US011542259B2

(12) United States Patent
Bannen et al.

(10) Patent No.: US 11,542,259 B2
(45) Date of Patent: Jan. 3, 2023

(54) COMPOUNDS FOR THE TREATMENT OF KINASE-DEPENDENT DISORDERS

(71) Applicant: Exelixis, Inc., Alameda, CA (US)

(72) Inventors: Lynne Canne Bannen, Novato, CA (US); Minna Bui, Oakland, CA (US); Faming Jiang, Castro Valley, CA (US); Kin Tso, San Francisco, CA (US); Yong Wang, South San Francisco, CA (US); Wei Xu, Danville, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 16/964,330

(22) PCT Filed: Jan. 25, 2019

(86) PCT No.: PCT/US2019/015297
§ 371 (c)(1),
(2) Date: Jul. 23, 2020

(87) PCT Pub. No.: WO2019/148044
PCT Pub. Date: Aug. 1, 2019

(65) Prior Publication Data

US 2021/0040076 A1 Feb. 11, 2021

Related U.S. Application Data

(60) Provisional application No. 62/622,702, filed on Jan. 26, 2018, provisional application No. 62/758,321, filed on Nov. 9, 2018.

(51) Int. Cl.

| | |
|---|---|
| ***C07D 413/12*** | (2006.01) |
| ***C07D 215/22*** | (2006.01) |
| ***C07D 401/12*** | (2006.01) |
| ***C07D 405/12*** | (2006.01) |
| ***C07D 413/10*** | (2006.01) |
| ***C07D 498/04*** | (2006.01) |

(52) U.S. Cl.
CPC ......... *C07D 413/12* (2013.01); *C07D 215/22* (2013.01); *C07D 401/12* (2013.01); *C07D 405/12* (2013.01); *C07D 413/10* (2013.01); *C07D 498/04* (2013.01)

(58) Field of Classification Search
CPC .. C07D 413/12; C07D 215/22; C07D 401/12; C07D 405/12; C07D 413/10; C07D 498/04
See application file for complete search history.

(56) References Cited

U.S. PATENT DOCUMENTS

2004/0053908 A1* 3/2004 Funahashi ............ C07D 215/36 514/408
2009/0053236 A1* 2/2009 Yamamoto ........... A61K 31/502 514/312
2010/0093727 A1* 4/2010 Xi ............................ A61P 9/10 546/113
2012/0035212 A1 2/2012 Brown et al.
2012/0070368 A1* 3/2012 Bannen .............. A61K 31/7068 424/130.1
2013/0337015 A1 12/2013 Wilson
2014/0121239 A1 5/2014 Aftab
2014/0200242 A1 7/2014 Wilson
2014/0221425 A1* 8/2014 Yun ......................... A61P 35/02 514/312
2014/0228401 A1 8/2014 Aftab et al.
2014/0256938 A1 9/2014 Wilson et al.
2014/0323522 A1 10/2014 Aftab et al.
2014/0330170 A1 11/2014 Holland (Continued)

FOREIGN PATENT DOCUMENTS

CN 104817497 A 8/2015
CN 105797123 A 7/2016

(Continued)

OTHER PUBLICATIONS

Package Insert for CABOMETYX, 21 pages, Dated Apr. 2016. (Year: 2016).*

(Continued)

*Primary Examiner* — Daniel R Carcanague

(74) *Attorney, Agent, or Firm* — Honigman LLP; Heidi M. Berven; Li Gao

(57) ABSTRACT

Disclosed herein are compounds of formula I. Compounds of formula I inhibit, regulate and/or modulate kinase receptor, particularly Axl and Mer signal transduction pathways related to the changes in cellular activities as mentioned above, compositions which contain these compounds, and methods of using them to treat kinase-dependent diseases and conditions. The present invention also provides methods for making compounds as mentioned above, and compositions which contain these compounds.

(I)

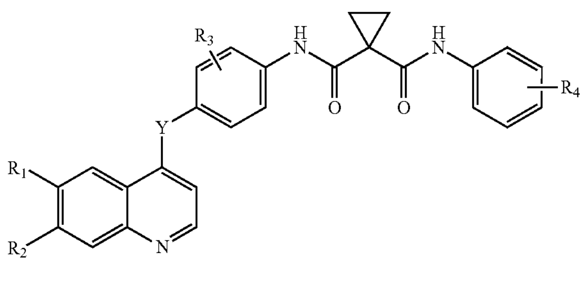

2 Claims, No Drawings

Specification includes a Sequence Listing.

(56) References Cited

U.S. PATENT DOCUMENTS

| | | | | |
|---|---|---|---|---|
| 2015/0133494 | A1 | 5/2015 | Aftab | |
| 2015/0202196 | A1 | 7/2015 | Bannen et al. | |
| 2016/0022662 | A1 | 1/2016 | DeCillis | |
| 2016/0031818 | A1 | 2/2016 | Aftab et al. | |
| 2016/0082019 | A1 | 3/2016 | Sweeney et al. | |
| 2017/0042880 | A1 | 2/2017 | Aftab et al. | |
| 2017/0044106 | A1 | 2/2017 | Aftab et al. | |
| 2017/0087143 | A1 | 3/2017 | Aftab et al. | |
| 2017/0217896 | A1 | 8/2017 | Xu et al. | |
| 2017/0224672 | A1 | 8/2017 | Aftab et al. | |
| 2017/0342033 | A1* | 11/2017 | Horn | A61K 31/47 |
| 2018/0009758 | A1 | 1/2018 | Horn | |
| 2018/0244667 | A1 | 8/2018 | Long et al. | |
| 2019/0091215 | A1 | 3/2019 | Aftab et al. | |
| 2019/0151302 | A1 | 5/2019 | Aftab et al. | |
| 2019/0209547 | A1 | 7/2019 | Aftab et al. | |
| 2019/0262330 | A1 | 8/2019 | Schwab et al. | |
| 2019/0375714 | A1* | 12/2019 | Si | A61K 31/4709 |
| 2020/0255382 | A1 | 8/2020 | Schwab et al. | |
| 2020/0268737 | A1 | 8/2020 | Shah et al. | |
| 2020/0330450 | A1 | 10/2020 | Smith et al. | |
| 2021/0030737 | A1 | 2/2021 | Tolaney et al. | |
| 2021/0032263 | A1* | 2/2021 | Bannen | C07D 471/04 |
| 2021/0040099 | A1* | 2/2021 | Bannen | A61P 35/00 |
| 2021/0261509 | A1 | 8/2021 | Shah | |
| 2021/0275515 | A1 | 9/2021 | Apolo | |
| 2022/0056138 | A1 | 2/2022 | Schwab et al. | |
| 2022/0089541 | A1* | 3/2022 | Bannen | C07D 215/48 |

FOREIGN PATENT DOCUMENTS

| | | | | |
|---|---|---|---|---|
| CN | 106400155 | A | 2/2017 | |
| EP | 2769976 | A1 | 8/2014 | |
| WO | 2005030140 | A2 | 4/2005 | |
| WO | 2010045095 | A1 | 4/2010 | |
| WO | 2011017639 | A1 | 2/2011 | |
| WO | 2012006960 | A1 | 1/2012 | |
| WO | 2012034055 | A2 | 3/2012 | |
| WO | 2016184434 | A1 | 11/2016 | |
| WO | 2019125798 | A1 | 6/2019 | |
| WO | WO-2020123800 | A1 * | 6/2020 | A61P 35/00 |
| WO | WO-2020154610 | A1 * | 7/2020 | A61P 35/00 |
| WO | WO-2020247019 | A1 * | 12/2020 | A61P 35/00 |
| WO | WO-2020247418 | A1 * | 12/2020 | A61P 35/00 |
| WO | WO-2021222673 | A1 * | 11/2021 | A61P 35/00 |
| WO | WO-2022026706 | A1 * | 2/2022 | A61P 35/00 |
| WO | WO-2022098828 | A1 * | 5/2022 | |

OTHER PUBLICATIONS

Parikh; European Journal of Medicinal Chemistry 2018, 143, 1103-1138. https://doi.org/10.1016/j.ejmech.2017.08.044 (Year: 2018).*

International Search Report for PCT/US2019/015297, dated May 13, 2019.

* cited by examiner

```
                              SEQUENCE LISTING


<160> NUMBER OF SEQ ID NOS: 45

<210> SEQ ID NO 1
<211> LENGTH: 587
<212> TYPE: PRT
<213> ORGANISM: Homo sapiens

<400> SEQUENCE: 1

Met Arg Pro Arg Gly Leu Pro Pro Leu Leu Val Val Leu Leu Gly Cys
1               5                   10                  15

Trp Ala Ser Val Ser Ala Gln Thr Asp Ala Thr Pro Ala Val Thr Thr
            20                  25                  30

Glu Gly Leu Asn Ser Thr Glu Ala Ala Leu Ala Thr Phe Gly Thr Phe
        35                  40                  45

Pro Ser Thr Arg Pro Pro Gly Thr Pro Arg Ala Pro Gly Pro Ser Ser
    50                  55                  60

Gly Pro Arg Pro Thr Pro Val Thr Asp Val Ala Val Leu Cys Val Cys
65                  70                  75                  80

Asp Leu Ser Pro Ala Gln Cys Asp Ile Asn Cys Cys Cys Asp Pro Asp
                85                  90                  95

Cys Ser Ser Val Asp Phe Ser Val Phe Ser Ala Cys Ser Val Pro Val
            100                 105                 110

Val Thr Gly Asp Ser Gln Phe Cys Ser Gln Lys Ala Val Ile Tyr Ser
        115                 120                 125

Leu Asn Phe Thr Ala Asn Pro Pro Gln Arg Val Phe Glu Leu Val Asp
    130                 135                 140

Gln Ile Asn Pro Ser Ile Phe Cys Ile His Ile Thr Asn Tyr Lys Pro
145                 150                 155                 160

Ala Leu Ser Phe Ile Asn Pro Glu Val Pro Asp Glu Asn Asn Phe Asp
                165                 170                 175

Thr Leu Met Lys Thr Ser Asp Gly Phe Thr Leu Asn Ala Glu Ser Tyr
            180                 185                 190

Val Ser Phe Thr Thr Lys Leu Asp Ile Pro Thr Ala Ala Lys Tyr Glu
        195                 200                 205

Tyr Gly Val Pro Leu Gln Thr Ser Asp Ser Phe Leu Arg Phe Pro Ser
    210                 215                 220

Ser Leu Thr Ser Ser Leu Cys Thr Asp Asn Asn Pro Ala Ala Phe Leu
225                 230                 235                 240

Val Asn Gln Ala Val Lys Cys Thr Arg Lys Ile Asn Leu Glu Gln Cys
                245                 250                 255

Glu Glu Ile Glu Ala Leu Ser Met Ala Phe Tyr Ser Ser Pro Glu Ile
            260                 265                 270

Leu Arg Val Pro Asp Ser Arg Lys Lys Val Pro Ile Thr Val Gln Ser
        275                 280                 285

Ile Val Ile Gln Ser Leu Asn Lys Thr Leu Thr Arg Arg Glu Asp Thr
    290                 295                 300
```

```
Asp Val Leu Gln Pro Thr Leu Val Asn Ala Gly His Phe Ser Leu Cys
305                 310                 315                 320

Val Asn Val Val Leu Glu Val Lys Tyr Ser Leu Thr Tyr Thr Asp Ala
                325                 330                 335

Gly Glu Val Thr Lys Ala Asp Leu Ser Phe Val Leu Gly Thr Val Ser
            340                 345                 350

Ser Val Val Val Pro Leu Gln Gln Lys Phe Glu Ile His Phe Leu Gln
        355                 360                 365

Glu Asn Thr Gln Pro Val Pro Leu Ser Gly Asn Pro Gly Tyr Val Val
    370                 375                 380

Gly Leu Pro Leu Ala Ala Gly Phe Gln Pro His Lys Gly Ser Gly Ile
385                 390                 395                 400

Ile Gln Thr Thr Asn Arg Tyr Gly Gln Leu Thr Ile Leu His Ser Thr
                405                 410                 415

Thr Glu Gln Asp Cys Leu Ala Leu Glu Gly Val Arg Thr Pro Val Leu
            420                 425                 430

Phe Gly Tyr Thr Met Gln Ser Gly Cys Lys Leu Arg Leu Thr Gly Ala
        435                 440                 445

Leu Pro Cys Gln Leu Val Ala Gln Lys Val Lys Ser Leu Leu Trp Gly
    450                 455                 460

Gln Gly Phe Pro Asp Tyr Val Ala Pro Phe Gly Asn Ser Gln Ala Gln
465                 470                 475                 480

Asp Met Leu Asp Trp Val Pro Ile His Phe Ile Thr Gln Ser Phe Asn
                485                 490                 495

Arg Lys Asp Ser Cys Gln Leu Pro Gly Ala Leu Val Ile Glu Val Lys
            500                 505                 510

Trp Thr Lys Tyr Gly Ser Leu Leu Asn Pro Gln Ala Lys Ile Val Asn
        515                 520                 525

Val Thr Ala Asn Leu Ile Ser Ser Ser Phe Pro Glu Ala Asn Ser Gly
    530                 535                 540

Asn Glu Arg Thr Ile Leu Ile Ser Thr Ala Val Thr Phe Val Asp Val
545                 550                 555                 560

Ser Ala Pro Ala Glu Ala Gly Phe Arg Ala Pro Pro Ala Ile Asn Ala
                565                 570                 575

Arg Leu Pro Phe Asn Phe Phe Phe Pro Phe Val
            580                 585


<210> SEQ ID NO 2
<211> LENGTH: 697
<212> TYPE: PRT
<213> ORGANISM: Homo sapiens

<400> SEQUENCE: 2

Met Gly Phe Gln Pro Pro Ala Ala Leu Leu Leu Arg Leu Phe Leu Leu
1               5                   10                  15

Gln Gly Ile Leu Arg Leu Leu Trp Gly Asp Leu Ala Phe Ile Pro Pro
            20                  25                  30

Phe Ile Arg Met Ser Gly Pro Ala Val Ser Ala Ser Leu Val Gly Asp
        35                  40                  45

Thr Glu Gly Val Thr Val Ser Leu Ala Val Leu Gln Asp Glu Ala Gly
    50                  55                  60

Ile Leu Pro Ile Pro Thr Cys Gly Val Leu Asn Asn Glu Thr Glu Asp
65                  70                  75                  80

Trp Ser Val Thr Val Ile Pro Gly Ala Lys Val Leu Glu Val Thr Val
```

-continued

```
                85                  90                  95
Arg Trp Lys Arg Gly Leu Asp Trp Cys Ser Ser Asn Glu Thr Asp Ser
            100                 105                 110
Phe Ser Glu Ser Pro Cys Ile Leu Gln Thr Leu Leu Val Ser Ala Ser
        115                 120                 125
His Asn Ser Ser Cys Ser Ala His Leu Leu Ile Gln Val Glu Ile Tyr
    130                 135                 140
Ala Asn Ser Ser Leu Thr His Asn Ala Ser Glu Asn Val Thr Val Ile
145                 150                 155                 160
Pro Asn Gln Val Tyr Gln Pro Leu Gly Pro Cys Pro Cys Asn Leu Thr
                165                 170                 175
Ala Gly Ala Cys Asp Val Arg Cys Cys Cys Asp Gln Glu Cys Ser Ser
            180                 185                 190
Asn Leu Thr Thr Leu Phe Arg Arg Ser Cys Phe Thr Gly Val Phe Gly
        195                 200                 205
Gly Asp Val Asn Pro Pro Phe Asp Gln Leu Cys Ser Ala Gly Thr Thr
    210                 215                 220
Thr Arg Gly Val Pro Asp Trp Phe Pro Phe Leu Cys Val Gln Ser Pro
225                 230                 235                 240
Leu Ala Asn Thr Pro Phe Leu Gly Tyr Phe Tyr His Gly Ala Val Ser
                245                 250                 255
Pro Lys Gln Asp Ser Ser Phe Glu Val Tyr Val Asp Thr Asp Ala Lys
            260                 265                 270
Asp Phe Ala Asp Phe Gly Tyr Lys Gln Gly Asp Pro Ile Met Thr Val
        275                 280                 285
Lys Lys Ala Tyr Phe Thr Ile Pro Gln Val Ser Leu Ala Gly Gln Cys
    290                 295                 300
Met Gln Asn Ala Pro Val Ala Phe Leu His Asn Phe Asp Val Lys Cys
305                 310                 315                 320
Val Thr Asn Leu Glu Leu Tyr Gln Glu Arg Asp Gly Ile Ile Asn Ala
                325                 330                 335
Lys Ile Lys Asn Val Ala Leu Gly Gly Ile Val Thr Pro Lys Val Ile
            340                 345                 350
Tyr Glu Glu Ala Thr Asp Leu Asp Lys Phe Ile Thr Asn Thr Glu Thr
        355                 360                 365
Pro Leu Asn Asn Gly Ser Thr Pro Arg Ile Val Asn Val Glu Glu His
    370                 375                 380
Tyr Ile Phe Lys Trp Asn Asn Asn Thr Ile Ser Glu Ile Asn Val Lys
385                 390                 395                 400
Ile Phe Arg Ala Glu Ile Asn Ala His Gln Lys Gly Ile Met Thr Gln
                405                 410                 415
Arg Phe Val Val Lys Phe Leu Ser Tyr Asn Ser Gly Asn Glu Glu Glu
            420                 425                 430
Leu Ser Gly Asn Pro Gly Tyr Gln Leu Gly Lys Pro Val Arg Ala Leu
        435                 440                 445
Asn Ile Asn Arg Met Asn Asn Val Thr Thr Leu His Leu Trp Gln Ser
    450                 455                 460
Ala Gly Arg Gly Leu Cys Thr Ser Ala Thr Phe Lys Pro Ile Leu Phe
465                 470                 475                 480
Gly Glu Asn Val Leu Ser Gly Cys Leu Leu Glu Val Gly Ile Asn Glu
                485                 490                 495
Asn Cys Thr Gln Leu Arg Glu Asn Ala Val Glu Arg Leu Asp Ser Leu
            500                 505                 510
```

```
Ile Gln Ala Thr His Val Ala Met Arg Gly Asn Ser Asp Tyr Ala Asp
        515                 520                 525

Leu Ser Asp Gly Trp Leu Glu Ile Ile Arg Val Asp Ala Pro Asp Pro
    530                 535                 540

Gly Ala Asp Pro Leu Ala Ser Ser Val Asn Gly Met Cys Leu Asp Ile
545                 550                 555                 560

Pro Ala His Leu Ser Ile Arg Ile Leu Ile Ser Asp Ala Gly Ala Val
                565                 570                 575

Glu Gly Ile Thr Gln Gln Glu Ile Leu Gly Val Glu Thr Arg Phe Ser
            580                 585                 590

Ser Val Asn Trp Gln Tyr Gln Cys Gly Leu Thr Cys Glu His Lys Ala
        595                 600                 605

Asp Leu Leu Pro Ile Ser Ala Ser Val Gln Phe Ile Lys Ile Pro Ala
    610                 615                 620

Gln Leu Pro His Pro Leu Thr Arg Phe Gln Ile Asn Tyr Thr Glu Tyr
625                 630                 635                 640

Asp Cys Asn Arg Asn Glu Val Cys Trp Pro Gln Leu Leu Tyr Pro Trp
                645                 650                 655

Thr Gln Tyr Tyr Gln Gly Glu Leu His Ser Gln Cys Val Ala Lys Gly
            660                 665                 670

Leu Leu Leu Leu Leu Phe Leu Thr Leu Ala Leu Phe Leu Ser Asn Pro
        675                 680                 685

Trp Thr Arg Ile Cys Lys Ala Tyr Ser
    690                 695


<210> SEQ ID NO 3
<211> LENGTH: 607
<212> TYPE: PRT
<213> ORGANISM: Homo sapiens

<400> SEQUENCE: 3

Met Arg Thr Pro Gln Leu Ala Leu Leu Gln Val Phe Phe Leu Val Phe
1               5                   10                  15

Pro Asp Gly Val Arg Pro Gln Pro Ser Ser Ser Pro Ser Gly Ala Val
            20                  25                  30

Pro Thr Ser Leu Glu Leu Gln Arg Gly Thr Asp Gly Gly Thr Leu Gln
        35                  40                  45

Ser Pro Ser Glu Ala Thr Ala Thr Arg Pro Ala Val Pro Gly Leu Pro
    50                  55                  60

Thr Val Val Pro Thr Leu Val Thr Pro Ser Ala Pro Gly Asn Arg Thr
65                  70                  75                  80

Val Asp Leu Phe Pro Val Leu Pro Ile Cys Val Cys Asp Leu Thr Pro
                85                  90                  95

Gly Ala Cys Asp Ile Asn Cys Cys Cys Asp Arg Asp Cys Tyr Leu Leu
            100                 105                 110

His Pro Arg Thr Val Phe Ser Phe Cys Leu Pro Gly Ser Val Arg Ser
        115                 120                 125

Ser Ser Trp Val Cys Val Asp Asn Ser Val Ile Phe Arg Ser Asn Ser
    130                 135                 140

Pro Phe Pro Ser Arg Val Phe Met Asp Ser Asn Gly Ile Arg Gln Phe
145                 150                 155                 160

Cys Val His Val Asn Asn Ser Asn Leu Asn Tyr Phe Gln Lys Leu Gln
                165                 170                 175

Lys Val Asn Ala Thr Asn Phe Gln Ala Leu Ala Ala Glu Phe Gly Gly
```

```
            180                 185                 190

Glu Ser Phe Thr Ser Thr Phe Gln Thr Gln Ser Pro Pro Ser Phe Tyr
        195                 200                 205

Arg Ala Gly Asp Pro Ile Leu Thr Tyr Phe Pro Lys Trp Ser Val Ile
    210                 215                 220

Ser Leu Leu Arg Gln Pro Ala Gly Val Gly Ala Gly Gly Leu Cys Ala
225                 230                 235                 240

Glu Ser Asn Pro Ala Gly Phe Leu Glu Ser Lys Ser Thr Thr Cys Thr
                245                 250                 255

Arg Phe Phe Lys Asn Leu Ala Ser Ser Cys Thr Leu Asp Ser Ala Leu
            260                 265                 270

Asn Ala Ala Ser Tyr Tyr Asn Phe Thr Val Leu Lys Val Pro Arg Ser
        275                 280                 285

Met Thr Asp Pro Gln Asn Met Glu Phe Gln Val Pro Val Ile Leu Thr
    290                 295                 300

Ser Gln Ala Asn Ala Pro Leu Leu Ala Gly Asn Thr Cys Gln Asn Val
305                 310                 315                 320

Val Ser Gln Val Thr Tyr Glu Ile Glu Thr Asn Gly Thr Phe Gly Ile
                325                 330                 335

Gln Lys Val Ser Val Ser Leu Gly Gln Thr Asn Leu Thr Val Glu Pro
            340                 345                 350

Gly Ala Ser Leu Gln Gln His Phe Ile Leu Arg Phe Arg Ala Phe Gln
        355                 360                 365

Gln Ser Thr Ala Ala Ser Leu Thr Ser Pro Arg Ser Gly Asn Pro Gly
    370                 375                 380

Tyr Ile Val Gly Lys Pro Leu Leu Ala Leu Thr Asp Asp Ile Ser Tyr
385                 390                 395                 400

Ser Met Thr Leu Leu Gln Ser Gln Gly Asn Gly Ser Cys Ser Val Lys
                405                 410                 415

Arg His Glu Val Gln Phe Gly Val Asn Ala Ile Ser Gly Cys Lys Leu
            420                 425                 430

Arg Leu Lys Lys Ala Asp Cys Ser His Leu Gln Gln Glu Ile Tyr Gln
        435                 440                 445

Thr Leu His Gly Arg Pro Arg Pro Glu Tyr Val Ala Ile Phe Gly Asn
    450                 455                 460

Ala Asp Pro Ala Gln Lys Gly Gly Trp Thr Arg Ile Leu Asn Arg His
465                 470                 475                 480

Cys Ser Ile Ser Ala Ile Asn Cys Thr Ser Cys Cys Leu Ile Pro Val
                485                 490                 495

Ser Leu Glu Ile Gln Val Leu Trp Ala Tyr Val Gly Leu Leu Ser Asn
            500                 505                 510

Pro Gln Ala His Val Ser Gly Val Arg Phe Leu Tyr Gln Cys Gln Ser
        515                 520                 525

Ile Gln Asp Ser Gln Gln Val Thr Glu Val Ser Leu Thr Thr Leu Val
    530                 535                 540

Asn Phe Val Asp Ile Thr Gln Lys Pro Gln Pro Pro Arg Gly Gln Pro
545                 550                 555                 560

Lys Met Asp Trp Lys Trp Pro Phe Asp Phe Phe Pro Phe Lys Val Ala
                565                 570                 575

Phe Ser Arg Gly Val Phe Ser Gln Lys Cys Ser Val Ser Pro Ile Leu
            580                 585                 590

Ile Leu Cys Leu Leu Leu Leu Gly Val Leu Asn Leu Glu Thr Met
        595                 600                 605
```

<210> SEQ ID NO 4
<211> LENGTH: 106
<212> TYPE: PRT
<213> ORGANISM: Homo sapiens

<400> SEQUENCE: 4

```
Met Ala Thr Pro Gly Pro Val Ile Pro Glu Val Pro Phe Glu Pro Ser
1               5                   10                  15

Lys Pro Pro Val Ile Glu Gly Leu Ser Pro Thr Val Tyr Arg Asn Pro
            20                  25                  30

Glu Ser Phe Lys Glu Lys Phe Val Arg Lys Thr Arg Glu Asn Pro Val
        35                  40                  45

Val Pro Ile Gly Cys Leu Ala Thr Ala Ala Ala Leu Thr Tyr Gly Leu
    50                  55                  60

Tyr Ser Phe His Arg Gly Asn Ser Gln Arg Ser Gln Leu Met Met Arg
65                  70                  75                  80

Thr Arg Ile Ala Ala Gln Gly Phe Thr Val Ala Ala Ile Leu Leu Gly
                85                  90                  95

Leu Ala Val Thr Ala Met Lys Ser Arg Pro
            100                 105
```

<210> SEQ ID NO 5
<211> LENGTH: 106
<212> TYPE: PRT
<213> ORGANISM: Homo sapiens

<400> SEQUENCE: 5

```
Met Ala Thr Leu Gly Phe Val Thr Pro Glu Ala Pro Phe Glu Ser Ser
1               5                   10                  15

Lys Pro Pro Ile Phe Glu Gly Leu Ser Pro Thr Val Tyr Ser Asn Pro
            20                  25                  30

Glu Gly Phe Lys Glu Lys Phe Leu Arg Lys Thr Arg Glu Asn Pro Val
        35                  40                  45

Val Pro Ile Gly Phe Leu Cys Thr Ala Ala Val Leu Thr Asn Gly Leu
    50                  55                  60

Tyr Cys Phe His Gln Gly Asn Ser Gln Cys Ser Arg Leu Met Met His
65                  70                  75                  80

Thr Gln Ile Ala Ala Gln Gly Phe Thr Ile Ala Ala Ile Leu Leu Gly
                85                  90                  95

Leu Ala Ala Thr Ala Met Lys Ser Pro Pro
            100                 105
```

<210> SEQ ID NO 6
<211> LENGTH: 132
<212> TYPE: PRT
<213> ORGANISM: Homo sapiens

<400> SEQUENCE: 6

```
Met Cys Ser Ala Gly Glu Leu Leu Arg Gly Gly Asp Gly Gly Glu Arg
1               5                   10                  15

Asp Glu Asp Gly Asp Ala Leu Ala Glu Arg Glu Ala Ala Gly Thr Gly
            20                  25                  30

Trp Asp Pro Gly Ala Ser Pro Arg Arg Arg Gly Gln Arg Pro Lys Glu
        35                  40                  45

Ser Glu Gln Asp Val Glu Asp Ser Gln Asn His Thr Gly Glu Pro Val
    50                  55                  60
```

```
Gly Asp Asp Tyr Lys Lys Met Gly Thr Leu Phe Gly Glu Leu Asn Lys
65                  70                  75                  80

Asn Leu Ile Asn Met Gly Phe Thr Arg Met Tyr Phe Gly Glu Arg Ile
                85                  90                  95

Val Glu Pro Val Ile Val Ile Phe Phe Trp Val Met Leu Trp Phe Leu
            100                 105                 110

Gly Leu Gln Ala Leu Gly Leu Val Ala Val Leu Cys Leu Val Ile Ile
        115                 120                 125

Tyr Val Gln Gln
    130


<210> SEQ ID NO 7
<211> LENGTH: 1104
<212> TYPE: PRT
<213> ORGANISM: Homo sapiens

<400> SEQUENCE: 7

Met Glu Arg Ser Pro Gly Glu Gly Pro Ser Pro Ser Pro Met Asp Gln
1               5                   10                  15

Pro Ser Ala Pro Ser Asp Pro Thr Asp Gln Pro Pro Ala Ala His Ala
            20                  25                  30

Lys Pro Asp Pro Gly Ser Gly Gly Gln Pro Ala Gly Pro Gly Ala Ala
        35                  40                  45

Gly Glu Ala Leu Ala Val Leu Thr Ser Phe Gly Arg Arg Leu Leu Val
    50                  55                  60

Leu Ile Pro Val Tyr Leu Ala Gly Ala Val Gly Leu Ser Val Gly Phe
65                  70                  75                  80

Val Leu Phe Gly Leu Ala Leu Tyr Leu Gly Trp Arg Arg Val Arg Asp
                85                  90                  95

Glu Lys Glu Arg Ser Leu Arg Ala Ala Arg Gln Leu Leu Asp Asp Glu
            100                 105                 110

Glu Gln Leu Thr Ala Lys Thr Leu Tyr Met Ser His Arg Glu Leu Pro
        115                 120                 125

Ala Trp Val Ser Phe Pro Asp Val Glu Lys Ala Glu Trp Leu Asn Lys
    130                 135                 140

Ile Val Ala Gln Val Trp Pro Phe Leu Gly Gln Tyr Met Glu Lys Leu
145                 150                 155                 160

Leu Ala Glu Thr Val Ala Pro Ala Val Arg Gly Ser Asn Pro His Leu
                165                 170                 175

Gln Thr Phe Thr Phe Thr Arg Val Glu Leu Gly Glu Lys Pro Leu Arg
            180                 185                 190

Ile Ile Gly Val Lys Val His Pro Gly Gln Arg Lys Glu Gln Ile Leu
        195                 200                 205

Leu Asp Leu Asn Ile Ser Tyr Val Gly Asp Val Gln Ile Asp Val Glu
    210                 215                 220

Val Lys Lys Tyr Phe Cys Lys Ala Gly Val Lys Gly Met Gln Leu His
225                 230                 235                 240

Gly Val Leu Arg Val Ile Leu Glu Pro Leu Ile Gly Asp Leu Pro Phe
                245                 250                 255

Val Gly Ala Val Ser Met Phe Phe Ile Arg Arg Pro Thr Leu Asp Ile
            260                 265                 270

Asn Trp Thr Gly Met Thr Asn Leu Leu Asp Ile Pro Gly Leu Ser Ser
        275                 280                 285

Leu Ser Asp Thr Met Ile Met Asp Ser Ile Ala Ala Phe Leu Val Leu
    290                 295                 300
```

-continued

```
Pro Asn Arg Leu Leu Val Pro Leu Val Pro Asp Leu Gln Asp Val Ala
305                 310                 315                 320

Gln Leu Arg Ser Pro Leu Pro Arg Gly Ile Ile Arg Ile His Leu Leu
                325                 330                 335

Ala Ala Arg Gly Leu Ser Ser Lys Asp Lys Tyr Val Lys Gly Leu Ile
            340                 345                 350

Glu Gly Lys Ser Asp Pro Tyr Ala Leu Val Arg Leu Gly Thr Gln Thr
        355                 360                 365

Phe Cys Ser Arg Val Ile Asp Glu Glu Leu Asn Pro Gln Trp Gly Glu
    370                 375                 380

Thr Tyr Glu Val Met Val His Glu Val Pro Gly Gln Glu Ile Glu Val
385                 390                 395                 400

Glu Val Phe Asp Lys Asp Pro Asp Lys Asp Asp Phe Leu Gly Arg Met
                405                 410                 415

Lys Leu Asp Val Gly Lys Val Leu Gln Ala Ser Val Leu Asp Asp Trp
            420                 425                 430

Phe Pro Leu Gln Gly Gly Gln Gly Gln Val His Leu Arg Leu Glu Trp
        435                 440                 445

Leu Ser Leu Leu Ser Asp Ala Glu Lys Leu Glu Gln Val Leu Gln Trp
    450                 455                 460

Asn Trp Gly Val Ser Ser Arg Pro Asp Pro Pro Ser Ala Ala Ile Leu
465                 470                 475                 480

Val Val Tyr Leu Asp Arg Ala Gln Asp Leu Pro Leu Lys Lys Gly Asn
                485                 490                 495

Lys Glu Pro Asn Pro Met Val Gln Leu Ser Ile Gln Asp Val Thr Gln
            500                 505                 510

Glu Ser Lys Ala Val Tyr Ser Thr Asn Cys Pro Val Trp Glu Glu Ala
        515                 520                 525

Phe Arg Phe Phe Leu Gln Asp Pro Gln Ser Gln Glu Leu Asp Val Gln
    530                 535                 540

Val Lys Asp Asp Ser Arg Ala Leu Thr Leu Gly Ala Leu Thr Leu Pro
545                 550                 555                 560

Leu Ala Arg Leu Leu Thr Ala Pro Glu Leu Ile Leu Asp Gln Trp Phe
                565                 570                 575

Gln Leu Ser Ser Ser Gly Pro Asn Ser Arg Leu Tyr Met Lys Leu Val
            580                 585                 590

Met Arg Ile Leu Tyr Leu Asp Ser Ser Glu Ile Cys Phe Pro Thr Val
        595                 600                 605

Pro Gly Cys Pro Gly Ala Trp Asp Val Asp Ser Glu Asn Pro Gln Arg
    610                 615                 620

Gly Ser Ser Val Asp Ala Pro Pro Arg Pro Cys His Thr Thr Pro Asp
625                 630                 635                 640

Ser Gln Phe Gly Thr Glu His Val Leu Arg Ile His Val Leu Glu Ala
                645                 650                 655

Gln Asp Leu Ile Ala Lys Asp Arg Phe Leu Gly Gly Leu Val Lys Gly
            660                 665                 670

Lys Ser Asp Pro Tyr Val Lys Leu Lys Leu Ala Gly Arg Ser Phe Arg
        675                 680                 685

Ser His Val Val Arg Glu Asp Leu Asn Pro Arg Trp Asn Glu Val Phe
    690                 695                 700

Glu Val Ile Val Thr Ser Val Pro Gly Gln Glu Leu Glu Val Glu Val
705                 710                 715                 720
```

-continued

```
Phe Asp Lys Asp Leu Asp Lys Asp Asp Phe Leu Gly Arg Cys Lys Val
                725                 730                 735

Arg Leu Thr Thr Val Leu Asn Ser Gly Phe Leu Asp Glu Trp Leu Thr
            740                 745                 750

Leu Glu Asp Val Pro Ser Gly Arg Leu His Leu Arg Leu Glu Arg Leu
        755                 760                 765

Thr Pro Arg Pro Thr Ala Ala Glu Leu Glu Glu Val Leu Gln Val Asn
    770                 775                 780

Ser Leu Ile Gln Thr Gln Lys Ser Ala Glu Leu Ala Ala Ala Leu Leu
785                 790                 795                 800

Ser Ile Tyr Met Glu Arg Ala Glu Asp Leu Pro Leu Arg Lys Gly Thr
                805                 810                 815

Lys His Leu Ser Pro Tyr Ala Thr Leu Thr Val Gly Asp Ser Ser His
            820                 825                 830

Lys Thr Lys Thr Ile Ser Gln Thr Ser Ala Pro Val Trp Asp Glu Ser
        835                 840                 845

Ala Ser Phe Leu Ile Arg Lys Pro His Thr Glu Ser Leu Glu Leu Gln
    850                 855                 860

Val Arg Gly Glu Gly Thr Gly Val Leu Gly Ser Leu Ser Leu Pro Leu
865                 870                 875                 880

Ser Glu Leu Leu Val Ala Asp Gln Leu Cys Leu Asp Arg Trp Phe Thr
                885                 890                 895

Leu Ser Ser Gly Gln Gly Gln Val Leu Leu Arg Ala Gln Leu Gly Ile
            900                 905                 910

Leu Val Ser Gln His Ser Gly Val Glu Ala His Ser His Ser Tyr Ser
        915                 920                 925

His Ser Ser Ser Ser Leu Ser Glu Glu Pro Glu Leu Ser Gly Gly Pro
    930                 935                 940

Pro His Ile Thr Ser Ser Ala Pro Glu Leu Arg Gln Arg Leu Thr His
945                 950                 955                 960

Val Asp Ser Pro Leu Glu Ala Pro Ala Gly Pro Leu Gly Gln Val Lys
                965                 970                 975

Leu Thr Leu Trp Tyr Tyr Ser Glu Glu Arg Lys Leu Val Ser Ile Val
            980                 985                 990

His Gly Cys Arg Ser Leu Arg Gln  Asn Gly Arg Asp Pro  Pro Asp Pro
        995                 1000                1005

Tyr Val  Ser Leu Leu Leu Leu  Pro Asp Lys Asn Arg  Gly Thr Lys
    1010                1015                1020

Arg Arg  Thr Ser Gln Lys Lys  Arg Thr Leu Ser Pro  Glu Phe Asn
    1025                1030                1035

Glu Arg  Phe Glu Trp Glu Leu  Pro Leu Asp Glu Ala  Gln Arg Arg
    1040                1045                1050

Lys Leu  Asp Val Ser Val Lys  Ser Asn Ser Ser Phe  Met Ser Arg
    1055                1060                1065

Glu Arg  Glu Leu Leu Gly Lys  Val Gln Leu Asp Leu  Ala Glu Thr
    1070                1075                1080

Asp Leu  Ser Gln Gly Val Ala  Arg Trp Tyr Asp Leu  Met Asp Asn
    1085                1090                1095

Lys Asp  Lys Gly Ser Ser
    1100
```

<210> SEQ ID NO 8
<211> LENGTH: 271
<212> TYPE: PRT

-continued

<213> ORGANISM: Homo sapiens

<400> SEQUENCE: 8

```
Met Arg Gly Asn Leu Ala Leu Val Gly Val Leu Ile Ser Leu Ala Phe
1               5                   10                  15

Leu Ser Leu Leu Pro Ser Gly His Pro Gln Pro Ala Gly Asp Asp Ala
            20                  25                  30

Cys Ser Val Gln Ile Leu Val Pro Gly Leu Lys Gly Asp Ala Gly Glu
        35                  40                  45

Lys Gly Asp Lys Gly Ala Pro Gly Arg Pro Gly Arg Val Gly Pro Thr
    50                  55                  60

Gly Glu Lys Gly Asp Met Gly Asp Lys Gly Gln Lys Gly Ser Val Gly
65                  70                  75                  80

Arg His Gly Lys Ile Gly Pro Ile Gly Ser Lys Gly Glu Lys Gly Asp
                85                  90                  95

Ser Gly Asp Ile Gly Pro Pro Gly Pro Asn Gly Glu Pro Gly Leu Pro
            100                 105                 110

Cys Glu Cys Ser Gln Leu Arg Lys Ala Ile Gly Glu Met Asp Asn Gln
        115                 120                 125

Val Ser Gln Leu Thr Ser Glu Leu Lys Phe Ile Lys Asn Ala Val Ala
    130                 135                 140

Gly Val Arg Glu Thr Glu Ser Lys Ile Tyr Leu Leu Val Lys Glu Glu
145                 150                 155                 160

Lys Arg Tyr Ala Asp Ala Gln Leu Ser Cys Gln Gly Arg Gly Gly Thr
                165                 170                 175

Leu Ser Met Pro Lys Asp Glu Ala Ala Asn Gly Leu Met Ala Ala Tyr
            180                 185                 190

Leu Ala Gln Ala Gly Leu Ala Arg Val Phe Ile Gly Ile Asn Asp Leu
        195                 200                 205

Glu Lys Glu Gly Ala Phe Val Tyr Ser Asp His Ser Pro Met Arg Thr
    210                 215                 220

Phe Asn Lys Trp Arg Ser Gly Glu Pro Asn Asn Ala Tyr Asp Glu Glu
225                 230                 235                 240

Asp Cys Val Glu Met Val Ala Ser Gly Gly Trp Asn Asp Val Ala Cys
                245                 250                 255

His Thr Thr Met Tyr Phe Met Cys Glu Phe Asp Lys Glu Asn Met
            260                 265                 270
```

<210> SEQ ID NO 9
<211> LENGTH: 847
<212> TYPE: PRT
<213> ORGANISM: Homo sapiens

<400> SEQUENCE: 9

```
Met Phe Lys Cys Trp Ser Val Val Leu Val Leu Gly Phe Ile Phe Leu
1               5                   10                  15

Glu Ser Glu Gly Arg Pro Thr Lys Glu Gly Gly Tyr Gly Leu Lys Ser
            20                  25                  30

Tyr Gln Pro Leu Met Arg Leu Arg His Lys Gln Glu Lys Asn Gln Glu
        35                  40                  45

Ser Ser Arg Val Lys Gly Phe Met Ile Gln Asp Gly Pro Phe Gly Ser
    50                  55                  60

Cys Glu Asn Lys Tyr Cys Gly Leu Gly Arg His Cys Val Thr Ser Arg
65                  70                  75                  80

Glu Thr Gly Gln Ala Glu Cys Ala Cys Met Asp Leu Cys Lys Arg His
```

-continued

```
                85                  90                  95

Tyr Lys Pro Val Cys Gly Ser Asp Gly Glu Phe Tyr Glu Asn His Cys
            100                 105                 110

Glu Val His Arg Ala Ala Cys Leu Lys Lys Gln Lys Ile Thr Ile Val
        115                 120                 125

His Asn Glu Asp Cys Phe Phe Lys Gly Asp Lys Cys Lys Thr Thr Glu
    130                 135                 140

Tyr Ser Lys Met Lys Asn Met Leu Leu Asp Leu Gln Asn Gln Lys Tyr
145                 150                 155                 160

Ile Met Gln Glu Asn Glu Asn Pro Asn Gly Asp Asp Ile Ser Arg Lys
                165                 170                 175

Lys Leu Leu Val Asp Gln Met Phe Lys Tyr Phe Asp Ala Asp Ser Asn
            180                 185                 190

Gly Leu Val Asp Ile Asn Glu Leu Thr Gln Val Ile Lys Gln Glu Glu
        195                 200                 205

Leu Gly Lys Asp Leu Phe Asp Cys Thr Leu Tyr Val Leu Leu Lys Tyr
    210                 215                 220

Asp Asp Phe Asn Ala Asp Lys His Leu Ala Leu Glu Glu Phe Tyr Arg
225                 230                 235                 240

Ala Phe Gln Val Ile Gln Leu Ser Leu Pro Glu Asp Gln Lys Leu Ser
                245                 250                 255

Ile Thr Ala Ala Thr Val Gly Gln Ser Ala Val Leu Ser Cys Ala Ile
            260                 265                 270

Gln Gly Thr Leu Arg Pro Pro Ile Ile Trp Lys Arg Asn Asn Ile Ile
        275                 280                 285

Leu Asn Asn Leu Asp Leu Glu Asp Ile Asn Asp Phe Gly Asp Asp Gly
    290                 295                 300

Ser Leu Tyr Ile Thr Lys Val Thr Thr Thr His Val Gly Asn Tyr Thr
305                 310                 315                 320

Cys Tyr Ala Asp Gly Tyr Glu Gln Val Tyr Gln Thr His Ile Phe Gln
                325                 330                 335

Val Asn Val Pro Pro Val Ile Arg Val Tyr Pro Glu Ser Gln Ala Arg
            340                 345                 350

Glu Pro Gly Val Thr Ala Ser Leu Arg Cys His Ala Glu Gly Ile Pro
        355                 360                 365

Lys Pro Gln Leu Gly Trp Leu Lys Asn Gly Ile Asp Ile Thr Pro Lys
    370                 375                 380

Leu Ser Lys Gln Leu Thr Leu Gln Ala Asn Gly Ser Glu Val His Ile
385                 390                 395                 400

Ser Asn Val Arg Tyr Glu Asp Thr Gly Ala Tyr Thr Cys Ile Ala Lys
                405                 410                 415

Asn Glu Ala Gly Val Asp Glu Asp Ile Ser Ser Leu Phe Val Glu Asp
            420                 425                 430

Ser Ala Arg Lys Thr Leu Ala Asn Ile Leu Trp Arg Glu Glu Gly Leu
        435                 440                 445

Gly Ile Gly Asn Met Phe Tyr Val Phe Tyr Glu Asp Gly Ile Lys Val
    450                 455                 460

Ile Gln Pro Ile Glu Cys Glu Phe Gln Arg His Ile Lys Pro Ser Glu
465                 470                 475                 480

Lys Leu Leu Gly Phe Gln Asp Glu Val Cys Pro Lys Ala Glu Gly Asp
                485                 490                 495

Glu Val Gln Arg Cys Val Trp Ala Ser Ala Val Asn Val Lys Asp Lys
            500                 505                 510
```

```
Phe Ile Tyr Val Ala Gln Pro Thr Leu Asp Arg Val Leu Ile Val Asp
        515                 520                 525

Val Gln Ser Gln Lys Val Val Gln Ala Val Ser Thr Asp Pro Val Pro
    530                 535                 540

Val Lys Leu His Tyr Asp Lys Ser His Asp Gln Val Trp Val Leu Ser
545                 550                 555                 560

Trp Gly Thr Leu Glu Lys Thr Ser Pro Thr Leu Gln Val Ile Thr Leu
                565                 570                 575

Ala Ser Gly Asn Val Pro His His Thr Ile His Thr Gln Pro Val Gly
            580                 585                 590

Lys Gln Phe Asp Arg Val Asp Asp Phe Phe Ile Pro Thr Thr Thr Leu
        595                 600                 605

Ile Ile Thr His Met Arg Phe Gly Phe Ile Leu His Lys Asp Glu Ala
    610                 615                 620

Ala Leu Gln Lys Ile Asp Leu Glu Thr Met Ser Tyr Ile Lys Thr Ile
625                 630                 635                 640

Asn Leu Lys Asp Tyr Lys Cys Val Pro Gln Ser Leu Ala Tyr Thr His
                645                 650                 655

Leu Gly Gly Tyr Tyr Phe Ile Gly Cys Lys Pro Asp Ser Thr Gly Ala
            660                 665                 670

Val Ser Pro Gln Val Met Val Asp Gly Val Thr Asp Ser Val Ile Gly
        675                 680                 685

Phe Asn Ser Asp Val Thr Gly Thr Pro Tyr Val Ser Pro Asp Gly His
    690                 695                 700

Tyr Leu Val Ser Ile Asn Asp Val Lys Gly Leu Val Arg Val Gln Tyr
705                 710                 715                 720

Ile Thr Ile Arg Gly Glu Ile Gln Glu Ala Phe Asp Ile Tyr Thr Asn
                725                 730                 735

Leu His Ile Ser Asp Leu Ala Phe Gln Pro Ser Phe Thr Glu Ala His
            740                 745                 750

Gln Tyr Asn Ile Tyr Gly Ser Ser Ser Thr Gln Thr Asp Val Leu Phe
        755                 760                 765

Val Glu Leu Ser Ser Gly Lys Val Lys Met Ile Lys Ser Leu Lys Glu
    770                 775                 780

Pro Leu Lys Ala Glu Glu Trp Pro Trp Asn Arg Lys Asn Arg Gln Ile
785                 790                 795                 800

Gln Asp Ser Gly Leu Phe Gly Gln Tyr Leu Met Thr Pro Ser Lys Asp
                805                 810                 815

Ser Leu Phe Ile Leu Asp Gly Arg Leu Asn Lys Leu Asn Cys Glu Ile
            820                 825                 830

Thr Glu Val Glu Lys Gly Asn Thr Val Ile Trp Val Gly Asp Ala
        835                 840                 845


<210> SEQ ID NO 10
<211> LENGTH: 470
<212> TYPE: PRT
<213> ORGANISM: Homo sapiens

<400> SEQUENCE: 10

Met Ser Arg Leu Gly Ala Leu Gly Gly Ala Arg Ala Gly Leu Gly Leu
1               5                   10                  15

Leu Leu Gly Thr Ala Ala Gly Leu Gly Phe Leu Cys Leu Leu Tyr Ser
            20                  25                  30

Gln Arg Trp Lys Arg Thr Gln Arg His Gly Arg Ser Gln Ser Leu Pro
```

-continued

```
        35                  40                  45

Asn Ser Leu Asp Tyr Thr Gln Thr Ser Asp Pro Gly Arg His Val Met
    50                  55                  60

Leu Leu Arg Ala Val Pro Gly Gly Ala Gly Asp Ala Ser Val Leu Pro
65                  70                  75                  80

Ser Leu Pro Arg Glu Gly Gln Glu Lys Val Leu Asp Arg Leu Asp Phe
                85                  90                  95

Val Leu Thr Ser Leu Val Ala Leu Arg Arg Glu Val Glu Glu Leu Arg
            100                 105                 110

Ser Ser Leu Arg Gly Leu Ala Gly Glu Ile Val Gly Glu Val Arg Cys
        115                 120                 125

His Met Glu Glu Asn Gln Arg Val Ala Arg Arg Arg Arg Phe Pro Phe
    130                 135                 140

Val Arg Glu Arg Ser Asp Ser Thr Gly Ser Ser Ser Val Tyr Phe Thr
145                 150                 155                 160

Ala Ser Ser Gly Ala Thr Phe Thr Asp Ala Glu Ser Glu Gly Gly Tyr
                165                 170                 175

Thr Thr Ala Asn Ala Glu Ser Asp Asn Glu Arg Asp Ser Asp Lys Glu
            180                 185                 190

Ser Glu Asp Gly Glu Asp Glu Val Ser Cys Glu Thr Val Lys Met Gly
        195                 200                 205

Arg Lys Asp Ser Leu Asp Leu Glu Glu Glu Ala Ala Ser Gly Ala Ser
    210                 215                 220

Ser Ala Leu Glu Ala Gly Gly Ser Ser Gly Leu Glu Asp Val Leu Pro
225                 230                 235                 240

Leu Leu Gln Gln Ala Asp Glu Leu His Arg Gly Asp Glu Gln Gly Lys
                245                 250                 255

Arg Glu Gly Phe Gln Leu Leu Leu Asn Asn Lys Leu Val Tyr Gly Ser
            260                 265                 270

Arg Gln Asp Phe Leu Trp Arg Leu Ala Arg Ala Tyr Ser Asp Met Cys
        275                 280                 285

Glu Leu Thr Glu Glu Val Ser Glu Lys Lys Ser Tyr Ala Leu Asp Gly
    290                 295                 300

Lys Glu Glu Ala Glu Ala Ala Leu Glu Lys Gly Asp Glu Ser Ala Asp
305                 310                 315                 320

Cys His Leu Trp Tyr Ala Val Leu Cys Gly Gln Leu Ala Glu His Glu
                325                 330                 335

Ser Ile Gln Arg Arg Ile Gln Ser Gly Phe Ser Phe Lys Glu His Val
            340                 345                 350

Asp Lys Ala Ile Ala Leu Gln Pro Glu Asn Pro Met Ala His Phe Leu
        355                 360                 365

Leu Gly Arg Trp Cys Tyr Gln Val Ser His Leu Ser Trp Leu Glu Lys
    370                 375                 380

Lys Thr Ala Thr Ala Leu Leu Glu Ser Pro Leu Ser Ala Thr Val Glu
385                 390                 395                 400

Asp Ala Leu Gln Ser Phe Leu Lys Ala Glu Glu Leu Gln Pro Gly Phe
                405                 410                 415

Ser Lys Ala Gly Arg Val Tyr Ile Ser Lys Cys Tyr Arg Glu Leu Gly
            420                 425                 430

Lys Asn Ser Glu Ala Arg Trp Trp Met Lys Leu Ala Leu Glu Leu Pro
        435                 440                 445

Asp Val Thr Lys Glu Asp Leu Ala Ile Gln Lys Asp Leu Glu Glu Leu
    450                 455                 460
```

Glu Val Ile Leu Arg Asp
465 470

<210> SEQ ID NO 11
<211> LENGTH: 495
<212> TYPE: PRT
<213> ORGANISM: Homo sapiens

<400> SEQUENCE: 11

Met Glu Asn Lys Ala Met Tyr Leu His Thr Val Ser Asp Cys Asp Thr
1 5 10 15

Ser Ser Ile Cys Glu Asp Ser Phe Asp Gly Arg Ser Leu Ser Lys Leu
20 25 30

Asn Leu Cys Glu Asp Gly Pro Cys His Lys Arg Arg Ala Ser Ile Cys
35 40 45

Cys Thr Gln Leu Gly Ser Leu Ser Ala Leu Lys His Ala Val Leu Gly
50 55 60

Leu Tyr Leu Leu Val Phe Leu Ile Leu Val Gly Ile Phe Ile Leu Ala
65 70 75 80

Val Ser Arg Pro Arg Ser Ser Pro Asp Asp Leu Lys Ala Leu Thr Arg
85 90 95

Asn Val Asn Arg Leu Asn Glu Ser Phe Arg Asp Leu Gln Leu Arg Leu
100 105 110

Leu Gln Ala Pro Leu Gln Ala Asp Leu Thr Glu Gln Val Trp Lys Val
115 120 125

Gln Asp Ala Leu Gln Asn Gln Ser Asp Ser Leu Leu Ala Leu Ala Gly
130 135 140

Ala Val Gln Arg Leu Glu Gly Ala Leu Trp Gly Leu Gln Ala Gln Ala
145 150 155 160

Val Gln Thr Glu Gln Ala Val Ala Leu Leu Arg Asp Arg Thr Gly Gln
165 170 175

Gln Ser Asp Thr Ala Gln Leu Glu Leu Tyr Gln Leu Gln Val Glu Ser
180 185 190

Asn Ser Ser Gln Leu Leu Leu Arg Arg His Ala Gly Leu Leu Asp Gly
195 200 205

Leu Ala Arg Arg Val Gly Ile Leu Gly Glu Glu Leu Ala Asp Val Gly
210 215 220

Gly Val Leu Arg Gly Leu Asn His Ser Leu Ser Tyr Asp Val Ala Leu
225 230 235 240

His Arg Thr Arg Leu Gln Asp Leu Arg Val Leu Val Ser Asn Ala Ser
245 250 255

Glu Asp Thr Arg Arg Leu Arg Leu Ala His Val Gly Met Glu Leu Gln
260 265 270

Leu Lys Gln Glu Leu Ala Met Leu Asn Ala Val Thr Glu Asp Leu Arg
275 280 285

Leu Lys Asp Trp Glu His Ser Ile Ala Leu Arg Asn Ile Ser Leu Ala
290 295 300

Lys Gly Pro Pro Gly Pro Lys Gly Asp Gln Gly Asp Glu Gly Lys Glu
305 310 315 320

Gly Arg Pro Gly Ile Pro Gly Leu Pro Gly Leu Arg Gly Leu Pro Gly
325 330 335

Glu Arg Gly Thr Pro Gly Leu Pro Gly Pro Lys Gly Asp Asp Gly Lys
340 345 350

Leu Gly Ala Thr Gly Pro Met Gly Met Arg Gly Phe Lys Gly Asp Arg

```
        355                 360                 365

Gly Pro Lys Gly Glu Lys Gly Glu Lys Gly Asp Arg Ala Gly Asp Ala
    370                 375                 380

Ser Gly Val Glu Ala Pro Met Met Ile Arg Leu Val Asn Gly Ser Gly
385                 390                 395                 400

Pro His Glu Gly Arg Val Glu Val Tyr His Asp Arg Arg Trp Gly Thr
                405                 410                 415

Val Cys Asp Asp Gly Trp Asp Lys Lys Asp Gly Asp Val Val Cys Arg
            420                 425                 430

Met Leu Gly Phe Arg Gly Val Glu Glu Val Tyr Arg Thr Ala Arg Phe
        435                 440                 445

Gly Gln Gly Thr Gly Arg Ile Trp Met Asp Asp Val Ala Cys Lys Gly
    450                 455                 460

Thr Glu Glu Thr Ile Phe Arg Cys Ser Phe Ser Lys Trp Gly Val Thr
465                 470                 475                 480

Asn Cys Gly His Ala Glu Asp Ala Ser Val Thr Cys Asn Arg His
                485                 490                 495


<210> SEQ ID NO 12
<211> LENGTH: 236
<212> TYPE: PRT
<213> ORGANISM: Homo sapiens

<400> SEQUENCE: 12

Met Thr Ala Glu Phe Leu Ser Leu Leu Cys Leu Gly Leu Cys Leu Gly
1               5                   10                  15

Tyr Glu Asp Glu Lys Lys Asn Glu Lys Pro Pro Lys Pro Ser Leu His
            20                  25                  30

Ala Trp Pro Ser Ser Val Val Glu Ala Glu Ser Asn Val Thr Leu Lys
        35                  40                  45

Cys Gln Ala His Ser Gln Asn Val Thr Phe Val Leu Arg Lys Val Asn
    50                  55                  60

Asp Ser Gly Tyr Lys Gln Glu Gln Ser Ser Ala Glu Asn Glu Ala Glu
65                  70                  75                  80

Phe Pro Phe Thr Asp Leu Lys Pro Lys Asp Ala Gly Arg Tyr Phe Cys
                85                  90                  95

Ala Tyr Lys Thr Thr Ala Ser His Glu Trp Ser Glu Ser Ser Glu His
            100                 105                 110

Leu Gln Leu Val Val Thr Asp Lys His Asp Glu Leu Glu Ala Pro Ser
        115                 120                 125

Met Lys Thr Asp Thr Arg Thr Ile Phe Val Ala Ile Phe Ser Cys Ile
    130                 135                 140

Ser Ile Leu Leu Leu Phe Leu Ser Val Phe Ile Ile Tyr Arg Cys Ser
145                 150                 155                 160

Gln His Ser Ser Ser Ser Glu Glu Ser Thr Lys Arg Thr Ser His Ser
                165                 170                 175

Lys Leu Pro Glu Gln Glu Ala Ala Glu Ala Asp Leu Ser Asn Met Glu
            180                 185                 190

Arg Val Ser Leu Ser Thr Ala Asp Pro Gln Gly Val Thr Tyr Ala Glu
        195                 200                 205

Leu Ser Thr Ser Ala Leu Ser Glu Ala Ala Ser Asp Thr Thr Gln Glu
    210                 215                 220

Pro Pro Gly Ser His Glu Tyr Ala Ala Leu Lys Val
225                 230                 235
```

-continued

<210> SEQ ID NO 13
<211> LENGTH: 180
<212> TYPE: PRT
<213> ORGANISM: Homo sapiens

<400> SEQUENCE: 13

```
Met Ala Ala Ala Glu Glu Glu Asp Gly Gly Pro Glu Gly Pro Asn Arg
1               5                   10                  15

Glu Arg Gly Gly Ala Gly Ala Thr Phe Glu Cys Asn Ile Cys Leu Glu
            20                  25                  30

Thr Ala Arg Glu Ala Val Val Ser Val Cys Gly His Leu Tyr Cys Trp
        35                  40                  45

Pro Cys Leu His Gln Trp Leu Glu Thr Arg Pro Glu Arg Gln Glu Cys
    50                  55                  60

Pro Val Cys Lys Ala Gly Ile Ser Arg Glu Lys Val Val Pro Leu Tyr
65                  70                  75                  80

Gly Arg Gly Ser Gln Lys Pro Gln Asp Pro Arg Leu Lys Thr Pro Pro
                85                  90                  95

Arg Pro Gln Gly Gln Arg Pro Ala Pro Glu Ser Arg Gly Gly Phe Gln
            100                 105                 110

Pro Phe Gly Asp Thr Gly Gly Phe His Phe Ser Phe Gly Val Gly Ala
        115                 120                 125

Phe Pro Phe Gly Phe Phe Thr Thr Val Phe Asn Ala His Glu Pro Phe
    130                 135                 140

Arg Arg Gly Thr Gly Val Asp Leu Gly Gln Gly His Pro Ala Ser Ser
145                 150                 155                 160

Trp Gln Asp Ser Leu Phe Leu Phe Leu Ala Ile Phe Phe Phe Phe Trp
                165                 170                 175

Leu Leu Ser Ile
            180
```

<210> SEQ ID NO 14
<211> LENGTH: 157
<212> TYPE: PRT
<213> ORGANISM: Homo sapiens

<400> SEQUENCE: 14

```
Met Leu Pro Glu Gln Gly Pro Gln Pro Ser Thr Met Pro Leu Trp Cys
1               5                   10                  15

Leu Leu Ala Ala Cys Thr Ser Leu Pro Arg Gln Ala Ala Thr Met Leu
            20                  25                  30

Glu Glu Ala Ala Ser Pro Asn Glu Ala Val His Ala Ser Thr Ser Gly
        35                  40                  45

Ser Gly Ala Leu Thr Asp Gln Thr Phe Thr Asp Leu Ser Ala Ala Glu
    50                  55                  60

Ala Ser Ser Glu Glu Val Pro Asp Phe Met Glu Val Pro His Ser Val
65                  70                  75                  80

His His Lys Ile Asn Cys Phe Phe Tyr Leu Glu Lys Gln Leu Cys Gln
                85                  90                  95

Leu Pro Ser Pro Leu Cys Leu Ser Ser Leu Leu Thr Leu Lys Leu Lys
            100                 105                 110

Thr Thr Val Pro Ala Pro Gly Arg Trp Trp Ser Phe Gln Pro His Lys
        115                 120                 125

Ala Phe Pro Leu Leu Val Gly Thr Pro Gly Ser Trp Gln Ser Thr Ile
    130                 135                 140
```

```
Asp Pro Ala Trp Ala Ala Pro Ser Gln Pro Ser Pro Gly
145                 150                 155


<210> SEQ ID NO 15
<211> LENGTH: 716
<212> TYPE: PRT
<213> ORGANISM: Homo sapiens

<400> SEQUENCE: 15

Met Met Ser Ile Arg Gln Arg Arg Glu Ile Arg Ala Thr Glu Val Ser
1               5                   10                  15

Glu Asp Phe Pro Ala Gln Glu Glu Asn Val Lys Leu Glu Asn Lys Leu
            20                  25                  30

Pro Ser Gly Cys Thr Ser Arg Arg Leu Trp Lys Ile Leu Ser Leu Thr
        35                  40                  45

Ile Gly Gly Thr Ile Ala Leu Cys Ile Gly Leu Leu Thr Ser Val Tyr
    50                  55                  60

Leu Ala Thr Leu His Glu Asn Asp Leu Trp Phe Ser Asn Ile Lys Glu
65                  70                  75                  80

Val Glu Arg Glu Ile Ser Phe Arg Thr Glu Cys Gly Leu Tyr Tyr Ser
                85                  90                  95

Tyr Tyr Lys Gln Met Leu Gln Ala Pro Thr Leu Val Gln Gly Phe His
            100                 105                 110

Gly Leu Ile Tyr Asp Asn Lys Thr Glu Ser Met Lys Thr Ile Asn Leu
        115                 120                 125

Leu Gln Arg Met Asn Ile Tyr Gln Glu Val Phe Leu Ser Ile Leu Tyr
    130                 135                 140

Arg Val Leu Pro Ile Gln Lys Tyr Leu Glu Pro Val Tyr Phe Tyr Ile
145                 150                 155                 160

Tyr Thr Leu Phe Gly Leu Gln Ala Ile Tyr Val Thr Ala Leu Tyr Ile
                165                 170                 175

Thr Ser Trp Leu Leu Ser Gly Thr Trp Leu Ser Gly Leu Leu Ala Ala
            180                 185                 190

Phe Trp Tyr Val Thr Asn Arg Ile Asp Thr Thr Arg Val Glu Phe Thr
        195                 200                 205

Ile Pro Leu Arg Glu Asn Trp Ala Leu Pro Phe Phe Ala Ile Gln Ile
    210                 215                 220

Ala Ala Ile Thr Tyr Phe Leu Arg Pro Asn Leu Gln Pro Leu Ser Glu
225                 230                 235                 240

Arg Leu Thr Leu Leu Ala Ile Phe Ile Ser Thr Phe Leu Phe Ser Leu
                245                 250                 255

Thr Trp Gln Phe Asn Gln Phe Met Met Leu Met Gln Ala Leu Val Leu
            260                 265                 270

Phe Thr Leu Asp Ser Leu Asp Met Leu Pro Ala Val Lys Ala Thr Trp
        275                 280                 285

Leu Tyr Gly Ile Gln Ile Thr Ser Leu Leu Leu Val Cys Ile Leu Gln
    290                 295                 300

Phe Phe Asn Ser Met Ile Leu Gly Ser Leu Leu Ile Ser Phe Asn Leu
305                 310                 315                 320

Ser Val Phe Ile Ala Arg Lys Leu Gln Lys Asn Leu Lys Thr Gly Ser
                325                 330                 335

Phe Leu Asn Arg Leu Gly Lys Leu Leu Leu His Leu Phe Met Val Leu
            340                 345                 350

Cys Leu Thr Leu Phe Leu Asn Asn Ile Ile Lys Lys Ile Leu Asn Leu
        355                 360                 365
```

Lys Ser Asp Glu His Ile Phe Lys Phe Leu Lys Ala Lys Phe Gly Leu
    370                 375                 380

Gly Ala Thr Arg Asp Phe Asp Ala Asn Leu Tyr Leu Cys Glu Glu Ala
385                 390                 395                 400

Phe Gly Leu Leu Pro Phe Asn Thr Phe Gly Arg Leu Ser Asp Thr Leu
                405                 410                 415

Leu Phe Tyr Ala Tyr Ile Phe Val Leu Ser Ile Thr Val Ile Val Ala
            420                 425                 430

Phe Val Val Ala Phe His Asn Leu Ser Asp Ser Thr Asn Gln Gln Ser
        435                 440                 445

Val Gly Lys Met Glu Lys Gly Thr Val Asp Leu Lys Pro Glu Thr Ala
    450                 455                 460

Tyr Asn Leu Ile His Thr Ile Leu Phe Gly Phe Leu Ala Leu Ser Thr
465                 470                 475                 480

Met Arg Met Lys Tyr Leu Trp Thr Ser His Met Cys Val Phe Ala Ser
                485                 490                 495

Phe Gly Leu Cys Ser Pro Glu Ile Trp Glu Leu Leu Leu Lys Ser Val
            500                 505                 510

His Leu Tyr Asn Pro Lys Arg Ile Cys Ile Met Arg Tyr Ser Val Pro
        515                 520                 525

Ile Leu Ile Leu Leu Tyr Leu Cys Tyr Lys Phe Trp Pro Gly Met Met
    530                 535                 540

Asp Glu Leu Ser Glu Leu Arg Glu Phe Tyr Asp Pro Asp Thr Val Glu
545                 550                 555                 560

Leu Met Asn Trp Ile Asn Ser Asn Thr Pro Arg Lys Ala Val Phe Ala
                565                 570                 575

Gly Ser Met Gln Leu Leu Ala Gly Val Lys Leu Cys Thr Gly Arg Thr
            580                 585                 590

Leu Thr Asn His Pro His Tyr Glu Asp Ser Ser Leu Arg Glu Arg Thr
        595                 600                 605

Arg Ala Val Tyr Gln Ile Tyr Ala Lys Arg Ala Pro Glu Glu Val His
    610                 615                 620

Ala Leu Leu Arg Ser Phe Gly Thr Asp Tyr Val Ile Leu Glu Asp Ser
625                 630                 635                 640

Ile Cys Tyr Glu Arg Arg His Arg Arg Gly Cys Arg Leu Arg Asp Leu
                645                 650                 655

Leu Asp Ile Ala Asn Gly His Met Met Asp Gly Pro Gly Glu Asn Asp
            660                 665                 670

Pro Asp Leu Lys Pro Ala Asp His Pro Arg Phe Cys Glu Glu Ile Lys
        675                 680                 685

Arg Asn Leu Pro Pro Tyr Val Ala Tyr Phe Thr Arg Val Phe Gln Asn
    690                 695                 700

Lys Thr Phe His Val Tyr Lys Leu Ser Arg Asn Lys
705                 710                 715

<210> SEQ ID NO 16
<211> LENGTH: 831
<212> TYPE: PRT
<213> ORGANISM: Homo sapiens

<400> SEQUENCE: 16

Met Lys Val His Met His Thr Lys Phe Cys Leu Ile Cys Leu Leu Thr
1               5                   10                  15

Phe Ile Phe His His Cys Asn His Cys His Glu Glu His Asp His Gly

-continued

```
            20                  25                  30

Pro Glu Ala Leu His Arg Gln His Arg Gly Met Thr Glu Leu Glu Pro
        35                  40                  45

Ser Lys Phe Ser Lys Gln Ala Ala Glu Asn Glu Lys Lys Tyr Tyr Ile
    50                  55                  60

Glu Lys Leu Phe Glu Arg Tyr Gly Glu Asn Gly Arg Leu Ser Phe Phe
65                  70                  75                  80

Gly Leu Glu Lys Leu Leu Thr Asn Leu Gly Leu Gly Glu Arg Lys Val
                85                  90                  95

Val Glu Ile Asn His Glu Asp Leu Gly His Asp His Val Ser His Leu
            100                 105                 110

Asp Ile Leu Ala Val Gln Glu Gly Lys His Phe His Ser His Asn His
        115                 120                 125

Gln His Ser His Asn His Leu Asn Ser Glu Asn Gln Thr Val Thr Ser
    130                 135                 140

Val Ser Thr Lys Arg Asn His Lys Cys Asp Pro Glu Lys Glu Thr Val
145                 150                 155                 160

Glu Val Ser Val Lys Ser Asp Asp Lys His Met His Asp His Asn His
                165                 170                 175

Arg Leu Arg His His His Arg Leu His His His Leu Asp His Asn Asn
            180                 185                 190

Thr His His Phe His Asn Asp Ser Ile Thr Pro Ser Glu Arg Gly Glu
        195                 200                 205

Pro Ser Asn Glu Pro Ser Thr Glu Thr Asn Lys Thr Gln Glu Gln Ser
    210                 215                 220

Asp Val Lys Leu Pro Lys Gly Lys Arg Lys Lys Lys Gly Arg Lys Ser
225                 230                 235                 240

Asn Glu Asn Ser Glu Val Ile Thr Pro Gly Phe Pro Pro Asn His Asp
                245                 250                 255

Gln Gly Glu Gln Tyr Glu His Asn Arg Val His Lys Pro Asp Arg Val
            260                 265                 270

His Asn Pro Gly His Ser His Val His Leu Pro Glu Arg Asn Gly His
        275                 280                 285

Asp Pro Gly Arg Gly His Gln Asp Leu Asp Pro Asp Asn Glu Gly Glu
    290                 295                 300

Leu Arg His Thr Arg Lys Arg Glu Ala Pro His Val Lys Asn Asn Ala
305                 310                 315                 320

Ile Ile Ser Leu Arg Lys Asp Leu Asn Glu Asp Asp His His His Glu
                325                 330                 335

Cys Leu Asn Val Thr Gln Leu Leu Lys Tyr Tyr Gly His Gly Ala Asn
            340                 345                 350

Ser Pro Ile Ser Thr Asp Leu Phe Thr Tyr Leu Cys Pro Ala Leu Leu
        355                 360                 365

Tyr Gln Ile Asp Ser Arg Leu Cys Ile Glu His Phe Asp Lys Leu Leu
    370                 375                 380

Val Glu Asp Ile Asn Lys Asp Lys Asn Leu Val Pro Glu Asp Glu Ala
385                 390                 395                 400

Asn Ile Gly Ala Ser Ala Trp Ile Cys Gly Ile Ile Ser Ile Thr Val
                405                 410                 415

Ile Ser Leu Leu Ser Leu Leu Gly Val Ile Leu Val Pro Ile Ile Asn
            420                 425                 430

Gln Gly Cys Phe Lys Phe Leu Leu Thr Phe Leu Val Ala Leu Ala Val
        435                 440                 445
```

```
Gly Thr Met Ser Gly Asp Ala Leu Leu His Leu Leu Pro His Ser Gln
    450                 455                 460

Gly Gly His Asp His Ser His Gln His Ala His Gly His Gly His Ser
465                 470                 475                 480

His Gly His Glu Ser Asn Lys Phe Leu Glu Glu Tyr Asp Ala Val Leu
                485                 490                 495

Lys Gly Leu Val Ala Leu Gly Gly Ile Tyr Leu Leu Phe Ile Ile Glu
            500                 505                 510

His Cys Ile Arg Met Phe Lys His Tyr Lys Gln Gln Arg Gly Lys Gln
        515                 520                 525

Lys Trp Phe Met Lys Gln Asn Thr Glu Glu Ser Thr Ile Gly Arg Lys
    530                 535                 540

Leu Ser Asp His Lys Leu Asn Asn Thr Pro Asp Ser Asp Trp Leu Gln
545                 550                 555                 560

Leu Lys Pro Leu Ala Gly Thr Asp Asp Ser Val Val Ser Glu Asp Arg
                565                 570                 575

Leu Asn Glu Thr Glu Leu Thr Asp Leu Glu Gly Gln Gln Glu Ser Pro
            580                 585                 590

Pro Lys Asn Tyr Leu Cys Ile Glu Glu Glu Lys Ile Ile Asp His Ser
        595                 600                 605

His Ser Asp Gly Leu His Thr Ile His Glu His Asp Leu His Ala Ala
    610                 615                 620

Ala His Asn His His Gly Glu Asn Lys Thr Val Leu Arg Lys His Asn
625                 630                 635                 640

His Gln Trp His His Lys His Ser His His Ser His Gly Pro Cys His
                645                 650                 655

Ser Gly Ser Asp Leu Lys Glu Thr Gly Ile Ala Asn Ile Ala Trp Met
            660                 665                 670

Val Ile Met Gly Asp Gly Ile His Asn Phe Ser Asp Gly Leu Ala Ile
        675                 680                 685

Gly Ala Ala Phe Ser Ala Gly Leu Thr Gly Gly Ile Ser Thr Ser Ile
    690                 695                 700

Ala Val Phe Cys His Glu Leu Pro His Glu Leu Gly Asp Phe Ala Val
705                 710                 715                 720

Leu Leu Lys Ala Gly Met Thr Val Lys Gln Ala Ile Val Tyr Asn Leu
                725                 730                 735

Leu Ser Ala Met Met Ala Tyr Ile Gly Met Leu Ile Gly Thr Ala Val
            740                 745                 750

Gly Gln Tyr Ala Asn Asn Ile Thr Leu Trp Ile Phe Ala Val Thr Ala
        755                 760                 765

Gly Met Phe Leu Tyr Val Ala Leu Val Asp Met Leu Pro Glu Met Leu
    770                 775                 780

His Gly Asp Gly Asp Asn Glu Glu His Gly Phe Cys Pro Val Gly Gln
785                 790                 795                 800

Phe Ile Leu Gln Asn Leu Gly Leu Leu Phe Gly Phe Ala Ile Met Leu
                805                 810                 815

Val Ile Ala Leu Tyr Glu Asp Lys Ile Val Phe Asp Ile Gln Phe
            820                 825                 830
```

<210> SEQ ID NO 17
<211> LENGTH: 600
<212> TYPE: PRT
<213> ORGANISM: Homo sapiens

<400> SEQUENCE: 17

```
Met Ala Ala Leu Ala Pro Val Gly Ser Pro Ala Ser Arg Gly Pro Arg
1               5                   10                  15

Leu Ala Ala Gly Leu Arg Leu Leu Pro Met Leu Gly Leu Leu Gln Leu
            20                  25                  30

Leu Ala Glu Pro Gly Leu Gly Arg Val His His Leu Ala Leu Lys Asp
        35                  40                  45

Asp Val Arg His Lys Val His Leu Asn Thr Phe Gly Phe Phe Lys Asp
    50                  55                  60

Gly Tyr Met Val Val Asn Val Ser Ser Leu Ser Leu Asn Glu Pro Glu
65                  70                  75                  80

Asp Lys Asp Val Thr Ile Gly Phe Ser Leu Asp Arg Thr Lys Asn Asp
                85                  90                  95

Gly Phe Ser Ser Tyr Leu Asp Glu Asp Val Asn Tyr Cys Ile Leu Lys
            100                 105                 110

Lys Gln Ser Val Ser Val Thr Leu Leu Ile Leu Asp Ile Ser Arg Ser
        115                 120                 125

Glu Val Arg Val Lys Ser Pro Pro Glu Ala Gly Thr Gln Leu Pro Lys
    130                 135                 140

Ile Ile Phe Ser Arg Asp Glu Lys Val Leu Gly Gln Ser Gln Glu Pro
145                 150                 155                 160

Asn Val Asn Pro Ala Ser Ala Gly Asn Gln Thr Gln Lys Thr Gln Asp
                165                 170                 175

Gly Gly Lys Ser Lys Arg Ser Thr Val Asp Ser Lys Ala Met Gly Glu
            180                 185                 190

Lys Ser Phe Ser Val His Asn Asn Gly Gly Ala Val Ser Phe Gln Phe
        195                 200                 205

Phe Phe Asn Ile Ser Thr Asp Asp Gln Glu Gly Leu Tyr Ser Leu Tyr
    210                 215                 220

Phe His Lys Cys Leu Gly Lys Glu Leu Pro Ser Asp Lys Phe Thr Phe
225                 230                 235                 240

Ser Leu Asp Ile Glu Ile Thr Glu Lys Asn Pro Asp Ser Tyr Leu Ser
                245                 250                 255

Ala Gly Glu Ile Pro Leu Pro Lys Leu Tyr Ile Ser Met Ala Phe Phe
            260                 265                 270

Phe Phe Leu Ser Gly Thr Ile Trp Ile His Ile Leu Arg Lys Arg Arg
        275                 280                 285

Asn Asp Val Phe Lys Ile His Trp Leu Met Ala Ala Leu Pro Phe Thr
    290                 295                 300

Lys Ser Leu Ser Leu Val Phe His Ala Ile Asp Tyr His Tyr Ile Ser
305                 310                 315                 320

Ser Gln Gly Phe Pro Ile Glu Gly Trp Ala Val Val Tyr Tyr Ile Thr
                325                 330                 335

His Leu Leu Lys Gly Ala Leu Leu Phe Ile Thr Ile Ala Leu Ile Gly
            340                 345                 350

Thr Gly Trp Ala Phe Ile Lys His Ile Leu Ser Asp Lys Asp Lys Lys
        355                 360                 365

Ile Phe Met Ile Val Ile Pro Leu Gln Val Leu Ala Asn Val Ala Tyr
    370                 375                 380

Ile Ile Ile Glu Ser Thr Glu Glu Gly Thr Thr Glu Tyr Gly Leu Trp
385                 390                 395                 400

Lys Asp Ser Leu Phe Leu Val Asp Leu Leu Cys Cys Gly Ala Ile Leu
                405                 410                 415
```

```
Phe Pro Val Val Trp Ser Ile Arg His Leu Gln Glu Ala Ser Ala Thr
            420                 425                 430

Asp Gly Lys Gly Asp Ser Met Gly Pro Leu Gln Gln Arg Ala Asn Leu
        435                 440                 445

Arg Ala Gly Ser Arg Ile Glu Ser His His Phe Ala Gln Ala Asp Leu
    450                 455                 460

Glu Leu Leu Ala Ser Ser Cys Pro Pro Ala Ser Val Ser Gln Arg Ala
465                 470                 475                 480

Gly Ile Thr Ala Ala Ile Asn Leu Ala Lys Leu Lys Leu Phe Arg His
                485                 490                 495

Tyr Tyr Val Leu Ile Val Cys Tyr Ile Tyr Phe Thr Arg Ile Ile Ala
            500                 505                 510

Phe Leu Leu Lys Leu Ala Val Pro Phe Gln Trp Lys Trp Leu Tyr Gln
        515                 520                 525

Leu Leu Asp Glu Thr Ala Thr Leu Val Phe Phe Val Leu Thr Gly Tyr
    530                 535                 540

Lys Phe Arg Pro Ala Ser Asp Asn Pro Tyr Leu Gln Leu Ser Gln Glu
545                 550                 555                 560

Glu Glu Asp Leu Glu Met Glu Ser Val Val Thr Thr Ser Gly Val Met
                565                 570                 575

Glu Ser Met Lys Lys Val Lys Lys Val Thr Asn Gly Ser Val Glu Pro
            580                 585                 590

Gln Gly Glu Trp Glu Gly Ala Val
        595                 600
```

<210> SEQ ID NO 18
<211> LENGTH: 1284
<212> TYPE: PRT
<213> ORGANISM: Homo sapiens

<400> SEQUENCE: 18

```
Met Ser Ser Gly Asp Pro Ala His Leu Gly Leu Cys Leu Trp Leu Trp
1               5                   10                  15

Leu Gly Ala Thr Leu Gly Arg Glu Gln Val Gln Ala Ser Gly Leu Leu
            20                  25                  30

Arg Leu Ala Val Leu Pro Glu Asp Arg Leu Gln Met Lys Trp Arg Glu
        35                  40                  45

Ser Glu Gly Ser Gly Leu Gly Tyr Leu Val Gln Val Lys Pro Met Ala
    50                  55                  60

Gly Asp Ser Glu Gln Glu Val Ile Leu Thr Thr Lys Thr Pro Lys Ala
65                  70                  75                  80

Thr Val Gly Gly Leu Ser Pro Ser Lys Gly Tyr Thr Leu Gln Ile Phe
                85                  90                  95

Glu Leu Thr Gly Ser Gly Arg Phe Leu Leu Ala Arg Arg Glu Phe Val
            100                 105                 110

Ile Glu Asp Leu Lys Ser Ser Ser Leu Asp Arg Ser Ser Gln Arg Pro
        115                 120                 125

Leu Gly Ser Gly Ala Pro Glu Pro Thr Pro Ser His Thr Gly Ser Pro
    130                 135                 140

Asp Pro Glu Gln Ala Ser Glu Pro Gln Val Ala Phe Thr Pro Ser Gln
145                 150                 155                 160

Asp Pro Arg Thr Pro Ala Gly Pro Gln Phe Arg Cys Leu Pro Pro Val
                165                 170                 175

Pro Ala Asp Met Val Phe Leu Val Asp Gly Ser Trp Ser Ile Gly His
```

```
            180                 185                 190

Ser His Phe Gln Gln Val Lys Asp Phe Leu Ala Ser Val Ile Ala Pro
        195                 200                 205

Phe Glu Ile Gly Pro Asp Lys Val Gln Val Gly Leu Thr Gln Tyr Ser
    210                 215                 220

Gly Asp Ala Gln Thr Glu Trp Asp Leu Asn Ser Leu Ser Thr Lys Glu
225                 230                 235                 240

Gln Val Leu Ala Ala Val Arg Arg Leu Arg Tyr Lys Gly Gly Asn Thr
                245                 250                 255

Phe Thr Gly Leu Ala Leu Thr His Val Leu Gly Gln Asn Leu Gln Pro
            260                 265                 270

Ala Ala Gly Leu Arg Pro Glu Ala Ala Lys Val Val Ile Leu Val Thr
        275                 280                 285

Asp Gly Lys Ser Gln Asp Asp Val His Thr Ala Ala Arg Val Leu Lys
    290                 295                 300

Asp Leu Gly Val Asn Val Phe Ala Val Gly Val Lys Asn Ala Asp Glu
305                 310                 315                 320

Ala Glu Leu Arg Leu Leu Ala Ser Pro Pro Arg Asp Ile Thr Val His
                325                 330                 335

Ser Val Leu Asp Phe Leu Gln Leu Gly Ala Leu Ala Gly Leu Leu Ser
            340                 345                 350

Arg Leu Ile Cys Gln Arg Leu Gln Gly Gly Ser Pro Arg Gln Gly Pro
        355                 360                 365

Ala Ala Ala Pro Ala Leu Asp Thr Leu Pro Ala Pro Thr Ser Leu Val
    370                 375                 380

Leu Ser Gln Val Thr Ser Ser Ser Ile Arg Leu Ser Trp Thr Pro Ala
385                 390                 395                 400

Pro Arg His Pro Leu Lys Tyr Leu Ile Val Trp Arg Ala Ser Arg Gly
                405                 410                 415

Gly Thr Pro Arg Glu Val Val Val Glu Gly Pro Ala Ala Ser Thr Glu
            420                 425                 430

Leu His Asn Leu Ala Ser Arg Thr Glu Tyr Leu Val Ser Val Phe Pro
        435                 440                 445

Ile Tyr Glu Gly Gly Val Gly Glu Gly Leu Arg Gly Leu Val Thr Thr
    450                 455                 460

Ala Pro Leu Pro Pro Pro Arg Ala Leu Thr Leu Ala Ala Val Thr Pro
465                 470                 475                 480

Arg Thr Val His Leu Thr Trp Gln Pro Ser Ala Gly Ala Thr His Tyr
                485                 490                 495

Leu Val Arg Cys Ser Pro Ala Ser Pro Lys Gly Glu Glu Glu Glu Arg
            500                 505                 510

Glu Val Gln Val Gly Arg Pro Glu Val Leu Leu Asp Gly Leu Glu Pro
        515                 520                 525

Gly Arg Asp Tyr Glu Val Ser Val Gln Ser Leu Arg Gly Pro Glu Gly
    530                 535                 540

Ser Glu Ala Arg Gly Ile Arg Ala Arg Thr Pro Thr Leu Ala Pro Pro
545                 550                 555                 560

Arg His Leu Gly Phe Ser Asp Val Ser His Asp Ala Ala Arg Val Phe
                565                 570                 575

Trp Glu Gly Ala Pro Arg Pro Val Arg Leu Val Arg Val Thr Tyr Val
            580                 585                 590

Ser Ser Glu Gly Gly His Ser Gly Gln Thr Glu Ala Pro Gly Asn Ala
        595                 600                 605
```

-continued

```
Thr Ser Ala Thr Leu Gly Pro Leu Ser Ser Ser Thr Thr Tyr Thr Val
    610                 615                 620

Arg Val Thr Cys Leu Tyr Pro Gly Gly Gly Ser Ser Thr Leu Thr Gly
625                 630                 635                 640

Arg Val Thr Thr Lys Lys Ala Pro Ser Pro Ser Gln Leu Ser Met Thr
                645                 650                 655

Glu Leu Pro Gly Asp Ala Val Gln Leu Ala Trp Val Ala Ala Ala Pro
            660                 665                 670

Ser Gly Val Leu Val Tyr Gln Ile Thr Trp Thr Pro Leu Gly Glu Gly
        675                 680                 685

Lys Ala His Glu Ile Ser Val Pro Gly Asn Leu Gly Thr Ala Val Leu
    690                 695                 700

Pro Gly Leu Gly Arg His Thr Glu Tyr Asp Val Thr Ile Leu Ala Tyr
705                 710                 715                 720

Tyr Arg Asp Gly Ala Arg Ser Asp Pro Val Ser Leu Arg Tyr Thr Pro
                725                 730                 735

Ser Thr Val Ser Arg Ser Pro Pro Ser Asn Leu Ala Leu Ala Ser Glu
            740                 745                 750

Thr Pro Asp Ser Leu Gln Val Ser Trp Thr Pro Pro Leu Gly Arg Val
        755                 760                 765

Leu His Tyr Trp Leu Thr Tyr Ala Pro Ala Ser Gly Leu Gly Pro Glu
    770                 775                 780

Lys Ser Val Ser Val Pro Gly Ala Arg Ser His Val Thr Leu Pro Asp
785                 790                 795                 800

Leu Gln Ala Ala Thr Lys Tyr Arg Val Leu Val Ser Ala Ile Tyr Ala
                805                 810                 815

Ala Gly Arg Ser Glu Ala Val Ser Ala Thr Gly Gln Thr Ala Cys Pro
            820                 825                 830

Ala Leu Arg Pro Asp Gly Ser Leu Pro Gly Phe Asp Leu Met Val Ala
        835                 840                 845

Phe Ser Leu Val Glu Lys Ala Tyr Ala Ser Ile Arg Gly Val Ala Met
    850                 855                 860

Glu Pro Ser Ala Phe Gly Gly Thr Pro Thr Phe Thr Leu Phe Lys Asp
865                 870                 875                 880

Ala Gln Leu Thr Arg Arg Val Ser Asp Val Tyr Pro Ala Pro Leu Pro
                885                 890                 895

Pro Glu His Thr Ile Val Phe Leu Val Arg Leu Leu Pro Glu Thr Pro
            900                 905                 910

Arg Glu Ala Phe Ala Leu Trp Gln Met Thr Ala Glu Asp Phe Gln Pro
        915                 920                 925

Leu Leu Gly Val Leu Leu Asp Ala Gly Lys Lys Ser Leu Thr Tyr Phe
    930                 935                 940

His Arg Asp Pro Arg Ala Ala Leu Gln Glu Ala Thr Phe Asp Pro Gln
945                 950                 955                 960

Glu Val Arg Lys Ile Phe Phe Gly Ser Phe His Lys Val His Val Ala
                965                 970                 975

Val Gly Arg Ser Lys Val Arg Leu Tyr Val Asp Cys Arg Lys Val Ala
            980                 985                 990

Glu Arg Pro Leu Gly Glu Met Gly  Ser Pro Pro Ala Ala  Gly Phe Val
        995                 1000                1005

Thr Leu  Gly Arg Leu Ala Lys  Ala Arg Gly Pro Arg  Ser Ser Ser
    1010                1015                1020
```

```
Ala Ala  Phe Gln Leu Gln Met  Leu Gln Ile Val Cys  Ser Asp Thr
    1025                1030                1035

Trp Ala  Asp Glu Asp Arg Cys  Cys Glu Leu Pro Ala  Ser Arg Asp
    1040                1045                1050

Gly Glu  Thr Cys Pro Ala Phe  Val Ser Ala Cys Ser  Cys Ser Ser
    1055                1060                1065

Glu Thr  Pro Gly Pro Pro Gly  Pro Gln Gly Pro Pro  Gly Leu Pro
    1070                1075                1080

Gly Arg  Asn Gly Thr Pro Gly  Glu Gln Gly Phe Pro  Gly Pro Arg
    1085                1090                1095

Gly Pro  Pro Gly Val Lys Gly  Glu Lys Gly Asp His  Gly Leu Pro
    1100                1105                1110

Gly Leu  Gln Gly His Pro Gly  His Gln Gly Ile Pro  Gly Arg Val
    1115                1120                1125

Gly Leu  Gln Gly Pro Lys Gly  Met Arg Gly Leu Glu  Gly Thr Ala
    1130                1135                1140

Gly Leu  Pro Gly Pro Pro Gly  Pro Arg Gly Phe Gln  Gly Met Ala
    1145                1150                1155

Gly Ala  Arg Gly Thr Ser Gly  Glu Arg Gly Pro Pro  Gly Thr Val
    1160                1165                1170

Gly Pro  Thr Gly Leu Pro Gly  Pro Lys Gly Glu Arg  Gly Glu Lys
    1175                1180                1185

Gly Glu  Pro Gln Ser Leu Ala  Thr Leu Tyr Gln Leu  Val Ser Gln
    1190                1195                1200

Ala Ser  His Val Ser Lys Phe  Asp Ser Phe His Glu  Asn Thr Arg
    1205                1210                1215

Pro Pro  Met Pro Ile Leu Glu  Gln Lys Leu Glu Pro  Gly Thr Glu
    1220                1225                1230

Pro Leu  Gly Ser Pro Gly Thr  Arg Ser Lys Ala Leu  Val Pro Gly
    1235                1240                1245

Glu Trp  Gly Arg Gly Gly Arg  His Leu Glu Gly Arg  Gly Glu Pro
    1250                1255                1260

Gly Ala  Val Gly Gln Met Gly  Ser Pro Gly Gln Gln  Gly Ala Ser
    1265                1270                1275

Thr Gln  Gly Leu Trp Glu
    1280


<210> SEQ ID NO 19
<211> LENGTH: 626
<212> TYPE: PRT
<213> ORGANISM: Homo sapiens

<400> SEQUENCE: 19

Met Ala Ala Arg Pro Ala Ala Thr Leu Ala Trp Ser Leu Leu Leu Leu
1               5                   10                  15

Ser Ser Ala Leu Leu Arg Glu Gly Cys Arg Ala Arg Phe Val Ala Glu
            20                  25                  30

Arg Asp Ser Glu Asp Asp Gly Glu Glu Pro Val Val Phe Pro Glu Ser
        35                  40                  45

Pro Leu Gln Ser Pro Thr Val Leu Val Ala Val Leu Ala Arg Asn Ala
    50                  55                  60

Ala His Thr Leu Pro His Phe Leu Gly Cys Leu Glu Arg Leu Asp Tyr
65                  70                  75                  80

Pro Lys Ser Arg Met Ala Ile Trp Ala Ala Thr Asp His Asn Val Asp
                85                  90                  95
```

-continued

```
Asn Thr Thr Glu Ile Phe Arg Glu Trp Leu Lys Asn Val Gln Arg Leu
            100                 105                 110

Tyr His Tyr Val Glu Trp Arg Pro Met Asp Glu Pro Glu Ser Tyr Pro
        115                 120                 125

Asp Glu Ile Gly Pro Lys His Trp Pro Thr Ser Arg Phe Ala His Val
    130                 135                 140

Met Lys Leu Arg Gln Ala Ala Leu Arg Thr Ala Arg Glu Lys Trp Ser
145                 150                 155                 160

Asp Tyr Ile Leu Phe Ile Asp Val Asp Asn Phe Leu Thr Asn Pro Gln
                165                 170                 175

Thr Leu Asn Leu Leu Ile Ala Glu Asn Lys Thr Ile Val Ala Pro Met
            180                 185                 190

Leu Glu Ser Arg Gly Leu Tyr Ser Asn Phe Trp Cys Gly Ile Thr Pro
        195                 200                 205

Lys Gly Phe Tyr Lys Arg Thr Pro Asp Tyr Val Gln Ile Arg Glu Trp
    210                 215                 220

Lys Arg Thr Gly Cys Phe Pro Val Pro Met Val His Ser Thr Phe Leu
225                 230                 235                 240

Ile Asp Leu Arg Lys Glu Ala Ser Asp Lys Leu Thr Phe Tyr Pro Pro
                245                 250                 255

His Gln Asp Tyr Thr Trp Thr Phe Asp Asp Ile Ile Val Phe Ala Phe
            260                 265                 270

Ser Ser Arg Gln Ala Gly Ile Gln Met Tyr Leu Cys Asn Arg Glu His
        275                 280                 285

Tyr Gly Tyr Leu Pro Ile Pro Leu Lys Pro His Gln Thr Leu Gln Glu
    290                 295                 300

Asp Ile Glu Asn Leu Ile His Val Gln Ile Glu Ala Met Ile Asp Arg
305                 310                 315                 320

Pro Pro Met Glu Pro Ser Gln Tyr Val Ser Val Val Pro Lys Tyr Pro
                325                 330                 335

Asp Lys Met Gly Phe Asp Glu Ile Phe Met Ile Asn Leu Lys Arg Arg
            340                 345                 350

Lys Asp Arg Arg Asp Arg Met Leu Arg Thr Leu Tyr Glu Gln Glu Ile
        355                 360                 365

Glu Val Lys Ile Val Glu Ala Val Asp Gly Lys Ala Leu Asn Thr Ser
    370                 375                 380

Gln Leu Lys Ala Leu Asn Ile Glu Met Leu Pro Gly Tyr Arg Asp Pro
385                 390                 395                 400

Tyr Ser Ser Arg Pro Leu Thr Arg Gly Glu Ile Gly Cys Phe Leu Ser
                405                 410                 415

His Tyr Ser Val Trp Lys Glu Val Ile Asp Arg Glu Leu Glu Lys Thr
            420                 425                 430

Leu Val Ile Glu Asp Asp Val Arg Phe Glu His Gln Phe Lys Lys Lys
        435                 440                 445

Leu Met Lys Leu Met Asp Asn Ile Asp Gln Ala Gln Leu Asp Trp Glu
    450                 455                 460

Leu Ile Tyr Ile Gly Arg Lys Arg Met Gln Val Lys Glu Pro Glu Lys
465                 470                 475                 480

Ala Val Pro Asn Val Ala Asn Leu Val Glu Ala Asp Tyr Ser Tyr Trp
                485                 490                 495

Thr Leu Gly Tyr Val Ile Ser Leu Glu Gly Ala Gln Lys Leu Val Gly
            500                 505                 510
```

```
Ala Asn Pro Phe Gly Lys Met Leu Pro Val Asp Glu Phe Leu Pro Val
        515                 520                 525

Met Tyr Asn Lys His Pro Val Ala Glu Tyr Lys Glu Tyr Tyr Glu Ser
    530                 535                 540

Arg Asp Leu Lys Ala Phe Ser Ala Glu Pro Leu Leu Ile Tyr Pro Thr
545                 550                 555                 560

His Tyr Thr Gly Gln Pro Gly Tyr Leu Ser Asp Thr Glu Thr Ser Thr
                565                 570                 575

Ile Trp Asp Asn Glu Thr Val Ala Thr Asp Trp Asp Arg Thr His Ala
            580                 585                 590

Trp Lys Ser Arg Lys Gln Ser Arg Ile Tyr Ser Asn Ala Lys Asn Thr
        595                 600                 605

Glu Ala Leu Pro Pro Pro Thr Ser Leu Asp Thr Val Pro Ser Arg Asp
    610                 615                 620

Glu Leu
625


<210> SEQ ID NO 20
<211> LENGTH: 610
<212> TYPE: PRT
<213> ORGANISM: Homo sapiens

<400> SEQUENCE: 20

Met Ala Gln Glu Ile Asp Leu Ser Ala Leu Lys Glu Leu Glu Arg Glu
1               5                   10                  15

Ala Ile Leu Gln Val Leu Tyr Arg Asp Gln Ala Val Gln Asn Thr Glu
            20                  25                  30

Glu Glu Arg Thr Arg Lys Leu Lys Thr His Leu Gln His Leu Arg Trp
        35                  40                  45

Lys Gly Ala Lys Asn Thr Asp Trp Glu His Lys Glu Lys Cys Cys Ala
    50                  55                  60

Arg Cys Gln Gln Val Leu Gly Phe Leu Leu His Arg Gly Ala Val Cys
65                  70                  75                  80

Arg Gly Cys Ser His Arg Val Cys Ala Gln Cys Arg Val Phe Leu Arg
                85                  90                  95

Gly Thr His Ala Trp Lys Cys Thr Val Cys Phe Glu Asp Arg Asn Val
            100                 105                 110

Lys Ile Lys Thr Gly Glu Trp Phe Tyr Glu Glu Arg Ala Lys Lys Phe
        115                 120                 125

Pro Thr Gly Gly Lys His Glu Thr Val Gly Gly Gln Leu Leu Gln Ser
    130                 135                 140

Tyr Gln Lys Leu Ser Lys Ile Ser Val Val Pro Pro Thr Pro Pro Pro
145                 150                 155                 160

Val Ser Glu Ser Gln Cys Ser Arg Ser Pro Gly Arg Leu Gln Glu Phe
                165                 170                 175

Gly Gln Phe Arg Gly Phe Asn Lys Ser Val Glu Asn Leu Phe Leu Ser
            180                 185                 190

Leu Ala Thr His Val Lys Lys Leu Ser Lys Ser Gln Asn Asp Met Thr
        195                 200                 205

Ser Glu Lys His Leu Leu Ala Thr Gly Pro Arg Gln Cys Val Gly Gln
    210                 215                 220

Thr Glu Arg Arg Ser Gln Ser Asp Thr Ala Val Asn Val Thr Thr Arg
225                 230                 235                 240

Lys Val Ser Ala Pro Asp Ile Leu Lys Pro Leu Asn Gln Glu Asp Pro
                245                 250                 255
```

```
Lys Cys Ser Thr Asn Pro Ile Leu Lys Gln Gln Asn Leu Pro Ser Ser
            260                 265                 270

Pro Ala Pro Ser Thr Ile Phe Ser Gly Gly Phe Arg His Gly Ser Leu
        275                 280                 285

Ile Ser Ile Asp Ser Thr Cys Thr Glu Met Gly Asn Phe Asp Asn Ala
    290                 295                 300

Asn Val Thr Gly Glu Ile Glu Phe Ala Ile His Tyr Cys Phe Lys Thr
305                 310                 315                 320

His Ser Leu Glu Ile Cys Ile Lys Ala Cys Lys Asn Leu Ala Tyr Gly
                325                 330                 335

Glu Glu Lys Lys Lys Lys Cys Asn Pro Tyr Val Lys Thr Tyr Leu Leu
            340                 345                 350

Pro Asp Arg Ser Ser Gln Gly Lys Arg Lys Thr Gly Val Gln Arg Asn
        355                 360                 365

Thr Val Asp Pro Thr Phe Gln Glu Thr Leu Lys Tyr Gln Val Ala Pro
    370                 375                 380

Ala Gln Leu Val Thr Arg Gln Leu Gln Val Ser Val Trp His Leu Gly
385                 390                 395                 400

Thr Leu Ala Arg Arg Val Phe Leu Gly Glu Val Ile Ile Pro Leu Ala
                405                 410                 415

Thr Trp Asp Phe Glu Asp Ser Thr Thr Gln Ser Phe Arg Trp His Pro
            420                 425                 430

Leu Arg Ala Lys Ala Glu Lys Tyr Glu Asp Ser Val Pro Gln Ser Asn
        435                 440                 445

Gly Glu Leu Thr Val Arg Ala Lys Leu Val Leu Pro Ser Arg Pro Arg
    450                 455                 460

Lys Leu Gln Glu Ala Gln Glu Gly Thr Asp Gln Pro Ser Leu His Gly
465                 470                 475                 480

Gln Leu Cys Leu Val Val Leu Gly Ala Lys Asn Leu Pro Val Arg Pro
                485                 490                 495

Asp Gly Thr Leu Asn Ser Phe Val Lys Gly Cys Leu Thr Leu Pro Asp
            500                 505                 510

Gln Gln Lys Leu Arg Leu Lys Ser Pro Val Leu Arg Lys Gln Ala Cys
        515                 520                 525

Pro Gln Trp Lys His Ser Phe Val Phe Ser Gly Val Thr Pro Ala Gln
    530                 535                 540

Leu Arg Gln Ser Ser Leu Glu Leu Thr Val Trp Asp Gln Ala Leu Phe
545                 550                 555                 560

Gly Met Asn Asp Arg Leu Leu Gly Gly Thr Arg Leu Gly Ser Lys Gly
                565                 570                 575

Asp Thr Ala Val Gly Gly Asp Ala Cys Ser Leu Ser Lys Leu Gln Trp
            580                 585                 590

Gln Lys Val Leu Ser Ser Pro Asn Leu Trp Thr Asp Met Thr Leu Val
        595                 600                 605

Leu His
    610


<210> SEQ ID NO 21
<211> LENGTH: 775
<212> TYPE: PRT
<213> ORGANISM: Homo sapiens

<400> SEQUENCE: 21

Met Asp Cys Arg Thr Lys Ala Asn Pro Asp Arg Thr Phe Asp Leu Val
```

-continued

```
1               5                   10                  15

Leu Lys Val Lys Cys His Ala Ser Glu Asn Glu Asp Pro Val Val Leu
            20                  25                  30

Trp Lys Phe Pro Glu Asp Phe Gly Asp Gln Glu Ile Leu Gln Ser Val
        35                  40                  45

Pro Lys Phe Cys Phe Pro Phe Asp Val Glu Arg Val Ser Gln Asn Gln
    50                  55                  60

Val Gly Gln His Phe Thr Phe Val Leu Thr Asp Ile Glu Ser Lys Gln
65                  70                  75                  80

Arg Phe Gly Phe Cys Arg Leu Thr Ser Gly Gly Thr Ile Cys Leu Cys
                85                  90                  95

Ile Leu Ser Tyr Leu Pro Trp Phe Glu Val Tyr Tyr Lys Leu Leu Asn
            100                 105                 110

Thr Leu Ala Asp Tyr Leu Ala Lys Glu Leu Glu Asn Asp Leu Asn Glu
        115                 120                 125

Thr Leu Arg Ser Leu Tyr Asn His Pro Val Pro Lys Ala Asn Thr Pro
    130                 135                 140

Val Asn Leu Ser Val Asn Gln Glu Ile Phe Ile Ala Cys Glu Gln Val
145                 150                 155                 160

Leu Lys Asp Gln Pro Ala Leu Val Pro His Ser Tyr Phe Ile Ala Pro
                165                 170                 175

Asp Val Thr Gly Leu Pro Thr Ile Pro Glu Ser Arg Asn Leu Thr Glu
            180                 185                 190

Tyr Phe Val Ala Val Asp Val Asn Asn Met Leu Gln Leu Tyr Ala Ser
        195                 200                 205

Met Leu His Glu Arg Arg Ile Val Ile Ile Ser Ser Lys Leu Ser Thr
    210                 215                 220

Leu Thr Ala Cys Ile His Gly Ser Ala Ala Leu Leu Tyr Pro Met Tyr
225                 230                 235                 240

Trp Gln His Ile Tyr Ile Pro Val Leu Pro Pro His Leu Leu Asp Tyr
                245                 250                 255

Cys Cys Ala Pro Met Pro Tyr Leu Ile Gly Ile His Ser Ser Leu Ile
            260                 265                 270

Glu Arg Val Lys Asn Lys Ser Leu Glu Asp Val Val Met Leu Asn Val
        275                 280                 285

Asp Thr Asn Thr Leu Glu Ser Pro Phe Ser Asp Leu Asn Asn Leu Pro
    290                 295                 300

Ser Asp Val Val Ser Ala Leu Lys Asn Lys Leu Lys Lys Gln Ser Thr
305                 310                 315                 320

Ala Thr Gly Asp Gly Val Ala Arg Ala Phe Leu Arg Ala Gln Ala Ala
                325                 330                 335

Leu Phe Gly Ser Tyr Arg Asp Ala Leu Arg Tyr Lys Pro Gly Glu Pro
            340                 345                 350

Ile Thr Phe Cys Glu Glu Ser Phe Val Lys His Arg Ser Ser Val Met
        355                 360                 365

Lys Gln Phe Leu Glu Thr Ala Ile Asn Leu Gln Leu Phe Lys Gln Phe
    370                 375                 380

Ile Asp Gly Arg Leu Ala Lys Leu Asn Ala Gly Arg Gly Phe Ser Asp
385                 390                 395                 400

Val Phe Glu Glu Glu Ile Thr Ser Gly Gly Phe Cys Gly Gly Asn Pro
                405                 410                 415

Arg Ser Tyr Gln Gln Trp Val His Thr Val Lys Lys Gly Gly Ala Leu
            420                 425                 430
```

```
Phe Asn Thr Ala Met Thr Lys Ala Thr Pro Ala Val Arg Thr Ala Tyr
        435                 440                 445

Lys Phe Ala Lys Asn His Ala Lys Leu Gly Leu Lys Glu Val Lys Ser
    450                 455                 460

Lys Leu Lys His Lys Glu Asn Glu Glu Asp Tyr Gly Thr Cys Ser Ser
465                 470                 475                 480

Ser Val Gln Tyr Thr Pro Val Tyr Lys Leu His Asn Glu Lys Gly Gly
                485                 490                 495

Asn Ser Glu Lys Arg Lys Leu Ala Gln Ala Arg Leu Lys Arg Pro Leu
            500                 505                 510

Lys Ser Leu Asp Gly Ala Leu Tyr Asp Asp Glu Asp Asp Asp Asp Ile
        515                 520                 525

Glu Arg Ala Ser Lys Leu Ser Ser Glu Asp Gly Glu Glu Ala Ser Ala
    530                 535                 540

Tyr Leu Tyr Glu Ser Asp Asp Ser Val Glu Thr Arg Val Lys Thr Pro
545                 550                 555                 560

Tyr Ser Gly Glu Met Asp Leu Leu Gly Glu Ile Leu Asp Thr Leu Ser
                565                 570                 575

Thr His Ser Ser Asp Gln Gly Lys Leu Ala Ala Ala Lys Ser Leu Asp
            580                 585                 590

Phe Phe Arg Ser Met Asp Asp Ile Asp Tyr Lys Pro Thr Asn Lys Ser
        595                 600                 605

Asn Ala Pro Ser Glu Asn Asn Leu Ala Phe Leu Cys Gly Gly Ser Gly
    610                 615                 620

Asp Gln Ala Glu Trp Asn Leu Gly Gln Asp Asp Ser Ala Leu His Gly
625                 630                 635                 640

Lys His Leu Pro Pro Ser Pro Arg Lys Arg Val Ser Ser Ser Gly Leu
                645                 650                 655

Thr Asp Ser Leu Phe Ile Leu Lys Glu Glu Asn Ser Asn Lys His Leu
            660                 665                 670

Gly Ala Asp Asn Val Ser Asp Pro Thr Ser Gly Leu Asp Phe Gln Leu
        675                 680                 685

Thr Ser Pro Glu Val Ser Gln Thr Asp Lys Gly Lys Thr Glu Lys Arg
    690                 695                 700

Glu Thr Leu Ser Gln Ile Ser Asp Asp Leu Leu Ile Pro Gly Leu Gly
705                 710                 715                 720

Arg His Ser Ser Thr Phe Val Pro Trp Glu Lys Glu Gly Lys Glu Ala
                725                 730                 735

Lys Glu Thr Ser Glu Asp Ile Gly Leu Leu His Glu Val Val Ser Leu
            740                 745                 750

Cys His Met Thr Ser Asp Phe Gln Gln Ser Leu Asn Ile Ser Asp Lys
        755                 760                 765

Asn Thr Asn Gly Asn Gln Thr
    770                 775
```

<210> SEQ ID NO 22
<211> LENGTH: 8797
<212> TYPE: PRT
<213> ORGANISM: Homo sapiens

<400> SEQUENCE: 22

```
Met Ala Thr Ser Arg Gly Ala Ser Arg Cys Pro Arg Asp Ile Ala Asn
1               5                   10                  15

Val Met Gln Arg Leu Gln Asp Glu Gln Glu Ile Val Gln Lys Arg Thr
```

-continued

```
            20                  25                  30

Phe Thr Lys Trp Ile Asn Ser His Leu Ala Lys Arg Lys Pro Pro Met
        35                  40                  45

Val Val Asp Asp Leu Phe Glu Asp Met Lys Asp Gly Val Lys Leu Leu
    50                  55                  60

Ala Leu Leu Glu Val Leu Ser Gly Gln Lys Leu Pro Cys Glu Gln Gly
65                  70                  75                  80

Arg Arg Met Lys Arg Ile His Ala Val Ala Asn Ile Gly Thr Ala Leu
                85                  90                  95

Lys Phe Leu Glu Gly Arg Lys Ile Lys Leu Val Asn Ile Asn Ser Thr
            100                 105                 110

Asp Ile Ala Asp Gly Arg Pro Ser Ile Val Leu Gly Leu Met Trp Thr
        115                 120                 125

Ile Ile Leu Tyr Phe Gln Ile Glu Glu Leu Thr Ser Asn Leu Pro Gln
    130                 135                 140

Leu Gln Ser Leu Ser Ser Ser Ala Ser Ser Val Asp Ser Ile Val Ser
145                 150                 155                 160

Ser Glu Thr Pro Ser Pro Pro Ser Lys Arg Lys Val Thr Thr Lys Ile
                165                 170                 175

Gln Gly Asn Ala Lys Lys Ala Leu Leu Lys Trp Val Gln Tyr Thr Ala
            180                 185                 190

Gly Lys Gln Thr Gly Ile Glu Val Lys Asp Phe Gly Lys Ser Trp Arg
        195                 200                 205

Ser Gly Val Ala Phe His Ser Val Ile His Ala Ile Arg Pro Glu Leu
    210                 215                 220

Val Asp Leu Glu Thr Val Lys Gly Arg Ser Asn Arg Glu Asn Leu Glu
225                 230                 235                 240

Asp Ala Phe Thr Ile Ala Glu Thr Glu Leu Gly Ile Pro Arg Leu Leu
                245                 250                 255

Asp Pro Glu Asp Val Asp Val Asp Lys Pro Asp Glu Lys Ser Ile Met
            260                 265                 270

Thr Tyr Val Ala Gln Phe Leu Lys His Tyr Pro Asp Ile His Asn Ala
        275                 280                 285

Ser Thr Asp Gly Gln Glu Asp Asp Glu Ile Leu Pro Gly Phe Pro Ser
    290                 295                 300

Phe Ala Asn Ser Val Gln Asn Phe Lys Arg Glu Asp Arg Val Ile Phe
305                 310                 315                 320

Lys Glu Met Lys Val Trp Ile Glu Gln Phe Glu Arg Asp Leu Thr Arg
                325                 330                 335

Ala Gln Met Val Glu Ser Asn Leu Gln Asp Lys Tyr Gln Ser Phe Lys
            340                 345                 350

His Phe Arg Val Gln Tyr Glu Met Lys Arg Lys Gln Ile Glu His Leu
        355                 360                 365

Ile Gln Pro Leu His Arg Asp Gly Lys Leu Ser Leu Asp Gln Ala Leu
    370                 375                 380

Val Lys Gln Ser Trp Asp Arg Val Thr Ser Arg Leu Phe Asp Trp His
385                 390                 395                 400

Ile Gln Leu Asp Lys Ser Leu Pro Ala Pro Leu Gly Thr Ile Gly Ala
                405                 410                 415

Trp Leu Tyr Arg Ala Glu Val Ala Leu Arg Glu Glu Ile Thr Val Gln
            420                 425                 430

Gln Val His Glu Glu Thr Ala Asn Thr Ile Gln Arg Lys Leu Glu Gln
        435                 440                 445
```

```
His Lys Asp Leu Leu Gln Asn Thr Asp Ala His Lys Arg Ala Phe His
    450                 455                 460

Glu Ile Tyr Arg Thr Arg Ser Val Asn Gly Ile Pro Val Pro Pro Asp
465                 470                 475                 480

Gln Leu Glu Asp Met Ala Glu Arg Phe His Phe Val Ser Ser Thr Ser
                485                 490                 495

Glu Leu His Leu Met Lys Met Glu Phe Leu Glu Leu Lys Tyr Arg Leu
            500                 505                 510

Leu Ser Leu Leu Val Leu Ala Glu Ser Lys Leu Lys Ser Trp Ile Ile
        515                 520                 525

Lys Tyr Gly Arg Arg Glu Ser Val Glu Gln Leu Leu Gln Asn Tyr Val
    530                 535                 540

Ser Phe Ile Glu Asn Ser Lys Phe Phe Glu Gln Tyr Glu Val Thr Tyr
545                 550                 555                 560

Gln Ile Leu Lys Gln Thr Ala Glu Met Tyr Val Lys Ala Asp Gly Ser
                565                 570                 575

Val Glu Glu Ala Glu Asn Val Met Lys Phe Met Asn Glu Thr Thr Ala
            580                 585                 590

Gln Trp Arg Asn Leu Ser Val Glu Val Arg Ser Val Arg Ser Met Leu
        595                 600                 605

Glu Glu Val Ile Ser Asn Trp Asp Arg Tyr Gly Asn Thr Val Ala Ser
    610                 615                 620

Leu Gln Ala Trp Leu Glu Asp Ala Glu Lys Met Leu Asn Gln Ser Glu
625                 630                 635                 640

Asn Ala Lys Lys Asp Phe Phe Arg Asn Leu Pro His Trp Ile Gln Gln
                645                 650                 655

His Thr Ala Met Asn Asp Ala Gly Asn Phe Leu Ile Glu Thr Cys Asp
            660                 665                 670

Glu Met Val Ser Arg Asp Leu Lys Gln Gln Leu Leu Leu Leu Asn Gly
        675                 680                 685

Arg Trp Arg Glu Leu Phe Met Glu Val Lys Gln Tyr Ala Gln Ala Asp
    690                 695                 700

Glu Met Asp Arg Met Lys Lys Glu Tyr Thr Asp Cys Val Val Thr Leu
705                 710                 715                 720

Ser Ala Phe Ala Thr Glu Ala His Lys Lys Leu Ser Glu Pro Leu Glu
                725                 730                 735

Val Ser Phe Met Asn Val Lys Leu Leu Ile Gln Asp Leu Glu Asp Ile
            740                 745                 750

Glu Gln Arg Val Pro Val Met Asp Ala Gln Tyr Lys Ile Ile Thr Lys
        755                 760                 765

Thr Ala His Leu Ile Thr Lys Glu Ser Pro Gln Glu Glu Gly Lys Glu
    770                 775                 780

Met Phe Ala Thr Met Ser Lys Leu Lys Glu Gln Leu Thr Lys Val Lys
785                 790                 795                 800

Glu Cys Tyr Ser Pro Leu Leu Tyr Glu Ser Gln Gln Leu Leu Ile Pro
                805                 810                 815

Leu Glu Glu Leu Glu Lys Gln Met Thr Ser Phe Tyr Asp Ser Leu Gly
            820                 825                 830

Lys Ile Asn Glu Ile Ile Thr Val Leu Glu Arg Glu Ala Gln Ser Ser
        835                 840                 845

Ala Leu Phe Lys Gln Lys His Gln Glu Leu Leu Ala Cys Gln Glu Asn
    850                 855                 860
```

```
Cys Lys Lys Thr Leu Thr Leu Ile Glu Lys Gly Ser Gln Ser Val Gln
865                 870                 875                 880

Lys Phe Val Thr Leu Ser Asn Val Leu Lys His Phe Asp Gln Thr Arg
                885                 890                 895

Leu Gln Arg Gln Ile Ala Asp Ile His Val Ala Phe Gln Ser Met Val
            900                 905                 910

Lys Lys Thr Gly Asp Trp Lys Lys His Val Glu Thr Asn Ser Arg Leu
        915                 920                 925

Met Lys Lys Phe Glu Glu Ser Arg Ala Glu Leu Glu Lys Val Leu Arg
    930                 935                 940

Ile Ala Gln Glu Gly Leu Glu Glu Lys Gly Asp Pro Glu Glu Leu Leu
945                 950                 955                 960

Arg Arg His Thr Glu Phe Phe Ser Gln Leu Asp Gln Arg Val Leu Asn
                965                 970                 975

Ala Phe Leu Lys Ala Cys Asp Glu Leu Thr Asp Ile Leu Pro Glu Gln
            980                 985                 990

Glu Gln Gln Gly Leu Gln Glu Ala  Val Arg Lys Leu His  Lys Gln Trp
        995                 1000                1005

Lys Asp  Leu Gln Gly Glu Ala  Pro Tyr His Leu Leu  His Leu Lys
    1010                1015                1020

Ile Asp  Val Glu Lys Asn Arg  Phe Leu Ala Ser Val  Glu Glu Cys
    1025                1030                1035

Arg Thr  Glu Leu Asp Arg Glu  Thr Lys Leu Met Pro  Gln Glu Gly
    1040                1045                1050

Ser Glu  Lys Ile Ile Lys Glu  His Arg Val Phe Phe  Ser Asp Lys
    1055                1060                1065

Gly Pro  His His Leu Cys Glu  Lys Arg Leu Gln Leu  Ile Glu Glu
    1070                1075                1080

Leu Cys  Val Lys Leu Pro Val  Arg Asp Pro Val Arg  Asp Thr Pro
    1085                1090                1095

Gly Thr  Cys His Val Thr Leu  Lys Glu Leu Arg Ala  Ala Ile Asp
    1100                1105                1110

Ser Thr  Tyr Arg Lys Leu Met  Glu Asp Pro Asp Lys  Trp Lys Asp
    1115                1120                1125

Tyr Thr  Ser Arg Phe Ser Glu  Phe Ser Ser Trp Ile  Ser Thr Asn
    1130                1135                1140

Glu Thr  Gln Leu Lys Gly Ile  Lys Gly Glu Ala Ile  Asp Thr Ala
    1145                1150                1155

Asn His  Gly Glu Val Lys Arg  Ala Val Glu Glu Ile  Arg Asn Gly
    1160                1165                1170

Val Thr  Lys Arg Gly Glu Thr  Leu Ser Trp Leu Lys  Ser Arg Leu
    1175                1180                1185

Lys Val  Leu Thr Glu Val Ser  Ser Glu Asn Glu Ala  Gln Lys Gln
    1190                1195                1200

Gly Asp  Glu Leu Ala Lys Leu  Ser Ser Ser Phe Lys  Ala Leu Val
    1205                1210                1215

Thr Leu  Leu Ser Glu Val Glu  Lys Met Leu Ser Asn  Phe Gly Asp
    1220                1225                1230

Cys Val  Gln Tyr Lys Glu Ile  Val Lys Asn Ser Leu  Glu Glu Leu
    1235                1240                1245

Ile Ser  Gly Ser Lys Glu Val  Gln Glu Gln Ala Glu  Lys Ile Leu
    1250                1255                1260

Asp Thr  Glu Asn Leu Phe Glu  Ala Gln Gln Leu Leu  Leu His His
```

-continued

```
    1265                1270                1275

Gln Gln  Lys Thr Lys Arg Ile  Ser Ala Lys Lys Arg  Asp Val Gln
    1280                1285                1290

Gln Gln  Ile Ala Gln Ala Gln  Gln Gly Glu Gly Gly  Leu Pro Asp
    1295                1300                1305

Arg Gly  His Glu Glu Leu Arg  Lys Leu Glu Ser Thr  Leu Asp Gly
    1310                1315                1320

Leu Glu  Arg Ser Arg Glu Arg  Gln Glu Arg Arg Ile  Gln Val Thr
    1325                1330                1335

Leu Arg  Lys Trp Glu Arg Phe  Glu Thr Asn Lys Glu  Thr Val Val
    1340                1345                1350

Arg Tyr  Leu Phe Gln Thr Gly  Ser Ser His Glu Arg  Phe Leu Ser
    1355                1360                1365

Phe Ser  Ser Leu Glu Ser Leu  Ser Ser Glu Leu Glu  Gln Thr Lys
    1370                1375                1380

Glu Phe  Ser Lys Arg Thr Glu  Ser Ile Ala Val Gln  Ala Glu Asn
    1385                1390                1395

Leu Val  Lys Glu Ala Ser Glu  Ile Pro Leu Gly Pro  Gln Asn Lys
    1400                1405                1410

Gln Leu  Leu Gln Gln Gln Ala  Lys Ser Ile Lys Glu  Gln Val Lys
    1415                1420                1425

Lys Leu  Glu Asp Thr Leu Glu  Glu Asp Ile Lys Thr  Met Glu Met
    1430                1435                1440

Val Lys  Thr Lys Trp Asp His  Phe Gly Ser Asn Phe  Glu Thr Leu
    1445                1450                1455

Ser Val  Trp Ile Thr Glu Lys  Glu Lys Glu Leu Asn  Ala Leu Glu
    1460                1465                1470

Thr Ser  Ser Ser Ala Met Asp  Met Gln Ile Ser Gln  Ile Lys Val
    1475                1480                1485

Thr Ile  Gln Glu Ile Glu Ser  Lys Leu Ser Ser Ile  Val Gly Leu
    1490                1495                1500

Glu Glu  Glu Ala Gln Ser Phe  Ala Gln Phe Val Thr  Thr Gly Glu
    1505                1510                1515

Ser Ala  Arg Ile Lys Ala Lys  Leu Thr Gln Ile Arg  Arg Tyr Gly
    1520                1525                1530

Glu Glu  Leu Arg Glu His Ala  Gln Cys Leu Glu Gly  Thr Ile Leu
    1535                1540                1545

Gly His  Leu Ser Gln Gln Gln  Lys Phe Glu Glu Asn  Leu Arg Lys
    1550                1555                1560

Ile Gln  Gln Ser Val Ser Glu  Phe Glu Asp Lys Leu  Ala Val Pro
    1565                1570                1575

Ile Lys  Ile Cys Ser Ser Ala  Thr Glu Thr Tyr Lys  Val Leu Gln
    1580                1585                1590

Glu His  Met Asp Leu Cys Gln  Ala Leu Glu Ser Leu  Ser Ser Ala
    1595                1600                1605

Ile Thr  Ala Phe Ser Ala Ser  Ala Arg Lys Val Val  Asn Arg Asp
    1610                1615                1620

Ser Cys  Val Gln Glu Ala Ala  Ala Leu Gln Gln Gln  Tyr Glu Asp
    1625                1630                1635

Ile Leu  Arg Arg Ala Lys Glu  Arg Gln Thr Ala Leu  Glu Asn Leu
    1640                1645                1650

Leu Ala  His Trp Gln Arg Leu  Glu Lys Glu Leu Ser  Ser Phe Leu
    1655                1660                1665
```

```
Thr Trp  Leu Glu Arg Gly Glu  Ala Lys Ala Ser Ser  Pro Glu Met
    1670                 1675                 1680

Asp Ile  Ser Ala Asp Arg Val  Lys Val Glu Gly Glu  Leu Gln Leu
    1685                 1690                 1695

Ile Gln  Ala Leu Gln Asn Glu  Val Val Ser Gln Ala  Ser Phe Tyr
    1700                 1705                 1710

Ser Lys  Leu Leu Gln Leu Lys  Glu Ser Leu Phe Ser  Val Ala Ser
    1715                 1720                 1725

Lys Asp  Asp Val Lys Met Met  Lys Leu His Leu Glu  Gln Leu Asp
    1730                 1735                 1740

Glu Arg  Trp Arg Asp Leu Pro  Gln Ile Ile Asn Lys  Arg Ile Asn
    1745                 1750                 1755

Phe Leu  Gln Ser Val Val Ala  Glu His Gln Gln Phe  Asp Glu Leu
    1760                 1765                 1770

Leu Leu  Ser Phe Ser Val Trp  Ile Lys Leu Phe Leu  Ser Glu Leu
    1775                 1780                 1785

Gln Thr  Thr Ser Glu Ile Ser  Ile Met Asp His Gln  Val Ala Leu
    1790                 1795                 1800

Thr Arg  His Lys Asp His Ala  Ala Glu Val Glu Ser  Lys Lys Gly
    1805                 1810                 1815

Glu Leu  Gln Ser Leu Gln Gly  His Leu Ala Lys Leu  Gly Ser Leu
    1820                 1825                 1830

Gly Arg  Ala Glu Asp Leu His  Leu Leu Gln Gly Lys  Ala Glu Asp
    1835                 1840                 1845

Cys Phe  Gln Leu Phe Glu Glu  Ala Ser Gln Val Val  Glu Arg Arg
    1850                 1855                 1860

Gln Leu  Ala Leu Ser His Leu  Ala Glu Phe Leu Gln  Ser His Ala
    1865                 1870                 1875

Ser Leu  Ser Gly Ile Leu Arg  Gln Leu Arg Gln Thr  Val Glu Ala
    1880                 1885                 1890

Thr Asn  Ser Met Asn Lys Asn  Glu Ser Asp Leu Ile  Glu Lys Asp
    1895                 1900                 1905

Leu Asn  Asp Ala Leu Gln Asn  Ala Lys Ala Leu Glu  Ser Ala Ala
    1910                 1915                 1920

Val Ser  Leu Asp Gly Ile Leu  Ser Lys Ala Gln Tyr  His Leu Lys
    1925                 1930                 1935

Ile Gly  Ser Ser Glu Gln Arg  Thr Ser Cys Arg Ala  Thr Ala Asp
    1940                 1945                 1950

Gln Leu  Cys Gly Glu Val Glu  Arg Ile Gln Asn Leu  Leu Gly Thr
    1955                 1960                 1965

Lys Gln  Ser Glu Ala Asp Ala  Leu Ala Val Leu Lys  Lys Ala Phe
    1970                 1975                 1980

Gln Asp  Gln Lys Glu Glu Leu  Leu Lys Ser Ile Glu  Asp Ile Glu
    1985                 1990                 1995

Glu Arg  Thr Asp Lys Glu Arg  Leu Lys Glu Pro Thr  Arg Gln Ala
    2000                 2005                 2010

Leu Gln  Gln Arg Leu Arg Val  Phe Asn Gln Leu Glu  Asp Glu Leu
    2015                 2020                 2025

Asn Ser  His Glu His Glu Leu  Cys Trp Leu Lys Asp  Lys Ala Lys
    2030                 2035                 2040

Gln Ile  Ala Gln Lys Asp Val  Ala Phe Ala Pro Glu  Val Asp Arg
    2045                 2050                 2055
```

```
Glu Ile  Asn Arg Leu Glu Val  Thr Trp Asp Asp Thr  Lys Arg Leu
    2060                 2065                 2070

Ile His  Glu Asn Gln Gly Gln  Cys Cys Gly Leu Ile  Asp Leu Met
    2075                 2080                 2085

Arg Glu  Tyr Gln Asn Leu Lys  Ser Ala Val Ser Lys  Val Leu Glu
    2090                 2095                 2100

Asn Ala  Ser Ser Val Ile Val  Thr Arg Thr Thr Ile  Lys Asp Gln
    2105                 2110                 2115

Glu Asp  Leu Lys Trp Ala Phe  Ser Lys His Glu Thr  Ala Lys Asn
    2120                 2125                 2130

Lys Met  Asn Tyr Lys Gln Lys  Asp Leu Asp Asn Phe  Thr Ser Lys
    2135                 2140                 2145

Gly Lys  His Leu Leu Ser Glu  Leu Lys Lys Ile His  Ser Ser Asp
    2150                 2155                 2160

Phe Ser  Leu Val Lys Thr Asp  Met Glu Ser Thr Val  Asp Lys Trp
    2165                 2170                 2175

Leu Asp  Val Ser Glu Lys Leu  Glu Glu Asn Met Asp  Arg Leu Arg
    2180                 2185                 2190

Val Ser  Leu Ser Ile Trp Asp  Asp Val Leu Ser Thr  Arg Asp Glu
    2195                 2200                 2205

Ile Glu  Gly Trp Ser Asn Asn  Cys Val Pro Gln Met  Ala Glu Asn
    2210                 2215                 2220

Ile Ser  Asn Leu Asp Asn His  Leu Arg Ala Glu Glu  Leu Leu Lys
    2225                 2230                 2235

Glu Phe  Glu Ser Glu Val Lys  Asn Lys Ala Leu Arg  Leu Glu Glu
    2240                 2245                 2250

Leu His  Ser Lys Val Asn Asp  Leu Lys Glu Leu Thr  Lys Asn Leu
    2255                 2260                 2265

Glu Thr  Pro Pro Asp Leu Gln  Phe Ile Glu Ala Asp  Leu Met Gln
    2270                 2275                 2280

Lys Leu  Glu His Ala Lys Glu  Ile Thr Glu Val Ala  Lys Gly Thr
    2285                 2290                 2295

Leu Lys  Asp Phe Thr Ala Gln  Ser Thr Gln Val Glu  Lys Phe Ile
    2300                 2305                 2310

Asn Asp  Ile Thr Thr Trp Phe  Thr Lys Val Glu Glu  Ser Leu Met
    2315                 2320                 2325

Asn Cys  Ala Gln Asn Glu Thr  Cys Glu Ala Leu Lys  Lys Val Lys
    2330                 2335                 2340

Asp Ile  Gln Lys Glu Leu Gln  Ser Gln Gln Ser Asn  Ile Ser Ser
    2345                 2350                 2355

Thr Gln  Glu Asn Leu Asn Ser  Leu Cys Arg Lys Tyr  His Ser Ala
    2360                 2365                 2370

Glu Leu  Glu Ser Leu Gly Arg  Ala Met Thr Gly Leu  Ile Lys Lys
    2375                 2380                 2385

His Glu  Ala Val Ser Gln Leu  Cys Ser Lys Thr Gln  Ala Ser Leu
    2390                 2395                 2400

Gln Glu  Ser Leu Glu Lys His  Phe Ser Glu Ser Met  Gln Glu Phe
    2405                 2410                 2415

Gln Glu  Trp Phe Leu Gly Ala  Lys Ala Ala Ala Lys  Glu Ser Ser
    2420                 2425                 2430

Asp Arg  Thr Gly Asp Ser Lys  Val Leu Glu Ala Lys  Leu His Asp
    2435                 2440                 2445

Leu Gln  Asn Ile Leu Asp Ser  Val Ser Asp Gly Gln  Ser Lys Leu
```

```
    2450                2455                2460

Asp Ala  Val Thr Gln Glu Gly  Gln Thr Leu Tyr Ala  His Leu Ser
    2465                2470                2475

Lys Gln  Ile Val Ser Ser Ile  Gln Glu Gln Ile Thr  Lys Ala Asn
    2480                2485                2490

Glu Glu  Phe Gln Ala Phe Leu  Lys Gln Cys Leu Lys  Asp Lys Gln
    2495                2500                2505

Ala Leu  Gln Asp Cys Ala Ser  Glu Leu Gly Ser Phe  Glu Asp Gln
    2510                2515                2520

His Arg  Lys Leu Asn Leu Trp  Ile His Glu Met Glu  Glu Arg Phe
    2525                2530                2535

Asn Thr  Glu Asn Leu Gly Glu  Ser Lys Gln His Ile  Pro Glu Lys
    2540                2545                2550

Lys Asn  Glu Val His Lys Val  Glu Met Phe Leu Gly  Glu Leu Leu
    2555                2560                2565

Ala Ala  Arg Glu Ser Leu Asp  Lys Leu Ser Gln Arg  Gly Gln Leu
    2570                2575                2580

Leu Ser  Glu Glu Gly His Gly  Ala Gly Gln Glu Gly  Arg Leu Cys
    2585                2590                2595

Ser Gln  Leu Leu Thr Ser His  Gln Asn Leu Leu Arg  Met Thr Lys
    2600                2605                2610

Glu Lys  Leu Arg Ser Cys Gln  Val Ala Leu Gln Glu  His Glu Ala
    2615                2620                2625

Leu Glu  Glu Ala Leu Gln Ser  Met Trp Phe Trp Val  Lys Ala Ile
    2630                2635                2640

Gln Asp  Arg Leu Ala Cys Ala  Glu Ser Thr Leu Gly  Ser Lys Asp
    2645                2650                2655

Thr Leu  Glu Lys Arg Leu Ser  Gln Ile Gln Asp Ile  Leu Leu Met
    2660                2665                2670

Lys Gly  Glu Gly Glu Val Lys  Leu Asn Met Ala Ile  Gly Lys Gly
    2675                2680                2685

Glu Gln  Ala Leu Arg Ser Ser  Asn Lys Glu Gly Gln  Arg Val Ile
    2690                2695                2700

Gln Thr  Gln Leu Glu Thr Leu  Lys Glu Val Trp Ala  Asp Ile Met
    2705                2710                2715

Ser Ser  Ser Val His Ala Gln  Ser Thr Leu Glu Ser  Val Ile Ser
    2720                2725                2730

Gln Trp  Asn Asp Tyr Val Glu  Arg Lys Asn Gln Leu  Glu Gln Trp
    2735                2740                2745

Met Glu  Ser Val Asp Gln Lys  Ile Glu His Pro Leu  Gln Pro Gln
    2750                2755                2760

Pro Gly  Leu Lys Glu Lys Phe  Val Leu Leu Asp His  Leu Gln Ser
    2765                2770                2775

Ile Leu  Ser Glu Ala Glu Asp  His Thr Arg Ala Leu  His Arg Leu
    2780                2785                2790

Ile Ala  Lys Ser Arg Glu Leu  Tyr Glu Lys Thr Glu  Asp Glu Ser
    2795                2800                2805

Phe Lys  Asp Thr Ala Gln Glu  Glu Leu Lys Thr Gln  Phe Asn Asp
    2810                2815                2820

Ile Met  Thr Val Ala Lys Glu  Lys Met Arg Lys Val  Glu Glu Ile
    2825                2830                2835

Val Lys  Asp His Leu Met Tyr  Leu Asp Ala Val His  Glu Phe Thr
    2840                2845                2850
```

Asp Trp Leu His Ser Ala Lys Glu Glu Leu His Arg Trp Ser Asp
2855 2860 2865

Met Ser Gly Asp Ser Ser Ala Thr Gln Lys Lys Leu Ser Lys Ile
2870 2875 2880

Lys Glu Leu Ile Asp Ser Arg Glu Ile Gly Ala Ser Arg Leu Ser
2885 2890 2895

Arg Val Glu Ser Leu Ala Pro Glu Val Lys Gln Asn Thr Thr Ala
2900 2905 2910

Ser Gly Cys Glu Leu Met His Thr Glu Met Gln Ala Leu Arg Ala
2915 2920 2925

Asp Trp Lys Gln Trp Glu Asp Ser Val Phe Gln Thr Gln Ser Cys
2930 2935 2940

Leu Glu Asn Leu Val Ser Gln Met Ala Leu Ser Glu Gln Glu Phe
2945 2950 2955

Ser Gly Gln Val Ala Gln Leu Glu Gln Ala Leu Glu Gln Phe Ser
2960 2965 2970

Ala Leu Leu Lys Thr Trp Ala Gln Gln Leu Thr Leu Leu Glu Gly
2975 2980 2985

Lys Asn Thr Asp Glu Glu Ile Val Glu Cys Trp His Lys Gly Gln
2990 2995 3000

Glu Ile Leu Asp Ala Leu Gln Lys Ala Glu Pro Arg Thr Glu Asp
3005 3010 3015

Leu Lys Ser Gln Leu Asn Glu Leu Cys Arg Phe Ser Arg Asp Leu
3020 3025 3030

Ser Thr Tyr Ser Gly Lys Val Ser Gly Leu Ile Lys Glu Tyr Asn
3035 3040 3045

Cys Leu Cys Leu Gln Ala Ser Lys Gly Cys Gln Asn Lys Glu Gln
3050 3055 3060

Ile Leu Gln Gln Arg Phe Arg Lys Ala Phe Arg Asp Phe Gln Gln
3065 3070 3075

Trp Leu Val Asn Ala Lys Ile Thr Thr Ala Lys Cys Phe Asp Ile
3080 3085 3090

Pro Gln Asn Ile Ser Glu Val Ser Thr Ser Leu Gln Lys Ile Gln
3095 3100 3105

Glu Phe Leu Ser Glu Ser Glu Asn Gly Gln His Lys Leu Asn Met
3110 3115 3120

Met Leu Ser Lys Gly Glu Leu Leu Ser Thr Leu Leu Thr Lys Glu
3125 3130 3135

Lys Ala Lys Gly Ile Gln Ala Lys Val Thr Ala Ala Lys Glu Asp
3140 3145 3150

Trp Lys Asn Phe His Ser Asn Leu His Gln Lys Glu Ser Ala Leu
3155 3160 3165

Glu Asn Leu Lys Ile Gln Met Lys Asp Phe Glu Val Ser Ala Glu
3170 3175 3180

Pro Ile Gln Asp Trp Leu Ser Lys Thr Glu Lys Met Val His Glu
3185 3190 3195

Ser Ser Asn Arg Leu Tyr Asp Leu Pro Ala Lys Arg Arg Glu Gln
3200 3205 3210

Gln Lys Leu Gln Ser Val Leu Glu Glu Ile His Cys Tyr Glu Pro
3215 3220 3225

Gln Leu Asn Arg Leu Lys Glu Lys Ala Gln Gln Leu Trp Glu Gly
3230 3235 3240

```
Gln Ala Ala Ser Lys Ser Phe Arg His Arg Val Ser Gln Leu Ser
    3245                3250                3255

Ser Gln Tyr Leu Ala Leu Ser Asn Leu Thr Lys Glu Lys Val Ser
    3260                3265                3270

Arg Leu Asp Arg Ile Val Ala Glu His Asn Gln Phe Ser Leu Gly
    3275                3280                3285

Ile Lys Glu Leu Gln Asp Trp Met Thr Asp Ala Ile His Met Leu
    3290                3295                3300

Asp Ser Tyr Cys His Pro Thr Ser Asp Lys Ser Val Leu Asp Ser
    3305                3310                3315

Arg Thr Leu Lys Leu Glu Ala Leu Leu Ser Val Lys Gln Glu Lys
    3320                3325                3330

Glu Ile Gln Met Lys Met Ile Val Thr Arg Gly Glu Ser Val Leu
    3335                3340                3345

Gln Asn Thr Ser Pro Glu Gly Ile Pro Thr Ile Gln Gln Gln Leu
    3350                3355                3360

Gln Ser Val Lys Asp Met Trp Ala Ser Leu Leu Ser Ala Gly Ile
    3365                3370                3375

Arg Cys Lys Ser Gln Leu Glu Gly Ala Leu Ser Lys Trp Thr Ser
    3380                3385                3390

Tyr Gln Asp Gly Val Arg Gln Phe Ser Gly Trp Met Asp Ser Met
    3395                3400                3405

Glu Ala Asn Leu Asn Glu Ser Glu Arg Gln His Ala Glu Leu Arg
    3410                3415                3420

Asp Lys Thr Thr Met Leu Gly Lys Ala Lys Leu Leu Asn Glu Glu
    3425                3430                3435

Val Leu Ser Tyr Ser Ser Leu Leu Glu Thr Ile Glu Val Lys Gly
    3440                3445                3450

Ala Gly Met Thr Glu His Tyr Val Thr Gln Leu Glu Leu Gln Asp
    3455                3460                3465

Leu Gln Glu Arg Tyr Arg Ala Ile Gln Glu Arg Ala Lys Glu Ala
    3470                3475                3480

Val Thr Lys Ser Glu Lys Leu Val Arg Leu His Gln Glu Tyr Gln
    3485                3490                3495

Arg Asp Leu Lys Ala Phe Glu Val Trp Leu Gly Gln Glu Gln Glu
    3500                3505                3510

Lys Leu Asp Gln Tyr Ser Val Leu Glu Gly Asp Ala His Thr His
    3515                3520                3525

Glu Thr Thr Leu Arg Asp Leu Gln Glu Leu Gln Val His Cys Ala
    3530                3535                3540

Glu Gly Gln Ala Leu Leu Asn Ser Val Leu His Thr Arg Glu Asp
    3545                3550                3555

Val Ile Pro Ser Gly Ile Pro Gln Ala Glu Asp Arg Ala Leu Glu
    3560                3565                3570

Ser Leu Arg Gln Asp Trp Gln Ala Tyr Gln His Arg Leu Ser Glu
    3575                3580                3585

Thr Arg Thr Gln Phe Asn Asn Val Val Asn Lys Leu Arg Leu Met
    3590                3595                3600

Glu Gln Lys Phe Gln Gln Val Asp Glu Trp Leu Lys Thr Ala Glu
    3605                3610                3615

Glu Lys Val Ser Pro Arg Thr Arg Arg Gln Ser Asn Arg Ala Thr
    3620                3625                3630

Lys Glu Ile Gln Leu His Gln Met Lys Lys Trp His Glu Glu Val
```

```
    3635                3640                3645

Thr Ala  Tyr Arg Asp Glu Val  Glu Glu Val Gly Ala  Arg Ala Gln
    3650                3655                3660

Glu Ile  Leu Asp Glu Ser His  Val Asn Ser Arg Met  Gly Cys Gln
    3665                3670                3675

Ala Thr  Gln Leu Thr Ser Arg  Tyr Gln Ala Leu Leu  Leu Gln Val
    3680                3685                3690

Leu Glu  Gln Ile Lys Phe Leu  Glu Glu Glu Ile Gln  Ser Leu Glu
    3695                3700                3705

Glu Ser  Glu Ser Ser Leu Ser  Ser Tyr Ser Asp Trp  Tyr Gly Ser
    3710                3715                3720

Thr His  Lys Asn Phe Lys Asn  Val Ala Thr Lys Ile  Asp Lys Val
    3725                3730                3735

Asp Thr  Val Met Met Gly Lys  Lys Leu Lys Thr Leu  Glu Val Leu
    3740                3745                3750

Leu Lys  Asp Met Glu Lys Gly  His Ser Leu Leu Lys  Ser Ala Arg
    3755                3760                3765

Glu Lys  Gly Glu Arg Ala Val  Lys Tyr Leu Glu Glu  Gly Glu Ala
    3770                3775                3780

Glu Arg  Leu Arg Lys Glu Ile  His Asp His Met Glu  Gln Leu Lys
    3785                3790                3795

Glu Leu  Thr Ser Thr Val Arg  Lys Glu His Met Thr  Leu Glu Lys
    3800                3805                3810

Gly Leu  His Leu Ala Lys Glu  Phe Ser Asp Lys Cys  Lys Ala Leu
    3815                3820                3825

Thr Gln  Trp Ile Ala Glu Tyr  Gln Glu Ile Leu His  Val Pro Glu
    3830                3835                3840

Glu Pro  Lys Met Glu Leu Tyr  Glu Lys Lys Ala Gln  Leu Ser Lys
    3845                3850                3855

Tyr Lys  Ser Leu Gln Gln Thr  Val Leu Ser His Glu  Pro Ser Val
    3860                3865                3870

Lys Ser  Val Arg Glu Lys Gly  Glu Ala Leu Leu Glu  Leu Val Gln
    3875                3880                3885

Asp Val  Thr Leu Lys Asp Lys  Ile Asp Gln Leu Gln  Ser Asp Tyr
    3890                3895                3900

Gln Asp  Leu Cys Ser Ile Gly  Lys Glu His Val Phe  Ser Leu Glu
    3905                3910                3915

Ala Lys  Val Lys Asp His Glu  Asp Tyr Asn Ser Glu  Leu Gln Glu
    3920                3925                3930

Val Glu  Lys Trp Leu Leu Gln  Met Ser Gly Arg Leu  Val Ala Pro
    3935                3940                3945

Asp Leu  Leu Glu Thr Ser Ser  Leu Glu Thr Ile Thr  Gln Gln Leu
    3950                3955                3960

Ala His  His Lys Ala Met Met  Glu Glu Ile Ala Gly  Phe Glu Asp
    3965                3970                3975

Arg Leu  Asn Asn Leu Gln Met  Lys Gly Asp Thr Leu  Ile Gly Gln
    3980                3985                3990

Cys Ala  Asp His Leu Gln Ala  Lys Leu Lys Gln Asn  Val His Ala
    3995                4000                4005

His Leu  Gln Gly Thr Lys Asp  Ser Tyr Ser Ala Ile  Cys Ser Thr
    4010                4015                4020

Ala Gln  Arg Met Tyr Gln Ser  Leu Glu His Glu Leu  Gln Lys His
    4025                4030                4035
```

-continued

```
Val Ser  Arg Gln Asp Thr Leu  Gln Gln Cys Gln Ala  Trp Leu Ser
    4040                 4045                 4050

Ala Val  Gln Pro Asp Leu Glu  Pro Ser Pro Gln Pro  Pro Leu Ser
    4055                 4060                 4065

Arg Ala  Glu Ala Ile Lys Gln  Val Lys His Phe Arg  Ala Leu Gln
    4070                 4075                 4080

Glu Gln  Ala Arg Thr Tyr Leu  Asp Leu Leu Cys Ser  Met Cys Asp
    4085                 4090                 4095

Leu Ser  Asn Ala Ser Val Lys  Thr Thr Ala Lys Asp  Ile Gln Gln
    4100                 4105                 4110

Thr Glu  Gln Thr Ile Glu Gln  Lys Leu Val Gln Ala  Gln Asn Leu
    4115                 4120                 4125

Thr Gln  Gly Trp Glu Glu Ile  Lys His Leu Lys Ser  Glu Leu Trp
    4130                 4135                 4140

Ile Tyr  Leu Gln Asp Ala Asp  Gln Gln Leu Gln Asn  Met Lys Arg
    4145                 4150                 4155

Arg His  Ser Glu Leu Glu Leu  Asn Ile Ala Gln Asn  Met Val Ser
    4160                 4165                 4170

Gln Val  Lys Asp Phe Val Lys  Lys Leu Gln Ser Lys  Gln Ala Ser
    4175                 4180                 4185

Val Asn  Thr Ile Ile Glu Lys  Val Asn Lys Leu Thr  Lys Lys Glu
    4190                 4195                 4200

Glu Ser  Pro Glu His Lys Glu  Ile Asn His Leu Asn  Asp Gln Trp
    4205                 4210                 4215

Leu Asp  Leu Cys Arg Gln Ser  Asn Asn Leu Cys Leu  Gln Arg Glu
    4220                 4225                 4230

Glu Asp  Leu Gln Arg Thr Arg  Asp Tyr His Asp Cys  Met Asn Val
    4235                 4240                 4245

Val Glu  Val Phe Leu Glu Lys  Phe Thr Thr Glu Trp  Asp Asn Leu
    4250                 4255                 4260

Ala Arg  Ser Asp Ala Glu Ser  Thr Ala Val His Leu  Glu Ala Leu
    4265                 4270                 4275

Lys Lys  Leu Ala Leu Ala Leu  Gln Glu Arg Lys Tyr  Ala Ile Glu
    4280                 4285                 4290

Asp Leu  Lys Asp Gln Lys Gln  Lys Met Ile Glu His  Leu Asn Leu
    4295                 4300                 4305

Asp Asp  Lys Glu Leu Val Lys  Glu Gln Thr Ser His  Leu Glu Gln
    4310                 4315                 4320

Arg Trp  Phe Gln Leu Glu Asp  Leu Ile Lys Arg Lys  Ile Gln Val
    4325                 4330                 4335

Ser Val  Thr Asn Leu Glu Glu  Leu Asn Val Val Gln  Ser Arg Phe
    4340                 4345                 4350

Gln Glu  Leu Met Glu Trp Ala  Glu Glu Gln Gln Pro  Asn Ile Ala
    4355                 4360                 4365

Glu Ala  Leu Lys Gln Ser Pro  Pro Pro Asp Met Ala  Gln Asn Leu
    4370                 4375                 4380

Leu Met  Asp His Leu Ala Ile  Cys Ser Glu Leu Glu  Ala Lys Gln
    4385                 4390                 4395

Met Leu  Leu Lys Ser Leu Ile  Lys Asp Ala Asp Arg  Val Met Ala
    4400                 4405                 4410

Asp Leu  Gly Leu Asn Glu Arg  Gln Val Ile Gln Lys  Ala Leu Ser
    4415                 4420                 4425
```

```
Asp Ala  Gln Ser His Val Asn  Cys Leu Ser Asp Leu  Val Gly Gln
    4430                 4435                 4440

Arg Arg  Lys Tyr Leu Asn Lys  Ala Leu Ser Glu Lys  Thr Gln Phe
    4445                 4450                 4455

Leu Met  Ala Val Phe Gln Ala  Thr Ser Gln Ile Gln  Gln His Glu
    4460                 4465                 4470

Arg Lys  Ile Met Phe Arg Glu  His Ile Cys Leu Leu  Pro Asp Asp
    4475                 4480                 4485

Val Ser  Lys Gln Val Lys Thr  Cys Lys Ser Ala Gln  Ala Ser Leu
    4490                 4495                 4500

Lys Thr  Tyr Gln Asn Glu Val  Thr Gly Leu Trp Ala  Gln Gly Arg
    4505                 4510                 4515

Glu Leu  Met Lys Glu Val Thr  Glu Gln Glu Lys Ser  Glu Val Leu
    4520                 4525                 4530

Gly Lys  Leu Gln Glu Leu Gln  Ser Val Tyr Asp Ser  Val Leu Gln
    4535                 4540                 4545

Lys Cys  Ser His Arg Leu Gln  Glu Leu Glu Lys Asn  Leu Val Ser
    4550                 4555                 4560

Arg Lys  His Phe Lys Glu Asp  Phe Asp Lys Ala Cys  His Trp Leu
    4565                 4570                 4575

Lys Gln  Ala Asp Ile Val Thr  Phe Pro Glu Ile Asn  Leu Met Asn
    4580                 4585                 4590

Glu Ser  Ser Glu Leu His Thr  Gln Leu Ala Lys Tyr  Gln Asn Ile
    4595                 4600                 4605

Leu Glu  Gln Ser Pro Glu Tyr  Glu Asn Leu Leu Leu  Thr Leu Gln
    4610                 4615                 4620

Arg Thr  Gly Gln Thr Ile Leu  Pro Ser Leu Asn Glu  Val Asp His
    4625                 4630                 4635

Ser Tyr  Leu Ser Glu Lys Leu  Asn Ala Leu Pro Arg  Gln Phe Asn
    4640                 4645                 4650

Val Ile  Val Ala Leu Ala Lys  Asp Lys Phe Tyr Lys  Val Gln Glu
    4655                 4660                 4665

Ala Ile  Leu Ala Arg Lys Glu  Tyr Ala Ser Leu Ile  Glu Leu Thr
    4670                 4675                 4680

Thr Gln  Ser Leu Ser Glu Leu  Glu Ala Gln Phe Leu  Arg Met Ser
    4685                 4690                 4695

Lys Val  Pro Thr Asp Leu Ala  Val Glu Glu Ala Leu  Ser Leu Gln
    4700                 4705                 4710

Asp Gly  Cys Arg Ala Ile Leu  Asp Glu Val Ala Gly  Leu Gly Glu
    4715                 4720                 4725

Ala Val  Asp Glu Leu Asn Gln  Lys Lys Glu Gly Phe  Arg Ser Thr
    4730                 4735                 4740

Gly Gln  Pro Trp Gln Pro Asp  Lys Met Leu His Leu  Val Thr Leu
    4745                 4750                 4755

Tyr His  Arg Leu Lys Arg Gln  Thr Glu Gln Arg Val  Ser Leu Leu
    4760                 4765                 4770

Glu Asp  Thr Thr Ser Ala Tyr  Gln Glu His Glu Lys  Met Cys Gln
    4775                 4780                 4785

Gln Leu  Glu Arg Gln Leu Lys  Ser Val Lys Glu Glu  Gln Ser Lys
    4790                 4795                 4800

Val Asn  Glu Glu Thr Leu Pro  Ala Glu Glu Lys Leu  Lys Met Tyr
    4805                 4810                 4815

His Ser  Leu Ala Gly Ser Leu  Gln Asp Ser Gly Ile  Val Leu Lys
```

4820 4825 4830

Arg Val Thr Ile His Leu Glu Asp Leu Ala Pro His Leu Asp Pro
4835 4840 4845

Leu Ala Tyr Glu Lys Ala Arg His Gln Ile Gln Ser Trp Gln Gly
4850 4855 4860

Glu Leu Lys Leu Leu Thr Ser Ala Ile Gly Glu Thr Val Thr Glu
4865 4870 4875

Cys Glu Ser Arg Met Val Gln Ser Ile Asp Phe Gln Thr Glu Met
4880 4885 4890

Ser Arg Ser Leu Asp Trp Leu Arg Arg Val Lys Ala Glu Leu Ser
4895 4900 4905

Gly Pro Val Tyr Leu Asp Leu Asn Leu Gln Asp Ile Gln Glu Glu
4910 4915 4920

Ile Arg Lys Ile Gln Ile His Gln Glu Glu Val Gln Ser Ser Leu
4925 4930 4935

Arg Ile Met Asn Ala Leu Ser His Lys Glu Lys Glu Lys Phe Thr
4940 4945 4950

Lys Ala Lys Glu Leu Ile Ser Ala Asp Leu Glu His Ser Leu Ala
4955 4960 4965

Glu Leu Ser Glu Leu Asp Gly Asp Ile Gln Glu Ala Leu Arg Thr
4970 4975 4980

Arg Gln Ala Thr Leu Thr Glu Ile Tyr Ser Gln Cys Gln Arg Tyr
4985 4990 4995

Tyr Gln Val Phe Gln Ala Ala Asn Asp Trp Leu Glu Asp Ala Gln
5000 5005 5010

Glu Leu Leu Gln Leu Ala Gly Asn Gly Leu Asp Val Glu Ser Ala
5015 5020 5025

Glu Glu Asn Leu Lys Ser His Met Glu Phe Phe Ser Thr Glu Asp
5030 5035 5040

Gln Phe His Ser Asn Leu Glu Glu Leu His Ser Leu Val Ala Thr
5045 5050 5055

Leu Asp Pro Leu Ile Lys Pro Thr Gly Lys Glu Asp Leu Glu Gln
5060 5065 5070

Lys Val Ala Ser Leu Glu Leu Arg Ser Gln Arg Met Ser Arg Asp
5075 5080 5085

Ser Gly Ala Gln Val Asp Leu Leu Gln Arg Cys Thr Ala Gln Trp
5090 5095 5100

His Asp Tyr Gln Lys Ala Arg Glu Glu Val Ile Glu Leu Met Asn
5105 5110 5115

Asp Thr Glu Lys Lys Leu Ser Glu Phe Ser Leu Leu Lys Thr Ser
5120 5125 5130

Ser Ser His Glu Ala Glu Glu Lys Leu Ser Glu His Lys Ala Leu
5135 5140 5145

Val Ser Val Val Asn Ser Phe His Glu Lys Ile Val Ala Leu Glu
5150 5155 5160

Glu Lys Ala Ser Gln Leu Glu Lys Thr Gly Asn Asp Ala Ser Lys
5165 5170 5175

Ala Thr Leu Ser Arg Ser Met Thr Thr Val Trp Gln Arg Trp Thr
5180 5185 5190

Arg Leu Arg Ala Val Ala Gln Asp Gln Glu Lys Ile Leu Glu Asp
5195 5200 5205

Ala Val Asp Glu Trp Thr Gly Phe Asn Asn Lys Val Lys Lys Ala
5210 5215 5220

```
Thr Glu  Met Ile Asp Gln Leu  Gln Asp Lys Leu Pro  Gly Ser Ser
    5225                 5230                 5235

Ala Glu  Lys Ala Ser Lys Ala  Glu Leu Leu Thr Leu  Leu Glu Tyr
    5240                 5245                 5250

His Asp  Thr Phe Val Leu Glu  Leu Glu Gln Gln Gln  Ser Ala Leu
    5255                 5260                 5265

Gly Met  Leu Arg Gln Gln Thr  Leu Ser Met Leu Gln  Asp Gly Ala
    5270                 5275                 5280

Ala Pro  Thr Pro Gly Glu Glu  Pro Pro Leu Met Gln  Glu Ile Thr
    5285                 5290                 5295

Ala Met  Gln Asp Arg Cys Leu  Asn Met Gln Glu Lys  Val Lys Thr
    5300                 5305                 5310

Asn Gly  Lys Leu Val Lys Gln  Glu Leu Lys Asp Arg  Glu Met Val
    5315                 5320                 5325

Glu Thr  Gln Ile Asn Ser Val  Lys Cys Trp Val Gln  Glu Thr Lys
    5330                 5335                 5340

Glu Tyr  Leu Gly Asn Pro Thr  Ile Glu Ile Asp Ala  Gln Leu Glu
    5345                 5350                 5355

Glu Leu  Gln Ile Leu Leu Thr  Glu Ala Thr Asn His  Arg Gln Asn
    5360                 5365                 5370

Ile Glu  Lys Met Ala Glu Glu  Gln Lys Glu Lys Tyr  Leu Gly Leu
    5375                 5380                 5385

Tyr Thr  Ile Leu Pro Ser Glu  Leu Ser Leu Gln Leu  Ala Glu Val
    5390                 5395                 5400

Ala Leu  Asp Leu Lys Ile Arg  Asp Gln Ile Gln Asp  Lys Ile Lys
    5405                 5410                 5415

Glu Val  Glu Gln Ser Lys Ala  Thr Ser Gln Glu Leu  Ser Arg Gln
    5420                 5425                 5430

Ile Gln  Lys Leu Ala Lys Asp  Leu Thr Thr Ile Leu  Thr Lys Leu
    5435                 5440                 5445

Lys Ala  Lys Thr Asp Asn Val  Val Gln Ala Lys Thr  Asp Gln Lys
    5450                 5455                 5460

Val Leu  Gly Glu Glu Leu Asp  Gly Cys Asn Ser Lys  Leu Met Glu
    5465                 5470                 5475

Leu Asp  Ala Ala Val Gln Lys  Phe Leu Glu Gln Asn  Gly Gln Leu
    5480                 5485                 5490

Gly Lys  Pro Leu Ala Lys Lys  Ile Gly Lys Leu Thr  Glu Leu His
    5495                 5500                 5505

Gln Gln  Thr Ile Arg Gln Ala  Glu Asn Arg Leu Ser  Lys Leu Asn
    5510                 5515                 5520

Gln Ala  Ala Ser His Leu Glu  Glu Tyr Asn Glu Met  Leu Glu Leu
    5525                 5530                 5535

Ile Leu  Lys Trp Ile Glu Lys  Ala Lys Val Leu Ala  His Gly Thr
    5540                 5545                 5550

Ile Ala  Trp Asn Ser Ala Ser  Gln Leu Arg Glu Gln  Tyr Ile Leu
    5555                 5560                 5565

His Gln  Thr Leu Leu Glu Glu  Ser Lys Glu Ile Asp  Ser Glu Leu
    5570                 5575                 5580

Glu Ala  Met Thr Glu Lys Leu  Gln Tyr Leu Thr Ser  Val Tyr Cys
    5585                 5590                 5595

Thr Glu  Lys Met Ser Gln Gln  Val Ala Glu Leu Gly  Arg Glu Thr
    5600                 5605                 5610
```

```
Glu Glu  Leu Arg Gln Met Ile  Lys Ile Arg Leu Gln  Asn Leu Gln
    5615                 5620                 5625

Asp Ala  Ala Lys Asp Met Lys  Lys Phe Glu Ala Glu  Leu Lys Lys
    5630                 5635                 5640

Leu Gln  Ala Ala Leu Glu Gln  Ala Gln Ala Thr Leu  Thr Ser Pro
    5645                 5650                 5655

Glu Val  Gly Arg Leu Ser Leu  Lys Glu Gln Leu Ser  His Arg Gln
    5660                 5665                 5670

His Leu  Leu Ser Glu Met Glu  Ser Leu Lys Pro Lys  Val Gln Ala
    5675                 5680                 5685

Val Gln  Leu Cys Gln Ser Ala  Leu Arg Ile Pro Glu  Asp Val Val
    5690                 5695                 5700

Ala Ser  Leu Pro Leu Cys His  Ala Ala Leu Arg Leu  Gln Glu Glu
    5705                 5710                 5715

Ala Ser  Arg Leu Gln His Thr  Ala Ile Gln Gln Cys  Asn Ile Met
    5720                 5725                 5730

Gln Glu  Ala Val Val Gln Tyr  Glu Gln Tyr Glu Gln  Glu Met Lys
    5735                 5740                 5745

His Leu  Gln Gln Leu Ile Glu  Gly Ala His Arg Glu  Ile Glu Asp
    5750                 5755                 5760

Lys Pro  Val Ala Thr Ser Asn  Ile Gln Glu Leu Gln  Ala Gln Ile
    5765                 5770                 5775

Ser Arg  His Glu Glu Leu Ala  Gln Lys Ile Lys Gly  Tyr Gln Glu
    5780                 5785                 5790

Gln Ile  Ala Ser Leu Asn Ser  Lys Cys Lys Met Leu  Thr Met Lys
    5795                 5800                 5805

Ala Lys  His Ala Thr Met Leu  Leu Thr Val Thr Glu  Val Glu Gly
    5810                 5815                 5820

Leu Ala  Glu Gly Thr Glu Asp  Leu Asp Gly Glu Leu  Leu Pro Thr
    5825                 5830                 5835

Pro Ser  Ala His Pro Ser Val  Val Met Met Thr Ala  Gly Arg Cys
    5840                 5845                 5850

His Thr  Leu Leu Ser Pro Val  Thr Glu Glu Ser Gly  Glu Glu Gly
    5855                 5860                 5865

Thr Asn  Ser Glu Ile Ser Ser  Pro Pro Ala Cys Arg  Ser Pro Ser
    5870                 5875                 5880

Pro Val  Ala Asn Thr Asp Ala  Ser Val Asn Gln Asp  Ile Ala Tyr
    5885                 5890                 5895

Tyr Gln  Ala Leu Ser Ala Glu  Arg Leu Gln Thr Asp  Ala Ala Lys
    5900                 5905                 5910

Ile His  Pro Ser Thr Ser Ala  Ser Gln Glu Phe Tyr  Glu Pro Gly
    5915                 5920                 5925

Leu Glu  Pro Ser Ala Thr Ala  Lys Leu Gly Asp Leu  Gln Arg Ser
    5930                 5935                 5940

Trp Glu  Thr Leu Lys Asn Val  Ile Ser Glu Lys Gln  Arg Thr Leu
    5945                 5950                 5955

Tyr Glu  Ala Leu Glu Arg Gln  Gln Lys Tyr Gln Asp  Ser Leu Gln
    5960                 5965                 5970

Ser Ile  Ser Thr Lys Met Glu  Ala Ile Glu Leu Lys  Leu Ser Glu
    5975                 5980                 5985

Ser Pro  Glu Pro Gly Arg Ser  Pro Glu Ser Gln Met  Ala Glu His
    5990                 5995                 6000

Gln Ala  Leu Met Asp Glu Ile  Leu Met Leu Gln Asp  Glu Ile Asn
```

```
    6005                6010                6015

Glu Leu  Gln Ser Ser Leu Ala  Glu Glu Leu Val Ser  Glu Ser Cys
    6020                6025                6030

Glu Ala  Asp Pro Ala Glu Gln  Leu Ala Leu Gln Ser  Thr Leu Thr
    6035                6040                6045

Val Leu  Ala Glu Arg Met Ser  Thr Ile Arg Met Lys  Ala Ser Gly
    6050                6055                6060

Lys Arg  Gln Leu Leu Glu Glu  Lys Leu Asn Asp Gln  Leu Glu Glu
    6065                6070                6075

Gln Arg  Gln Glu Gln Ala Leu  Gln Arg Tyr Arg Cys  Glu Ala Asp
    6080                6085                6090

Glu Leu  Asp Ser Trp Leu Leu  Ser Thr Lys Ala Thr  Leu Asp Thr
    6095                6100                6105

Ala Leu  Ser Pro Pro Lys Glu  Pro Met Asp Met Glu  Ala Gln Leu
    6110                6115                6120

Met Asp  Cys Gln Asn Met Leu  Val Glu Ile Glu Gln  Lys Val Val
    6125                6130                6135

Ala Leu  Ser Glu Leu Ser Val  His Asn Glu Asn Leu  Leu Leu Glu
    6140                6145                6150

Gly Lys  Ala His Thr Lys Asp  Glu Ala Glu Gln Leu  Ala Gly Lys
    6155                6160                6165

Leu Arg  Arg Leu Lys Gly Ser  Leu Leu Glu Leu Gln  Arg Ala Leu
    6170                6175                6180

His Asp  Lys Gln Leu Asn Met  Gln Gly Thr Ala Gln  Glu Lys Glu
    6185                6190                6195

Glu Ser  Asp Val Asp Leu Thr  Ala Thr Gln Ser Pro  Gly Val Gln
    6200                6205                6210

Glu Trp  Leu Ala Gln Ala Arg  Thr Thr Trp Thr Gln  Gln Arg Gln
    6215                6220                6225

Ser Ser  Leu Gln Gln Gln Lys  Glu Leu Glu Gln Glu  Leu Ala Glu
    6230                6235                6240

Gln Lys  Ser Leu Leu Arg Ser  Val Ala Ser Arg Gly  Glu Glu Ile
    6245                6250                6255

Leu Ile  Gln His Ser Ala Ala  Glu Thr Ser Gly Asp  Ala Gly Glu
    6260                6265                6270

Lys Pro  Asp Val Leu Ser Gln  Glu Leu Gly Met Glu  Gly Glu Lys
    6275                6280                6285

Ser Ser  Ala Glu Asp Gln Met  Arg Met Lys Trp Glu  Ser Leu His
    6290                6295                6300

Gln Glu  Phe Ser Thr Lys Gln  Lys Leu Leu Gln Asn  Val Leu Glu
    6305                6310                6315

Gln Glu  Gln Glu Gln Val Leu  Tyr Ser Arg Pro Asn  Arg Leu Leu
    6320                6325                6330

Ser Gly  Val Pro Leu Tyr Lys  Gly Asp Val Pro Thr  Gln Asp Lys
    6335                6340                6345

Ser Ala  Val Thr Ser Leu Leu  Asp Gly Leu Asn Gln  Ala Phe Glu
    6350                6355                6360

Glu Val  Ser Ser Gln Ser Gly  Gly Ala Lys Arg Gln  Ser Ile His
    6365                6370                6375

Leu Glu  Gln Lys Leu Tyr Asp  Gly Val Ser Ala Thr  Ser Thr Trp
    6380                6385                6390

Leu Asp  Asp Val Glu Glu Arg  Leu Phe Val Ala Thr  Ala Leu Leu
    6395                6400                6405
```

```
Pro Glu Glu Thr Glu Thr Cys Leu Phe Asn Gln Glu Ile Leu Ala
    6410                6415                6420

Lys Asp Ile Lys Glu Met Ser Glu Glu Met Asp Lys Asn Lys Asn
    6425                6430                6435

Leu Phe Ser Gln Ala Phe Pro Glu Asn Gly Asp Asn Arg Asp Val
    6440                6445                6450

Ile Glu Asp Thr Leu Gly Cys Leu Leu Gly Arg Leu Ser Leu Leu
    6455                6460                6465

Asp Ser Val Val Asn Gln Arg Cys His Gln Met Lys Glu Arg Leu
    6470                6475                6480

Gln Gln Ile Leu Asn Phe Gln Asn Asp Leu Lys Val Leu Phe Thr
    6485                6490                6495

Ser Leu Ala Asp Asn Lys Tyr Ile Ile Leu Gln Lys Leu Ala Asn
    6500                6505                6510

Val Phe Glu Gln Pro Val Ala Glu Gln Ile Glu Ala Ile Gln Gln
    6515                6520                6525

Ala Glu Asp Gly Leu Lys Glu Phe Asp Ala Gly Ile Ile Glu Leu
    6530                6535                6540

Lys Arg Arg Gly Asp Lys Leu Gln Val Glu Gln Pro Ser Met Gln
    6545                6550                6555

Glu Leu Ser Lys Leu Gln Asp Met Tyr Asp Glu Leu Met Met Ile
    6560                6565                6570

Ile Gly Ser Arg Arg Ser Gly Leu Asn Gln Asn Leu Thr Leu Lys
    6575                6580                6585

Ser Gln Tyr Glu Arg Ala Leu Gln Asp Leu Ala Asp Leu Leu Glu
    6590                6595                6600

Thr Gly Gln Glu Lys Met Ala Gly Asp Gln Lys Ile Ile Val Ser
    6605                6610                6615

Ser Lys Glu Glu Ile Gln Gln Leu Leu Asp Lys His Lys Glu Tyr
    6620                6625                6630

Phe Gln Gly Leu Glu Ser His Met Ile Leu Thr Glu Thr Leu Phe
    6635                6640                6645

Arg Lys Ile Ile Ser Phe Ala Val Gln Lys Glu Thr Gln Phe His
    6650                6655                6660

Thr Glu Leu Met Ala Gln Ala Ser Ala Val Leu Lys Arg Ala His
    6665                6670                6675

Lys Arg Gly Val Glu Leu Glu Tyr Ile Leu Glu Thr Trp Ser His
    6680                6685                6690

Leu Asp Glu Asp Gln Gln Glu Leu Ser Arg Gln Leu Glu Val Val
    6695                6700                6705

Glu Ser Ser Ile Pro Ser Val Gly Leu Val Glu Glu Asn Glu Asp
    6710                6715                6720

Arg Leu Ile Asp Arg Ile Thr Leu Tyr Gln His Leu Lys Ser Ser
    6725                6730                6735

Leu Asn Glu Tyr Gln Pro Lys Leu Tyr Gln Val Leu Asp Asp Gly
    6740                6745                6750

Lys Arg Leu Leu Ile Ser Ile Ser Cys Ser Asp Leu Glu Ser Gln
    6755                6760                6765

Leu Asn Gln Leu Gly Glu Cys Trp Leu Ser Asn Thr Asn Lys Met
    6770                6775                6780

Ser Lys Glu Leu His Arg Leu Glu Thr Ile Leu Lys His Trp Thr
    6785                6790                6795
```

Arg Tyr Gln Ser Glu Ser Ala Asp Leu Ile His Trp Leu Gln Ser
6800 6805 6810

Ala Lys Asp Arg Leu Glu Phe Trp Thr Gln Gln Ser Val Thr Val
6815 6820 6825

Pro Gln Glu Leu Glu Met Val Arg Asp His Leu Asn Ala Phe Leu
6830 6835 6840

Glu Phe Ser Lys Glu Val Asp Ala Gln Ser Ser Leu Lys Ser Ser
6845 6850 6855

Val Leu Ser Thr Gly Asn Gln Leu Leu Arg Leu Lys Lys Val Asp
6860 6865 6870

Thr Ala Thr Leu Arg Ser Glu Leu Ser Arg Ile Asp Ser Gln Trp
6875 6880 6885

Thr Asp Leu Leu Thr Asn Ile Pro Ala Val Gln Glu Lys Leu His
6890 6895 6900

Gln Leu Gln Met Asp Lys Leu Pro Ser Arg His Ala Ile Ser Glu
6905 6910 6915

Val Met Ser Trp Ile Ser Leu Met Glu Asn Val Ile Gln Lys Asp
6920 6925 6930

Glu Asp Asn Ile Lys Asn Ser Ile Gly Tyr Lys Ala Ile His Glu
6935 6940 6945

Tyr Leu Gln Lys Tyr Lys Gly Phe Lys Ile Asp Ile Asn Cys Lys
6950 6955 6960

Gln Leu Thr Val Asp Phe Val Asn Gln Ser Val Leu Gln Ile Ser
6965 6970 6975

Ser Gln Asp Val Glu Ser Lys Arg Ser Asp Lys Thr Asp Phe Ala
6980 6985 6990

Glu Gln Leu Gly Ala Met Asn Lys Ser Trp Gln Ile Leu Gln Gly
6995 7000 7005

Leu Val Thr Glu Lys Ile Gln Leu Leu Glu Gly Leu Leu Glu Ser
7010 7015 7020

Trp Ser Glu Tyr Glu Asn Asn Val Gln Cys Leu Lys Thr Trp Phe
7025 7030 7035

Glu Thr Gln Glu Lys Arg Leu Lys Gln Gln His Arg Ile Gly Asp
7040 7045 7050

Gln Ala Ser Val Gln Asn Ala Leu Lys Asp Cys Gln Asp Leu Glu
7055 7060 7065

Asp Leu Ile Lys Ala Lys Glu Lys Glu Val Glu Lys Ile Glu Gln
7070 7075 7080

Asn Gly Leu Ala Leu Ile Gln Asn Lys Lys Glu Asp Val Ser Ser
7085 7090 7095

Ile Val Met Ser Thr Leu Arg Glu Leu Gly Gln Thr Trp Ala Asn
7100 7105 7110

Leu Asp His Met Val Gly Gln Leu Lys Ile Leu Leu Lys Ser Val
7115 7120 7125

Leu Asp Gln Trp Ser Ser His Lys Val Ala Phe Asp Lys Ile Asn
7130 7135 7140

Ser Tyr Leu Met Glu Ala Arg Tyr Ser Leu Ser Arg Phe Arg Leu
7145 7150 7155

Leu Thr Gly Ser Leu Glu Ala Val Gln Val Gln Val Asp Asn Leu
7160 7165 7170

Gln Asn Leu Gln Asp Asp Leu Glu Lys Gln Glu Arg Ser Leu Gln
7175 7180 7185

Lys Phe Gly Ser Ile Thr Asn Gln Leu Leu Lys Glu Cys His Pro

```
    7190                7195                7200

Pro Val  Thr Glu Thr Leu Thr  Asn Thr Leu Lys Glu  Val Asn Met
    7205                7210                7215

Arg Trp  Asn Asn Leu Leu Glu  Glu Ile Ala Glu Gln  Leu Gln Ser
    7220                7225                7230

Ser Lys  Ala Leu Leu Gln Leu  Trp Gln Arg Tyr Lys  Asp Tyr Ser
    7235                7240                7245

Lys Gln  Cys Ala Ser Thr Val  Gln Gln Gln Glu Asp  Arg Thr Asn
    7250                7255                7260

Glu Leu  Leu Lys Ala Ala Thr  Asn Lys Asp Ile Ala  Asp Asp Glu
    7265                7270                7275

Val Ala  Thr Trp Ile Gln Asp  Cys Asn Asp Leu Leu  Lys Gly Leu
    7280                7285                7290

Gly Thr  Val Lys Asp Ser Leu  Phe Phe Leu His Glu  Leu Gly Glu
    7295                7300                7305

Gln Leu  Lys Gln Gln Val Asp  Ala Ser Ala Ala Ser  Ala Ile Gln
    7310                7315                7320

Ser Asp  Gln Leu Ser Leu Ser  Gln His Leu Cys Ala  Leu Glu Gln
    7325                7330                7335

Ala Leu  Cys Lys Gln Gln Thr  Ser Leu Gln Ala Gly  Val Leu Asp
    7340                7345                7350

Tyr Glu  Thr Phe Ala Lys Ser  Leu Glu Ala Leu Glu  Ala Trp Ile
    7355                7360                7365

Val Glu  Ala Glu Glu Ile Leu  Gln Gly Gln Asp Pro  Ser His Ser
    7370                7375                7380

Ser Asp  Leu Ser Thr Ile Gln  Glu Arg Met Glu Glu  Leu Lys Gly
    7385                7390                7395

Gln Met  Leu Lys Phe Ser Ser  Met Ala Pro Asp Leu  Asp Arg Leu
    7400                7405                7410

Asn Glu  Leu Gly Tyr Arg Leu  Pro Leu Asn Asp Lys  Glu Ile Lys
    7415                7420                7425

Arg Met  Gln Asn Leu Asn Arg  His Trp Ser Leu Ile  Ser Ser Gln
    7430                7435                7440

Thr Thr  Glu Arg Phe Ser Lys  Leu Gln Ser Phe Leu  Leu Gln His
    7445                7450                7455

Gln Thr  Phe Leu Glu Lys Cys  Glu Thr Trp Met Glu  Phe Leu Val
    7460                7465                7470

Gln Thr  Glu Gln Lys Leu Ala  Val Glu Ile Ser Gly  Asn Tyr Gln
    7475                7480                7485

His Leu  Leu Glu Gln Gln Arg  Ala His Glu Leu Phe  Gln Ala Glu
    7490                7495                7500

Met Phe  Ser Arg Gln Gln Ile  Leu His Ser Ile Ile  Ile Asp Gly
    7505                7510                7515

Gln Arg  Leu Leu Glu Gln Gly  Gln Val Asp Asp Arg  Asp Glu Phe
    7520                7525                7530

Asn Leu  Lys Leu Thr Leu Leu  Ser Asn Gln Trp Gln  Gly Val Ile
    7535                7540                7545

Arg Arg  Ala Gln Gln Arg Arg  Gly Ile Ile Asp Ser  Gln Ile Arg
    7550                7555                7560

Gln Trp  Gln Arg Tyr Arg Glu  Met Ala Glu Lys Leu  Arg Lys Trp
    7565                7570                7575

Leu Val  Glu Val Ser Tyr Leu  Pro Met Ser Gly Leu  Gly Ser Val
    7580                7585                7590
```

Pro Ile Pro Leu Gln Gln Ala Arg Thr Leu Phe Asp Glu Val Gln
7595 7600 7605

Phe Lys Glu Lys Val Phe Leu Arg Gln Gln Gly Ser Tyr Ile Leu
7610 7615 7620

Thr Val Glu Ala Gly Lys Gln Leu Leu Leu Ser Ala Asp Ser Gly
7625 7630 7635

Ala Glu Ala Ala Leu Gln Ala Glu Leu Ala Glu Ile Gln Glu Lys
7640 7645 7650

Trp Lys Ser Ala Ser Met Arg Leu Glu Glu Gln Lys Lys Lys Leu
7655 7660 7665

Ala Phe Leu Leu Lys Asp Trp Glu Lys Cys Glu Lys Gly Ile Ala
7670 7675 7680

Asp Ser Leu Glu Lys Leu Arg Thr Phe Lys Lys Lys Leu Ser Gln
7685 7690 7695

Ser Leu Pro Asp His His Glu Glu Leu His Ala Glu Gln Met Arg
7700 7705 7710

Cys Lys Glu Leu Glu Asn Ala Val Gly Ser Trp Thr Asp Asp Leu
7715 7720 7725

Thr Gln Leu Ser Leu Leu Lys Asp Thr Leu Ser Ala Tyr Ile Ser
7730 7735 7740

Ala Asp Asp Ile Ser Ile Leu Asn Glu Arg Val Glu Leu Leu Gln
7745 7750 7755

Arg Gln Trp Glu Glu Leu Cys His Gln Leu Ser Leu Arg Arg Gln
7760 7765 7770

Gln Ile Gly Glu Arg Leu Asn Glu Trp Ala Val Phe Ser Glu Lys
7775 7780 7785

Asn Lys Glu Leu Cys Glu Trp Leu Thr Gln Met Glu Ser Lys Val
7790 7795 7800

Ser Gln Asn Gly Asp Ile Leu Ile Glu Glu Met Ile Glu Lys Leu
7805 7810 7815

Lys Lys Asp Tyr Gln Glu Glu Ile Ala Ile Ala Gln Glu Asn Lys
7820 7825 7830

Ile Gln Leu Gln Gln Met Gly Glu Arg Leu Ala Lys Ala Ser His
7835 7840 7845

Glu Ser Lys Ala Ser Glu Ile Glu Tyr Lys Leu Gly Lys Val Asn
7850 7855 7860

Asp Arg Trp Gln His Leu Leu Asp Leu Ile Ala Ala Arg Val Lys
7865 7870 7875

Lys Leu Lys Glu Thr Leu Val Ala Val Gln Gln Leu Asp Lys Asn
7880 7885 7890

Met Ser Ser Leu Arg Thr Trp Leu Ala His Ile Glu Ser Glu Leu
7895 7900 7905

Ala Lys Pro Ile Val Tyr Asp Ser Cys Asn Ser Glu Glu Ile Gln
7910 7915 7920

Arg Lys Leu Asn Glu Gln Gln Glu Leu Gln Arg Asp Ile Glu Lys
7925 7930 7935

His Ser Thr Gly Val Ala Ser Val Leu Asn Leu Cys Glu Val Leu
7940 7945 7950

Leu His Asp Cys Asp Ala Cys Ala Thr Asp Ala Glu Cys Asp Ser
7955 7960 7965

Ile Gln Gln Ala Thr Arg Asn Leu Asp Arg Arg Trp Arg Asn Ile
7970 7975 7980

```
Cys Ala  Met Ser Met Glu Arg  Arg Leu Lys Ile Glu  Glu Thr Trp
    7985                 7990                 7995

Arg Leu  Trp Gln Lys Phe Leu  Asp Asp Tyr Ser Arg  Phe Glu Asp
    8000                 8005                 8010

Trp Leu  Lys Ser Ser Glu Arg  Thr Ala Ala Phe Pro  Ser Ser Ser
    8015                 8020                 8025

Gly Val  Ile Tyr Thr Val Ala  Lys Glu Glu Leu Lys  Lys Phe Glu
    8030                 8035                 8040

Ala Phe  Gln Arg Gln Val His  Glu Cys Leu Thr Gln  Leu Glu Leu
    8045                 8050                 8055

Ile Asn  Lys Gln Tyr Arg Arg  Leu Ala Arg Glu Asn  Arg Thr Asp
    8060                 8065                 8070

Ser Ala  Cys Ser Leu Lys Gln  Met Val His Glu Gly  Asn Gln Arg
    8075                 8080                 8085

Trp Asp  Asn Leu Gln Lys Arg  Val Thr Ser Ile Leu  Arg Arg Leu
    8090                 8095                 8100

Lys His  Phe Ile Gly Gln Arg  Glu Glu Phe Glu Thr  Ala Arg Asp
    8105                 8110                 8115

Ser Ile  Leu Val Trp Leu Thr  Glu Met Asp Leu Gln  Leu Thr Asn
    8120                 8125                 8130

Ile Glu  His Phe Ser Glu Cys  Asp Val Gln Ala Lys  Ile Lys Gln
    8135                 8140                 8145

Leu Lys  Ala Phe Gln Gln Glu  Ile Ser Leu Asn His  Asn Lys Ile
    8150                 8155                 8160

Glu Gln  Ile Ile Ala Gln Gly  Glu Gln Leu Ile Glu  Lys Ser Glu
    8165                 8170                 8175

Pro Leu  Asp Ala Ala Ile Ile  Glu Glu Glu Leu Asp  Glu Leu Arg
    8180                 8185                 8190

Arg Tyr  Cys Gln Glu Val Phe  Gly Arg Val Glu Arg  Tyr His Lys
    8195                 8200                 8205

Lys Leu  Ile Arg Leu Pro Leu  Pro Asp Asp Glu His  Asp Leu Ser
    8210                 8215                 8220

Asp Arg  Glu Leu Glu Leu Glu  Asp Ser Ala Ala Leu  Ser Asp Leu
    8225                 8230                 8235

His Trp  His Asp Arg Ser Ala  Asp Ser Leu Leu Ser  Pro Gln Pro
    8240                 8245                 8250

Ser Ser  Asn Leu Ser Leu Ser  Leu Ala Gln Pro Leu  Arg Ser Glu
    8255                 8260                 8265

Arg Ser  Gly Arg Asp Thr Pro  Ala Ser Val Asp Ser  Ile Pro Leu
    8270                 8275                 8280

Glu Trp  Asp His Asp Tyr Asp  Leu Ser Arg Asp Leu  Glu Ser Ala
    8285                 8290                 8295

Met Ser  Arg Ala Leu Pro Ser  Glu Asp Glu Glu Gly  Gln Asp Asp
    8300                 8305                 8310

Lys Asp  Phe Tyr Leu Arg Gly  Ala Val Gly Leu Ser  Gly Asp His
    8315                 8320                 8325

Ser Ala  Leu Glu Ser Gln Ile  Arg Gln Leu Gly Lys  Ala Leu Asp
    8330                 8335                 8340

Asp Ser  Arg Phe Gln Ile Gln  Gln Thr Glu Asn Ile  Ile Arg Ser
    8345                 8350                 8355

Lys Thr  Pro Thr Gly Pro Glu  Leu Asp Thr Ser Tyr  Lys Gly Tyr
    8360                 8365                 8370

Met Lys  Leu Leu Gly Glu Cys  Ser Ser Ser Ile Asp  Ser Val Lys
```

```
    8375                8380                8385

Arg Leu  Glu His Lys Leu Lys  Glu Glu Glu Glu Ser  Leu Pro Gly
    8390                8395                8400

Phe Val  Asn Leu His Ser Thr  Glu Thr Gln Thr Ala  Gly Val Ile
    8405                8410                8415

Asp Arg  Trp Glu Leu Leu Gln  Ala Gln Ala Leu Ser  Lys Glu Leu
    8420                8425                8430

Arg Met  Lys Gln Asn Leu Gln  Lys Trp Gln Gln Phe  Asn Ser Asp
    8435                8440                8445

Leu Asn  Ser Ile Trp Ala Trp  Leu Gly Asp Thr Glu  Glu Glu Leu
    8450                8455                8460

Glu Gln  Leu Gln Arg Leu Glu  Leu Ser Thr Asp Ile  Gln Thr Ile
    8465                8470                8475

Glu Leu  Gln Ile Lys Lys Leu  Lys Glu Leu Gln Lys  Ala Val Asp
    8480                8485                8490

His Arg  Lys Ala Ile Ile Leu  Ser Ile Asn Leu Cys  Ser Pro Glu
    8495                8500                8505

Phe Thr  Gln Ala Asp Ser Lys  Glu Ser Arg Asp Leu  Gln Asp Arg
    8510                8515                8520

Leu Ser  Gln Met Asn Gly Arg  Trp Asp Arg Val Cys  Ser Leu Leu
    8525                8530                8535

Glu Glu  Trp Arg Gly Leu Leu  Gln Asp Ala Leu Met  Gln Cys Gln
    8540                8545                8550

Gly Phe  His Glu Met Ser His  Gly Leu Leu Leu Met  Leu Glu Asn
    8555                8560                8565

Ile Asp  Arg Arg Lys Asn Glu  Ile Val Pro Ile Asp  Ser Asn Leu
    8570                8575                8580

Asp Ala  Glu Ile Leu Gln Asp  His His Lys Gln Leu  Met Gln Ile
    8585                8590                8595

Lys His  Glu Leu Leu Glu Ser  Gln Leu Arg Val Ala  Ser Leu Gln
    8600                8605                8610

Asp Met  Ser Cys Gln Leu Leu  Val Asn Ala Glu Gly  Thr Asp Cys
    8615                8620                8625

Leu Glu  Ala Lys Glu Lys Val  His Val Ile Gly Asn  Arg Leu Lys
    8630                8635                8640

Leu Leu  Leu Lys Glu Val Ser  Arg His Ile Lys Glu  Leu Glu Lys
    8645                8650                8655

Leu Leu  Asp Val Ser Ser Ser  Gln Gln Asp Leu Ser  Ser Trp Ser
    8660                8665                8670

Ser Ala  Asp Glu Leu Asp Thr  Ser Gly Ser Val Ser  Pro Thr Ser
    8675                8680                8685

Gly Arg  Ser Thr Pro Asn Arg  Gln Lys Thr Pro Arg  Gly Lys Cys
    8690                8695                8700

Ser Leu  Ser Gln Pro Gly Pro  Ser Val Ser Ser Pro  His Ser Arg
    8705                8710                8715

Ser Thr  Lys Gly Gly Ser Asp  Ser Ser Leu Ser Glu  Pro Gly Pro
    8720                8725                8730

Gly Arg  Ser Gly Arg Gly Phe  Leu Phe Arg Val Leu  Arg Ala Ala
    8735                8740                8745

Leu Pro  Leu Gln Leu Leu Leu  Leu Leu Leu Ile Gly  Leu Ala Cys
    8750                8755                8760

Leu Val  Pro Met Ser Glu Glu  Asp Tyr Ser Cys Ala  Leu Ser Asn
    8765                8770                8775
```

```
Asn Phe  Ala Arg Ser Phe His  Pro Met Leu Arg Tyr  Thr Asn Gly
    8780                 8785                 8790

Pro Pro  Pro Leu
    8795


<210> SEQ ID NO 23
<211> LENGTH: 431
<212> TYPE: PRT
<213> ORGANISM: Homo sapiens

<400> SEQUENCE: 23

Met Arg Arg Leu Arg Arg Leu Ala His Leu Val Leu Phe Cys Pro Phe
1               5                   10                  15

Ser Lys Arg Leu Gln Gly Arg Leu Pro Gly Leu Arg Val Arg Cys Ile
            20                  25                  30

Phe Leu Ala Trp Leu Gly Val Phe Ala Gly Ser Trp Leu Val Tyr Val
        35                  40                  45

His Tyr Ser Ser Tyr Ser Glu Arg Cys Arg Gly His Val Cys Gln Val
    50                  55                  60

Val Ile Cys Asp Gln Tyr Arg Lys Gly Ile Ile Ser Gly Ser Val Cys
65                  70                  75                  80

Gln Asp Leu Cys Glu Leu His Met Val Glu Trp Arg Thr Cys Leu Ser
                85                  90                  95

Val Ala Pro Gly Gln Gln Val Tyr Ser Gly Leu Trp Arg Asp Lys Asp
            100                 105                 110

Val Thr Ile Lys Cys Gly Ile Glu Glu Thr Leu Asp Ser Lys Ala Arg
        115                 120                 125

Ser Asp Ala Ala Pro Arg Arg Glu Leu Val Leu Phe Asp Lys Pro Thr
    130                 135                 140

Arg Gly Thr Ser Ile Lys Glu Phe Arg Glu Met Thr Leu Ser Phe Leu
145                 150                 155                 160

Lys Ala Asn Leu Gly Asp Leu Pro Ser Leu Pro Ala Leu Val Gly Gln
                165                 170                 175

Val Leu Leu Met Ala Asp Phe Asn Lys Asp Asn Arg Val Ser Leu Ala
            180                 185                 190

Glu Ala Lys Ser Val Trp Ala Leu Leu Gln Arg Asn Glu Phe Leu Leu
        195                 200                 205

Leu Leu Ser Leu Gln Glu Lys Glu His Ala Ser Arg Leu Leu Gly Tyr
    210                 215                 220

Cys Gly Asp Leu Tyr Leu Thr Glu Gly Val Pro His Gly Ala Trp His
225                 230                 235                 240

Ala Ala Ala Leu Pro Pro Leu Leu Arg Pro Leu Leu Pro Pro Ala Leu
                245                 250                 255

Gln Gly Ala Leu Gln Gln Trp Leu Gly Pro Ala Trp Pro Trp Arg Ala
            260                 265                 270

Lys Ile Ala Ile Gly Leu Leu Glu Phe Val Glu Glu Leu Phe His Gly
        275                 280                 285

Ser Tyr Gly Thr Phe Tyr Met Cys Glu Thr Thr Leu Ala Asn Val Gly
    290                 295                 300

Tyr Thr Ala Thr Tyr Asp Phe Lys Met Ala Asp Leu Gln Gln Val Ala
305                 310                 315                 320

Pro Glu Ala Thr Val Arg Arg Phe Leu Gln Gly Arg Arg Cys Glu His
                325                 330                 335

Ser Thr Asp Cys Thr Tyr Gly Arg Asp Cys Arg Ala Pro Cys Asp Arg
```

```
            340                 345                 350

Leu Met Arg Gln Cys Lys Gly Asp Leu Ile Gln Pro Asn Leu Ala Lys
        355                 360                 365

Val Cys Ala Leu Leu Arg Gly Tyr Leu Leu Pro Gly Ala Pro Ala Asp
    370                 375                 380

Leu Arg Glu Glu Leu Gly Thr Gln Leu Arg Thr Cys Thr Thr Leu Ser
385                 390                 395                 400

Gly Leu Ala Ser Gln Val Glu Ala His His Ser Leu Val Leu Ser His
                405                 410                 415

Leu Lys Thr Leu Leu Trp Lys Lys Ile Ser Asn Thr Lys Tyr Ser
            420                 425                 430


<210> SEQ ID NO 24
<211> LENGTH: 441
<212> TYPE: PRT
<213> ORGANISM: Homo sapiens

<400> SEQUENCE: 24

Met Gly Gly Pro Arg Ala Trp Ala Leu Leu Cys Leu Gly Leu Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
    50                  55                  60

Pro Met Ser Cys Pro Gly Ser Ser Tyr Arg Thr Val Val Arg Pro Thr
65                  70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Ala Ser Ser Ala Ser Leu
            100                 105                 110

Glu Pro Met Trp Ser Gly Ser Thr Met Arg Arg Met Ala Leu Arg Pro
        115                 120                 125

Thr Ala Phe Ser Gly Cys Leu Asn Cys Ser Lys Val Ser Glu Leu Thr
    130                 135                 140

Glu Arg Leu Lys Val Leu Glu Ala Lys Met Thr Met Leu Thr Val Ile
145                 150                 155                 160

Glu Gln Pro Val Pro Pro Thr Pro Ala Thr Pro Glu Asp Pro Ala Pro
                165                 170                 175

Leu Trp Gly Pro Pro Pro Ala Gln Gly Ser Pro Gly Asp Gly Gly Leu
            180                 185                 190

Gln Asp Gln Val Gly Ala Trp Gly Leu Pro Gly Pro Thr Gly Pro Lys
        195                 200                 205

Gly Asp Ala Gly Ser Arg Gly Pro Met Gly Met Arg Gly Pro Pro Gly
    210                 215                 220

Pro Gln Gly Pro Pro Gly Ser Pro Gly Arg Ala Gly Ala Val Gly Thr
225                 230                 235                 240

Pro Gly Glu Arg Gly Pro Pro Gly Pro Pro Gly Pro Pro Gly Pro Pro
                245                 250                 255

Gly Pro Pro Ala Pro Val Gly Pro Pro His Ala Arg Ile Ser Gln His
            260                 265                 270

Gly Asp Pro Leu Leu Ser Asn Thr Phe Thr Glu Thr Asn Asn His Trp
        275                 280                 285
```

-continued

```
Pro Gln Gly Pro Thr Gly Pro Pro Gly Pro Pro Gly Pro Met Gly Pro
    290                 295                 300

Pro Gly Pro Pro Gly Pro Thr Gly Val Pro Gly Ser Pro Gly His Ile
305                 310                 315                 320

Gly Pro Pro Gly Pro Thr Gly Pro Lys Gly Ile Ser Gly His Pro Gly
                325                 330                 335

Glu Lys Gly Glu Arg Gly Leu Arg Gly Glu Pro Gly Pro Gln Gly Ser
            340                 345                 350

Ala Gly Gln Arg Gly Glu Pro Gly Pro Lys Gly Asp Pro Gly Glu Lys
        355                 360                 365

Ser His Trp Gly Glu Gly Leu His Gln Leu Arg Glu Ala Leu Lys Ile
    370                 375                 380

Leu Ala Glu Arg Val Leu Ile Leu Glu Thr Met Ile Gly Leu Tyr Glu
385                 390                 395                 400

Pro Glu Leu Gly Ser Gly Ala Gly Pro Ala Gly Thr Gly Thr Pro Ser
                405                 410                 415

Leu Leu Arg Gly Lys Arg Gly Gly His Ala Thr Asn Tyr Arg Ile Val
            420                 425                 430

Ala Pro Arg Ser Arg Asp Glu Arg Gly
        435                 440


<210> SEQ ID NO 25
<211> LENGTH: 409
<212> TYPE: PRT
<213> ORGANISM: Homo sapiens

<400> SEQUENCE: 25

Met Glu Glu Ser Trp Glu Ala Ala Pro Gly Gly Gln Ala Gly Ala Glu
1               5                   10                  15

Leu Pro Met Glu Pro Val Gly Ser Leu Val Pro Thr Leu Glu Gln Pro
            20                  25                  30

Gln Val Pro Ala Lys Val Arg Gln Pro Glu Gly Pro Glu Ser Ser Pro
        35                  40                  45

Ser Pro Ala Gly Ala Val Glu Lys Ala Ala Gly Ala Gly Leu Glu Pro
    50                  55                  60

Ser Ser Lys Lys Lys Pro Pro Ser Pro Arg Pro Gly Ser Pro Arg Val
65                  70                  75                  80

Pro Pro Leu Ser Leu Gly Tyr Gly Val Cys Pro Glu Pro Pro Ser Pro
                85                  90                  95

Gly Pro Ala Leu Val Lys Leu Pro Arg Asn Gly Glu Ala Pro Gly Ala
            100                 105                 110

Glu Pro Ala Pro Ser Ala Trp Ala Pro Met Glu Leu Gln Val Asp Val
        115                 120                 125

Arg Val Lys Pro Val Gly Ala Ala Gly Gly Ser Ser Thr Pro Ser Pro
    130                 135                 140

Arg Pro Ser Thr Arg Phe Leu Lys Val Pro Val Pro Glu Ser Pro Ala
145                 150                 155                 160

Phe Ser Arg His Ala Asp Pro Ala His Gln Leu Leu Leu Arg Ala Pro
                165                 170                 175

Ser Gln Gly Gly Thr Trp Gly Arg Arg Ser Pro Leu Ala Ala Ala Arg
            180                 185                 190

Thr Glu Ser Gly Cys Asp Ala Glu Gly Arg Ala Ser Pro Ala Glu Gly
        195                 200                 205

Ser Ala Gly Ser Pro Gly Ser Pro Thr Cys Cys Arg Cys Lys Glu Leu
    210                 215                 220
```

```
Gly Leu Glu Lys Glu Asp Ala Ala Leu Leu Pro Arg Ala Gly Leu Asp
225                 230                 235                 240

Gly Asp Glu Lys Leu Pro Arg Ala Val Thr Leu Thr Gly Leu Pro Met
                245                 250                 255

Tyr Val Lys Ser Leu Tyr Trp Ala Leu Ala Phe Met Ala Val Leu Leu
            260                 265                 270

Ala Val Ser Gly Val Val Ile Val Val Leu Ala Ser Arg Ala Gly Ala
        275                 280                 285

Arg Cys Gln Gln Cys Pro Pro Gly Trp Val Leu Ser Glu Glu His Cys
    290                 295                 300

Tyr Tyr Phe Ser Ala Glu Ala Gln Ala Trp Glu Ala Ser Gln Ala Phe
305                 310                 315                 320

Cys Ser Ala Tyr His Ala Thr Leu Pro Leu Leu Ser His Thr Gln Asp
                325                 330                 335

Phe Leu Gly Arg Tyr Pro Val Ser Arg His Ser Trp Val Gly Ala Trp
            340                 345                 350

Arg Gly Pro Gln Gly Trp His Trp Ile Asp Glu Ala Pro Leu Pro Pro
        355                 360                 365

Gln Leu Leu Pro Glu Asp Gly Glu Asp Asn Leu Asp Ile Asn Cys Gly
    370                 375                 380

Ala Leu Glu Glu Gly Thr Leu Val Ala Ala Asn Cys Ser Thr Pro Arg
385                 390                 395                 400

Pro Trp Val Cys Ala Lys Gly Thr Gln
                405


<210> SEQ ID NO 26
<211> LENGTH: 904
<212> TYPE: PRT
<213> ORGANISM: Homo sapiens

<400> SEQUENCE: 26

Met Glu Trp Gly Ser Glu Ser Ala Ala Val Arg Arg His Arg Val Gly
1               5                   10                  15

Val Glu Arg Arg Glu Gly Ala Ala Ala Ala Pro Pro Pro Glu Arg Glu
            20                  25                  30

Ala Arg Ala Gln Glu Pro Leu Val Asp Gly Cys Ser Gly Gly Gly Arg
        35                  40                  45

Thr Arg Lys Arg Ser Pro Gly Gly Ser Gly Gly Ala Ser Arg Gly Ala
    50                  55                  60

Gly Thr Gly Leu Ser Glu Val Arg Ala Ala Leu Gly Leu Ala Leu Tyr
65                  70                  75                  80

Leu Ile Ala Leu Arg Thr Leu Val Gln Leu Ser Leu Gln Gln Leu Val
                85                  90                  95

Leu Arg Gly Ala Ala Gly His Arg Gly Glu Phe Asp Ala Leu Gln Ala
            100                 105                 110

Arg Asp Tyr Leu Glu His Ile Thr Ser Ile Gly Pro Arg Thr Thr Gly
        115                 120                 125

Ser Pro Glu Asn Glu Ile Leu Thr Val His Tyr Leu Leu Glu Gln Ile
    130                 135                 140

Lys Leu Ile Glu Val Gln Ser Asn Ser Leu His Lys Ile Ser Val Asp
145                 150                 155                 160

Val Gln Arg Pro Thr Gly Ser Phe Ser Ile Asp Phe Leu Gly Gly Phe
                165                 170                 175

Thr Ser Tyr Tyr Asp Asn Ile Thr Asn Val Val Val Lys Leu Glu Pro
```

```
            180                 185                 190

Arg Asp Gly Ala Gln His Ala Val Leu Ala Asn Cys His Phe Asp Ser
        195                 200                 205

Val Ala Asn Ser Pro Gly Ala Ser Asp Asp Ala Val Ser Cys Ser Val
    210                 215                 220

Met Leu Glu Val Leu Arg Val Leu Ser Thr Ser Ser Glu Ala Leu His
225                 230                 235                 240

His Ala Val Ile Phe Leu Phe Asn Gly Ala Glu Glu Asn Val Leu Gln
                245                 250                 255

Ala Ser His Gly Phe Ile Thr Gln His Pro Trp Ala Ser Leu Ile Arg
            260                 265                 270

Ala Phe Ile Asn Leu Glu Ala Ala Gly Val Gly Gly Lys Glu Leu Val
        275                 280                 285

Phe Gln Thr Gly Pro Glu Asn Pro Trp Leu Val Gln Ala Tyr Val Ser
    290                 295                 300

Ala Ala Lys His Pro Phe Ala Ser Val Val Ala Gln Glu Val Phe Gln
305                 310                 315                 320

Ser Gly Ile Ile Pro Ser Asp Thr Asp Phe Arg Ile Tyr Arg Asp Phe
                325                 330                 335

Gly Asn Ile Pro Gly Ile Asp Leu Ala Phe Ile Glu Asn Gly Tyr Ile
            340                 345                 350

Tyr His Thr Lys Tyr Asp Thr Ala Asp Arg Ile Leu Thr Asp Ser Ile
        355                 360                 365

Gln Arg Ala Gly Asp Asn Ile Leu Ala Val Leu Lys His Leu Ala Thr
    370                 375                 380

Ser Asp Met Leu Ala Ala Ala Ser Lys Tyr Arg His Gly Asn Met Val
385                 390                 395                 400

Phe Phe Asp Val Leu Gly Leu Phe Val Ile Ala Tyr Pro Ser Arg Ile
                405                 410                 415

Gly Ser Ile Ile Asn Tyr Met Val Val Met Gly Val Val Leu Tyr Leu
            420                 425                 430

Gly Lys Lys Phe Leu Gln Pro Lys His Lys Thr Gly Asn Tyr Lys Lys
        435                 440                 445

Asp Phe Leu Cys Gly Leu Gly Ile Thr Leu Ile Ser Trp Phe Thr Ser
    450                 455                 460

Leu Val Thr Val Leu Ile Ile Ala Val Phe Ile Ser Leu Ile Gly Gln
465                 470                 475                 480

Ser Leu Ser Trp Tyr Asn His Phe Tyr Val Ser Val Cys Leu Tyr Gly
                485                 490                 495

Thr Ala Thr Val Ala Lys Ile Ile Leu Ile His Thr Leu Ala Lys Arg
            500                 505                 510

Phe Tyr Tyr Met Asn Ala Ser Ala Gln Tyr Leu Gly Glu Val Phe Phe
        515                 520                 525

Asp Ile Ser Leu Phe Val His Cys Cys Phe Leu Val Thr Leu Thr Tyr
    530                 535                 540

Gln Gly Leu Cys Ser Ala Phe Ile Ser Ala Val Trp Val Ala Phe Pro
545                 550                 555                 560

Leu Leu Thr Lys Leu Cys Val His Lys Asp Phe Lys Gln His Gly Ala
                565                 570                 575

Gln Gly Lys Phe Ile Ala Phe Tyr Leu Leu Gly Met Phe Ile Pro Tyr
            580                 585                 590

Leu Tyr Ala Leu Tyr Leu Ile Trp Ala Val Phe Glu Met Phe Thr Pro
        595                 600                 605
```

```
Ile Leu Gly Arg Ser Gly Ser Glu Ile Pro Pro Asp Val Val Leu Ala
    610                 615                 620

Ser Ile Leu Ala Gly Cys Thr Met Ile Leu Ser Ser Tyr Phe Ile Asn
625                 630                 635                 640

Phe Ile Tyr Leu Ala Lys Ser Thr Lys Lys Thr Met Leu Thr Leu Thr
                645                 650                 655

Leu Val Cys Ala Ile Thr Phe Leu Leu Val Cys Ser Gly Thr Phe Phe
            660                 665                 670

Pro Tyr Ser Ser Asn Pro Ala Asn Pro Lys Pro Lys Arg Val Phe Leu
        675                 680                 685

Gln His Met Thr Arg Thr Phe His Asp Leu Glu Gly Asn Ala Val Lys
    690                 695                 700

Arg Asp Ser Gly Ile Trp Ile Asn Gly Phe Asp Tyr Thr Gly Ile Ser
705                 710                 715                 720

His Ile Thr Pro His Ile Pro Glu Ile Asn Asp Ser Ile Arg Ala His
                725                 730                 735

Cys Glu Glu Asn Ala Pro Leu Cys Gly Phe Pro Trp Tyr Leu Pro Val
            740                 745                 750

His Phe Leu Ile Arg Lys Asn Trp Tyr Leu Pro Ala Pro Glu Val Ser
        755                 760                 765

Pro Arg Asn Pro Pro His Phe Arg Leu Ile Ser Lys Glu Gln Thr Pro
    770                 775                 780

Trp Asp Ser Ile Lys Leu Thr Phe Glu Ala Thr Gly Pro Ser His Met
785                 790                 795                 800

Ser Phe Tyr Val Arg Ala His Lys Gly Ser Thr Leu Ser Gln Trp Ser
                805                 810                 815

Leu Gly Asn Gly Thr Pro Val Thr Ser Lys Gly Gly Asp Tyr Phe Val
            820                 825                 830

Phe Tyr Ser His Gly Leu Gln Ala Ser Ala Trp Gln Phe Trp Ile Glu
        835                 840                 845

Val Gln Val Ser Glu Glu His Pro Glu Gly Met Val Thr Val Ala Ile
    850                 855                 860

Ala Ala His Tyr Leu Ser Gly Glu Asp Lys Arg Ser Pro Gln Leu Asp
865                 870                 875                 880

Ala Leu Lys Glu Lys Phe Pro Asp Trp Thr Phe Pro Ser Ala Trp Val
                885                 890                 895

Cys Thr Tyr Asp Leu Phe Val Phe
            900


<210> SEQ ID NO 27
<211> LENGTH: 202
<212> TYPE: PRT
<213> ORGANISM: Homo sapiens

<400> SEQUENCE: 27

Met Glu Arg Gly Ala Gly Ala Lys Leu Leu Pro Leu Leu Leu Leu Leu
1               5                   10                  15

Arg Ala Thr Gly Phe Thr Cys Ala Gln Thr Asp Gly Arg Asn Gly Tyr
            20                  25                  30

Thr Ala Val Ile Glu Val Thr Ser Gly Gly Pro Trp Gly Asp Trp Ala
        35                  40                  45

Trp Pro Glu Met Cys Pro Asp Gly Phe Phe Ala Ser Gly Phe Ser Leu
    50                  55                  60

Lys Val Glu Pro Pro Gln Gly Ile Pro Gly Asp Asp Thr Ala Leu Asn
```

```
65                  70                  75                  80

Gly Ile Arg Leu His Cys Ala Arg Gly Asn Val Leu Gly Asn Thr His
                85                  90                  95

Val Val Glu Ser Gln Ser Gly Ser Trp Gly Glu Trp Ser Glu Pro Leu
            100                 105                 110

Trp Cys Arg Gly Gly Ala Tyr Leu Val Ala Phe Ser Leu Arg Val Glu
        115                 120                 125

Ala Pro Thr Thr Leu Gly Asp Asn Thr Ala Ala Asn Asn Val Arg Phe
    130                 135                 140

Arg Cys Ser Asp Gly Glu Glu Leu Gln Gly Pro Gly Leu Ser Trp Gly
145                 150                 155                 160

Asp Phe Gly Asp Trp Ser Asp His Cys Pro Lys Gly Ala Cys Gly Leu
                165                 170                 175

Gln Thr Lys Ile Gln Gly Pro Arg Gly Leu Gly Asp Asp Thr Ala Leu
            180                 185                 190

Asn Asp Ala Arg Leu Phe Cys Cys Arg Ser
        195                 200


<210> SEQ ID NO 28
<211> LENGTH: 147
<212> TYPE: PRT
<213> ORGANISM: Homo sapiens

<400> SEQUENCE: 28

Met Gly Phe Ile Phe Ser Lys Ser Met Asn Glu Ser Met Lys Asn Gln
1               5                   10                  15

Lys Glu Phe Met Leu Met Asn Ala Arg Leu Gln Leu Glu Arg Gln Leu
            20                  25                  30

Ile Met Gln Ser Glu Met Arg Glu Arg Gln Met Ala Met Gln Ile Ala
        35                  40                  45

Trp Ser Arg Glu Phe Leu Lys Tyr Phe Gly Thr Phe Phe Gly Leu Ala
    50                  55                  60

Ala Ile Ser Leu Thr Ala Gly Ala Ile Lys Lys Lys Lys Pro Ala Phe
65                  70                  75                  80

Leu Val Pro Ile Val Pro Leu Ser Phe Ile Leu Thr Tyr Gln Tyr Asp
                85                  90                  95

Leu Gly Tyr Gly Thr Leu Leu Glu Arg Met Lys Gly Glu Ala Glu Asp
            100                 105                 110

Ile Leu Glu Thr Glu Lys Ser Lys Leu Gln Leu Pro Arg Gly Met Ile
        115                 120                 125

Thr Phe Glu Ser Ile Glu Lys Ala Arg Lys Glu Gln Ser Arg Phe Phe
    130                 135                 140

Ile Asp Lys
145


<210> SEQ ID NO 29
<211> LENGTH: 758
<212> TYPE: PRT
<213> ORGANISM: Homo sapiens

<400> SEQUENCE: 29

Met Arg Lys Gln Gly Val Ser Ser Lys Arg Leu Gln Ser Ser Gly Arg
1               5                   10                  15

Ser Gln Ser Lys Gly Arg Arg Gly Ala Ser Leu Ala Arg Glu Pro Glu
            20                  25                  30

Val Glu Glu Glu Met Glu Lys Ser Ala Leu Gly Gly Gly Lys Leu Pro
```

-continued

```
        35                  40                  45

Arg Gly Ser Trp Arg Ser Ser Pro Gly Arg Ile Gln Ser Leu Lys Glu
    50                  55                  60

Arg Lys Gly Leu Glu Leu Glu Val Val Ala Lys Thr Phe Leu Leu Gly
65                  70                  75                  80

Pro Phe Gln Phe Val Arg Asn Ser Leu Ala Gln Leu Arg Glu Lys Val
                85                  90                  95

Gln Glu Leu Gln Ala Arg Arg Phe Ser Ser Arg Thr Thr Leu Gly Ile
            100                 105                 110

Ala Val Phe Val Ala Ile Leu His Trp Leu His Leu Val Thr Leu Phe
        115                 120                 125

Glu Asn Asp Arg His Phe Ser His Leu Ser Ser Leu Glu Arg Glu Met
    130                 135                 140

Thr Phe Arg Thr Glu Met Gly Leu Tyr Tyr Ser Tyr Phe Lys Thr Ile
145                 150                 155                 160

Ile Glu Ala Pro Ser Phe Leu Glu Gly Leu Trp Met Ile Met Asn Asp
                165                 170                 175

Arg Leu Thr Glu Tyr Pro Leu Ile Ile Asn Ala Ile Lys Arg Phe His
            180                 185                 190

Leu Tyr Pro Glu Val Ile Ile Ala Ser Trp Tyr Cys Thr Phe Met Gly
        195                 200                 205

Ile Met Asn Leu Phe Gly Leu Glu Thr Lys Thr Cys Trp Asn Val Thr
    210                 215                 220

Arg Ile Glu Pro Leu Asn Glu Val Gln Ser Cys Glu Gly Leu Gly Asp
225                 230                 235                 240

Pro Ala Cys Phe Tyr Val Gly Val Ile Phe Ile Leu Asn Gly Leu Met
                245                 250                 255

Met Gly Leu Phe Phe Met Tyr Gly Ala Tyr Leu Ser Gly Thr Gln Leu
            260                 265                 270

Gly Gly Leu Ile Thr Val Leu Cys Phe Phe Phe Asn His Gly Glu Ala
        275                 280                 285

Thr Arg Val Met Trp Thr Pro Pro Leu Arg Glu Ser Phe Ser Tyr Pro
    290                 295                 300

Phe Leu Val Leu Gln Met Cys Ile Leu Thr Leu Ile Leu Arg Thr Ser
305                 310                 315                 320

Ser Asn Asp Arg Arg Pro Phe Ile Ala Leu Cys Leu Ser Asn Val Ala
                325                 330                 335

Phe Met Leu Pro Trp Gln Phe Ala Gln Phe Ile Leu Phe Thr Gln Ile
            340                 345                 350

Ala Ser Leu Phe Pro Met Tyr Val Val Gly Tyr Ile Glu Pro Ser Lys
        355                 360                 365

Phe Gln Lys Ile Ile Tyr Met Asn Met Ile Ser Val Thr Leu Ser Phe
    370                 375                 380

Ile Leu Met Phe Gly Asn Ser Met Tyr Leu Ser Ser Tyr Tyr Ser Ser
385                 390                 395                 400

Ser Leu Leu Met Thr Trp Ala Ile Ile Leu Lys Arg Asn Glu Ile Gln
                405                 410                 415

Lys Leu Gly Val Ser Lys Leu Asn Phe Trp Leu Ile Gln Gly Ser Ala
            420                 425                 430

Trp Trp Cys Gly Thr Ile Ile Leu Lys Phe Leu Thr Ser Lys Ile Leu
        435                 440                 445

Gly Val Ser Asp His Ile Arg Leu Ser Asp Leu Ile Ala Ala Arg Ile
    450                 455                 460
```

```
Leu Arg Tyr Thr Asp Phe Asp Thr Leu Ile Tyr Thr Cys Ala Pro Glu
465                 470                 475                 480

Phe Asp Phe Met Glu Lys Ala Thr Pro Leu Arg Tyr Thr Lys Thr Leu
                485                 490                 495

Leu Leu Pro Val Val Met Val Ile Thr Cys Phe Ile Phe Lys Lys Thr
            500                 505                 510

Val Arg Asp Ile Ser Tyr Val Leu Ala Thr Asn Ile Tyr Leu Arg Lys
        515                 520                 525

Gln Leu Leu Glu His Ser Glu Leu Ala Phe His Thr Leu Gln Leu Leu
    530                 535                 540

Val Phe Thr Ala Leu Ala Ile Leu Ile Met Arg Leu Lys Met Phe Leu
545                 550                 555                 560

Thr Pro His Met Cys Val Met Ala Ser Leu Ile Cys Ser Arg Gln Leu
                565                 570                 575

Phe Gly Trp Leu Phe Arg Arg Val Arg Phe Glu Lys Val Ile Phe Gly
            580                 585                 590

Ile Leu Thr Val Met Ser Ile Gln Gly Tyr Ala Asn Leu Arg Asn Gln
        595                 600                 605

Trp Ser Ile Ile Gly Glu Phe Asn Asn Leu Pro Gln Glu Glu Leu Leu
    610                 615                 620

Gln Trp Ile Lys Tyr Ser Thr Thr Ser Asp Ala Val Phe Ala Gly Ala
625                 630                 635                 640

Met Pro Thr Met Ala Ser Ile Lys Leu Ser Thr Leu His Pro Ile Val
                645                 650                 655

Asn His Pro His Tyr Glu Asp Ala Asp Leu Arg Ala Arg Thr Lys Ile
            660                 665                 670

Val Tyr Ser Thr Tyr Ser Arg Lys Ser Ala Lys Glu Val Arg Asp Lys
        675                 680                 685

Leu Leu Glu Leu His Val Asn Tyr Tyr Val Leu Glu Glu Ala Trp Cys
    690                 695                 700

Val Val Arg Thr Lys Pro Gly Cys Ser Met Leu Glu Ile Trp Asp Val
705                 710                 715                 720

Glu Asp Pro Ser Asn Ala Ala Asn Pro Pro Leu Cys Ser Val Leu Leu
                725                 730                 735

Glu Asp Ala Arg Pro Tyr Phe Thr Thr Val Phe Gln Asn Ser Val Tyr
            740                 745                 750

Arg Val Leu Lys Val Asn
        755


<210> SEQ ID NO 30
<211> LENGTH: 316
<212> TYPE: PRT
<213> ORGANISM: Homo sapiens

<400> SEQUENCE: 30

Met Ala Ser Ala Asp Glu Leu Thr Phe His Glu Phe Glu Glu Ala Thr
1               5                   10                  15

Asn Leu Leu Ala Asp Thr Pro Asp Ala Ala Thr Thr Ser Arg Ser Asp
            20                  25                  30

Gln Leu Thr Pro Gln Gly His Val Ala Val Ala Val Gly Ser Gly Gly
        35                  40                  45

Ser Tyr Gly Ala Glu Asp Glu Val Glu Glu Glu Ser Asp Lys Ala Ala
    50                  55                  60

Leu Leu Gln Glu Gln Gln Gln Gln Gln Gln Pro Gly Phe Trp Thr Phe
```

65 70 75 80

Ser Tyr Tyr Gln Ser Phe Phe Asp Val Asp Thr Ser Gln Val Leu Asp
85 90 95

Arg Ile Lys Gly Ser Leu Leu Pro Arg Pro Gly His Asn Phe Val Arg
100 105 110

His His Leu Arg Asn Arg Pro Asp Leu Tyr Gly Pro Phe Trp Ile Cys
115 120 125

Ala Thr Leu Ala Phe Val Leu Ala Val Thr Gly Asn Leu Thr Leu Val
130 135 140

Leu Ala Gln Arg Arg Asp Pro Ser Ile His Tyr Ser Pro Gln Phe His
145 150 155 160

Lys Val Thr Val Ala Gly Ile Ser Ile Tyr Cys Tyr Ala Trp Leu Val
165 170 175

Pro Leu Ala Leu Trp Gly Phe Leu Arg Trp Arg Lys Gly Val Gln Glu
180 185 190

Arg Met Gly Pro Tyr Thr Phe Leu Glu Thr Val Cys Ile Tyr Gly Tyr
195 200 205

Ser Leu Phe Val Phe Ile Pro Met Val Val Leu Trp Leu Ile Pro Val
210 215 220

Pro Trp Leu Gln Trp Leu Phe Gly Ala Leu Ala Leu Gly Leu Ser Ala
225 230 235 240

Ala Gly Leu Val Phe Thr Leu Trp Pro Val Val Arg Glu Asp Thr Arg
245 250 255

Leu Val Ala Thr Val Leu Leu Ser Val Val Val Leu Leu His Ala Leu
260 265 270

Leu Ala Met Gly Cys Lys Leu Tyr Phe Phe Gln Ser Leu Pro Pro Glu
275 280 285

Asn Val Ala Pro Pro Pro Gln Ile Thr Ser Leu Pro Ser Asn Ile Ala
290 295 300

Leu Ser Pro Thr Leu Pro Gln Ser Leu Ala Pro Ser
305 310 315

<210> SEQ ID NO 31
<211> LENGTH: 241
<212> TYPE: PRT
<213> ORGANISM: Homo sapiens

<400> SEQUENCE: 31

Met Lys Phe Ile Leu Leu Trp Ala Leu Leu Asn Leu Thr Val Ala Leu
1 5 10 15

Ala Phe Asn Pro Asp Tyr Thr Val Ser Ser Thr Pro Pro Tyr Leu Val
20 25 30

Tyr Leu Lys Ser Asp Tyr Leu Pro Cys Ala Gly Val Leu Ile His Pro
35 40 45

Leu Trp Val Ile Thr Ala Ala His Cys Asn Leu Pro Lys Leu Arg Val
50 55 60

Ile Leu Gly Val Thr Ile Pro Ala Asp Ser Asn Glu Lys His Leu Gln
65 70 75 80

Val Ile Gly Tyr Glu Lys Met Ile His His Pro His Phe Ser Val Thr
85 90 95

Ser Ile Asp His Asp Ile Met Leu Ile Lys Leu Lys Thr Glu Ala Glu
100 105 110

Leu Asn Asp Tyr Val Lys Leu Ala Asn Leu Pro Tyr Gln Thr Ile Ser
115 120 125

```
Glu Asn Thr Met Cys Ser Val Ser Thr Trp Ser Tyr Asn Val Cys Asp
    130                 135                 140

Ile Tyr Lys Glu Pro Asp Ser Leu Gln Thr Val Asn Ile Ser Val Ile
145                 150                 155                 160

Ser Lys Pro Gln Cys Arg Asp Ala Tyr Lys Thr Tyr Asn Ile Thr Glu
                165                 170                 175

Asn Met Leu Cys Val Gly Ile Val Pro Gly Arg Arg Gln Pro Cys Lys
            180                 185                 190

Glu Val Ser Ala Ala Pro Ala Ile Cys Asn Gly Met Leu Gln Gly Ile
        195                 200                 205

Leu Ser Phe Ala Asp Gly Cys Val Leu Arg Ala Asp Val Gly Ile Tyr
    210                 215                 220

Ala Lys Ile Phe Tyr Tyr Ile Pro Trp Ile Glu Asn Val Ile Gln Asn
225                 230                 235                 240

Asn


<210> SEQ ID NO 32
<211> LENGTH: 1172
<212> TYPE: PRT
<213> ORGANISM: Homo sapiens

<400> SEQUENCE: 32

Met Ser Pro Asp Val Pro Leu Leu Asn Asp Tyr Lys Gln Asp Phe Phe
1               5                   10                  15

Leu Lys Arg Phe Pro Gln Thr Val Leu Gly Gly Pro Arg Phe Lys Leu
            20                  25                  30

Gly Tyr Cys Ala Pro Pro Tyr Ile Tyr Val Asn Gln Ile Ile Leu Phe
        35                  40                  45

Leu Met Pro Trp Val Trp Gly Gly Val Gly Thr Leu Leu Tyr Gln Leu
    50                  55                  60

Gly Ile Leu Lys Asp Tyr Tyr Thr Ala Ala Leu Ser Gly Gly Leu Met
65                  70                  75                  80

Leu Phe Thr Ala Phe Val Ile Gln Phe Thr Ser Leu Tyr Ala Lys Asn
                85                  90                  95

Lys Ser Thr Thr Val Glu Arg Ile Leu Thr Thr Asp Ile Leu Ala Glu
            100                 105                 110

Glu Asp Glu His Glu Phe Thr Ser Cys Thr Gly Ala Glu Thr Val Lys
        115                 120                 125

Phe Leu Ile Pro Gly Lys Lys Tyr Val Ala Asn Thr Val Phe His Ser
    130                 135                 140

Ile Leu Ala Gly Leu Ala Cys Gly Leu Gly Thr Trp Tyr Leu Leu Pro
145                 150                 155                 160

Asn Arg Ile Thr Leu Leu Tyr Gly Ser Thr Gly Gly Thr Ala Leu Leu
                165                 170                 175

Phe Phe Phe Gly Trp Met Thr Leu Cys Ile Ala Glu Tyr Ser Leu Ile
            180                 185                 190

Val Asn Thr Ala Thr Glu Thr Ala Thr Phe Gln Thr Gln Asp Thr Tyr
        195                 200                 205

Glu Ile Ile Pro Leu Met Arg Pro Leu Tyr Ile Phe Phe Phe Val Ser
    210                 215                 220

Val Asp Leu Ala His Arg Phe Val Val Asn Met Pro Ala Leu Glu His
225                 230                 235                 240

Met Asn Gln Ile Leu His Ile Leu Phe Val Phe Leu Pro Phe Leu Trp
                245                 250                 255
```

Ala Leu Gly Thr Leu Pro Pro Pro Asp Ala Leu Leu Leu Trp Ala Met
260 265 270

Glu Gln Val Leu Glu Phe Gly Leu Gly Gly Ser Ser Met Ser Thr His
275 280 285

Leu Arg Leu Leu Val Met Phe Ile Met Ser Ala Gly Thr Ala Ile Ala
290 295 300

Ser Tyr Phe Ile Pro Ser Thr Val Gly Val Val Leu Phe Met Thr Gly
305 310 315 320

Phe Gly Phe Leu Leu Ser Leu Asn Leu Ser Asp Met Gly His Lys Ile
325 330 335

Gly Thr Lys Ser Lys Asp Leu Pro Ser Gly Pro Glu Lys His Phe Ser
340 345 350

Trp Lys Glu Cys Leu Phe Tyr Ile Ile Ile Leu Val Leu Ala Leu Leu
355 360 365

Glu Thr Ser Leu Leu His His Phe Ala Gly Phe Ser Gln Ile Ser Lys
370 375 380

Ser Asn Ser Gln Ala Ile Val Gly Tyr Gly Leu Met Ile Leu Leu Ile
385 390 395 400

Ile Leu Trp Ile Leu Arg Glu Ile Gln Ser Val Tyr Ile Ile Gly Ile
405 410 415

Phe Arg Asn Pro Phe Tyr Pro Lys Asp Val Gln Thr Val Thr Val Phe
420 425 430

Phe Glu Lys Gln Thr Arg Leu Met Lys Ile Gly Ile Val Arg Arg Ile
435 440 445

Leu Leu Thr Leu Val Ser Pro Phe Ala Met Ile Ala Phe Leu Ser Leu
450 455 460

Asp Ser Ser Leu Gln Gly Leu His Ser Val Ser Val Cys Ile Gly Phe
465 470 475 480

Thr Arg Ala Phe Arg Met Val Trp Gln Asn Thr Glu Asn Ala Leu Leu
485 490 495

Glu Thr Val Ile Val Ser Thr Val His Leu Ile Ser Ser Thr Asp Ile
500 505 510

Trp Trp Asn Arg Ser Leu Asp Thr Gly Leu Arg Leu Leu Leu Val Gly
515 520 525

Ile Ile Arg Asp Arg Leu Ile Gln Phe Ile Ser Lys Leu Gln Phe Ala
530 535 540

Val Thr Val Leu Leu Thr Ser Trp Thr Glu Lys Lys Gln Arg Arg Lys
545 550 555 560

Thr Thr Ala Thr Leu Cys Ile Leu Asn Ile Val Phe Ser Pro Phe Val
565 570 575

Leu Val Ile Ile Val Phe Ser Thr Leu Leu Ser Ser Pro Leu Leu Pro
580 585 590

Leu Phe Thr Leu Pro Val Phe Leu Val Gly Phe Pro Arg Pro Ile Gln
595 600 605

Ser Trp Pro Gly Ala Ala Gly Thr Thr Ala Cys Val Cys Ala Asp Thr
610 615 620

Val Tyr Tyr Tyr Gln Met Val Pro Arg Leu Thr Ala Val Leu Gln Thr
625 630 635 640

Ala Met Ala Ala Gly Ser Leu Gly Leu Leu Leu Pro Gly Ser His Tyr
645 650 655

Leu Gly Arg Phe Gln Asp Arg Leu Met Trp Ile Met Ile Leu Glu Cys
660 665 670

Gly Tyr Thr Tyr Cys Ser Ile Asn Ile Lys Gly Leu Glu Leu Gln Glu

```
        675                 680                 685

Thr Ser Cys His Thr Ala Glu Ala Arg Arg Val Asp Glu Val Phe Glu
    690                 695                 700

Asp Ala Phe Glu Gln Glu Tyr Thr Arg Val Cys Ser Leu Asn Glu His
705                 710                 715                 720

Phe Gly Asn Val Leu Thr Pro Cys Thr Val Leu Pro Val Lys Leu Tyr
                725                 730                 735

Ser Asp Ala Arg Asn Val Leu Ser Gly Ile Ile Asp Ser His Glu Asn
            740                 745                 750

Leu Lys Glu Phe Lys Gly Asp Leu Ile Lys Val Leu Val Trp Ile Leu
        755                 760                 765

Val Gln Tyr Cys Ser Lys Arg Pro Gly Met Lys Glu Asn Val His Asn
    770                 775                 780

Thr Glu Asn Lys Gly Lys Ala Pro Leu Met Leu Pro Ala Leu Asn Thr
785                 790                 795                 800

Leu Pro Pro Pro Lys Ser Pro Glu Asp Ile Asp Ser Leu Asn Ser Glu
                805                 810                 815

Thr Phe Asn Asp Trp Ser Asp Asp Asn Ile Phe Asp Asp Glu Pro Thr
            820                 825                 830

Ile Lys Lys Val Ile Glu Glu Lys His Gln Leu Lys Asp Leu Pro Gly
        835                 840                 845

Thr Asn Leu Phe Ile Pro Gly Ser Val Glu Ser Gln Arg Val Gly Asp
    850                 855                 860

His Ser Thr Gly Thr Val Pro Glu Asn Asp Leu Tyr Lys Ala Val Leu
865                 870                 875                 880

Leu Gly Tyr Pro Ala Val Asp Lys Gly Lys Gln Glu Asp Met Pro Tyr
                885                 890                 895

Ile Pro Leu Met Glu Phe Ser Cys Ser His Ser His Leu Val Cys Leu
            900                 905                 910

Pro Ala Glu Trp Arg Thr Ser Cys Met Pro Ser Ser Lys Met Lys Glu
        915                 920                 925

Met Ser Ser Leu Phe Pro Glu Asp Trp Tyr Gln Phe Val Leu Arg Gln
    930                 935                 940

Leu Glu Cys Tyr His Ser Glu Glu Lys Ala Ser Asn Val Leu Glu Glu
945                 950                 955                 960

Ile Ala Lys Asp Lys Val Leu Lys Asp Phe Tyr Val His Thr Val Met
                965                 970                 975

Thr Cys Tyr Phe Ser Leu Phe Gly Ile Asp Asn Met Ala Pro Ser Pro
            980                 985                 990

Gly His Ile Leu Arg Val Tyr Gly  Gly Val Leu Pro Trp  Ser Val Ala
        995                 1000                1005

Leu Asp  Trp Leu Thr Glu Lys  Pro Glu Leu Phe Gln  Leu Ala Leu
    1010                1015                1020

Lys Ala  Phe Arg Tyr Thr Leu  Lys Leu Met Ile Asp  Lys Ala Ser
    1025                1030                1035

Leu Gly  Pro Ile Glu Asp Phe  Arg Glu Leu Ile Lys  Tyr Leu Glu
    1040                1045                1050

Glu Tyr  Glu Arg Asp Trp Tyr  Ile Gly Leu Val Ser  Asp Glu Lys
    1055                1060                1065

Trp Lys  Glu Ala Ile Leu Gln  Glu Lys Pro Tyr Leu  Phe Ser Leu
    1070                1075                1080

Gly Tyr  Asp Ser Asn Met Gly  Ile Tyr Thr Gly Arg  Val Leu Ser
    1085                1090                1095
```

```
Leu Gln  Glu Leu Leu Ile Gln  Val Gly Lys Leu Asn  Pro Glu Ala
    1100                 1105                 1110

Val Arg  Gly Gln Trp Ala Asn  Leu Ser Trp Glu Leu  Leu Tyr Ala
    1115                 1120                 1125

Thr Asn  Asp Asp Glu Glu Arg  Tyr Ser Ile Gln Ala  His Pro Leu
    1130                 1135                 1140

Leu Leu  Arg Asn Leu Thr Val  Gln Ala Ala Glu Pro  Pro Leu Gly
    1145                 1150                 1155

Tyr Pro  Ile Tyr Ser Ser Lys  Pro Leu His Ile His  Leu Tyr
    1160                 1165                 1170
```

<210> SEQ ID NO 33
<211> LENGTH: 346
<212> TYPE: PRT
<213> ORGANISM: Homo sapiens

<400> SEQUENCE: 33

```
Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
            20                  25                  30

Lys Thr Pro Ala Gln Pro Gln Leu Lys Ala Ala Asn Cys Cys Glu Glu
        35                  40                  45

Val Lys Glu Leu Lys Ala Gln Val Ala Asn Leu Ser Ser Leu Leu Ser
    50                  55                  60

Glu Leu Asn Lys Lys Gln Glu Arg Asp Trp Val Ser Val Val Met Gln
65                  70                  75                  80

Val Met Glu Leu Glu Ser Asn Ser Lys Arg Met Glu Ser Arg Leu Thr
                85                  90                  95

Asp Ala Glu Ser Lys Tyr Ser Glu Met Asn Asn Gln Ile Asp Ile Met
            100                 105                 110

Gln Leu Gln Ala Ala Gln Thr Val Thr Gln Thr Ser Ala Asp Ala Ile
        115                 120                 125

Tyr Asp Cys Ser Ser Leu Tyr Gln Lys Asn Tyr Arg Ile Ser Gly Val
    130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile Gln Arg
                165                 170                 175

Arg Lys Ser Gly Leu Val Ser Phe Tyr Arg Asp Trp Lys Gln Tyr Lys
            180                 185                 190

Gln Gly Phe Gly Ser Ile Arg Gly Asp Phe Trp Leu Gly Asn Glu His
        195                 200                 205

Ile His Arg Leu Ser Arg Gln Pro Thr Arg Leu Arg Val Glu Met Glu
    210                 215                 220

Asp Trp Glu Gly Asn Leu Arg Tyr Ala Glu Tyr Ser His Phe Val Leu
225                 230                 235                 240

Gly Asn Glu Leu Asn Ser Tyr Arg Leu Phe Leu Gly Asn Tyr Thr Gly
                245                 250                 255

Asn Val Gly Asn Asp Ala Leu Gln Tyr His Asn Asn Thr Ala Phe Ser
            260                 265                 270

Thr Lys Asp Lys Asp Asn Asp Asn Cys Leu Asp Lys Cys Ala Gln Leu
        275                 280                 285

Arg Lys Gly Gly Tyr Trp Tyr Asn Cys Cys Thr Asp Ser Asn Leu Asn
```

```
    290                 295                 300

Gly Val Tyr Tyr Arg Leu Gly Glu His Asn Lys His Leu Asp Gly Ile
305                 310                 315                 320

Thr Trp Tyr Gly Trp His Gly Ser Thr Tyr Ser Leu Lys Arg Val Glu
                325                 330                 335

Met Lys Ile Arg Pro Glu Asp Phe Lys Pro
            340                 345


<210> SEQ ID NO 34
<211> LENGTH: 752
<212> TYPE: PRT
<213> ORGANISM: Homo sapiens

<400> SEQUENCE: 34

Met Ala Glu Pro Gln Ala Glu Ser Glu Pro Leu Leu Gly Gly Ala Arg
1               5                   10                  15

Gly Gly Gly Gly Asp Trp Pro Ala Gly Leu Thr Thr Tyr Arg Ser Ile
            20                  25                  30

Gln Val Gly Pro Gly Ala Ala Ala Arg Trp Asp Leu Cys Ile Asp Gln
        35                  40                  45

Ala Val Val Phe Ile Glu Asp Ala Ile Gln Tyr Arg Ser Ile Asn His
    50                  55                  60

Arg Val Asp Ala Ser Ser Met Trp Leu Tyr Arg Arg Tyr Tyr Ser Asn
65                  70                  75                  80

Val Cys Gln Arg Thr Leu Ser Phe Thr Ile Phe Leu Ile Leu Phe Leu
                85                  90                  95

Ala Phe Ile Glu Thr Pro Ser Ser Leu Thr Ser Thr Ala Asp Val Arg
            100                 105                 110

Tyr Arg Ala Ala Pro Trp Glu Pro Pro Cys Gly Leu Thr Glu Ser Val
        115                 120                 125

Glu Val Leu Cys Leu Leu Val Phe Ala Ala Asp Leu Ser Val Lys Gly
    130                 135                 140

Tyr Leu Phe Gly Trp Ala His Phe Gln Lys Asn Leu Trp Leu Leu Gly
145                 150                 155                 160

Tyr Leu Val Val Leu Val Val Ser Leu Val Asp Trp Thr Val Ser Leu
                165                 170                 175

Ser Leu Val Cys His Glu Pro Leu Arg Ile Arg Arg Leu Leu Arg Pro
            180                 185                 190

Phe Phe Leu Leu Gln Asn Ser Ser Met Met Lys Lys Thr Leu Lys Cys
        195                 200                 205

Ile Arg Trp Ser Leu Pro Glu Met Ala Ser Val Gly Leu Leu Leu Ala
    210                 215                 220

Ile His Leu Cys Leu Phe Thr Met Phe Gly Met Leu Leu Phe Ala Gly
225                 230                 235                 240

Gly Lys Gln Asp Asp Gly Gln Asp Arg Glu Arg Leu Thr Tyr Phe Gln
                245                 250                 255

Asn Leu Pro Glu Ser Leu Thr Ser Leu Leu Val Leu Leu Thr Thr Ala
            260                 265                 270

Asn Asn Pro Asp Val Met Ile Pro Ala Tyr Ser Lys Asn Arg Ala Tyr
        275                 280                 285

Ala Ile Phe Phe Ile Val Phe Thr Val Ile Gly Ser Leu Phe Leu Met
    290                 295                 300

Asn Leu Leu Thr Ala Ile Ile Tyr Ser Gln Phe Arg Gly Tyr Leu Met
305                 310                 315                 320
```

```
Lys Ser Leu Gln Thr Ser Leu Phe Arg Arg Arg Leu Gly Thr Arg Ala
                325                 330                 335

Ala Phe Glu Val Leu Ser Ser Met Val Gly Glu Gly Gly Ala Phe Pro
            340                 345                 350

Gln Ala Val Gly Val Lys Pro Gln Asn Leu Leu Gln Val Leu Gln Lys
        355                 360                 365

Val Gln Leu Asp Ser Ser His Lys Gln Ala Met Met Glu Lys Val Arg
    370                 375                 380

Ser Tyr Gly Ser Val Leu Leu Ser Ala Glu Glu Phe Gln Lys Leu Phe
385                 390                 395                 400

Asn Glu Leu Asp Arg Ser Val Val Lys Glu His Pro Pro Arg Pro Glu
                405                 410                 415

Tyr Gln Ser Pro Phe Leu Gln Ser Ala Gln Phe Leu Phe Gly His Tyr
            420                 425                 430

Tyr Phe Asp Tyr Leu Gly Asn Leu Ile Ala Leu Ala Asn Leu Val Ser
        435                 440                 445

Ile Cys Val Phe Leu Val Leu Asp Ala Asp Val Leu Pro Ala Glu Arg
    450                 455                 460

Asp Asp Phe Ile Leu Gly Ile Leu Asn Cys Val Phe Ile Val Tyr Tyr
465                 470                 475                 480

Leu Leu Glu Met Leu Leu Lys Val Phe Ala Leu Gly Leu Arg Gly Tyr
                485                 490                 495

Leu Ser Tyr Pro Ser Asn Val Phe Asp Gly Leu Leu Thr Val Val Leu
            500                 505                 510

Leu Val Leu Glu Ile Ser Thr Leu Ala Val Tyr Arg Leu Pro His Pro
        515                 520                 525

Gly Trp Arg Pro Glu Met Val Gly Leu Leu Ser Leu Trp Asp Met Thr
    530                 535                 540

Arg Met Leu Asn Met Leu Ile Val Phe Arg Phe Leu Arg Ile Ile Pro
545                 550                 555                 560

Ser Met Lys Leu Met Ala Val Val Ala Ser Thr Val Leu Gly Leu Val
                565                 570                 575

Gln Asn Met Arg Ala Phe Gly Gly Ile Leu Val Val Val Tyr Tyr Val
            580                 585                 590

Phe Ala Ile Ile Gly Ile Asn Leu Phe Arg Gly Val Ile Val Ala Leu
        595                 600                 605

Pro Gly Asn Ser Ser Leu Ala Pro Ala Asn Gly Ser Ala Pro Cys Gly
    610                 615                 620

Ser Phe Glu Gln Leu Glu Tyr Trp Ala Asn Asn Phe Asp Asp Phe Ala
625                 630                 635                 640

Ala Ala Leu Val Thr Leu Trp Asn Leu Met Val Val Asn Asn Trp Gln
                645                 650                 655

Val Phe Leu Asp Ala Tyr Arg Arg Tyr Ser Gly Pro Trp Ser Lys Ile
            660                 665                 670

Tyr Phe Val Leu Trp Trp Leu Val Ser Ser Val Ile Trp Val Asn Leu
        675                 680                 685

Phe Leu Ala Leu Ile Leu Glu Asn Phe Leu His Lys Trp Asp Pro Arg
    690                 695                 700

Ser His Leu Gln Pro Leu Ala Gly Thr Pro Glu Ala Thr Tyr Gln Met
705                 710                 715                 720

Thr Val Glu Leu Leu Phe Arg Asp Ile Leu Glu Glu Pro Gly Glu Asp
                725                 730                 735

Glu Leu Thr Glu Arg Leu Ser Gln His Pro His Leu Trp Leu Cys Arg
```

```
740                 745                 750


<210> SEQ ID NO 35
<211> LENGTH: 272
<212> TYPE: PRT
<213> ORGANISM: Homo sapiens

<400> SEQUENCE: 35

Met Gln Trp Asn Val Pro Arg Thr Val Ser Arg Leu Ala Arg Arg Thr
1               5                   10                  15

Cys Leu Glu Pro His Asn Ala Gly Leu Phe Gly His Cys Gln Asn Val
            20                  25                  30

Lys Gly Pro Leu Leu Leu Tyr Asn Ala Glu Ser Lys Val Val Leu Val
        35                  40                  45

Gln Gly Pro Gln Lys Gln Trp Leu His Leu Ser Ala Ala Gln Cys Val
    50                  55                  60

Ala Lys Glu Arg Arg Pro Leu Asp Ala His Pro Pro Gln Pro Gly Val
65                  70                  75                  80

Leu Arg His Lys Gln Gly Lys Gln His Val Ser Phe Arg Arg Val Phe
                85                  90                  95

Ser Ser Ser Ala Thr Ala Gln Gly Thr Pro Glu Lys Lys Glu Glu Pro
            100                 105                 110

Asp Pro Leu Gln Asp Lys Ser Ile Ser Leu Tyr Gln Arg Phe Lys Lys
        115                 120                 125

Thr Phe Arg Gln Tyr Gly Lys Val Leu Ile Pro Val His Leu Ile Thr
    130                 135                 140

Ser Gly Val Trp Phe Gly Thr Phe Tyr Tyr Ala Ala Leu Lys Gly Val
145                 150                 155                 160

Asn Val Val Pro Phe Leu Glu Leu Ile Gly Leu Pro Asp Ser Val Val
                165                 170                 175

Ser Ile Leu Lys Asn Ser Gln Ser Gly Asn Ala Leu Thr Ala Tyr Ala
            180                 185                 190

Leu Phe Lys Ile Ala Thr Pro Ala Arg Tyr Thr Val Thr Leu Gly Gly
        195                 200                 205

Thr Ser Val Thr Val Lys Tyr Leu Arg Ser His Gly Tyr Met Ser Thr
    210                 215                 220

Pro Pro Pro Val Lys Glu Tyr Leu Gln Asp Arg Met Glu Glu Thr Lys
225                 230                 235                 240

Glu Leu Ile Thr Glu Lys Met Glu Glu Thr Lys Asp Arg Leu Thr Glu
                245                 250                 255

Lys Leu Gln Glu Thr Lys Glu Lys Val Ser Phe Lys Lys Lys Val Glu
            260                 265                 270


<210> SEQ ID NO 36
<211> LENGTH: 402
<212> TYPE: PRT
<213> ORGANISM: Homo sapiens

<400> SEQUENCE: 36

Met Met Val Ala Leu Arg Gly Ala Ser Ala Leu Leu Val Leu Phe Leu
1               5                   10                  15

Ala Ala Phe Leu Pro Pro Pro Gln Cys Thr Gln Asp Pro Ala Met Val
            20                  25                  30

His Tyr Ile Tyr Gln Arg Phe Arg Val Leu Glu Gln Gly Leu Glu Lys
        35                  40                  45

Cys Thr Gln Ala Thr Arg Ala Tyr Ile Gln Glu Phe Gln Glu Phe Ser
```

```
    50                  55                  60

Lys Asn Ile Ser Val Met Leu Gly Arg Cys Gln Thr Tyr Thr Ser Glu
65                  70                  75                  80

Tyr Lys Ser Ala Val Gly Asn Leu Ala Leu Arg Val Glu Arg Ala Gln
                85                  90                  95

Arg Glu Ile Asp Tyr Ile Gln Tyr Leu Arg Glu Ala Asp Glu Cys Ile
            100                 105                 110

Glu Ser Glu Asp Lys Thr Leu Ala Glu Met Leu Leu Gln Glu Ala Glu
        115                 120                 125

Glu Glu Lys Lys Ile Arg Thr Leu Leu Asn Ala Ser Cys Asp Asn Met
    130                 135                 140

Leu Met Gly Ile Lys Ser Leu Lys Ile Val Lys Lys Met Met Asp Thr
145                 150                 155                 160

His Gly Ser Trp Met Lys Asp Ala Val Tyr Asn Ser Pro Lys Val Tyr
                165                 170                 175

Leu Leu Ile Gly Ser Arg Asn Asn Thr Val Trp Glu Phe Ala Asn Ile
            180                 185                 190

Arg Ala Phe Met Glu Asp Asn Thr Lys Pro Ala Pro Arg Lys Gln Ile
        195                 200                 205

Leu Thr Leu Ser Trp Gln Gly Thr Gly Gln Val Ile Tyr Lys Gly Phe
    210                 215                 220

Leu Phe Phe His Asn Gln Ala Thr Ser Asn Glu Ile Ile Lys Tyr Asn
225                 230                 235                 240

Leu Gln Lys Arg Thr Val Glu Asp Arg Met Leu Leu Pro Gly Gly Val
                245                 250                 255

Gly Arg Ala Leu Val Tyr Gln His Ser Pro Ser Thr Tyr Ile Asp Leu
            260                 265                 270

Ala Val Asp Glu His Gly Leu Trp Ala Ile His Ser Gly Pro Gly Thr
        275                 280                 285

His Ser His Leu Val Leu Thr Lys Ile Glu Pro Gly Thr Leu Gly Val
    290                 295                 300

Glu His Ser Trp Asp Thr Pro Cys Arg Ser Gln Asp Ala Glu Ala Ser
305                 310                 315                 320

Phe Leu Leu Cys Gly Val Leu Tyr Val Val Tyr Ser Thr Gly Gly Gln
                325                 330                 335

Gly Pro His Arg Ile Thr Cys Ile Tyr Asp Pro Leu Gly Thr Ile Ser
            340                 345                 350

Glu Glu Asp Leu Pro Asn Leu Phe Phe Pro Lys Arg Pro Arg Ser His
        355                 360                 365

Ser Met Ile His Tyr Asn Pro Arg Asp Lys Gln Leu Tyr Ala Trp Asn
    370                 375                 380

Glu Gly Asn Gln Ile Ile Tyr Lys Leu Gln Thr Lys Arg Lys Leu Pro
385                 390                 395                 400

Leu Lys


<210> SEQ ID NO 37
<211> LENGTH: 246
<212> TYPE: PRT
<213> ORGANISM: Homo sapiens

<400> SEQUENCE: 37

Met Gly Pro Gln His Leu Arg Leu Val Gln Leu Phe Cys Leu Leu Gly
1               5                   10                  15

Ala Ile Ser Thr Leu Pro Arg Ala Gly Ala Leu Leu Cys Tyr Glu Ala
```

```
            20                  25                  30

Thr Ala Ser Arg Phe Arg Ala Val Ala Phe His Asn Trp Lys Trp Leu
        35                  40                  45

Leu Met Arg Asn Met Val Cys Lys Leu Gln Glu Gly Cys Glu Glu Thr
    50                  55                  60

Leu Val Phe Ile Glu Thr Gly Thr Ala Arg Gly Val Val Gly Phe Lys
65                  70                  75                  80

Gly Cys Ser Ser Ser Ser Ser Tyr Pro Ala Gln Ile Ser Tyr Leu Val
                85                  90                  95

Ser Pro Pro Gly Val Ser Ile Ala Ser Tyr Ser Arg Val Cys Arg Ser
            100                 105                 110

Tyr Leu Cys Asn Asn Leu Thr Asn Leu Glu Pro Phe Val Lys Leu Lys
        115                 120                 125

Ala Ser Thr Pro Lys Ser Ile Thr Ser Ala Ser Cys Ser Cys Pro Thr
    130                 135                 140

Cys Val Gly Glu His Met Lys Asp Cys Leu Pro Asn Phe Val Thr Thr
145                 150                 155                 160

Asn Ser Cys Pro Leu Ala Ala Ser Thr Cys Tyr Ser Ser Thr Leu Lys
                165                 170                 175

Phe Gln Ala Gly Phe Leu Asn Thr Thr Phe Leu Leu Met Gly Cys Ala
            180                 185                 190

Arg Glu His Asn Gln Leu Leu Ala Asp Phe His His Ile Gly Ser Ile
        195                 200                 205

Lys Val Thr Glu Val Leu Asn Ile Leu Glu Lys Ser Gln Ile Val Gly
    210                 215                 220

Ala Ala Ser Ser Arg Gln Asp Pro Ala Trp Gly Val Val Leu Gly Leu
225                 230                 235                 240

Leu Phe Ala Phe Arg Asp
                245


<210> SEQ ID NO 38
<211> LENGTH: 2845
<212> TYPE: PRT
<213> ORGANISM: Homo sapiens

<400> SEQUENCE: 38

Met Ala Leu Gly Lys Val Leu Ala Met Ala Leu Val Leu Ala Leu Ala
1               5                   10                  15

Val Leu Gly Ser Leu Ser Pro Gly Ala Arg Ala Gly Asp Cys Lys Gly
            20                  25                  30

Gln Arg Gln Val Leu Arg Glu Ala Pro Gly Phe Val Thr Asp Gly Ala
        35                  40                  45

Gly Asn Tyr Ser Val Asn Gly Asn Cys Glu Trp Leu Ile Glu Ala Pro
    50                  55                  60

Ser Pro Gln His Arg Ile Leu Leu Asp Phe Leu Phe Leu Asp Thr Glu
65                  70                  75                  80

Cys Thr Tyr Asp Tyr Leu Phe Val Tyr Asp Gly Asp Ser Pro Arg Gly
                85                  90                  95

Pro Leu Leu Ala Ser Leu Ser Gly Ser Thr Arg Pro Pro Pro Ile Glu
            100                 105                 110

Ala Ser Ser Gly Lys Met Leu Leu His Leu Phe Ser Asp Ala Asn Tyr
        115                 120                 125

Asn Leu Leu Gly Phe Asn Ala Ser Phe Arg Phe Ser Leu Cys Pro Gly
    130                 135                 140
```

-continued

```
Gly Cys Gln Ser His Gly Gln Cys Gln Pro Pro Gly Val Cys Ala Cys
145                 150                 155                 160

Glu Pro Gly Trp Gly Gly Pro Asp Cys Gly Leu Gln Glu Cys Ser Ala
                165                 170                 175

Tyr Cys Gly Ser His Gly Thr Cys Ala Ser Pro Leu Gly Pro Cys Arg
            180                 185                 190

Cys Glu Pro Gly Phe Leu Gly Arg Ala Cys Asp Leu His Leu Trp Glu
        195                 200                 205

Asn Gln Gly Ala Gly Trp Trp His Asn Val Ser Ala Arg Asp Pro Ala
    210                 215                 220

Phe Ser Ala Arg Ile Gly Ala Ala Gly Ala Phe Leu Ser Pro Pro Gly
225                 230                 235                 240

Leu Leu Ala Val Phe Gly Gly Gln Asp Leu Asn Asn Ala Leu Gly Asp
                245                 250                 255

Leu Val Leu Tyr Asn Phe Ser Ala Asn Thr Trp Glu Ser Trp Asp Leu
            260                 265                 270

Ser Pro Ala Pro Ala Ala Arg His Ser His Val Ala Val Ala Trp Ala
        275                 280                 285

Gly Ser Leu Val Leu Met Gly Gly Glu Leu Ala Asp Gly Ser Leu Thr
    290                 295                 300

Asn Asp Val Trp Ala Phe Ser Pro Leu Gly Arg Gly His Trp Glu Leu
305                 310                 315                 320

Leu Ala Pro Pro Ala Ser Ser Ser Ser Gly Pro Pro Gly Leu Ala Gly
                325                 330                 335

His Ala Ala Ala Leu Val Asp Asp Val Trp Leu Tyr Val Ser Gly Gly
            340                 345                 350

Arg Thr Pro His Asp Leu Phe Ser Ser Gly Leu Phe Arg Phe Arg Leu
        355                 360                 365

Asp Ser Thr Ser Gly Gly Tyr Trp Glu Gln Val Ile Pro Ala Gly Gly
    370                 375                 380

Arg Pro Pro Ala Ala Thr Gly His Ser Met Val Phe His Ala Pro Ser
385                 390                 395                 400

Arg Ala Leu Leu Val His Gly Gly His Arg Pro Ser Thr Ala Arg Phe
                405                 410                 415

Ser Val Arg Val Asn Ser Thr Glu Leu Phe His Val Asp Arg His Val
            420                 425                 430

Trp Thr Thr Leu Lys Gly Arg Asp Gly Leu Gln Gly Pro Arg Glu Arg
        435                 440                 445

Ala Phe His Thr Ala Ser Val Leu Gly Asn Tyr Met Val Val Tyr Gly
    450                 455                 460

Gly Asn Val His Thr His Tyr Gln Glu Glu Lys Cys Tyr Glu Asp Gly
465                 470                 475                 480

Ile Phe Phe Tyr His Leu Gly Cys His Gln Trp Val Ser Gly Ala Glu
                485                 490                 495

Leu Ala Pro Pro Gly Thr Pro Glu Gly Arg Ala Ala Pro Pro Ser Gly
            500                 505                 510

Arg Tyr Ser His Val Ala Ala Val Leu Gly Gly Ser Val Leu Leu Val
        515                 520                 525

Ala Gly Gly Tyr Ser Gly Arg Pro Arg Gly Asp Leu Met Ala Tyr Lys
    530                 535                 540

Val Pro Pro Phe Val Phe Gln Ala Pro Ala Pro Asp Tyr His Leu Asp
545                 550                 555                 560

Tyr Cys Ser Met Tyr Thr Asp His Ser Val Cys Ser Arg Asp Pro Glu
```

-continued

```
                565                 570                 575

Cys Ser Trp Cys Gln Gly Ala Cys Gln Ala Ala Pro Pro Pro Gly Thr
            580                 585                 590

Pro Leu Gly Ala Cys Pro Ala Ala Ser Cys Leu Gly Leu Gly Arg Leu
        595                 600                 605

Leu Gly Asp Cys Gln Ala Cys Leu Ala Phe Ser Ser Pro Thr Ala Pro
    610                 615                 620

Pro Arg Gly Pro Gly Thr Leu Gly Trp Cys Val His Asn Glu Ser Cys
625                 630                 635                 640

Leu Pro Arg Pro Glu Gln Ala Arg Cys Arg Gly Glu Gln Ile Ser Gly
                645                 650                 655

Thr Val Gly Trp Trp Gly Pro Ala Pro Val Phe Val Thr Ser Leu Glu
            660                 665                 670

Ala Cys Val Thr Gln Ser Phe Leu Pro Gly Leu His Leu Leu Thr Phe
        675                 680                 685

Gln Gln Pro Pro Asn Thr Ser Gln Pro Asp Lys Val Ser Ile Val Arg
    690                 695                 700

Ser Thr Thr Ile Thr Leu Thr Pro Ser Ala Glu Thr Asp Val Ser Leu
705                 710                 715                 720

Val Tyr Arg Gly Phe Ile Tyr Pro Met Leu Pro Gly Gly Pro Gly Gly
                725                 730                 735

Pro Gly Ala Glu Asp Val Ala Val Trp Thr Arg Ala Gln Arg Leu His
            740                 745                 750

Val Leu Ala Arg Met Ala Arg Gly Pro Asp Thr Glu Asn Met Glu Glu
        755                 760                 765

Val Gly Arg Trp Val Ala His Gln Glu Lys Glu Thr Arg Arg Leu Gln
    770                 775                 780

Arg Pro Gly Ser Ala Arg Leu Phe Pro Leu Pro Gly Arg Asp His Lys
785                 790                 795                 800

Tyr Ala Val Glu Ile Gln Gly Gln Leu Asn Gly Ser Ala Gly Pro Gly
                805                 810                 815

His Ser Glu Leu Thr Leu Leu Trp Asp Arg Thr Gly Val Pro Gly Gly
            820                 825                 830

Ser Glu Ile Ser Phe Phe Phe Leu Glu Pro Tyr Arg Ser Ser Ser Cys
        835                 840                 845

Thr Ser Tyr Ser Ser Cys Leu Gly Cys Leu Ala Asp Gln Gly Cys Gly
    850                 855                 860

Trp Cys Leu Thr Ser Ala Thr Cys His Leu Arg Gln Gly Gly Ala His
865                 870                 875                 880

Cys Gly Asp Asp Gly Ala Gly Gly Ser Leu Leu Val Leu Val Pro Thr
                885                 890                 895

Leu Cys Pro Leu Cys Glu Glu His Arg Asp Cys His Ala Cys Thr Gln
            900                 905                 910

Asp Pro Phe Cys Glu Trp His Gln Ser Thr Ser Arg Lys Gly Asp Ala
        915                 920                 925

Ala Cys Ser Arg Arg Gly Arg Gly Arg Gly Ala Leu Lys Ser Pro Glu
    930                 935                 940

Glu Cys Pro Pro Leu Cys Ser Gln Arg Leu Thr Cys Glu Asp Cys Leu
945                 950                 955                 960

Ala Asn Ser Ser Gln Cys Ala Trp Cys Gln Ser Thr His Thr Cys Phe
                965                 970                 975

Leu Phe Ala Ala Tyr Leu Ala Arg Tyr Pro His Gly Gly Cys Arg Gly
            980                 985                 990
```

-continued

```
Trp Asp Asp Ser Val His Ser Glu  Pro Arg Cys Arg Ser  Cys Asp Gly
        995                 1000                 1005

Phe Leu  Thr Cys His Glu Cys  Leu Gln Ser His Glu  Cys Gly Trp
    1010                 1015                 1020

Cys Gly  Asn Glu Asp Asn Pro  Thr Leu Gly Arg Cys  Leu Gln Gly
    1025                 1030                 1035

Asp Phe  Ser Gly Pro Leu Gly  Gly Gly Asn Cys Ser  Leu Trp Val
    1040                 1045                 1050

Gly Glu  Gly Leu Gly Leu Pro  Val Ala Leu Pro Ala  Arg Trp Ala
    1055                 1060                 1065

Tyr Ala  Arg Cys Pro Asp Val  Asp Glu Cys Arg Leu  Gly Leu Ala
    1070                 1075                 1080

Arg Cys  His Pro Arg Ala Thr  Cys Leu Asn Thr Pro  Leu Ser Tyr
    1085                 1090                 1095

Glu Cys  His Cys Gln Arg Gly  Tyr Gln Gly Asp Gly  Ile Ser His
    1100                 1105                 1110

Cys Asn  Arg Thr Cys Leu Glu  Asp Cys Gly His Gly  Val Cys Ser
    1115                 1120                 1125

Gly Pro  Pro Asp Phe Thr Cys  Val Cys Asp Leu Gly  Trp Thr Ser
    1130                 1135                 1140

Asp Leu  Pro Pro Pro Thr Pro  Ala Pro Gly Pro Pro  Ala Pro Arg
    1145                 1150                 1155

Cys Ser  Arg Asp Cys Gly Cys  Ser Phe His Ser His  Cys Arg Lys
    1160                 1165                 1170

Arg Gly  Pro Gly Phe Cys Asp  Glu Cys Gln Asp Trp  Thr Trp Gly
    1175                 1180                 1185

Glu His  Cys Glu Arg Cys Arg  Pro Gly Ser Phe Gly  Asn Ala Thr
    1190                 1195                 1200

Gly Ser  Arg Gly Cys Arg Pro  Cys Gln Cys Asn Gly  His Gly Asp
    1205                 1210                 1215

Pro Arg  Arg Gly His Cys Asp  Asn Leu Ser Gly Leu  Cys Phe Cys
    1220                 1225                 1230

Gln Asp  His Thr Glu Gly Ala  His Cys Gln Leu Cys  Ser Pro Gly
    1235                 1240                 1245

Tyr Tyr  Gly Asp Pro Arg Ala  Gly Gly Ser Cys Phe  Arg Glu Cys
    1250                 1255                 1260

Gly Gly  Arg Ala Leu Leu Thr  Asn Val Ser Ser Val  Ala Leu Gly
    1265                 1270                 1275

Ser Arg  Arg Val Gly Gly Leu  Leu Pro Pro Gly Gly  Gly Ala Ala
    1280                 1285                 1290

Arg Ala  Gly Pro Gly Leu Ser  Tyr Cys Val Trp Val  Val Ser Ala
    1295                 1300                 1305

Thr Glu  Glu Leu Gln Pro Cys  Ala Pro Gly Thr Leu  Cys Pro Pro
    1310                 1315                 1320

Leu Thr  Leu Thr Phe Ser Pro  Asp Ser Ser Thr Pro  Cys Thr Leu
    1325                 1330                 1335

Ser Tyr  Val Leu Ala Phe Asp  Gly Phe Pro Arg Phe  Leu Asp Thr
    1340                 1345                 1350

Gly Val  Val Gln Ser Asp Arg  Ser Leu Ile Ala Ala  Phe Cys Gly
    1355                 1360                 1365

Gln Arg  Arg Asp Arg Pro Leu  Thr Val Gln Ala Leu  Ser Gly Leu
    1370                 1375                 1380
```

-continued

```
Leu Val  Leu His Trp Glu Ala  Asn Gly Ser Ser Ser  Trp Gly Phe
    1385                 1390                 1395

Asn Ala  Ser Val Gly Ser Ala  Arg Cys Gly Ser Gly  Gly Pro Gly
    1400                 1405                 1410

Ser Cys  Pro Val Pro Gln Glu  Cys Val Pro Gln Asp  Gly Ala Ala
    1415                 1420                 1425

Gly Ala  Gly Leu Cys Arg Cys  Pro Gln Gly Trp Ala  Gly Pro His
    1430                 1435                 1440

Cys Arg  Met Ala Leu Cys Pro  Glu Asn Cys Asn Ala  His Thr Gly
    1445                 1450                 1455

Ala Gly  Thr Cys Asn Gln Ser  Leu Gly Val Cys Ile  Cys Ala Glu
    1460                 1465                 1470

Gly Phe  Gly Gly Pro Asp Cys  Ala Thr Lys Leu Asp  Gly Gly Gln
    1475                 1480                 1485

Leu Val  Trp Glu Thr Leu Met  Asp Ser Arg Leu Ser  Ala Asp Thr
    1490                 1495                 1500

Ala Ser  Arg Phe Leu His Arg  Leu Gly His Thr Met  Val Asp Gly
    1505                 1510                 1515

Pro Asp  Ala Thr Leu Trp Met  Phe Gly Gly Leu Gly  Leu Pro Gln
    1520                 1525                 1530

Gly Leu  Leu Gly Asn Leu Tyr  Arg Tyr Ser Val Ser  Glu Arg Arg
    1535                 1540                 1545

Trp Thr  Gln Met Leu Ala Gly  Ala Glu Asp Gly Gly  Pro Gly Pro
    1550                 1555                 1560

Ser Pro  Arg Ser Phe His Ala  Ala Ala Tyr Val Pro  Ala Gly Arg
    1565                 1570                 1575

Gly Ala  Met Tyr Leu Leu Gly  Gly Leu Thr Ala Gly  Gly Val Thr
    1580                 1585                 1590

Arg Asp  Phe Trp Val Leu Asn  Leu Thr Thr Leu Gln  Trp Arg Gln
    1595                 1600                 1605

Glu Lys  Ala Pro Gln Thr Val  Glu Leu Pro Ala Val  Ala Gly His
    1610                 1615                 1620

Thr Leu  Thr Ala Arg Arg Gly  Leu Ser Leu Leu Leu  Val Gly Gly
    1625                 1630                 1635

Tyr Ser  Pro Glu Asn Gly Phe  Asn Gln Gln Leu Leu  Glu Tyr Gln
    1640                 1645                 1650

Leu Ala  Thr Gly Thr Trp Val  Ser Gly Ala Gln Ser  Gly Thr Pro
    1655                 1660                 1665

Pro Thr  Gly Leu Tyr Gly His  Ser Ala Val Tyr His  Glu Ala Thr
    1670                 1675                 1680

Asp Ser  Leu Tyr Val Phe Gly  Gly Phe Arg Phe His  Val Glu Leu
    1685                 1690                 1695

Ala Ala  Pro Ser Pro Glu Leu  Tyr Ser Leu His Cys  Pro Asp Arg
    1700                 1705                 1710

Thr Trp  Ser Leu Leu Ala Pro  Ser Gln Gly Ala Lys  Arg Asp Arg
    1715                 1720                 1725

Met Arg  Asn Val Arg Gly Ser  Ser Arg Gly Leu Gly  Gln Val Pro
    1730                 1735                 1740

Gly Glu  Gln Pro Gly Ser Trp  Gly Phe Arg Glu Val  Arg Lys Lys
    1745                 1750                 1755

Met Ala  Leu Trp Ala Ala Leu  Ala Gly Thr Gly Gly  Phe Leu Glu
    1760                 1765                 1770

Glu Ile  Ser Pro His Leu Lys  Glu Pro Arg Pro Arg  Leu Phe His
```

```
    1775                1780                1785

Ala Ser  Ala Leu Leu Gly Asp  Thr Met Val Val Leu  Gly Gly Arg
    1790                1795                1800

Ser Asp  Pro Asp Glu Phe Ser  Ser Asp Val Leu Leu  Tyr Gln Val
    1805                1810                1815

Asn Cys  Asn Ala Trp Leu Leu  Pro Asp Leu Thr Arg  Ser Ala Ser
    1820                1825                1830

Val Gly  Pro Pro Met Glu Glu  Ser Val Ala His Ala  Val Ala Ala
    1835                1840                1845

Val Gly  Ser Arg Leu Tyr Ile  Ser Gly Gly Phe Gly  Gly Val Ala
    1850                1855                1860

Leu Gly  Arg Leu Leu Ala Leu  Thr Leu Pro Pro Asp  Pro Cys Arg
    1865                1870                1875

Leu Leu  Ser Ser Pro Glu Ala  Cys Asn Gln Ser Gly  Ala Cys Thr
    1880                1885                1890

Trp Cys  His Gly Ala Cys Leu  Ser Gly Asp Gln Ala  His Arg Leu
    1895                1900                1905

Gly Cys  Gly Gly Ser Pro Cys  Ser Pro Met Pro Arg  Ser Pro Glu
    1910                1915                1920

Glu Cys  Arg Arg Leu Arg Thr  Cys Ser Glu Cys Leu  Ala Arg His
    1925                1930                1935

Pro Arg  Thr Leu Gln Pro Gly  Asp Gly Glu Ala Ser  Thr Pro Arg
    1940                1945                1950

Cys Lys  Trp Cys Thr Asn Cys  Pro Glu Gly Ala Cys  Ile Gly Arg
    1955                1960                1965

Asn Gly  Ser Cys Thr Ser Glu  Asn Asp Cys Arg Ile  Asn Gln Arg
    1970                1975                1980

Glu Val  Phe Trp Ala Gly Asn  Cys Ser Glu Ala Ala  Cys Gly Ala
    1985                1990                1995

Ala Asp  Cys Glu Gln Cys Thr  Arg Glu Gly Lys Cys  Met Trp Thr
    2000                2005                2010

Arg Gln  Phe Lys Arg Thr Gly  Glu Thr Arg Arg Ile  Leu Ser Val
    2015                2020                2025

Gln Pro  Thr Tyr Asp Trp Thr  Cys Phe Ser His Ser  Leu Leu Asn
    2030                2035                2040

Val Ser  Pro Met Pro Val Glu  Ser Ser Pro Pro Leu  Pro Cys Pro
    2045                2050                2055

Thr Pro  Cys His Leu Leu Pro  Asn Cys Thr Ser Cys  Leu Asp Ser
    2060                2065                2070

Lys Gly  Ala Asp Gly Gly Trp  Gln His Cys Val Trp  Ser Ser Ser
    2075                2080                2085

Leu Gln  Gln Cys Leu Ser Pro  Ser Tyr Leu Pro Leu  Arg Cys Met
    2090                2095                2100

Ala Gly  Gly Cys Gly Arg Leu  Leu Arg Gly Pro Glu  Ser Cys Ser
    2105                2110                2115

Leu Gly  Cys Ala Gln Ala Thr  Gln Cys Ala Leu Cys  Leu Arg Arg
    2120                2125                2130

Pro His  Cys Gly Trp Cys Ala  Trp Gly Gly Gln Asp  Gly Gly Gly
    2135                2140                2145

Arg Cys  Met Glu Gly Gly Leu  Ser Gly Pro Arg Asp  Gly Leu Thr
    2150                2155                2160

Cys Gly  Arg Pro Gly Ala Ser  Trp Ala Phe Leu Ser  Cys Pro Pro
    2165                2170                2175
```

Glu Asp Glu Cys Ala Asn Gly His His Asp Cys Asn Glu Thr Gln
2180 2185 2190

Asn Cys His Asp Gln Pro His Gly Tyr Glu Cys Ser Cys Lys Thr
2195 2200 2205

Gly Tyr Thr Met Asp Asn Met Thr Gly Leu Cys Arg Pro Val Cys
2210 2215 2220

Ala Gln Gly Cys Val Asn Gly Ser Cys Val Glu Pro Asp His Cys
2225 2230 2235

Arg Cys His Phe Gly Phe Val Gly Arg Asn Cys Ser Thr Glu Cys
2240 2245 2250

Arg Cys Asn Arg His Ser Glu Cys Ala Gly Val Gly Ala Arg Asp
2255 2260 2265

His Cys Leu Leu Cys Arg Asn His Thr Lys Gly Ser His Cys Glu
2270 2275 2280

Gln Cys Leu Pro Leu Phe Val Gly Ser Ala Val Gly Gly Gly Thr
2285 2290 2295

Cys Arg Pro Cys His Ala Phe Cys Arg Gly Asn Ser His Ile Cys
2300 2305 2310

Ile Ser Arg Lys Glu Leu Gln Met Ser Lys Gly Glu Pro Lys Lys
2315 2320 2325

Tyr Ser Leu Asp Pro Glu Glu Ile Glu Asn Trp Val Thr Glu Gly
2330 2335 2340

Pro Ser Glu Asp Glu Ala Val Cys Val Asn Cys Gln Asn Asn Ser
2345 2350 2355

Tyr Gly Glu Lys Cys Glu Ser Cys Leu Gln Gly Tyr Phe Leu Leu
2360 2365 2370

Asp Gly Lys Cys Thr Lys Cys Gln Cys Asn Gly His Ala Asp Thr
2375 2380 2385

Cys Asn Glu Gln Asp Gly Thr Gly Cys Pro Cys Gln Asn Asn Thr
2390 2395 2400

Glu Thr Gly Thr Cys Gln Gly Ser Ser Pro Ser Asp Arg Arg Asp
2405 2410 2415

Cys Tyr Lys Tyr Gln Cys Ala Lys Cys Arg Glu Ser Phe His Gly
2420 2425 2430

Ser Pro Leu Gly Gly Gln Gln Cys Tyr Arg Leu Ile Ser Val Glu
2435 2440 2445

Gln Glu Cys Cys Leu Asp Pro Thr Ser Gln Thr Asn Cys Phe His
2450 2455 2460

Glu Pro Lys Arg Arg Ala Leu Gly Pro Gly Arg Thr Val Leu Phe
2465 2470 2475

Gly Val Gln Pro Lys Phe Thr Asn Val Asp Ile Arg Leu Thr Leu
2480 2485 2490

Asp Val Thr Phe Gly Ala Val Asp Leu Tyr Val Ser Thr Ser Tyr
2495 2500 2505

Asp Thr Phe Val Val Arg Val Ala Pro Asp Thr Gly Val His Thr
2510 2515 2520

Val His Ile Gln Pro Pro Pro Ala Pro Pro Pro Pro Pro Pro Pro
2525 2530 2535

Ala Asp Gly Gly Pro Arg Gly Ala Gly Asp Pro Gly Gly Ala Gly
2540 2545 2550

Ala Ser Ser Gly Pro Gly Ala Pro Ala Glu Pro Arg Val Arg Glu
2555 2560 2565

-continued

Val Trp Pro Arg Gly Leu Ile Thr Tyr Val Thr Val Thr Glu Pro
2570 2575 2580

Ser Ala Val Leu Val Val Arg Gly Val Arg Asp Arg Leu Val Ile
2585 2590 2595

Thr Tyr Pro His Glu His His Ala Leu Lys Ser Ser Arg Phe Tyr
2600 2605 2610

Leu Leu Leu Leu Gly Val Gly Asp Pro Ser Gly Pro Gly Ala Asn
2615 2620 2625

Gly Ser Ala Asp Ser Gln Gly Leu Leu Phe Phe Arg Gln Asp Gln
2630 2635 2640

Ala His Ile Asp Leu Phe Val Phe Phe Ser Val Phe Phe Ser Cys
2645 2650 2655

Phe Phe Leu Phe Leu Ser Leu Cys Val Leu Leu Trp Lys Ala Lys
2660 2665 2670

Gln Ala Leu Asp Gln Arg Gln Glu Gln Arg Arg His Leu Gln Glu
2675 2680 2685

Met Thr Lys Met Ala Ser Arg Pro Phe Ala Lys Val Thr Val Cys
2690 2695 2700

Phe Pro Pro Asp Pro Thr Ala Pro Ala Ser Ala Trp Lys Pro Ala
2705 2710 2715

Gly Leu Pro Pro Pro Ala Phe Arg Arg Ser Glu Pro Phe Leu Ala
2720 2725 2730

Pro Leu Leu Leu Thr Gly Ala Gly Gly Pro Trp Gly Pro Met Gly
2735 2740 2745

Gly Gly Cys Cys Pro Pro Ala Ile Pro Ala Thr Thr Ala Gly Leu
2750 2755 2760

Arg Ala Gly Pro Ile Thr Leu Glu Pro Thr Glu Asp Gly Met Ala
2765 2770 2775

Gly Val Ala Thr Leu Leu Leu Gln Leu Pro Gly Gly Pro His Ala
2780 2785 2790

Pro Asn Gly Ala Cys Leu Gly Ser Ala Leu Val Thr Leu Arg His
2795 2800 2805

Arg Leu His Glu Tyr Cys Gly Gly Gly Gly Gly Ala Gly Gly Ser
2810 2815 2820

Gly His Gly Thr Gly Ala Gly Arg Lys Gly Leu Leu Ser Gln Asp
2825 2830 2835

Asn Leu Thr Ser Met Ser Leu
2840 2845

<210> SEQ ID NO 39
<211> LENGTH: 586
<212> TYPE: PRT
<213> ORGANISM: Homo sapiens

<400> SEQUENCE: 39

Met Ala Glu Gly Val Pro Ala Ser Pro Ser Ser Gly Glu Gly Ser Arg
1 5 10 15

Gly Pro His Ser Gly Val Ile Gln Trp Leu Val Asp Asn Phe Cys Ile
20 25 30

Cys Glu Glu Cys Ser Val Pro Arg Cys Leu Met Tyr Glu Ile Tyr Val
35 40 45

Glu Thr Cys Gly Gln Asn Thr Glu Asn Gln Val Asn Pro Ala Thr Phe
50 55 60

Gly Lys Leu Val Arg Leu Val Phe Pro Asp Leu Gly Thr Arg Arg Leu
65 70 75 80

```
Gly Thr Arg Gly Ser Ala Arg Tyr His Tyr Asp Gly Ile Cys Ile Lys
                85                  90                  95

Lys Ser Ser Phe Phe Tyr Ala Gln Tyr Cys Tyr Leu Ile Gly Glu Lys
            100                 105                 110

Arg Tyr His Ser Gly Asp Ala Ile Ala Phe Glu Lys Ser Thr Asn Tyr
        115                 120                 125

Asn Ser Ile Ile Gln Gln Glu Ala Thr Cys Glu Asp His Ser Pro Met
    130                 135                 140

Lys Thr Asp Pro Val Gly Ser Pro Leu Ser Glu Phe Arg Arg Cys Pro
145                 150                 155                 160

Phe Leu Glu Gln Glu Gln Ala Lys Lys Tyr Ser Cys Asn Met Met Ala
                165                 170                 175

Phe Leu Ala Asp Glu Tyr Cys Asn Tyr Cys Arg Asp Ile Leu Arg Asn
            180                 185                 190

Val Glu Asp Leu Leu Thr Ser Phe Trp Lys Ser Leu Gln Gln Asp Thr
        195                 200                 205

Val Met Leu Met Ser Leu Pro Asp Val Cys Gln Leu Phe Lys Cys Tyr
    210                 215                 220

Asp Val Gln Leu Tyr Lys Gly Ile Glu Asp Val Leu Leu His Asp Phe
225                 230                 235                 240

Leu Glu Asp Val Ser Ile Gln Tyr Leu Lys Ser Val Gln Leu Phe Ser
                245                 250                 255

Lys Lys Phe Lys Leu Trp Leu Leu Asn Ala Leu Glu Gly Val Pro Ala
            260                 265                 270

Leu Leu Gln Ile Ser Lys Leu Lys Glu Val Thr Leu Phe Val Lys Arg
        275                 280                 285

Leu Arg Arg Lys Thr Tyr Leu Ser Asn Met Ala Lys Thr Met Arg Met
    290                 295                 300

Val Leu Lys Ser Lys Arg Arg Val Ser Val Leu Lys Ser Asp Leu Gln
305                 310                 315                 320

Ala Ile Ile Asn Gln Gly Thr Leu Ala Thr Ser Lys Lys Ala Leu Ala
                325                 330                 335

Ser Asp Arg Ser Gly Ala Asp Glu Leu Glu Asn Asn Pro Glu Met Lys
            340                 345                 350

Cys Leu Arg Asn Leu Ile Ser Leu Leu Gly Thr Ser Thr Asp Leu Arg
        355                 360                 365

Val Phe Leu Ser Cys Leu Ser Ser His Leu Gln Ala Phe Val Phe Gln
    370                 375                 380

Thr Ser Arg Ser Lys Glu Glu Phe Thr Lys Leu Ala Ala Ser Phe Gln
385                 390                 395                 400

Leu Arg Trp Asn Leu Leu Leu Thr Ala Val Ser Lys Ala Met Thr Leu
                405                 410                 415

Cys His Arg Asp Ser Phe Gly Ser Trp His Leu Phe His Leu Leu Leu
            420                 425                 430

Leu Glu Tyr Met Ile His Ile Leu Gln Ser Cys Leu Glu Glu Glu Glu
        435                 440                 445

Glu Glu Glu Asp Met Gly Thr Val Lys Glu Met Leu Pro Asp Asp Pro
    450                 455                 460

Thr Leu Gly Gln Pro Asp Gln Ala Leu Phe His Ser Leu Asn Ser Ser
465                 470                 475                 480

Leu Ser Gln Ala Cys Ala Ser Pro Ser Met Glu Pro Leu Gly Val Met
                485                 490                 495
```

```
Pro Thr His Met Gly Gln Gly Arg Tyr Pro Val Gly Val Ser Asn Met
            500                 505                 510

Val Leu Arg Ile Leu Gly Phe Leu Val Asp Thr Ala Met Gly Asn Lys
        515                 520                 525

Leu Ile Gln Val Leu Leu Glu Asp Glu Thr Thr Glu Ser Ala Val Lys
    530                 535                 540

Leu Ser Leu Pro Met Gly Gln Glu Ala Leu Ile Thr Leu Lys Asp Gly
545                 550                 555                 560

Gln Gln Phe Val Ile Gln Ile Ser Asp Val Pro Gln Ser Ser Glu Asp
                565                 570                 575

Ile Tyr Phe Arg Glu Asn Asn Ala Asn Val
            580                 585


<210> SEQ ID NO 40
<211> LENGTH: 459
<212> TYPE: PRT
<213> ORGANISM: Homo sapiens

<400> SEQUENCE: 40

Met Glu Gly Ser Ala Ser Pro Pro Glu Lys Pro Arg Ala Arg Pro Ala
1               5                   10                  15

Ala Ala Val Leu Cys Arg Gly Pro Val Glu Pro Leu Val Phe Leu Ala
            20                  25                  30

Asn Phe Ala Leu Val Leu Gln Gly Pro Leu Thr Thr Gln Tyr Leu Trp
        35                  40                  45

His Arg Phe Ser Ala Asp Leu Gly Tyr Asn Gly Thr Arg Gln Arg Gly
    50                  55                  60

Gly Cys Ser Asn Arg Ser Ala Asp Pro Thr Met Gln Glu Val Glu Thr
65                  70                  75                  80

Leu Thr Ser His Trp Thr Leu Tyr Met Asn Val Gly Gly Phe Leu Val
                85                  90                  95

Gly Leu Phe Ser Ser Thr Leu Leu Gly Ala Trp Ser Asp Ser Val Gly
            100                 105                 110

Arg Arg Pro Leu Leu Val Leu Ala Ser Leu Gly Leu Leu Leu Gln Ala
        115                 120                 125

Leu Val Ser Val Phe Val Val Gln Leu Gln Leu His Val Gly Tyr Phe
    130                 135                 140

Val Leu Gly Arg Ile Leu Cys Ala Leu Leu Gly Asp Phe Gly Gly Leu
145                 150                 155                 160

Leu Ala Ala Ser Phe Ala Ser Val Ala Asp Val Ser Ser Ser Arg Ser
                165                 170                 175

Arg Thr Phe Arg Met Ala Leu Leu Glu Ala Ser Ile Gly Val Ala Gly
            180                 185                 190

Met Leu Ala Ser Leu Leu Gly Gly His Trp Leu Arg Ala Gln Gly Tyr
        195                 200                 205

Ala Asn Pro Phe Trp Leu Ala Leu Ala Leu Leu Ile Ala Met Thr Leu
    210                 215                 220

Tyr Ala Ala Phe Cys Phe Gly Glu Thr Leu Lys Glu Pro Lys Ser Thr
225                 230                 235                 240

Arg Leu Phe Thr Phe Arg His His Arg Ser Ile Val Gln Leu Tyr Val
                245                 250                 255

Ala Pro Ala Pro Glu Lys Ser Arg Lys His Leu Ala Leu Tyr Ser Leu
            260                 265                 270

Ala Ile Phe Val Val Ile Thr Val His Phe Gly Ala Gln Asp Ile Leu
        275                 280                 285
```

```
Thr Leu Tyr Glu Leu Ser Thr Pro Leu Cys Trp Asp Ser Lys Leu Ile
    290                 295                 300

Gly Tyr Gly Ser Ala Ala Gln His Leu Pro Tyr Leu Thr Ser Leu Leu
305                 310                 315                 320

Ala Leu Lys Leu Leu Gln Tyr Cys Leu Ala Asp Ala Trp Val Ala Glu
                325                 330                 335

Ile Gly Leu Ala Phe Asn Ile Leu Gly Met Val Val Phe Ala Phe Ala
            340                 345                 350

Thr Ile Thr Pro Leu Met Phe Thr Gly Tyr Gly Leu Leu Phe Leu Ser
        355                 360                 365

Leu Val Ile Thr Pro Val Ile Arg Ala Lys Leu Ser Lys Leu Val Arg
    370                 375                 380

Glu Thr Glu Gln Gly Ala Leu Phe Ser Ala Val Ala Cys Val Asn Ser
385                 390                 395                 400

Leu Ala Met Leu Thr Ala Ser Gly Ile Phe Asn Ser Leu Tyr Pro Ala
                405                 410                 415

Thr Leu Asn Phe Met Lys Gly Phe Pro Phe Leu Leu Gly Ala Gly Leu
            420                 425                 430

Leu Leu Ile Pro Ala Val Leu Ile Gly Met Leu Glu Lys Ala Asp Pro
        435                 440                 445

His Leu Glu Phe Gln Gln Phe Pro Gln Ser Pro
    450                 455
```

```
<210> SEQ ID NO 41
<211> LENGTH: 173
<212> TYPE: PRT
<213> ORGANISM: Homo sapiens

<400> SEQUENCE: 41

Met His Trp Lys Met Leu Leu Leu Leu Leu Leu Tyr Tyr Asn Ala Glu
1               5                   10                  15

Ala Ser Met Cys His Arg Trp Ser Arg Ala Val Leu Phe Pro Ala Ala
            20                  25                  30

His Arg Pro Lys Arg Ser Ser Ser Leu Pro Leu Asn Pro Val Leu Gln
        35                  40                  45

Thr Ser Leu Glu Glu Val Glu Leu Leu Tyr Glu Phe Leu Leu Ala Glu
    50                  55                  60

Leu Glu Ile Ser Pro Asp Leu Gln Ile Ser Ile Lys Asp Glu Glu Leu
65                  70                  75                  80

Ala Ser Leu Arg Lys Ala Ser Asp Phe Arg Thr Val Cys Asn Asn Val
                85                  90                  95

Ile Pro Lys Ser Ile Pro Asp Ile Arg Arg Leu Ser Ala Ser Leu Ser
            100                 105                 110

Ser His Pro Gly Ile Leu Lys Lys Glu Asp Phe Glu Arg Thr Val Leu
        115                 120                 125

Thr Leu Ala Tyr Thr Ala Tyr Arg Thr Ala Leu Ser His Gly His Gln
    130                 135                 140

Lys Asp Ile Trp Ala Gln Ser Leu Val Ser Leu Phe Gln Ala Leu Arg
145                 150                 155                 160

His Asp Leu Met Arg Ser Ser Gln Pro Gly Val Pro Pro
                165                 170
```

```
<210> SEQ ID NO 42
<211> LENGTH: 245
<212> TYPE: PRT
```

<213> ORGANISM: Homo sapiens

<400> SEQUENCE: 42

Met Thr Leu Phe Pro Val Leu Leu Phe Leu Val Ala Gly Leu Leu Pro
1 5 10 15

Ser Phe Pro Ala Asn Glu Asp Lys Asp Pro Ala Phe Thr Ala Leu Leu
20 25 30

Thr Thr Gln Thr Gln Val Gln Arg Glu Ile Val Asn Lys His Asn Glu
35 40 45

Leu Arg Arg Ala Val Ser Pro Pro Ala Arg Asn Met Leu Lys Met Glu
50 55 60

Trp Asn Lys Glu Ala Ala Ala Asn Ala Gln Lys Trp Ala Asn Gln Cys
65 70 75 80

Asn Tyr Arg His Ser Asn Pro Lys Asp Arg Met Thr Ser Leu Lys Cys
85 90 95

Gly Glu Asn Leu Tyr Met Ser Ser Ala Ser Ser Ser Trp Ser Gln Ala
100 105 110

Ile Gln Ser Trp Phe Asp Glu Tyr Asn Asp Phe Asp Phe Gly Val Gly
115 120 125

Pro Lys Thr Pro Asn Ala Val Val Gly His Tyr Thr Gln Val Val Trp
130 135 140

Tyr Ser Ser Tyr Leu Val Gly Cys Gly Asn Ala Tyr Cys Pro Asn Gln
145 150 155 160

Lys Val Leu Lys Tyr Tyr Tyr Val Cys Gln Tyr Cys Pro Ala Gly Asn
165 170 175

Trp Ala Asn Arg Leu Tyr Val Pro Tyr Glu Gln Gly Ala Pro Cys Ala
180 185 190

Ser Cys Pro Asp Asn Cys Asp Asp Gly Leu Cys Thr Asn Gly Cys Lys
195 200 205

Tyr Glu Asp Leu Tyr Ser Asn Cys Lys Ser Leu Lys Leu Thr Leu Thr
210 215 220

Cys Lys His Gln Leu Val Arg Asp Ser Cys Lys Ala Ser Cys Asn Cys
225 230 235 240

Ser Asn Ser Ile Tyr
245

<210> SEQ ID NO 43
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 43

Lys Lys Ser Arg Gly Asp Tyr Met Thr Met Gln Ile Gly
1 5 10

<210> SEQ ID NO 44
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 44

Gly Gly Met Glu Asp Ile Tyr Phe Glu Phe Met Gly Gly Lys Lys Lys
1 5 10 15

-continued

```
<210> SEQ ID NO 45
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 45

Lys Lys Lys Gly Gln Glu Glu Glu Tyr Val Phe Ile Glu
1               5                   10
```

COMPOUNDS FOR THE TREATMENT OF KINASE-DEPENDENT DISORDERS

CROSS-REFERENCE TO RELATED APPLICATIONS

This application is a United States National Phase filing of PCT/US2019/015297, filed Jan. 25, 2019, which claims the benefit of priority to U.S. Provisional Application No. 62/622,702, filed Jan. 26, 2018 and U.S. Provisional Application No. 62/758,321, filed Nov. 9, 2018, the entire contents of which are incorporated herein by reference.

FIELD OF THE INVENTION

The invention relates to compounds that modulate cellular activities such as proliferation, differentiation, programmed cell death, migration, and chemoinvasion by modulating protein kinase enzymatic activity. Even more specifically, the invention relates to compounds which inhibit, regulate, and/or modulate Axl and Mer receptor tyrosine kinases, compositions which contain these compounds, methods of using them to treat kinase-dependent diseases and conditions, synthesis of the compounds, and processes for formulating the compounds for pharmaceutical purposes.

BACKGROUND OF THE INVENTION

Human Axl belongs to the TAM subfamily of receptor tyrosine kinases that includes Mer. TAM kinases are characterized by an extracellular ligand binding domain consisting of two immunoglobulin-like domains and two fibronectin type III domains. Axl is overexpressed in a number of tumor cell types and was initially cloned from patients with chronic myelogenous leukemia. When overexpressed, Axl exhibits transforming potential. Axl signaling is believed to cause tumor growth through activation of proliferative and anti-apoptotic signaling pathways. Axl has been associated with cancers such as lung cancer, myeloid leukemia, uterine cancer, ovarian cancer, gliomas, melanoma, thyroid cancer, renal cell carcinoma, osteosarcoma, gastric cancer, prostate cancer, and breast cancer. The over-expression of Axl results in a poor prognosis for patients with the indicated cancers.

Activation of Mer, like Axl, conveys downstream signaling pathways that cause tumor growth and activation. Mer binds ligands such as the soluble protein Gas-6. Gas-6 binding to Mer induces autophosphorylation of Mer on its intracellular domain, resulting in downstream signal activation. Over-expression of Mer in cancer cells leads to increased metastasis, most likely by generation of soluble Mer extracellular domain protein as a decoy receptor. Tumor cells secrete a soluble form of the extracellular Mer receptor which reduces the ability of soluble Gas-6 ligand to activate Mer on endothelial cells, leading to cancer progression.

Therefore a need exists for compounds that inhibit TAM receptor tyrosine kinases such as Axl and Mer for the treatment of selected cancers.

SUMMARY OF THE INVENTION

In one aspect, the present invention provides a compound of formula I:

I

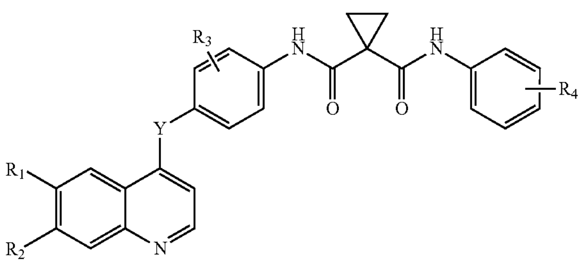

or a pharmaceutically acceptable salt thereof, wherein:

$R_1$ is selected from the group consisting of —H, —CN, —CO—$NR_5R_6$, —$CO_2R_7$, optionally substituted aryl, optionally substituted heteroaryl, optionally substituted ($C_1$-$C_6$) alkyl, optionally substituted ($C_3$-$C_8$) cycloalkyl, optionally substituted ($C_3$-$C_6$) heterocycloalkyl, —$SO_2NR_8R_9$, and —($SO_2$)—($C_1$-$C_6$) alkyl;

wherein when $R_1$ is selected from the group consisting of —CN, —CO—$NR_5R_6$, —$CO_2R_7$, optionally substituted aryl, optionally substituted heteroaryl, optionally substituted ($C_3$-$C_8$) cycloalkyl, optionally substituted ($C_3$-$C_6$) heterocycloalkyl, —$SO_2NR_8R_9$, and —($SO_2$)—($C_1$-$C_6$) alkyl, $R_2$ is —H, halo, —$NR_5R_6$, or optionally substituted ($C_1$-$C_6$) alkoxy;

wherein when $R_1$ is —H, optionally substituted ($C_1$-$C_6$) alkyl, or optionally substituted ($C_1$-$C_6$) alkoxy, $R_2$ is —CO—$NR_5R_6$; or —$CO_2R_7$;

or $R_1$ and $R_2$ taken together with the atoms to which they are attached to form optionally substituted cycloalkyl or optionally substituted heterocyloalkyl;

$R_3$ is selected from the group consisting of —H, optionally substituted ($C_1$-$C_6$) alkyl, —CN, and halo;

$R_4$ is —H or halo;

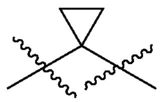 [SMILES: *C1(*)CC1]

is optionally substituted with one, two, three, or four groups independently selected from the group consisting of halo and ($C_1$-$C_6$) alkyl, wherein "∿∿∿" indicate points of attachment;

$R_5$ and $R_6$ are each independently —H, optionally substituted ($C_1$-$C_6$) alkyl, or optionally substituted ($C_1$-$C_6$) alkoxy;

$R_7$ is —H or optionally substituted ($C_1$-$C_6$) alkyl $R_8$ and $R_9$ are each independently —H or optionally substituted ($C_1$-$C_6$) alkyl;

or $R_8$ and $R_9$ may connect to form an optionally substituted heterocycle; and Y is selected from the group consisting of O, S, SO, $SO_2$, NH, and N—($C_1$-$C_6$ alkyl).

Another aspect provides a compound of formula A:

A

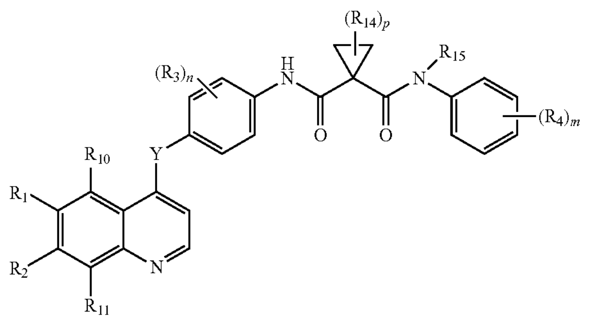

or a pharmaceutically acceptable salt thereof, wherein (i) $R_1$ is selected from the group consisting of ($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, 4-10 membered heterocycloalkyl, —CN, —NHOH, —C(O)$R^a$, —C(O)$NR^aR^a$, —C(O)NHO$R^a$, —C(O)O$R^a$, —C(O)$NR^aS(O)_2R^a$, —OC(O)$NR^aR^a$, C(═$NR^a$)$R^a$, —C(═NOH)$R^a$, —C(═NOH)$NR^a$, —C(═NCN)$NR^aR^a$, —C(═$NR^a$)$NR^aR^a$, —S(O)$NR^aR^a$, —$S(O)_2NR^a$C(O)$R^a$, —P(O)$R^aR^a$, —P(O)($OR^a$)($OR^a$), —$B(OH)_2$, —$B(OR^a)_2$, and $S(O)_2NR^aR^a$; and $R_2$ is selected from —H, halo, ($C_1$-$C_6$) alkyl, ($C_2$-$C_6$) alkenyl, ($C_2$-$C_6$) alkynyl, ($C_1$-$C_6$) haloalkyl, ($C_1$-$C_6$) haloalkoxy, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, (4-14 membered heterocycloalkyl)-($C_1$-$C_4$) alkylene-, —CN, —$NO_2$, —$OR^a$, —NHO$R^a$, —C(O)$R^a$, —C(O)$NR^aR^a$, —C(O)NHO$R^a$, —C(O)O$R^a$, —C(O)$NR^aS(O)_2R^a$, —OC(O)$R^a$, —OC(O)$NR^aR^a$, —NH$R^a$, —$NR^aR^a$, —$NR^a$C(O)$R^a$, —$NR^a$C(═$NR^a$)$R^a$, —$NR^a$C(O)O$R^a$, —$NR^a$C(O)$NR^aR^a$, —C(═$NR^a$)$R^a$, —C(═NOH)$R^a$, —C(═NOH)$NR^a$, —C(═NCN)$NR^aR^a$, —$NR^a$C(═NCN)$NR^aR^a$, —C(═$NR^a$)$NR^aR^a$, —$NR^a$C(═$NR^a$)$NR^aR^a$, —$NR^a$S(O)$R^a$, —$NR^aS(O)_2R^a$, —$NR^aS(O)_2NR^aR^a$, —S(O)$R^a$, —S(O)$NR^aR^a$, —$S(O)_2R^a$, —$S(O)_2NR^a$C(O)$R^a$, —P(O)$R^aR^a$, —P(O)($OR^a$)($OR^a$), —$B(OH)_2$, —$B(OR^a)_2$, and —$S(O)_2NR^aR^a$, wherein the ($C_1$-$C_6$) alkyl, ($C_2$-$C_6$) alkenyl, ($C_2$-$C_6$) alkynyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, and (4-14 membered heterocycloalkyl)-($C_1$-$C_4$) alkylene- of $R_1$ or $R_2$ are each optionally substituted with 1, 2, 3, 4, or 5 independently selected $R^b$ substituents, provided when $R_1$ is 5-7 membered heteroaryl or 5-7 membered heterocycloalkyl and $R_2$ is $C_{1-6}$ alkoxy, then the 5-7 membered heteroaryl or 5-7 membered heterocycloalkyl does not connect to the fused phenyl ring of the quinoline moiety through a ring nitrogen atom; or (ii) $R_1$ is selected from —H, halo, ($C_1$-$C_6$) alkyl, ($C_2$-$C_6$) alkenyl, ($C_2$-$C_6$) alkynyl, ($C_1$-$C_6$) haloalkyl, ($C_1$-$C_6$)haloalkoxy, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, (4-14 membered heterocycloalkyl)-($C_1$-$C_4$) alkylene-, —CN, —$NO_2$, —$OR^a$, —$SR^a$, —NHO$R^a$, —C(O)$R^a$, —C(O)$NR^aR^a$, —C(O)NHO$R^a$, —C(O)O$R^a$, —C(O)$NR^aS(O)_2R^a$, —OC(O)$R^a$, —OC(O)$NR^aR^a$, —NH$R^a$, —$NR^aR^a$, —$NR^a$C(O)$R^a$, —$NR^a$C(═$NR^a$)$R^a$, —$NR^a$C(O)O$R^a$, —$NR^a$C(O)$NR^aR^a$, —C(═$NR^a$)$R^a$, —C(═NOH)$R^a$, —C(═NOH)$NR^a$, —C(═NCN)$NR^aR^a$, —$NR^a$C(═NCN)$NR^aR^a$, —C(═$NR^a$)$NR^aR^a$, —$NR^a$C(═$NR^a$)$NR^aR^a$, —$NR^a$S(O)$R^a$, —$NR^aS(O)_2R^a$, —$NR^aS(O)_2NR^aR^a$, —S(O)$R^a$, —S(O)$NR^aR^a$, —$S(O)_2R^a$, —$S(O)_2NR^a$C(O)$R^a$, —P(O)$R^aR^a$, —P(O)($OR^a$)($OR^a$), —$B(OH)_2$, —$B(OR^a)_2$, and —$S(O)_2NR^aR^a$, wherein the ($C_1$-$C_6$) alkyl, ($C_2$-$C_6$) alkenyl, ($C_2$-$C_6$) alkynyl, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, and (4-14 membered heterocycloalkyl)-($C_1$-$C_4$) alkylene- of $R_1$ or $R_2$ are each optionally substituted with 1, 2, 3, 4, or 5 independently selected $R^b$ substituents; and $R_2$ is selected from the group consisting of ($C_2$-$C_6$) alkenyl, ($C_2$-$C_6$) alkynyl, —CN, —NHOH, —C(O)$R^a$, —C(O)$NR^aR^a$, —C(O)NHO$R^a$, —C(O)O$R^a$, —C(O)$NR^aS(O)_2R^a$, —OC(O)$NR^aR^a$, C(═$NR^a$)$R^a$, —C(═NOH)$R^a$, —C(═NOH)$NR^a$, —C(═NCN)$NR^aR^a$, —$NR^a$C(═NCN)$NR^aR^a$, —C(═$NR^a$)$NR^aR^a$, —S(O)$NR^aR^a$, —$S(O)_2NR^a$C(O)$R^a$, —P(O)$R^aR^a$, —P(O)($OR^a$)($OR^a$), —$B(OH)_2$, —$B(OR^a)_2$, and $S(O)_2NR^aR^a$, provided when $R_1$ is 5-7 membered heteroaryl or 5-7 membered heterocycloalkyl and $R_2$ is $C_{1-6}$ alkoxy, then the 5-7 membered heteroaryl or 5-7 membered heterocycloalkyl of $R_1$ does not connect to the fused phenyl ring of the quinoline moiety through a ring nitrogen atom, (iii) $R_1$ and $R_2$ taken together with the atoms to which they are attached form a fused ($C_3$-$C_7$) cycloalkyl ring or a fused 4- to 10-membered heterocycloalkyl ring, wherein the fused ($C_3$-$C_7$) cycloalkyl ring and fused 4- to 10-membered heterocycloalkyl ring are each optionally substituted with 1, 2, or 3 independently selected $R^b$ substituents, provided that the compound is not 1-[2-(4-Fluoro-phenyl)-acetyl]-cyclopropanecarboxylic acid [3-fluoro-4-(7,8,10,11,13,14-hexahydro-6,9,12,15-tetraoxa-1-aza-cyclododeca[b]naphthalen-4-yloxy)-phenyl]-amide;

$R_{10}$ and $R_{11}$ are each independently selected from the group consisting of —H, halo, ($C_1$-$C_6$) alkyl, ($C_1$-$C_6$) haloalkyl, ($C_1$-$C_6$) haloalkoxy, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, (4-14 membered heterocycloalkyl)-($C_1$-$C_4$) alkylene-, —CN, —$NO_2$, —$OR^a$, —$SR^a$, —NHO$R^a$, —C(O)$R^a$, —C(O)$NR^aR^a$, —C(O)O$R^a$, —C(O)$NR^aS(O)_2R^a$, —OC(O)$R^a$, —OC(O)$NR^aR^a$, —$NR^aR^a$, —$NR^a$C(O)$R^a$, —$NR^a$C(═$NR^a$)$R^a$, —$NR^a$C(O)O$R^a$, —$NR^a$C(O)NR-$^aR^a$, —C(═$NR^a$)$R^a$, —C(═NOH)$R^a$, —C(═NOH)$NR^a$, —C(═NCN)$NR^aR^a$, —$NR^a$C(═NCN)$NR^aR^a$, —C(═$NR^a$)$NR^aR^a$, —$NR^a$C(═$NR^a$)$NR^aR^a$, —$NR^a$S(O)$R^a$, —$NR^aS(O)_2R^a$, —$NR^aS(O)_2NR^aR^a$, —S(O)$R^a$, —S(O)$NR^aR^a$, —$S(O)_2R^a$, —$S(O)_2NR^a$C(O)$R^a$, —P(O)$R^aR^a$, —P(O)($OR^a$)($OR^a$), —$B(OH)_2$, —$B(OR^a)_2$, and $S(O)_2NR^aR^a$, wherein the ($C_1$-$C_6$) alkyl, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, and (4-14 membered heterocycloalkyl)-($C_1$-$C_4$) alkylene- of $R_1$ or $R_2$ are each optionally substituted with 1, 2, 3, 4, or 5 independently selected $R^b$ substituents;

each $R_3$ is independently selected from the group consisting of —H, halo, —OH, —CN, optionally substituted ($C_1$-$C_6$) alkyl, ($C_1$-$C_6$) alkoxy, ($C_1$-$C_6$) haloalkoxy, —$NH_2$, —NH($C_1$-$C_6$)alkyl, —N($C_1$-$C_6$ alkyl)$_2$, and ($C_3$-$C_6$) cycloalkyl, wherein the ($C_1$-$C_6$) alkoxy, —NH($C_1$-$C_6$)alkyl, —N($C_1$-$C_6$ alkyl)$_2$, and ($C_3$-$C_6$) cycloalkyl of $R_3$ are each optionally substituted with 1, 2, or 3 independently selected $R^g$ substituents;

each $R_{14}$ is independently selected from the group consisting of halo, —OH, —$NH_2$, —CN, ($C_1$-$C_6$) alkyl, ($C_1$-$C_6$) alkoxy, ($C_1$-$C_6$) haloalkyl, ($C_1$-$C_6$) haloalkoxy, —COOH, —NH($C_1$-$C_6$)alkyl, —N($C_1$-$C_6$ alkyl)$_2$, phenyl, phenyl-($C_1$-$C_2$) alkylene, ($C_3$-$C_6$) cycloalkyl, ($C_3$-$C_6$) cycloalkyl-($C_1$-$C_4$) alkylene-, 4- to 6-membered heterocycloalkyl, (4- to 6-membered heterocycloalkyl)-($C_1$-$C_4$) alkylene-, 5- to 6-membered heteroaryl, (5- to 6-membered heteroaryl)-($C_1$-$C_4$) alkylene-, and —$OR^e$, wherein the ($C_1$-$C_6$) alkyl, phenyl, phenyl-($C_1$-$C_2$) alkylene, ($C_3$-$C_6$) cycloalkyl, ($C_3$-$C_6$) cycloalkyl-($C_1$-$C_4$) alkylene-, 4- to 6-membered heterocycloalkyl, (4- to 6-membered heterocycloalkyl)-($C_1$-$C_4$) alkylene-, 5- to 6-membered heteroaryl, and (5- to 6-membered heteroaryl)-($C_1$-$C_4$) alkylene- of $R_{14}$ are each optionally substituted with 1, 2, or 3 independently selected $R^g$ substituents, $R_{15}$ is H or $C_{1-6}$ alkyl;

each $R_4$ is independently selected from the group consisting of —H, halo, —OH, —$COOR^e$, —$CONR^eR^e$, —CN, —$NH_2$, —NH(($C_1$-$C_6$) alkyl), —N(($C_1$-$C_6$) alkyl)$_2$, ($C_1$-$C_6$) alkyl, ($C_1$-$C_6$) alkoxy, ($C_1$-$C_6$) haloalkyl, ($C_1$-$C_6$) haloalkoxy, —$CONR^aR^a$, —$NR^aCOR^a$, —$NR^aCONR^aR^a$, —$SO_2R^a$, —$NR^aS(O)_2R^a$, —$NR^aS(O)_2NR^aR^a$, ($C_3$-$C_6$)cycloalkyl, 4- to 6-membered heterocycloalkyl, phenyl, 5- or 6-membered heteroaryl, ($C_3$-$C_6$) cycloalkyl-($C_1$-$C_4$) alkylene-, (4- to 6-membered heterocycloalkyl)-($C_1$-$C_4$) alkylene-, phenyl-($C_1$-$C_2$) alkylene, and (5- or 6-membered heteroaryl)-($C_1$-$C_4$) alkylene-, wherein the ($C_1$-$C_6$) alkyl, ($C_3$-$C_6$) cycloalkyl, 4- to 6-membered heterocycloalkyl, phenyl, 5- or 6-membered heteroaryl, ($C_3$-$C_6$) cycloalkyl-($C_1$-$C_4$) alkylene-, (4- to 6-membered heterocycloalkyl)-($C_1$-$C_4$) alkylene-, phenyl-($C_1$-$C_2$) alkylene, and (5- or 6-membered heteroaryl)-($C_1$-$C_4$) alkylene- of $R_4$ are each optionally substituted with 1, 2, or 3 independently selected $R^f$ substituents;

each $R^a$ is independently selected from the group consisting of —H, —CN, ($C_1$-$C_6$) alkyl, ($C_1$-$C_6$) haloalkyl, ($C_2$-$C_6$) alkenyl, ($C_2$-$C_6$) alkynyl, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, and (4-14 membered heterocycloalkyl)-($C_1$-$C_4$) alkylene-, wherein the ($C_1$-$C_6$) alkyl, ($C_1$-$C_6$) haloalkyl, ($C_2$-$C_6$) alkenyl, ($C_2$-$C_6$) alkynyl, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, and (4-14 membered heterocycloalkyl)-($C_1$-$C_4$) alkylene- of $R^a$ are each optionally substituted with 1, 2, 3, 4, or 5 independently selected $R^d$ substituents;

each $R^b$ is independently selected from the group consisting of halo, oxo, ($C_1$-$C_6$) alkyl, ($C_2$-$C_6$) alkenyl, ($C_2$-$C_6$) alkynyl, ($C_1$-$C_6$) haloalkyl, ($C_1$-$C_6$) haloalkoxy, ($C_6$-$C_{10}$) aryl, ($C_3$-$C_{10}$) cycloalkyl, 5-10 membered heteroaryl, 4-10 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-10 membered heteroaryl)-($C_1$-$C_4$) alkylene-, (4-10 membered heterocycloalkyl)-($C_1$-$C_4$) alkylene-, —CN, —OH, —$NH_2$, —$NO_2$, —$NHOR^c$, —$OR^c$, —$SR^c$, —$C(O)R^c$, —$C(O)NR^cR^c$, —$C(O)OR^c$, —$C(O)NR^cS(O)_2R^c$, —$OC(O)R^c$, —$OC(O)NR^cR^c$, —$C(=NOH)R^c$, —$C(=NOH)NR^c$, —$C(=NCN)NR^cR^c$, —$NR^cC(=NCN)NR^cR^c$, —$C(=NR^c)NR^cR^c$, —$NR^cC(=NR^c)NR^cR^c$, —$NR^cR^c$, —$NR^cC(O)R^c$, —$NR^cC(=NR^c)R^c$, —$NR^cC(O)OR^c$, —$NR^cC(O)NR^cR^c$, —$NR^cS(O)R^c$, —$NR^cS(O)_2R^c$, —$NR^cS(O)_2NR^cR^c$, —$S(O)R^c$, —$S(O)NR^cR^c$, —$S(O)_2R^c$, —$S(O)_2NR^cC(O)R^c$, —$P(O)R^cR^c$, —$P(O)(OR^c)(OR^c)$, —$B(OH)_2$, —$B(OR^c)_2$, and —$S(O)_2NR^cR^c$, wherein the ($C_1$-$C_6$) alkyl, ($C_1$-$C_6$) haloalkyl, ($C_1$-$C_6$) haloalkoxy, ($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, 4-10 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-10 membered heteroaryl)-($C_1$-$C_4$) alkylene-, and (4-10 membered heterocycloalkyl)-($C_1$-$C_4$) alkylene- of $R^b$ are each further optionally substituted with 1, 2, or 3 independently selected $R^d$ substituents;

each $R^c$ is independently selected from the group consisting of —H, ($C_1$-$C_6$) alkyl, ($C_1$-$C_6$) haloalkyl, ($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, 4-10 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-10 membered heteroaryl)-($C_1$-$C_4$) alkylene-, and (4-10 membered heterocycloalkyl)-($C_1$-$C_4$) alkylene-, wherein the ($C_1$-$C_6$) alkyl, ($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, 4-10 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-10 membered heteroaryl)-($C_1$-$C_4$) alkylene-, and (4-10 membered heterocycloalkyl)-($C_1$-$C_4$) alkylene- of $R^c$ are each optionally substituted with 1, 2, 3, 4, or 5 independently selected $R^f$ substituents;

each $R^d$ is independently selected from the group consisting of ($C_1$-$C_6$) alkyl, ($C_1$-$C_6$) haloalkyl, halo, ($C_6$-$C_{10}$) aryl, 5-10 membered heteroaryl, ($C_3$-$C_{10}$) cycloalkyl, 4-10 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-10 membered heteroaryl)-($C_1$-$C_4$) alkylene-, (4-10 membered heterocycloalkyl)-($C_1$-$C_4$) alkylene-, —CN, —$NH_2$, —$NHOR^e$, —$OR^e$, —$SR^e$, —$C(O)R^e$, —$C(O)NR^eR^e$, —$C(O)OR^e$, —$OC(O)R^e$, —$OC(O)NR^eR^e$, —$NR^eR^e$, —$NR^eC(O)R^e$, —$NR^eC(O)NR^eR^e$, —$NR^eC(O)OR^e$, —$C(=NR^e)NR^eR^e$, —$NR^eC(=NR^e)NR^eR^e$, —$NR^eC(=NOH)NR^eR^e$, —$NR^eC(=NCN)NR^eR^e$, —$S(O)R^e$, —$S(O)NR^eR^e$, —$S(O)_2R^e$, —$NR^eS(O)_2R^e$, —$NR^eS(O)_2NR^eR^e$, and —$S(O)_2NR^eR^e$, wherein the ($C_1$-$C_6$) alkyl, ($C_1$-$C_6$) haloalkyl, ($C_6$-$C_{10}$) aryl, 5-10 membered heteroaryl, ($C_3$-$C_{10}$) cycloalkyl, 4-10 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-10 membered heteroaryl)-($C_1$-$C_4$) alkylene-, and (4-10 membered heterocycloalkyl)-($C_1$-$C_4$) alkylene- of $R^d$ are each optionally substituted with 1, 2, or 3 independently selected $R^f$ substituents;

each $R^e$ is independently selected from the group consisting of —H, ($C_1$-$C_6$) alkyl, ($C_3$-$C_6$) cycloalkyl, ($C_3$-$C_6$) cycloalkyl-($C_1$-$C_4$) alkylene-, ($C_6$-$C_{10}$) aryl, ($C_6$-$C_{10}$) aryl-($C_1$-$C_4$) alkylene-, 5- or 6-membered heteroaryl, (5- or 6-membered heteroaryl)-($C_1$-$C_4$) alkylene-, 4-7-membered heterocycloalkyl, (4-7-membered heterocycloalkyl)-($C_1$-$C_4$) alkylene-, ($C_1$-$C_6$) haloalkyl, ($C_1$-$C_6$) haloalkoxy, ($C_2$-$C_4$) alkenyl, and ($C_2$-$C_4$) alkynyl, wherein the ($C_1$-$C_4$) alkyl, ($C_3$-$C_6$) cycloalkyl, ($C_6$-$C_{10}$) aryl, 5 or 6-membered heteroaryl, 4-7-membered heterocycloalkyl, ($C_6$-$C_{10}$) aryl-($C_1$-$C_4$) alkylene-, (5- or 6-membered heteroaryl)-($C_1$-$C_4$) alkylene-, (4-7-membered heterocycloalkyl)-($C_1$-$C_4$) alkylene-, ($C_2$-$C_4$) alkenyl, and ($C_2$-$C_4$) alkynyl of $R^e$ are each optionally substituted with 1, 2, or 3 $R^f$ substituents, or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents, or any two $R^e$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo, —OH, —CN, —COOH, —$NH_2$, —NH—($C_1$-$C_6$) alkyl, —N(($C_1$-$C_6$) alky)$_2$, ($C_1$-$C_6$) alkyl, ($C_1$-$C_6$) alkoxy, ($C_1$-$C_6$) alkylthio, ($C_1$-$C_6$) haloalkyl, ($C_1$-$C_6$) haloalkoxy, phenyl, 5-6 membered heteroaryl, 4-6 membered heterocycloalkyl, and ($C_3$-$C_6$) cycloalkyl, wherein the ($C_1$-$C_6$) alkyl, phenyl, ($C_3$-$C_6$) cycloalkyl, 4-6 membered heterocycloalkyl, and 5-6 membered heteroaryl of $R^f$ are each optionally substituted with 1, 2, or 3 substituents selected from halo, —OH, —CN, —COOH, —$NH_2$, ($C_1$-$C_4$) alkyl, ($C_1$-$C_4$) alkoxy, ($C_1$-$C_4$) haloalkyl, ($C_1$-$C_4$) haloalkoxy, phenyl, ($C_3$-$C_{10}$) cycloalkyl, 5-6 membered heteroaryl, and 4-6 membered heterocycloalkyl;

each $R^g$ is independently selected from the group consisting of halo, —OH, —CN, —COOH, —COO—($C_1$-$C_4$) alkyl, —$NH_2$, —NH—($C_1$-$C_6$) alkyl, —N(($C_1$-$C_6$) alky)$_2$, ($C_1$-$C_6$) alkyl, ($C_1$-$C_6$) alkoxy, ($C_1$-$C_6$) alkylthio, ($C_1$-$C_6$) haloalkyl, ($C_1$-$C_6$)haloalkoxy, phenyl, 5-6 membered heteroaryl, 4-6 membered heterocycloalkyl, and ($C_3$-$C_6$) cycloalkyl;

Y is selected from —O—, —S—, —SO—, —$SO_2$—, —NH—, and N(($C_1$-$C_6$) alkyl)-;

the ring nitrogen atom on the quinoline moiety in Formula A is optionally oxidized;

the subscript n is an integer of 1, 2, 3, or 4;

the subscript m is an integer of 1, 2, 3, 4, or 5; and the subscript p is an integer of 0, 1, 2, 3, or 4.

Another aspect provides methods of using compounds of formula I or a pharmaceutically acceptable salt thereof for the treatment of a disease, disorder, or syndrome mediated at least in part by modulating in vivo activity of a protein kinase.

A further aspect provides processes for making compounds of formula A and of formula I.

These and other aspects and embodiments are described below.

DETAILED DESCRIPTION OF THE INVENTION

Abbreviations and Definitions

The following abbreviations and terms have the indicated meanings throughout:

| Abbreviation | Meaning |
|---|---|
| Ac | Acetyl |
| anhyd | Anhydrous |
| Aq | Aqueous |
| Ar | Argon |
| Boc | Tert-butoxycarbonyl |
| Br | Broad |
| ° C. | Degrees Celsius |
| c- | Cyclo |
| calcd | Calculated |
| CBZ | CarboBenZoxy = benzyloxycarbonyl |
| d | Doublet |
| dd | Doublet of doublets |
| ddd | Doublet of doublets of doublets |

-continued

| Abbreviation | Meaning |
|---|---|
| dt | Doublet of triplets |
| DCM | Dichloromethane |
| DMF | N,N-Dimethylformamide |
| DMSO | Dimethyl sulfoxide |
| Dppf | 1,1'-bis(diphenylphosphano)ferrocene |
| EA | Elemental Analysis |
| EI | Electron Impact ionization |
| eq or equiv | Equivalent |
| Fmoc | Fluorenylmethyloxycarbonyl |
| g | Gram(s) |
| h or hr | Hour(s) |
| HPLC | High pressure liquid chromatography |
| $H_2$ | Hydrogen |
| L | Liter(s) |
| LiHMDS | Lithium bis(trimethylsilyl)azide |
| M | Molar or molarity |
| m | Multiplet |
| MHz | Megahertz (frequency) |
| Min | Minute(s) |
| mL | Milliliter(s) |
| Mp | Melting point |
| m/z | Mass to charge ratio |
| μL | Microliter(s) |
| Mol | Mole(s) |
| MS | Mass spectral analysis |
| $N_2$ | Nitrogen |
| N | Normal or normality |
| nM | Nanomolar |
| NMR | Nuclear magnetic resonance spectroscopy |
| Pd/C | Palladium on carbon |
| Q | Quartet |
| RT | Room temperature |
| s | Singlet |
| soln | Solution |
| S/C | Substrate/catalyst ratio |
| t or tr | Triplet |
| THF | Tetrahydrofuran |
| TLC | Thin layer chromatography |
| v/v | Volume to volume |

The symbol "—" means a single bond, and "═" means a double bond.

As used herein, the singular forms "a," "an," and "the" include plural reference unless the context clearly dictates otherwise.

When a variable is defined generically, with a number of possible substituents, each individual radical can be defined with our without the bond. For example, if $R^z$ can be hydrogen, this can be indicated as "—H" or "H" in the definition of $R^z$.

When chemical structures are depicted or described, unless explicitly stated otherwise, all carbons are assumed to have hydrogen substitution to conform to a valence of four. For example, in the structure on the left-hand side of the schematic below, there are nine hydrogens implied. The nine hydrogens are depicted in the right-hand structure. Sometimes a particular atom in a structure is described in textual formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

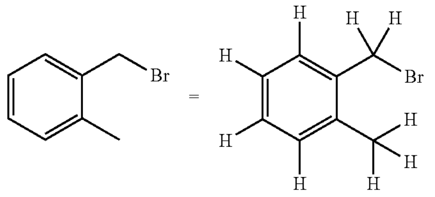

If a group "R" is depicted as "floating" on a ring system, as for example in the formula:

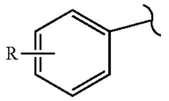

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

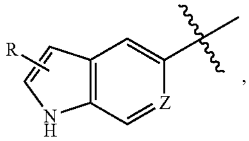 , 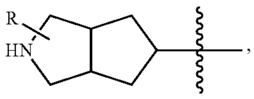 , and 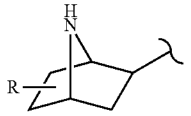

then, unless otherwise defined, a substituent "R" may reside on any atom of the fused ring system, assuming replacement of a depicted hydrogen (for example the —NH— in the formula above), implied hydrogen (for example, in the formula above, where the hydrogens are not shown but understood to be present), or expressly defined hydrogen (for example, where in the formula above, "Z" equals =CH—) from one of the ring atoms, so long as a stable structure is formed. In the example depicted, the "R" group may reside on either the 5-membered or the 6-membered ring of the fused ring system. When a group "R" is depicted as existing on a ring system containing saturated carbons, for example in the formula:

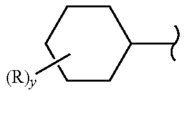

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group, there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

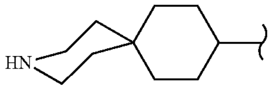

"Halogen" or "halo" refers to fluorine, chlorine, bromine, or iodine.

The term "$C_{n-m}$" or "$C_n$-$C_m$" indicates a range which includes the endpoints, wherein n and m are integers and indicate the number of carbons. Examples include $C_{1-4}$, $C_1$-$C_4$, $C_{1-6}$, $C_1$-$C_6$, and the like.

"Alkyl" refers to a branched or straight hydrocarbon chain of one to eight carbon atoms, such as methyl, ethyl, n-propyl, isopropyl, n-butyl, isobutyl, sec-butyl, t-butyl, pentyl, hexyl, and heptyl. ($C_1$-$C_6$)alkyl is preferred. The term "$C_{n-m}$ alkyl" or ($C_n$-$C_m$) alkyl, refers to an alkyl group having n to m carbon atoms. When optionally substituted, one or more hydrogen atoms of the alkyl group (e.g., from 1 to 4, from 1 to 2, or 1) may be replaced with a moiety as described below under "Optional Substitution." In some aspects, the alkyl group is unsubstituted or not optionally substituted.

"Alkylene" refers to an optionally substituted bivalent saturated aliphatic radical having from 1 to 10 carbon atoms, 1 to 8 carbon atoms, 1 to 6 carbon atoms, 1 to 4 carbon atoms, or 1 to 2 carbon atoms. When optionally substituted, one or more hydrogen atoms of the alkylene group (e.g., from 1 to 4, from 1 to 2, or 1) may be replaced with a moiety as described below under "Optional Substitution." In some aspects, the alkylene group is unsubstituted or not optionally substituted. The term "$C_{n-m}$ alkylene" refers to an alkylene group having n to m carbon atoms. Examples of alkylene groups include, but are not limited to, methylene, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkenyl" refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" or ($C_n$-$C_m$) alkenyl refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

The term "alkynyl" refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" or ($C_n$-$C_m$) alkynyl refers to an alkynyl group having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

"Alkoxy" refers to a moiety of the formula —OR', wherein R' is an ($C_1$-$C_6$)alkyl moiety as defined herein. The term "$C_{n-m}$ alkoxy" or ($C_n$-$C_m$) alkoxy refers to an alkoxy group, the alkyl group of which has n to m carbons.

Examples of alkoxy moieties include, but are not limited to, methoxy, ethoxy, isopropoxy, and the like.

An alkoxy group can be unsubstituted or optionally substituted. When optionally substituted, one or more hydrogen atoms of the alkoxy group (e.g., from 1 to 4, from 1 to 2, or 1) may be replaced with a moiety as described below under "Optional Substitution," with the proviso that no hydrogen atom alpha to the ether oxygen is replaced by a hydroxy, amino, or thio group. In some aspects, the alkoxy group is unsubstituted or not optionally substituted.

"Alkoxycarbonyl" refers to a group —C(O)—R' wherein R' is ($C_1$-$C_6$)alkoxy as defined herein.

The term "amino" refers to a group of formula —$NH_2$.

The term "carbamyl" refers to a group of formula —C(O)$NH_2$.

The term "carbonyl", employed alone or in combination with other terms, refers to a —C(═O)— group, which also may be written as C(O).

The term "cyano" or "nitrile" refers to a group of formula —C≡N, which also may be written as —CN or CN.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (═O) substituents.

The term "sulfide" refers to a sulfur atom as a divalent substituent, forming a thiocarbonyl group (C═S) when attached to carbon.

The term "heteroatom" used herein is meant to include boron, phosphorus, sulfur, oxygen, and nitrogen.

The term "haloalkyl" as used herein refers to an alkyl group in which one or more of the hydrogen atoms has been replaced by a halogen atom. The term "$C_{n-m}$ haloalkyl" or ($C_n$-$C_m$) haloalkyl refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" or ($C_n$-$C_m$) haloalkoxy refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

"Aryl" means a monovalent six- to fourteen-membered, mono- or bi-carbocyclic ring (e.g., having two fused rings), wherein the monocyclic ring is aromatic and at least one of the rings in the bicyclic ring is aromatic. The term "$C_{n-m}$ aryl" or "($C_n$-$C_m$) aryl" refers to an aryl group having from n to m ring carbon atoms. In some embodiments, aryl groups have from 6 to about 10 carbon atoms. In some embodiments aryl groups have 6 carbon atoms. In some embodiments aryl groups have 10 carbon atoms. Unless stated otherwise, the valency of the group may be located on any atom of any ring within the radical, valency rules permitting. Representative examples include phenyl, naphthyl, and indanyl, and the like.

An aryl group can be unsubstituted or optionally substituted. When optionally substituted, one or more hydrogen atoms of the aryl group (e.g., from 1 to 5, from 1 to 2, or 1) may be replaced with a moiety as described below under "Optional Substitution." In some aspects, the alkoxy group is unsubstituted or not optionally substituted.

"Arylene" means a divalent six- to fourteen-membered, mono- or bi-carbocyclic ring, wherein the monocyclic ring is aromatic and at least one of the rings in the bicyclic ring is aromatic. Representative examples include phenylene, naphthylene, and indenylene, and the like.

"Cycloalkyl" refers to a non-aromatic hydrocarbon ring system (monocyclic, bicyclic, or polycyclic), including cyclized alkyl and alkenyl groups. The term "$C_{n-m}$ cycloalkyl" or "($C_n$-$C_m$) cycloalkyl" refers to a cycloalkyl that has n to m ring member carbon atoms. Cycloalkyl groups can include mono- or polycyclic (e.g., having 2, 3, or 4 fused rings) groups and spirocycles. Cycloalkyl groups can have 3, 4, 5, 6, 7, 8, 9, 10, 11, 12, 13, or 14 ring-forming carbons ($C_{3-14}$). In some embodiments, the cycloalkyl group has 3 to 14 members, 3 to 10 members, 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl, or cyclohexyl. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl. In some embodiments, cycloalkyl includes a single saturated carbocyclic ring of three to eight ring carbons, such as cyclopropyl, cyclobutyl, cyclopentyl, and cyclohexyl. Cycloalkyl may optionally be substituted with one or more substituents, such as one, two, or three substituents. In some embodiments, the cycloalkyl substituent is selected from the group consisting of ($C_1$-$C_6$)alkyl, hydroxy, ($C_1$-$C_6$)alkoxy, halo($C_1$-$C_6$)alkyl, halo($C_1$-$C_6$)alkoxy, halo, amino, mono- and di($C_1$-$C_6$)alkylamino, hetero($C_1$-$C_6$)alkyl, acyl, aryl, and heteroaryl.

A cycloalkyl group can be unsubstituted or optionally substituted. When optionally substituted, one or more hydrogen atoms of the cycloalkyl group (e.g., from 1 to 4, from 1 to 2, or 1) may be replaced with a moiety as described below under "Optional Substitution." In some aspects, a substituted cycloalkyl group can incorporate an exo- or endocyclic alkene (e.g., cyclohex-2-en-1-yl). In some aspects, a cycloalkyl group is unsubstituted or not optionally substituted.

"Cycloalkyloxycarbonyl" means a group —C(O)—OR' wherein R' is ($C_3$-$C_6$)cycloalkyl as defined herein.

"Phenyloxycarbonyl" refers to a group —C(O)—Ophenyl.

"Heteroaryl" means a monocyclic, fused bicyclic, or fused tricyclic, monovalent radical of 5 to 14 ring atoms containing one or more, preferably one, two, three, or four ring heteroatoms independently selected from —O—, —S(O)$_n$— (n is 0, 1, or 2), —N—, and —N(R')—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(═NH)— group. R' is hydrogen, alkyl, hydroxy, alkoxy, acyl, or alkylsulfonyl. Unless stated otherwise, the valency may be located on any atom of any ring of the heteroaryl group, valency rules permitting. In particular, when the point of valency is located on the nitrogen, an additional nitrogen substituent is not present. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, and N-oxide or a protected derivative thereof.

A five-membered heteroaryl ring is a heteroaryl group having five ring atoms wherein one or more (e.g., 1, 2, 3, or 4) ring atoms are independently selected from N, O, and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl ring is a heteroaryl group having six ring atoms wherein one or more (e.g., 1, 2, 3, or 4) ring atoms are independently selected from N, O, and S. Exemplary six-membered ring heteroaryls are pyridyl, pyrazinyl, pyrimidinyl, triazinyl, and pyridazinyl.

"Heteroarylene" means a monocyclic, fused bicyclic, or fused tricyclic, divalent radical of 5 to 14 ring atoms containing one or more, preferably one, two, three, or four ring heteroatoms independently selected from —O—, —S(O)$_n$— (n is 0, 1, or 2), —N—, and —N(R$^{19}$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^{19}$ is hydrogen, alkyl, or alkenyl. Unless stated otherwise, the valencies may be located on any atom of any ring of the heteroarylene group, valency rules permitting. In particular, when the point of valency is located on the nitrogen, an additional nitrogen substituent is not present. More specifically, the term heteroaryl includes, but is not limited to, thien-diyl, benzo[d]isoxazol-diyl, benzo[d]isothiazol-diyl, 1H-indazol-diyl (optionally substituted at the N1 position with R$^{19}$), benzo[d]oxazol-diyl, benzo[d]thiazol-diyl, 1H-benzo[d]imidazol-diyl (optionally substituted at the N1 position with R$^{19}$), 1H-benzo[d][1,2,3]triazol-diyl (optionally substituted at the N1 position with R$^{19}$), imidazo[1,2-c]pyridin-diyl, cinnolin-diyl, quinolin-diyl, pyridin-diyl, 1-oxido-pyridin-diyl, [1,2,4]triazolo[4,3-a]pyridin-diyl, and 2,3-dihydroimidazo[1,2-a]pyridin-diyl, and the like.

As used herein, "heterocycloalkyl" or "heterocyclo" refer to a non-aromatic ring or ring system, which may optionally contain one or more alkenylene groups as part of the ring structure, which has at least one heteroatom ring member independently selected from boron, nitrogen, sulfur, oxygen, and phosphorus, and which has 4-14 ring members, 4-10 ring members, 4-7 ring members, or 4-6 ring members. Included within the term "heterocycloalkyl" are monocyclic 4-, 5-, 6-, and 7-membered heterocycloalkyl groups. Heterocycloalkyl groups can include mono- or bicyclic or polycyclic (e.g., having two or three fused or bridged rings) ring systems or spirocycles. In some embodiments, the heterocycloalkyl group is a monocyclic group having 1, 2, or 3 heteroatoms independently selected from nitrogen, sulfur, and oxygen. Ring-forming carbon atoms and heteroatoms of a heterocycloalkyl group can be optionally oxidized to form an oxo or sulfido group or other oxidized linkage (e.g., C(O), S(O), C(S), S(O)$_2$, N-oxide, and the like) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, and the like. A heterocycloalkyl group containing a fused aromatic ring can be attached through any ring-forming atom, including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, 4,5,6,7-tetrahydrothiazolo[5,4-c]pyridinyl, and thiomorpholino.

"Heterocycloalkyl" or "heterocyclo," can be unsubstituted or optionally substituted. When optionally substituted, one or more hydrogen atoms of the group (e.g., from 1 to 4, from 1 to 2, or 1) may be replaced with a moiety independently selected from fluoro, hydroxy, alkoxy, amino, alkylamino, acylamino, thio, and alkylthio. In some aspects, a substituted heterocycyl group can incorporate an exo- or endocyclic alkene (e.g., cyclohex-2-en-1-yl). In some aspects, the heterocycyl group is unsubstituted or not optionally substituted.

Optional Substitution

A group is optionally substituted herein unless expressly provided otherwise. The term "optionally substituted" refers to being substituted or unsubstituted. In certain embodiments, alkyl, alkenyl, alkynyl, carbocycloalkyl, heterocyclyoalkyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" "substituted" or "unsubstituted" cyclyoalkyl, "substituted" or "unsubstituted" heterocycloalkyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen (halo), —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(═O)$R^{aa}$, —$CO_2H$, —CHO, —$C(OR^{cc})_2$, —$CO_2R^{aa}$, —OC(═O)$R^{aa}$, —$OCO_2R^{aa}$, —C(═O)$N(R^{bb})_2$, —OC(═O)$N(R^{bb})_2$, —$NR^{bb}$C(═O)$R^{aa}$, —$NR^{bb}CO_2R^{aa}$, —$NR^{bb}$C(═O)$N(R^{bb})_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)$N(R^{bb})_2$, —OC(═$NR^{bb}$)$N(R^{bb})_2$, —$NR^{bb}$C(═$NR^{bb}$)$N(R^{bb})_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —$Si(R^{aa})_3$, —$OSi(R^{aa})_3$—C(═S)$N(R^{bb})_2$, —C(═O)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$_2R^{aa}$, —OP(═O)$_2R^{aa}$, —P(═O)$(R^{aa})_2$, —OP(═O)$(R^{aa})_2$, —OP(═O)$(OR^{cc})_2$, —P(═O)$_2N(R^{bb})_2$, —OP(═O)$_2N(R^{bb})_2$, —P(═O)$(NR^{bb})_2$, —OP(═O)$(NR^{bb})_2$, —$NR^{bb}$P(═O)$(OR^{cc})_2$, —$NR^{bb}$P(═O)$(NR^{bb})_2$, —$OP(R^{cc})_2$, —$OP(R^{cc})_3$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, ($C_3$-$C_{10}$) carbocycloalkyl, 3-14 membered heterocycloalkyl, ($C_6$-$C_{14}$) aryl, and 5-14 membered heteroaryl, wherein each alkyl, alkenyl, alkynyl, cycloalkyl, heterocycloalkyl, aryl, and heteroaryl is independently substituted with 0, 1, 2, 3, 4, or 5 $R^d$ groups;

or two geminal hydrogens on a carbon atom are replaced with the group ═O, ═S, ═$NN(R^{bb})_2$, ═$NNR^{bb}$C(═O)$R^{aa}$, ═$NNR^{bb}$C(═O)$OR^{aa}$, ═$NNR^{bb}$S(═O)$_2R^{aa}$, ═$NR^{bb}$, or ═$NOR^{cc}$;

each instance of $R^{aa}$ is, independently, selected from ($C_1$-$C_{10}$) alkyl, ($C_1$-$C_{10}$) perhaloalkyl, ($C_2$-$C_{10}$) alkenyl, ($C_2$-$C_{10}$) alkynyl, ($C_3$-$C_{10}$) cycloalkyl, 3-14 membered heterocycloalkyl, ($C_6$-$C_{14}$) aryl, and 5-14 membered heteroaryl, or two $R^{aa}$ groups are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 $R^{dd}$ groups;

each instance of $R^{bb}$ is, independently, selected from hydrogen, ($C_1$-$C_{10}$) perhaloalkyl, ($C_2$-$C_{10}$) alkenyl, ($C_2$-$C_{10}$) alkynyl, ($C_3$-$C_{10}$) cycloalkyl, $C_{6-14}$ aryl, and 5-14 membered heteroaryl, or two $R^{bb}$ groups are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 $R^{dd}$ groups;

each instance of $R^{cc}$ is, independently, selected from hydrogen, ($C_1$-$C_{10}$) alkyl, ($C_1$-$C_{10}$) perhaloalkyl, ($C_2$-$C_{10}$) alkenyl, ($C_2$-$C_{10}$) alkynyl, ($C_3$-$C_{10}$) cycloalkyl, 3-14 membered heterocycloalkyl, ($C_6$-$C_{14}$) aryl, and 5-14 membered heteroaryl, or two $R^{cc}$ groups are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}$C(═$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$_2R^{ee}$, —P(═O)$(R^{ee})_2$, —OP(═O)$(R^{ee})_2$, —OP(═O)$(OR^{ee})_2$, ($C_1$-$C_{10}$) alkyl, ($C_1$-$C_{10}$) perhaloalkyl, ($C_2$-$C_{10}$) alkenyl, ($C_2$-$C_{10}$) alkynyl, ($C_3$-$C_{10}$) cycloalkyl, 3-10 membered heterocycloalkyl, ($C_6$-$C_{10}$) aryl, 5-10 membered heteroaryl, wherein each alkyl, alkenyl, alkynyl, cycloalkyl, heterocycloalkyl, aryl, and heteroaryl is independently substituted with 0, 1, 2, 3, 4, or 5 $R^{gg}$ groups, or two geminal $R^{dd}$ substituents can be joined to form ═O or ═S;

each instance of $R^{ee}$ is, independently, selected from ($C_1$-$C_6$) alkyl, ($C_1$-$C_6$) perhaloalkyl, ($C_2$-$C_6$) alkenyl, ($C_2$-$C_6$) alkynyl, ($C_3$-$C_{10}$) cycloalkyl, ($C_6$-$C_{10}$) aryl, 3-10 membered heterocycloalkyl, and 3-10 membered heteroaryl, wherein each alkyl, alkenyl, alkynyl, heteroalkyl, heteroalkenyl, heteroalkynyl, cycloalkyl, heterocycloalkyl, aryl, and heteroaryl is independently substituted with 0, 1, 2, 3, 4, or 5 $R^{gg}$ groups;

each instance of $R^{ff}$ is, independently, selected from hydrogen, ($C_1$-$C_6$) alkyl, ($C_1$-$C_6$) perhaloalkyl, ($C_2$-$C_6$) alkenyl, ($C_2$-$C_6$) alkynyl, ($C_3$-$C_{10}$) cycloalkyl, ($C_6$-$C_{10}$) aryl, and 5-10 membered heteroaryl, or two $R^{ff}$ groups are joined to form a 3-10 membered heterocycloalkyl or 5-10 membered heteroaryl ring, wherein each alkyl, alkenyl, alkynyl, cycloalkyl, heterocycloalkyl, aryl, and heteroaryl is independently substituted with 0, 1, 2, 3, 4, or 5 $R^{gg}$ groups; and each instance of $R^{gg}$ is, independently, halogen, —CN, —$NO_2$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)$^+X^-$, —$NH_3^+X^-$, —N($OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2$($C_{1-6}$ alkyl), —OC(═O)($C_{1-6}$ alkyl), —$OCO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(═NH)$NH_2$, —$NHSO_2$($C_{1-6}$ alkyl), —$SO_2N$($C_{1-6}$ alkyl)$_2$, —$SO_2NH$($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$-C(═S)N($C_{1-6}$ alkyl)$_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═O)$_2$($C_{1-6}$ alkyl), —P(═O)($C_{1-6}$ alkyl)$_2$, —OP(═O)($C_{1-6}$ alkyl)$_2$, —OP(═O)($OC_{1-6}$ alkyl)$_2$, ($C_1$-$C_6$) alkyl, ($C_1$-$C_6$) perhaloalkyl, ($C_2$-$C_6$) alkenyl, ($C_2$-$C_6$) alkynyl, ($C_3$-$C_{10}$) cycloalkyl, ($C_6$-$C_{10}$) aryl, 3-10 membered heterocycloalkyl, 5-10 membered heteroaryl; or two geminal $R^{gg}$ substituents can be joined to form ═O or ═S; wherein $X^-$ is a counterion.

As noted previously, nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{c}$, —$SO_2OR^{cc}$, —$SOR^{aa}$, —C(═S)$N(R^{cc})_2$, —C(═O)$SR^{cc}$, —C(═S)$SR^{cc}$, —P(═$O)_2R^{aa}$, —P(═O)$(R^{aa})_2$, —P(═$O)_2N(R^{cc})_2$, —P(═)$(NR^{cc})_2$, ($C_1$-$C_{10}$) alkyl, ($C_1$-$C_{10}$) perhaloalkyl, ($C_2$-$C_{10}$) alkenyl, ($C_2$-$C_{10}$) alkynyl, ($C_3$-$C_{10}$) cycloalkyl, 3-14 membered heterocycloalkyl, ($C_6$-$C_{14}$) aryl, and 5-14 membered heteroaryl, or two $R^{cc}$ groups attached to an N atom are joined to form a 3-14 membered heterocycloalkyl or 5-14 membered heteroaryl ring, wherein each alkyl, alkenyl, alkynyl, cycloalkyl, heterocycloalkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is a nitrogen protecting group (also referred to herein as an “amino protecting group”). Nitrogen protecting groups include, but are not limited to, —OH, —$OR^{aa}$, —$N(R^{cc})_2$, —C(═O)$R^{aa}$, —C(═O)$N(R^{cc})_2$, —$CO_2R^{aa}$, —$SO_2R^{aa}$, —C(═$NR^{cc}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, ($C_1$-$C_{10}$) alkyl (e.g., aralkyl, heteroaralkyl), ($C_2$-$C_{10}$) alkenyl, ($C_2$-$C_{10}$) alkynyl, ($C_3$-$C_{10}$) cycloalkyl, 3-14 membered heterocycloalkyl, ($C_6$-$C_{14}$) aryl, and 5-14 membered heteroaryl groups, wherein each alkyl, alkenyl, alkynyl, cycloalkyl, heterocycloalkyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenyl acetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., C(═O)$OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenyl ethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., S(═$O)_2$R") include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzyl sulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethyl silyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{b}b)N(R^{bb})_2$, $—S(=O)R^{aa}$, $—SO_2R^{aa}$, $—Si(R^{aa})_3$, $—P(R^{cc})_2$, $—P(R^{cc})_3$, $—P(=O)_2R^{aa}$, $—P(=O)(R^{aa})_2$, $—P(=O)(OR^{cc})_2$, $—P(=O)_2N(R^{bb})_2$, and $—P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxy ethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenyl selenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenyl sulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3$, $—P(=O)_2R^{aa}$, $—P(=O)(R^{aa})_2$, $—P(=O)(OR^{cc})_2$, $—P(=O)_2N(R^{bb})_2$, and $—P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), $—OR^{aa}$ (when the O atom is attached to a carbonyl group, wherein $R^{aa}$ is as defined herein), $—O(C{=}O)R^{LG}$, or $—O(SO)_2R^{LG}$ (e.g., tosyl, mesyl, besyl), wherein $R^{LG}$ is optionally substituted alkyl, optionally substituted aryl, or optionally substituted heteroaryl. In certain embodiments, the leaving group is a halogen.

The terms for which definitions are given above are specifically exemplified in the Examples.

"Yield" for each of the reactions described herein is expressed as a percentage of the theoretical yield.

"Patient" for the purposes of the present invention includes humans and any other animals, particularly mammals, and other organisms. Thus the methods are applicable to both human therapy and veterinary applications. In a preferred embodiment the patient is a mammal, and in a most preferred embodiment the patient is human. Examples of the preferred mammals include mice, rats, other rodents, rabbits, dogs, cats, swine, cattle, sheep, horses, and primates.

"Kinase-dependent diseases or conditions" refer to pathologic conditions that depend on the activity of one or more kinases. Kinases either directly or indirectly participate in the signal transduction pathways of a variety of cellular activities including proliferation, adhesion, migration, differentiation, and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

"Therapeutically effective amount" is an amount of a compound of the invention that, when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Head and neck: squamous cell carcinomas of the head and neck, laryngeal and hypopharyngeal cancer, nasal cavity and paranasal sinus cancer, nasopharyngeal cancer, salivary gland cancer, oral and oropharyngeal cancer; Lung: bronchogenic carcinoma (squamous cell, undifferentiated small cell, undifferentiated large cell, adenocarcinoma, non-small cell lung cancer), alveolar (bronchiolar) carcinoma, bronchial adenoma, sarcoma, lymphoma, chondromatous hamartoma, mesothelioma; Colon: colorectal cancer, adenocarcinoma, gastrointestinal stromal tumors, lymphoma, carcinoids, Turcot Syndrome; Gastrointestinal: gastric cancer, gastroesophageal junction adenocarcinoma, esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Breast: metastatic breast cancer, ductal carcinoma in situ, invasive ductal carcinoma, tubular carcinoma, medullary carcinoma, mucinous carcinoma, lobular carcinoma in situ, triple negative breast cancer; Genitourinary tract: kidney (adenocarcinoma, Wilm's tumor [nephroblastoma], lymphoma, leukemia, renal cell carcinoma), bladder and urethra (squamous cell carcinoma, transitional cell carcinoma, adenocarcinoma, urothelial carcinoma), prostate (adenocarcinoma, sarcoma, castrate resistant prostate cancer), testis (seminoma, teratoma, embryonal carcinoma, teratocarcinoma, choriocarcinoma, sarcoma, interstitial cell carcinoma, fibroma, fibroadenoma, adenomatoid tumors, lipoma), clear cell carcinoma, papillary carcinoma; Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma, and giant cell tumors; Thyroid: medullary thyroid cancer, differentiated thyroid cancer, papillary thyroid cancer, follicular thyroid cancer, hurthle cell cancer, and anaplastic thyroid cancer; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial cancer), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable salts" includes "pharmaceutically acceptable acid addition salts" and "pharmaceutically acceptable base addition salts." "Pharmaceutically acceptable acid addition salts" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salts" include those derived from inorganic bases such as sodium, potassium, lithium, ammonium, calcium, magnesium, iron, zinc, copper, manganese, aluminum salts, and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines, and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, di cyclohexylamine, choline, and caffeine. (See, for example, S. M. Berge, et al., "Pharmaceutical Salts," J. Pharm. Sci., 1977; 66:1-19 which is incorporated herein by reference.)

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

Compounds of the invention can also include all isotopes of atoms occurring in the intermediates or final compounds. Isotopes include those atoms having the same atomic number but different mass numbers. For example, isotopes of hydrogen include tritium and deuterium.

Any one of the process steps or sequences disclosed and/or claimed herein can be performed under an inert gas atmosphere, more particularly under argon or nitrogen. In addition, the methods of the present invention may be carried out as semi-continuous or continuous processes, more preferably as continuous processes.

Moreover, many of the process steps and sequences that are described herein can be telescoped.

In general, the nomenclature used in this Application is based on naming conventions adopted by the International Union of Pure and Applied Chemistry (IUPAC). Chemical structures shown herein were prepared using CHEMDRAW®. Any open valency appearing on a carbon, oxygen, or nitrogen atom in the structures herein indicates the presence of a hydrogen atom.

EMBODIMENTS OF THE INVENTION

One aspect provides a compound of formula A:

A

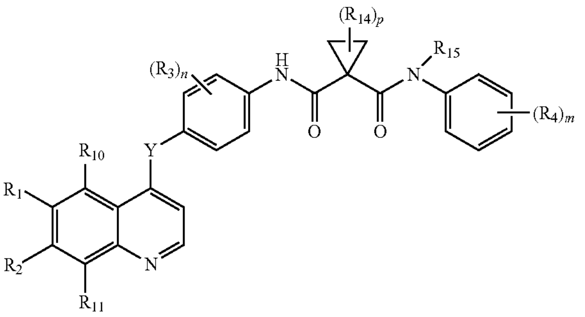

or a pharmaceutically acceptable salt thereof, wherein the variables and substituents in formula A are as defined in the Summary of the Invention.

In one embodiment of this aspect, the compound of formula A is a compound of formula A-1.

A-1

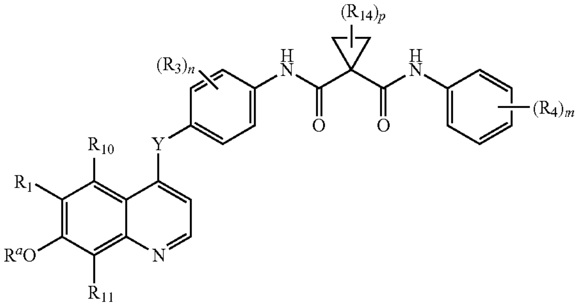

In another embodiment of this aspect, the compound of formula A is a compound of formula A-2.

A-2

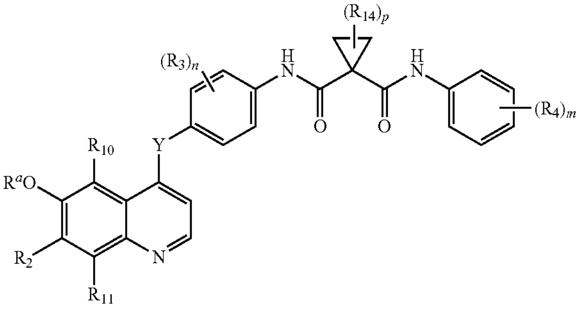

In a further embodiment of this aspect, the compound of formula A is a compound of formula A-3:

A-3

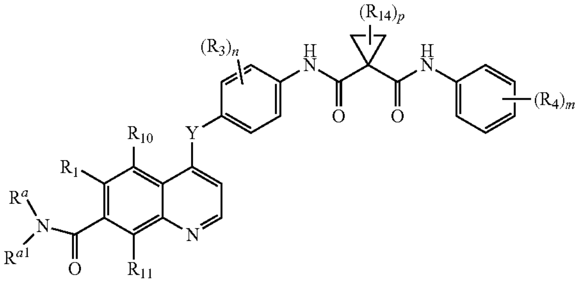

wherein $R^{a1}$ is —H or ($C_1$-$C_6$) alkyl.

In a further embodiment, $R_1$ in the compound of formula A-3 is —H.

In a further embodiment of this aspect, the compound of formula A is a compound of formula A-4:

A-4

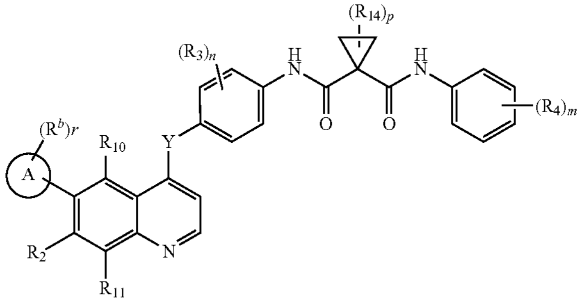

wherein ring A is 5- to 14-membered heteroaryl; and the subscript r is 1, 2, 3, or 4.

In this embodiment, $R_2$ is —H.

In a further embodiment, r in formula A-4 is 1 or 2.

In a further embodiment of formula A: $R_1$ is —H, optionally substituted ($C_1$-$C_6$) alkyl, halo, —$OR^a$, —$NO_2$, —$NH_2$, —$NHR^a$, —$NR^aR^a$, —$SR^a$, —$SOR^a$, or —$S(O)_2R^a$, and $R_2$ is selected from the group consisting of ($C_2$-$C_6$) alkenyl, ($C_2$-$C_6$) alkynyl, ($C_6$-$C_{10}$) aryl, ($C_3$-$C_{10}$) cycloalkyl, —CN, —$NHOR^a$, —$C(O)R^a$, —$C(O)NR^aR^a$, —$C(O)NHOR^a$, —$C(O)OR^a$, —$C(O)NR^aS(O)_2R^a$, —$OC(O)NR^aR^a$, $NR^aC(O)R^a$, —$NR^aC(=NR^a)R^a$, —$NR^aC(O)OR^a$, —$NR^aC(O)NR^aR^a$, —$C(=NR^a)R^a$, —$C(=NOH)R^a$, —$C(=NOR^a)R^a$, —$C(=NOH)NR^a$, —$C(=NCN)NR^aR^a$, —$NR^aC(=NCN)NR^aR^a$, —$C(=NR^a)NR^aR^a$, —$NR^aC(=NR^a)NR^aR^a$, —$NR^aS(O)R^a$, —$NR^aS(O)_2R^a$, —$NR^aS(O)_2NR^aR^a$, —$S(O)R^a$, —$S(O)NR^aR^a$, —$S(O)_2R^a$, —$S(O)_2NR^aC(O)R^a$, —$P(O)R^aR^a$, —$P(O)(OR^a)(OR^a)$, —$B(OH)_2$, —$B(OR^a)_2$, and —$S(O)_2NR^aR^a$.

In one embodiment of this embodiment, $R_1$ is —H.

In a further embodiment: $R_1$ is selected from the group consisting of ($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, 4-10 membered heterocycloalkyl, —CN, —$NHOR^a$, —$C(O)R^a$, —$C(O)NR^aR^a$, —$C(O)NHOR^a$, —$C(O)OR^a$, —$C(O)NR^aS(O)_2R^a$, —$OC(O)NR^aR^a$, —$NR^aC(O)R^a$, —$NR^aC(=NR^a)R^a$, —$NR^aC(O)OR^a$, —$NR^aC(O)NR^aR^a$, —$C(=NR^a)R^a$, —$C(=NOH)R^a$, —$C(=NOH)NR^a$, —$C(=NOR^a)R^a$, —$C(=NCN)NR^aR^a$, —$NR^aC(=NCN)NR^aR^a$, —$C(=NR^a)NR^aR^a$, —$NR^aC(=NR^a)NR^aR^a$, —$NR^aS(O)R^a$, —$NR^aS(O)_2R^a$, —$NR^aS(O)_2NR^aR^a$, —$S(O)R^a$, —$S(O)NR^aR^a$, —$S(O)_2R^a$, —$S(O)_2NR^aC(O)R^a$, —$P(O)R^aR^a$, —$P(O)(OR^a)(OR^a)$, —$B(OH)_2$, —$B(OR^a)_2$, and —$S(O)_2NR^aR^a$; and $R_2$ is —H, optionally substituted ($C_1$-$C_6$) alkyl, halo, —$OR^a$, —$NO_2$, —$NH_2$, —$NHR^a$, —$NR^aR^a$, —$SR^a$, —$SOR^a$, or —$S(O)_2R^a$.

In one embodiment of this embodiment, $R_2$ is —H.

In another embodiment:

$R_1$ is ($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, 4-10 membered heterocycloalkyl, —CN, —$NHOR^a$, —$C(O)R^a$, —$C(O)NR^aR^a$, —$C(O)NHOR^a$, —$C(O)OR^a$, —$C(O)NR^aS(O)_2R^a$, —$OC(O)NR^aR^a$, —$NR^aC(O)R^a$, —$NR^aC(=NR^a)R^a$, —$NR^aC(O)OR^a$, —$NR^aC(O)NR^aR^a$, —$C(=NR^a)R^a$, —$C(=NOH)R^a$, —$C(=NOR^a)R^a$, —$C(=NOH)NR^a$, —$C(=NCN)NR^aR^a$, —$NR^aC(=NCN)NR^aR^a$, —$C(=NR^a)NR^aR^a$, —$NR^aC(=NR^a)NR^aR^a$, —$NR^aS(O)R^a$, —$NR^aS(O)_2R^a$, —$NR^aS(O)_2NR^aR^a$, —$S(O)R^a$, —$S(O)NR^aR^a$, —$S(O)_2R^a$, —$S(O)_2NR^aC(O)R^a$, —$P(O)R^aR^a$, —$P(O)(OR^a)(OR^a)$, —$B(OH)_2$, —$B(OR^a)_2$, or —$S(O)_2NR^aR^a$; and $R_2$ is selected from the group consisting of —H, halo, ($C_1$-$C_6$) alkyl, ($C_2$-$C_6$) alkenyl, ($C_2$-$C_6$) alkynyl, ($C_1$-$C_6$) haloalkyl, ($C_1$-$C_6$) haloalkoxy, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, (4-14 membered heterocycloalkyl)-($C_1$-$C_4$) alkylene-, —CN, —$NO_2$, —$OR^a$, —$SR^a$, —$NHOR^a$, —$C(O)R^a$, —$C(O)NR^aR^a$, —$C(O)NHOR^a$, —$C(O)OR^a$, —$C(O)NR^aS(O)_2R^a$, —$OC(O)R^a$, —$OC(O)NR^aR^a$, —$NHR^a$, —$NR^aR^a$, —$NR^aC(O)R^a$, —$NR^aC(=NR^a)R^a$, —$NR^aC(O)OR^a$, —$NR^aC(O)NR^aR^a$, —$C(=NR^a)R^a$, —$C(=NOH)R^a$, —$C(=NOH)NR^a$, —$C(=NOR^a)R^a$, —$C(=NCN)NR^aR^a$, —$NR^aC(=NCN)NR^aR^a$, —$C(=NR)NR^aR^a$, —$NR^aC(=NR)NR^aR^a$, —$NR^aS(O)R^a$, —$NR^aS(O)_2R^a$, —$NR^aS(O)_2NR^aR^a$, —$S(O)R^a$, —$S(O)NR^aR^a$, —$S(O)_2R^a$, —$S(O)_2NR^aC(O)R^a$, —$P(O)R^aR^a$, —$P(OR^a)(OR^a)(OR^a)$, —$B(OH)_2$, —$B(OR^a)_2$; and —$S(O)_2NR^aR^a$.

In one embodiment of this embodiment, $R_2$ is —H.

In another embodiment:

$R_1$ is selected from the group consisting of —H, halo, ($C_1$-$C_6$) alkyl, ($C_2$-$C_6$) alkenyl, ($C_2$-$C_6$) alkynyl, ($C_1$-$C_6$) haloalkyl, ($C_1$-$C_6$) haloalkoxy, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, (4-14 membered heterocycloalkyl)-($C_1$-$C_4$) alkylene-, —CN, —$NO_2$, —$OR^a$, —$SR^a$, —$NHOR^a$, —$C(O)R^a$, —$C(O)NR^aR^a$, —$C(O)NHOR^a$, —$C(O)OR^a$, —$C(O)NR^aS(O)_2R^a$, —$OC(O)R^a$, —$OC(O)NR^aR^a$, —$NHR^a$, —$NR^aR^a$, —$NR^aC(O)R^a$, —$NR^aC(=NR^a)R^a$, —$NR^aC(O)OR^a$, —$NR^aC(O)NR^aR^a$, —$C(=NR^a)R^a$, —$C(=NOH)R^a$, —$C(=NOR^a)R^a$, —$C(=NOH)NR^a$, —$C(=NCN)NR^aR^a$, —$NR^aC(=NCN)NR^aR^a$, —$C(=NR)NR^aR^a$, —$NR^aC(=NR)NR^aR^a$, —$NR^aS(O)R^a$, —$NR^aS(O)_2R^a$, —$NR^aS(O)_2NR^aR^a$, —$S(O)R^a$, —$S(O)NR^aR^a$, —$S(O)_2R^a$, —$S(O)_2NR^aC(O)R^a$, —$P(O)R^aR^a$, —$P(O)(OR^a)(OR^a)$, —$B(OH)_2$, —$B(OR^a)_2$, and —$S(O)_2NR^aR^a$; and In one embodiment of this embodiment, $R_1$ is —H.

In another further embodiment:

$R_1$ and $R_2$ taken together with the atoms to which they are attached form a fused ($C_3$-$C_7$) cycloalkyl ring or a fused 4- to 10-membered heterocycloalkyl ring; wherein the fused ($C_3$-$C_7$) cycloalkyl ring or a fused 4- to 10-membered heterocycloalkyl ring are each optionally substituted with 1, 2, or 3 independently selected $R^b$ substituents, provided that the compound is not 1-[2-(4-Fluoro-phenyl)-acetyl]-cyclopropanecarboxylic acid [3-fluoro-4-(7,8,10,11,13,14-hexahydro-6,9,12,15-tetraoxa-1-aza-cyclododeca[b]naphthalen-4-yloxy)-phenyl]-amide.

In a further embodiment: $R_1$ and $R_2$ taken together with the atoms to which they are attached form a fused ($C_3$-$C_7$) cycloalkyl ring or a fused 4- to 10-membered heterocycloalkyl ring, wherein the fused ($C_3$-$C_7$) cycloalkyl ring or a fused 4- to 10-membered heterocycloalkyl ring are each optionally substituted with 1, 2, or 3 independently selected $R^b$ substituents, provided that the compound is not a compound having the formula:

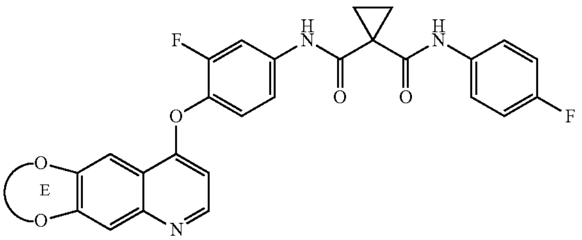 [SMILES: O=C(Nc1ccc(F)cc1)C1(C(=O)Nc2ccc(Oc3ccnc4cc(O)c(O)cc34)c(F)c2)CC1]

wherein ring E is a fused 4- to 10-membered heterocycloalkyl.

In another embodiment, $R_1$ in the compound of formula A, A-1, or A-3 is selected from the group consisting of —H, ($C_1$-$C_6$) alkyl, ($C_2$-$C_6$) alkenyl, ($C_2$-$C_6$) alkynyl, —C(═NO—($C_1$-$C_6$) alkyl)$R^a$, —CN, —C(O)O$R^a$, —C(O)N$R^aR^a$, —C(O)NHO$R^a$, —S(O)$_2$N$R^aR^a$, phenyl, 5- to 6-membered heteroaryl, ($C_3$-$C_6$) cycloalkyl, and 4- to 6-membered heterocycloalkyl.

In another embodiment, $R_1$ is selected from the group consisting of —H, ($C_1$-$C_6$) alkyl, ($C_2$-$C_6$) alkenyl, ($C_2$-$C_6$) alkynyl, —C(═NO—($C_1$-$C_6$) alkyl)$R^a$, —CN, —C(O)O$R^a$, —C(O)N$R^aR^a$, —C(O)NHO$R^a$, —S(O)$_2$N$R^aR^a$, phenyl, 5- to 6-membered heteroaryl, ($C_3$-$C_6$) cycloalkyl, and 4- to 6-membered heterocycloalkyl; and $R_2$ is H, optionally substituted ($C_1$-$C_6$) alkyl, halo, —O$R^a$, —N$O_2$, —N$H_2$, —NH$R^a$, —N$R^aR^a$, —S$R^a$, —SO$R^a$, or —S(O)$_2R^a$.

In another embodiment, $R_1$ is selected from the group consisting of —H, ($C_1$-$C_6$) alkyl, ($C_2$-$C_6$) alkenyl, ($C_2$-$C_6$) alkynyl, —C(═NO—($C_1$-$C_6$) alkyl)$R^a$, —CN, —C(O)O$R^a$, —C(O)N$R^aR^a$, —C(O)NHO$R^a$, —S(O)$_2$N$R^aR^a$, phenyl, 5- to 6-membered heteroaryl, ($C_3$-$C_6$) cycloalkyl: and 4- to 6-membered heterocycloalkyl; and $R_2$ is selected from the group consisting of —H, halo, ($C_1$-$C_6$) alkyl, ($C_2$-$C_6$) alkenyl, ($C_2$-$C_6$) alkynyl, ($C_1$-$C_6$) haloalkyl, ($C_1$-$C_6$) haloalkoxy, ($C_6$-$C_{10}$) aryl, ($C_3$-$C_{10}$) cycloalkyl, ($C_6$-$C_{10}$) aryl-($C_1$-$C_4$) alkyl ene-, ($C_3$-$C_{10}$) cycloalkyl-($C_1$-$C_4$) alkylene-, (5-14 membered heteroaryl)-(C $C_4$) alkylene-, (4-14 membered heterocycloalkyl)-($C_1$-$C_4$) alkylene-, —CN, —N$O_2$, —O$R^a$, —S$R^a$, —NHO$R^a$, —C(O)$R^a$, —C(O)N$R^aR^a$, —C(O)NHO$R^a$, —C(O)O$R^a$, —C(O)N$R^a$S(O)$_2R^a$, —OC(O)$R^a$, —OC(O)N$R^aR^a$, —NH$R^a$, —N$R^aR^a$, —N$R^a$C(O)$R^a$, —N$R^a$C(═N$R^a$)$R^a$, —N$R^a$C(O)O$R^a$, —N$R^a$C(O)N$R^aR^a$, —C(═N$R^a$)$R^a$, —C(═NOH)$R^a$, —C(═NOH)N$R^a$, —C(═NO$R^a$)$R^a$, —C(═NCN)N$R^aR^a$, —N$R^a$C(═NCN)N$R^aR^a$, —C(═N$R^a$)N$R^aR^a$, —N$R^a$C(═N$R^a$)N$R^aR^a$, —N$R^a$S(O)$R^a$, —N$R^a$S(O)$_2R^a$, —N$R^a$S(O)$_2$N$R^aR^a$, —S(O)$R^a$, —S(O)N$R^aR^a$, —S(O)$_2R^a$, —S(O)$_2$N$R^a$C(O)$R^a$, —P(O)$R^aR^a$, —P(O)(O$R^a$)(O$R^a$), —B(OH)$_2$, —B(O$R^a$)$_2$; and —S(O)$_2$N$R^aR^a$.

In another embodiment, $R_1$ is selected from the group consisting of —H, ($C_1$-$C_6$) alkyl, ($C_2$-$C_6$) alkenyl, ($C_2$-$C_6$) alkynyl, —C(═NO—($C_1$-$C_6$) alkyl)$R^a$, —CN, —C(O)O$R^a$, —C(O)N$R^aR^a$, —C(O)NHO$R^a$, —S(O)$_2$N$R^aR^a$, phenyl, 5- to 6-membered heteroaryl, —($C_3$-$C_6$) cycloalkyl, and 4- to 6-membered heterocycloalkyl; and $R_2$ is ($C_2$-$C_6$) alkenyl, ($C_2$-$C_6$) alkynyl, —CN, —NHO$R^a$, —C(O)$R^a$, —C(O)N$R^aR^a$, —C(O)NHO$R^a$, —C(O)O$R^a$, —C(O)N$R^a$S(O)$_2R^a$, —OC(O)N$R^aR^a$, —N$R^a$C(O)$R^a$, —N$R^a$C(═N$R^a$)$R^a$, —N$R^a$C(O)O$R^a$, —N$R^a$C(O)N$R^aR^a$, —C(═N$R^a$)$R^a$, —C(═NOH)$R^a$, —C(═NOH)N$R^a$, —C(═NO$R^a$)$R^a$, —C(═NCN)N$R^aR^a$, —N$R^a$C(═NCN)N$R^aR^a$, —C(═N$R^a$)N$R^aR^a$, —N$R^a$C(═N$R^a$)N$R^aR^a$, —N$R^a$S(O)$R^a$, —N$R^a$S(O)$_2R^a$, —N$R^a$S(O)$_2$N$R^aR^a$, —S(O)$R^a$, —S(O)N$R^aR^a$, —S(O)$_2R^a$, —S(O)$_2$N$R^a$C(O)$R^a$, —P(O)$R^aR^a$, —P(O)(O$R^a$)(O$R^a$), —B(OH)$_2$, —B(O$R^a$)$_2$, or —S(O)$_2$N$R^aR^a$.

In a further embodiment, $R_1$ is —H, $R^a$NHC(O)—, $R^a$OC(O)—, ($C_1$-$C_6$) alkyl, ($C_1$-$C_6$) alkoxy, or —C(═NO—$CH_3$)$R^a$, and $R_2$ is selected from 2-methoxyethylamino, azetidin-1-yl, methylamino, 3-morpholinopropoxy, 2-methoxyethoxy, 2-hydroxyethoxy, propoxy, 2-hydroxypropoxy, methoxycarbonyl, carboxy, carbamoyl, methylcarbamoyl, (2-hydroxyethoxy)carbamoyl, (2,2-dihydroxyethoxy)carbamoyl, (oxetan-3-yloxy)carbamoyl, methoxycarbamoyl, 2-trimethylsilylethynyl, ethynyl, sulfamoyl, acetyl, and —C(═NO$CH_3$)$CH_3$.

In a further embodiment of formula A, and A-2, and $R_2$ is selected from the group consisting of —H, ($C_1$-$C_6$) alkyl, ($C_2$-$C_6$) alkenyl, ($C_2$-$C_6$) alkynyl, —C(═NO—($C_1$-$C_6$) alkyl)$R^a$, —CN, —C(O)O$R^a$, —C(O)N$R^aR^a$, —C(O)NHO$R^a$, and —S(O)$_2$N$R^aR^a$.

In a further embodiment, $R_1$ is —H, optionally substituted ($C_1$-$C_6$) alkyl, halo, —O$R^a$, —N$O_2$, —N$H_2$, —NH$R^a$, —N$R^aR^a$, —S$R^a$, —SO$R^a$, or S(O)$_2R^a$, and $R_2$ is selected from the group consisting of —H, ($C_1$-$C_6$) alkyl, ($C_2$-$C_6$) alkenyl, ($C_2$-$C_6$) alkynyl, —C(═NO—($C_1$-$C_6$) alkyl)$R^a$, —CN, —C(O)O$R^a$, —C(O)N$R^aR^a$, —C(O)NHO$R^a$, —S(O)$_2$N$R^aR^a$, phenyl, and ($C_3$-$C_6$) cycloalkyl.

In a further embodiment, $R_1$ is selected from the group consisting of —H, optionally substituted ($C_1$-$C_6$) alkyl, halo, —O$R^a$, —N$O_2$, —N$H_2$, —NH$R^a$, —N$R^aR^a$, —S$R^a$, —SO$R^a$, and —S(O)$_2R^a$, and $R_2$ is selected from the group consisting of —H, ($C_1$-$C_6$) alkyl, ($C_2$-$C_6$) alkenyl, ($C_2$-$C_6$) alkynyl, —C(═NO—($C_1$-$C_6$) alkyl)$R^a$, —CN, —C(O)O$R^a$, —C(O)N$R^aR^a$, —C(O)NHO$R^a$, —S(O)$_2$N$R^aR^a$.

In a further embodiment, $R_1$ is selected from the group consisting of ($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, 4-10 membered heterocycloalkyl, —CN, —NHO$R^a$, —C(O)$R^a$, —C(O)N$R^aR^a$, —C(O)NHO$R^a$, —C(O)O$R^a$, —C(O)N$R^a$S(O)$_2R^a$, —OC(O)N$R^aR^a$, —N$R^a$C(O)$R^a$, —N$R^a$C(═N$R^a$)$R^a$, —N$R^a$C(O)O$R^a$, —N$R^a$C(O)N$R^aR^a$, —C(═N$R^a$)$R^a$, —C(═NOH)$R^a$, —C(═NOH)N$R^a$, —C(═NO$R^a$)$R^a$, —C(═NCN)N$R^aR^a$, —N$R^a$C(═NCN)N$R^aR^a$, —C(═N$R^a$)N$R^aR^a$, —N$R^a$C(═N$R^a$)N$R^aR^a$, —N$R^a$S(O)$R^a$, —N$R^a$S(O)$_2R^a$, —N$R^a$S(O)$_2$N$R^aR^a$, —S(O)$R^a$, —S(O)N$R^aR^a$, —S(O)$_2R^a$, —S(O)$_2$N$R^a$C(O)$R^a$, —P(O)$R^aR^a$, —P(O)(O$R^a$)(O$R^a$), —B(OH)$_2$, —B(O$R^a$)$_2$, and —S(O)$_2$N$R^aR^a$; and $R_2$ is selected from the group consisting of —H, ($C_1$-$C_6$) alkyl, ($C_2$-$C_6$) alkenyl, ($C_2$-$C_6$) alkynyl, —C(═NO—($C_1$-$C_6$) alkyl)$R^a$, —CN, —C(O)O$R^a$, —C(O)N$R^aR^a$, —C(O)NHO$R^a$, —S(O)$_2$N$R^aR^a$.

In a further embodiment, $R_1$ is selected from the group consisting of —H, halo, ($C_1$-$C_6$) alkyl, ($C_2$-$C_6$) alkenyl, ($C_2$-$C_6$) alkynyl, ($C_1$-$C_6$) haloalkyl, ($C_1$-$C_6$) haloalkoxy, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, (4-14 membered heterocycloalkyl)-($C_1$-$C_4$) alkylene-, —CN, —$NO_2$, —$OR^a$, —$SR^a$, —$NHOR^a$, —$C(O)R^a$, —$C(O)NR^aR^a$, —$C(O)NHOR^a$, —$C(O)OR^a$, —$C(O)NR^aS(O)_2R^a$, —$OC(O)R^a$, —$OC(O)NR^aR^a$, —$NHR^a$, —$NR^aR^a$, —$NR^aC(O)R^a$, —$NR^aC(=NR^a)R^a$, —$NR^aC(O)OR^a$, —$NR^aC(O)NR^aR^a$, —$C(=NR^a)R^a$, —$C(=NOH)R^a$, —$C(=NOR^a)R^a$, —$C(=NOH)NR^a$, —$C(=NCN)NR^aR^a$, —$NR^aC(=NCN)NR^aR^a$, —$C(=NR^a)NR^aR^a$, —$NR^aC(=NR^a)NR^aR^a$, —$NR^aS(O)R^a$, —$NR^aS(O)_2R^a$, —$NR^aS(O)_2NR^aR^a$, —$S(O)R^a$, —$S(O)NR^aR^a$, —$S(O)_2R^a$, —$S(O)_2NR^aC(O)R^a$, —$P(O)R^aR^a$, —$P(O)(OR^a)(OR^a)$, —$B(OH)_2$, —$B(OR^a)_2$, and —$S(O)_2NR^aR^a$; and $R_2$ is selected from the group consisting of —H, ($C_1$-$C_6$) alkyl, ($C_2$-$C_6$) alkenyl, ($C_2$-$C_6$) alkynyl, —C(=NO—($C_1$-$C_6$) alkyl)$R^a$, —CN, —$C(O)OR^a$, —$C(O)NR^aR^a$, —$C(O)NHOR^a$, —$S(O)_2NR^aR^a$.

In a further embodiment, $R_1$ is selected from the group consisting of 2-methoxyethylamino, azetidin-1-yl, methylamino, 3-morpholinopropoxy, 2-methoxyethoxy, 2-hydroxyethoxy, propoxy, 2-hydroxypropoxy, methoxycarbonyl, carboxy, carbamoyl, methylcarbamoyl, 2-oxazolyl, pyrazol-3-yl, pyrazol-4-yl, 4-isoxazolyl, 3,5-dimethylisoxazol-4-yl, 1-methyl-pyrazol-4-yl, 2-methyl-pyrazol-3-yl, 2-ethyl-pyrazol-3-yl, 2-(2-hydroxyethyl)-pyrazol-3-yl, 2-(2,2,2-trifluoroethyl)-pyrazol-3-yl, 2-(2-fluoroethyl)-pyrazol-3-yl, difluoroethyl)-pyrazol-3-yl, 2-trifluoromethyl-pyrazol-3-yl, 2-difluoromethyl-pyrazol-3-yl, 1-methyl-imidazol-4-yl, 1-methyl-imidazol-2-yl, 1H-imidazol-2-yl, (2-hydroxyethoxy)carbamoyl, (2,2-dihydroxyethoxy)carbamoyl, (oxetan-3-yloxy)carbamoyl, methoxycarbamoyl, 2-trimethylsilylethynyl, ethynyl, 1,3,4-oxadiazol-3-yl, 1H-1,2,3-triazol-5-yl, sulfamoyl, acetyl, and $C(=NOCH_3)CH_3$; and $R_2$ is —H, —$R^aNHC(O)$—, —$R^aOC(O)$—, ($C_1$-$C_6$) alkyl, ($C_1$-$C_6$) alkoxy, or —$C(=NO—CH_3)R^a$.

In a further embodiment of formula A-4, the subscript r is 1 or 2.

In a further embodiment of the above aspect and embodiments, $R_{10}$ and $R_{11}$ are each —H.

In a further embodiment of the above aspect and embodiments, the subscript n is 1.

In a further embodiment of the above aspect and embodiments, the subscript m is 1.

In a further embodiment of the above aspect and embodiments, the subscript p is 1.

Another embodiment, a compound of formula A is a compound of formula B:

B

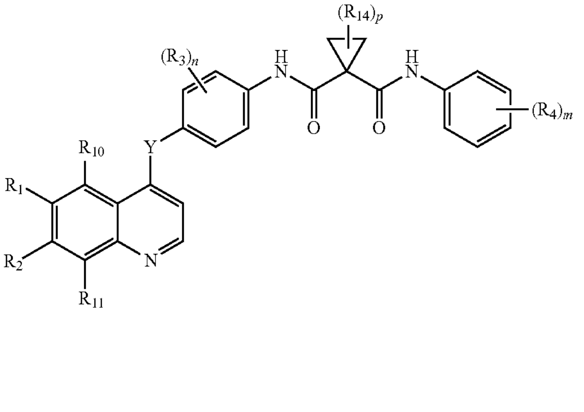

or a pharmaceutically acceptable salt thereof, wherein $R_1$ and $R_2$ are as defined in (i), (ii), or (iii) of formula A; and $R_3$, $R_{10}$, $R_{11}$, $R_{14}$, $R_4$, n, p, m and Y are as defined as follows:

each $R_3$ is independently selected from the group consisting of —H, halo, —OH, —CN, optionally substituted ($C_1$-$C_6$) alkyl, ($C_1$-$C_6$) alkoxy, ($C_1$-$C_6$) haloalkoxy, —$NH_2$, —NH($C_1$-$C_6$)alkyl, —N($C_1$-$C_6$ alkyl)$_2$, and ($C_3$-$C_6$) cycloalkyl, wherein ($C_1$-$C_6$) alkoxy, —NH($C_1$-$C_6$)alkyl, —N($C_1$-$C_6$ alkyl)$_2$, and ($C_3$-$C_6$) cycloalkyl are each optionally substituted;

each of $R_{10}$ and $R_{11}$ is independently selected from the group consisting of —H, ($C_1$-$C_6$) alkyl, ($C_1$-$C_6$) alkoxy, and ($C_1$-$C_6$) haloalkoxy;

each $R_{14}$ is independently selected from the group consisting of -halo, —OH, —$NH_2$, —CN, ($C_1$-$C_6$) alkyl, ($C_1$-$C_6$) alkoxy, ($C_1$-$C_6$) haloalkyl, ($C_1$-$C_6$) haloalkoxy, —COOH, —NH($C_1$-$C_6$)alkyl, —N($C_1$-$C_6$ alkyl)$_2$, phenyl, phenyl-($C_1$-$C_2$) alkylene, ($C_3$-$C_6$) cycloalkyl, ($C_3$-$C_6$) cycloalkyl-($C_1$-$C_4$) alkylene-, 4- to 6-membered heterocycloalkyl, (4- to 6-membered heterocycloalkyl)-($C_1$-$C_4$) alkylene-, 5- to 6-membered heteroaryl, (5- to 6-membered heteroaryl)-($C_1$-$C_4$) alkylene-, and —OR', wherein the ($C_1$-$C_6$) alkyl, phenyl, phenyl-($C_1$-$C_2$) alkylene, ($C_3$-$C_6$) cycloalkyl, ($C_3$-$C_6$) cycloalkyl-($C_1$-$C_4$) alkylene-, 4- to 6-membered heterocycloalkyl, (4- to 6-membered heterocycloalkyl)-($C_1$-$C_4$) alkylene-, 5- to 6-membered heteroaryl, and (5- to 6-membered heteroaryl)-($C_1$-$C_4$) alkylene- of $R_{14}$ are each optionally substituted;

each $R_4$ is independently selected from —H, halo, —OH, ($C_1$-$C_6$) alkyl, ($C_1$-$C_6$) alkoxy, ($C_1$-$C_6$) haloalkyl, and ($C_1$-$C_6$) haloalkoxy, wherein the ($C_1$-$C_6$) alkyl are each ($C_1$-$C_6$) alkoxy, ($C_1$-$C_6$) haloalkyl, and ($C_1$-$C_6$) haloalkoxy are each independently optionally substituted;

each $R^a$ is independently selected from —H, ($C_1$-$C_6$) alkyl, ($C_1$-$C_6$) haloalkyl, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, and (4-14 membered heterocycloalkyl)-($C_1$-$C_4$) alkylene-, wherein ($C_1$-$C_6$) alkyl, ($C_1$-$C_6$) haloalkyl, ($C_6$-$C_{10}$) aryl, ($C_3$-$C_{10}$) cycloalkyl, 5-14 membered heteroaryl, 4-14 membered heterocycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, and (4-14 membered heterocycloalkyl)-($C_1$-$C_4$) alkylene- are each independently optionally substituted;

n, p, and m are each independently integers of 0 to 3; and

Y is selected from —O—, —S—, —SO—, —$SO_2$— —NH—, and —N(($C_1$-$C_6$) alkyl)-.

In one embodiment of formula A and B:

(i) $R_1$ is selected from the group consisting of:

($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, and 4-10 membered heterocycloalkyl, wherein the ($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, and 4-10 membered heterocycloalkyl are each independently optionally substituted, —CN, —$P(O)R^aR^a$, $P(O)(OR^a)_2$, $B(OH)_2$, $B(OR^a)_2$, $X_2R^a$, wherein $X_2$ is —NHO—, —NH—S(O)—, —N—($C_1$-$C_6$)alkyl-S(O)—, —NH—$S(O)_2$—, —N—($C_1$-$C_6$) alkyl-$S(O)_2R^a$—, —NH—S(O)—NH—, —N—($C_1$-$C_6$) alkyl-S(O)NH—, —NH—$S(O)_2$NH—, —N—($C_1$-$C_6$) alkyl-$S(O)_2$NH—, —$S(O)_2$NHC(O)—, and

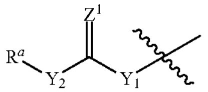

wherein "" indicates the point of attachment, wherein:

$Y_1$ is absent, or is —NH—, —N—($C_1$-$C_6$) alkyl-, or —O—, $Y_2$ is absent, or is —O—, —NH—, —NHO—, —N—($C_1$-$C_6$) alkyl-, —$N_2H_2$—, —NH—S(O)—, or —NH—$S(O)_2$—; or $Y_2$ is or optionally substituted

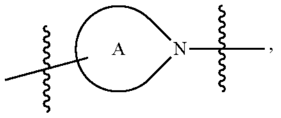

wherein "" indicates points of attachment, wherein ring A is a 3, 4, 5, 6, or 7-membered ring; and $Z^1$ is O, NH, N—($C_1$-$C_6$) alkyl, NOH, NO—($C_1$-$C_6$) alkyl, or NCN; and $R_2$ is:

—H or a group selected from the group consisting of:

($C_1$-$C_6$) alkyl, halo, —$NO_2$, and $X_1R^a$, wherein $X_1$ is —O—, —S—, —SO—, —$SO_2$—, —$SO_2$NH—, —$SO_2NR^a$—, —NH—, and —N—($C_1$-$C_6$) alkyl-, wherein ($C_1$-$C_6$) alkyl is optionally substituted.

In another embodiment of formula A and B:

(ii) $R_1$ is selected from the group consisting of:

($C_2$-$C_6$) alkenyl, ($C_2$-$C_6$) alkynyl, ($C_6$-$C_{10}$) aryl, ($C_3$-$C_{10}$) cycloalkyl, 5-10 membered heteroaryl, and 4-10 membered heterocycloalkyl, wherein ($C_2$-$C_6$) alkenyl, ($C_2$-$C_6$) alkynyl, ($C_6$-$C_{10}$) aryl, ($C_3$-$C_{10}$) cycloalkyl, 5-14 membered heteroaryl, and 4-14 membered heterocycloalkyl are each independently optionally substituted;

P(O)$R^aR^a$, P(O)($OR^a$)($OR^a$), $B(OH)_2$, $B(OR^a)_2$, CN, $X_2R^a$, wherein $X_2$ is —NHO—, —NH—S(O)—, —N—($C_1$-$C_6$)alkyl-S(O)—, —NH—$S(O)_2$—, —N—($C_1$-$C_6$) alkyl-$S(O)_2R^a$—, —NH—S(O)—NH—, —N—($C_1$-$C_6$) alkyl-S(O)NH—, —NH—S(O)$_2$NH—, —N—($C_1$-$C_6$) alkyl-$S(O)_2$NH—, —S(O)—, —$S(O)_2$—, —$S(O)_2$NHC(O), and

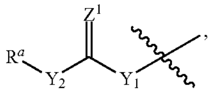

wherein:

$Y_1$ is absent, or is NH—, —N—($C_1$-$C_6$) alkyl-, or —O—, $Y_2$ is absent, or is —O—, —NH—, —NHO—, —N—($C_1$-$C_6$) alkyl-, —$N_2H_2$—, —NH—S(O)—, or —NH—$S(O)_2$, or $Y_2$ is optionally substituted

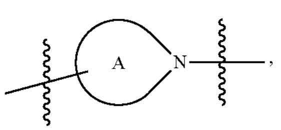

wherein "" indicates points of attachment, wherein ring A is a 3, 4, 5, 6, or 7-membered ring;

$Z^1$ is —O—, —NH—, —N—($C_1$-$C_6$) alkyl-, —NOH—, —NO—($C_1$-$C_6$) alkyl-, or —NCN—; and $R_2$ is selected from the group consisting of H, halo, ($C_1$-$C_6$) alkyl, ($C_2$-$C_6$) alkenyl, ($C_2$-$C_6$) alkynyl, ($C_1$-$C_6$) haloalkyl, ($C_1$-$C_6$) haloalkoxy, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, and (4-14 membered heterocycloalkyl)-($C_1$-$C_4$) alkylene-, wherein ($C_2$-$C_6$) alkenyl, ($C_2$-$C_6$) alkynyl, ($C_1$-$C_6$) haloalkyl, ($C_1$-$C_6$) haloalkoxy, ($C_6$-$C_{10}$) aryl, ($C_3$-$C_{10}$) cycloalkyl, ($C_6$-$C_{10}$) aryl-($C_1$-$C_4$) alkylene-, ($C_3$-$C_{10}$) cycloalkyl-($C_1$-$C_4$) alkylene-, (5-14 membered heteroaryl)-($C_1$-$C_4$) alkylene-, and (4-14 membered heterocycloalkyl)-($C_1$-$C_4$) alkylene- are each independently optionally substituted, CN, $NO_2$, P(O)$R^aR^a$, P(O)($OR^a$)($OR^a$), $B(OH)_2$, $B(OR^a)_2$, $X_1R^a$, wherein $X_1$ is —O—, —S—, —NH—, or —N—($C_1$-$C_6$)—, —NHO—, —NH—S(O)—, —N—($C_1$-$C_6$) alkyl-S(O)—, —NH—$S(O)_2$—, —N—($C_1$-$C_6$) alkyl-$S(O)_2$—, —NH—S(O)—NH—, —N—($C_1$-$C_6$) alkyl-S(O)NH—, —NH—$S(O)_2$NH—, —N—($C_1$-$C_6$) alkyl-$S(O)_2$NH—, —$S(O)_2$NHC(O)—, —NH—S(O)$R^a$—, —N—($C_1$-$C_6$) alkyl-S(O)$R^a$—, —NH—$S(O)_2R^a$—, —N—($C_1$-$C_6$) alkyl-$S(O)_2R^a$—, and

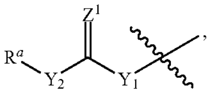

wherein:

$Y_1$ is absent or is —NH—, —N—($C_1$-$C_6$) alkyl-, or —O—;

$Y_2$ is absent or is —O—, —NH—, —NHO—, —N—($C_1$-$C_6$) alkyl-, —$N_2H_2$—, —NH—S(O)—, or —NH—$S(O)_2$—, or $Y_2$ is optionally substituted

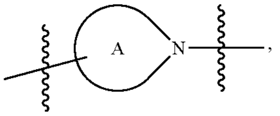

wherein ring A is a 3, 4, 5, 6, or 7-membered ring and wherein "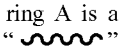" indicates points of attachment; and $Z^1$ is O, NH, N—($C_1$-$C_6$) alkyl, NOH, NO—($C_1$-$C_6$) alkyl, or NCN.

In another embodiment of formula A and B:

(iii) $R_1$ and $R_2$ taken together with the atoms to which they are attached form a 4- to 10-membered heterocycloalkyl ring optionally substituted with 1, 2, or 3 groups independently selected from the group consisting of halo, ($C_1$-$C_6$) alkyl, ($C_1$-$C_6$) haloalkyl, ($C_1$-$C_6$) haloalkoxy, —CN, —OH, —$NH_2$, provided that the compound is not 1-[2-(4-Fluoro-phenyl)-acetyl]-cyclopropanecarboxylic acid [3-fluoro-4-(7,8,10,11,13,14-hexahydro-6,9,12,15-tetraoxa-1-aza-cyclododeca[b]naphthalen-4-yloxy)-phenyl]-amide.

In a further embodiment of the compound of formula A and B:

$R_1$ is —H, —CN, ($C_1$-$C_6$) alkyl, ($C_3$-$C_{10}$) cycloalkyl, ($C_6$-$C_{10}$) aryl, 4-10 membered heterocycloalkyl, 5-10 membered heteroaryl, —$S(O)_2NHR^a$, —$P(O)R^aR^a$, —$OR^a$, or

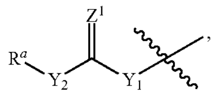

wherein "∿∿∿" indicates the point of attachment, wherein:

$Y_1$ is absent or is NH—, —N—($C_1$-$C_6$) alkyl-, or —O—;

$Y_2$ is absent or is —O—, —NH—, —NHO—, —N—($C_1$-$C_6$) alkyl-, —NH—NH—, —NH—S(O)—, or NH—$S(O)_2$; and $Z^1$ is —O, —NH, —N—($C_1$-$C_6$) alkyl, —N—OH, or —N—O($C_1$-$C_6$)alkyl.

In another embodiment of the of formula A and B:

$R_2$ is —H, halo, —$X_1R^a$, ($C_2$-$C_6$) alkenyl, ($C_2$-$C_6$) alkynyl, or

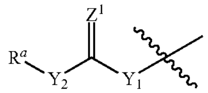

wherein "∿∿∿" indicates the point of attachment, wherein:

$Y_1$ is absent or is NH, N—($C_1$-$C_6$) alkyl, or O;

$Y_2$ is absent or is O, NH, NHO, N—($C_1$-$C_6$) alkyl, $N_2H_2$, NH—S(O), or NH—$S(O)_2$; and $Z^1$ is —O, —NH, —N—($C_1$-$C_6$) alkyl, —NOH—, or —N—O($C_1$-$C_6$)alkyl.

In another embodiment of formula A and B, $R_3$ is —H or halo.

In another embodiment of formula A and B, $R_4$ is —H or halo.

In another embodiment of formula A and B, wherein $R_{14}$ is —H or halo.

In another embodiment of formula A and B, Y is —O—.

In another embodiment, the compound of B is a compound of either formula B-1 or B-2:

B-1

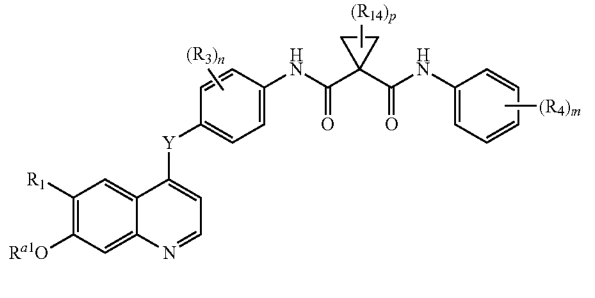

-continued

B-2

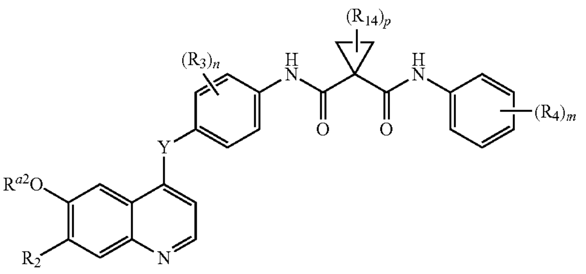

or a pharmaceutically acceptable salt thereof.

In one embodiment of formula B-1:

$R^{a1}$ is optionally substituted ($C_1$-$C_6$) alkyl;

$R_1$ is —H, —CN, optionally substituted 3-6 membered cycloalkyl, optionally substituted phenyl, optionally substituted 4-6 membered heterocycloalkyl, optionally substituted 5-6 membered heteroaryl, —$SO_2$—($C_1$-$C_6$) alkyl, —$SO_2NH_2$, —$SO_2$—NH($C_1$-$C_6$) alkyl, P(O)(($C_1$-$C_6$) alkyl)$_2$, or

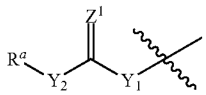

wherein "∿∿∿" indicates the point of attachment, wherein:

$Y_1$ is absent;

$Y_2$ is absent or is —O—, —NH—, —NHO—, —NH—NH—, —N—($C_1$-$C_6$) alkyl-; or $Y_2$ is optionally substituted

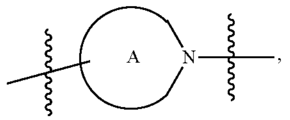

wherein ring A is a 3, 4, 5, 6, or 7-membered ring, wherein "∿∿∿" indicates points of attachment;

$Z^1$ is O, NH, N—($C_1$-$C_6$) alkyl, NHO, or NO—($C_1$-$C_6$) alkyl; and $R^a$ is —H, —($C_1$-$C_6$) alkyl, 4-6-membered heterocycloalkyl, 3-6-membered cycloalkyl, —($C_2$-$C_6$) alkylene-OH, —$CH_2CHOH$—($C_2$-$C_6$) alkylene-OH, —($C_2$-$C_6$) alkylene-$NH_2$, —($C_2$-$C_6$) alkylene-NH ($C_1$-$C_6$), —($C_2$-$C_6$) alkylene-N($C_1$-$C_6$)$_2$, or —($C_2$-$C_6$) alkylene-N-(4-6-membered heterocycloalkyl);

In another embodiment of formula B-1:

$R^{a1}$ is ($C_1$-$C_6$) alkyl;

$R_1$ is —H, —CN, optionally substituted cyclopropyl, optionally substituted phenyl, optionally substituted 4-6 membered azetidinyl, optionally substituted pyrollidinyl, optionally substituted piperidinyl, optionally substituted oxetanyl, optionally substituted oxazolyl, optionally substituted pyridinyl, optionally substituted imidazolyl, optionally substituted pyrrolyl, optionally substituted furanyl, optionally substituted pyrazolyl, optionally substituted oxadiazolyl, —$SO_2$—($C_1$-$C_6$) alkyl, —$SO_2NH_2$, —$SO_2$—NH($C_1$-$C_6$) alkyl, or P(O)(($C_1$-$C_6$) alkyl)$_2$; or $R_1$ is

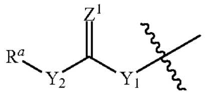, wherein:

$Y_1$ is absent;

$Y_2$ is O, NH, NHO, NH—NH, or N—($C_1$-$C_6$) alkyl; or $Y_2$ is optionally substituted azetidinyl;

$Z^1$ is O, NH, or N—($C_1$-$C_6$) alkyl; and $R^a$ is H, ($C_1$-$C_6$) alkyl, —($C_2$-$C_6$) alkylene-OH, —$CH_2CHOH$—($C_2$-$C_6$) alkylene-OH, —($C_2$-$C_6$) alkylene-$NH_2$, —($C_2$-$C_6$) alkylene-NH($C_1$-$C_6$) alkyl, —($C_2$-$C_6$) alkylene-N(($C_1$-$C_6$) alkyl)$_2$, —($C_2$-$C_6$) alkylene-heterocycloalkyl), or 4-6 membered heterocycloalkyl, wherein heterocycloalkyl is optionally substituted.

In one embodiment of formula B-2:

$R^{a2}$ is optionally substituted ($C_1$-$C_6$) alkyl;

$R_2$ is

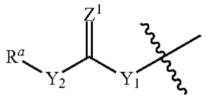

wherein "∿∿∿" indicates the point of attachment, wherein:

$Y_1$ is absent;

$Y_2$ is absent or is —O— or —NH—; and $Z^1$ is O; and $R^a$ is —H or —($C_1$-$C_6$) alkyl.

In another embodiment of formula B-2:

$R^{a2}$ is ($C_1$-$C_6$) alkyl;

$R_2$ is

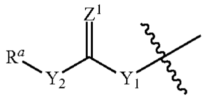

wherein "∿∿∿" indicates the point of attachment, wherein:

$Y_1$ is absent;

$Y_2$ is absent or is —O— or —NH—; and $Z^1$ is O or NO—($C_1$-$C_6$) alkyl; and $R^a$ is —H or —($C_1$-$C_6$) alkyl.

In another embodiment of formula B-1, $R^{a1}$ is methoxy.

In another embodiment of formula B-2, $R^{a2}$ is methoxy.

In another embodiment, the compound of formula B is a compound of either formula B-3 or B-4:

B-3

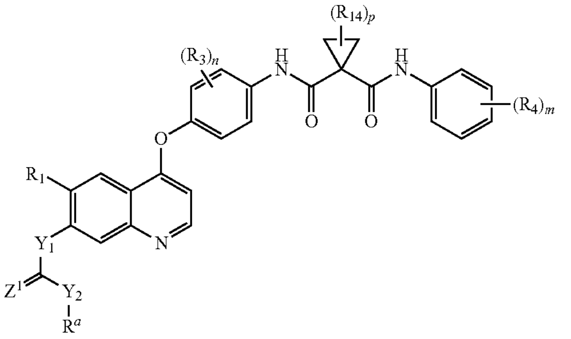

B-4

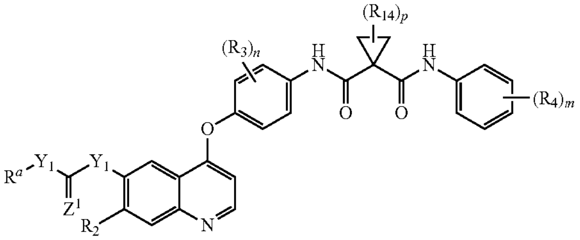

or a pharmaceutically acceptable salt thereof.

In one embodiment of formula B-3:

$R_1$ is —H or ($C_1$-$C_6$) alkyl; and $Y_1$ is absent;

$Y_2$ is absent or is —O—, —NHO—, or —NH—; and $Z^1$ is O or NO—($C_1$-$C_6$) alkyl; and $R^a$ is —H or —($C_1$-$C_6$) alkyl.

In another embodiment of formula B-3:

$R_1$ is —H or methyl;

$Y_1$ is absent;

$Y_2$ is absent or is —O—, —NHO—, or —NH—; and $Z^1$ is O or NO-Me; and $R^a$ is —H or Me.

In another embodiment of formula B-3:

$R_1$ and $R^a$, together with the atoms to which they are attached, form a 4-6 membered heterocycloalkyl ring optionally substituted with halo, ($C_1$-$C_6$) alkyl, or ($C_1$-$C_6$) haloalkyl.

In one embodiment of formula B-4:

$Y_1$ is absent;

$Y_2$ is O, NH, NHO, NH—NH, or N—($C_1$-$C_6$) alkyl; or $Y_2$ is optionally substituted azetidinyl;

$Z^1$ is O, NH, NO—($C_1$-$C_6$) alkyl, or N—($C_1$-$C_6$) alkyl; and $R^a$ is H, ($C_1$-$C_6$) alkyl, —($C_2$-$C_6$) alkylene-OH, —$CH_2CHOH$—($C_2$-$C_6$) alkylene-OH, —($C_2$-$C_6$) alkylene-$NH_2$, —($C_2$-$C_6$) alkylene-NH($C_1$-$C_6$) alkyl, —($C_2$-$C_6$) alkylene-N(($C_1$-$C_6$) alkyl)$_2$, —($C_2$-$C_6$) alkylene-optionally substituted 4-6 membered heterocycloalkyl), or optionally substituted 4-6 membered heterocycloalkyl;

$R_2$ is —H, —F, —$C_1$, —Br, —($C_1$-$C_6$)alkoxy, —O—($C_2$-$C_6$)alkylene-OH, —O—($C_2$-$C_6$)alkylene-O—($C_1$-$C_6$ alkyl), ($C_2$-$C_6$)alkylene-O—($C_1$-$C_6$) alkyl, —$NH_2$, —NH—($C_1$-$C_6$ alkyl), NH—($C_1$-$C_6$)alkylene-(optionally substituted 4-6 membered heterocycloalkyl), or —NH—($C_2$-$C_6$)alkylene-O—($C_1$-$C_6$ alkyl).

In another embodiment of formula B-4:

$Y_1$ is absent;

$Y_2$ is O, NH, NHO, NH—NH, or N—($C_1$-$C_6$) alkyl; or $Y_2$ is optionally substituted azetidinyl;

$Z^1$ is O, NH, NO—($C_1$-$C_6$) alkyl, N—($C_1$-$C_6$) alkyl; and $R^a$ is —H, methyl, ethyl, —($C_2$-$C_6$) alkylene-OH, —$CH_2CHOH$—($C_2$-$C_6$) alkylene-OH, —($C_2$-$C_6$) alkylene-$NH_2$, —($C_2$-$C_6$) alkylene-NHMe, —($C_2$-$C_6$) alkylene-N$(Me)_2$, —($C_1$-$C_6$) alkylene-morpholinyl), —($C_1$-$C_6$) alkylene-piperidinyl), ($C_1$-$C_6$)alkylene-(optionally substituted pyrrolidinyl), optionally substituted azetidinyl, or optionally substituted oxetanyl;

$R_2$ is —H, —F, —$C_1$, —Br, methoxy, —O—($C_2$-$C_6$) alkylene-OH, —O—($C_2$-$C_6$)alkylene-OMe, —$NH_2$, —NH—($C_1$-$C_6$ alkyl), —NH—($C_2$-$C_6$)alkylene-OMe, —NH—($C_2$-$C_6$)alkylene-(optionally substituted morpholinyl), or —NH—($C_2$-$C_6$)alkylene-O—($C_1$-$C_6$ alkyl).

In another embodiment of formula B-4:

$R_2$ and $R^a$, together with the atoms to which they are attached, form a 4-6 membered heterocycloalkyl ring optionally substituted with halo, ($C_1$-$C_6$) alkyl, or ($C_1$-$C_6$) haloalkyl.

In another embodiment, the compound of formula B is a compound of formula B-5.

B-5

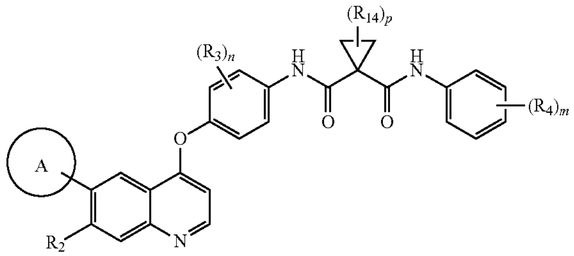

or a pharmaceutically acceptable salt thereof, wherein ring A in formula B-5 is an optionally substituted 5-6 membered heteroaryl or aryl.

In one embodiment of formula B-5:

Ring A is an optionally substituted ($C_6$-$C_{10}$) aryl, optionally substituted ($C_3$-$C_{10}$) cycloalkyl, optionally substituted 5-10 membered heteroaryl, or optionally substituted 4-10 membered heterocycloalkyl; and $R_2$ is H, or ($C_1$-$C_6$)alkoxy.

In another embodiment of formula B-5:

Ring A is an optionally substituted phenyl, optionally substituted cyclopropyl, optionally substituted pyridyl, optionally substituted imidazolyl, optionally substituted pyrrolyl, optionally substituted furanyl, optionally substituted pyrazolyl, optionally substituted oxazolyl, optionally substituted azetidinyl, or optionally substituted oxetanyl; and $R_2$ is H, or methoxy.

Another embodiment of a compound of formula A and B is a compound of formula C:

C

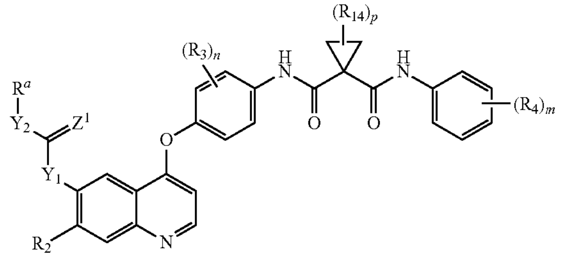

or a pharmaceutically acceptable salt thereof, wherein:

$Y_1$ is absent;

$Y_2$ is O, NH, NHO, NH—NH, or N—($C_1$-$C_6$) alkyl; or $Y_2$ is optionally substituted azetidinyl;

Z is O, NH, NO—($C_1$-$C_6$) alkyl, or N—($C_1$-$C_6$) alkyl;

$R^a$ is —H, ($C_1$-$C_6$) alkyl, —($C_2$-$C_6$) alkylene-OH, —$CH_2CHOH$—($C_2$-$C_6$) alkylene-OH, —($C_2$-$C_6$) alkylene-$NH_2$, —($C_2$-$C_6$) alkylene-NH($C_1$-$C_6$) alkyl, —($C_2$-$C_6$) alkylene-N(($C_1$-$C_6$) alkyl$)_2$, —($C_2$-$C_6$) alkylene-optionally substituted 4-6 membered heterocycloalkyl), or optionally substituted 4-6 membered heterocycloalkyl;

$R_2$ is —H, —F, —Cl, —Br, —($C_1$-$C_6$)alkoxy, —O—($C_2$-$C_6$)alkylene-OH, —O—($C_2$-$C_6$)alkylene-O—($C_1$-$C_6$ alkyl), ($C_2$-$C_6$)alkylene-O—($C_1$-$C_6$) alkyl, —$NH_2$, —NH—($C_1$-$C_6$ alkyl), NH—($C_1$-$C_6$)alkylene-(optionally substituted 4-6 membered heterocycloalkyl), NH—($C_2$-$C_6$)alkylene-O—($C_1$-$C_6$ alkyl); and n and m are each independently integers of 0 to 3

In another embodiment of formula C:

$Y_1$ is absent;

$Y_2$ is O, NH, NHO, NH—NH, or N—($C_1$-$C_6$) alkyl; or $Y_2$ is optionally substituted azetidinyl;

$Z^1$ is O, NH, NO—($C_1$-$C_6$) alkyl, or N—($C_1$-$C_6$) alkyl;

$R^a$ is —H, methyl, ethyl, —($C_2$-$C_6$) alkylene-OH, —$CH_2CHOH$—($C_2$-$C_6$) alkylene-OH, —($C_2$-$C_6$) alkylene-$NH_2$, —($C_2$-$C_6$) alkylene-NHMe, —($C_2$-$C_6$) alkylene-N$(Me)_2$, —($C_1$-$C_6$) alkylene-morpholinyl), —($C_1$-$C_6$) alkylene-piperidinyl), ($C_1$-$C_6$)alkylene-(optionally substituted pyrrolidinyl), optionally substituted azetidinyl, or optionally substituted oxetanyl;

$R_2$ is —H, —F, —$C_1$, —Br, methoxy, —O—($C_2$-$C_6$) alkylene-OH, —O—($C_2$-$C_6$)alkylene-OMe, —$NH_2$, —NH—($C_1$-$C_6$ alkyl), NH—($C_2$-$C_6$)alkylene-OMe, —NH—($C_2$-$C_6$)alkylene-(optionally substituted morpholinyl), or —NH—($C_2$-$C_6$)alkylene-O—($C_1$-$C_6$ alkyl); and and n and m or each 0 or 1.

In another embodiment of formula C:

$R_2$ and $R^a$, together with the atoms to which they are attached, form a 4-6 membered heterocycloalkyl ring optionally substituted with halo, ($C_1$-$C_6$) alkyl, and ($C_1$-$C_6$) haloalkyl; and n and m are each independently integers of 0 to 3.

Another embodiment of formula C is a compound of formula C-1.

C-1

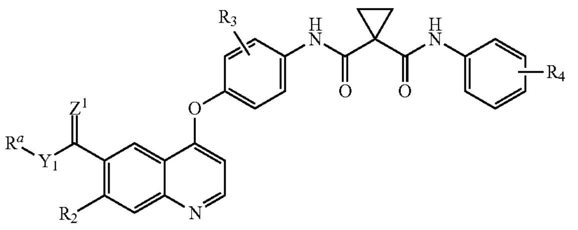

or a pharmaceutically acceptable salt thereof, wherein:

$Y_2$ is O, NH, NHO, NH—NH, or N—($C_1$-$C_6$) alkyl; or $Y_2$ is optionally substituted azetidinyl;

$Z^1$ is O, NH, NO—($C_1$-$C_6$) alkyl, or N—($C_1$-$C_6$) alkyl;

$R^a$ is —H, methyl, ethyl, —($C_2$-$C_6$) alkylene-OH, —$CH_2CHOH$—($C_2$-$C_6$) alkylene-OH, —($C_2$-$C_6$) alkylene-$NH_2$, —($C_2$-$C_6$) alkylene-NHMe, —($C_2$-$C_6$) alkylene-N$(Me)_2$, —($C_1$-$C_6$) alkylene-morpholinyl), —($C_1$-$C_6$) alkylene-piperidinyl) ($C_1$-$C_6$)alkylene-(optionally substituted pyrrolidinyl), optionally substituted azetidinyl, or optionally substituted oxetanyl;

$R_2$ is —H, —F, —Cl, —Br, methoxy, —O—($C_2$-$C_6$) alkylene-OH, —O—($C_2$-$C_6$)alkylene-OMe, —$NH_2$, —NH—($C_1$-$C_6$ alkyl), —NH—($C_2$-$C_6$)alkylene-OMe, —NH—($C_2$-$C_6$)alkylene-(optionally substituted morpholinyl), or —NH—($C_2$-$C_6$)alkylene-O—($C_1$-$C_6$ alkyl); and and n and m are each independently 0 or 1.

Another embodiment of formula A and B is a compound of formula D:

D

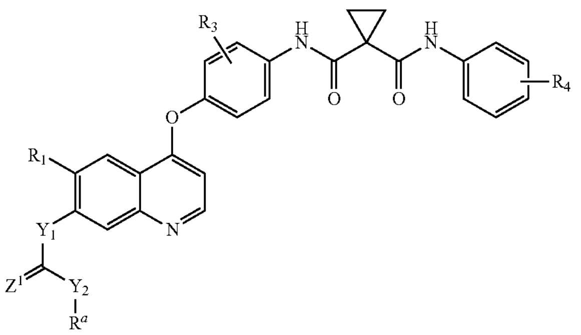

In one embodiment of formula D:

$R_1$ is —H or ($C_1$-$C_6$) alkyl; and $Y_1$ is absent;

$Y_2$ is absent or is —O—, —NHO—, or —NH—; and $Z^1$ is O or NO—($C_1$-$C_6$) alkyl;

$R^a$ is —H or —($C_1$-$C_6$) alkyl; and n and m are each independently integers of 0 to 3.

In another embodiment of formula D:

$R_1$ is —H or methyl;

$Y_1$ is absent;

$Y_2$ is absent or is —O—, —NHO—, or —NH—; and $Z^1$ is O or NO-Me; and $R^a$ is —H, or -Me.

n and m are each independently integers of 0 to 1.

In another embodiment of formula D:

$R_1$ and $R^a$, together with the atoms to which they are attached, form a 4-6 membered heterocycloalkyl ring optionally substituted with halo, ($C_1$-$C_6$) alkyl, or ($C_1$-$C_6$) haloalkyl; and n and m are each independently integers of 0 to 1.

Another embodiment of formula D is a compound of formula D-1.

D-1

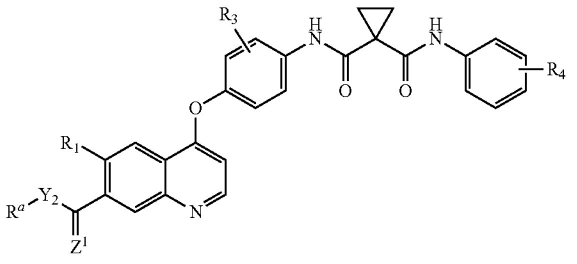

Another embodiment of formula A and B is a compound of formula E:

E

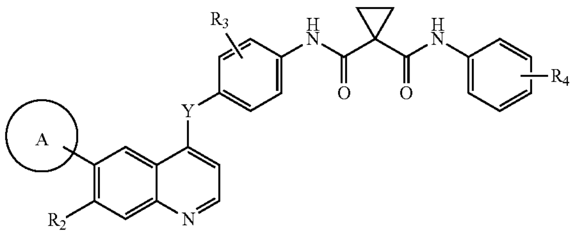

or a pharmaceutically acceptable salt thereof, wherein:

Ring A is an optionally substituted ($C_6$-$C_{10}$) aryl, optionally substituted ($C_3$-$C_{10}$) cycloalkyl, optionally substituted 5-10 membered heteroaryl, or optionally substituted 4-10 membered heterocycloalkyl; and $R_2$ is H or ($C_1$-$C_6$)alkoxy.

In another embodiment of formula E:

Ring A is an optionally substituted phenyl, optionally substituted cyclopropyl, optionally substituted pyridyl, optionally substituted imidazolyl, optionally substituted pyrrolyl, optionally substituted furanyl, optionally substituted pyrazolyl, optionally substituted oxazolyl, optionally substituted azetidinyl, or optionally substituted oxetanyl; and $R_2$ is H or methoxy.

Another embodiment of formula A and B is a compound of formula F:

F

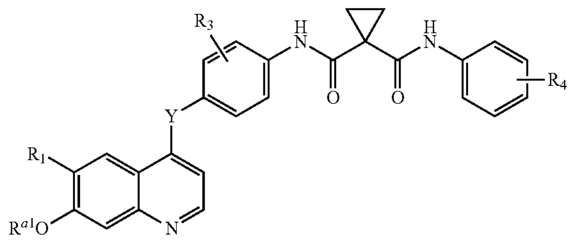

or a pharmaceutically acceptable salt thereof, wherein $R^{a1}$ is optionally substituted ($C_1$-$C_6$) alkyl;

$R_1$ is —H, —CN, optionally substituted 3-6 membered cycloalkyl, optionally substituted phenyl, optionally substituted 4-6 membered heterocycloalkyl, optionally substituted 5-6 membered heteroaryl, —$SO_2$—($C_1$-$C_6$) alkyl, —$SO_2NH_2$, —$SO_2$—NH($C_1$-$C_6$) alkyl, or P(O)(($C_1$-$C_6$) alkyl)$_2$, or

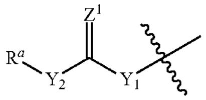

wherein “ ” indicates the point of attachment, wherein:

$Y_1$ is absent;

$Y_2$ is absent or is —O—, —NH—, —NHO—, —NH—NH—, —N—($C_1$-$C_6$) alkyl-; or $Y_2$ is optionally substituted

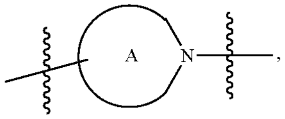

wherein ring A is a 3, 4, 5, 6, or 7-membered ring, wherein “ ” indicates points of attachment;

$Z^1$ is O, NH, N—($C_1$-$C_6$) alkyl, NHO, or NO—($C_1$-$C_6$) alkyl; and $R^a$ is —H, —($C_1$-$C_6$) alkyl, 4-6-membered heterocycloalkyl, 3-6-membered cycloalkyl, —($C_2$-$C_6$) alkylene-OH, —$CH_2$CHOH—($C_2$-$C_6$) alkylene-OH, —($C_2$-$C_6$) alkylene-$NH_2$, —($C_2$-$C_6$) alkylene-NH ($C_1$-$C_6$), —($C_2$-$C_6$) alkylene-N($C_1$-$C_6$)$_2$, —($C_2$-$C_6$) alkylene-N-(4-6-membered heterocycloalkyl);

In another embodiment of formula F:

$R^{a1}$ is methyl;

$R_1$ is —H, —CN, optionally substituted cyclopropyl, optionally substituted phenyl, optionally substituted 4-6 membered azetidinyl, optionally substituted pyrollidinyl, optionally substituted piperidinyl, optionally substituted oxetanyl, optionally substituted oxazolyl, optionally substituted pyridinyl, optionally substituted imidazolyl, optionally substituted pyrrolyl, optionally substituted furanyl, optionally substituted pyrazolyl, optionally substituted oxadiazolyl, —$SO_2$—($C_1$-$C_6$) alkyl, —$SO_2NH_2$, —$SO_2$—NH($C_1$-$C_6$) alkyl, or P(O)(($C_1$-$C_6$) alkyl)$_2$; or $R_1$ is

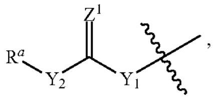

wherein:

$Y_1$ is absent;

$Y_2$ is O, NH, NHO, NH—NH, or N—($C_1$-$C_6$) alkyl; or $Y_2$ is optionally substituted azetidinyl;

$Z^1$ is O, NH, or N—($C_1$-$C_6$) alkyl; and $R^a$ is H, ($C_1$-$C_6$) alkyl, —($C_2$-$C_6$) alkylene-OH, —$CH_2$CHOH—($C_2$-$C_6$) alkylene-OH, —($C_2$-$C_6$) alkylene-$NH_2$, —($C_2$-$C_6$) alkylene-NH($C_1$-$C_6$) alkyl, —($C_2$-$C_6$) alkylene-N(($C_1$-$C_6$) alkyl)$_2$, —($C_2$-$C_6$) alkylene-heterocycloalkyl), and 4-6 membered heterocycloalkyl, wherein heterocycloalkyl is optionally substituted.

Another embodiment of formula A and B is a compound of formula G:

G

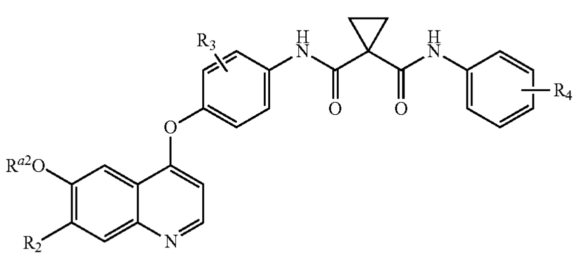

or a pharmaceutically acceptable salt thereof, wherein:

$R^{a1}$ is optionally substituted ($C_1$-$C_6$) alkyl;

$R_2$ is

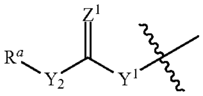

wherein “ ” indicates the point of attachment, wherein:

$Y_1$ is absent;

$Y_2$ is absent or is —O—, or —NH—; and $Z^1$ is O; and $R^a$ is —H or —($C_1$-$C_6$) alkyl.

In another embodiment of formula G:

$R^{a2}$ is methyl;

$R_2$ is

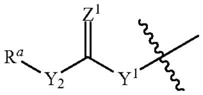

wherein “ ” indicates the point of attachment, wherein:

$Y_1$ is absent;

$Y_2$ is absent or is —O—, or —NH—; and $Z^1$ is O or NO—($C_1$-$C_6$) alkyl; and $R^a$ is —H, or —($C_1$-$C_6$) alkyl.

Another embodiment of formula A and B is a compound for modulating kinase activity according to Formula H:

H

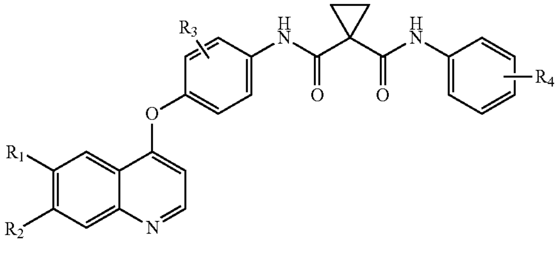

or a pharmaceutically acceptable salt thereof, wherein:

$R_1$ is selected from the group consisting of —H, —CN, —CO—$NR_5R_6$, —$CO_2R_7$, optionally substituted aryl, optionally substituted heteroaryl, optionally substituted ($C_1$-$C_6$) alkyl, optionally substituted ($C_3$-$C_8$) cycloalkyl, optionally substituted ($C_3$-$C_6$) heterocycloalkyl, —$SO_2NR_8R_9$, or —($SO_2$)($C_1$-$C_6$) alkyl;

wherein when $R_1$ is selected from the group consisting of —CN, —CO—$NR_5R_6$, —$CO_2R_7$, optionally substituted aryl, optionally substituted heteroaryl, optionally substituted ($C_3$-$C_8$) cycloalkyl, optionally substituted ($C_3$-$C_6$) heterocycloalkyl, —$SO_2NR_8R_9$, and —($SO_2$)—($C_1$-$C_6$) alkyl, $R_2$ is H, halo, $NR_5R_6$, or optionally substituted ($C_1$-$C_6$) alkoxy;

wherein when $R_1$ is —H, optionally substituted ($C_1$-$C_6$) alkyl, or optionally substituted ($C_1$-$C_6$) alkoxy, $R_2$ is —CO—$NR_5R_6$ or —$CO_2R_7$;

or $R_1$ and $R_2$ taken together with the atoms to which they are attached to form optionally substituted cycloalkyl or optionally substituted heterocyloalkyl;

$R_3$ is selected from the group consisting of H, optionally substituted ($C_1$-$C_6$) alkyl, —CN, and halo;

$R_4$ is —H or halo;

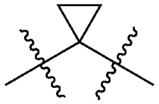 [SMILES: *C1(*)CC1]

is optionally substituted with one, two, three, or four groups independently selected from the group consisting of halo and ($C_1$-$C_6$) alkyl, wherein “” indicate points of attachment;

$R_5$ and $R_6$ are each independently H; optionally substituted ($C_1$-$C_6$) alkyl; or optionally substituted $C_1$-$C_6$ alkoxy;

$R_7$ is —H or optionally substituted ($C_1$-$C_6$) alkyl;

$R_8$ and $R_9$ are each independently —H or optionally substituted ($C_1$-$C_6$) alkyl; or $R_8$ and $R_9$ may connect to form optionally substituted heterocycle; and Y is selected from the group consisting of O, S, SO, $SO_2$, NH, and N—(($C_1$-$C_6$) alkyl).

In one embodiment of a compound of formula I, Y is O.

In another embodiment, $R_3$ is —H.

In another embodiment,

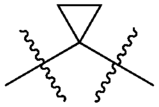 [SMILES: *C1(*)CC1]

is not substituted.

In another embodiment, $R_4$ is halo.

In another embodiment, $R_4$ is para fluoro.

In another embodiment, $R_2$ is —H, halo, or optionally substituted ($C_1$-$C_6$)-alkoxy.

In another embodiment, $R_1$ is —CN.

In another embodiment, $R_1$ is —$CO_2H$.

In another embodiment, $R_1$ is —$CO_2$-Me.

In another embodiment, $R_1$ is —CO—$NHR_6$.

In another embodiment, $R_1$ is —CO—$NH_2$.

In another embodiment, $R_1$ is —CO—$NMeR_6$.

In another embodiment, $R_3$ is —H or halo.

In another embodiment, $R_1$ is selected from the group consisting of —CN, —($SO_2$)$NH_2$, —OMe, —($SO_2$)$CH_3$

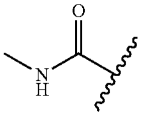, 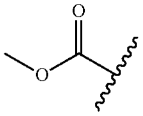, 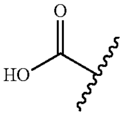,

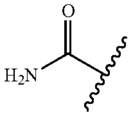, 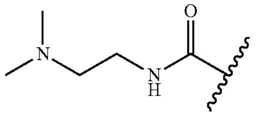,

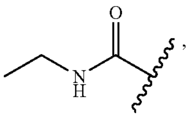, 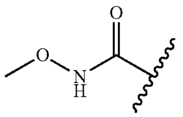,

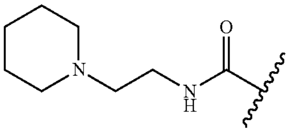,

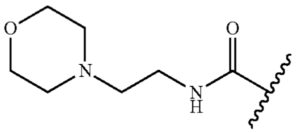, 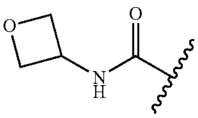,

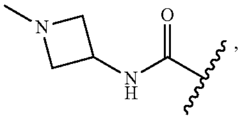, 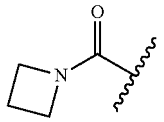,

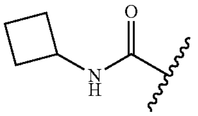, 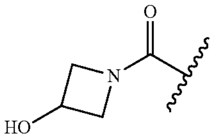,

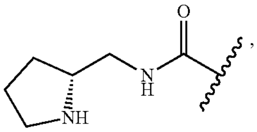, 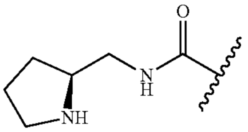,

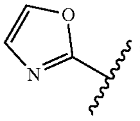, 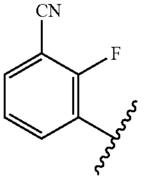, 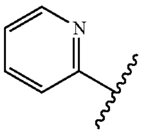,

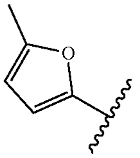, 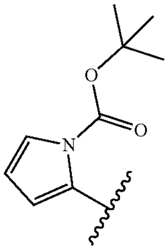 ,

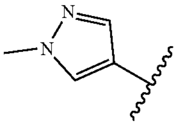, 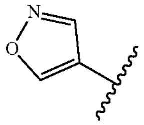, 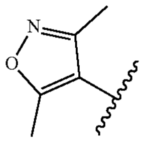,

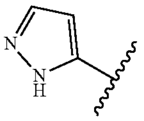, 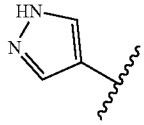, 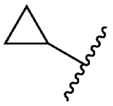,

-continued

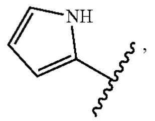, 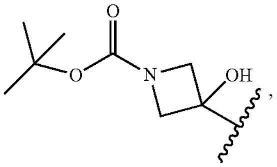,

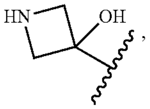, 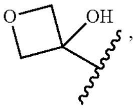, 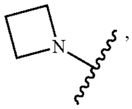,

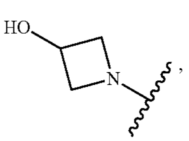, 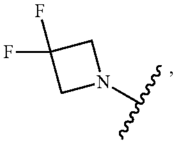,

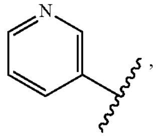, 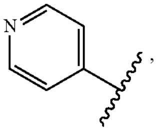, 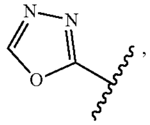,

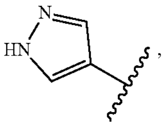, and 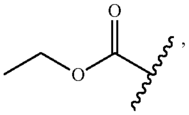, wherein “ ” is the point of attachment.

In another embodiment, $R_1$ is selected from the group consisting of

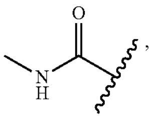, 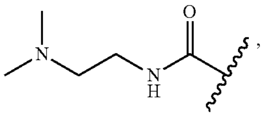,

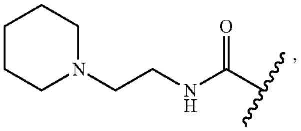,

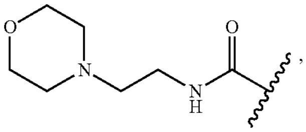, 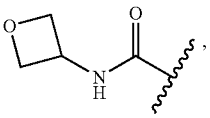,

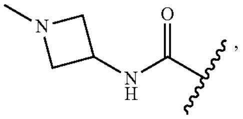, 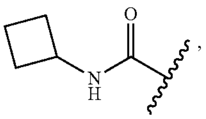,

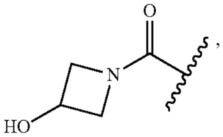,

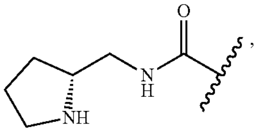, and

-continued

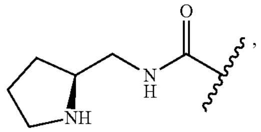, wherein “ ” is the point of attachment.

In another embodiment, $R_1$ selected from the group consisting of

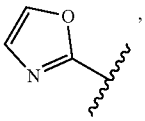, 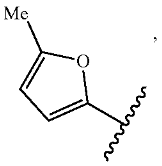, 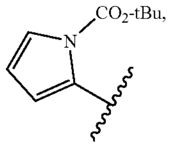

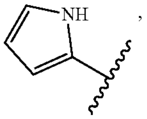, 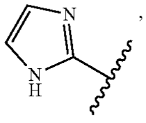, 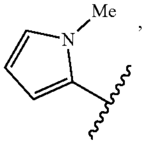,

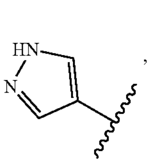, 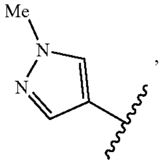, 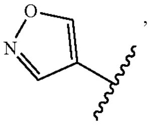,

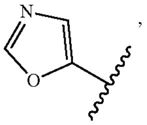, 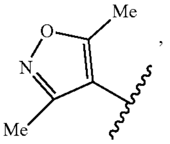, 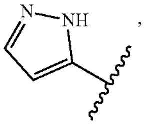,

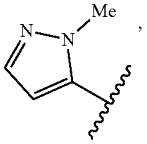, wherein “ ” is the point of attachment.

In another embodiment, $R_2$ is selected from the group consisting of —H, —CN, —Br, —F, —Cl, —OMe, —$CH_3$,

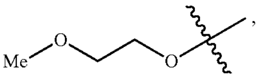, 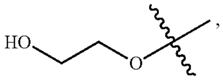,

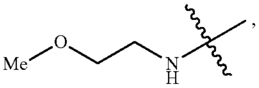,

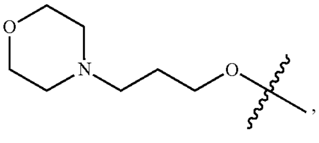, $CH_2NH_2$, $NH_2$, NHMe,

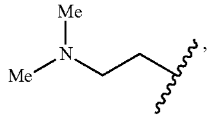,
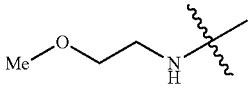,
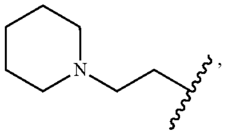,
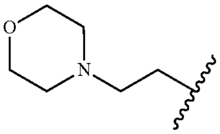, and
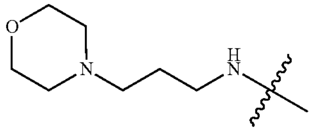, wherein "" is the point of attachment.

In another embodiment, $R_1$ is —H, methyl, or methoxy.

In another embodiment, $R_2$ is —$CO_2H$.

In another embodiment, $R_1$ is —$CO_2$-Me.

In another embodiment, $R_1$ is —CO—$NHR_6$.

In another embodiment, $R_1$ is —CO—$NH_2$.

In another embodiment, $R_1$ is —CO—$NMeR_6$.

In another embodiment, $R_1$ is selected from the group consisting of

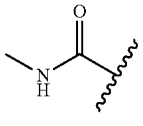,
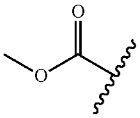,
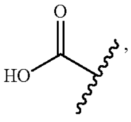, and

-continued

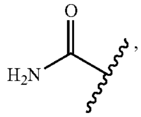,

In another embodiment, $R_1$ and $R_2$ are taken together to form

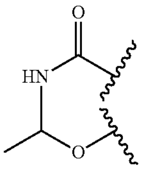.

In a further embodiment, the compound of formula I is a compound of formula I-1:

I-1

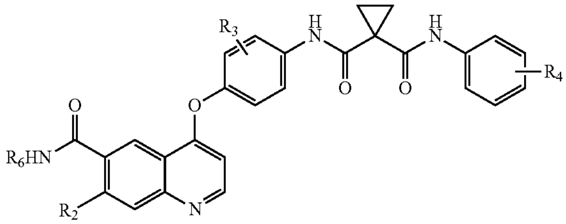

wherein $R_6$ is ($C_1$-$C_6$) alkyl, $R_2$ is ($C_1$-$C_6$) alkoxy, $R_3$ is —H or halo, and $R_4$ is halo.

In another aspect, the invention provides a compound of formula A or A-I which is provided in Table 1 below.

TABLE 1

Specific compounds of the invention

| No. | Structure | Name |
| --- | --- | --- |
| 5 | 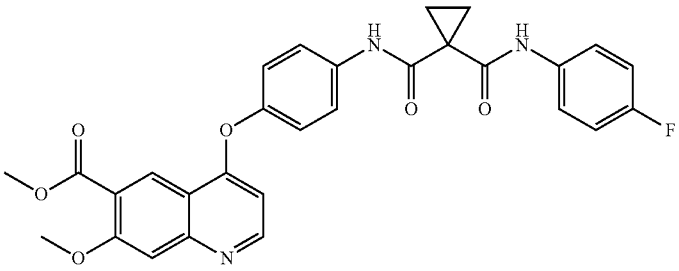 [SMILES: COC(=O)c1cc2c(Oc3ccc(NC(=O)C4(C(=O)Nc5ccc(F)cc5)CC4)cc3)ccnc2cc1OC] | methyl 4-[4-[[1-[(4-fluorophenyl)carbamoyl]-cyclopropanecarbonyl]amino]-phenoxy]-7-methoxyquinoline-6-carboxylate |
| 6 | 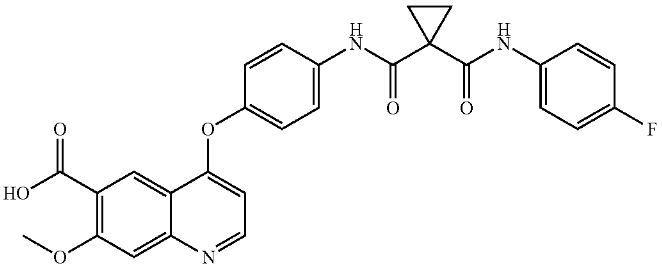 [SMILES: COc1cc2nccc(Oc3ccc(NC(=O)C4(C(=O)Nc5ccc(F)cc5)CC4)cc3)c2cc1C(=O)O] | 4-[4-[[1-[(4-fluorophenyl)carbamoyl]-cyclopropanecarbonyl]amino]-phenoxy]-7-methoxyquinoline-6-carboxylic acid |

TABLE 1-continued

| Specific compounds of the invention | | |
|---|---|---|
| No. | Structure | Name |
| 7 | 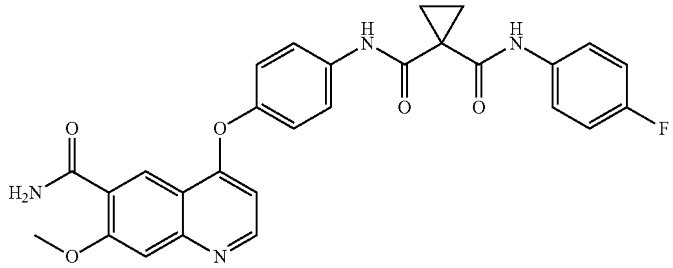 [SMILES: COc1cc2nccc(Oc3ccc(NC(=O)C4(C(=O)Nc5ccc(F)cc5)CC4)cc3)c2cc1C(N)=O] | 1-N-[4-(6-carbamoyl-7-methoxyquinolin-4-yl)oxyphenyl]-1-N'-(4-fluorophenyl)cyclopropane-1,1-dicarboxamide |
| 8 | 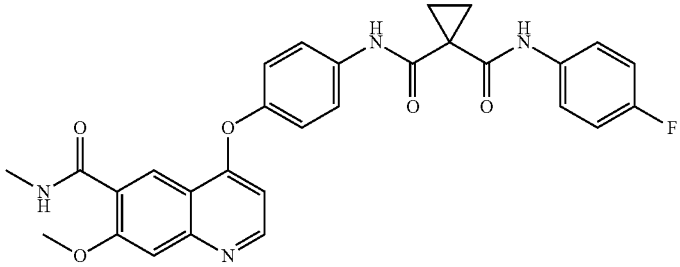 [SMILES: CNC(=O)c1cc2c(Oc3ccc(NC(=O)C4(C(=O)Nc5ccc(F)cc5)CC4)cc3)ccnc2cc1OC] | 1-N'-(4-fluorophenyl)-1-N-[4-[7-methoxy-6-(methylcarbamoyl)quinoln-4-yl]oxyphenyl]cyclopropane-1,1-dicarboxamide |
| 9 | 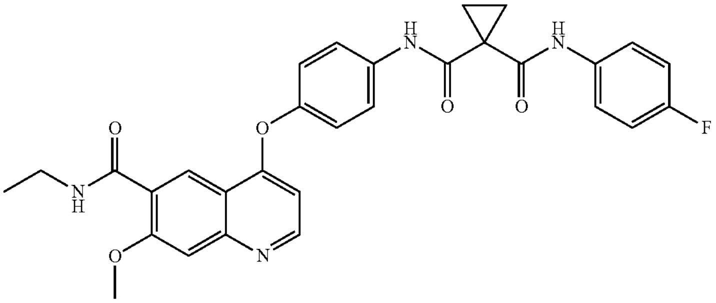 [SMILES: CCNC(=O)c1cc2c(Oc3ccc(NC(=O)C4(C(=O)Nc5ccc(F)cc5)CC4)cc3)ccnc2cc1OC] | 1-N-[4-[6-(ethylcarbamoyl)-7-methoxyquinolin-4-yl]oxyphenyl]-1-N'-(4-fluorophenyl)cyclopropane-1,1-dicarboxamide |
| 10 | 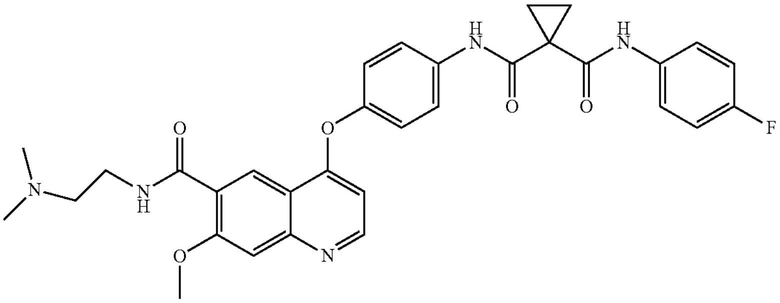 [SMILES: COc1cc2nccc(Oc3ccc(NC(=O)C4(C(=O)Nc5ccc(F)cc5)CC4)cc3)c2cc1C(=O)NCCN(C)C] | 1-N-[4-[6-[2-(dimethylamino)ethylcarbamoyl]-7-methoxyquinolin-4-yl]oxyphenyl]-1-N'-(4-fluorophenyl)cyclopropane-1,1-dicarboxamide |
| 11 | 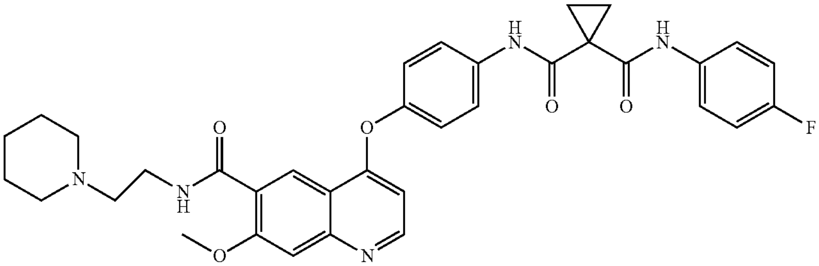 [SMILES: COc1cc2nccc(Oc3ccc(NC(=O)C4(C(=O)Nc5ccc(F)cc5)CC4)cc3)c2cc1C(=O)NCCN1CCCCC1] | 1-N'-(4-fluorophenyl)-N-[4-[7-methoxy-6-(2-piperidin-1-ylethylcarbamoyl)quinolin-4-yl]oxyphenyl]cyclopropane-1,1-dicarboxamide |

TABLE 1-continued

| Specific compounds of the invention | | |
|---|---|---|
| No. | Structure | Name |
| 12 | 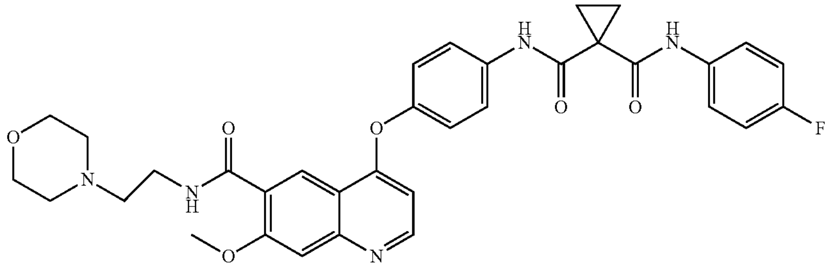 [SMILES: COc1cc2nccc(Oc3ccc(NC(=O)C4(C(=O)Nc5ccc(F)cc5)CC4)cc3)c2cc1C(=O)NCCN1CCOCC1] | 1-N'-(4-fluorophenyl)-1-N-[4-[7-methoxy-6-(2-morpholin-4-ylethylcarbamoyl)quinolin-4-yl]oxyphenyl]cyclopropane-1,1-dicarboxamide |
| 13 | 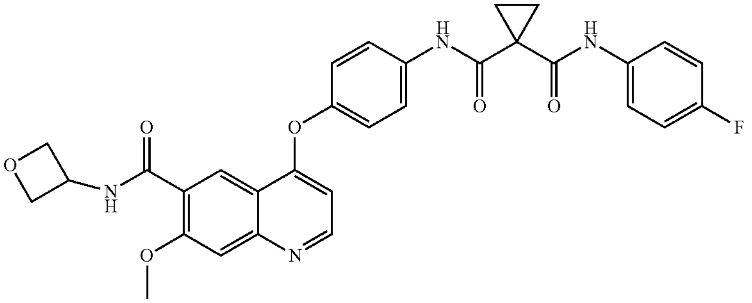 [SMILES: COc1cc2nccc(Oc3ccc(NC(=O)C4(C(=O)Nc5ccc(F)cc5)CC4)cc3)c2cc1C(=O)NC1COC1] | 1-N'-(4-fluorophenyl)-1-N-[4-[7-methoxy-6-(oxetan-3-ylcarbamoyl)quinolin-4-yl]oxyphenyl]cyclopropane-1,1-dicarboxamide |
| 14 | 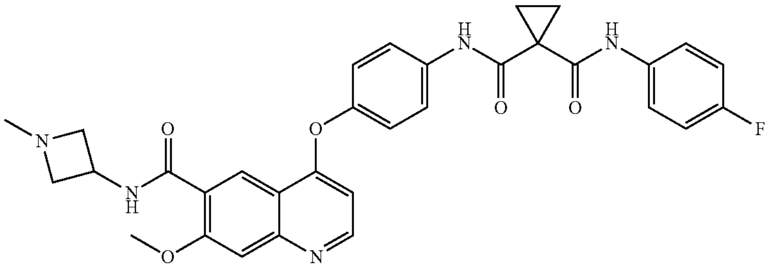 [SMILES: COc1cc2nccc(Oc3ccc(NC(=O)C4(C(=O)Nc5ccc(F)cc5)CC4)cc3)c2cc1C(=O)NC1CN(C)C1] | 1-N'-(4-fluorophenyl)-1-N-[4-[7-methoxy-6-[(1-methylazetidin-3-yl)carbamoyl]quinolin-4-yl]oxyphenyl]cyclopropane-1,1-dicarboxamide |
| 15 | 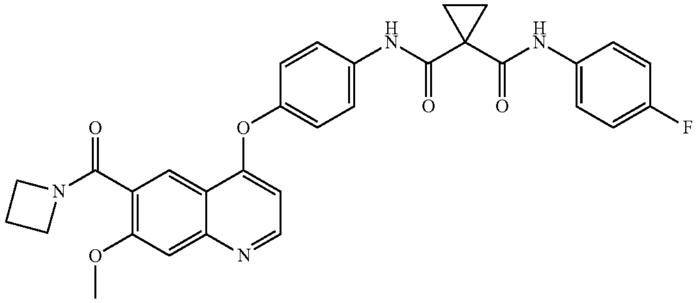 [SMILES: COc1cc2nccc(Oc3ccc(NC(=O)C4(C(=O)Nc5ccc(F)cc5)CC4)cc3)c2cc1C(=O)N1CCC1] | 1-N-[4-[6-(azetidine-1-carbonyl)-7-methoxyquinolin-4-yl]oxyphenyl]-1-N'-(4-fluorophenyl)cyclopropane-1,1-dicarboxamide |
| 16 | 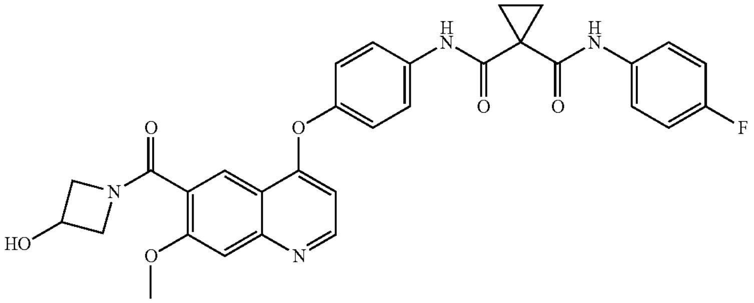 [SMILES: COc1cc2nccc(Oc3ccc(NC(=O)C4(C(=O)Nc5ccc(F)cc5)CC4)cc3)c2cc1C(=O)N1CC(O)C1] | 1-N'-(4-fluorophenyl)-1-N-[4-[6-(3-hydroxyazetidine-1-carbonyl)-7-methoxyquinolin-4-yl]oxyphenyl]cyclopropane-1,1-dicarboxamide |

TABLE 1-continued

| Specific compounds of the invention | | |
|---|---|---|
| No. | Structure | Name |
| 17 | 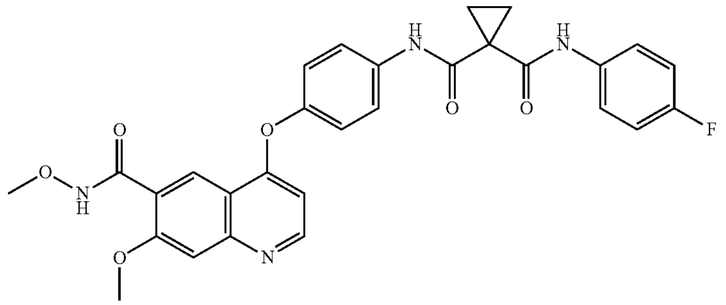 [SMILES: CONC(=O)c1cc2c(Oc3ccc(NC(=O)C4(C(=O)Nc5ccc(F)cc5)CC4)cc3)ccnc2cc1OC] | 1-N'-(4-fluorophenyl)-1-N-[4-[7-methoxy-6-(methoxycarbamoyl) quinolin-4-yl]oxyphenyl]cyclopropane-1,1-dicarboxamide |
| 20 | 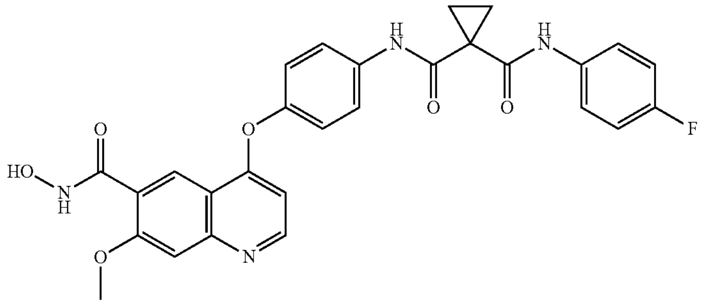 [SMILES: COc1cc2nccc(Oc3ccc(NC(=O)C4(C(=O)Nc5ccc(F)cc5)CC4)cc3)c2cc1C(=O)NO] | 1-N'-(4-fluorophenyl)-1-N-[4-[6-(hydroxycarbamoyl)-7-methoxyquinolin-4-yl]oxyphenyl]cyclopropane-1,1-dicarboxamide |
| 21 | 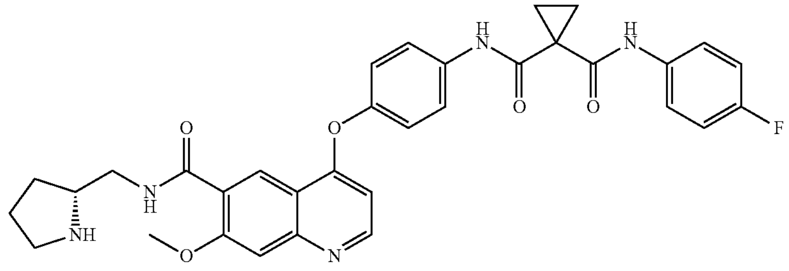 [SMILES: COc1cc2nccc(Oc3ccc(NC(=O)C4(C(=O)Nc5ccc(F)cc5)CC4)cc3)c2cc1C(=O)NC[C@H]1CCCN1] | 1-N'-(4-fluorophenyl)-1-N-[4-[7-methoxy-6-[[(2R)-pyrrolidin-2-yl]methylcarbamoyl]quinolin-4-yl]oxyphenyl]cyclopropane-1,1-dicarboxamide |
| 22 | 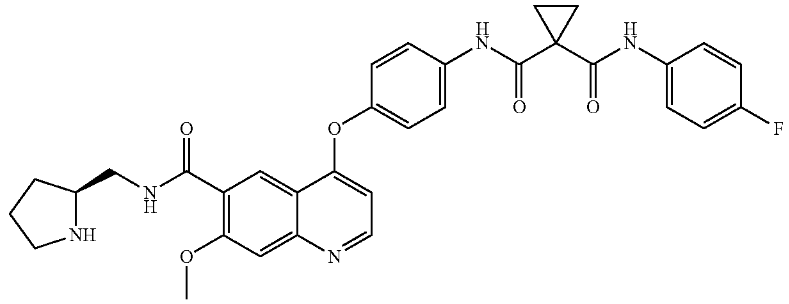 [SMILES: COc1cc2nccc(Oc3ccc(NC(=O)C4(C(=O)Nc5ccc(F)cc5)CC4)cc3)c2cc1C(=O)NC[C@@H]1CCCN1] | 1-N'-(4-fluorophenyl)-1-N-[4-[7-methoxy-6-[[(2S)-pyrrolidin-2-yl]methylcarbamoyl]quinolin-4-yl]oxyphenyl]cyclopropane-1,1-dicarboxamide |
| 26 | 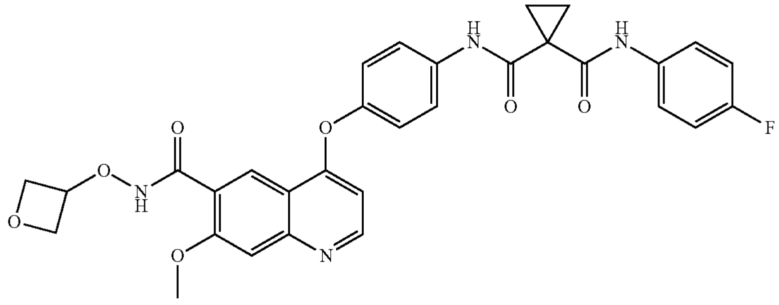 [SMILES: COc1cc2nccc(Oc3ccc(NC(=O)C4(C(=O)Nc5ccc(F)cc5)CC4)cc3)c2cc1C(=O)NOC1COC1] | 1-N'-(4-fluorophenyl)-1-N-[4-[7-methoxy-6-(oxetan-3-yloxycarbamoyl)quinolin-4-yl]oxyphenyl]cyclopropane-1,1-dicarboxamide |

TABLE 1-continued

| Specific compounds of the invention | | |
|---|---|---|
| No. | Structure | Name |
| 27 | 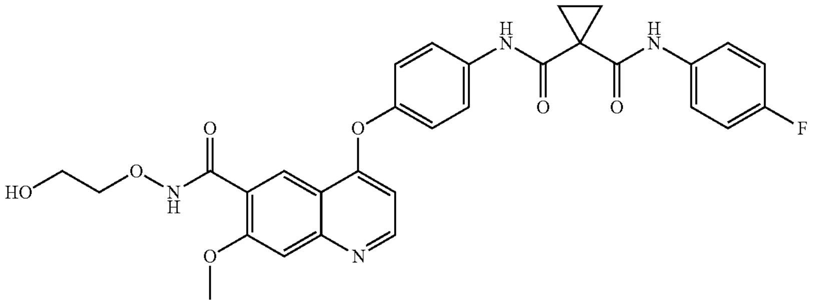 [SMILES: COc1cc2nccc(Oc3ccc(NC(=O)C4(C(=O)Nc5ccc(F)cc5)CC4)cc3)c2cc1C(=O)NOCCO] | 1-N'-(4-fluorophenyl)-1-N-[4-[6-(2-hydroxyethoxycarbamoyl)-7-methoxyquinolin-4-yl]oxyphenyl]cyclopropane-1,1-dicarboxamide |
| 30 | 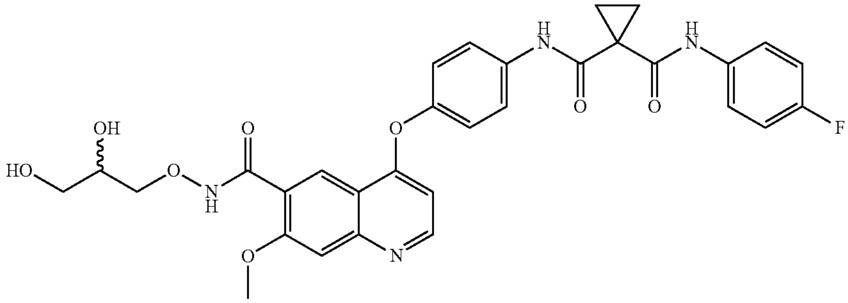 [SMILES: COc1cc2nccc(Oc3ccc(NC(=O)C4(C(=O)Nc5ccc(F)cc5)CC4)cc3)c2cc1C(=O)NOCC(O)CO] | 1-N-[4-[6-(2,3-dihydroxypropoxycarbamoyl)-7-methoxyquinolin-4-yl]oxyphenyl]-1-N'-(4-fluorophenyl)cyclopropane-1,1-dicarboxamide Enantiomer 1 |
| 31 | 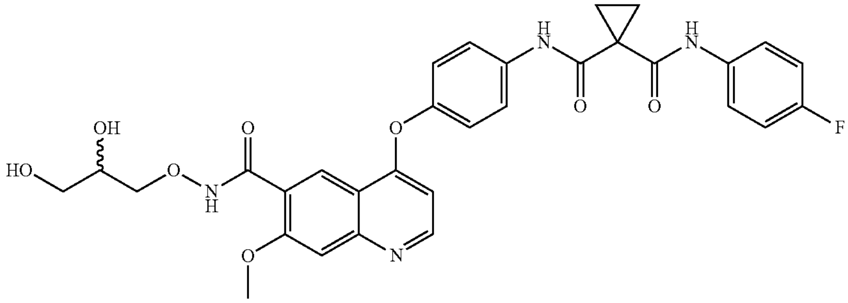 [SMILES: COc1cc2nccc(Oc3ccc(NC(=O)C4(C(=O)Nc5ccc(F)cc5)CC4)cc3)c2cc1C(=O)NOCC(O)CO] | 1-N-[4-[6-(2,3-dihydroxypropoxycarbamoyl)-7-methoxyquinolin-4-yl]oxyphenyl]-1-N'-(4-fluorophenyl)cyclopropane-1,1-dicarboxamide Enantiomer 2 |
| 32 | 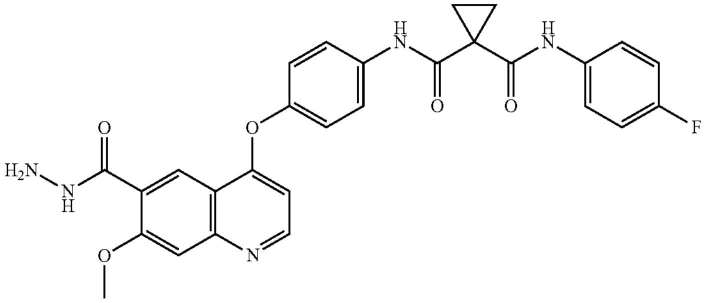 [SMILES: COc1cc2nccc(Oc3ccc(NC(=O)C4(C(=O)Nc5ccc(F)cc5)CC4)cc3)c2cc1C(=O)NN] | 1-N'-(4-fluorophenyl)-1-N-[4-[6-(hydrazinecarbonyl)-7-methoxyquinolin-4-yl]oxyphenyl]cyclopropane-1,1-dicarboxamide |
| 34 | 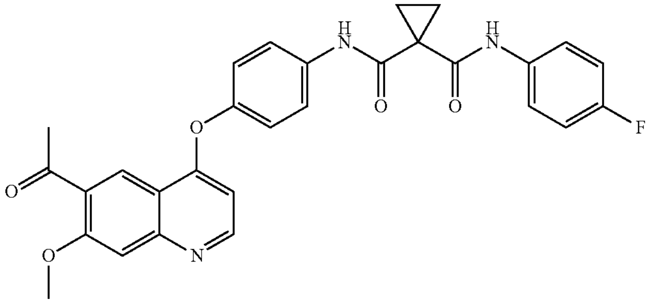 [SMILES: COc1cc2nccc(Oc3ccc(NC(=O)C4(C(=O)Nc5ccc(F)cc5)CC4)cc3)c2cc1C(C)=O] | 1-N-[4-(6-acetyl-7-methoxyquinolin-4-yl)oxyphenyl]-1-N'-(4-fluorophenyl)cyclopropane-1,1-dicarboxamide |

TABLE 1-continued

| Specific compounds of the invention | | |
|---|---|---|
| No. | Structure | Name |
| 35 | 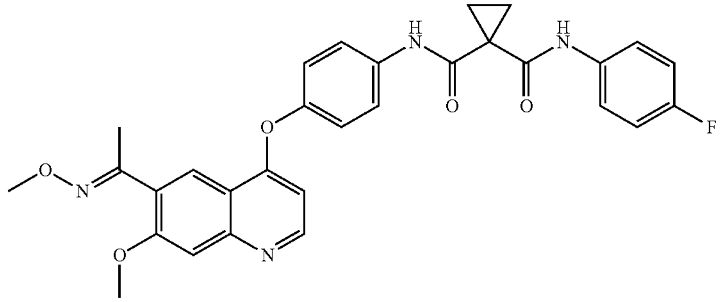 [SMILES: CO/N=C(\C)c1cc2c(Oc3ccc(NC(=O)C4(C(=O)Nc5ccc(F)cc5)CC4)cc3)ccnc2cc1OC] | 1-N'-(4-fluorophenyl)-1-N-[4-[7-methoxy-6-[(E)-N-methoxy-C-methylcarbonimidoyl]quinolin-4-yl]oxyphenyl]cyclopropane-1,1-dicarboxamide |
| 36 | 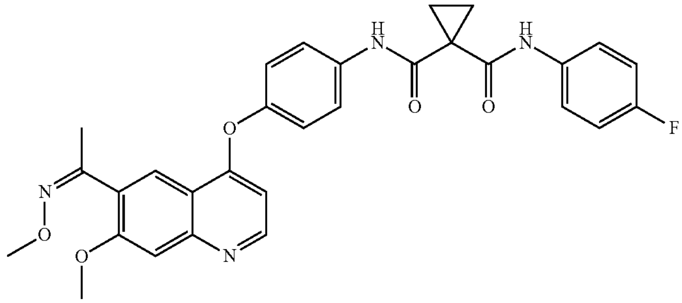 [SMILES: CO/N=C(/C)c1cc2c(Oc3ccc(NC(=O)C4(C(=O)Nc5ccc(F)cc5)CC4)cc3)ccnc2cc1OC] | 1-N'-(4-fluorophenyl)-1-N-[4-[7-methoxy-6-[(Z)-N-methoxy-C-methylcarbonimidoyl]quinolin-4-yl]oxyphenyl]cyclopropane-1,1-dicarboxamide |
| 37 | 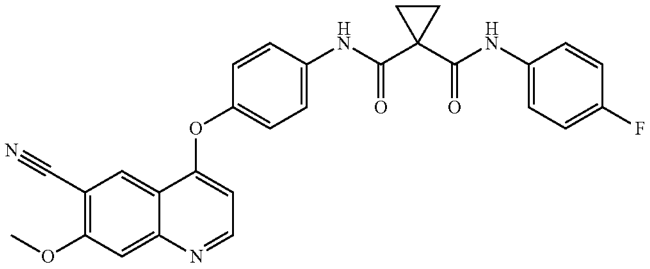 [SMILES: COc1cc2nccc(Oc3ccc(NC(=O)C4(C(=O)Nc5ccc(F)cc5)CC4)cc3)c2cc1C#N] | 1-N-[4-(6-cyano-7-methoxyquinolin-4-yl)oxyphenyl]-1-N'-(4-fluorophenyl)cyclopropane-1,1-dicarboxamide |
| 45 | 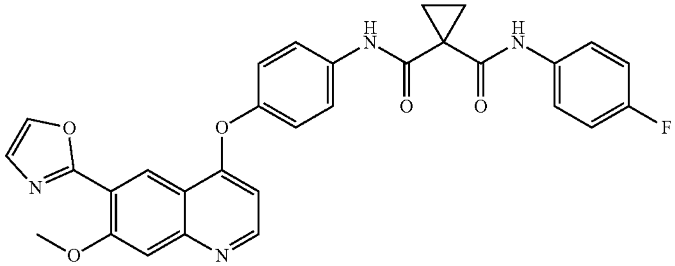 [SMILES: COc1cc2nccc(Oc3ccc(NC(=O)C4(C(=O)Nc5ccc(F)cc5)CC4)cc3)c2cc1-c1ncco1] | 1-N'-(4-fluorophenyl)-1-N-[4-[7-methoxy-6-(1,3-oxazol-2-yl)quinolin-4-yl]oxyphenyl]cyclopropane-1,1-dicarboxamide |
| 50 | 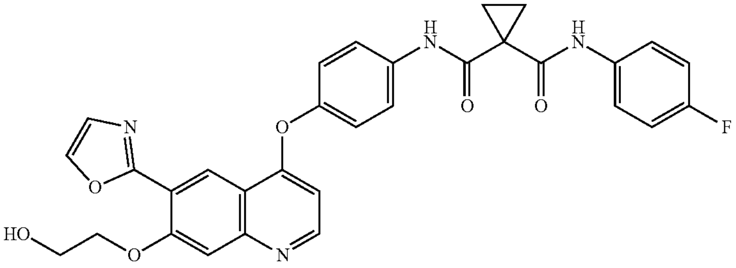 [SMILES: O=C(Nc1ccc(F)cc1)C1(C(=O)Nc2ccc(Oc3ccnc4cc(OCCO)c(-c5ncco5)cc34)cc2)CC1] | 1-N'-(4-fluorophenyl)-1-N-[4-[7-(2-hydroxyethoxy)-6-(1,3-oxazol-2-yl)quinolin-4-yl]oxyphenyl]cyclopropane-1,1-dicarboxamide |

TABLE 1-continued

| Specific compounds of the invention | | |
|---|---|---|
| No. | Structure | Name |
| 51 | 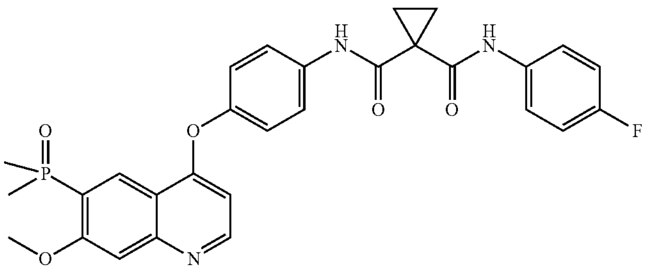 [SMILES: COc1cc2nccc(Oc3ccc(NC(=O)C4(C(=O)Nc5ccc(F)cc5)CC4)cc3)c2cc1P(C)(C)=O] | 1-N-[4-(6-dimethylphosphoryl-7-methoxyquinolin-4-yl)oxyphenyl]-1-N'-(4-fluorophenyl)cyclopropane-1,1-dicarboxamide |
| 58 | 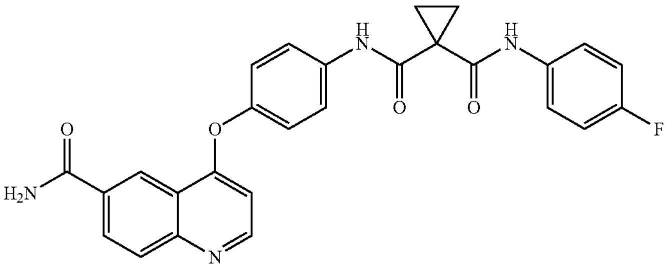 [SMILES: NC(=O)c1ccc2nccc(Oc3ccc(NC(=O)C4(C(=O)Nc5ccc(F)cc5)CC4)cc3)c2c1] | 1-N-[4-(6-carbamoylquinolin-4-yl)oxyphenyl]-1-N'-(4-fluorophenyl)cyclopropane-1,1-dicarboxamide |
| 59 | 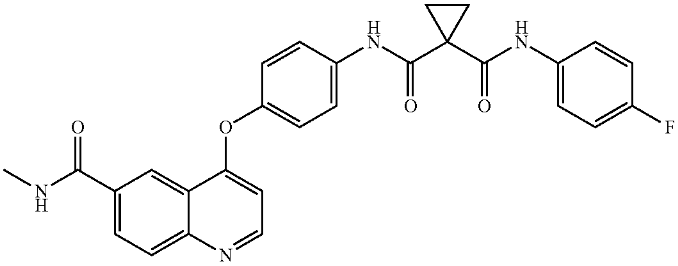 [SMILES: CNC(=O)c1ccc2nccc(Oc3ccc(NC(=O)C4(C(=O)Nc5ccc(F)cc5)CC4)cc3)c2c1] | 1-N'-(4-fluorophenyl)-1-N-[4-[6-(methylcarbamoyl)quinolin-4-yl]oxyphenyl]cyclopropane-1,1-dicarboxamide |
| 60 | 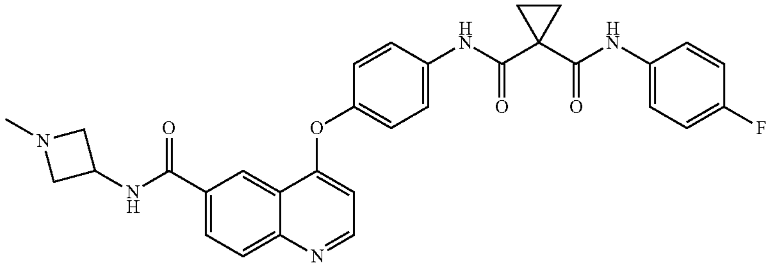 [SMILES: CN1CC(NC(=O)c2ccc3nccc(Oc4ccc(NC(=O)C5(C(=O)Nc6ccc(F)cc6)CC5)cc4)c3c2)C1] | 1-N'-(4-fluorophenyl)-1-N-[4-[6-[(1-methylazetidin-3-yl)carbamoyl]quinolin-4-yl]oxyphenyl]cyclopropane-1,1-dicarboxamide |
| 67 | 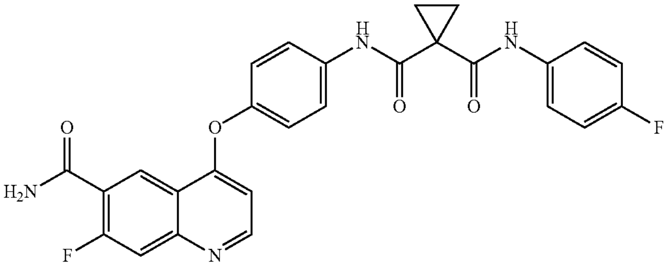 | 1-N-[4-(6-carbamoyl-7-fluoroquinolin-4-yl)oxyphenyl]-1-N'-(4-fluorophenyl)cyclopropane-1,1-dicarboxamide |

TABLE 1-continued

Specific compounds of the invention

| No. | Structure | Name |
| --- | --- | --- |
| 68 | 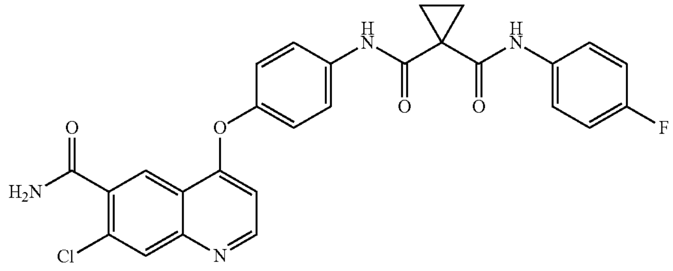 | 1-N-[4-(6-carbamoyl-7-chloroquinolin-4-yl)-oxyphenyl]-1-N'-(4-fluorophenyl)cyclopropane-1,1-dicarboxamide |
| 69 | 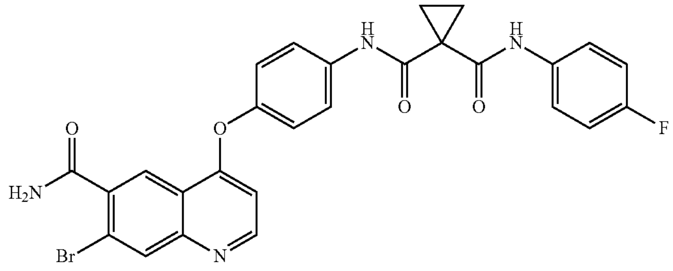 [SMILES: NC(=O)c1cc2c(Oc3ccc(NC(=O)C4(C(=O)Nc5ccc(F)cc5)CC4)cc3)ccnc2cc1F] | 1-N-[4-(7-bromo-6-carbamoylquinolin-4-yl)oxyphenyl]-1-N'-(4-fluorophenyl)cyclopropane-1,1-dicarboxamide |
| 70 | 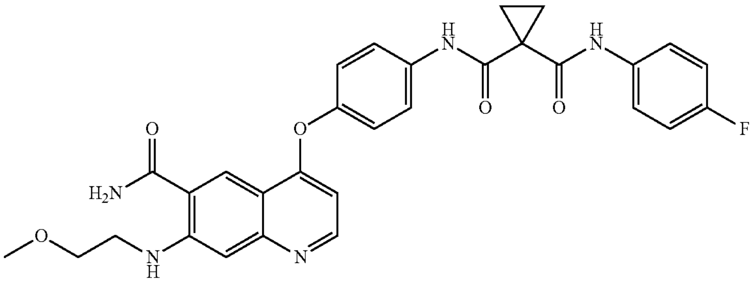 [SMILES: COCCNc1cc2nccc(Oc3ccc(NC(=O)C4(C(=O)Nc5ccc(F)cc5)CC4)cc3)c2cc1C(N)=O] | 1-N-[4-[6-carbamoyl-7-(2-methoxyethylamino)quinolin-4-yl]oxyphenyl]-1-N'-(4-fluorophenyl)cyclopropane-1,1-dicarboxamide |
| 71 | 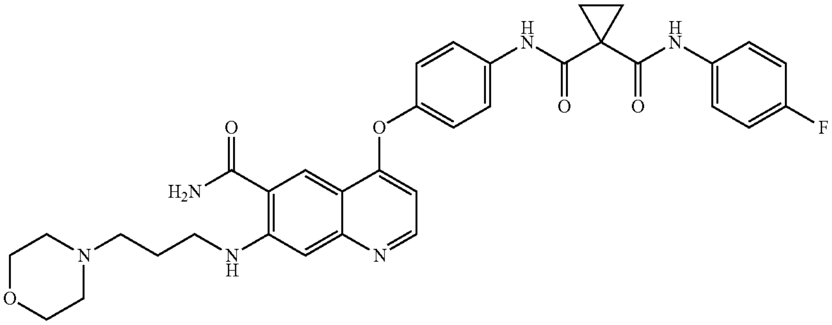 [SMILES: NC(=O)c1cc2c(Oc3ccc(NC(=O)C4(C(=O)Nc5ccc(F)cc5)CC4)cc3)ccnc2cc1NCCCN1CCOCC1] | 1-N-[4-[6-carbamoyl-7-(3-morpholin-4-ylpropylamino)quinolin-4-yl]oxyphenyl]-1-N'-(4-fluorophenyl)cyclopropane-1,1dicarboxamide |
| 72 | 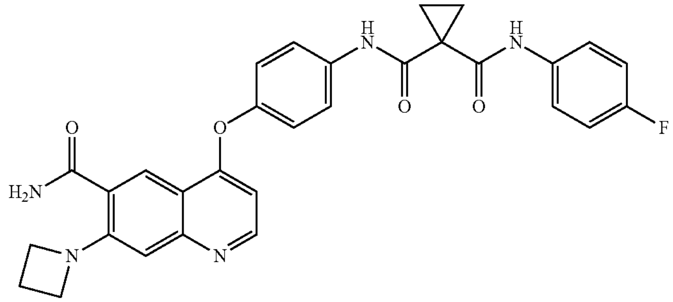 [SMILES: NC(=O)c1cc2c(Oc3ccc(NC(=O)C4(C(=O)Nc5ccc(F)cc5)CC4)cc3)ccnc2cc1N1CCC1] | 1-N-[4-[7-(azetidin-1-yl)-6-carbamoylquinolin-4-yl]oxyphenyl]-1-N'-(4-fluorophenyl)cyclopropane-1,1-dicarboxamide |

TABLE 1-continued

| Specific compounds of the invention | | |
|---|---|---|
| No. | Structure | Name |
| 81 | 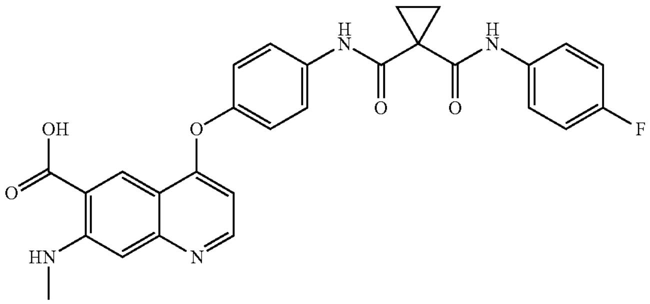 | 4-[4-[[1-[(4-fluorophenyl)carbamoyl]-cyclopropanecarbonyl]amino]-phenoxy]-7-(methylamino)quinoline-6-carboxylic acid |
| 82 | 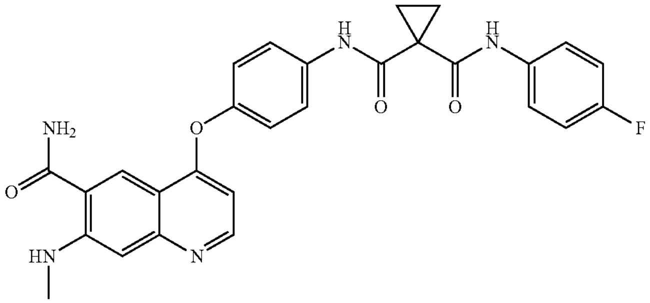 [SMILES: CNc1cc2nccc(Oc3ccc(NC(=O)C4(C(=O)Nc5ccc(F)cc5)CC4)cc3)c2cc1C(=O)O] | 1-N-[4-[6-carbamoyl-7-(methylamino)quinolin-4-yl]oxyphenyl]-1-N'-(4-fluorophenyl)cyclopropane-1,1-dicarboxamide |
| 83 | 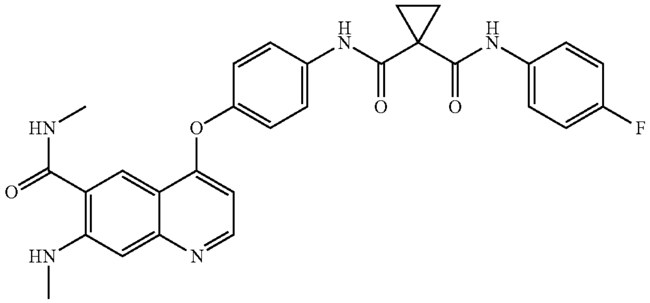 [SMILES: CNC(=O)c1cc2c(Oc3ccc(NC(=O)C4(C(=O)Nc5ccc(F)cc5)CC4)cc3)ccnc2cc1NC] | 1-N'-(4-fluorophenyl)-1-N-[4-[7-(methylamino)-6-(methylcarbamoyl)quinolin-4-yl]oxyphenyl]cyclopropane-1,1-dicarboxamide |
| 84 | 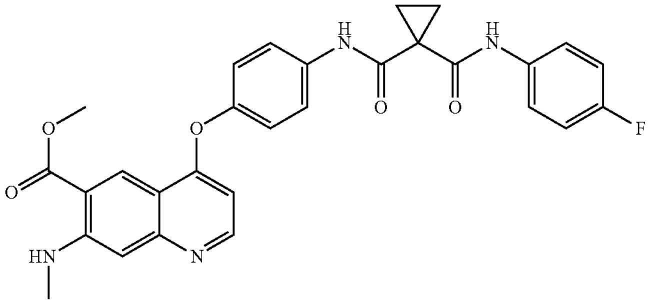 [SMILES: CNc1cc2nccc(Oc3ccc(NC(=O)C4(C(=O)Nc5ccc(F)cc5)CC4)cc3)c2cc1C(=O)OC] | methyl 4-[4-[[1-[(4-fluorophenyl)carbamoyl]-cyclopropanecarbonyl]-amino]-phenoxy]-7-(methylamino)quinoline-6-carboxylate |
| 87 | 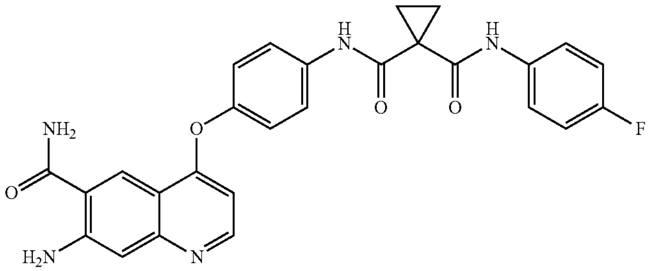 | 1-N-[4-(7-amino-6-carbamoylquinolin-4-yl)oxyphenyl]-1-N'-(4-fluorophenyl)cyclopropane-1,1-dicarboxamide |

TABLE 1-continued

Specific compounds of the invention

| No. | Structure | Name |
| --- | --- | --- |
| 88 | 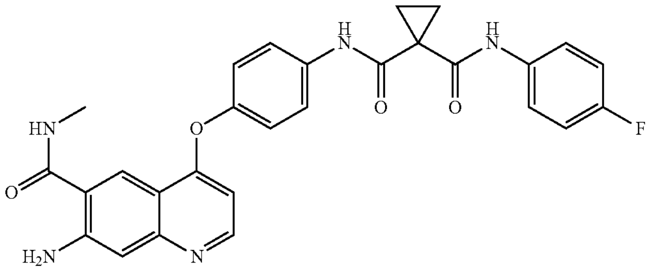 [SMILES: CNC(=O)c1cc2c(Oc3ccc(NC(=O)C4(C(=O)Nc5ccc(F)cc5)CC4)cc3)ccnc2cc1N] | 1-N-[4-[7-amino-6-(methylcarbamoyl)quinolin-4-yl]oxyphenyl]-1-N'-(4-fluorophenyl)cyclopropane-1,1-dicarboxamide |
| 89 | 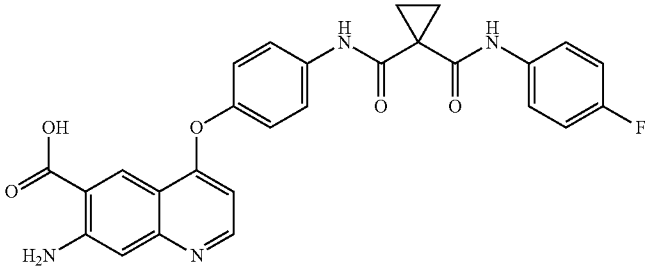 [SMILES: Nc1cc2nccc(Oc3ccc(NC(=O)C4(C(=O)Nc5ccc(F)cc5)CC4)cc3)c2cc1C(=O)O] | 7-amino-4-[4-[[1-[(4-fluorophenyl)carbamoyl]-cyclopropanecarbonyl]-amino]phenoxy]-quinoline-6-carboxylic acid |
| 90 | 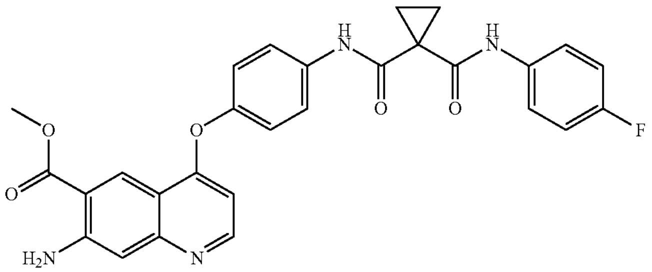 [SMILES: COC(=O)c1cc2c(Oc3ccc(NC(=O)C4(C(=O)Nc5ccc(F)cc5)CC4)cc3)ccnc2cc1N] | methyl 7-amino-4-[4-[[1-[(4-fluorophenyl)carbamoyl]-cyclopropanecarbonyl]-amino]phenoxy]-quinoline-6-carboxylate |
| 92 | 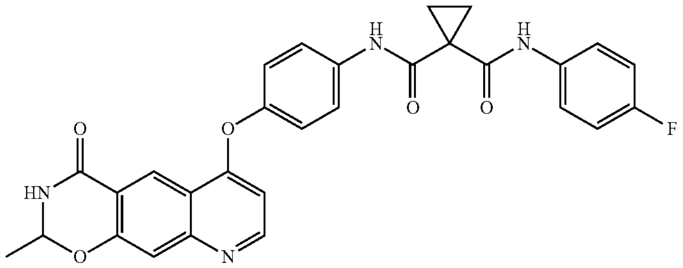 [SMILES: CC1NC(=O)c2cc3c(Oc4ccc(NC(=O)C5(C(=O)Nc6ccc(F)cc6)CC5)cc4)ccnc3cc2O1] | 1-N'-(4-fluorophenyl)-1-N-[4-[(2-methyl-4-oxo-2,3-dihydropyrido[3,2-g][1,3]benzoxazin-6-yl)oxy]phenyl]cyclopropane-1,1-dicarboxamide |
| 96 | 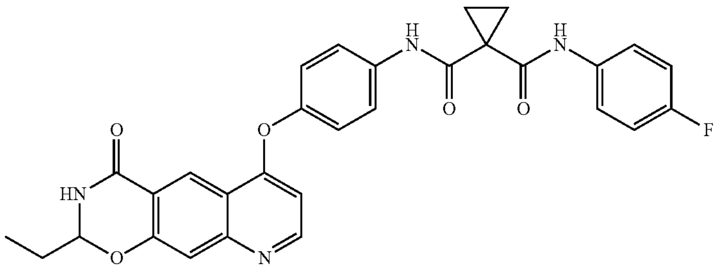 [SMILES: CCC1NC(=O)c2cc3c(Oc4ccc(NC(=O)C5(C(=O)Nc6ccc(F)cc6)CC5)cc4)ccnc3cc2O1] | 1-N-[4-[(2-ethyl-4-oxo-2,3-dihydropyrido[3,2-g][1,3]benzoxazin-6-yl)oxy]phenyl]-1-N'-(4-fluorophenyl)cyclopropane-1,1-dicarboxamide |

TABLE 1-continued

Specific compounds of the invention

| No. | Structure | Name |
| --- | --- | --- |
| 98 | 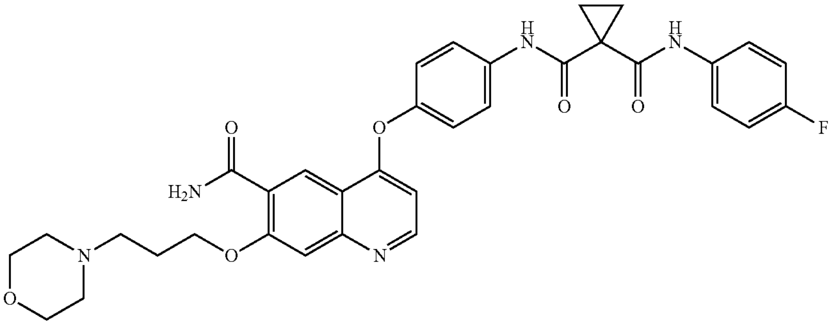 [SMILES: NC(=O)c1cc2c(Oc3ccc(NC(=O)C4(C(=O)Nc5ccc(F)cc5)CC4)cc3)ccnc2cc1OCCCN1CCOCC1] | 1-N-[4-[6-carbamoyl-7-(3-morpholin-4-ylpropoxy)quinolin-4-yl]oxyphenyl]-1-N'-(4-fluorophenyl)cyclopropane-1,1-dicarboxamide |
| 103 | 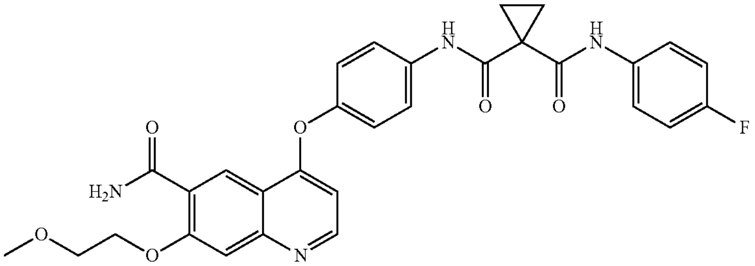 [SMILES: COCCOc1cc2nccc(Oc3ccc(NC(=O)C4(C(=O)Nc5ccc(F)cc5)CC4)cc3)c2cc1C(N)=O] | 1-N-[4-[6-carbamoyl-7-(2-methoxyethoxy)quinolin-4-yl]oxyphenyl]-1-N'-(4-fluorophenyl)cyclopropane-1,1-dicarboxamide |
| 106 | 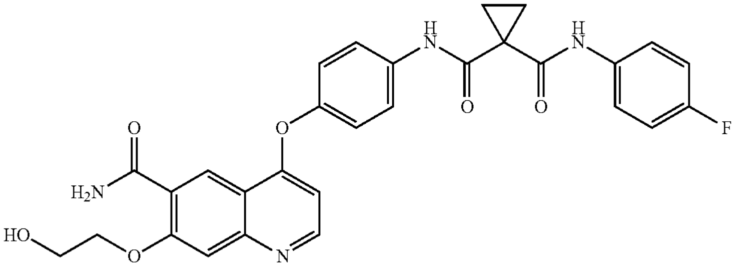 [SMILES: NC(=O)c1cc2c(Oc3ccc(NC(=O)C4(C(=O)Nc5ccc(F)cc5)CC4)cc3)ccnc2cc1OCCO] | 1-N-[4-[6-carbamoyl-7-(2-hydroxyethoxy)quinolin-4-yl]oxyphenyl]-1-N'-(4-fluorophenyl)cyclopropane-1,1-dicarboxamide |
| 110 | 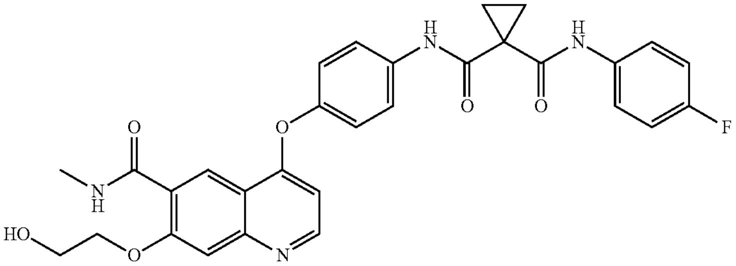 [SMILES: CNC(=O)c1cc2c(Oc3ccc(NC(=O)C4(C(=O)Nc5ccc(F)cc5)CC4)cc3)ccnc2cc1OCCO] | 1-N'-(4-fluorophenyl)-1-N-[4-[7-(2-hydroxyethoxy)-6-(methylcarbamoyl)quinolin-4-yl]oxyphenyl]cyclopropane-1,1-dicarboxamide |
| 115 | 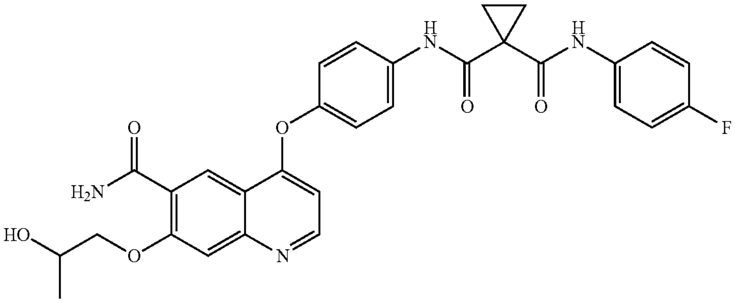 [SMILES: CC(O)COc1cc2nccc(Oc3ccc(NC(=O)C4(C(=O)Nc5ccc(F)cc5)CC4)cc3)c2cc1C(N)=O] | 1-N-[4-[6-carbamoyl-7-(2-hydroxypropoxy)quinolin-4-yl]oxyphenyl]-1-N'-(4-fluorophenyl)cyclopropane-1,1-dicarboxamide |

TABLE 1-continued

| Specific compounds of the invention | | |
|---|---|---|
| No. | Structure | Name |
| 116 | 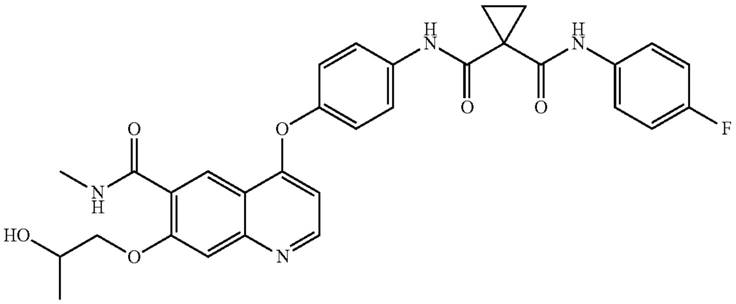 [SMILES: CNC(=O)c1cc2c(Oc3ccc(NC(=O)C4(C(=O)Nc5ccc(F)cc5)CC4)cc3)ccnc2cc1OCC(C)O] | 1-N'-(4-fluorophenyl)-1-N-[4-[7-(2-hydroxypropoxy)-6-(methylcarbamoyl)quinolin-4-yl]oxyphenyl]cyclopropane-1,1-dicarboxamide |
| 125 | 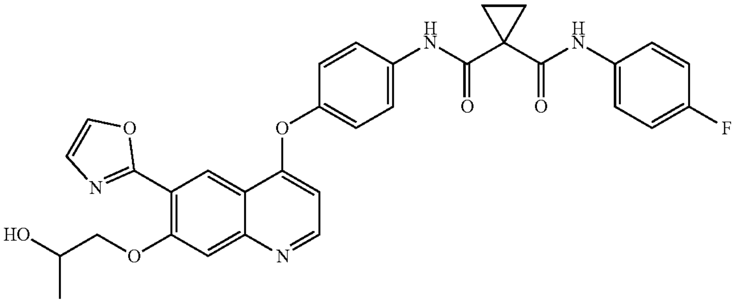 [SMILES: CC(O)COc1cc2nccc(Oc3ccc(NC(=O)C4(C(=O)Nc5ccc(F)cc5)CC4)cc3)c2cc1-c1ncco1] | 1-N'-(4-fluorophenyl)-1-N-[4-[7-(2-hydroxypropoxy)-6-(1,3-oxazol-2-yl)quinolin-4-yl]oxyphenyl]cyclopropane-1,1-dicarboxamide |
| 128 | 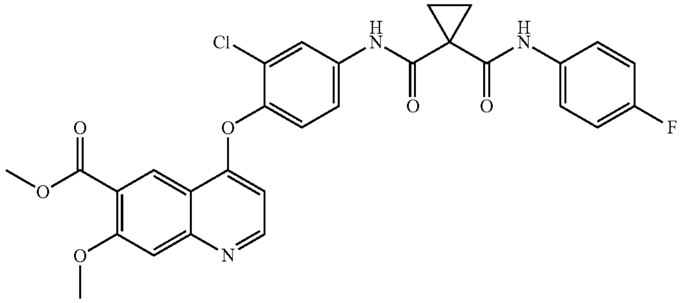 [SMILES: COC(=O)c1cc2c(Oc3ccc(NC(=O)C4(C(=O)Nc5ccc(F)cc5)CC4)cc3Cl)ccnc2cc1OC] | methyl 4-[2-chloro-4-[[1-[(4-fluorophenyl)carbamoyl]-cyclopropanecarbonyl]-amino]phenoxy]-7-methoxyquinoline-6-carboxylate |
| 129 | 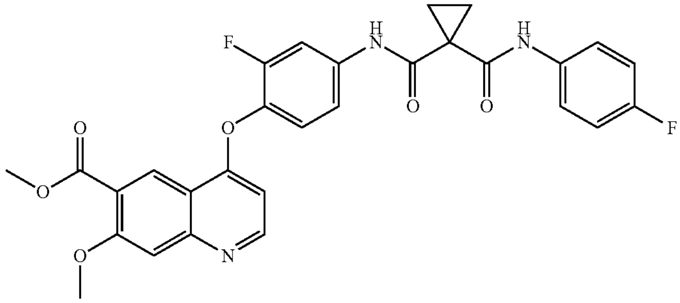 [SMILES: COC(=O)c1cc2c(Oc3ccc(NC(=O)C4(C(=O)Nc5ccc(F)cc5)CC4)cc3F)ccnc2cc1OC] | methyl 4-[2-fluoro-4-[[1-[(4-fluorophenyl)carbamoyl]-cyclopropanecarbonyl]-amino]phenoxy]-7-methoxyquinoline-6-carboxylate |
| 130 | 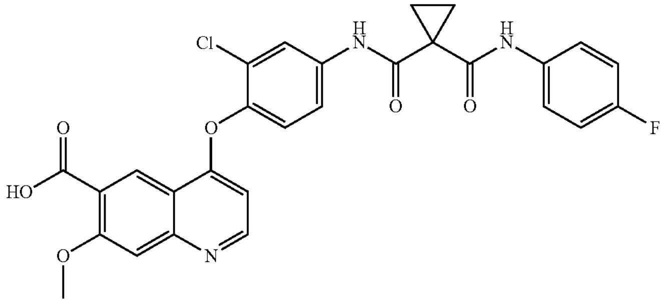 [SMILES: COc1cc2nccc(Oc3ccc(NC(=O)C4(C(=O)Nc5ccc(F)cc5)CC4)cc3Cl)c2cc1C(=O)O] | 4-[2-chloro-4-[[1-[(4-fluorophenyl)carbamoyl]-cyclopopanecarbonyl]-amino]phenoxy]-7-methoxyquinoline-6-carboxylic acid |

TABLE 1-continued

| Specific compounds of the invention | | |
|---|---|---|
| No. | Structure | Name |
| 131 | 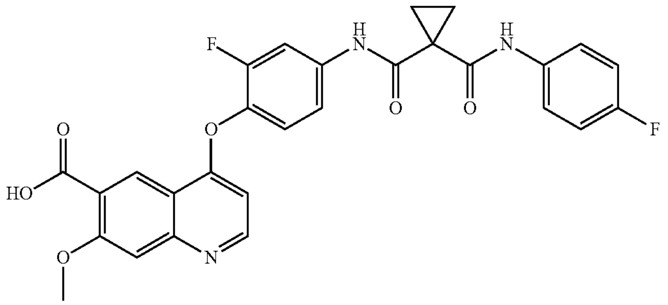 [SMILES: COc1cc2nccc(Oc3ccc(NC(=O)C4(C(=O)Nc5ccc(F)cc5)CC4)cc3F)c2cc1C(=O)O] | 4-[2-fluoro-4-[[1-[(4-fluorophenyl)carbamoyl]-cyclopropanecarbonyl]-amino]phenoxy]-7-methoxyquinoline-6-carboxylic acid |
| 132 | 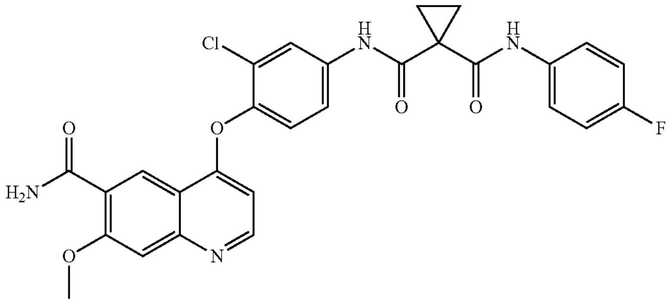 [SMILES: COc1cc2nccc(Oc3ccc(NC(=O)C4(C(=O)Nc5ccc(F)cc5)CC4)cc3F)c2cc1C(N)=O] | 1-N'-[4-(6-carbamoyl-7-methoxyquinolin-4-yl)oxy-3-chlorophenyl]-1-N-(4-fluorophenyl)cyclopropane-1,1-dicarboxamide |
| 133 | 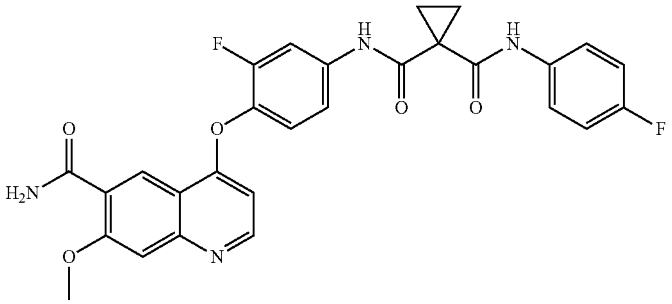 | 1-N'-[4-(6-carbamoyl-7-methoxyquinolin-4-yl)oxy-3-fluorophenyl]-1-N-(4-fluorophenyl)cyclopropane-1,1-dicarboxamide |
| 134 | 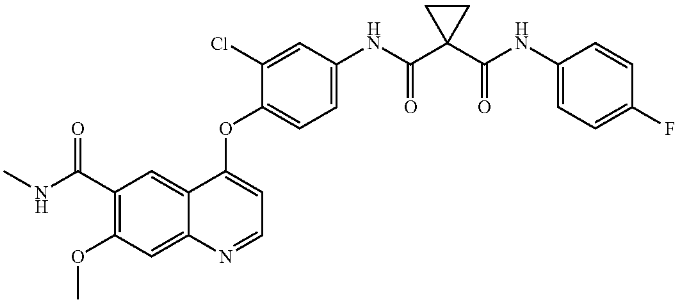 | 1-N'-[3-chloro-4-[7-methoxy-6 (methylcarbamoyl)quinolin-4-yl]oxyphenyl]-1-N-(4-fluorophenyl)cyclopropane-1,1-dicarboxamide |
| 135 | 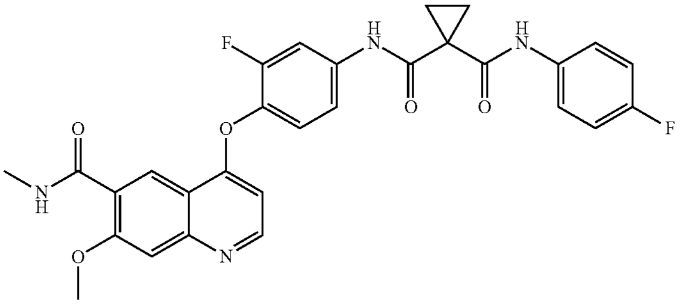 [SMILES: CNC(=O)c1cc2c(Oc3ccc(NC(=O)C4(C(=O)Nc5ccc(F)cc5)CC4)cc3Cl)ccnc2cc1OC] | 1-N'-[3-fluoro-4-[7-methoxy-6 (methylcarbamoyl)quinolin-4-yl]oxyphenyl]-1-N-(4-fluorophenyl)cyclopropane-1,1-dicarboxamide |

TABLE 1-continued

| Specific compounds of the invention | | |
|---|---|---|
| No. | Structure | Name |
| 140 | 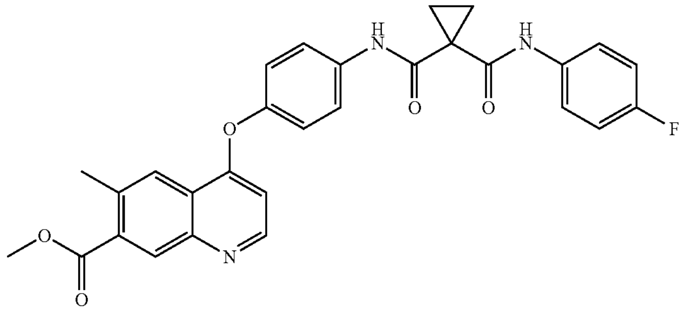 [SMILES: COC(=O)c1cc2nccc(Oc3ccc(NC(=O)C4(C(=O)Nc5ccc(F)cc5)CC4)cc3)c2cc1C] | methyl 4-[4-[[1-[(4-fluorophenyl)carbamoyl]-cyclopropanecarbonyl]-amino]phenoxy]-6-methylquinoline-7-carboxylate |
| 141 | 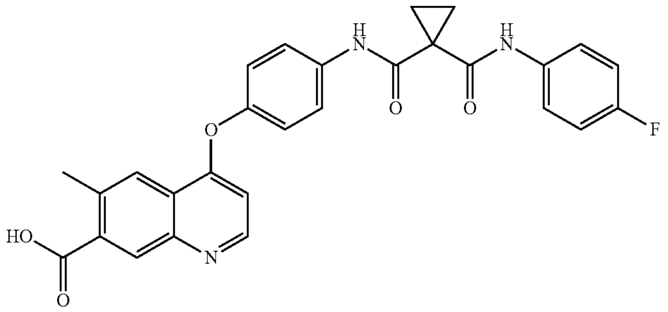 [SMILES: Cc1cc2c(Oc3ccc(NC(=O)C4(C(=O)Nc5ccc(F)cc5)CC4)cc3)ccnc2cc1C(=O)O] | 4-[4-[[1-[(4-fluorophenyl)carbamoyl]-cyclopropanecarbonyl]-amino]phenoxy]-6-methylquinoline-7-carboxylic acid |
| 142 | 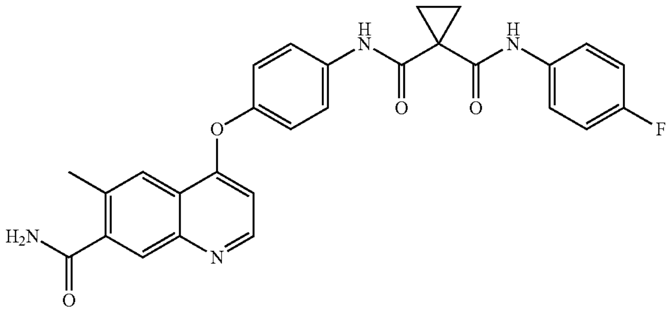 [SMILES: Cc1cc2c(Oc3ccc(NC(=O)C4(C(=O)Nc5ccc(F)cc5)CC4)cc3)ccnc2cc1C(N)=O] | 1-N-[4-(7-carbamoyl-6-methylquinolin-4-yl)oxyphenyl]-1-N'-(4-fluorophenyl)cyclopropane-1,1-dicarboxamide |
| 143 | 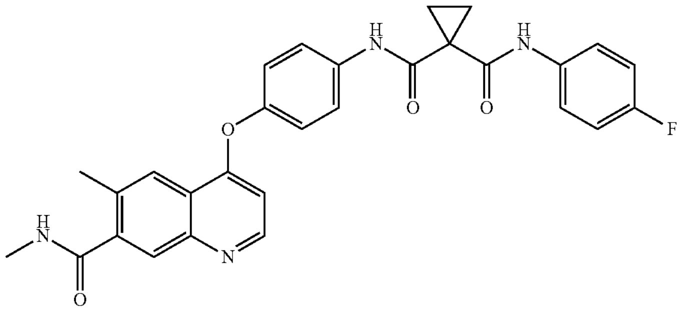 [SMILES: CNC(=O)c1cc2nccc(Oc3ccc(NC(=O)C4(C(=O)Nc5ccc(F)cc5)CC4)cc3)c2cc1C] | 1-N'-(4-fluorophenyl)-1-N-[4-[6-methyl-7-(methylcarbamoyl)quinolin-4-yl]oxyphenyl]cyclopropane-1,1-dicarboxamide |
| 150 | 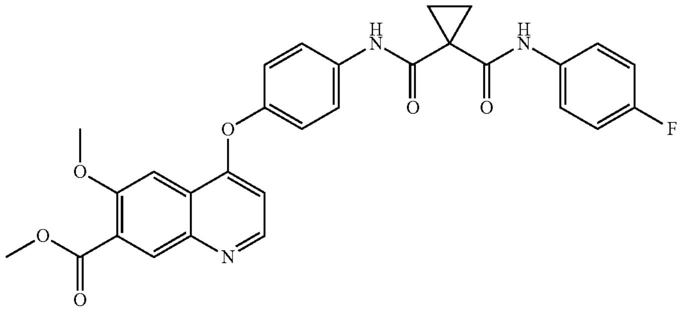 [SMILES: COC(=O)c1cc2nccc(Oc3ccc(NC(=O)C4(C(=O)Nc5ccc(F)cc5)CC4)cc3)c2cc1OC] | methyl 4-[4-[[1-[(4-fluorophenyl)carbamoyl]-cyclopropanecarbonyl]-amino]phenoxy]-6-methoxyquinoline-7-carboxylate |

TABLE 1-continued

| Specific compounds of the invention | | |
|---|---|---|
| No. | Structure | Name |
| 151 | 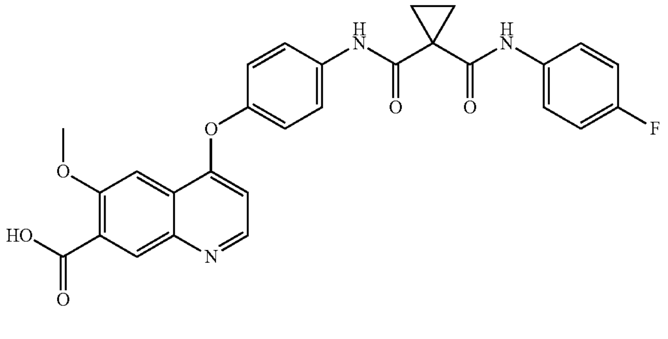 [SMILES: COc1cc2c(Oc3ccc(NC(=O)C4(C(=O)Nc5ccc(F)cc5)CC4)cc3)ccnc2cc1C(=O)O] | 4-[4-[[1-[(4-fluorophenyl)carbamoyl]-cyclopropanecarbonyl]-amino]phenoxy]-6-methoxyquinoline-7-carboxylic acid |
| 152 | 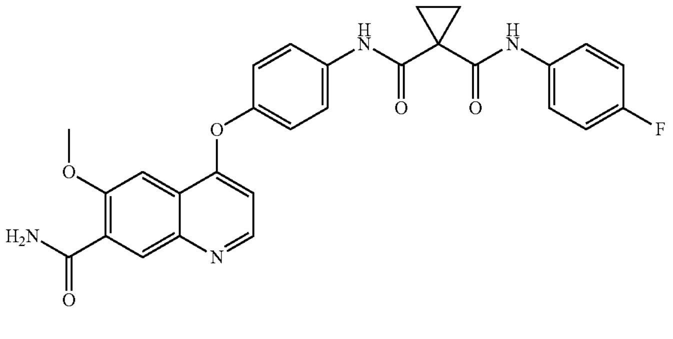 [SMILES: COc1cc2c(Oc3ccc(NC(=O)C4(C(=O)Nc5ccc(F)cc5)CC4)cc3)ccnc2cc1C(N)=O] | 1-N-[4-(7-carbamoyl-6-methoxyquinolin-4-yl)oxyphenyl]-1-N'-(4-fluorophenyl)cyclopropane-1,1-dicarboxamide |
| 153 | 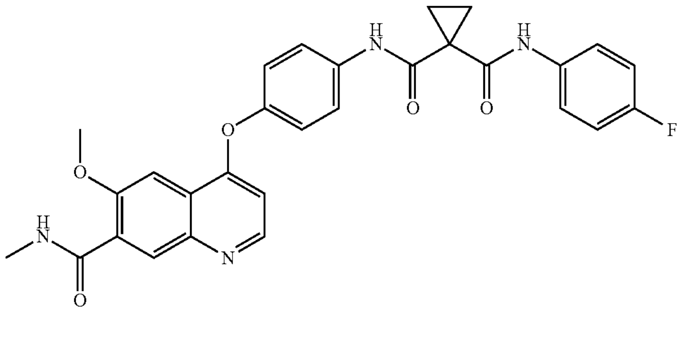 [SMILES: CNC(=O)c1cc2nccc(Oc3ccc(NC(=O)C4(C(=O)Nc5ccc(F)cc5)CC4)cc3)c2cc1OC] | 1-N'-(4-fluorophenyl)-1-N-[4-[6-methoxy-7-(methylcarbamoyl)quinolin-4-yl]oxyphenyl]cyclopropane-1,1-dicarboxamide |
| 162 | 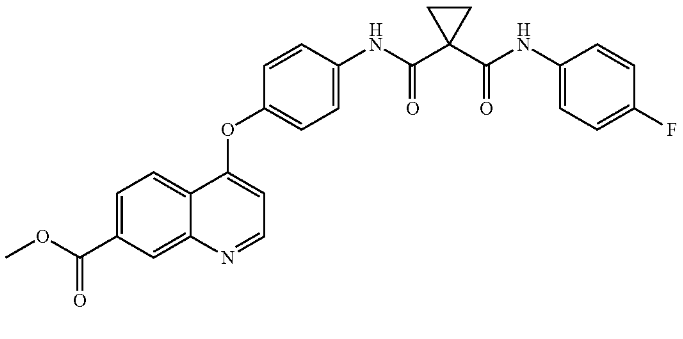 [SMILES: COC(=O)c1ccc2c(Oc3ccc(NC(=O)C4(C(=O)Nc5ccc(F)cc5)CC4)cc3)ccnc2c1] | methyl 4-[4-[[1-[(4-fluorophenyl)carbamoyl]-cyclopropanecarbonyl]-amino]phenoxy]-quinoline-7-carboxylate |

TABLE 1-continued

Specific compounds of the invention

| No. | Structure | Name |
| --- | --- | --- |
| 163 | 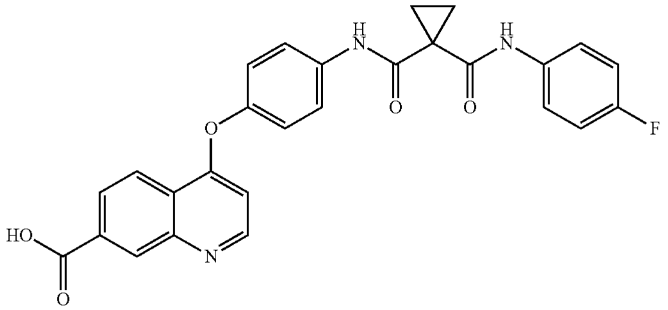 [SMILES: O=C(O)c1ccc2c(Oc3ccc(NC(=O)C4(C(=O)Nc5ccc(F)cc5)CC4)cc3)ccnc2c1] | 4-[4-[[1-[(4-fluorophenyl)carbamoyl]-cyclopropanecarbonyl]-amino]phenoxy]-quinoline-7-carboxylic acid |
| 164 | 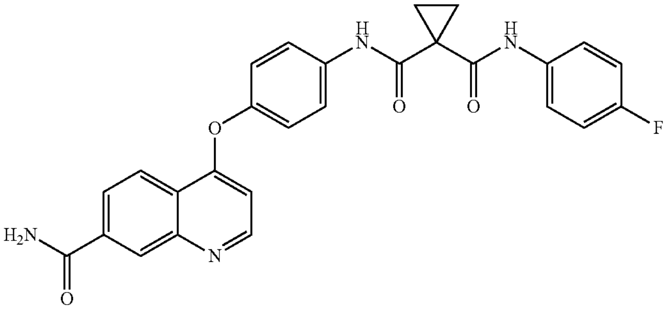 [SMILES: NC(=O)c1ccc2c(Oc3ccc(NC(=O)C4(C(=O)Nc5ccc(F)cc5)CC4)cc3)ccnc2c1] | 1-N-[4-(7-carbamoylquinolin-4-yl)oxyphenyl]-1-N'-(4-fluorophenyl)cyclopropane-1,1-dicarboxamide |
| 165 | 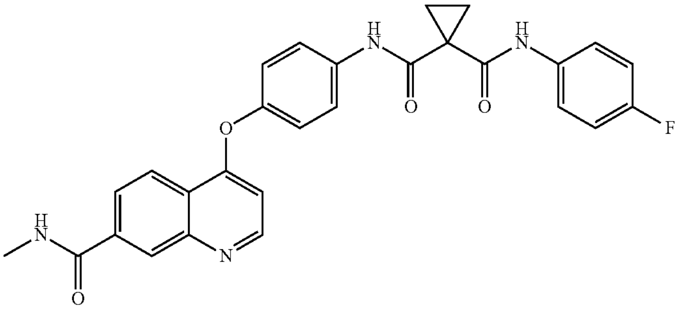 [SMILES: CNC(=O)c1ccc2c(Oc3ccc(NC(=O)C4(C(=O)Nc5ccc(F)cc5)CC4)cc3)ccnc2c1] | 1-N'-(4-fluorophenyl)-1-N-[4-[7-(methylcarbamoyl)quinolin-4-yl]oxyphenyl]cyclopropane-1,1-dicarboxamide |
| 166 | 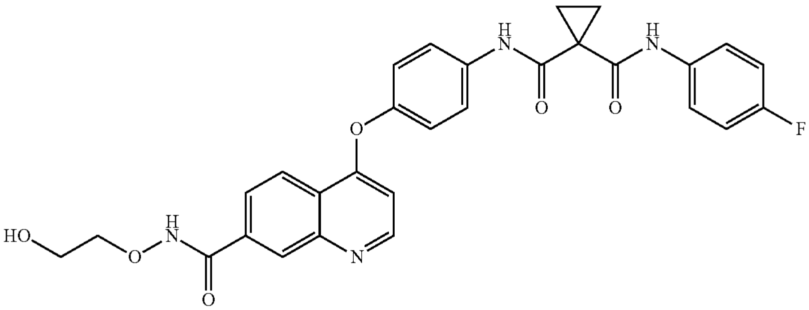 [SMILES: O=C(NOCCO)c1ccc2c(Oc3ccc(NC(=O)C4(C(=O)Nc5ccc(F)cc5)CC4)cc3)ccnc2c1] | 1-N'-(4-fluorophenyl)-1-N-[4-[7-(2-hydroxyethoxycarbamoyl)-quinolin-4-yl]oxyphenyl]cyclopropane-1,1-dicarboxamide |
| 167 | 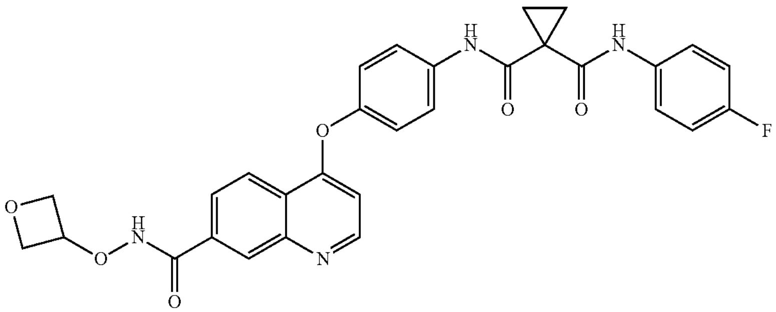 [SMILES: O=C(NOC1COC1)c1ccc2c(Oc3ccc(NC(=O)C4(C(=O)Nc5ccc(F)cc5)CC4)cc3)ccnc2c1] | 1-N'-(4-fluorophenyl)-1-N-[4-[7-(oxetan-3-yloxycarbamoyl)quinolin-4-yl]oxyphenyl]cyclopropane-1,1-dicarboxamide |

TABLE 1-continued

| Specific compounds of the invention | | |
|---|---|---|
| No. | Structure | Name |
| 169 | 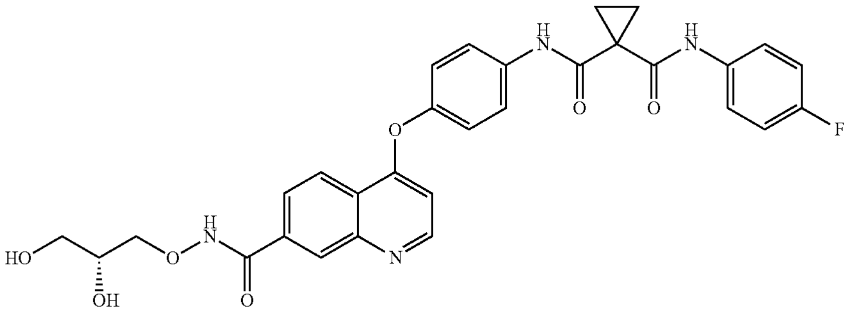 [SMILES: O=C(NOC[C@H](O)CO)c1ccc2c(Oc3ccc(NC(=O)C4(C(=O)Nc5ccc(F)cc5)CC4)cc3)ccnc2c1] | 1-N-[4-[7-[[(2R)-2,3-dihydroxypropoxy]carbamoyl]-quinolin-4-yl]oxyphenyl]-1-N'-(4-fluorophenyl)cyclopropane-1,1-dicarboxamide |
| 170 | 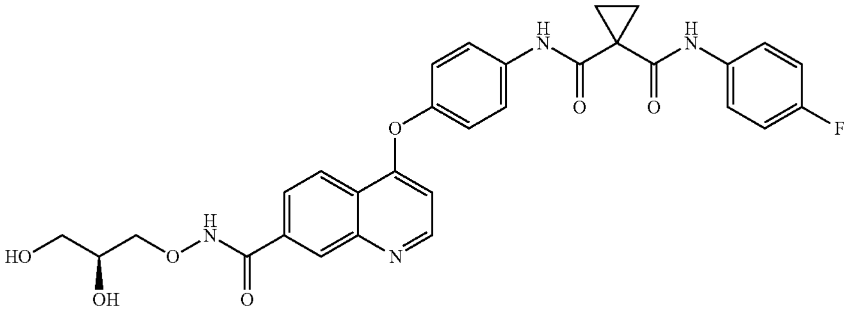 [SMILES: O=C(NOC[C@@H](O)CO)c1ccc2c(Oc3ccc(NC(=O)C4(C(=O)Nc5ccc(F)cc5)CC4)cc3)ccnc2c1] | 1-N-[4-[7-[[(2S)-2,3-dihydroxypropoxy]carbamoyl]-quinolin-4-yl]oxyphenyl]-1-N'-(4-fluorophenyl)cyclopropane-1,1-dicarboxamide |
| 175 | 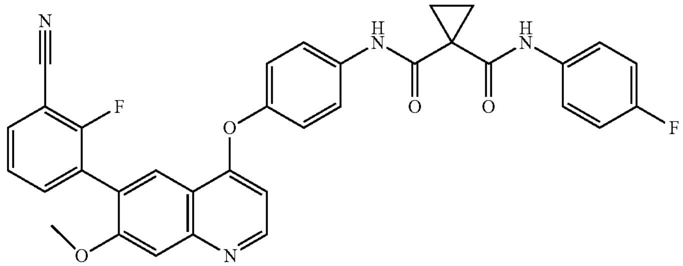 [SMILES: COc1cc2nccc(Oc3ccc(NC(=O)C4(C(=O)Nc5ccc(F)cc5)CC4)cc3)c2cc1-c1cccc(C#N)c1F] | 1-N-[4-[6-(3-cyano-2-fluorophenyl)-7-methoxyquinolin-4-yl]oxyphenyl]-1-N'-(4-fluorophenyl)cyclopropane-1,1-dicarboxamide |
| 176 | 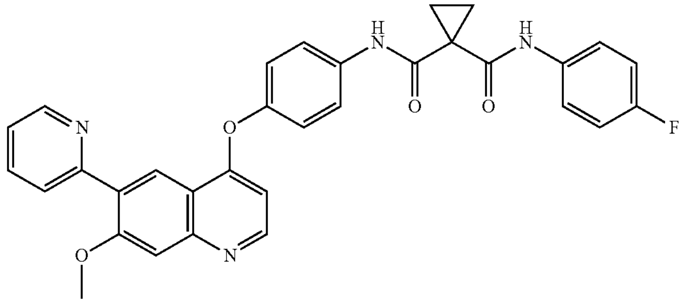 [SMILES: COc1cc2nccc(Oc3ccc(NC(=O)C4(C(=O)Nc5ccc(F)cc5)CC4)cc3)c2cc1-c1ccccn1] | 1-N'-(4-fluorophenyl)-1-N-[4-(7-methoxy-6-pyridin-2-ylquinolin-4-yl)oxyphenyl]cyclopropane-1,1-dicarboxamide |
| 177 | 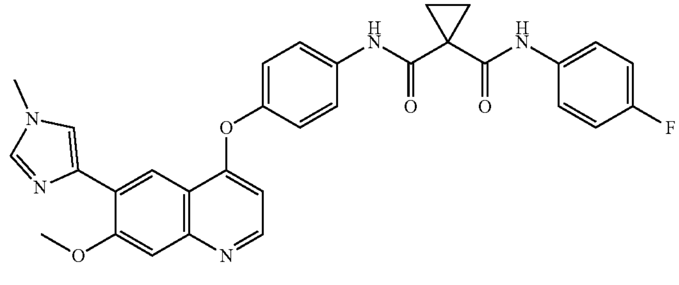 [SMILES: COc1cc2nccc(Oc3ccc(NC(=O)C4(C(=O)Nc5ccc(F)cc5)CC4)cc3)c2cc1-c1cn(C)cn1] | 1-N'-(4-fluorophenyl)-1-N-[4-[7-methoxy-6-(1-methylimidazol-4-yl)quinolin-4-yl]oxyphenyl]cyclopropane-1,1-dicarboxamide |

TABLE 1-continued

| Specific compounds of the invention | | |
|---|---|---|
| No. | Structure | Name |
| 180 | 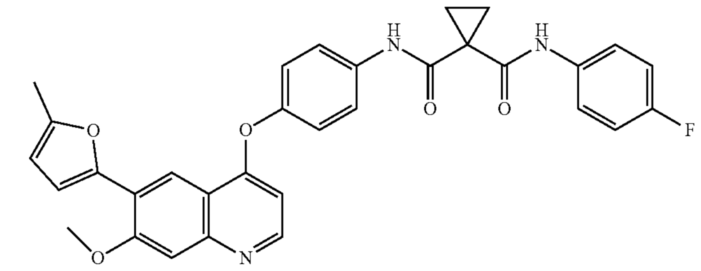 [SMILES: COc1cc2nccc(Oc3ccc(NC(=O)C4(C(=O)Nc5ccc(F)cc5)CC4)cc3)c2cc1-c1ccc(C)o1] | 1-N'-(4-fluorophenyl)-1-N-[4-[7-methoxy-6-(5-methylfuran-2-yl)quinolin-4-yl]oxyphenyl]cyclopropane-1,1-dicarboxamide |
| 181 | 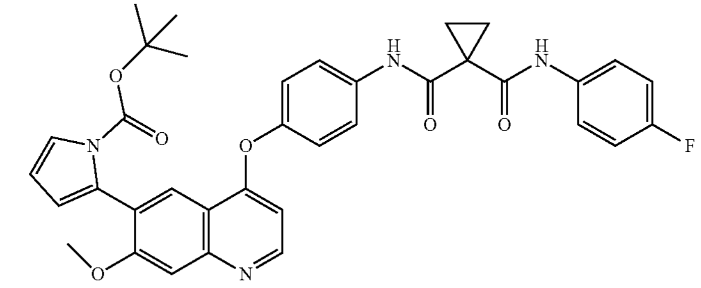 [SMILES: COc1cc2nccc(Oc3ccc(NC(=O)C4(C(=O)Nc5ccc(F)cc5)CC4)cc3)c2cc1-c1cccn1C(=O)OC(C)(C)C] | tert-butyl 2-[4-[4-[[1-[(4-fluorophenyl)carbamoyl]-cyclopropanecarbonyl]-amino]phenoxy]-7-methoxyquinolin-6-yl]pyrrole-1-carboxylate |
| 182 | 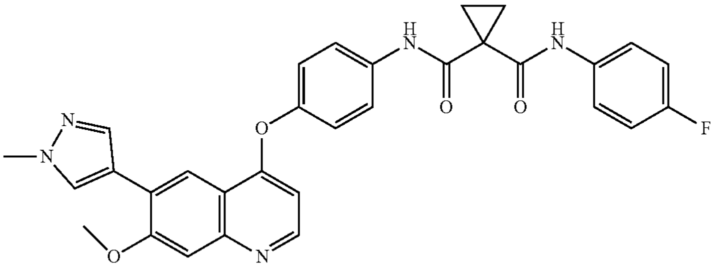 [SMILES: COc1cc2nccc(Oc3ccc(NC(=O)C4(C(=O)Nc5ccc(F)cc5)CC4)cc3)c2cc1-c1cnn(C)c1] | 1-N'-(4-fluorophenyl)-1-N-[4-[7-methoxy-6-(1-methylpyrazol-4-yl)quinolin-4-yl]oxyphenyl]cyclopropane-1,1-dicarboxamide |
| 183 | 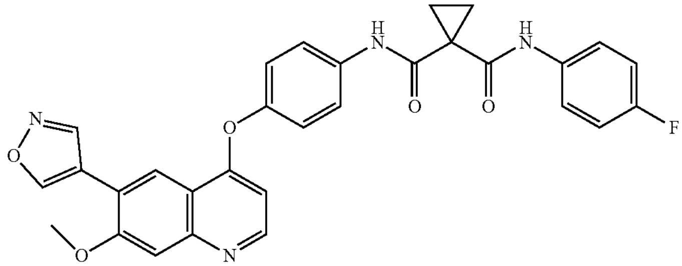 [SMILES: COc1cc2nccc(Oc3ccc(NC(=O)C4(C(=O)Nc5ccc(F)cc5)CC4)cc3)c2cc1-c1cnoc1] | 1-N'-(4-fluorophenyl)-1-N-[4-[7-methoxy-6-(1,2-oxazol-4-yl)quinolin-4-yl]oxyphenyl]cyclopropane-1,1-dicarboxamide |
| 184 | 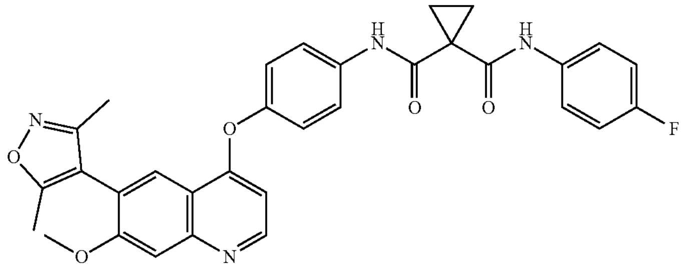 [SMILES: COc1cc2nccc(Oc3ccc(NC(=O)C4(C(=O)Nc5ccc(F)cc5)CC4)cc3)c2cc1-c1c(C)noc1C] | 1-N-[4-[6-(3,5-dimethyl-1,2-oxazol-4-yl)-7-methoxyquinolin-4-yl]oxyphenyl]-1-N'-(4-fluorophenyl)cyclopropane-1,1-dicarboxamide |

TABLE 1-continued

| Specific compounds of the invention | | |
|---|---|---|
| No. | Structure | Name |
| 185 | 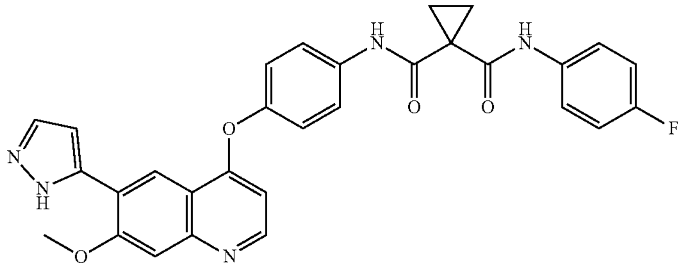 [SMILES: COc1cc2nccc(Oc3ccc(NC(=O)C4(C(=O)Nc5ccc(F)cc5)CC4)cc3)c2cc1-c1ccn[nH]1] | 1-N'-(4-fluorophenyl)-1-N-[4-[7-methoxy-6-(1H-pyrazol-5-yl)quinolin-4-yl]oxyphenyl]cyclopropane-1,1-dicarboxamide |
| 186 | 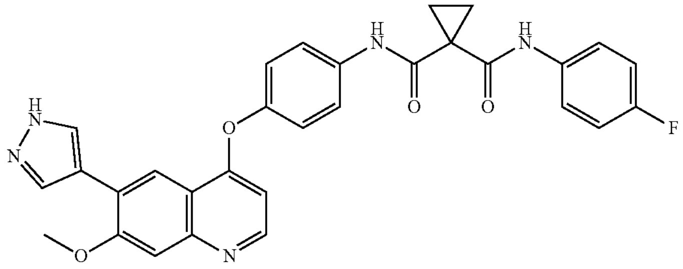 [SMILES: COc1cc2nccc(Oc3ccc(NC(=O)C4(C(=O)Nc5ccc(F)cc5)CC4)cc3)c2cc1-c1cn[nH]c1] | 1-N'-(4-fluorophenyl)-1-N-[4-[7-methoxy-6-(1H-pyrazol-4-yl)quinolin-4-yl]oxyphenyl]cyclopropane-1,1-dicarboxamide |
| 187 | 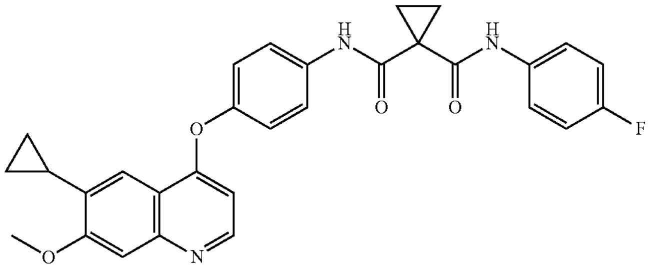 [SMILES: COc1cc2nccc(Oc3ccc(NC(=O)C4(C(=O)Nc5ccc(F)cc5)CC4)cc3)c2cc1C1CC1] | 1-N-[4-(6-cyclopropyl-7-methoxyquinolin-4-yl)oxyphenyl]-1-N'-(4-fluorophenyl)cyclopropane-1,1-dicarboxamide |
| 188 | 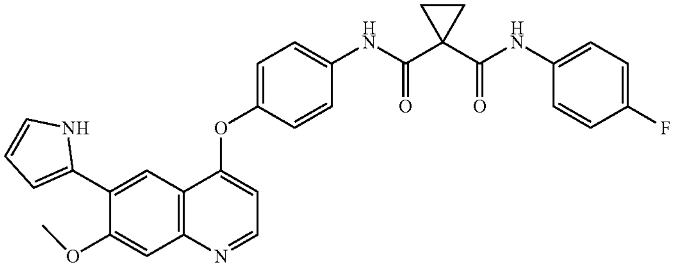 [SMILES: COc1cc2nccc(Oc3ccc(NC(=O)C4(C(=O)Nc5ccc(F)cc5)CC4)cc3)c2cc1-c1ccc[nH]1] | 1-N'-(4-fluorophenyl)-1-N-[4-[7-methoxy-6-(1H-pyrrol-2-yl)quinolin-4-yl]oxyphenyl]cyclopropane-1,1-dicarboxamide |
| 191 | 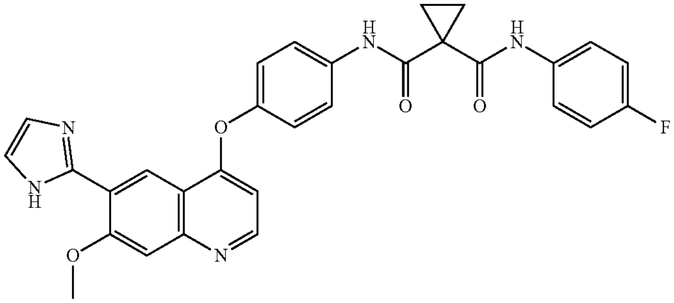 [SMILES: COc1cc2nccc(Oc3ccc(NC(=O)C4(C(=O)Nc5ccc(F)cc5)CC4)cc3)c2cc1-c1ncc[nH]1] | 1-N'-(4-fluorophenyl)-1-N-[4-[6-(1H-imidazol-2-yl)-7-methoxyquinolin-4-yl]oxyphenyl]cyclopropane-1,1-dicarboxamide |

TABLE 1-continued

| Specific compounds of the invention | | |
|---|---|---|
| No. | Structure | Name |
| 192 | 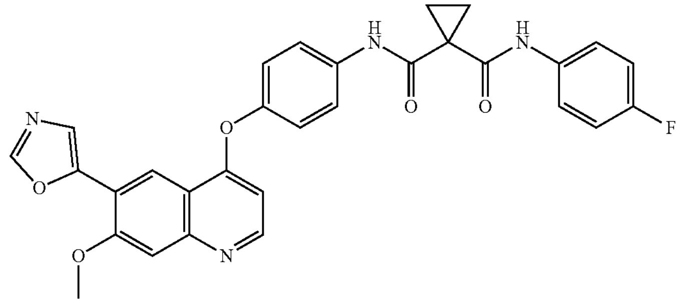 [SMILES: COc1cc2nccc(Oc3ccc(NC(=O)C4(C(=O)Nc5ccc(F)cc5)CC4)cc3)c2cc1-c1cnco1] | 1-N'-(4-fluorophenyl)-1-N-[4-[7-methoxy-6-(1,3-oxazol-5-yl)quinolin-4-yl]oxyphenyl]cyclopropane-1,1-dicarboxamide |
| 193 | 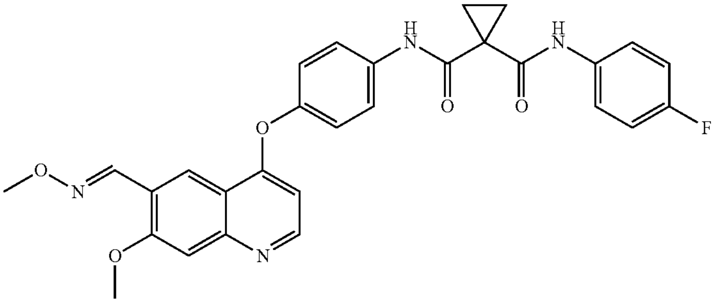 [SMILES: CO/N=C/c1cc2c(Oc3ccc(NC(=O)C4(C(=O)Nc5ccc(F)cc5)CC4)cc3)ccnc2cc1OC] | 1-N'-(4-fluorophenyl)-1-N-[4-[7-methoxy-6-[(E)-methoxyiminomethyl]quinolin-4-yl]oxyphenyl]cyclopropane-1,1-dicarboxamide |
| 195 | 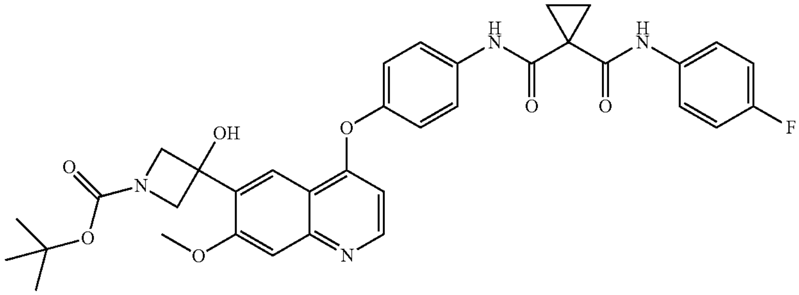 [SMILES: COc1cc2nccc(Oc3ccc(NC(=O)C4(C(=O)Nc5ccc(F)cc5)CC4)cc3)c2cc1C1(O)CN(C(=O)OC(C)(C)C)C1] | tert-butyl 3-[4-[4-[[1-[(4-fluorophenyl)carbamoyl]-cyclopropanecarbonyl]-amino]phenoxy]-7-methoxyquinolin-6-yl]-3-hydroxyazetidine-1-carboxylate |
| 196 | 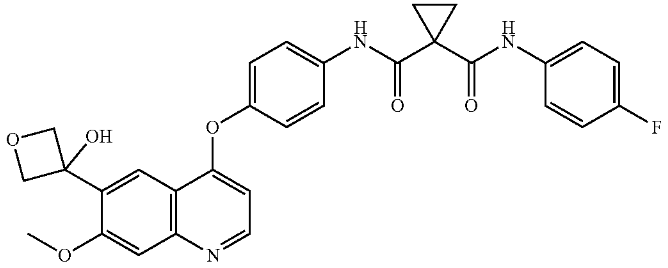 [SMILES: COc1cc2nccc(Oc3ccc(NC(=O)C4(C(=O)Nc5ccc(F)cc5)CC4)cc3)c2cc1C1(O)COC1] | 1-N'-(4-fluorophenyl)-1-N-[4-[6-(3-hydroxyoxetan-3-yl)-7-methoxyquinolin-4-yl]oxyphenyl]cyclopropane-1,1-dicarboxamide |
| 197 | 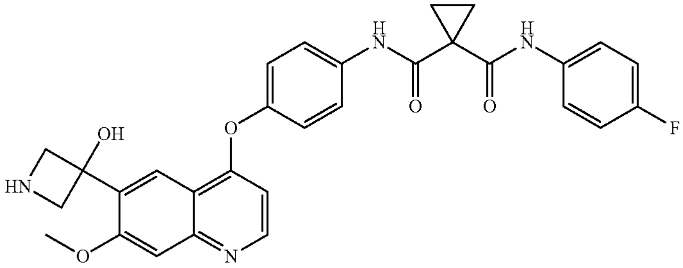 [SMILES: COc1cc2nccc(Oc3ccc(NC(=O)C4(C(=O)Nc5ccc(F)cc5)CC4)cc3)c2cc1C1(O)CNC1] | 1-N'-(4-fluorophenyl)-1-N-[4-[6-(3-hydroxyazetidin-3-yl)-7-methoxyquinolin-4-yl]oxyphenyl]cyclopropane-1,1-dicarboxamide |

TABLE 1-continued

| Specific compounds of the invention | | |
|---|---|---|
| No. | Structure | Name |
| 198 | 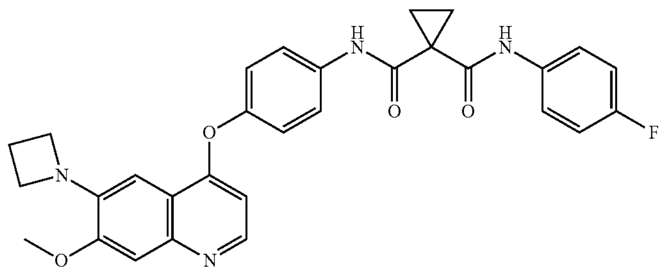 [SMILES: COc1cc2nccc(Oc3ccc(NC(=O)C4(C(=O)Nc5ccc(F)cc5)CC4)cc3)c2cc1N1CCC1] | 1-N-[4-[6-(azetidin-1-yl)-7-methoxyquinolin-4-yl]oxyphenyl]-1-N'-(4-fluorophenyl)cyclopropane-1,1-dicarboxamide |
| 199 | 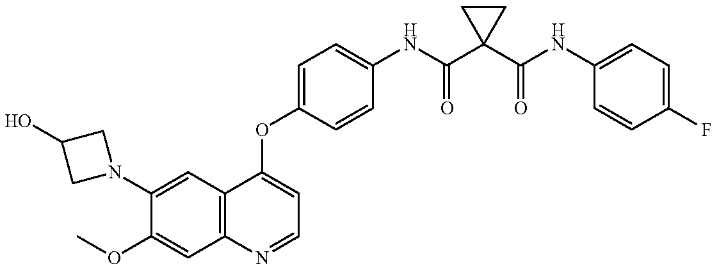 [SMILES: COc1cc2nccc(Oc3ccc(NC(=O)C4(C(=O)Nc5ccc(F)cc5)CC4)cc3)c2cc1N1CC(O)C1] | 1-N'-(4-fluorophenyl)-1-N-[4-[6-(3-hydroxyazetidin-1-yl)-7-methoxyquinolin-4-yl]oxyphenyl]cyclopropane-1,1-dicarboxamide |
| 200 | 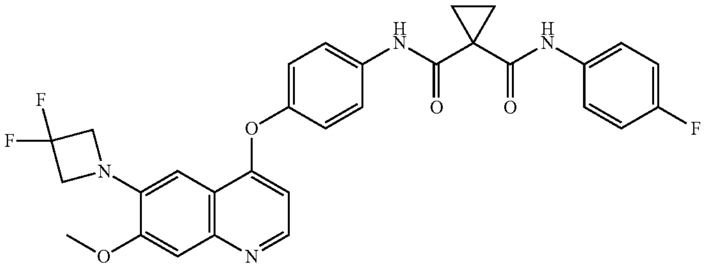 [SMILES: COc1cc2nccc(Oc3ccc(NC(=O)C4(C(=O)Nc5ccc(F)cc5)CC4)cc3)c2cc1N1CC(F)(F)C1] | 1-N-[4-[6-(3,3-difluoroazetidin-1-yl)-7-methoxyquinolin-4-yl]oxyphenyl]-1-N'-(4-fluorophenyl)cyclopropane-1,1-dicarboxamide |
| 201 | 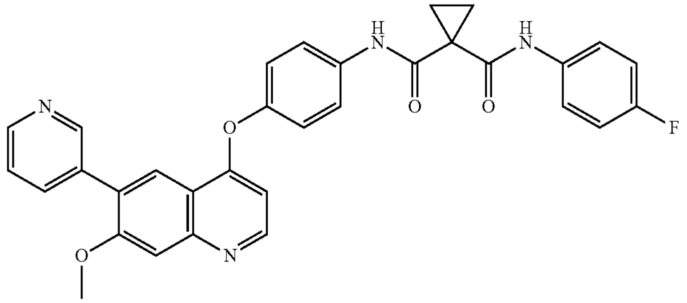 [SMILES: COc1cc2nccc(Oc3ccc(NC(=O)C4(C(=O)Nc5ccc(F)cc5)CC4)cc3)c2cc1-c1cccnc1] | 1-N'-(4-fluorophenyl)-1-N-[4-(7-methoxy-6-pyridin-3-ylquinolin-4-yl)oxyphenyl]cyclopropane-1,1-dicarboxamide |
| 202 | 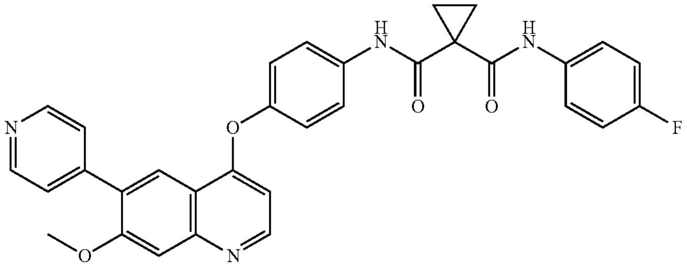 [SMILES: COc1cc2nccc(Oc3ccc(NC(=O)C4(C(=O)Nc5ccc(F)cc5)CC4)cc3)c2cc1-c1ccncc1] | 1-N'-(4-fluorophenyl)-1-N-[4-(7-methoxy-6-pyridin-4-ylquinolin-4-yl)oxyphenyl]cyclopropane-1,1-dicarboxamide |

TABLE 1-continued

| Specific compounds of the invention | | |
|---|---|---|
| No. | Structure | Name |
| 204 | 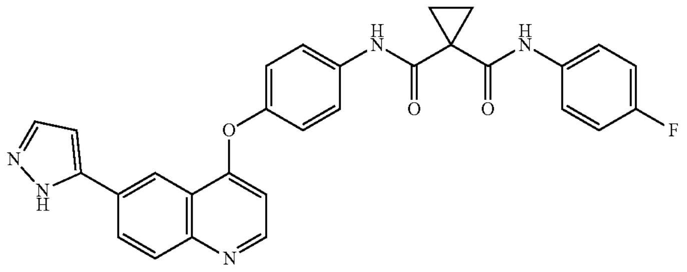 [SMILES: O=C(Nc1ccc(F)cc1)C1(C(=O)Nc2ccc(Oc3ccnc4ccc(-c5ccn[nH]5)cc34)cc2)CC1] | 1-N'-(4-fluorophenyl)-1-N-[4-[6-(1H-pyrazol-5-yl)quinolin-4-yl]oxyphenyl]cyclopropane-1,1-dicarboxamide |
| 206 | 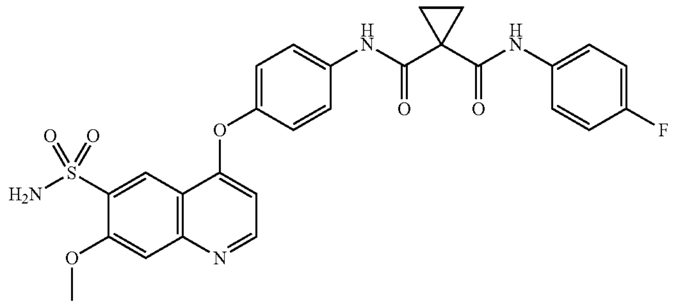 [SMILES: COc1cc2nccc(Oc3ccc(NC(=O)C4(C(=O)Nc5ccc(F)cc5)CC4)cc3)c2cc1S(N)(=O)=O] | 1-N'-(4-fluorophenyl)-1-N-[4-(7-methoxy-6-sulfamoylquinolin-4-yl)oxyphenyl]cyclopropane-1,1-dicarboxamide |
| 207 | 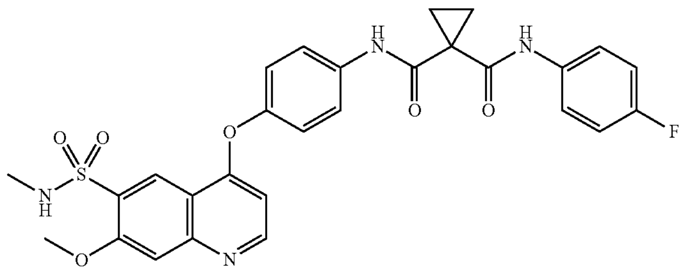 [SMILES: CNS(=O)(=O)c1cc2c(Oc3ccc(NC(=O)C4(C(=O)Nc5ccc(F)cc5)CC4)cc3)ccnc2cc1OC] | 1-N'-(4-fluorophenyl)-1-N-[4-[7-methoxy-6-(methylsulfamoyl)quinolin-4-yl]oxyphenyl]cyclopropane-1,1-dicarboxamide |
| 208 | 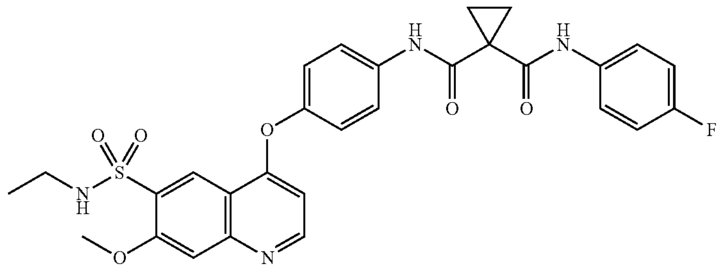 [SMILES: CCNS(=O)(=O)c1cc2c(Oc3ccc(NC(=O)C4(C(=O)Nc5ccc(F)cc5)CC4)cc3)ccnc2cc1OC] | 1-N-[4-[6-(ethylsulfamoyl)-7-methoxyquinolin-4-yl]oxyphenyl]-1-N'-(4-fluorophenyl)cyclopropane-1,1-dicarboxamide |
| 209 | 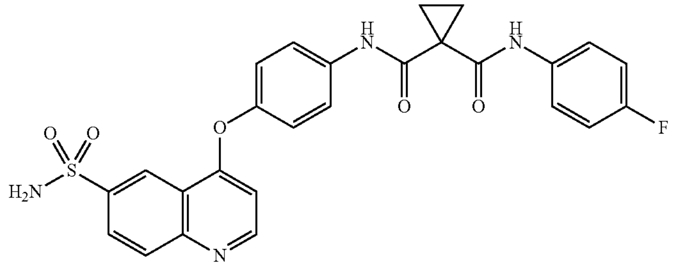 [SMILES: NS(=O)(=O)c1ccc2nccc(Oc3ccc(NC(=O)C4(C(=O)Nc5ccc(F)cc5)CC4)cc3)c2c1] | 1-N'-(4-fluorophenyl)-1-N-[4-(6-sulfamoylquinolin-4-yl)oxyphenyl]cyclopropane-1,1-dicarboxamide |

TABLE 1-continued

| Specific compounds of the invention | | |
|---|---|---|
| No. | Structure | Name |
| 210 | 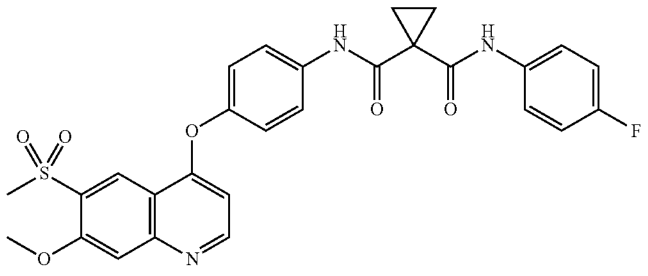 [SMILES: COc1cc2nccc(Oc3ccc(NC(=O)C4(C(=O)Nc5ccc(F)cc5)CC4)cc3)c2cc1S(C)(=O)=O] | 1-N'-(4-fluorophenyl)-1-N-[4-(7-methoxy-6-methylsulfonylquinolin-4-yl)oxyphenyl]cyclopropane-1,1-dicarboxamide |
| 213 | 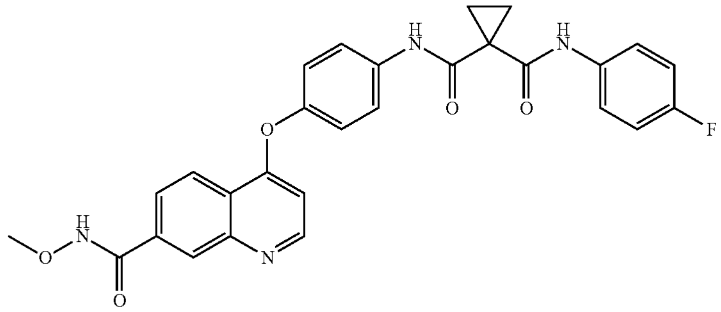 [SMILES: CONC(=O)c1ccc2c(Oc3ccc(NC(=O)C4(C(=O)Nc5ccc(F)cc5)CC4)cc3)ccnc2c1] | 1-N'-(4-fluorophenyl)-1-N-[4-[7-(methoxycarbamoyl)quinolin-4-yl]oxyphenyl]cyclopropane-1,1-dicarboxamide |
| 214 | 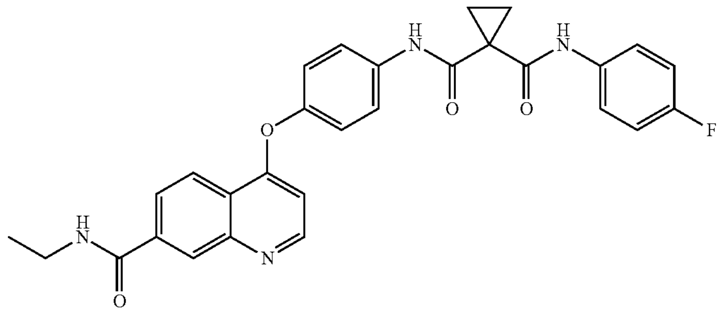 [SMILES: CCNC(=O)c1ccc2c(Oc3ccc(NC(=O)C4(C(=O)Nc5ccc(F)cc5)CC4)cc3)ccnc2c1] | 1-N-[4-[7-(ethylcarbamoyl)quinolin-4-yl]oxyphenyl]-1-N'-(4-fluorophenyl)cyclopropane-1,1-dicarboxamide |
| 220 | 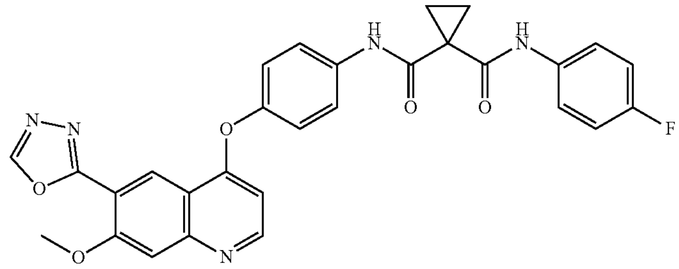 [SMILES: COc1cc2nccc(Oc3ccc(NC(=O)C4(C(=O)Nc5ccc(F)cc5)CC4)cc3)c2cc1-c1nnco1] | 1-N'-(4-fluorophenyl)-1-N-[4-[7-methoxy-6-(1,3,4-oxadiazol-2-yl)quinolin-4-yl]oxyphenyl]cyclopropane-1,1-dicarboxamide |
| 221 | 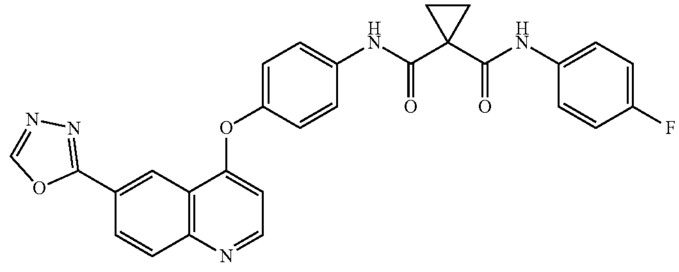 [SMILES: O=C(Nc1ccc(F)cc1)C1(C(=O)Nc2ccc(Oc3ccnc4ccc(-c5nnco5)cc34)cc2)CC1] | 1-N'-(4-fluorophenyl)-1-N-[4-[6-(1,3,4-oxadiazol-2-yl)quinolin-4-yl]oxyphenyl]cyclopropane-1,1-dicarboxamide |

TABLE 1-continued

| Specific compounds of the invention | | |
|---|---|---|
| No. | Structure | Name |
| 254 | 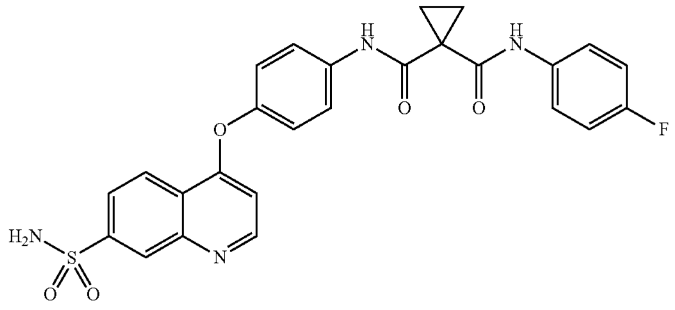 [SMILES: NS(=O)(=O)c1ccc2c(Oc3ccc(NC(=O)C4(C(=O)Nc5ccc(F)cc5)CC4)cc3)ccnc2c1] | 1-N'-(4-fluorophenyl)-1-N-[4-(7-sulfamoylquinolin-4-yl)oxyphenyl]cyclopropane-1,1-dicarboxamide |
| 255 | 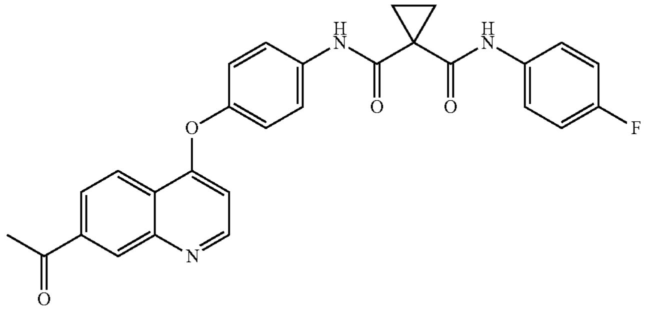 [SMILES: CC(=O)c1ccc2c(Oc3ccc(NC(=O)C4(C(=O)Nc5ccc(F)cc5)CC4)cc3)ccnc2c1] | 1-N-[4-(7-acetylquinolin-4-yl)oxyphenyl]-1-N'-(4-fluorophenyl)cyclopropane-1,1-dicarboxamide; or |
| 256 | 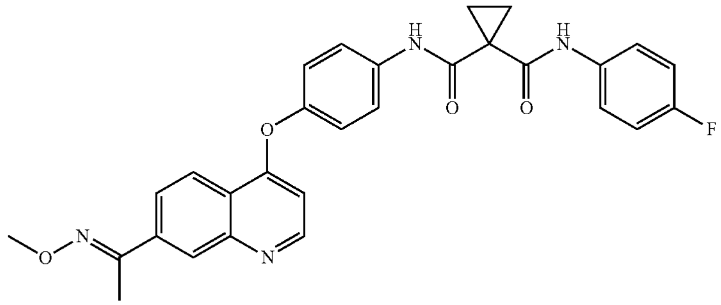 [SMILES: CO/N=C(\C)c1ccc2c(Oc3ccc(NC(=O)C4(C(=O)Nc5ccc(F)cc5)CC4)cc3)ccnc2c1] | 1-N'-(4-fluorophenyl)-1-N-[4-[7-[(E)-N-methoxy-C-methylcarbonimidoyl]quinolin-4-yl]oxyphenyl]cyclopropane-1,1-dicarboxamide |
| 262 | 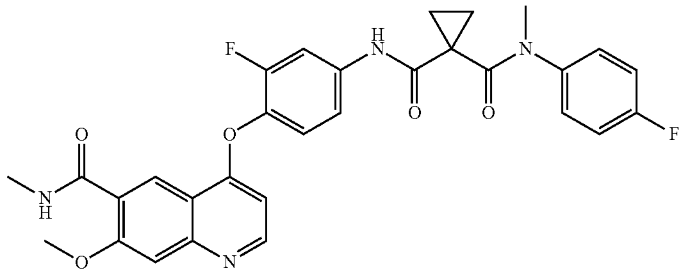 [SMILES: CNC(=O)c1cc2c(Oc3ccc(NC(=O)C4(C(=O)N(C)c5ccc(F)cc5)CC4)cc3F)ccnc2cc1OC] | 1-N-[3-fluoro-4-[7-methoxy-6-(methylcarbamoyl)quinolin-4-yl]oxyphenyl]-1-N'-(4-fluorophenyl)-1-N'-methylcyclopropane-1,1-dicarboxamide |

TABLE 1-continued

Specific compounds of the invention

| No. | Structure | Name |
|---|---|---|
| 263 | 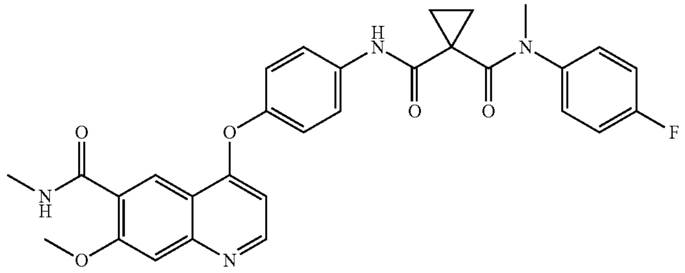 [SMILES: CNC(=O)c1cc2c(Oc3ccc(NC(=O)C4(C(=O)N(C)c5ccc(F)cc5)CC4)cc3)ccnc2cc1OC] | 1-N'-(4-fluorophenyl)-1-N-[4-[7-methoxy-6-(methylcarbamoyl)quinolin-4-yl]oxyphenyl]-1-N'-methylcyclopropane-1,1-dicarboxamide |
| 264 | 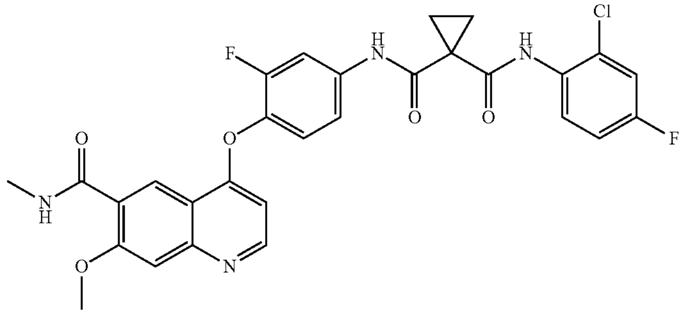 [SMILES: CNC(=O)c1cc2c(Oc3ccc(NC(=O)C4(C(=O)Nc5ccc(F)cc5Cl)CC4)cc3F)ccnc2cc1OC] | 1-N'-(2-chloro-4-fluorophenyl)-1-N-[3-fluoro-4-[7-methoxy-6-(methylcarbamoyl)quinolin-4-yl]oxyphenyl]cyclopropane-1,1-dicarboxamide |
| 265 | 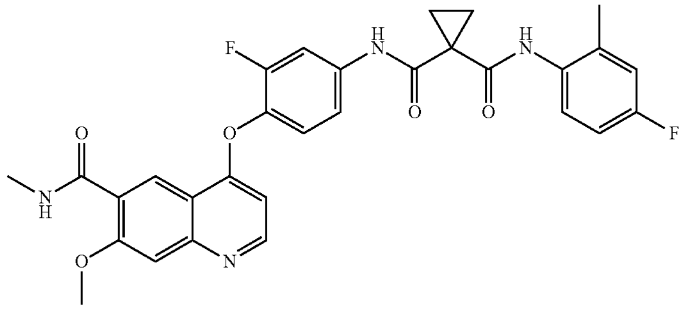 [SMILES: CNC(=O)c1cc2c(Oc3ccc(NC(=O)C4(C(=O)Nc5ccc(F)cc5C)CC4)cc3F)ccnc2cc1OC] | 1-N-[3-fluoro-4-[7-methoxy-6-(methylcarbamoyl)quinolin-4-yl]oxyphenyl]-1-N'-(4-fluoro-2-methylphenyl)cyclopropane-1,1-dicarboxamide |
| 267 | 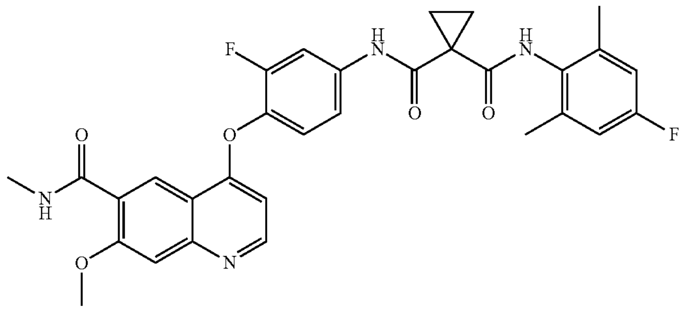 [SMILES: CNC(=O)c1cc2c(Oc3ccc(NC(=O)C4(C(=O)Nc5c(C)cc(F)cc5C)CC4)cc3F)ccnc2cc1OC] | 1-N'-(4-fluoro-2,6-dimethylphenyl)-1-N-[3-fluoro-4-[7-methoxy-6-(methylcarbamoyl)quinolin-4-yl]oxyphenyl]cyclopropane-1,1-dicarboxamide |
| 268 | 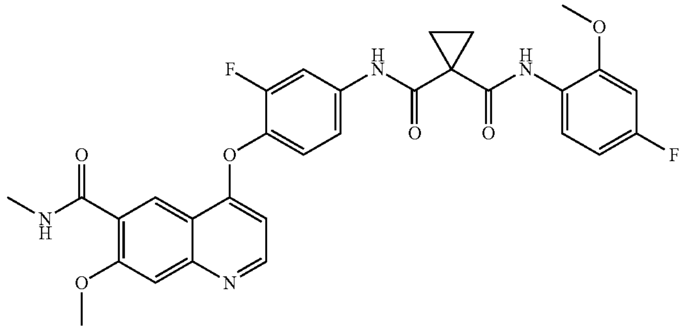 [SMILES: CNC(=O)c1cc2c(Oc3ccc(NC(=O)C4(C(=O)Nc5ccc(F)cc5OC)CC4)cc3F)ccnc2cc1OC] | 1-N-[3-fluoro-4-[7-methoxy-6-(methylcarbamoyl)quinolin-4-yl]oxyphenyl]-1-N'-(4-fluoro-2-methoxyphenyl)cyclopropane-1,1-dicarboxamide |

TABLE 1-continued

| Specific compounds of the invention | | |
|---|---|---|
| No. | Structure | Name |
| 269 | 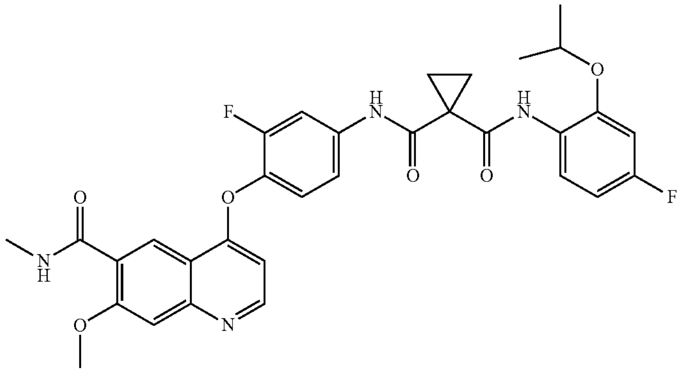 [SMILES: CNC(=O)c1cc2c(Oc3ccc(NC(=O)C4(C(=O)Nc5ccc(F)cc5OC(C)C)CC4)cc3F)ccnc2cc1OC] | 1-N-[3-fluoro-4-[7-methoxy-6-(methylcarbamoyl)quinolin-4-yl]oxyphenyl]-1-N'-(4-fluoro-2-propan-2-yloxyphenyl)cyclopropane-1,1-dicarboxamide |
| 270 | 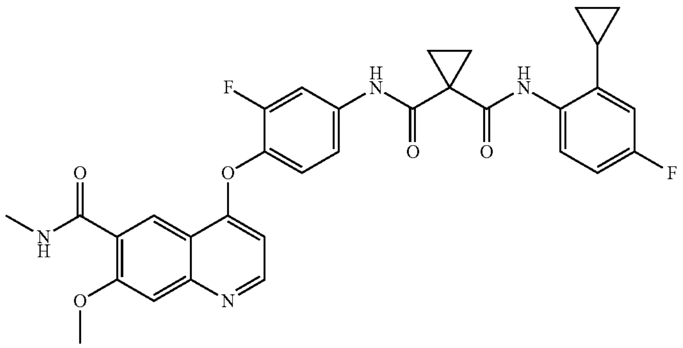 [SMILES: CNC(=O)c1cc2c(Oc3ccc(NC(=O)C4(C(=O)Nc5ccc(F)cc5C5CC5)CC4)cc3F)ccnc2cc1OC] | 1-N'-(2-cyclopropyl-4-fluorophenyl)-1-N-[3-fluoro-4-[7-methoxy-6-(methylcarbamoyl)quinolin-4-yl]oxyphenyl]cyclopropane-1,1-dicarboxamide |
| 273 | 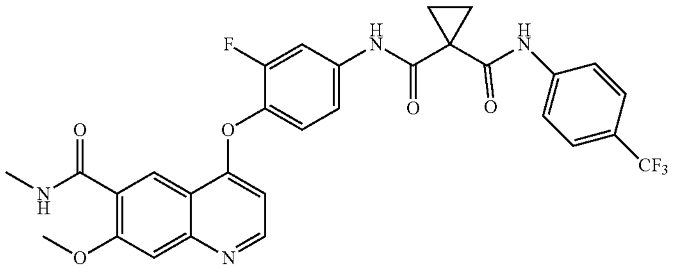 [SMILES: CNC(=O)c1cc2c(Oc3ccc(NC(=O)C4(C(=O)Nc5ccc(C(F)(F)F)cc5)CC4)cc3F)ccnc2cc1OC] | 1-N'-[3-fluoro-4-[7-methoxy-6-(methylcarbamoyl)quinolin-4-yl]oxyphenyl]-1-N-[4-(trifluoromethyl)phenyl]-cyclopropane-1,1-dicarboxamide |
| 274 | 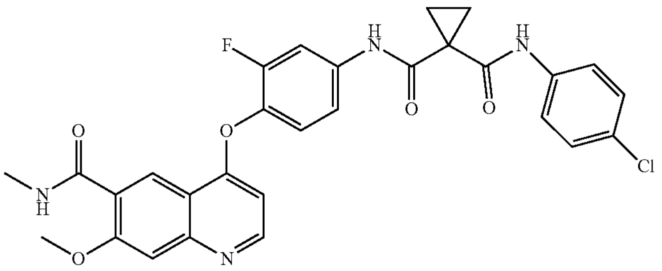 [SMILES: CNC(=O)c1cc2c(Oc3ccc(NC(=O)C4(C(=O)Nc5ccc(Cl)cc5)CC4)cc3F)ccnc2cc1OC] | 1-N-(4-chlorophenyl)-1-N'-[3-fluoro-4-[7-methoxy-6-(methylcarbamoyl)quinolin-4-yl]oxyphenyl]cyclopropane-1,1-dicarboxamide |
| 278 | 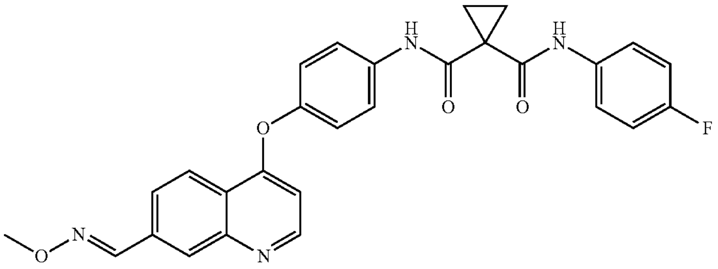 [SMILES: CO/N=C/c1ccc2c(Oc3ccc(NC(=O)C4(C(=O)Nc5ccc(F)cc5)CC4)cc3)ccnc2c1] | 1-N'-(4-fluorophenyl)-1-N-[4-[7-[(E)-methoxyiminomethyl]quinolin-4-yl]oxyphenyl]cyclopropane-1,1-dicarboxamide |

TABLE 1-continued

| Specific compounds of the invention | | |
|---|---|---|
| No. | Structure | Name |
| 279 | 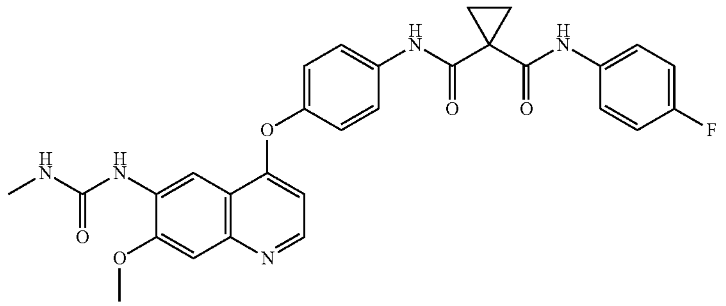 [SMILES: CNC(=O)Nc1cc2c(Oc3ccc(NC(=O)C4(C(=O)Nc5ccc(F)cc5)CC4)cc3)ccnc2cc1OC] | 1-N'-(4-fluorophenyl)-1-N-[4-[7-methoxy-6-(methylcarbamoylamino)quinolin-4-yl]oxyphenyl]cyclopropane-1,1-dicarboxamide |
| 280 | 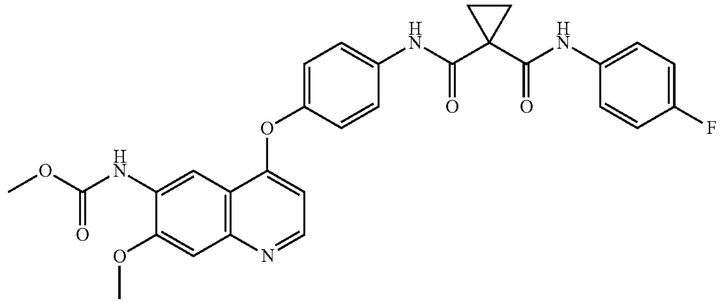 [SMILES: COC(=O)Nc1cc2c(Oc3ccc(NC(=O)C4(C(=O)Nc5ccc(F)cc5)CC4)cc3)ccnc2cc1OC] | methyl N-[4-[4-[[1-[(4-fluorophenyl)carbamoyl]-cyclopropanecarbonyl]-amino]phenoxy]-7-methoxyquinolin-6-yl]carbamate |
| 281 | 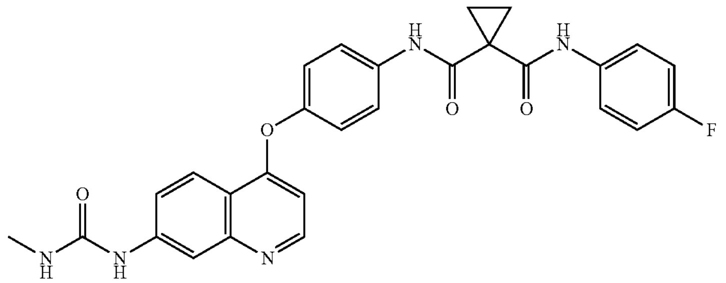 [SMILES: CNC(=O)Nc1ccc2c(Oc3ccc(NC(=O)C4(C(=O)Nc5ccc(F)cc5)CC4)cc3)ccnc2c1] | 1-N'-(4-fluorophenyl)-1-N-[4-[7-(methylcarbamoylamino)quinolin-4-yl]oxyphenyl]cyclopropane-1,1-dicarboxamide |
| 282 | 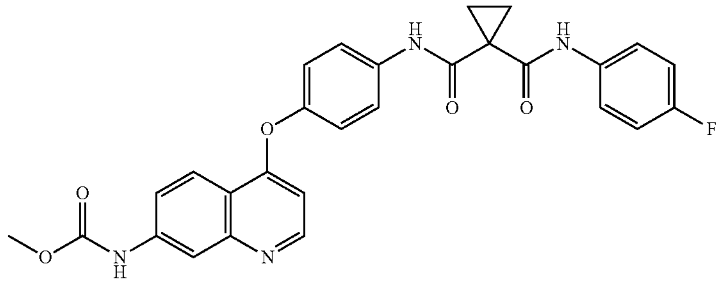 [SMILES: COC(=O)Nc1ccc2c(Oc3ccc(NC(=O)C4(C(=O)Nc5ccc(F)cc5)CC4)cc3)ccnc2c1] | methyl N-[4-[4-[[1-[(4-fluorophenyl)carbamoyl]-cyclopropanecarbonyl]-amino]phenoxy]quinolin-7-yl]carbamate |
| 283 | 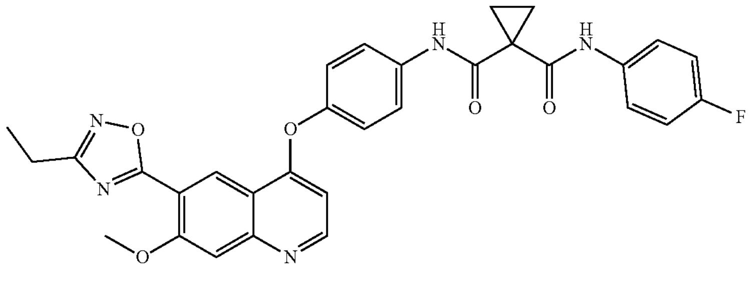 [SMILES: CCc1noc(-c2cc3c(Oc4ccc(NC(=O)C5(C(=O)Nc6ccc(F)cc6)CC5)cc4)ccnc3cc2OC)n1] | 1-N-[4-[6-(3-ethyl-1,2,4-oxadiazol-5-yl)-7-methoxyquinolin-4-yl]oxyphenyl]-1-N'-(4-fluorophenyl)cyclopropane-1,1-dicarboxamide |

TABLE 1-continued

Specific compounds of the invention

| No. | Structure | Name |
|---|---|---|
| 289 | 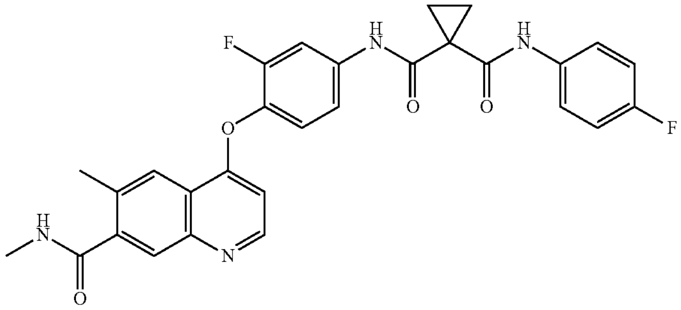 [SMILES: CNC(=O)c1cc2nccc(Oc3ccc(NC(=O)C4(C(=O)Nc5ccc(F)cc5)CC4)cc3F)c2cc1C] | 1-N'-[3-fluoro-4-[6-methyl-7-(methylcarbamoyl)quinolin-4-yl]oxyphenyl]-1-N-(4-fluorophenyl)cyclopropane-1,1-dicarboxamide |
| 290 | 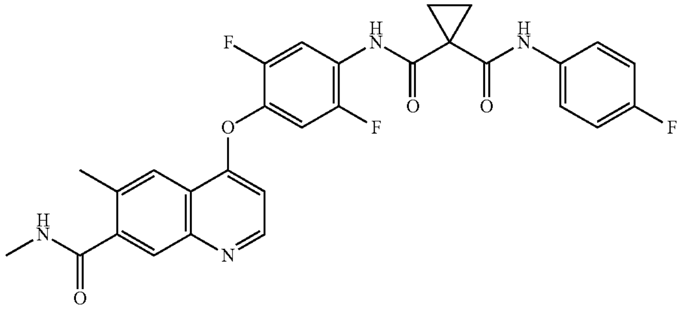 [SMILES: CNC(=O)c1cc2nccc(Oc3cc(F)c(NC(=O)C4(C(=O)Nc5ccc(F)cc5)CC4)cc3F)c2cc1C] | 1-N'-[2,5-difluoro-4-[6-methyl-7-(methylcarbamoyl)quinolin-4-yl]oxyphenyl]-1-N-(4-fluorophenyl)cyclopropane-1,1-dicarboxamide |
| 291 | 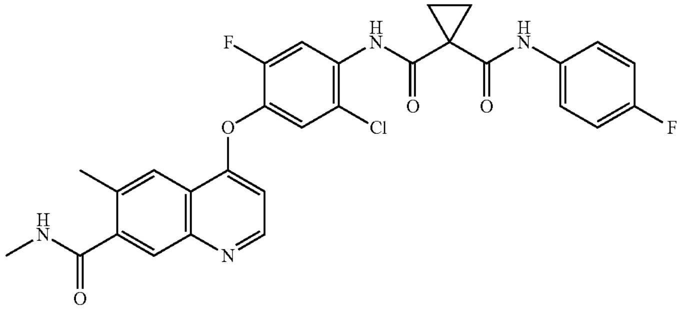 | 1-N'-[2-chloro-5-fluoro-4-[6-methyl-7-(methylcarbamoyl)quinolin-4-yl]oxyphenyl]-1-N-(4-fluorophenyl)cyclopropane-1,1-dicarboxamide |
| 292 | 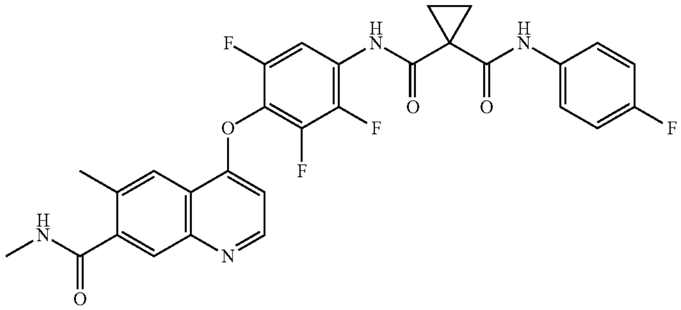 [SMILES: CNC(=O)c1cc2nccc(Oc3c(F)cc(NC(=O)C4(C(=O)Nc5ccc(F)cc5)CC4)c(F)c3F)c2cc1C] | 1-N-(4-fluorophenyl)-1-N'-[2,3,5-trifluoro-4-[6-methyl-7-(methylcarbamoyl)quinolin-4-yl]oxyphenyl]cyclopropane-1,1-dicarboxamide |
| 293 | 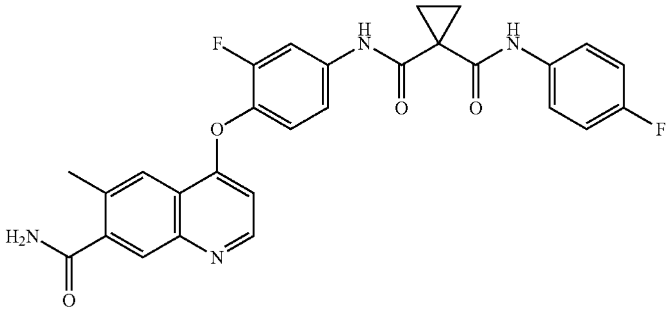 [SMILES: Cc1cc2c(Oc3ccc(NC(=O)C4(C(=O)Nc5ccc(F)cc5)CC4)cc3F)ccnc2cc1C(N)=O] | 1-N'-[4-(7-carbamoyl-6-methylquinolin-4-yl)oxy-3-fluorophenyl]-1-N-(4-fluorophenyl)cyclopropane-1,1-dicarboxamide |

TABLE 1-continued

| No. | Structure | Name |
| --- | --- | --- |
| 294 | 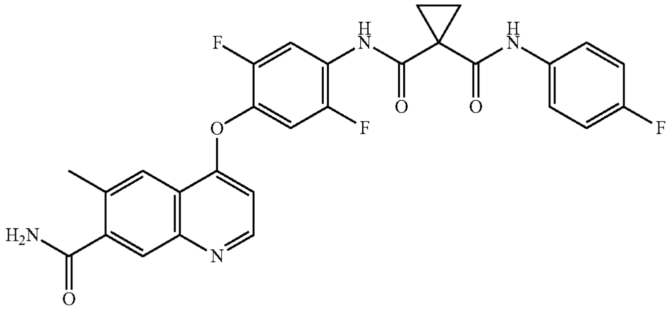 [SMILES: Cc1cc2c(Oc3cc(F)c(NC(=O)C4(C(=O)Nc5ccc(F)cc5)CC4)cc3F)ccnc2cc1C(N)=O] | 1-N'-[4-(7-carbamoyl-6-methylquinolin-4-yl)oxy-2,5-difluorophenyl]-1-N-(4-fluorophenyl)cyclopropane-1,1-dicarboxamide |
| 301 | 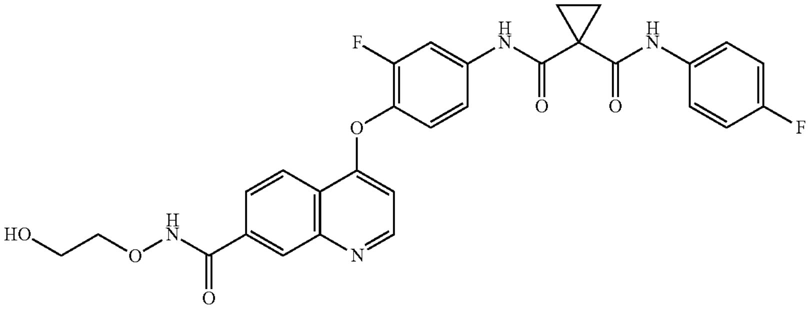 [SMILES: O=C(NOCCO)c1ccc2c(Oc3ccc(NC(=O)C4(C(=O)Nc5ccc(F)cc5)CC4)cc3F)ccnc2c1] | 1-N'-[3-fluoro-4-[7-(2-hydroxyethoxycarbamoyl)quinolin-4-yl]oxyphenyl]-1-N-(4-fluorophenyl)cyclopropane-1,1-dicarboxamide |
| 302 | 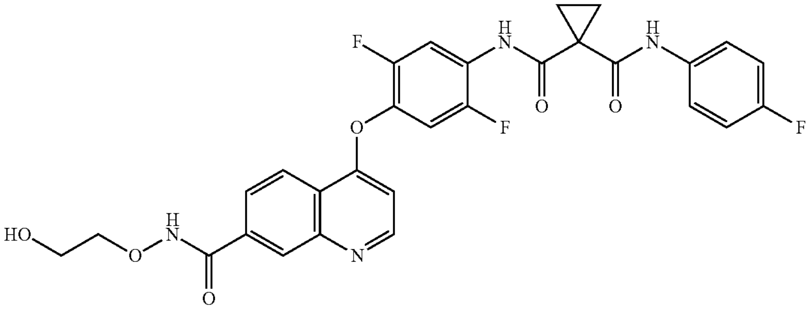 [SMILES: O=C(NOCCO)c1ccc2c(Oc3cc(F)c(NC(=O)C4(C(=O)Nc5ccc(F)cc5)CC4)cc3F)ccnc2c1] | 1-N'-[2,5-difluoro-4-[7-(2-hydroxyethoxycarbamoyl)-quinolin-4-yl]oxyphenyl]-1-N-(4-fluorophenyl)cyclopropane-1,1-dicarboxamide |

Specific compounds of the invention or a pharmaceutically acceptable salt thereof.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as, for example, tablets, suppositories, pills, soft elastic and hard gelatin capsules, powders, solutions, suspensions, aerosols, and the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, and the like. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate, and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, and the like.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate, and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, and the like, a compound(s) of the invention, or a pharmaceutically acceptable salt thereof, and optional pharmaceutical adjuvants in a carrier, such as, for example, water, saline, aqueous dextrose, glycerol, ethanol, and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, and dimethylformamide; oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol, and sorbitan esters, microcrystalline cellulose, aluminum metahydroxide, bentonite, agar-agar, and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol, or a suppository wax, which are solid at ordinary temperatures but liquid at body temperature and therefore melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound (s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode, and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Combination Therapy

A compound as disclosed herein can be administered as a single therapy or in combination ("co-administered") with one or more additional therapies for the treatment of a disease or disorder, for instance a disease or disorder associated with hyper-proliferation such as cancer. Therapies that may be used in combination with a compound disclosed herein include: (i) surgery; (ii) radiotherapy (for example, gamma radiation, neutron beam radiotherapy, electron beam radiotherapy, proton therapy, brachytherapy, and systemic radioactive isotopes); (iii) endocrine therapy; (iv) adjuvant therapy, immunotherapy, CAR T-cell therapy; and (v) other chemotherapeutic agents.

The term "co-administered" ("co-administering") refers to either simultaneous administration, or any manner of separate sequential administration, of a compound of Formula I' or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents for cancer treatment can be found, for instance, at https://www.cancer.gov/about-cancer/treatment/drugs (last visited Jan. 22, 2019) and in publically available sources such as Cancer Principles and Practice of Oncology by V. T. Devita and S. Hellman (editors), $11^{th}$ edition (2018), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound as disclosed herein or a pharmaceutically acceptable salt thereof and at least one immunotherapy. Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN™ (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3epitope) IgG antibody (ImClone System); IMC-C225 which is a chimeric anti-EGFR IgG antibody (ImClone System); VITAXIN™ which is a humanized anti-alpha V beta 3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-alpha antibody (CAT/BASF); CDP870 is a humanized anti-TNF-alpha. Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-alpha. IgG4 antibody (Celltech); LDP-02 is a humanized anti-alpha4 beta7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$beta_2$ antibody (Cambridge Ab Tech). Others are provided in later paragraphs.

Immunotherapies that can be used in combination with a compound as disclosed herein include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

In various embodiments, an immunological therapy or an immunological therapeutic agent can include, one or more of the following: an adoptive cell transfer, an angiogenesis inhibitor, Bacillus Calmette-Guerin therapy, biochemotherapy, a cancer vaccine, a chimeric antigen receptor (CAR) T-cell therapy, a cytokine therapy, gene therapy, an immune checkpoint modulator, an immunoconjugate, a radioconjugate, an oncolytic virus therapy, or a targeted drug therapy. The function or at least one of the functions of the immunological therapy or immunological therapeutic agent, collectively referred to herein as an "immunotherapeutic agent".

The present disclosure provides a method for preventing, treating, reducing, inhibiting or controlling a neoplasia, a tumor or a cancer in a subject in need thereof, involving administering a therapeutically effective amount of a combination comprising a compound of Formula I' and an immunotherapeutic agent. In one non-limiting embodiment, the method comprises administering a therapeutically effective amount of a combination comprising a compound of Formula I' in combination with an immunotherapeutic agent. In various embodiments, the combination provides a cooperative effect, an additive effect, or a synergistic effect in reducing the number of cancer cells when treated with the combination as compared to each treatment alone. In some embodiments, administration of a therapeutically effective amount of a combination comprising a compound of Formula I' and an immunotherapeutic agent, results in synergistic anti-tumor activity and/or antitumor activity that is more potent than the additive effect of administration of a compound of Formula I' or immunotherapeutic agent alone.

Human cancers harbor numerous genetic and epigenetic alterations, generating neoantigens potentially recognizable by the immune system (Sjoblom et al. (2006) Science 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

The present disclosure provides a combination of a compound of Formula I' and an immunotherapeutic agent. These exemplified combinations can be used to treat a subject with a cancer. In various embodiments, immunotherapeutic agents that find utility in the present compositions, formulations, and methods can include one or more agents or therapies, including: an adoptive cell transfer, an angiogenesis inhibitor, *Bacillus* Calmette-Guerin therapy, biochemotherapy, a cancer vaccine, a chimeric antigen receptor (CAR) T-cell therapy, a cytokine therapy, gene therapy, an immune checkpoint modulator, for example an immune checkpoint inhibitor, an immunoconjugate, a radioconjugate, an oncolytic virus therapy, or a targeted drug therapy.

In certain embodiments of the present disclosure, a therapeutically effective combination comprises a compound of Formula I' and an immunotherapeutic agent. In various related embodiments, the compound of Formula I' enhances the activity of the immunotherapeutic agent.

In certain embodiments of each of the aforementioned aspects, as well as other aspects and embodiments described elsewhere herein, the immunotherapeutic agent enhances the activity of the compound of Formula I'.

In certain embodiments of each of the aforementioned aspects, as well as other aspects and embodiments described elsewhere herein, the compound of Formula I' and the immunotherapeutic agent act synergistically. In various embodiments described herein, an exemplary immunotherapeutic agent is an immune cell (e.g. T-cell, dendritic cell, a natural killer cell and the like) modulator chosen from an agonist or an activator of a costimulatory molecule, wherein the modulator is a monoclonal antibody, a bispecific antibody comprising one or more immune checkpoint antigen binding moieties, a trispecific antibody, or an immune cell-engaging multivalent antibody/fusion protein/construct known in the art). In some embodiments, the immunotherapeutic agent can be an antibody that modulates a costimulatory molecule, bind to an antigen on the surface of an immune cell, or a cancer cell. In each of these different embodiments, the antibody modulator can be a monoclonal antibody, a polyclonal antibody, a bispecific antibody, a trispecific or multispecific format antibody, a fusion protein, or a fragment thereof, for example, a Diabody, a Single-chain (sc)-diabody (scFv)2, a Miniantibody, a Minibody, a Barnase-barstar, a scFv-Fc, a sc(Fab)2, a Trimeric antibody construct, a Triabody antibody construct, a Trimerbody antibody construct, a Tribody antibody constuct, a Collabody antibody construct, a (scFv-TNFa)3, or a F(ab)3/DNL antibody construct.

In certain embodiments of each of the aforementioned aspects, as well as other aspects and embodiments described elsewhere herein, the immunotherapeutic agent is an agent that modulates immune responses, for example, a checkpoint inhibitor or a checkpoint agonist. In some embodiments, the immunotherapeutic agent is an agent that enhances anti-tumor immune responses. In some embodiments, the immunotherapeutic agent is an agent that increases cell-mediated immunity. In some embodiments, the immunotherapeutic agent is an agent that increases T-cell activity. In some embodiments, the immunotherapeutic agent is an agent that increases cytolytic T-cell (CTL) activity. In some embodiments, the immunotherapeutic agent is an antibody modulator that targets PD-1, PD-L1, PD-L2, CEACAM (e.g., CEACAM-1, -3 and/or -5), CTLA-4, TIM-3, LAG-3, VISTA, BTLA, TIGIT, LAIR1, CD160, 2B4, TGF beta, OX40, 41BB, LIGHT, CD40, GITR, TGF-beta, TIM-3, SIRP-alpha, VSIG8, BTLA, SIGLEC7, SIGLEC9, ICOS, B7H3, B7H4, FAS, and/or BTNL2 among others known in the art. In some embodiments, the immunotherapeutic agent is an agent that increases natural killer (NK) cell activity. In some embodiments, the immunotherapeutic agent is an agent that inhibits suppression of an immune response. In some embodiments, the immunotherapeutic agent is an agent that inhibits suppressor cells or suppressor cell activity. In some embodiments, the immunotherapeutic agent is an agent or therapy that inhibits Treg activity. In some embodiments, the immunotherapeutic agent is an agent that inhibits the activity of inhibitory immune checkpoint receptors. In some embodiments, the combination of the present disclosure comprises a compound of Formula I' and an immunotherapeutic agent, wherein the immunotherapeutic agent includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, ICOS, SLAM (e.g., SLAMF7), HVEM, LIGHT, CD2, CD27, CD28, CDS, ICAM-1, LFA-1 (CD11a/CD18), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

In some embodiments, the immunotherapeutic agent is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a modulator of SIRP-alpha activity, a modulator of TIGIT activity, a modulator of VSIG8 activity, a modulator of BTLA activity, a modulator of SIGLEC7 activity, a modulator of SIGLEC9 activity, a modulator of ICOS activity, a modulator of B7H3 activity, a modulator of B7H4 activity, a modulator of FAS activity, a modulator of BTNL2 activity, a cytokine, a chemokine, an interferon, an interleukin, a lymphokine, a member of the tumor necrosis factor (TNF) family, or an immunostimulatory oligonucleotide. In some embodiments, the immunotherapeutic agent is an immune checkpoint modulator (e.g., an immune checkpoint inhibitor e.g. an inhibitor of PD-1 activity, a modulator of PD-L1 activity, a modulator of PD-L2 activity, a modulator of CTLA-4, or a CD40 agonist (e.g., an anti-CD40 antibody molecule), (xi) an OX40 agonist (e.g., an anti-OX40 antibody molecule), or (xii) a CD27 agonist (e.g., an anti-CD27 antibody molecule). In one embodiment, the immunomodulator is an inhibitor of PD-1, PD-L1, PD-L2, CTLA-4, TIM-3, LAG-3, CEACAM (e.g., CEACAM-1, -3 and/or -5), VISTA, BTLA, TIGIT, LAIR1, CD160, 2B4 and/or TGF beta. In one embodiment, the inhibitor of an immune checkpoint molecule inhibits PD-1, PD-L1, LAG-3, TIM-3, CEACAM (e.g., CEACAM-1, -3 and/or -5), CTLA-4, or any combination thereof.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof for example, a monoclonal antibody, a bispecific antibody comprising one or more immune checkpoint antigen binding moieties, a trispecific antibody, or an immune cell-engaging multivalent antibody/fusion protein/construct known in the art that binds to the inhibitory molecule; e.g., an antibody or fragment thereof (also referred to herein as "an antibody molecule") that binds to PD-1, PD-L1, PD-L2, CEACAM (e.g., CEACAM-1, -3 and/or -5), CTLA-4, TIM-3, LAG-3, VISTA, BTLA, TIGIT, LAIR1, CD160, 2B4, TGF beta, or a combination thereof.

In some embodiments, where the combination comprises a compound of Formula I' and an immunotherapeutic agent, wherein the immunotherapeutic agent is a monoclonal antibody or a bispecific antibody. For example, the monoclonal or bispecific antibody may specifically bind a member of the c-Met pathway and/or an immune checkpoint modulator (e.g., the bispecific antibody binds to both a hepatocyte growth factor receptor (HGFR) and an immune checkpoint modulator described herein, such as an antibody that binds PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2 or CD27). In particular embodiments, the bispecific antibody specifically binds a human HGFR protein and one of PD-1, PD-L1, and CTLA-4.

In some embodiments, the immunotherapeutic agent is a cytokine, for example, a chemokine, an interferon, an interleukin, lymphokine, or a member of the tumor necrosis factor family. In some embodiments, the cytokine is IL-2, IL15, or interferon-gamma.

In some embodiments of any of the above aspects or those described elsewhere herein, the cancer is selected from the group consisting of lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma, glioblastoma multiforme, cervical cancer, stomach cancer, bladder cancer, head and neck cancer, and hepatoma.

In some embodiments of any of the above aspects or those described elsewhere herein, the subject's cancer or tumor does not respond to immune checkpoint inhibition (e.g., to any immune checkpoint inhibitor described herein, such as a PD-1 antagonist or PD-L1 antagonist) or the subject's cancer or tumor has progressed following an initial response to immune checkpoint inhibition (e.g., to any immune checkpoint inhibitor described herein, such as a PD-1 antagonist or PD-L1 antagonist).

In some embodiments of any of the above aspects or those described elsewhere herein, the subject is a human.

A checkpoint inhibitor can be any molecule, agent, treatment and/or method of inhibiting an immune checkpoint, and/or promoting an inhibitor of an immune checkpoint, e.g., by promoting an intrinsic immune checkpoint inhibitor; inhibiting a transcription factor involved in the expression of an immune checkpoint; and/or by acting in concert with some additional extrinsic factor. For example, a checkpoint inhibitor could include a treatment that inhibits transcription factors involved the expression of immune checkpoint genes, or promotes the expression of transcription factors for tumor-suppressor genes, e.g., BACH2 (Luan et al., (2016). Transcription Factors and Checkpoint Inhibitor Expression with Age: Markers of Immunosenescence. Blood, 128(22), 5983). Moreover, a checkpoint inhibitor can inhibit the transcription of immune checkpoint genes; the modification and/or processing of immune checkpoint mRNA; the translation of immune checkpoint proteins; and/or molecules involved in immunity or the immune checkpoint pathway, e.g., PD-1 transcription factors such as HIF-1, STAT3, NF-κB, and AP-1, or the activation of common oncogenic pathways such as JAK/STAT, RAS/ERK, or PI3K/AKT/mTOR (Zerdes et al., Genetic, transcriptional and post-translational regulation of the programmed death protein ligand 1 in cancer: biology and clinical correlations, Oncogene volume 37, pages 4639-4661 (2018), the disclosure of which is incorporated herein by reference in its entirety).

Checkpoint inhibitors can include treatments, molecules, agents, and/or methods that regulate immune checkpoints at the transcriptional level, e.g., using the RNA-interference pathway co-suppression, and/or post-transcriptional gene silencing (PTGS) (e.g., microRNAs, miRNA; silencing-RNA, small-interfering-RNA, or short-interfering-RNA (siRNA). Transcriptional regulation of checkpoint molecules has been shown to involve mir-16, which has been shown to target the 3'UTR of the checkpoint mRNAs CD80, CD274 (PD-L1) and CD40 (Leibowitz et al., Post-transcriptional regulation of immune checkpoint genes by mir-16 in melanoma, Annals of Oncology (2017) 28; v428-v448). Mir-33a has also been shown to be involved in regulating the expression of PD-1 in cases of lung adenocarcinoma (Boldini et al., Role of microRNA-33a in regulating the expression of PD-1 in lung adenocarcinoma, Cancer Cell Int. 2017; 17: 105, the disclosure of which is incorporated herein by reference in its entirety).

T-cell-specific aptamer-siRNA chimeras have been suggested as a highly specific method of inhibiting molecules in the immune checkpoint pathway (Hossain et al., The aptamer-siRNA conjugates: reprogramming T cells for cancer therapy, Ther. Deliv. 2015 January; 6(1): 1-4, the disclosure of which is incorporated herein by reference in its entirety).

Alternatively, members of the immune checkpoint pathway can be inhibited using treatments that affect associated pathways, e.g., metabolism. For example, oversupplying the glycolytic intermediate pyruvate in mitochondria from CAD macrophages promoted expression of PD-L1 via induction of the bone morphogenetic protein 4/phosphorylated SMAD1/5/IFN regulatory factor 1 (BMP4/p-SMAD1/5/IRF1) signaling pathway. Accordingly, implementing treatments that modulate the metabolic pathway can result in subsequent modulation of the immunoinhibitory PD-1/PD-L1 checkpoint pathway (Watanabe et al., Pyruvate controls the checkpoint inhibitor PD-L1 and suppresses T cell immunity, J Clin Invest. 2017 Jun. 30; 127(7): 2725-2738).

Checkpoint immunity can be regulated via oncolytic viruses that selectively replicate within tumor cells and induce acute immune responses in the tumor-microenvironment, i.e., by acting as genetic vectors that carry specific agents (e.g., antibodies, miRNA, siRNA, and the like) to cancer cells and effecting their oncolysis and secretion of cytokines and chemokines to synergize with immune checkpoint inhibition (Shi et al., Cancer Immunotherapy: A Focus on the Regulation of Immune Checkpoints, Int J Mol Sci. 2018 May; 19(5): 1389). Currently, there are clinical trials underway that utilize the following viruses as checkpoint inhibitors: poliovirus, measles virus, adenoviruses, poxviruses, herpes simplex virus (HSV), coxsackieviruses, reovirus, Newcastle disease virus (NDV), T-VEC (a herpes virus encoded with GM-CSF (granulocyte-macrophage colony stimulating factor)), and H101 (Shi et al., supra).

Checkpoint inhibitors can operate at the translational level of checkpoint immunity. The translation of mRNA into protein represents a key event in the regulation of gene expression, thus inhibition of immune checkpoint translation is a method in which the immune checkpoint pathway can be inhibited.

Inhibition of the immune checkpoint pathway can occur at any stage of the immune checkpoint translational process. For example, drugs, molecules, agents, treatments, and/or methods can inhibit the initiation process (whereby the 40*S* ribosomal subunit is recruited to the 5' end of the mRNA and scans the 5'UTR of the mRNA toward its 3' end. Inhibition can occur by targeting the anticodon of the initiator methionyl-transfer RNA (tRNA) (Met-tRNAi), its base-pairing with the start codon, or the recruitment of the 60S subunit to begin elongation and sequential addition of amino acids in the translation of immune-checkpoint-specific genes. Alternatively, a checkpoint inhibitor can inhibit checkpoints at the translational level by preventing the formation of the ternary complex (TC), i.e., eukaryotic initiation factor (eIF)2 (or one or more of its α, β, and γ subunits); GTP; and Met-tRNAi.

Checkpoint inhibition can occur via destabilization of eIF2α by precluding its phosphorylation via protein kinase R (PKR), PERK, GCN2, or HRI, or by precluding TCs from associating with the 40S ribosome and/or other initiation factors, thus preventing the preinitiation complex (PIC) from forming; inhibiting the eIF4F complex and/or its cap-binding protein eIF4E, the scaffolding protein eIF4G, or eIF4A helicase. Methods discussing the translational control of cancer are discussed in Truitt et al., New frontiers in translational control of the cancer genome, Nat Rev Cancer. 2016 Apr. 26; 16(5): 288-304, the disclosure of which is incorporated herein by reference in its entirety.

Checkpoint inhibitors can also include treatments, molecules, agents, and/or methods that regulate immune checkpoints at the cellular and/or protein level, e.g., by inhibiting an immune checkpoint receptor. Inhibition of checkpoints can occur via the use of antibodies, antibody fragments, antigen-binding fragments, small-molecules, and/or other drugs, agents, treatments, and/or methods.

Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response ('block' the immune response) against tumor tissues. In contrast to the majority of anti-cancer agents, checkpoint inhibitors do not target tumor cells directly, but rather target lymphocyte receptors or their ligands in order to enhance the endogenous antitumor activity of the immune system. (Pardoll, 2012, Nature Reviews Cancer 12:252-264).

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of antibody (Ab), ipilimumab (YERVOY®), that binds to and inhibits CTLA-4 for the treatment of patients with advanced melanoma (Hodi et al. (2010) N Engl J Med 363:711-23) and the development of antibodies such as nivolumab and pembrolizumab (formerly lambrolizumab; USAN Council Statement (2013) Pembrolizumab: Statement on a nonproprietary name adopted by the USAN Council (ZZ-165), Nov. 27, 2013) that bind specifically to the Programmed Death-1 (PD-1) receptor and block the inhibitory PD-1/PD-1 ligand pathway (Topalian et al. (2012a) N Engl J Med 366:2443-54; Topalian et al. (2012b) Curr Opin Immunol 24:207-12; Topalian et al. (2014) J Clin Oncol 32(10):1020-30; Hamid et al. (2013) N Engl J Med 369:134-144; Hamid and Carvajal (2013) Expert Opin Biol Ther 13(6):847-61; McDermott and Atkins (2013) Cancer Med 2(5):662-73).

PD-1 is a key immune checkpoint receptor expressed by activated T and B cells and mediates immunosuppression.

Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al. (2014) In vitro characterization of the anti-PD-1 antibody nivolumab, BMS-936558, and in vivo toxicology in non-human primates. Nivolumab has been approved for the treatment of patients with unresectable or metastatic melanoma and disease progression following ipilimumab and, if BRAF V600 mutation positive, a BRAF inhibitor and for the treatment of squamous non-small cell lung cancer.

Recent data suggest a secondary mechanism of anti-CTLA-4 antibodies, which could occur within the tumor itself. CTLA-4 has been found to be expressed in tumors at higher levels on regulatory T-cells (also referred to herein as "Treg cells") as compared with intra-tumoral effector T-cells (also referred to herein as "Teff cells"), resulting in the hypothesis of anti-CTLA-4 preferentially impacting the Treg cell. "Therapeutic use of anti-CTLA-4 antibodies", Christian U. Blank and Alexander Enk, International Immunology, Vol. 27, No. 1, pp. 3-10. A recent study of a PD-1 and CTLA-4 combination show that the combination blockade of the CTLA-4 and PD-1 pathways also cooperates to increase the ratio of Teff cells to both regulatory T-cells and MDSCs, thereby reducing suppression and promoting inflammation in the tumor microenvironment. "Combination of CTLA-4 and PD-1 blockade expands infiltrating T-cells and reduces regulatory T and myeloid cells within B16 melanoma tumors", Curran et al., PNAS|Mar. 2, 2010; vol. 107 (no. 9); pp. 4275-4280, the disclosure of which is incorporated herein by reference in its entirety. The combination of a checkpoint inhibitor and another therapeutic agent(s) may enhance or prolong anti-tumor response of the checkpoint inhibitor and/or effects of the therapeutic agent. In this regard, WO 2015/069770 discloses a combination treatment based on activating the adaptive immune response, in particular the combination of CTLA-4 and PD-1 inhibitors, for the treatment of cancer. The disclosure of WO 2015/069770 is incorporated by reference in its entirety in the disclosure of this application.

One mechanism by which the checkpoint blockade anti-CTLA-4 antibodies mediate anti-tumor effect is by decreasing regulatory T-cells. Due to the distinct mechanism of action of anti-CTLA-4 antibodies, they can successfully combine with the anti-PD1 checkpoint blockade antibodies which work to release the suppressive signaling conferred to effector T-cells. Dual blockade with these antibodies combine to improve anti-tumor response both preclinically (Proc Natl Acad Sci USA 2010, 107, 4275-4280) and in the clinic (N Engl J Med 2013, 369, 122-133; N Engl J Med 2015, 372, 2006-2017).

CTLA-4 attenuates the early activation of naïve and memory T cells through interactions with its ligands B7-1 (CD80) and B7-2 (CD86) (FIG. 1A). PD-1 is an receptor expressed on the surface of activated mature T cells, activated NK cells, B cells, monocytes and multiple normal tissues and plays a crucial role in the maintenance of peripheral tolerance [20-21] (FIG. 1A). In contrast to CTLA-4, PD-1 acts via interactions with its ligands PD-L1 (also known as B7-H1 or CD274) and is involved mainly in T cell activity modulation in peripheral tissues as well as providing a major immune resistance mechanism within the tumor microenvironment.

In some embodiments, the immunotherapeutic agent is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, or an immunostimulatory oligonucleotide. In some embodiments, the immune checkpoint modulator, i.e. is an inhibitor or antagonist, or is an activator or agonist, for example, a CD28 modulator, a 4-1BB modulator, an OX40 modulator, a CD27 modulator, a CD80 modulator, a CD86 modulator, a CD40 modulator, or a GITR modulator, a Lag-3 modulator, a 41BB modulator, a LIGHT modulator, a CD40 modulator, a GITR modulator, a TGF-beta modulator, a TIM-3 modulator, a SIRP-alpha modulator, a TIGIT modulator, a VSIG8 modulator, a BTLA modulator, a SIGLEC7 modulator, a SIGLEC9 modulator, a ICOS modulator, a B7H3 modulator, a B7H4 modulator, a FAS modulator, and/or a BTNL2 modulator. In some embodiments, the immunotherapeutic agent is an immune checkpoint modulator as described above (e.g., an immune checkpoint modulator antibody, which can be in the form of a monoclonal antibody, a bispecific antibody comprising one or more immune checkpoint antigen binding moieties, a trispecific antibody, or an immune cell-engaging multivalent antibody/fusion protein/construct known in the art).

Combination treatments with immune checkpoint inhibitor immunotherapeutic agent may include antibodies that specifically target immune system checkpoints such as CTLA4, PD1 and PD-L1 are one of the most promising new avenues of immunotherapy for cancer and other diseases. Additional checkpoint targets, such as TIM-3, LAG-3, various B-7 ligands, CHK 1 and CHK2 kinases, BTLA, A2aR, and others, are also under investigation. Currently, three checkpoint inhibitors have received rapid approval from the U.S. Food and Drug Administration for cancer treatment, including ipilimumab (Yervoy®), a CTLA-4 inhibitor, and pembrolizumab (Keytruda®) and nivolumab (Opdivo®), both PD-1 inhibitors. In addition, several checkpoint inhibitor agents are in clinical trials.

Programmed Cell Death Protein 1, (PD-1 or CD279), a 55-kD type 1 transmembrane protein, is a member of the CD28 family of T cell co-stimulatory receptors that include immunoglobulin superfamily member CD28, CTLA-4, inducible co-stimulator (ICOS), and BTLA. PD-1 is highly expressed on activated T cells and B cells. PD-1 expression can also be detected on memory T-cell subsets with variable levels of expression. Two ligands specific for PD-1 have been identified: programmed death-ligand 1 (PD-L1, also known as B7-H1 or CD274) and PD-L2 (also known as B7-DC or CD273). PD-L1 and PD-L2 have been shown to down-regulate T cell activation upon binding to PD-1 in both mouse and human systems (Okazaki et al., Int Immunol., 2007; 19: 813-824). The interaction of PD-1 with its ligands, PD-L1 and PD-L2, which are expressed on antigen-presenting cells (APCs) and dendritic cells (DCs), transmits negative regulatory stimuli to down-modulate the activated T cell immune response. Blockade of PD-1 suppresses this negative signal and amplifies T cell responses.

Numerous studies indicate that the cancer microenvironment manipulates the PD-L1-/PD-1 signaling pathway and that induction of PD-L1 expression is associated with inhibition of immune responses against cancer, thus permitting cancer progression and metastasis. The PD-L1/PD-1 signaling pathway is a primary mechanism of cancer immune evasion for several reasons. First, and most importantly, this pathway is involved in negative regulation of immune responses of activated T effector cells, found in the periphery. Second, PD-L1 is up-regulated in cancer microenvironments, while PD-1 is also up-regulated on activated tumor infiltrating T cells, thus possibly potentiating a vicious cycle of inhibition. Third, this pathway is intricately involved in both innate and adaptive immune regulation through bi-directional signaling. These factors make the PD-1/PD-L1 complex a central point through which cancer can manipulate immune responses and promote its own progression.

CTLA-4 (also known as Cytotoxic T-lymphocyte-associated protein 4, CTLA4, CTLA-4, CD152, cluster of differentiation 152; ALPS5, CD, CELIAC3, GRD4, GSE, and IDDM12). CTLA-4 is a ~24.6-kDa single-pass type I membrane protein that plays an inhibitory role in T-cell function. CTLA-4 was originally identified by differential screening of a murine cytolytic T cell cDNA library, See Brunet et al., A new member of the immunoglobulin superfamily—CTLA-4, Nature. 1987 Jul. 16-22; 328(6127):267-70. CTLA- has been shown to interact with the b7 family ligands CD80 (also known as Cluster of differentiation 80, and B7-1); and CD86 (also known as Cluster of Differentiation 86 or B7-2). See Linsley et al., CTLA-4 is a second receptor for the B cell activation antigen B7, J Exp Med. 1991 Sep. 1; 174(3):561-9. Sequence comparison between the human CTLA-4 DNA encoding region, and that of CD28, reveals significant homology between both sequences, with the greatest similarity between juxtamembrane and cytoplasmic regions; accordingly, CTLA-4 is implicated in abrogating/reducing T-cell activity, and opposes the activity of CD28. CTLA-4 deficient mice have been shown to exhibit massive lymphoproliferation. Chambers et al., Lymphoproliferation in CTLA-4-deficient mice is mediated by costimulation-dependent activation of CD4+ T cells, Immunity. 1997 December; 7(6):885-95. It has been reported that CTLA-4 blockade augments T-cell responses both in vitro and in vivo, enhances an induced autoimmune disease, and exacerbates antitumor immunity. (See Luhder, J. Exp. Med. 1998; 187:427-432; Walunas et al., Immunity. 1994; 1:405-413; Kearney, J. Immunol. 1995; 155:1032-1036); Leach, Science 1996; 271:1734-1736). CTLA-4 has also been reported as having alternative and/or additional impact on the initial character of the T-cell immune response (Chambers, Curr. Opin. Immunol. 1997; 9:396-404; Bluestone, J. Immunol. 1997; 158:1989-1993; Thompson, Immunity 1997; 7:445-450).

The first immune-checkpoint inhibitor to be tested in a clinical trial was ipilimumab (Yervoy, Bristol-Myers Squibb), an CTLA-4 mAb. CTLA-4 belongs to the immunoglobulin superfamily of receptors, which also includes PD-1, BTLA, TIM-3, and V-domain immunoglobulin suppressor of T cell activation (VISTA). Anti-CTLA-4 mAb is a powerful checkpoint inhibitor which removes "the break" from both naive and antigen-experienced cells. Therapy enhances the antitumor function of CD8+ T cells, increases the ratio of CD8+ T cells to Foxp3+ T regulatory cells, and inhibits the suppressive function of T regulatory cells. The major drawback to anti-CTLA-4 mAb therapy is the generation of autoimmune toxicities due to on-target effects of an over-exuberant immune system which has lost the ability to turn itself down. It has been reported that up to 25% of patients treated with ipilimumab developed serious grade 3-4 adverse events/autoimmune-type side effects including dermatitis, enterocolitis, hepatitis, endocrinopathies (including hypophysitis, thyroiditis, and adrenalitis), arthritis, uveitis, nephritis, and aseptic meningitis. In contrast to the anti-CTLA-4 experience, anti-PD-1 therapy appears to be better-tolerated and induces a relatively lower rate of autoimmune-type side effects.

In some embodiments, the immunotherapeutic agent is an agent that inhibits the activity of PD-1. In some embodiments, the immunotherapeutic agent is an agent that inhibits the activity of PD-L1 and/or PD-L2. In some embodiments, the immunotherapeutic agent is an agent that inhibits the activity of CTLA-4. In some embodiments, the immunotherapeutic agent is an agent that inhibits the activity of CD80 and/or CD86. In some embodiments, the immunotherapeutic agent is an agent that inhibits the activity of TIGIT. In some embodiments, the immunotherapeutic agent is an agent that inhibits the activity of KIR. In some embodiments, the immunotherapeutic agent is an agent that enhances or stimulates the activity of activating immune checkpoint receptors.

In some of the embodiments of the methods described herein, the immunotherapeutic agent is a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, or an IDO1 antagonist.

In some embodiments, the PD-1 antagonist is an antibody that specifically binds PD-1. In some embodiments, the antibody that binds PD-1 is pembrolizumab (KEYTRUDA®, MK-3475; Merck), pidilizumab (CT-011; Curetech Ltd.), nivolumab (OPDIVO®, BMS-936558, MDX-1106; Bristol Myer Squibb), MEDI0680 (AMP-514; AstraZenenca/MedImmune), REGN2810 (Regeneron Pharmaceuticals), BGB-A317 (BeiGene Ltd.), PDR-001 (Novartis), or STI-A1110 (Sorrento Therapeutics). In some embodiments, the antibody that binds PD-1 is described in PCT Publication WO 2014/179664, for example, an antibody identified as APE2058, APE1922, APE1923, APE1924, APE 1950, or APE1963 (Anaptysbio), or an antibody containing the CDR regions of any of these antibodies. In other embodiments, the PD-1 antagonist is a fusion protein that includes the extracellular domain of PD-L1 or PD-L2, for example, AMP-224 (AstraZeneca/MedImmune). In other embodiments, the PD-1 antagonist is a peptide inhibitor, for example, AUNP-12 (Aurigene).

In some embodiments, the PD-L1 antagonist is an antibody that specifically binds PD-L1. In some embodiments, the antibody that binds PD-L1 is atezolizumab (RG7446, MPDL3280A; Genentech), MEDI4736 (AstraZeneca/MedImmune), BMS-936559 (MDX-1105; Bristol Myers Squibb), avelumab (MSB0010718C; Merck KGaA), KD033 (Kadmon), the antibody portion of KD033, or STI-A1014 (Sorrento Therapeutics). In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that contains the CDR regions of any of these antibodies, the disclosure of which is incorporated herein by reference in its entirety.

In some embodiments, the CTLA-4 antagonist is an antibody that specifically binds CTLA-4. In some embodiments, the antibody that binds CTLA-4 is ipilimumab (YERVOY®; Bristol Myer Squibb) or tremelimumab (CP-675,206; Pfizer). In some embodiments, the CTLA-4 antagonist a CTLA-4 fusion protein or soluble CTLA-4 receptor, for example, KARR-102 (Kahr Medical Ltd.).

In some embodiments, the LAG3 antagonist is an antibody that specifically binds LAG3. In some embodiments, the antibody that binds LAG3 is IMP701 (Prima BioMed), IMP731 (Prima BioMed/GlaxoSmithKline), BMS-986016 (Bristol Myer Squibb), LAG525 (Novartis), and GSK2831781 (GlaxoSmithKline). In some embodiments, the LAG3 antagonist includes a soluble LAG3 receptor, for example, IMP321 (Prima BioMed).

In some embodiments, the KIR antagonist is an antibody that specifically binds KIR. In some embodiments, the antibody that binds KIR is lirilumab (Bristol Myer Squibb/Innate Pharma).

In some embodiments, the immunotherapeutic agent used in the combinations disclosed herein (e.g., in combination with a compound of Formula I') is an activator or agonist of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CD28, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand.

In some embodiments, the OX40 agonist includes OX40 ligand, or an OX40-binding portion thereof. For example, the OX40 agonist may be MEDI6383 (AstraZeneca). In some embodiments, the OX40 agonist is an antibody that specifically binds OX40. In some embodiments, the antibody that binds OX40 is MEDI6469 (AstraZeneca/MedImmune), MEDI0562 (AstraZeneca/MedImmune), or MOXR0916 (RG7888; Genentech). In some embodiments, the OX40 agonist is a vector (e.g., an expression vector or virus, such as an adenovirus) capable of expressing OX40 ligand. In some embodiments the OX40-expressing vector is Delta-24-RGDOX (DNAtrix) or DNX2401 (DNAtrix).

In some embodiments, the 4-1BB (CD137) agonist is a binding molecule, such as an anticalin. In some embodiments, the anticalin is PRS-343 (Pieris AG). In some embodiments, the 4-1BB agonist is an antibody that specifically binds 4-1BB. In some embodiments, antibody that binds 4-1BB is PF-2566 (PF-05082566; Pfizer) or urelumab (BMS-663513; Bristol Myer Squibb).

In some embodiments, the CD27 agonist is an antibody that specifically binds CD27. In some embodiments, the antibody that binds CD27 is varlilumab (CDX-1127; Celldex).

In some embodiments, the GITR agonist comprises GITR ligand or a GITR-binding portion thereof. In some embodiments, the GITR agonist is an antibody that specifically binds GITR. In some embodiments, the antibody that binds GITR is TRX518 (GITR, Inc.), MK-4166 (Merck), or INBRX-110 (Five Prime Therapeutics/Inhibrx).

TIM-3 has been identified as another important inhibitory receptor expressed by exhausted CD8+ T cells. In mouse models of cancer, it has been shown that the most dysfunctional tumor-infiltrating CD8+ T cells actually co-express PD-1 and TIM-3.

LAG-3 is another recently identified inhibitory receptor that acts to limit effector T-cell function and augment the suppressive activity of T regulatory cells. It has recently been revealed that PD-1 and LAG-3 are extensively co-expressed by tumor-infiltrating T cells in mice, and that combined blockade of PD-1 and LAG-3 provokes potent synergistic antitumor immune responses in mouse models of cancer.

PD-1 pathway blockade can be combined with vaccines or other a compound of Formula I' antibodies for improved therapeutic efficacy (Hirano, F. et al, Cancer Res., 65(3): 1089-1096 (2005); Li, B. et al, Clin. Cancer Res., 15: 1507-1509 (2009); and Curran, M. A. et al, Proc. Natl. Acad. Set, 107(9):4275-4280 (2010)).

In some embodiments, immunotherapeutic agents useful in the compositions and methods described herein may include a monoclonal antibody, a bispecific antibody comprising one or more immune checkpoint antigen binding moieties, a trispecific antibody, or an immune cell-engaging multivalent antibody/fusion protein/construct known in the art that target specifically both PD-1 and ligand PD-L1.

PD-1 (also known as Programmed Death 1, CD279, PDCD1) is a cell surface receptor with a critical role in regulating the balance between stimulatory and inhibitory signals in the immune system and maintaining peripheral tolerance (Ishida, Y et al. 1992 EMBO J. 11 3887; Kier, Mary E et al. 2008 Annu Rev Immunol 26 677-704; Okazaki, Taku et al. 2007 International Immunology 19 813-824). PD-1 is an inhibitory member of the immunoglobulin super-family with homology to CD28. The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Expression of PD-1 is inducible on T cells, B cells, natural killer (NK) cells and monocytes, for example upon lymphocyte activation via T cell receptor (TCR) or B cell receptor (BCR) signalling (Kier, Mary E et al. 2008 Annu Rev Immunol 26 677-704; Agata, Y et al 1996 Int Immunol 8 765-72). PD-1 is a receptor for the ligands CD80, CD86, PD-L1 (B7-H1, CD274) and PD-L2 (B7-DC, CD273), which are cell surface expressed members of the B7 family (Freeman, Gordon et al. 2000 J Exp Med 192 1027; Latchman, Y et al. 2001 Nat Immunol 2 261). Upon ligand engagement, PD-1 recruits phosphatases such as SHP-1 and SHP-2 to its intracellular tyrosine motifs which subsequently dephosphorylate effector molecules activated by TCR or BCR signalling (Chemnitz, J et al. 2004 J Immunol 173 945-954; Riley, James L 2009 Immunological Reviews 229 114-125) In this way, PD-1 transduces inhibitory signals into T and B cells only when it is engaged simultaneously with the TCR or BCR.

PD-1 has been demonstrated to down-regulate effector T cell responses via both cell-intrinsic and cell-extrinsic functional mechanisms. Inhibitory signaling through PD-1 induces a state of unresponsiveness in T cells, resulting in the cells being unable to clonally expand or produce optimal levels of effector cytokines. PD-1 may also induce apoptosis in T cells via its ability to inhibit survival signals from co-stimulation, which leads to reduced expression of key anti-apoptotic molecules such as Bcl-XL (Kier, Mary E et al. 2008 Annu Rev Immunol 26 677-704). In addition to these direct effects, recent publications have implicated PD-1 as being involved in the suppression of effector cells by promoting the induction and maintenance of regulatory T cells (TREG). For example, PD-L1 expressed on dendritic cells was shown to act in synergy with TGF-β to promote the induction of CD4+ FoxP3+ TREG with enhanced suppressor function (Francisco, Loise M et al. 2009 J Exp Med 206 3015-3029).

TIM-3 (also known as T-cell immunoglobulin and mucin-domain containing-3, TIM-3, Hepatitis A virus cellular receptor 2, HAVCR2, HAVcr-2, KIM-3, TIMD-3, TIMD3, Tim-3, and CD366) is a ~33.4-kDa single-pass type I membrane protein involved in immune responses (Sanchez-Fueyo et al., Tim-3 inhibits T helper type 1-mediated autoand alloimmune responses and promotes immunological tolerance, Nat. Immunol. 4:1093-1101 (2003)).

TIM-3 is selectively expressed on Th1-cells, and phagocytic cells (e.g., macrophages and dendritic cells). The use of siRNA or a blocking antibody to reduce the expression of human resulted in increased secretion of interferon γ (IFN-γ) from CD4 positive T-cells, implicating the inhibitory role of TIM-3 in human T cells. Analysis of clinical samples from autoimmune disease patients showed no expression of TIM-3 in CD4 positive cells. In particular, expression level of TIM-3 is lower and secretion of IFN-γ is higher in T cell clones derived from the cerebrospinal fluid of patients with multiple sclerosis than those in clones derived from normal healthy persons (Koguchi K et al., J Exp Med. 203:1413-8. (2006)).

TIM-3 is the receptor for the ligands Galectin-9, which is a member of galectin family, molecules ubiquitously expressed on a variety of cell types and which binds β-galactoside; Phospatidyl serine (PtdSer) (DeKryff et al., T cell/transmembrane, Ig, and mucin-3 allelic variants differentially recognize phosphatidylserine and mediate phagocytosis of apoptotic cells, J Immunol. 2010 Feb. 15; 184(4): 1918-30); High Mobility Group Protein 1 (also known as HMGB1, HMG1, HMG3, SBP-1, HMG-1, and high mobility group box 1) Chiba et al., Tumor-infiltrating DCs suppress nucleic acid-mediated innate immune responses through interactions between the receptor TIM-3 and the alarmin HMGB1, Nat Immunol. 2012 September; 13(9): 832-42); and Carcinoembryonic Antigen Related Cell Adhesion Molecule 1 (also known as CEACAM1, BGP, BGP1, BGPI, carcinoembryonic antigen related cell adhesion molecule 1) (Huang et al., CEACAM1 regulates TIM-3-mediated tolerance and exhaustion, Nature. 2015 Jan. 15; 517 (7534):386-90).

BTLA (also known as B- and T-lymphocyte attenuator, BTLA1, CD272, and B and T lymphocyte associated) is a ~27.3-kDa single-pass type I membrane protein involved in lymphocyte inhibition during immune response. BTLA is constitutively expressed in both B and T cells. BTLA interacts with HVEM (herpes virus-entry mediator), a member of the tumor-necrosis factor receptor (TNFR) family (Gonzalez et al., Proc. Natl. Acad. Sci. USA, 2005, 102: 1116-21). The interaction of BTLA, which belongs to the CD28 family of the immunoglobulin superfamily, and HVEM, a costimulatory tumor-necrosis factor (TNF) receptor (TNFR), is unique in that it defines a cross talk between these two families of receptors. BTLA contains a membrane proximal immunoreceptor tyrosine-based inhibitory motif (ITIM) and membrane distal immunoreceptor tyrosine-based switch motif (ITSM). Disruption of either the ITIM or ITSM abrogated the ability of BTLA to recruit either SHP1 or SHP2, suggesting that BTLA recruits SHP1 and SHP2 in a manner distinct from PD-1 and both tyrosine motifs are required to block T cell activation. The BTLA cytoplasmic tail also contains a third conserved tyrosine-containing motif within the cytoplasmic domain, similar in sequence to a Grb-2 recruitment site (YXN). Also, a phosphorylated peptide containing this BTLA N-terminal tyrosine motif can interact with GRB2 and the p85 subunit of PI3K in vitro, although the functional effects of this interaction remain unexplored in vivo (Gavrieli et al., Bioochem. Biophysi Res Commun, 2003, 312, 1236-43). BTLA is the receptor for the ligands PTPN6/SHP-1; PTPN11/SHP-2; TNFRSF14/HVEM; and B7H4.

VISTA (also known as V-domain Ig suppressor of T cell activation VSIR, B7-H5, B7H5, GI24, PP2135, SISP1, DD1alpha, VISTA, C10orf54, chromosome 10 open reading frame 54, PD-1H, and V-set immunoregulatory receptor) is a ~33.9-kDa single-pass type I membrane protein involved in T-cell inhibitory response, embryonic stem cells differentiation via BMP4 signaling inhibition, and MMP14-mediated MMP2 activation (Yoon et al., Control of signaling-mediated clearance of apoptotic cells by the tumor suppressor p53, Science. 2015 Jul. 31; 349(6247): 1261669). VISTA interacts with the ligand VSIG-3 (Wang et al., VSIG-3 as a ligand of VISTA inhibits human T-cell function, Immunology. 2019 January; 156(1):74-85)

LAG-3 (also known as Lymphocyte-activation gene 3, LAG3, CD223, and lymphocyte activating 3) is a ~57.4-kDa single-pass type I membrane protein involved in lymphocyte activation that also binds to HLA class-II antigens. LAG-3 is a member of the immunoglobulin supergene family, and is expressed on activated T cells (Huard et al., 1994, Immunogenetics 39:213), NK cells (Triebel et al., 1990, J. Exp. Med. 171:1393-1405), regulatory T cells (Huang et al., 2004, Immunity 21:503-513; Camisaschi et al., 2010, J Immunol. 184:6545-6551; Gagliani et al., 2013, Nat Med 19:739-746), and plasmacytoid dendritic cells (DCs) (Workman et al., 2009, J Immunol 182:1885-1891). LAG-3 is a membrane protein encoded by a gene located on chromosome 12, and is structurally and genetically related to CD4. Similar to CD4, LAG-3 can interact with MHC class II molecules on the cell surface (Baixeras et al., 1992, J. Exp. Med. 176:327-337; Huard et al., 1996, Eur. J. Immunol. 26:1180-1186). It has been suggested that the direct binding of LAG-3 to MHC class II plays a role in down-regulating antigen-dependent stimulation of CD4+ T lymphocytes (Huard et al., 1994, Eur. J. Immunol. 24:3216-3221) and LAG-3 blockade has also been shown to reinvigorate CD8+ lymphocytes in both tumor or self-antigen (Gross et al., 2007, J Clin Invest. 117:3383-3392) and viral models (Blackburn et al., 2009, Nat. Immunol. 10:29-37). Further, the intra-cytoplasmic region of LAG-3 can interact with LAP (LAG-3-associated protein), which is a signal transduction molecule involved in the downregulation of the CD3/TCR activation pathway (Iouzalen et al., 2001, Eur. J. Immunol. 31:2885-2891). Moreover, CD4+CD25+ regulatory T cells (Treg) have been shown to express LAG-3 upon activation, which contributes to the suppressor activity of Treg cells (Huang, C. et al., 2004, Immunity 21:503-513). LAG-3 can also negatively regulate T cell homeostasis by Treg cells in both T cell-dependent and independent mechanisms (Workman, C. J. and Vignali, D. A., 2005, J. Immunol. 174:688-695).

LAG-3 has been shown to interact with MHC class II molecules (Huard et al., CD4/major histocompatibility complex class II interaction analyzed with CD4- and lymphocyte activation gene-3 (LAG-3)-Ig fusion proteins, Eur J Immunol. 1995 September; 25(9):2718-21).

Additionally, several kinases are known to be checkpoint inhibitors. For example, CHEK-1, CHEK-2, and A2aR.

CHEK-1 (also known as CHK 1 kinase, CHK1, and checkpoint kinase 1) is a ~54.4-kDa serine/threonine-protein kinase that is involved with checkpoint-mediated cell cycle arrest, and the activation of DNA repair in response to the DNA damage and/or unreplicated DNA.

CHEK-2 (also known as CHK2 kinase, CDS1, CHK2, HuCds1, LFS2, PP1425, RAD53, hCds1, and checkpoint kinase 2) is a ~60.9 kDa. serine/threonine-protein kinase involved in checkpoint-mediated cell cycle arrest, DNA-repair activation, and double-strand break-mediated apoptosis.

A2aR (also known as adenosine A2A receptor, ADORA2A, adenosine A2a receptor, A2aR, ADORA2, and RDC8) is a ~44.7-kDa multi-pass membrane receptor for adenosine and other ligands.

In various embodiments, the immunotherapeutic agent can comprise an antibody or an antigen binding fragment thereof. Within this definition, immune checkpoint inhibitors include bispecific antibodies and immune cell-engaging multivalent antibody/fusion protein/constructs known in the art. In some embodiments, immunotherapeutic agents which comprise bispecific antibodies may include bispecific antibodies that are bivalent and bind either the same epitope of the immune checkpoint molecule, two different epitopes of the same immune checkpoint molecule or different epitopes of two different immune checkpoints.

Persons of ordinary skill in the art can implement several bispecific antibody formats known in the field to target one or more of CTLA4, PD1, PD-L1 TIM-3, LAG-3, various B-7 ligands, B7H3, B7H4, CHK 1 and CHK2 kinases, BTLA, A2aR, OX40, 41BB, LIGHT, CD40, GITR, TGF-beta, SIRP-alpha, TIGIT, VSIG8, SIGLEC7, SIGLEC9, ICOS, FAS, BTNL2 and other for use in the combination described herein.

In various embodiments, the immunotherapeutic agent can include am immune cell-engaging multivalent antibody/fusion protein/construct.

In an embodiment of the disclosure, the checkpoint inhibitor, in combination with a compound of Formula I', is used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression.

In a further embodiment of the disclosure, there is provided a combination therapy for treating cancer, comprising a compound of Formula I' and blockade of checkpoint inhibitors with the potential to elicit potent and durable immune responses with enhanced therapeutic benefit and more manageable toxicity.

In a further embodiment of the disclosure, there is provided a combination therapy for treating cancer, comprising a compound of Formula I' and an immune checkpoint inhibitor. In an embodiment of the disclosure is provided a method for treating cancer and/or preventing the establishment of metastases by employing a checkpoint inhibitor which act synergistically with a compound of Formula I'.

In further embodiments, methods of the disclosure include, one or more of the following: 1) reducing or inhibiting growth, proliferation, mobility or invasiveness of tumor or cancer cells that potentially or do develop metastases, 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established, 4) reducing or inhibiting formation or establishment of additional metastasis after the metastasis has been formed or established, 5) prolonged overall survival, 6) prolonged progression free survival, or 7) disease stabilization.

In an embodiment of the disclosure, administration of the immunotherapeutic agent, in combination therapy with a compound of Formula I', provides a detectable or measurable improvement in a condition of a given subject, such as alleviating or ameliorating one or more adverse (physical) symptoms or consequences associated with the presence of a cell proliferative or cellular hyperproliferative disorder, neoplasia, tumor or cancer, or metastasis, i e., a therapeutic benefit or a beneficial effect.

A therapeutic benefit or beneficial effect is any objective or subjective, transient, temporary, or long-term improvement in the condition or pathology, or a reduction in onset, severity, duration or frequency of adverse symptom associated with or caused by cell proliferation or a cellular hyperproliferative disorder such as a neoplasia, tumor or cancer, or metastasis. It may lead to improved survival. A satisfactory clinical endpoint of a treatment method in accordance with the disclosure is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumor or cancer, or metastasis. A therapeutic benefit or improvement therefore may be, but is not limited to destruction of target proliferating cells (e.g., neoplasia, tumor or cancer, or metastasis) or ablation of one or more, most or all pathologies, adverse symptoms or complications associated with or caused by cell proliferation or the cellular hyperproliferative disorder such as a neoplasia, tumor or cancer, or metastasis. However, a therapeutic benefit or improvement need not be a cure or complete destruction of all target proliferating cells (e.g., neoplasia, tumor or cancer, or metastasis) or ablation of all pathologies, adverse symptoms or complications associated with or caused by cell proliferation or the cellular hyperproliferative disorder such as a neoplasia, tumor or cancer, or metastasis. For example, partial destruction of a tumor or cancer cell mass, or a stabilization of the tumor or cancer mass, size or cell numbers by inhibiting progression or worsening of the tumor or cancer, can reduce mortality and prolong lifespan even if only for a few days, weeks or months, even though a portion or the bulk of the tumor or cancer mass, size or cells remain.

Specific non-limiting examples of therapeutic benefit include a reduction in neoplasia, tumor or cancer, or metastasis volume (size or cell mass) or numbers of cells, inhibiting or preventing an increase in neoplasia, tumor or cancer volume (e.g., stabilizing), slowing or inhibiting neoplasia, tumor or cancer progression, worsening or metastasis, or inhibiting neoplasia, tumor or cancer proliferation, growth or metastasis.

In an embodiment of the disclosure, administration of the immunotherapeutic agent, in combination therapy with a compound of Formula I', provides a detectable or measurable improvement or overall response according to the irRC (as derived from time-point response assessments and based on tumor burden), including one of more of the following: (i) irCR—complete disappearance of all lesions, whether measurable or not, and no new lesions (confirmation by a repeat, consecutive assessment no less than 4 weeks from the date first documented), (ii) irPR—decrease in tumor burden .gtoreq.50% relative to baseline (confirmed by a consecutive assessment at least 4 weeks after first documentation).

Optionally, any method described herein may not take effect immediately. For example, treatment may be followed by an increase in the neoplasia, tumor or cancer cell numbers or mass, but over time eventual stabilization or reduction in tumor cell mass, size or numbers of cells in a given subject may subsequently occur.

Additional adverse symptoms and complications associated with neoplasia, tumor, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of adverse symptom or complication associated with or caused by a cellular hyperproliferative disorder, an improvement in the subjects quality of life and/or well-being, such as increased energy, appetite, psychological well-being, are all particular non-limiting examples of therapeutic benefit.

A therapeutic benefit or improvement therefore can also include a subjective improvement in the quality of life of a treated subject. In additional embodiment, a method prolongs or extends lifespan (survival) of the subject. In a further embodiment, a method improves the quality of life of the subject.

In one embodiment, administration of the immunotherapeutic agent, in combination therapy with a compound of Formula I', results in a clinically relevant improvement in one or more markers of disease status and progression selected from one or more of the following: (i): overall survival, (ii): progression-free survival, (iii): overall response rate, (iv): reduction in metastatic disease, (v): circulating levels of tumor antigens such as carbohydrate antigen 19.9 (CA19.9) and carcinoembryonic antigen (CEA) or others depending on tumor, (vii) nutritional status (weight, appetite, serum albumin), (viii): pain control or analgesic use, (ix): CRP/albumin ratio.

Treatment with a compound of Formula I' in combination with an immunotherapeutic agent gives rise to more complex immunity including not only the development of innate immunity and type-1 immunity, but also immunoregulation which more efficiently restores appropriate immune functions.

In various exemplary methods, a checkpoint inhibitor antibody (monoclonal or polyclonal, bispecific, trispecific, or an immune cell-engaging multivalent antibody/fusion protein/construct) directed to a checkpoint molecule of interest (e.g., PD-1) may be sequenced and the polynucleotide sequence may then be cloned into a vector for expression or propagation. The sequence encoding the antibody or antigen-binding fragment thereof of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, methods for producing the recombinant antibodies can include the steps of culturing a host cell containing isolated nucleic acid(s) encoding the antibodies of the present disclosure. Methods for culturing a host cell containing isolated nucleic acid(s) encoding the antibodies of the present disclosure can be done in a variety of ways, depending on the nature of the antibody. In some embodiments, in the case where the antibodies of the disclosure are full length traditional antibodies, for example, a heavy chain variable region and a light chain variable region under conditions such that an antibody is produced and can be isolated.

In general, nucleic acids are provided that encode the antibodies or antigen-binding fragments thereof of the present disclosure. Such polynucleotides encode for both the variable and constant regions of each of the heavy and light chains, although other combinations are also contemplated by the present disclosure. The present disclosure also contemplates oligonucleotide fragments derived from the disclosed polynucleotides and nucleic acid sequences complementary to these polynucleotides.

The polynucleotides can be in the form of RNA, DNA, cDNA, genomic DNA, nucleic acid analogs, and synthetic DNA. The DNA may be double-stranded or single-stranded, and if single stranded, may be the coding (sense) strand or non-coding (anti-sense) strand. The coding sequence that encodes the polypeptide may be identical to the coding sequence or may be a different coding sequence, which sequence, as a result of the redundancy or degeneracy of the genetic code, encodes the same polypeptides.

In some embodiments, nucleic acid(s) encoding the antibodies of the present disclosure are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, and the like) or other components (selection genes, and the like), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, and the like.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, and the like), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, Va. USA. including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

Exemplary and illustrative recombinant methods for antibody molecular biology, expression, purification, and screening are described, for example, in Antibody Engineering, edited by Kontermann & Dubel, Springer, Heidelberg, 2001 and 2010 Hayhurst & Georgiou, 2001, Curr. Opin. Chem. Biol. 5:683-689; Maynard & Georgiou, 2000, Annu. Rev. Biomed. Eng. 2:339-76; and Morrison, S. (1985)

Science 229:1202, the disclosures of which are incorporated herein by reference in their entireties.

In various embodiments, the polynucleotide sequence encoding the selected variable heavy and light chains may be used for genetic manipulation to humanize the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Immune checkpoint modulator antibodies of the present disclosure can be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or in yeast cells (e.g. *Pichia pastoris* or *Saccharomyces cerevisiae*. Methods for expressing antibodies recombinantly in plants or yeast have been disclosed. See, for example, Peeters, et al. Vaccine 19:2756, 2001; Lonberg, N. and D. Huszar Int. Rev. Immunol 13:65, 1995; and Horwitz, A. H. et al., Proc. Natl. Acad. Sci. 85:8678-8682; the disclosures of which are hereby incorporated by reference in their entireties. Methods for making derivatives of antibodies, e.g., domain, single chain, and the like are known in the art.

Immunoassays and flow cytometry sorting techniques such as fluorescence activated cell sorting (FACS) can also be employed to isolate antibodies that are specific for checkpoint molecules.

In some embodiments, a polynucleotide comprises a sequence encoding the heavy chain and/or the light chain variable regions of the checkpoint inhibitor antibody or antigen-binding fragment thereof of the present disclosure. The sequence encoding the antibody or antigen-binding fragment thereof of interest may be maintained in a vector in a host cell and the host cell can then be expanded and frozen for future use. Vectors (including expression vectors) and host cells are further described herein.

The disclosure includes affinity matured checkpoint modulator antibodies. For example, affinity matured antibodies can be produced by procedures known in the art (Marks et al., 1992, Bio/Technology, 10:779-783; Barbas et al., 1994, Proc Nat. Acad. Sci. USA 91:3809-3813. One way of characterizing a CDR of an antibody and/or altering (such as improving) the binding affinity of a polypeptide, such as an antibody, termed "library scanning mutagenesis". An exemplary method for providing affinity matures antibodies and antigen-binding fragments can include replacing one or more amino acid positions in the CDR with two or more (such as 3, 4, 5, 6, 7, 8, 9, 10, 11, 12, 13, 14, 15, 16, 17, 18, 19, or 20) amino acids using art recognized methods. a library of clones are generated, each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a KD of about 10 nM or lower. The library of clones can then be recombinantly introduced into a selection construct using any method known in the art for selection, including phage display, yeast display, and ribosome display.

The antibodies may also be modified, e.g., in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the KD of the antibody directed to a checkpoint molecule, to increase or decrease kon or to alter the binding specificity of the antibody. Techniques in site-directed mutagenesis are well-known in the art. See, e.g., Sambrook et al. and Ausubel et al.

Pharmaceutical compositions containing a compound of Formula I' according to the present disclosure will comprise an effective amount of a compound of Formula I', an immunotherapeutic agent, and/or both, typically dispersed in a pharmaceutically acceptable carrier. The phrases "pharmaceutically or pharmacologically acceptable" refers to molecular entities and compositions that do not produce adverse, allergic or other untoward reaction when administered to animal, such as, for example, a human, as appropriate. The preparation of an pharmaceutical composition that contains a compound of Formula I' will be known to those of skill in the art in light of the present disclosure, as exemplified by Remington's Pharmaceutical Sciences, 18th Ed. Mack Printing Company, 1990, Moreover, for animal (e.g., human) administration, it will be understood that preparations should meet sterility, pyrogenicity, general safety and purity standards. A specific example of a pharmacologically acceptable carrier for a combination compositions, containing a compound of Formula I' in admixture with an immunotherapeutic agent as described herein is borate buffer or sterile saline solution (0.9% NaCl).

Formulations of the an immunotherapeutic agent, for example an immune checkpoint modulator antibody used in accordance with the present disclosure can be prepared for storage by mixing an antibody having the desired degree of purity with optional pharmaceutically acceptable carriers, excipients or stabilizers as amply described and illustrated in Remington's Pharmaceutical Sciences 16th edition, Osol, A. Ed. [1980], in the form of lyophilized formulations or aqueous solutions and/or suspensions. Acceptable carriers, excipients, buffers or stabilizers are nontoxic to recipients at the dosages and concentrations employed, and include suitable aqueous and/or non-aqueous excipients that may be employed in the pharmaceutical compositions of the disclosure, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, buffers such as phosphate, citrate, and other organic acids. Antioxidants may be included, for example, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like; preservatives (such as octade-cyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues). Other exemplary pharmaceutically acceptable excipients may include polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In one illustrative embodiment, the pharmaceutical compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. In some embodiments, the checkpoint inhibitor antibodies or antigen-binding fragments thereof of the present disclosure are formulated for and can be lyophilized for storage and reconstituted in a suitable excipient prior to use according to art-known lyophilization and reconstitution techniques. In one exemplary pharmaceutical composition containing one or more checkpoint inhibitor antibodies or antigen-binding fragment thereof, the composition is formulated as a sterile, preservative-free solution of one or more checkpoint inhibitor antibodies or antigen-binding fragment thereof for intravenous or subcutaneous administration. The formulation can be supplied as either a single-use, prefilled pen, as a single-use, for example containing about 1 mL prefilled glass syringe, or as a single-use institutional use vial. Preferably, the pharmaceutical composition containing the checkpoint inhibitor antibody or antigen-binding fragment thereof is clear and colorless, with a pH of about 6.9-5.0, preferably a pH of 6.5-5.0, and even more preferably a pH ranging from about 6.0 to about 5.0. In various embodiments, the formulations comprising the pharmaceutical compositions can contain from about 500 mg to about 10 mg, or from about 400 mg to about 20 mg, or from about 300 mg to about 30 mg or from about 200 mg to about 50 mg of the checkpoint inhibitor antibody or antigen-binding fragment thereof per mL of solution when reconstituted and administered to the subject. Exemplary injection or infusion excipients can include mannitol, citric acid monohydrate, dibasic sodium phosphate dihydrate, monobasic sodium phosphate dihydrate, polysorbate 80, sodium chloride, sodium citrate and water for parenteral administration, for example, intravenously, intramuscularly, intraperitoneally, or subcutaneous administration.

In another exemplary embodiment, one or more immunotherapeutic agents, or an antigen-binding fragment thereof is formulated for intravenous or subcutaneous administration as a sterile aqueous solution containing 1-75 mg/mL, or more preferably, about 5-60 mg/mL, or yet more preferably, about 10-50 mg/mL, or even more preferably, about 10-40 mg/mL of antibody, with sodium acetate, polysorbate 80, and sodium chloride at a pH ranging from about 5 to 6. Preferably, the intravenous or subcutaneous formulation is a sterile aqueous solution containing 5, 10, 15, 20, 25, 30, 35, 40, 45, or 50 mg/mL of the immunotherapeutic agent, for example, an immune checkpoint inhibitor antibody or an antigen-binding fragment thereof, with 20 mM sodium acetate, 0.2 mg/mL polysorbate 80, and 140 mM sodium chloride at pH 5.5. Further, a solution comprising a checkpoint inhibitor antibody or an antigen-binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 5-500 mg of an immunotherapeutic agent or antigen-binding fragment thereof of the present disclosure, 10 mM histidine, 5% sucrose, and 0.01% polysorbate 80 at pH 5.8, with or without a compound of Formula I'. This composition may be provided as a lyophilized powder. When the powder is reconstituted at full volume, the composition retains the same formulation. Alternatively, the powder may be reconstituted at half volume, in which case the composition comprises 10-500 mg of an immunotherapeutic agent or antigen-binding fragment thereof of the present disclosure, 20 mM histidine, 10% sucrose, and 0.02% polysorbate 80 at pH 5.8.

In one embodiment, part of the dose is administered by an intravenous bolus and the rest by infusion of the immunotherapeutic agent formulation. For example, from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof, may be given as a bolus, and the rest of the antibody dose may be administered by intravenous injection. A predetermined dose of the immunotherapeutic agent, or antigen-binding fragment thereof, may be administered, for example, over a period of an hour to two hours to five hours.

In a further embodiment, part of the dose is administered by a subcutaneous injection and/or infusion in the form of a bolus and the rest by infusion of the immunotherapeutic agent formulation. In some exemplary doses, the immunotherapeutic agent formulation can be administered subcutaneously in a dose ranging from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof. In some embodiments the dose may be given as a bolus, and the rest of the immunotherapeutic agent dose may be administered by subcutaneous or intravenous injection. A predetermined dose of the immunotherapeutic agent, or antigen-binding fragment thereof, may be administered, for example, over a period of an hour to two hours to five hours.

The formulation herein may also contain more than one active compound as necessary for the particular indication being treated, preferably those with complementary activities that do not adversely affect each other. For example, it may be desirable to provide one or more immunotherapeutic agents with other specificities. Alternatively, or in addition, the composition may comprise an anti-inflammatory agent, a chemotherapeutic agent, a cytotoxic agent, a cytokine, a growth inhibitory agent and/or a small molecule antagonist. Such molecules are suitably present in combination in amounts that are effective for the purpose intended.

The formulations to be used for in vivo administration should be sterile, or nearly so. This is readily accomplished by filtration through sterile filtration membranes.

In various embodiments, illustrative formulations of the pharmaceutical compositions described herein can be prepared using methods widely known in the field of pharmaceutical formulations. In general, such preparatory methods can include the step of bringing the active ingredient into association with a carrier or one or more other accessory ingredients, and then, if desirable, packaging the product into a desired single- or multi-dose unit.

In some embodiments, the composition comprising a compound of Formula I' can be also delivered in a vesicle, and the immunotherapeutic agent can be delivered in the same liposome formulation, or in a separate formulation that is compatible with the liposomal formulation containing the compound of Formula I', In some illustrative examples, a liposome containing one or more liposomal surface moieties for example, polyethylene glycol, antibodies and antibody fragments thereof that target a desired tumor surface antigen, receptor, growth factor, glycoprotein, glycolipid or neoantigen, which are selectively transported into specific cells or organs, thus enhance targeted drug delivery.

In another embodiment, a compound of Formula I' can be delivered in a vesicle, in particular a liposome (see Langer, Science 249:1527-1533 (1990); Treat et al., in LIPOSOMES IN THE THERAPY OF INFECTIOUS DISEASE AND CANCER, Lopez-Berestein and Fidler (eds.), Liss, N.Y., pp. 353-365 (1989); Lopez-Berestein, ibid., pp. 317-327; see generally ibid.).

In yet another embodiment, a compound of Formula I', or the composition containing the combination, or a composition containing the immunotherapeutic agent, can be delivered in a controlled release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, controlled release of the compound of Formula I' can comprise polymeric materials to provide sustained, intermediate, pulsatile, or alternate release (see MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). Other controlled-release systems discussed in the review by Langer (Science 249:1527-1533 (1990)) can be used.

The optimum concentration of the active ingredient(s) in the chosen medium can be determined empirically, according to procedures well known to the skilled artisan, and will depend on the ultimate pharmaceutical formulation desired and the use to be employed.

The present disclosure also provides a pharmaceutical pack or kit comprising one or more containers filled with one or more of the ingredients of the pharmaceutical compositions of the disclosure, which at minimum will include a compound of Formula I' and one or more checkpoint inhibitor antibodies or antigen-binding fragment thereof as described herein. In other embodiments, the kit may contain one or more further containers providing a pharmaceutically acceptable excipient, for example a diluent. In one embodiment a kit may comprise at least one container, wherein the container can include a compound of Formula I', a checkpoint inhibitor antibody or an antigen-binding fragment thereof of the present disclosure. The kit may also include a set of instructions for preparing and administering the final pharmaceutical composition to the subject in need thereof, for the treatment of a checkpoint molecule-mediated disease or disorder.

Some embodiments of the present disclosure, the immunotherapeutic agent is a population of immune cells, which can be administered in combination with a compound of Formula I' to treat a subject with cancer. In some embodiments, the immunotherapeutic agent is a population of immune cells, such as leukocytes (nucleated white blood cells), comprising (e.g., expressing) a receptor that binds to an antigen of interest. A leukocyte of the present disclosure may be, for example, a neutrophil, eosinophil, basophil, lymphocyte or a monocyte. In some embodiments, a leukocyte is a lymphocyte. Examples of lymphocytes include T cells, B cells, Natural Killer (NK) cells or NKT cells. In some embodiments, a T-cell is a CD4+ Th (T helper) cell, a CD8+ cytotoxic T cell, a γδT cell or a regulatory (suppressor) T cell. In some embodiments, an immune cell is a dendritic cell.

Immune cells of the present disclosure, in some embodiments, are genetically engineered to express an antigen-binding receptor. A cell is considered "engineered" if it contains an engineered (exogenous) nucleic acid. Engineered nucleic acids of the present disclosure may be introduced into a cell by any known (e.g., conventional) method. For example, an engineered nucleic acid may be introduced into a cell by electroporation (see, e.g., Heiser W. C. Transcription Factor Protocols: Methods in Molecular Biology™ 2000; 130: 117-134), chemical (e.g., calcium phosphate or lipid), transfection (see, e.g., Lewis W. H., et al., Somatic Cell Genet. 1980 May; 6(3): 333-47; Chen C., et al., Mol Cell Biol. 1987 August; 7(8): 2745-2752), fusion with bacterial protoplasts containing recombinant plasmids (see, e.g., Schaffner W. Proc Natl Acad Sci USA. 1980 April; 77(4): 2163-7), microinjection of purified DNA directly into the nucleus of the cell (see, e.g., Capecchi M. R. Cell. 1980 November; 22(2 Pt 2): 479-88), or retrovirus transduction.

Some aspects of the present disclosure provide an "adoptive cell" approach, which involves isolating immune cells (e.g., T-cells) from a subject with cancer, genetically engineering the immune cells (e.g., to express an antigen-binding receptor, such as a chimeric antigen receptor), expanding the cells ex vivo, and then re-introducing the immune cells into the subject. This method results in a greater number of engineered immune cells in the subject relative to what could be achieved by conventional gene delivery and vaccination methods. In some embodiments, immune cells are isolated from a subject, expanded ex vivo without genetic modification, and then re-introduced into the subject.

Immune cells of the present disclosure comprise receptors that bind to antigens, such as an antigen encoded by an exogenously delivered nucleic acid, as provided herein. In some embodiments, a leukocyte is modified (e.g., genetically modified) to express a receptor that binds to an antigen. The receptor may be, in some embodiments, a naturally-occurring antigen receptor (normally expressed on the immune cell), recombinant antigen receptor (not normally expressed on the immune cell) or a chimeric antigen receptor (CAR). Naturally-occurring and recombinant antigen receptors encompassed by the present disclosure include T cell receptors, B cell receptors, NK cell receptors, NKT cell receptors and dendritic cell receptors. A “chimeric antigen receptor” refers to an artificial immune cell receptor that is engineered to recognize and bind to an antigen expressed by tumor cells. Generally, a CAR is designed for a T cell and is a chimera of a signaling domain of the T-cell receptor (TcR) complex and an antigen-recognizing domain (e.g., a single chain fragment (scFv) of an antibody) (Enblad et al., Human Gene Therapy. 2015; 26(8):498-505), the disclosure of which is incorporated herein by reference in its entirety.

In some embodiments, an antigen binding receptor is a chimeric antigen receptor (CAR). A T cell that expressed a CAR is referred to as a “CAR T cell.” A CAR T cell receptor, in some embodiments, comprises a signaling domain of the T-cell receptor (TcR) complex and an antigen-recognizing domain (e.g., a single chain fragment (scFv) of an antibody) (Enblad et al., Human Gene Therapy. 2015; 26(8):498-505) the disclosure of which is incorporated herein by reference in its entirety.

There are four generations of CARs, each of which contains different components. First generation CARs join an antibody-derived scFv to the CD3zeta (zeta. or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TcR CD3-zeta chain. Third-generation costimulatory domains may include, e.g., a combination of CD3z, CD27, CD28, 4-1BB, ICOS, or OX40. CARs, in some embodiments, contain an ectodomain (e.g., CD3), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26):4017-4023; Kakarla and Gottschalk, Cancer J. 2014; 20(2):151-155) the disclosure of which is incorporated herein by reference in its entirety.

In some embodiments, the chimeric antigen receptor (CAR) is a T-cell redirected for universal cytokine killing (TRUCK), also known as a fourth generation CAR. TRUCKs are CAR-redirected T-cells used as vehicles to produce and release a transgenic cytokine that accumulates in the targeted tissue, e.g., a targeted tumor tissue. The transgenic cytokine is released upon CAR engagement of the target. TRUCK cells may deposit a variety of therapeutic cytokines in the target. This may result in therapeutic concentrations at the targeted site and avoid systemic toxicity.

CARs typically differ in their functional properties. The CD3zeta signaling domain of the T-cell receptor, when engaged, will activate and induce proliferation of T-cells but can lead to anergy (a lack of reaction by the body’s defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency. Fourth generation CARs are additionally modified with a constitutive or inducible expression cassette for a transgenic cytokine, which is released by the CAR T-cell to modulate the T-cell response. See, for example, Enblad et al., Human Gene Therapy. 2015; 26(8):498-505; Chmielewski and Hinrich, Expert Opinion on Biological Therapy. 2015; 15(8): 1145-1154 the disclosures of which are incorporated herein by reference in their entireties.

In some embodiments, an illustrative immunotherapeutic agent is a first generation chimeric antigen receptor CAR. In some embodiments, a chimeric antigen receptor is a third generation CAR. In some embodiments, a chimeric antigen receptor is a second generation CAR. In some embodiments, a chimeric antigen receptor is a third generation CAR. In some embodiments, the chimeric antigen receptor is a fourth generation CAR or a T-cell redirected for universal cytokine killing (TRUCK).

In some embodiments, a chimeric antigen receptor (CAR) comprises an extracellular domain comprising an antigen binding domain, a transmembrane domain, and a cytoplasmic domain. In some embodiments, a CAR is fully human. In some embodiments, the antigen binding domain of a CAR is specific for one or more antigens. In some embodiments, a “spacer” domain or “hinge” domain is located between an extracellular domain (comprising the antigen binding domain) and a transmembrane domain of a CAR, or between a cytoplasmic domain and a transmembrane domain of the CAR. A “spacer domain” refers to any oligopeptide or polypeptide that functions to link the transmembrane domain to the extracellular domain and/or the cytoplasmic domain in the polypeptide chain. A “hinge domain” refers to any oligopeptide or polypeptide that functions to provide flexibility to the CAR, or domains thereof, or to prevent steric hindrance of the CAR, or domains thereof. In some embodiments, a spacer domain or hinge domain may comprise up to 300 amino acids (e.g., 10 to 100 amino acids, or 5 to 20 amino acids). In some embodiments, one or more spacer domain(s) may be included in other regions of a CAR.

In some embodiments, a CAR of the disclosure comprises an antigen binding domain, such as a single chain FIT (scFv) specific for a tumor antigen. The choice of binding domain depends upon the type and number of ligands that define the surface of a target cell. For example, the antigen binding domain may be chosen to recognize a ligand that acts as a cell surface marker on target cells associated with a particular disease state, such as cancer or an autoimmune disease. Thus, examples of cell surface markers that may act as ligands for the antigen binding domain in the CAR of the present disclosure include those associated with cancer cells and/or other forms of diseased cells. In some embodiments, a CAR is engineered to target a tumor antigen of interest by way of engineering a desired antigen binding domain that specifically binds to an antigen on a tumor cell encoded by an engineered nucleic acid, as provided herein.

An antigen binding domain (e.g., an scFv) that “specifically binds” to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antigen binding domain (e.g., an scFv) that specifically binds to a first target antigen may or may not specifically bind to a second target antigen. As such, "specific binding" does not necessarily require (although it can include) exclusive binding.

In some embodiments, immune cells expressing a CAR are genetically modified to recognize multiple targets or antigens, which permits the recognition of unique target or antigen expression patterns on tumor cells. Examples of CARs that can bind multiple targets include: "split signal CARs," which limit complete immune cell activation to tumors expressing multiple antigens; "tandem CARs" (TanCARs), which contain ectodomains having two scFvs; and "universal ectodomain CARs," which incorporate avidin or a fluorescein isothiocyanate (FITC)-specific scFv to recognize tumor cells that have been incubated with tagged monoclonal antibodies (Mabs).

A CAR is considered "bispecific" if it recognizes two distinct antigens (has two distinct antigen recognition domains). In some embodiments, a bispecific CAR is comprised of two distinct antigen recognition domains present in tandem on a single transgenic receptor (referred to as a TanCAR; see, e.g., Grada Z et al. Molecular Therapy Nucleic Acids 2013; 2:e105, incorporated herein by reference in its entirety). Thus, methods, in some embodiments, comprise delivering to a tumor a combination comprising a compound of Formula I' and an immunotherapeutic agent, wherein the immunotherapeutic agent is an engineered nucleic acid that encodes an antigen, or delivering to a tumor an engineered nucleic acid that induces expression of a self-antigen, and delivering to the tumor an immune cell expressing a bispecific CAR that binds to two antigens, one of which is encoded by the engineered nucleic acid.

In some embodiments, a CAR is an antigen-specific inhibitory CAR (iCAR), which may be used, for example, to avoid off-tumor toxicity (Fedorov, V D et al. Sci. Transl. Med. published online Dec. 11, 2013, incorporated herein by reference in its entirety). iCARs contain an antigen-specific inhibitory receptor, for example, to block nonspecific immunosuppression, which may result from extra tumor target expression. iCARs may be based, for example, on inhibitory molecules CTLA-4 or PD-1. In some embodiments, these iCARs block T cell responses from T cells activated by either their endogenous T cell receptor or an activating CAR. In some embodiments, this inhibiting effect is temporary.

In some embodiments, CARs may be used in adoptive cell transfer, wherein immune cells are removed from a subject and modified so that they express receptors specific to an antigen, e.g., a tumor-specific antigen. The modified immune cells, which may then recognize and kill the cancer cells, are reintroduced into the subject (Pule, et al., Cytotherapy. 2003; 5(3): 211-226; Maude et al., Blood. 2015; 125(26): 4017-4023, each of which is incorporated herein by reference in their entireties).

According to other aspects of the disclosure, the tumor antigenic component in the vaccine of the invention is any natural or synthetic tumor-associated protein or peptide or combination of tumor-associated proteins and/or peptides or glycoproteins or glycopeptides. In still yet other aspects, the antigenic component can be patient-specific or common to many or most patients with a particular type of cancer. According to one aspect, the antigenic component consists of a cell lysate derived from tumor tissue removed from the patient being treated. In another aspect, the lysate can be engineered or synthesized from exosomes derived from tumor tissue. In yet another aspect, the antigenic component consists of a cell lysate derived from tumor tissue extracted from one or more unrelated individuals or from tumor-cell lines.

In various embodiments, an illustrative immunotherapeutic agent comprises one or more cancer vaccines, for use in combination with a compound of Formula I'. The tumor-associated antigen component of the vaccine may be manufactured by any of a variety of well-known techniques. For individual protein components, the antigenic protein is isolated from tumor tissue or a tumor-cell line by standard chromatographic means such as high-pressure liquid chromatography or affinity chromatography or, alternatively, it is synthesized by standard recombinant DNA technology in a suitable expression system, such as *E. coli*, yeast or plants. The tumor-associated antigenic protein is then purified from the expression system by standard chromatographic means. In the case of peptide antigenic components, these are generally prepared by standard automated synthesis. Proteins and peptides can be modified by addition of amino acids, lipids and other agents to improve their incorporation into the delivery system of the vaccine (such as a multilamellar liposome). For a tumor-associated antigenic component derived from the patient's own tumor, or tumors from other individuals, or cell lines, the tumor tissue, or a single cell suspension derived from the tumor tissue, is typically homogenized in a suitable buffer. The homogenate can also be fractionated, such as by centrifugation, to isolate particular cellular components such as cell membranes or soluble material. The tumor material can be used directly or tumor-associated antigens can be extracted for incorporation in the vaccine using a buffer containing a low concentration of a suitable agent such as a detergent. An example of a suitable detergent for extracting antigenic proteins from tumor tissue, tumor cells, and tumor-cell membranes is diheptanoyl phosphatidylcholine. Exosomes derived from tumor tissue or tumor cells, whether autologous or heterologous to the patient, can be used for the antigenic component for incorporation in the vaccine or as a starting material for extraction of tumor-associated antigens.

In some embodiments of the present disclosure, a cancer vaccine, wherein the cancer vaccine includes at least one tumor-associated antigen, at least one immunostimulant, and optionally, at least one cell-based immunotherapeutic agent, in some embodiments, the immunostimulant component in the cancer vaccine of the disclosure is any Biological Response Modifier (BRM) with the ability to enhance the therapeutic cancer vaccine's effectiveness to induce humoral and cellular immune responses against cancer cells in a patient. According to one aspect, the immunostimulant is a cytokine or combination of cytokines. Examples of such cytokines include the interferons, such as IFN-gamma, the interleukins, such as IL-2, IL-15 and IL-23, the colony stimulating factors, such as M-CSF and GM-CSF, and tumor necrosis factor. According to another aspect, the immunostimulant component of the disclosed cancer vaccine includes one or more adjuvant-type immunostimulatory agents such as APC Toll-like Receptor agonists or costimulatory/cell adhesion membrane proteins, with or without immunostimulatory cytokines. Examples of Toll-like Receptor agonists include lipid A and CpG, and costimulatory/adhesion proteins such as CD80, CD86, and ICAM-1.

In some embodiments, the immunostimulant is selected from the group consisting of IFN-gamma (IFN-$\gamma$), IL-2, IL-15, IL-23, M-CSF, GM-CSF, tumor necrosis factor, lipid A, CpG, CD80, CD86, and ICAM-1, or combinations thereof. According to other aspects, the cell-based immunotherapeutic agent is selected from the group consisting of dendritic cells, tumor-infiltrating T lymphocytes, chimeric antigen receptor-modified T effector cells directed to the patient's tumor type, B lymphocytes, natural killer cells, bone marrow cells, and any other cell of a patient's immune system, or combinations thereof. In one aspect, the cancer vaccine immunostimulant includes one or more cytokines, such as interleukin 2 (IL-2), GM-CSF, M-CSF, and interferon-gamma (IFN-γ), one or more Toll-like Receptor agonists and/or adjuvants, such as monophosphoryl lipid A, lipid A, muramyl dipeptide (MDP) lipid conjugate and double stranded RNA, or one or more costimulatory membrane proteins and/or cell adhesion proteins, such CD80, CD86 and ICAM-1, or any combination of the above. In one aspect, the cancer vaccine includes an immunostimulant that is a cytokine selected from the group consisting of interleukin 2 (IL-2), GM-CSF, M-CSF, and interferon-gamma (IFN-γ). In another aspect, the cancer vaccine includes an immunostimulant that is a Toll-like Receptor agonist and/or adjuvant selected from the group consisting of monophosphoryl lipid A, lipid A, and muramyl dipeptide (MDP) lipid conjugate and double stranded RNA. In yet another aspect, the cancer vaccine includes an immunostimulant that is a costimulatory membrane protein and/or cell adhesion protein selected from the group consisting of CD80, CD86, and ICAM-1.

In various embodiments, an immunotherapeutic agent can include a cancer vaccine, wherein the cancer vaccine incorporates any tumor antigen that can be potentially used to construct a fusion protein according to the invention and particularly the following:

(a) cancer-testis antigens including NY-ESO-1, SSX2, SCP1 as well as RAGE, BAGE, GAGE and MAGE family polypeptides, for example, GAGE-1, GAGE-2, MAGE-1 MAGE-2, MAGE-3, MAGE-4, MAGE-5, MAGE-6, and MAGE-12, which can be used, for example, to address melanoma, lung, head and neck, NSCLC, breast, gastrointestinal, and bladder tumors; (b) mutated antigens, including p53, associated with various solid tumors, e.g., colorectal, lung, head and neck cancer; p21/Ras associated with, e.g., melanoma, pancreatic cancer and colorectal cancer; CDK4, associated with, e.g., melanoma; MUM1 associated with, e.g., melanoma; caspase-8 associated with, e.g., head and neck cancer; CIA 0205 associated with, e.g., bladder cancer; HLA-A2-R1701, beta catenin associated with, e.g., melanoma; TCR associated with, e.g., T-cell non-Hodgkin lymphoma; BCR-abl associated with, e.g., chronic myelogenous leukemia; triosephosphate isomerase; KIA 0205; CDC-27, and LDLR-FUT; (c) over-expressed antigens, including, Galectin 4 associated with, e.g., colorectal cancer; Galectin 9 associated with, e.g., Hodgkin's disease; proteinase 3 associated with, e.g., chronic myelogenous leukemia; WT 1 associated with, e.g., various leukemias; carbonic anhydrase associated with, e.g., renal cancer; aldolase A associated with, e.g., lung cancer; PRAME associated with, e.g., melanoma; HER-2/neu associated with, e.g., breast, colon, lung and ovarian cancer; mammaglobin, alpha-fetoprotein associated with, e.g., hepatoma; KSA associated with, e.g., colorectal cancer; gastrin associated with, e.g., pancreatic and gastric cancer; telomerase catalytic protein, MUC-1 associated with, e.g., breast and ovarian cancer; G-250 associated with, e.g., renal cell carcinoma; p53 associated with, e.g., breast, colon cancer; and carcinoembryonic antigen associated with, e.g., breast cancer, lung cancer, and cancers of the gastrointestinal tract such as colorectal cancer; (d) shared antigens, including melanoma-melanocyte differentiation antigens such as MART-1/Melan A; gp100; MC1R; melanocyte-stimulating hormone receptor; tyrosinase; tyrosinase related protein-1/TRP1 and tyrosinase related protein-2/TRP2 associated with, e.g., melanoma; (e) prostate associated antigens including PAP, PSA, PSMA, PSH-P1, PSM-P1, PSM-P2, associated with e.g., prostate cancer; (f) immunoglobulin idiotypes associated with myeloma and B cell lymphomas. In certain embodiments, the one or more TAA can be selected from pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotrophic virus antigens, TSP-180, p185erbB2, pl 80erbB-3, c-met, mn-23H1, TAG-72-4, CA 19-9, CA 72-4, CAM 17.1, NuMa, K-ras, pi 6, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS or any combinations thereof.

In some embodiments, cancer vaccines of the present disclosure for use in combination with a compound of Formula I' can include a tumor antigen comprising the entire amino acid sequence, a portion of it, or specific immunogenic epitopes of one of the following human proteins: TCTN1 (SEO ID NO. 1: Gene ID: ENSG00000204852), TCTN2 (SEO ID NO. 2; Gene ID: ENSG00000168778), TCTN3 (SEO ID NO. 3; Gene ID: ENSG000001 19977), HIGD2A (SEO ID NO. 4; Gene ID: ENSG00000146066), HIGD2B (SEO ID NO. 5; Gene ID: ENSG00000175202), C40RF32 (SEO ID NO. 6; Gene ID: ENSG00000174749), FAM62A (E-SYT1, SEO ID NO. 7; Gene ID: ENSG00000139641), COLEC 11 (SEO ID NO. 8; Gene ID: ENSG000001 18004), FSTL5 (SEO ID NO. 9; Gene ID: ENSG00000168843), FAM82A2 (SEQ ID NO. 10; Gene ID: ENSG00000137824), SCARA5 (SEO ID NO. 11; Gene ID: ENSG00000168079), VSTM1 (SEO ID NO. 12; Gene ID: ENSG00000189068), RNF5 (§ Q ID NO. 13; Gene ID: ENSG00000183574), UNQ6126 (SEO ID NO. 14; Gene ID: gi|169216088), DPY19L3 (SEO ID NO. 15; Gene ID: ENSG00000178904), SLC39A10 (§ Q ID NO. 16; gene ID: ENSG00000196950), GPR107 (SEO ID NO. 17; Gene ID: ENSG00000148358), COL20A1 (SEO ID NO. 18; Gene ID: ENSG00000101203), GLT25D2 (SEO ID NO. 19; Gene ID: ENSG00000198756), SYTL3 (SEO ID NO. 20; Gene ID: ENSG00000164674), DENND1B (SEO ID NO. 21; Gene ID: ENSG00000162701), C6orf98 (SEO ID NO. 22; Gene ID: EG: 387079), FAM69B (SEO ID NO. 23; Gene ID: ENSG00000165716), EMID1 (SEO ID NO. 24; Gene ID: OTTHUMG00000030824), KLRG2 (SEO ID NO. 25; GENE ID: ENSG00000188883), ERMP1 (SEO ID NO. 26; GENE ID: ENSG00000099219), VMO1 (SEO ID NO. 27; Gene ID: ENSG00000182853), C9orf46 (SEQ ID NO. 28; Gene ID: ENSG00000107020), F1137107 (SEO ID NO. 29; Gene ID: ENSG00000177990), YIPF2 (SEO ID NO. 30; Gene ID: ENSG00000130733), TRYX3 (SEQ ID NO. 31; PRSS58, ENSG00000258223.2), C14orf135 (SEO ID NO. 32; Gene ID: ENSG00000126773), ANGPTL7 (SEO ID NO. 33; Gene ID: ENSG00000171819), TPCN2 (SEO ID NO. 34; Gene ID: ENSG00000162341), C18orf19 (SEO ID NO. 35; Gene ID: ENSG00000177150), OLFML1 (SEO ID NO. 36; Gene ID: ENSG00000183801), LYPD4 (SEO ID NO. 37; Gene ID: ENSG00000101203), MEGF8 (SEO ID NO. 38; Gene ID: ENSG00000105429), F1142986 (SEO ID NO. 39; Gene ID: ENSG00000196460), SLC46A1 (SEO ID NO. 40; Gene ID: ENSG00000076351), FAM180A (SEO ID NO. 41; Gene ID: ENSG00000189320), CRISP-3 (SEO ID NO. 42; GENE ID: ENSG00000096006), or combinations thereof. These tumor antigens are disclosed in WO2010/086162, WO2010/086163, WO2011/051278, WO2011/051276, WO2011/051277, WO2011/051280, WO2011/051271, WO2011/135068, WO2014/198919, the content of which is herein incorporated by reference in their entireties.

In various embodiments, an illustrative immunotherapeutic agent may include an mRNA operable to encode any one or more of the aforementioned cancer antigens useful for synthesizing a cancer vaccine. In some illustrative embodiments, the mRNA based cancer vaccine may have one or more of the following properties: a) the mRNA encoding each cancer antigen is interspersed by cleavage sensitive sites; b) the mRNA encoding each cancer antigen is linked directly to one another without a linker; c) the mRNA encoding each cancer antigen is linked to one another with a single nucleotide linker; d) each cancer antigen comprises a 20-40 amino acids and includes a centrally located SNP mutation; e) at least 40% of the cancer antigens have a highest affinity for class I MHC molecules from the subject; f) at least 40% of the cancer antigens have a highest affinity for class II MHC molecules from the subject; g) at least 40% of the cancer antigens have a predicted binding affinity of IC>500 nM for HLA-A, HLA-B and/or DRB1; h) the mRNA encodes 1 to 15 cancer antigens; i) 10-60% of the cancer antigens have a binding affinity for class I MHC and 10-60% of the cancer antigens have a binding affinity for class II MHC; and/or j) the mRNA encoding the cancer antigens is arranged such that the cancer antigens are ordered to minimize pseudo-epitopes.

In various embodiments, the combination comprising a compound of Formula I' and a cancer vaccine immunotherapeutic agent as disclosed herein can be used to illicit an immune response in a subject against a cancer antigen. The method involves administering to the subject a RNA vaccine comprising at least one RNA polynucleotide having an open reading frame encoding at least one antigenic polypeptide or an immunogenic fragment thereof, thereby inducing in the subject an immune response specific to the antigenic polypeptide or an immunogenic fragment thereof, in combination with administering a compound of Formula I' either in the same composition or a separate composition, administered at the same time, or sequentially dosed, wherein the anti-antigenic polypeptide antibody titer in the subject is increased following vaccination relative to anti-antigenic polypeptide antibody titer in a subject vaccinated with a prophylactically effective dose of a traditional vaccine against the cancer. An “anti-antigenic polypeptide antibody” is a serum antibody the binds specifically to the antigenic polypeptide.

A prophylactically effective dose is a therapeutically effective dose that prevents advancement of cancer at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, and the like. In exemplary embodiments, a traditional vaccine is a vaccine that has achieved regulatory approval and/or is registered by a national drug regulatory body, for example the Food and Drug Administration (FDA) in the United States or the European Medicines Agency (EMA.)

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the cancer.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In preferred aspects, RNA vaccine immunotherapeutic agents of the present disclosure (e.g., mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, and the like.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.) In exemplary aspects of the invention, antigen-specific antibodies are measured in units of g/ml or are measured in units of IU/L (International Units per liter) or mIU/ml (milli International Units per ml). In exemplary embodiments of the invention, an efficacious vaccine produces >0.5 μg/mL, >0.1 μg/mL, >0.2 μg/mL, >0.35 μg/mL, >0.5 μg/mL, >1 μg/mL, >2 μg/mL, >5 μg/mL or >10 μg/mL. In exemplary embodiments of the invention, an efficacious vaccine produces >10 mIU/mL, >20 mIU/mL, >50 mIU/mL, >100 mIU/mL, >200 mIU/mL, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay. Also provided are nucleic acid vaccines comprising one or more RNA polynucleotides having an open reading frame encoding a first antigenic polypeptide or a concatemeric polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Immunotherapeutic agents comprising a nucleic acid vaccine comprising one or more RNA polynucleotides having an open reading frame comprising at least one chemical modification or optionally no nucleotide modification, the open reading frame encoding a first antigenic polypeptide or a concatemeric polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 μg and 400 μg of one or more RNA polynucleotides having an open reading frame comprising at least one chemical modification or optionally no nucleotide modification, the open reading frame encoding a first antigenic polypeptide or a concatemeric polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a tumor in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 μg/kg and 400 μg/kg of a nucleic acid vaccine comprising one or more RNA polynucleotides having an open reading frame encoding a first antigenic polypeptide or a concatemeric polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

In some embodiments, an illustrative immunotherapeutic agent can include one or more interfering RNAs that can be administered in combination with a compound of Formula I'. An “RNA interfering agent” as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi). Short interfering RNA" (siRNA), also referred to herein as “small interfering RNA” is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methyl cytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

Antigens which can be targeted for synthesizing a corresponding antisense RNA molecule can include any antigen that is specific for one or more tumors, for example, antigens exemplified above with reference to cancer vaccines.

In some embodiments, a combination of an immunotherapeutic agent and a compound of Formula I' can include a bispecific antibody immunotherapeutic agent. The bispecific antibody can include a protein construct having a first antigen binding moiety and a second antigen binding site that binds to a cytotoxic immune cell. The first antigen binding site can bind to a tumor antigen that is specifically being treated with the combination of the present invention. For example, the first antigen binding moiety may bind to a non-limiting example of tumor antigens selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin αVβ3, Integrin α5β1, MUC1, ERBB2, ERBB3, MET, IGF1R, EPHA3, TRAILR1, TRAILR2, RANKL, FAP and Tenascin among others. In some embodiments, the first antigen binding moiety has specificity to a protein or a peptide that is overexpressed on a tumor cell as compared to a corresponding non-tumor cell. In some embodiments, the first antigen binding moiety has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor.

The second antigen-binding moiety is any molecule that specifically binds to an antigen or protein or polypeptide expressed on the surface of a cytotoxic immune cell (a CIK cell). Exemplary non-limiting antigens expressed on the surface of the cytotoxic immune cells suitable for use with the present disclosure may include CD2, CD3, CD4, CD5, CD8, CD11a, CD11 b, CD14, CD16a, CD27, CD28, CD45, CD45RA, CD56, CD62L, the Fc receptor, LFA, LFA-1, TCRαβ, CCR7, macrophage inflammatory protein 1a, perforin, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In some embodiments, the second antigen binding moiety binds to CD3 of the cytotoxic immune cell, e.g., CIK cell. In some embodiments, the second antigen binding moiety binds to CD56 of the cytotoxic immune cell. In some embodiments, the second antigen binding moiety binds to the Fc receptor of the cytotoxic immune cell. In some embodiments, the Fc region of the bispecific antibody binds to the Fc receptor of the cytotoxic immune cell. In some embodiments, a second antigen-binding moiety is any molecule that specifically binds to an antigen expressed on the surface of a cytotoxic immune cell (e.g., a CIK cell). The second antigen binding moiety is specific for an antigen on a cytotoxic immune cell. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells. The second antigen binding moiety specifically binds to an antigen expressed on the surface of a cytotoxic immune cell. Exemplary non-limiting antigens expressed on the surface of the cytotoxic immune cells suitable for modulation with the present disclosure may include CD2, CD3, CD4, CD5, CD8, CD11a, CD11 b, CD14, CD16a, CD27, CD28, CD45, CD45RA, CD56, CD62L, the Fc receptor, LFA, LFA-1, TCRαβ, CCR7, macrophage inflammatory protein 1a, perforin, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In other embodiments, the bispecific antibody modulator is an activator of a costimulatory molecule (e.g., an OX40 agonist). In one embodiment, the OX40 agonist is a bispecific antibody molecule to OX40 and another tumor antigen or a costimulatory antigen. The OX40 agonist can be administered alone, or in combination with other immunomodulators, e.g., in combination with an inhibitor (for example an antibody construct) of PD-1, PD-L1, CTLA-4, CEACAM (e.g., CEACAM-1, -3 and/or -5), TIM-3 or LAG-3. In some embodiments, the anti-OX40 antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, an OX40 antibody molecule is administered in combination with an anti-PD-1 antibody molecule (e.g., an anti-PD-1 molecule as described herein). The OX40 antibody molecule and the anti-PD-1 antibody molecule may be in the form of separate antibody composition, or as a bispecific antibody molecule. In other embodiments, the OX40 agonist can be administered in combination with other costimulatory molecule, e.g., an agonist of GITR, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand. In some embodiments, the second antigen binding moiety binds to the Fc receptor on the cytotoxic immune cell, e.g., CIK cell.

In some embodiments, the bispecific antibody immunotherapeutic agent has specificities for a tumor antigen and a CIK cell, which brings the tumor antigen expressing tumor cell in close proximity of the CIK cell, leading to the elimination of the tumor cell through anti-tumor cytotoxicity of CIK cell. In some embodiments, the bispecific antibody has specificity for a tumor antigen but does not have specificity for a CIK cell, however, the Fc region of the bispecific antibody can bind to the Fc receptor of the CIK cell, which in turn brings the tumor cell in close proximity of the CIK cell, leading to the elimination of the tumor cell through anti-tumor cytotoxicity of CIK cell. In some embodiments, the bispecific antibody has specificity for a CIK cell but does not have specificity for tumor cell, however, the Fc region of the bispecific antibody can bind to the Fc receptor of the tumor cell, which in turn brings the tumor cell in close proximity of the CIK cell, leading to the elimination of the tumor cell through anti-tumor cytotoxicity of CIK cell.

In some embodiments, a combination of an immunotherapeutic agent and a compound of Formula I' can include an immune cell-engaging multivalent antibody/fusion protein/construct immunotherapeutic agent. In various embodiments, an exemplary immunotherapeutic agent can include immune cell-engaging multivalent antibody/fusion protein/construct which may comprise a recombinant structure, for example, all engineered antibodies that do not imitate the original IgG structure. Here, different strategies to multimerize antibody fragments are utilized. For example, shortening the peptide linker between the V domains forces the scFv to self-associate into a dimer (diabody; 55 kDa). Bispecific diabodies are formed by the noncovalent association of two VHA-VLB and VHB-VLA fragments expressed in the same cell. This leads to the formation of heterodimers with two different binding sites. Single-chain diabodies (sc-diabodies) are bispecific molecules where the VHA-VLB and VHB-VLA fragments are linked together by an additional third linker. Tandem-diabodies (Tandabs) are tetravalent bispecific antibodies generated by two scDiabodies.

Also included are the di-diabodies known in the art. This 130-kDa molecule is formed by the fusion of a diabody to the N-terminus of the CH3 domain of an IgG, resulting in an IgG-like structure. Further diabody derivatives are the triabody and the tetra-body, which fold into trimeric and tetrameric fragments by shortening the linker to <5 or 0-2 residues. Also exemplified are $(scFv)_2$ constructs known as 'bispecific T cell engager' (BITE). BITEs are bispecific single-chain antibodies consisting of two scFv antibody fragments, joined via a flexible linker, that are directed against a surface antigen on target cells and CD3 on T cells. Also exemplified are bivalent (Fab)2 and trivalent (Fab)3 antibody formats. Also exemplified are minibodies and trimerbodies generated from scFvs. Exemplary constructs useful to target tumor antigens as can include one or more of: Diabody, Single-chain (sc)-diabody (scFv)2, Minianti-body, Minibody, Barnase-barstar, scFv-Fc, sc(Fab)2, Trimeric antibody constructs, Triabody antibody constructs, Trimerbody antibody constructs, Tribody antibody constructs, Collabody antibody constructs, (scFv-TNFa)3, F(ab) 3/DNL. In each of these exemplified constructs, at least one binding moiety may bind to an antigen or protein or polypeptide expressed on the surface of a cytotoxic immune cell, and at least one binding moiety will bind specifically to an antigen on a cytotoxic immune cell. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells.

In some embodiments, a combination of an immunotherapeutic agent and a compound of Formula I' can include a radioconjugate immunotherapeutic agent.

In various embodiments, a radioconjugate is a small molecule or large molecule (herein referred to as a "cell targeting agent"), for example and polypeptide, an antibody or an antibody fragment thereof, that is coupled to or otherwise affixed to a radionuclide, or a plurality of radionuclides, such that the binding of the radioconjugate to its target (a protein or molecule on or in a cancer cell), will lead to the death or morbidity of said cancer cell. In various embodiments, the radioconjugate can be a cell targeting agent labelled with a radionuclide, or the cell targeting agent may be coupled or otherwise affixed to a particle, or microparticle, or nanoparticle containing a plurality of radionuclides, wherein the radionuclides are the same or different. Methods for synthesizing radioconjugates are known in the art, and may include the class of immunoglobulin or antigen binding parts thereof, that are conjugated to a toxic radionuclide.

In some embodiments, the molecule that binds to the cancer cell can be known as a "cell targeting agent". As used herein, an exemplary cell targeting agent can allow the drug-containing nanoparticles or radionuclide to target the specific types of cells of interest. Examples of cell targeting agents include, but are not limited to, small molecules (e.g., folate, adenosine, purine) and large molecule (e.g., peptide or antibody) that bind to or target a tumor associated antigen. Examples of tumor associated antigens include, but are not limited to, adenosine receptors, alpha v beta 3, aminopeptidase P, alpha fetoprotein, cancer antigen 125, carcinoembryonic antigen, cCaveolin-1, chemokine receptors, clusterin, oncofetal antigens, CD20, epithelial tumor antigen, melanoma associated antigen, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyosinase, and tyrosine kinases. In some embodiments, the cell targeting agent is folate or a folate derivative that binds specifically to folate receptors (FRs). In some embodiments, the cell targeting agent is an antibody, a bispecific antibody, a trispecific antibody or an antigen binding construct thereof, that specifically binds to a cancer antigen selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin αVβ3, Integrin α5β1, MUC1, ERBB2, ERBB3, MET, IGF1R, EPHA3, TRAILR1, TRAILR2, RANKL, FAP and Tenascin among others.

The use of folate as a targeting agent in the radioconjugate also allow both tumor cells and regulatory T (Treg) cells to be targeted for destruction. It is well accepted that high numbers of Treg cells suppress tumor immunity. Specifically, Treg cells suppress (foreign and self) reactive T cells without killing them through contact-dependent or cytokine (e.g., IL-10, TGF-.beta., and the like) secretion. FR4 is selectively upregulated on Treg cells. It has been shown that antibody blockade of FR4 depleted Treg cells and provoked tumor immunity in tumor-bearing mice. Thus, folate-coated PBM nanoparticles carrying a cytotoxic agent would take FR-expressing cells for their destruction, which would both directly (i.e., BrCa cell) and indirectly (i.e., breast tumor associated and peripheral Treg cells) inhibit tumor progression.

In another further embodiment, the targeting agent is an antibody or peptide, or immune cell-engaging multivalent antibody/fusion protein/constructs capable of binding tumor associated antigens consisting of but not limited to: adenosine receptors, alpha v beta 3, aminopeptidase P, alpha fetoprotein, cancer antigen 125, carcinoembryonic antigen, caveolin-1, chemokine receptors, clusterin, oncofetal antigens, CD20, Human Growth Factor Receptor (HGFR), epithelial tumor antigen, melanoma associated antigen, MUC1, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyrosinase, tyrosine kinases, and the like.

In one embodiment, the treatment method includes the co-administration of a compound as disclosed herein or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from antimicrotubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agents" include chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478; alkylating agents such as thiotepa and CYTOXAN®; cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5 alpha-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma 1I and calicheamicin omega 1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Ore.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX®; and (ix) pharmaceutically acceptable salts, acids and derivatives of any of the above.

Chemotherapeutic agents also include antibodies, as described above, including alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nivolumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-8744695, Wyeth Research and Abbott Laboratories) which is a recombinant exclusively human-sequence, full-length IgG.sub.1 .lamda. antibody genetically modified to recognize interleukin-12 p40 protein.

Chemotherapeutic agents also include "tyrosine kinase inhibitors" including the EGFR inhibitors; small molecule HER2 tyrosine kinase inhibitor such as Mubritonib (TAK165, Takeda); CP-724.714, (Axon Medchem BV, an oral selective inhibitor of the ErbB2 receptor tyrosine kinase); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase 1 inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; antisense molecules (e.g. those that bind to HER-encoding nucleic acid); quinoxalines (U.S. Pat. No. 5,804,396); tryphostins (U.S. Pat. No. 5,804,396); Affinitac (ISIS 3521; Isis/Lilly); PKI166 (Novartis); Semaxinib (Pfizer); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca). Tyrosine kinase inhibitors also include Erlotinib (Tarceva®), Gefitinib (Iressa®), Dasatinib (Sprycel®), Nilotinib (Tasigna®), Crizotinib (Xalkori®), Ruxolitinib (Jakafi®), Vemurafenib (Zelboraf®), Vandetanib (Caprelsag), Pazopanib (Votrient®), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, veliparib, vismodegib, volasertib, cobimetinib (Cotellic®), and others.

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNF alpha) blockers such as etanercept (Enbrel), infliximab (Remicade), adalimumab (1-Iumira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/132 blockers such as Anti-lymphotoxin alpha (LTa); miscellaneous investigational agents such as thioplatin, PS-341, phenylbutyrate, ET-18-$OCH_3$, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE) pixantrone; farnesyltransferase inhibitors such as lonafamib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include Poly ADP ribose polymerase (PARP) inhibitors: olaparib (Lynparza®), rucaprib (Rubraca®) niraparib (Zejula®), talzoparib (Talzenna®).

Effective combinations of compounds of Formula I' or any formulas as described herein with other agents may be identified through preclinical and clinical testing of the combinations, and will depend on many factors, including disease type and stage of development, overall health of the patient, toxicities and side effects of the agents, and the like.

In some embodiments, compounds as disclosed herein may be used in combination therapy with any of the kinase inhibitors disclosed herein for the treatment of diseases such as cancer. Exemplary kinase inhibitors include imatinib, baricitinib gefitinib, erlotinib, sorafenib, dasatinib, sunitinib, lapatinib, nilotinib, pirfenidone, pazopanib, crizotinib, vemurafenib, vandetanib, ruxolitinib, axitinib, bosutinib, regorafenib, tofacitinib, cabozantinib, ponatinib, trametinib, dabrafenib, afatinib, ibrutinib, ceritinib, idelalisib, nintedanib, palbociclib, lenvatinib, cobimetinib, XL-147, XL-765, XL-499, and XL-880. In some embodiments, a compound as described herein can be used in combination with a HSP90 inhibitor (e.g., XL888), liver X receptor (LXR) modulators, retinoid-related orphan receptor gamma (RORγ) modulators, a CK1 inhibitor, a CK1-α inhibitor, a Wnt pathway inhibitor (e.g., SST-215), or a mineralocorticoid receptor inhibitor, (e.g., esaxerenone or XL-550) for the treatment of a disease disclosed herein such as cancer.

In some embodiments, for treatment of cancer, compounds as disclosed herein may be used in combination with inhibitors of PD-1 or inhibitors of PD-L1, e.g., an anti-PD-1 monoclonal antibody or an anti-PD-L1 monoclonal antibody, for example, nivolumab (Opdivo), pembrolizumab (Keytruda, MK-3475), atezolizumab, avelumab, AMP-224, AMP-514, PDR001, durvalumab, pidilizumab (CT-011), CK-301, BMS 936559, and MPDL3280A; CTLA-4 inhibitors, e.g., an anti-CTLA-4 antibody, for example, ipilimumab (Yervoy) and tremelimumab; and phosphatidylserine inhibitors, for example, bavituximab (PGN401); antibodies to cytokines (IL-10, TGF-β, and the like); other anti-cancer agents such as cemiplimab.

In some embodiments, a compound as described herein can be used in combination with a vaccination protocol for the treatment of cancer. In some embodiments, a compound as described herein can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa*.

In some embodiments, compounds as disclosed herein may be used in combination with inhibitors of PARP, for example, olaparib (Lynparza®), rucaprib (Rubraca®) niraparib (Zejula®), talzoparib (Talzenna®).

The amount of both the compound disclosed herein or salt thereof and the additional one or more additional therapeutic agent (in those compositions which comprise an additional therapeutic agent as described above) that may be combined with carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound disclosed herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-10,000 μg/kg body weight/day of the additional therapeutic agent can be administered.

Labeled Compounds and Assay Methods

Another aspect of the present invention relates to labeled compounds of the invention (radio-labeled, fluorescent-labeled, and the like) that would be useful not only in imaging techniques but also in assays, both in vitro and in vivo, for localizing and quantitating TAM kinases in tissue samples, including human, and for identifying TAM kinase ligands by inhibition binding of a labeled compound. Accordingly, the present invention includes TAM kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The radionuclide that is incorporated in the instant radio-labeled compounds will depend on the specific application of that radio-labeled compound. For example, for in vitro metalloprotease labeling and competition assays, compounds that incorporate $^{3}H$, $^{14}C$, $^{82}Br$, $^{125}I$, $^{131}I$, or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$, or $^{77}Br$ will generally be most useful.

It is understood that a "radio-labeled" or "labeled compound" is a compound that has incorporated at least one radionuclide. In some embodiments, the radionuclide is selected from the group consisting of $^{3H}$, $^{14}C$, $^{125}I$, $^{35}S$, and $^{82}Br$.

The present invention can further include synthetic methods for incorporating radio-isotopes into compounds of the invention. Synthetic methods for incorporating radio-isotopes into organic compounds are well known in the art, and a person of ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a TAM by monitoring its concentration variation when contacting with the TAM kinases, through tracking of the labeling. For example, a test compound (labeled) can be evaluated for its ability to reduce binding of another compound which is known to bind to a TAM kinase (i.e., standard compound). Accordingly, the ability of a test compound to compete with the standard compound for binding to the TAM kinase directly correlates to its binding affinity. Conversely, in some other screening assays, the standard compound is labeled, and test compounds are unlabeled. Accordingly, the concentration of the labeled standard compound is monitored in order to evaluate the competition between the standard compound and the test compound, and the relative binding affinity of the test compound is thus ascertained.

Synthesis

Compounds of this invention can be made by the synthetic procedures described below. The starting materials and reagents used in preparing these compounds are either available from commercial suppliers such as Sigma Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, $4^{th}$ Edition); and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure and over a temperature range from about −78° C. to about 150° C., more preferably from about 0° C. to about 125° C., and most preferably at about room (or ambient) temperature, e.g., about 20° C. Unless otherwise stated (as in the case of a hydrogenation), all reactions are performed under an atmosphere of nitrogen.

The compounds disclosed and claimed herein have asymmetric carbon atoms or quaternized nitrogen atoms in their structure and may be prepared through the syntheses described herein as single stereoisomers, racemates, or mixtures of enantiomers and diastereomers. The compounds may also exist as geometric isomers. All such single stereoisomers, racemates, and geometric isomers, and mixtures thereof are intended to be within the scope of this invention.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereomeric salts or complexes which may be separated, for example, by crystallization; via formation of diastereomeric derivatives which may be separated, for example, by crystallization; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomers may be synthesized by asymmetric synthesis using optically active reagents, substrates, catalysts, or solvents, or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The methods of the present invention may be carried out as semi-continuous or continuous processes, more preferably as continuous processes.

The present invention as described above unless indicated otherwise may be carried out in the presence of a solvent or a mixture of two or more solvents. In particular the solvent is an aqueous or an organic solvent such as the ether-like solvent (e.g. tetrahydrofuran, methyltetrahydrofuran, diisopropyl ether, t-butylmethyl ether, or dibutyl ether), aliphatic hydrocarbon solvent (e.g. hexane, heptane, or pentane), saturated alicyclic hydrocarbon solvent (e.g. cyclohexane or cyclopentane), or aromatic solvent (e.g. toluene, o-, m-, or p-xylene, or t-butyl-benzene), or mixture thereof.

The starting materials and reagents, which do not have their synthetic route explicitly disclosed herein, are generally available from commercial sources or are readily prepared using methods well known to the person skilled in the art.

Processes

One aspect provides a process of making a compound of Formula I:

I

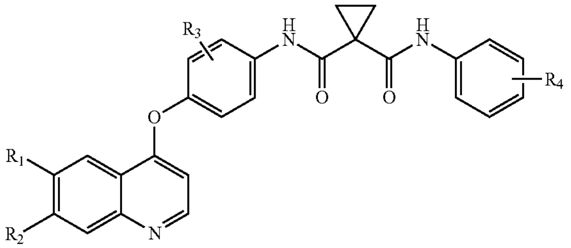

or a pharmaceutically acceptable salt thereof, comprising:

reacting a compound of formula II:

II

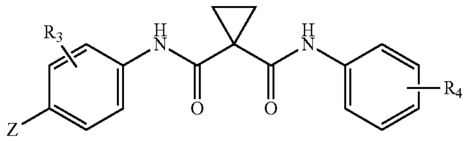

wherein Z is selected from the group consisting of $NH_2$, SH, and OH;

with a compound of formula III:

III

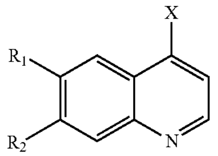

wherein X is a leaving group;

$R_1$ is selected from the group consisting of —H, —CN, —CO—$NR_5R_6$, —$CO_2R_7$, optionally substituted aryl, optionally substituted heteroaryl, optionally substituted ($C_1$-$C_6$) alkyl, optionally substituted ($C_3$-$C_8$) cycloalkyl, optionally substituted ($C_3$-$C_6$) heterocycloalkyl, —$SO_2NR_8R_9$, and —($SO_2$)—($C_1$-$C_6$) alkyl;

wherein when $R_1$ is selected from the group consisting of —CN, —CO—$NR_5R_6$, —$CO_2R_7$, optionally substituted aryl, optionally substituted heteroaryl, optionally substituted ($C_3$-$C_8$) cycloalkyl, optionally substituted ($C_3$-$C_6$) heterocycloalkyl, —$SO_2NR_8R_9$, and —($SO_2$)—($C_1$-$C_6$) alkyl, $R_2$ is —H, halo, —$NR_5R_6$, or optionally substituted ($C_1$-$C_6$) alkoxy;

wherein when $R_1$ is —H, optionally substituted ($C_1$-$C_6$) alkyl, or optionally substituted ($C_1$-$C_6$) alkoxy, $R_2$ is —CO—$NR_5R_6$, or —$CO_2R_7$;

or $R_1$ and $R_2$ taken together with the atoms to which they are attached to form optionally substituted cycloalkyl or optionally substituted heterocyloalkyl;

$R_3$ is selected from the group consisting of H, optionally substituted ($C_1$-$C_6$) alkyl, —CN, and halo;

$R_4$ is —H or halo;

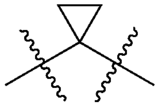 [SMILES: *C1(*)CC1]

is optionally substituted with one, two, three, or four groups independently selected from the group consisting of halo; and ($C_1$-$C_6$) alkyl, wherein "" indicate points of attachment;

$R_5$ and $R_6$ are each independently H, optionally substituted ($C_1$-$C_6$) alkyl, or optionally substituted ($C_1$-$C_6$) alkoxy;

$R_7$ is —H or optionally substituted ($C_1$-$C_6$) alkyl $R_8$ and $R_9$ are each independently —H or optionally substituted ($C_1$-$C_6$) alkyl; or $R_8$ and $R_9$ may connect to form optionally substituted heterocycle; and Y is selected from the group consisting of O, S, SO, $SO_2$, NH, and N—(($C_1$-$C_6$) alkyl).

Another aspect is a process for making a compound of Formula I:

I

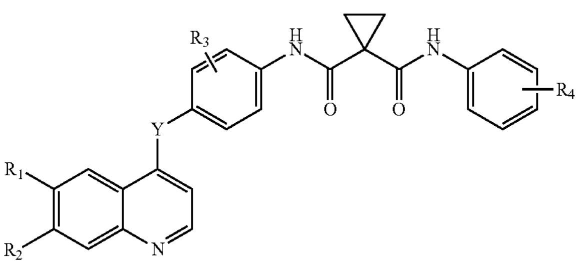

or a pharmaceutically acceptable salt thereof, comprising: reacting a compound of formula IV:

IV

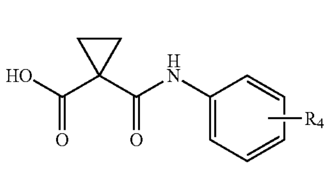

with a compound of formula V:

V

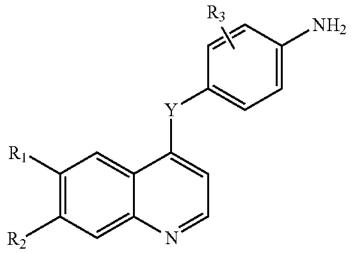

$R_1$ is selected from the group consisting of —H, —CN, —CO—$NR_5R_6$, —$CO_2R_7$, optionally substituted aryl, optionally substituted heteroaryl, optionally substituted ($C_1$-$C_6$) alkyl, optionally substituted ($C_3$-$C_8$) cycloalkyl, optionally substituted ($C_3$-$C_6$) heterocycloalkyl, —$SO_2NR_8R_9$, and ($SO_2$)—($C_1$-$C_6$) alkyl;

wherein when $R_1$ is selected from the group consisting of —CN, —CO—$NR_5R_6$, —$CO_2R_7$, optionally substituted aryl, optionally substituted heteroaryl, optionally substituted ($C_3$-$C_8$) cycloalkyl, optionally substituted ($C_3$-$C_6$) heterocycloalkyl, —$SO_2NR_8R_9$, and —($SO_2$)—($C_1$-$C_6$) alkyl, $R_2$ is —H, halo, —$NR_5R_6$, or optionally substituted ($C_1$-$C_6$) alkoxy;

wherein when $R_1$ is —H, optionally substituted ($C_1$-$C_6$) alkyl, or optionally substituted ($C_1$-$C_6$) alkoxy, $R_2$ is —CO—$NR_5R_6$, optionally substituted heteroaryl, or —$CO_2R_7$;

or $R_1$ and $R_2$ taken together with the atoms to which they are attached to form optionally substituted cycloalkyl or optionally substituted heterocyloalkyl;

$R_3$ is selected from the group consisting of —H, optionally substituted ($C_1$-$C_6$) alkyl, —CN, and halo;

$R_4$ is —H or halo;

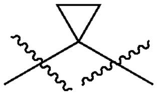 [SMILES: *C1(*)CC1]

is optionally substituted with one, two, three, or four groups independently selected from the group consisting of halo, and $C_1$-$C_6$ alkyl, wherein "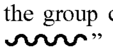" indicate points of attachment;

$R_5$ and $R_6$ are each independently —H, optionally substituted ($C_1$-$C_6$) alkyl, or optionally substituted ($C_1$-$C_6$) alkoxy;

$R_7$ is —H or optionally substituted ($C_1$-$C_6$) alkyl;

$R_8$ and $R_9$ are each independently —H or optionally substituted ($C_1$-$C_6$) alkyl; or $R_8$ and $R_9$ may connect to form optionally substituted heterocycle; and Y is selected from the group consisting of O, S, SO, $SO_2$, NH, and N—($C_1$-$C_6$ alkyl).

In one embodiment, compounds of Formula V are made by a process comprising reacting a compound of Formula VI:

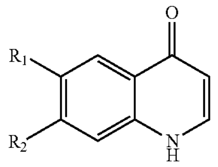

VI with a compound of Formula VII:

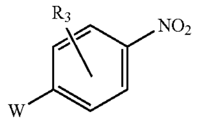

VII to form a compound of Formula VIII:

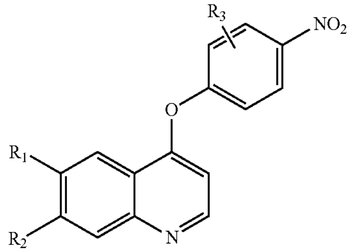

VIII and reducing the compound of Formula VIII to provide a compound of Formula V wherein:

$R_1$ is selected from the group consisting of —H, —CN, —CO—$NR_5R_6$, —$CO_2R_7$, optionally substituted aryl, optionally substituted heteroaryl, optionally substituted ($C_1$-$C_6$) alkyl, optionally substituted ($C_3$-$C_8$) cycloalkyl, optionally substituted ($C_3$-$C_6$) heterocycloalkyl, —$SO_2NR_8R_9$, and —($SO_2$)—($C_1$-$C_6$) alkyl;

wherein when $R_1$ is selected from the group consisting of —CN, —CO—$NR_5R_6$, —$CO_2R_7$, optionally substituted aryl, optionally substituted heteroaryl, optionally substituted ($C_3$-$C_8$) cycloalkyl, optionally substituted ($C_3$-$C_6$) heterocycloalkyl, —$SO_2NR_8R_9$, and —($SO_2$)—($C_1$-$C_6$) alkyl, $R_2$ is —H, halo, —$NR_5R_6$, or optionally substituted ($C_1$-$C_6$) alkoxy;

wherein when $R_1$ is —H, optionally substituted ($C_1$-$C_6$) alkyl, or optionally substituted ($C_1$-$C_6$) alkoxy, $R_2$ is —CO—$NR_5R_6$, or —$CO_2R_7$;

or $R_1$ and $R_2$ taken together with the atoms to which they are attached to form optionally substituted cycloalkyl or optionally substituted heterocyloalkyl;

$R_3$ is selected from the group consisting of —H, optionally substituted ($C_1$-$C_6$) alkyl, —CN, and halo; and W is halo.

The following examples are provided for the purpose of further illustration and are not intended to limit the scope of the claimed invention.

EXAMPLES

Example 1: Methyl 4-[4-[[1-[(4-fluorophenyl)carbamoyl]cyclopropane-carbonyl]amino]phenoxy]-7-methoxyquinoline-6-carboxylate (5)

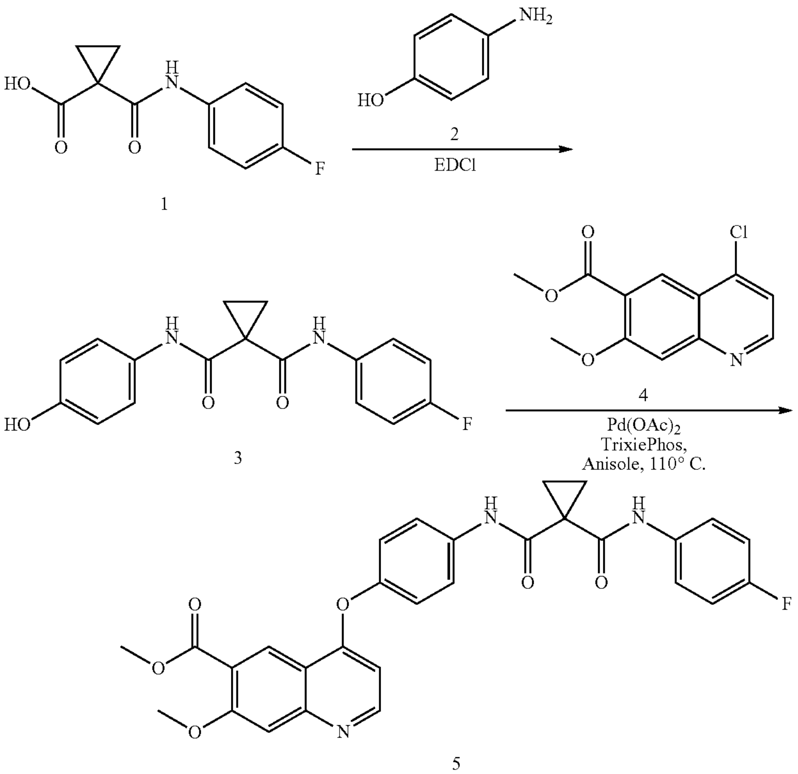

N-(4-Fluorophenyl)-N-(4-hydroxyphenyl)cyclopropane-1,1-dicarboxamide (3): To a solution of Compound 1 (10 g, 44.80 mmol, 1 eq) and Compound 2 (5.87 g, 53.8 mmol, 1.2 eq) in dimethyl acetamide (DMA) (60 mL) was added 3-(ethyliminomethyleneamino)-N,N-dimethyl-propan-1-amine hydrochloride (EDCI) (10.31 g, 53.8 mmol, 1.2 eq). The mixture was stirred vigorously at 20° C. until the reaction was complete. The mixture was poured into aqueous (aq) saturated $NaHCO_3$ (400 mL) and extracted with EtOAc (4×100 mL). The combined organic phases were washed with aq saturated NaCl (100 mL), dried over anhyd (anhyd) $Na_2SO_4$, and concentrated. Compound 3 (21 g, crude) (50% purity) was obtained. $^1H$ NMR (400 MHz, DMSO-$d_6$) δ 10.16 (br s, 1H), 9.72 (br s, 1H), 7.61 (dd, 2H), 7.34 (d, 2H), 7.13 (t, 2H) 6.68 (d, 2H), 1.42 (s, 4H); MS (EI) for $C_{17}H_{15}FN_2O_3$. found 314.9 (MH+).

Methyl 4-[4-[[1-[(4-fluorophenyl)carbamoyl]cyclopropane-carbonyl]amino]phenoxy]-7-methoxyquinoline-6-carboxylate (5): A mixture of Compound 3 (5.99 g, 9.5 mmol, 1.2 eq), Compound 4 (2 g, 8.0 mmol, 1.0 eq), $Pd(OAc)_2$ (89 mg, 397.4 0.05 eq), rac-2-(Di-tert-butylphosphino)-1,1'-binaphthyl (TrixiePhos, 316.71 mg, 794.7 0.1 eq), and $K_3PO_4$ (2.53 g, 11.9 mmol, 1.5 eq) in anisole (50 mL) was stirred at 110° C. for 2 hours (h) under an atmosphere of nitrogen. The mixture was filtered, and the filtrate was concentrated. The residue was purified by flash silica gel chromatography (1:1 petroleum ether:EtOAc to 20:1 EtOAc:MeOH). Compound 5 was obtained (2.6 g, 61.8% yield). $^1H$ NMR (400 MHz, $CDCl_3$) δ 9.38 (s, 1H), 8.80 (s, 1H), 8.63 (d, 2H), 7.64 (d, 2H), 7.54-7.41 (m, 3H), 7.18 (d, 2H), 7.09-7.01 (m, 2H), 6.43 (d, 1H), 4.05 (s, 3H), 3.97 (s, 3H), 1.78-1.72 (m, 2H), 1.69-1.63 (m, 2H); MS (EI) for $C_{29}H_{24}FN_3O_6$. found 530.0 (MH+).

Example 2: 4-[4-[[1-[(4-Fluorophenyl)carbamoyl]cyclopropane-carbonyl]amino]phenoxy]-7-methoxyquinoline-6-carboxylic Acid (6)

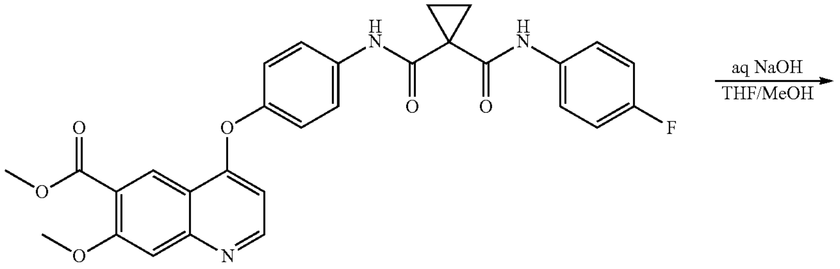

5

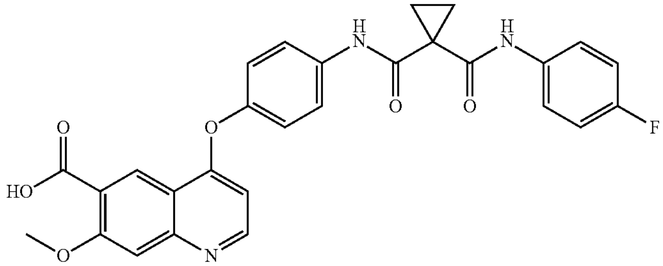

6

4-[4-[[1-[(4-Fluorophenyl)carbamoyl]cyclopropane-carbonyl]amino]phenoxy]-7-methoxyquinoline-6-carboxylic acid (6): To a solution of Compound 5 (1.8 g, 3.4 mmol, 1 eq) in tetrahydrofuran (THF) (15 mL) and MeOH (15 mL) was added 2 M aq NaOH (7 mL, 4.1 eq). The mixture was stirred at 6-13° C. for 4 h. The mixture was adjusted to a pH of approximately 8 with 1 M aq HCl and concentrated to remove solvent. Water (50 mL) was added, and the mixture was adjusted to a pH of approximately 6 with 1 M aq HCl. The resulting precipitate was filtered, washed with water (2×10 mL), and dried under vacuum. Compound 6 was obtained (1.7 g, 97.0% yield). $^1El$ NMR (400 MHz, DMSO-$d_6$) δ 10.22 (s, 1H), 10.08 (s, 1H), 8.65 (d, 1H), 8.48 (s, 1H), 7.77 (d, 2H), 7.64 (dd, 2H) 7.47 (s, 1H), 7.25 (d, 2H), 7.15 (t, 2H), 6.45 (d, 1H), 3.96 (s, 3H), 1.47 (s, 4H); MS (EI) for $C_{28}H_{22}FN_3O_6$. found 516.1 (MH+).

Example 3: 1-N-[4-(6-Carbamoyl-7-methoxyquinolin-4-yl)oxyphenyl]-1-N'-(4-fluorophenyl)cyclopropane-1,1-dicarboxamide (7)

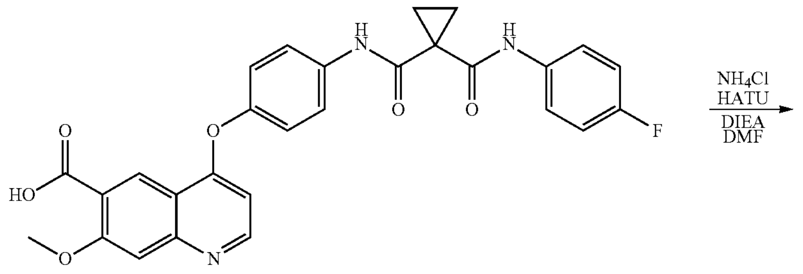

6

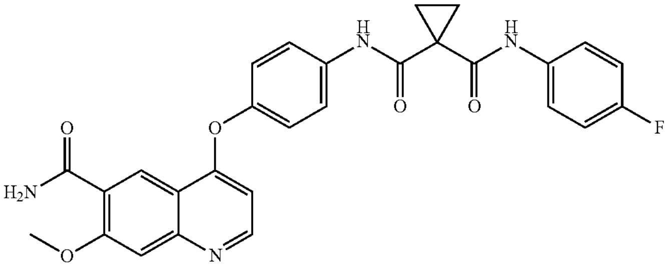

7

1-N-[4-(6-Carbamoyl-7-methoxyquinolin-4-yl)oxyphenyl]-1-N'-(4-fluorophenyl)cyclopropane-1,1-dicarboxamide (7): A solution of Compound 6 (350 mg, 679.0 μmol, 1 eq), 1-[bis(dimethylamino)methylene]-1H-1,2,3-triazolo[4,5-b]pyridinium 3-oxide hexafluorophosphate (HATU) (388 mg, 1.0 mmol, 1.5 eq), and diisopropylethylamine (DIEA or DIPEA) (352 mg, 2.7 mmol, 474 uL, 4.0 eq) in dimethylformamide (DMF) (10 mL) was stirred at 6-10° C. for 1 h, after which was added $NH_4Cl$ (73 mg, 1.4 mmol, 2.0 eq), and the mixture was stirred at 6-10° C. for an additional 17 h. The mixture was filtered, and the resulting filtrate was concentrated and purified by prep HPLC (Column: Waters Xbridge 150 mm*25 mm*5 μm, gradient: 32-62% of acetonitrile in 10 mM aq $NH_4HCO_3$, flow rate: 25 mL/min). Compound 7 was obtained (90.1 mg, 25.8% yield). $^1H$ NMR (400 MHz, DMSO-$d_6$) δ 10.20 (s, 1H), 10.06 (s, 1H), 8.68 (s, 1H), 8.66 (d, 1H) 7.86 (br s, 1H), 7.81-7.72 (m, 3H), 7.68-7.61 (m, 2H), 7.51 (s, 1H), 7.26 (d, 2H), 7.19-7.11 (m, 2H), 6.46 (d, 1H), 4.03 (s, 3H), 1.47 (s, 4H); MS (EI) for $C_{28}H_{23}FN_4O_5$. found 515.1 (MH+).

Example 4: 1-N'-(4-Fluorophenyl)-1-N-[4-[7-methoxy-6-(methylcarbamoyl)quinolin-4-yl]oxyphenyl]cyclopropane-1,1-dicarboxamide (8)

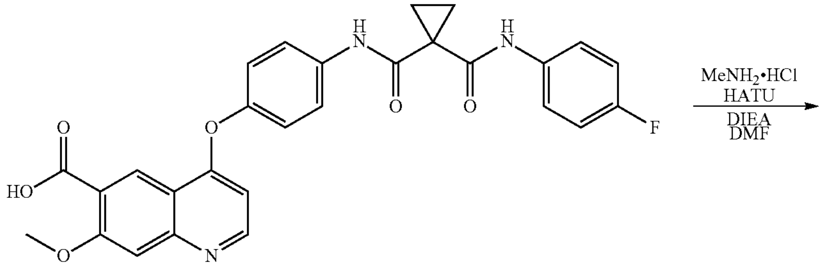

6

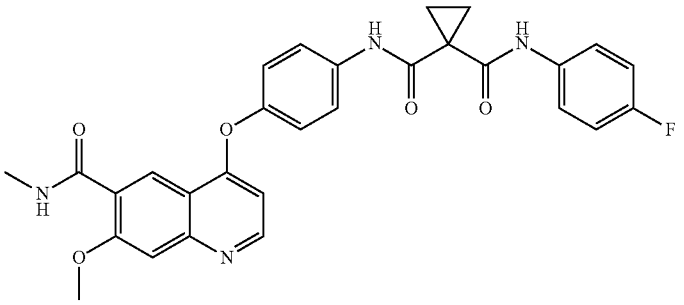

8

1-N'-(4-Fluorophenyl)-1-N-[4-[7-methoxy-6-(methylcarbamoyl)quinolin-4-yl]oxyphenyl]cyclopropane-1,1-dicarboxamide (8): A solution of Compound 6 (300 mg, 582.0 μmol, 1 eq), HATU (332 mg, 873.2 μmol, 1.5 eq), and DIEA (301 mg, 2.3 mmol, 406 μL, 4 eq) in DMF (10 mL) was stirred at 6-10° C. for 1 h. Methanamine hydrochloride (79 mg, 1.2 mmol, 2.0 eq) was added, and the mixture was stirred at 6-10° C. for 17 h. The mixture was filtered, and the resulting filtrate was purified by prep HPLC (Column: Waters Xbridge 150 mm*25 mm*5 μm, gradient: 33-63% of acetonitrile in 10 mM aq $NH_4HCO_3$, flow rate: 25 mL/min). Compound 8 was obtained (105.4 mg, 34.3% yield). $^1$H NMR (400 MHz, DMSO-$d_6$) δ 10.20 (s, 1H), 10.06 (s, 1H), 8.65 (d, 1H), 8.61 (s, 1H), 8.42-8.33 (m, 1H), 7.77 (d, 2H), 7.68-7.61 (m, 2H), 7.51 (s, 1H), 7.25 (d, 2H), 7.19-7.11 (m, 2H), 6.46 (d, 1H), 4.02 (s, 3H), 2.84 (d, 3H) 1.47 (s, 4H); MS (EI) for $C_{29}H_{25}FN_4O_5$. found 529.1 (MH+).

The following compounds were prepared in a method analogous to Compound 8 in Example 4:

1-N-[4-[6-(Ethylcarbamoyl)-7-methoxyquinolin-4-yl]oxyphenyl]-1-N'-(4-fluorophenyl)cyclopropane-1,1-dicarboxamide (9): $^1$H NMR (400 MHz, DMSO-$d_6$) δ 10.20 (s, 1H), 10.06 (s, 1H), 8.65 (d, 1H), 8.56 (s, 1H), 8.40 (br t, 1H), 7.78 (br d, 2H), 7.64 (dd, 2H), 7.51 (s, 1H), 7.25 (d, 2H), 7.15 (t, 2H), 6.46 (d, 1H), 4.02 (s, 3H), 3.37-3.29 (m, 2H), 1.48 (s, 4H), 1.15 (t, 3H); MS (EI) for $C_{30}H_{27}FN_4O_5$. found 543.2 (MH+).

1-N-[4-[6-[2-(Dimethylamino)ethylcarbamoyl]-7-methoxyquinolin-4-yl]oxyphenyl]-1-N'-(4-fluorophenyl)cyclopropane-1,1-dicarboxamide (10): $^1$H NMR (400 MHz, $CDCl_3$) δ 9.38 (s, 1H), 9.23 (s, 1H), 9.16 (s, 1H), 8.61 (d, 1H), 8.50 (s, 1H), 7.68 (d, 2H), 7.49-7.46 (m, 3H), 7.12 (d, 2H), 7.03 (t, 2H), 6.43 (d, 1H), 4.11 (s, 3H), 3.66 (q, 2H), 2.68 (t, 2H), 2.41 (s, 6H), 1.70 (s, 4H); MS (EI) for $C_{32}H_{32}FN_5O_5$. found 586.2 (MH+).

1-N'-(4-Fluorophenyl)-1-N-[4-[7-methoxy-6-(2-piperidin-1-ylethylcarbamoyl)quinolin-4-yl]oxyphenyl]cyclopropane-1,1-dicarboxamide (11): $^1$H NMR (400 MHz, $CDCl_3$) δ 9.79 (s, 1H), 9.63 (s, 1H), 9.13 (s, 1H), 8.68 (s, 1H), 8.58 (d, 1H), 7.74 (d, 2H), 7.49-7.41 (m, 3H), 7.06-6.96 (m, 4H), 6.38 (d, 1H), 4.13 (s, 3H), 3.65 (q, 2H), 2.60 (t, 2H), 2.49 (s, 4H), 1.70-1.65 (m, 8H), 1.51 (s, 2H); MS (EI) for $C_{35}H_{36}FN_5O_5$. found 626.3 (MH+).

1-N'-(4-Fluorophenyl)-1-N-[4-[7-methoxy-6-(2-morpholin-4-ylethylcarbamoyl)quinolin-4-yl]oxyphenyl]cyclopropane-1,1-dicarboxamide (12): $^1$H NMR (400 MHz, $CDCl_3$) δ 9.26 (s, 1H), 9.24 (s, 1H), 8.95 (s, 1H), 8.63 (d, 1H), 8.46 (s, 1H), 7.65 (d, 2H), 7.52 (s, 1H), 7.50-7.47 (m, 2H), 7.16 (d, 2H), 7.05 (t, 2H), 6.46 (d, 1H), 4.15 (s, 3H), 3.79 (t, 4H), 3.68-3.64 (m, 2H), 2.65 (t, 2H), 2.57 (s, 4H), 1.70 (d, 4H); MS (EI) for $C_{34}H_{34}FN_5O_6$. found 628.3 (MH+).

1-N'-(4-Fluorophenyl)-1-N-[4-[7-methoxy-6-(oxetan-3-ylcarbamoyl)quinolin-4-yl]oxyphenyl]cyclopropane-1,1-dicarboxamide (13): $^1$H NMR (400 MHz, $CDCl_3$) δ 9.34 (s, 1H), 9.22 (s, 1H), 8.92 (s, 1H), 8.64 (d, 1H), 8.47 (d, 1H), 7.65 (d, 2H), 7.55 (s, 1H), 7.50-7.46 (m, 2H), 7.14 (d, 2H), 7.05 (t, 2H), 6.47 (d, 1H), 5.36-5.27 (m, 1H), 5.06 (t, 2H), 4.68 (t, 2H), 4.17 (s, 3H), 1.71 (s, 4H); MS (EI) for $C_{31}H_{27}FN_4O_6$. found 571.2 (MH+).

1-N'-(4-Fluorophenyl)-1-N-[4-[7-methoxy-6-[(1-methylazetidin-3-yl)carbamoyl]quinolin-4-yl]oxyphenyl]cyclopropane-1,1-dicarboxamide (14): $^1$H NMR (400 MHz, $CDCl_3$) δ 9.60 (s, 2H), 9.11 (s, 1H), 8.58 (d, 1H), 8.34 (d, 1H), 7.67 (d, 2H), 7.53-7.37 (m, 3H), 7.06 (d, 2H), 6.98 (t, 2H), 6.40 (d, 1H), 4.82-4.66 (m, 1H), 4.12 (s, 3H), 3.73 (t, 2H), 3.10 (t, 2H), 2.38 (s, 3H), 1.74-1.60 (m, 4H); MS (EI) for $C_{32}H_{30}FN_5O_5$. found 584.9 (MH+).

1-N-[4-[6-(Azetidine-1-carbonyl)-7-methoxyquinolin-4-yl]oxyphenyl]-1-N'-(4-fluorophenyl)cyclopropane-1,1-dicarboxamide (15): $^1$H NMR (400 MHz, $CDCl_3$) δ 9.40 (s, 1H), 9.22 (br s, 1H), 8.59 (d, 1H), 8.32 (s, 1H), 7.63 (d, 2H), 7.49 (td, 9.2 Hz, 3H), 7.13 (d, 2H), 7.04 (t, 2H), 6.43 (d, 1H), 4.28 (t, 2H), 4.08-3.98 (m, 5H), 2.37-2.32 (m, 2H), 1.77-1.64 (m, 4H); MS (EI) for $C_{31}H_{27}FN_4O_5$. found 554.8 (MH+).

1-N'-(4-Fluorophenyl)-1-N-[4-[6-(3-hydroxyazetidine-1-carbonyl)-7-methoxyquinolin-4-yl]oxyphenyl]cyclopropane-1,1-dicarboxamide (16): $^1$H NMR (400 MHz, $CDCl_3$) δ 9.43 (s, 1H), 9.18 (s, 1H), 8.60 (s, 1H), 8.31 (s, 1H), 7.61 (d, 2H), 7.50-7.46 (m, 3H), 7.11 (d, 2H), 7.06-7.00 (m, 2H), 6.45 (d, 1H), 4.75-4.70 (m, 1H), 4.51-4.47 (m, 1H), 4.19-4.13 (m, 1H), 4.11-4.07 (m, 1H), 4.01 (s, 3H), 3.95-3.91 (m, 1H), 1.75-1.73 (m, 2H), 1.72-1.69 (m, 2H); MS (EI) for $C_{31}H_{27}FN_4O_6$. found 571.0 (MH+).

1-N'-(4-Fluorophenyl)-1-N-[4-[7-methoxy-6-(methoxycarbamoyl)quinolin-4-yl]oxyphenyl]cyclopropane-1,1-dicarboxamide (17): $^1$H NMR (400 MHz, DMSO-$d_6$) δ 11.27 (br s, 1H), 10.20 (br s, 1H), 10.06 (br s, 1H), 8.65 (d, 1H), 8.44 (s, 1H), 7.76 (d, 2H), 7.63 (d, 2H), 7.49 (s, 1H), 7.25 (d, 2H), 6.46 (d, 2H), 6.93 (d, 1H), 3.98 (s, 3H), 3.74 (s, 3H), 1.47 (s, 4H); MS (EI) for $C_{29}H_{25}FN_4O_6$. found 545.1 (MH+).

t-Butyl (R)-2-((4-(4-(1-((4-fluorophenyl)carbamoyl)cyclopropane-1-carboxamido)phenoxy)-7-methoxyquinoline-6-carboxamido)methyl)pyrrolidine-1-carboxylate (18): MS (EI) for $C_{38}H_{40}FN_5O_7$. found 698.3 (MH+).

t-Butyl (S)-2-((4-(4-(1-((4-fluorophenyl)carbamoyl)cyclopropane-1-carboxamido)phenoxy)-7-methoxyquinoline-6-carboxamido)methyl)pyrrolidine-1-carboxylate (19): MS (EI) for $C_{38}H_{40}FN_5O_7$. found 698.3 (MH+).

1-N'-(4-Fluorophenyl)-1-N-[4-[6-(hydroxycarbamoyl)-7-methoxyquinolin-4-yl]oxyphenyl]cyclopropane-1,1-dicarboxamide hydrochloride (20): $^1$H NMR (400 MHz, DMSO-$d_6$) δ 11.08 (s, 1H), 10.32 (s, 1H), 10.04 (s, 1H), 8.97-8.88 (m, 1H), 8.54 (s, 1H), 7.84 (d, 2H), 7.72-7.58 (m, 3H), 7.35 (d, 2H), 7.15 (t, 2H), 6.86-6.75 (m, 1H), 4.04 (s, 3H), 1.48 (d, 4H); MS (EI) for $C_{28}H_{23}FN_4O_6$. found 531.0 (MH+).

Example 5: 1-N'-(4-Fluorophenyl)-1-N-[4-[7-methoxy-6-[[(2R)-pyrrolidin-2-yl]methylcarbamoyl]quinolin-4-yl]oxyphenyl]cyclopropane-1,1-dicarboxamide (21)

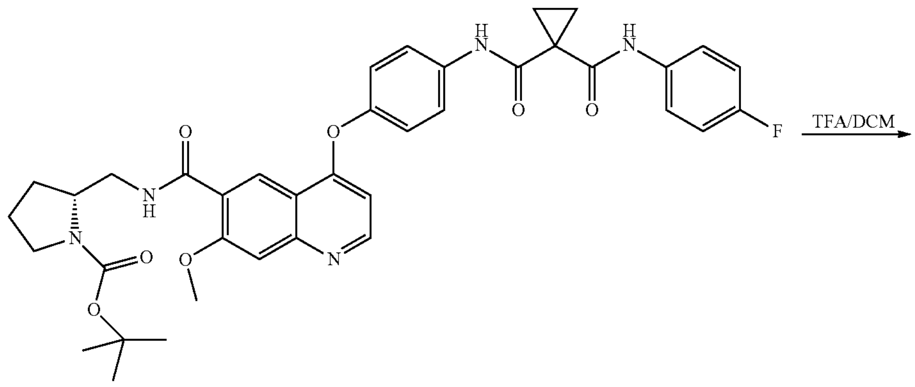

18

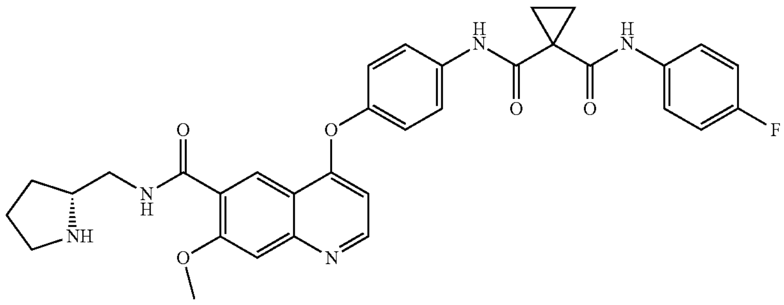

21

1-N'-(4-Fluorophenyl)-1-N-[4-[7-methoxy-6-[[(2R)-pyrrolidin-2-yl]methylcarbamoyl]quinolin-4-yl]oxyphenyl]cyclopropane-1,1-dicarboxamide (21): To a mixture of Compound 18 (67 mg, 96.0 μmol, 1 eq) in dichloromethane (DCM) (3 mL) was added trifluoroacetic acid (TFA; 1 mL) in one portion at 30° C. The mixture was stirred at 30° C. for 0.5 h, after which the reaction mixture was concentrated under vacuum. The resulting residue was purified by prep HPLC (column: Waters Xbridge 150*25*5 μm; mobile phase: [water (0.05% ammonia hydroxide v/v)-acetonitrile (ACN]; B %: 50%) to give Compound 21 (24.4 mg, 42.5% yield). $^{1}$H NMR (400 MHz, DMSO-$d_6$) δ 9.52-9.35 (m, 2H), 9.14 (s, 1H), 8.59 (d, 1H), 8.42 (br t, 1H), 7.68 (d, 2H), 7.51-7.44 (m, 3H), 7.09 (d, 2H), 7.06-6.97 (m, 2H), 6.42 (d, 1H), 4.13 (s, 3H), 3.69 (td, 1H), 3.55-3.47 (m, 1H), 3.45-3.37 (m, 1H), 3.01 (t, 2H), 2.01-1.79 (m, 8H), 1.58-1.45 (m, 1H); MS (EI) for $C_{33}H_{32}FN_5O_5$. found 598.3 (MH+).

The following compound was prepared from Compound 19 in a manner analogous to the method used to convert Compound 18 to Compound 21 in Example 5:

1-N'-(4-Fluorophenyl)-1-N-[4-[7-methoxy-6-[[(2S)-pyrrolidin-2-yl]methylcarbamoyl]quinolin-4-yl]oxyphenyl]cyclopropane-1,1-dicarboxamide (22): $^{1}$H NMR (400 MHz, $CDCl_3$) δ 9.47 (s, 2H), 9.15 (s, 1H), 8.60 (d, 1H), 8.40 (t, 1H), 7.7-7.67 (m, 2H), 7.49-7.45 (m, 3H), 7.10-7.04 (m, 2H), 7.03-6.99 (m, 2H), 6.41 (d, 1H), 4.11 (s, 3H), 3.71-3.65 (m, 1H), 3.50-3.37 (m, 2H), 3.02-2.96 (m, 2H), 2.01-1.95 (m, 2H), 1.84-1.75 (m, 2H), 1.71-1.66 (m, 4H), 1.55-1.48 (m, 1H); MS (EI) for $C_{33}H_{32}FN_5O_5$. found 598.3 (MH+).

Example 6: 1-N'-(4-Fluorophenyl)-1-N-[4-[7-methoxy-6-(oxetan-3-yloxycarbamoyl)quinolin-4-yl]oxyphenyl]cyclopropane-1,1-dicarboxamide (26)

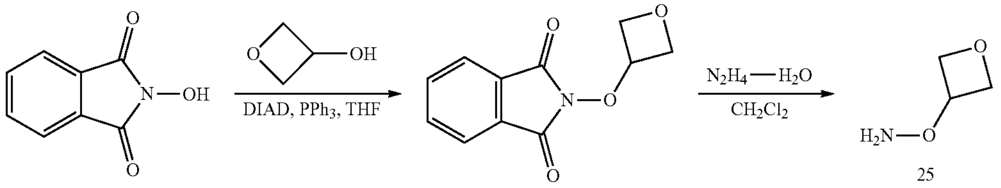

23 24 25

-continued

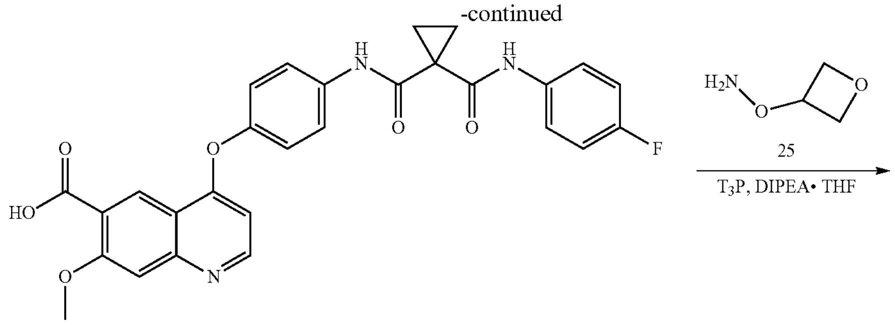

6

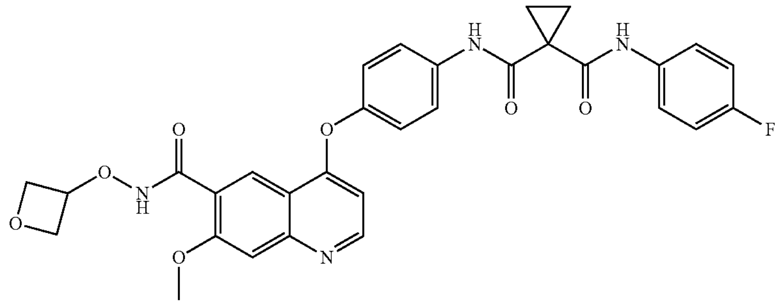

26

2-(Oxetan-3-yloxy)isoindoline-1,3-dione (24): To a solution of Compound 23 (1.32 g, 8.1 mmol, 1.2 eq) and oxetan-3-ol (500 mg, 6.8 mmol, 1 eq) in THF (30 mL) were added $PPh_3$ (3.54 g, 13.5 mmol, 2 eq) and diisopropyl azodicarboxylate (DIAD) (2.81 g, 13.9 mmol, 2.7 mL, 2.1 eq) in portions at 0° C. The resulting mixture was stirred at 20° C. for 15 h to give a brown solution. The mixture was concentrated with silica gel and purified by flash silica gel chromatography (0 to approximately 70% EtOAc in Petroleum ether gradient). The resulting residue was subjected to a second purification by flash silica gel chromatography using the same solvent system to obtain Compound 24 (300 mg, 10.14% yield, 50% purity). MS (EI) for $C_{11}H_9NO_4$. found 219.8 (MH+).

O-(Oxetan-3-yl)hydroxylamine (25): To a solution of Compound 24 (280 mg, 1.3 mmol, 1 eq) in DCM (5 mL) was added $NH_2NH_2$—$H_2O$ (95.92 mg, 1.9 mmol, 93.13 uL, 1.5 eq) at 0° C., and the resulting mixture stirred for 1 h to give a white suspension. The mixture was filtered and washed with DCM (5 mL), and the filtrate was concentrated. Crude Compound 25 (150 mg) was used in the next step without further purification.

1-N'-(4-Fluorophenyl)-1-N-[4-[7-methoxy-6-(oxetan-3-yloxycarbamoyl)quinolin-4-yl]oxyphenyl]cyclopropane-1,1-dicarboxamide (26): To a solution of Compound 6 (100 mg, 194.0 μmol, 1 eq) and Compound 25 (20.74 mg, 232.8 μmol, 1.2 eq) in THF (3 mL) were added propylphosphonic anhydride ($T_3P$) (185.17 mg, 582.0 μmol, 173.06 uL, 3 eq) and DIEA (75.22 mg, 582.0 μmol, 101.37 μL, 3 eq), and the resulting mixture was stirred at 20° C. for 10 h. The mixture was concentrated, and the resulting residue was purified by prep HPLC (column: YMC-Actus Triart C18 150*30 mm*5 μm; mobile phase: [water (0.05% ammonia hydroxide v/v)-ACN]; B %: 25%-65%, 10 min) to give Compound 26 (5.3 mg, 4.66% yield). $^1H$ NMR (400 MHz, DMSO-$d_6$) δ 11.66 (s, 1H), 10.21 (br s, 1H), 10.06 (br s, 1H), 8.67 (d, 1H), 8.42 (s, 1H), 7.78 (d, 2H), 7.64-7.86 (m, 2H), 7.51 (s, 1H), 7.26 (d, 2H), 7.13-7.18 (m, 2H), 6.47 (d, 1H), 5.07-5.09 (m, 1H), 4.73-4.76 (m, 2H), 4.63-4.66 (m, 2H), 3.99 (s, 3H), 1.48 (s, 4H); MS (EI) for $C_{31}H_{27}FN_4O_7$. found 587.1 (MH+).

The following compounds were prepared from Compound 6 in a manner analogous to the method used to form Compound 26 from Compound 6 in the last step of Example 6:

1-N'-(4-Fluorophenyl)-1-N-[4-[6-(2-hydroxyethoxycarbamoyl)-7-methoxyquinolin-4-yl]oxyphenyl]cyclopropane-1,1-dicarboxamide (27): $^1H$ NMR (400 MHz, DMSO-$d_6$) δ 11.47 (s, 1H), 10.22 (s, 1H), 10.07 (s, 1H), 8.67 (d, 1H), 8.46 (s, 1H), 7.78 (d, 2H), 7.61-7.67 (m, 2H), 7.51 (s, 1H), 7.26 (d, 2H), 7.12-7.18 (m, 2H), 6.47 (d, 1H), 4.82 (t, 1H), 4.00 (s, 3H), 3.97 (t, 2H), 3.65 (q, 2H), 1.48 (s, 4H); MS (EI) for $C_{30}H_{27}FN_4O_7$. found 575.1 (MH+).

N-(4-((6-(((2,2-Dimethyl-1,3-dioxolan-4-yl)methoxy)carbamoyl)-7-methoxyquinolin-4-yl)oxy)phenyl)-N-(4-fluorophenyl)cyclopropane-1,1-dicarboxamide (28). MS (EI) for $C_{34}H_{33}FN_4O_8$. found 645.0 (MH+).

Example 7: 1-N-[4-[6-(2,3-Dihydroxypropoxycarbamoyl)-7-methoxyquinolin-4-yl]oxyphenyl]-1-N'-(4-fluorophenyl)cyclopropane-1,1-dicarboxamide, enantiomers 1 (30) and 2 (31)

1-N-[4-[6-(2,3-Dihydroxypropoxycarbamoyl)-7-methoxyquinolin-4-yl]oxyphenyl]-1-N'-(4-fluorophenyl) cyclopropane-1,1-dicarboxamide, enantiomers 1 (30) and 2 (31).

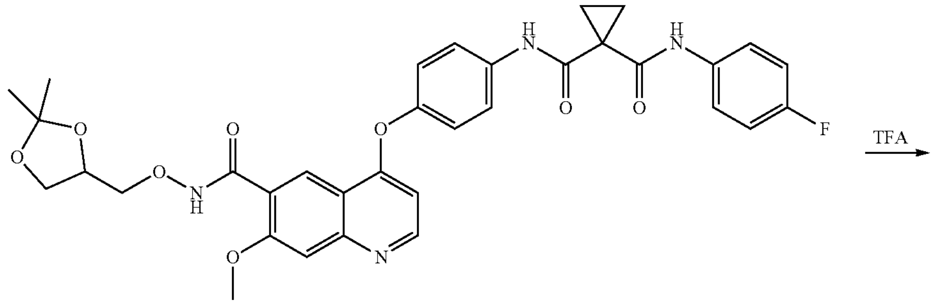

28

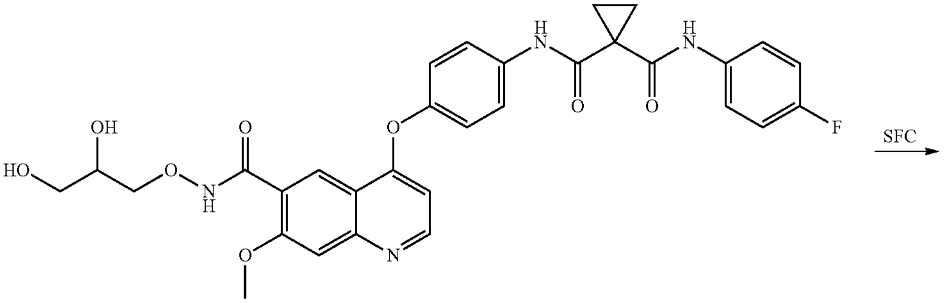

29 Racemate

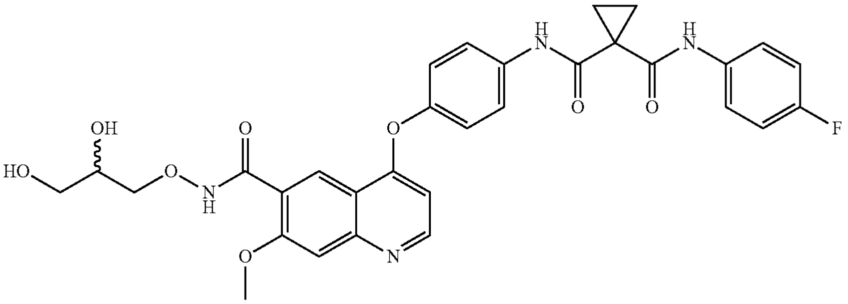

30 Enantiomer 1
31 Enantiomer 2

1-N-[4-[6-(2,3-Dihydroxypropoxycarbamoyl)-7-methoxyquinolin-4-yl]oxyphenyl]-1-N'-(4-fluorophenyl) cyclopropane-1,1-dicarboxamide, racemate (29): To a solution of Compound 28 (300 mg, 465.37 μmol, 1 eq) in DCM (10 mL) was added TFA (53.06 mg, 465.37 μmol, 34.46 uL, 1 eq), and the resulting mixture was stirred at 20° C. for 10 h. Two additional aliquots of TFA totaling 0.35 mL were added, and stirring continued at 20° C. for a total of another 5 h to give a brown solution. The reaction mixture was concentrated in vacuo, and the resulting residue was purified by prep-HPLC (column: Agela DuraShell 150 mm*25 mm*5 μm; mobile phase: [water (0.225% FA)-ACN]; B %: 11%-51%, 10 min) to give compound 29 (85 mg, 30.21%) $^1$H NMR (400 MHz, DMSO-$d_6$) δ 11.54 (br s, 1H), 10.22 (br s, 1H), 10.07 (br s, 1H), 8.67 (d, 1H), 8.49 (s, 1H), 7.77 (d, 2H), 7.64-7.67 (m, 2H), 7.52 (s, 1H), 7.26 (d, Hz, 2H), 7.14-7.16 (m, 2H), 6.47 (d, 1H), 5.00 (br s, 1H), 4.67 (br s, 1H), 3.99-4.02 (m, 4H), 3.78-3.85 (m, 2H), 3.39-3.42 (m, 2H), 1.48 (s, 4H); MS (EI) for $C_{31}H_{29}FN_4O_8$. found 605.4 (MH+).

The individual enantiomers of the racemic Compound 29 (85 mg, 140.59 μmol, 1 eq) were separated using SFC (column: DAICEL CHIRALPAK AD (250 mm*30 mm, 10 um); mobile phase: [0.1% NH3H2O IPA]; B %: 45%-45%, min) to give Compound 30 (53.0 mg, 62.35%) and Compound 31 (21.3 mg, 25.06% yield). Compound 30: $^1$H NMR (400 MHz, DMSO-$d_6$) δ 11.54 (br s, 1H), 10.22 (br s, 1H), 10.07 (br s, 1H), 8.67 (d, 1H), 8.49 (s, 1H), 7.77 (d, 2H), 7.64-7.67 (m, 2H), 7.52 (s, 1H), 7.26 (d, 2H), 7.14-7.16 (m, 2H), 6.47 (d, 1H), 5.00 (d, 1H), 4.67 (t, 1H), 3.99-4.03 (m, 4H), 3.78-3.93 (m, 2H), 3.39-3.47 (m, 2H), 1.48 (s, 4H); MS (EI) for $C_{31}H_{29}FN_4O_8$. found 605.3 (MH+). Compound 31: $^1$H NMR (400 MHz, DMSO-$d_6$) δ 11.54 (br s, 1H), 10.23 (br s, 1H), 10.08 (br s, 1H), 8.67 (d, 1H), 8.49 (s, 1H), 7.79 (d, 2H), 7.64-7.67 (m, 2H), 7.51 (s, 1H), 7.26 (d, 2H), 7.14-7.18 (m, 2H), 6.47 (d, 1H), 5.03 (br s, 1H), 4.69 (br s, 1H), 4.00-4.04 (m, 4H), 3.76-3.86 (m, 2H), 3.52-3.56 (m, 2H), 1.48 (s, 4H); MS (EI) for $C_{31}H_{29}FN_4O_8$. found 605.0 (MH+).

Example 8: 1-N'-(4-Fluorophenyl)-1-N-[4-[6-(hydrazinecarbonyl)-7-methoxyquinolin-4-yl]oxyphenyl]cyclopropane-1,1-dicarboxamide (32)

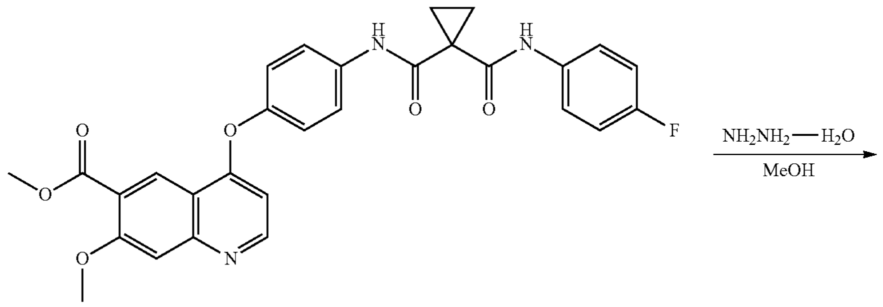

5

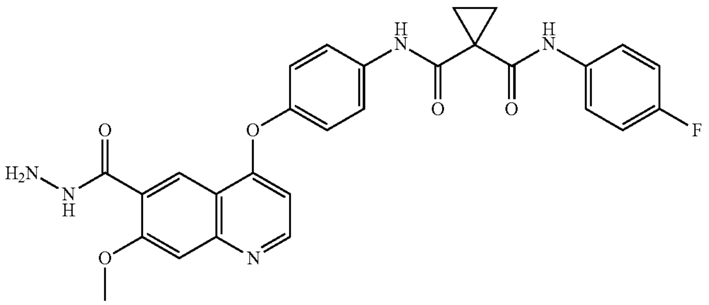

32

1-N'-(4-Fluorophenyl)-1-N-[4-[6-(hydrazinecarbonyl)-7-methoxyquinolin-4-yl]oxyphenyl]cyclopropane-1,1-dicarboxamide (32): To a solution of Compound 5 (100 mg, 188.85 μmol, 1 eq) in MeOH (5 mL) was added $NH_2NH_2$—$H_2O$ (28.36 mg, 566.56 μmol, 27.54 uL, 3eq). The resulting mixture was stirred at 50° C. for 2 h and then concentrated in vacuo. The residue was triturated with MeOH (3 mL), and the resulting residue was filtered to give Compound 32 (56.6 mg, 53.77% yield). $^1H$ NMR (400 MHz, DMSO-$d_6$) δ 10.21 (s, 1H), 10.06 (s, 1H), 9.51 (br s, 1H), 8.66 (d, 1H), 8.53 (s, 1H), 7.78 (d, 2H), 7.69-7.60 (m, 2H), 7.51 (s, 1H), 7.26 (d, 2H), 7.16 (t, 2H), 6.48 (d, 1H), 4.62 (br d, 2H), 4.01 (s, 3H), 1.48 (s, 4H); MS (EI) for $C_{28}H_{24}FN_5O_5$. found 530.2 (MH+).

Example 9: 1-N-[4-(6-Acetyl-7-methoxyquinolin-4-yl)oxyphenyl]-1-N'-(4-fluorophenyl)cyclopropane-1,1-dicarboxamide (34)

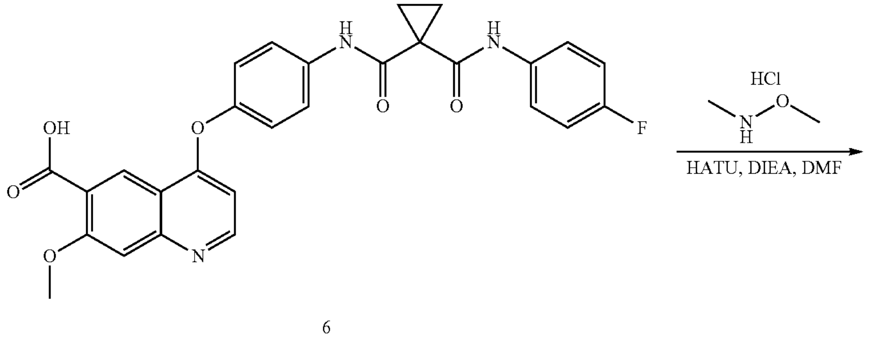

6

-continued

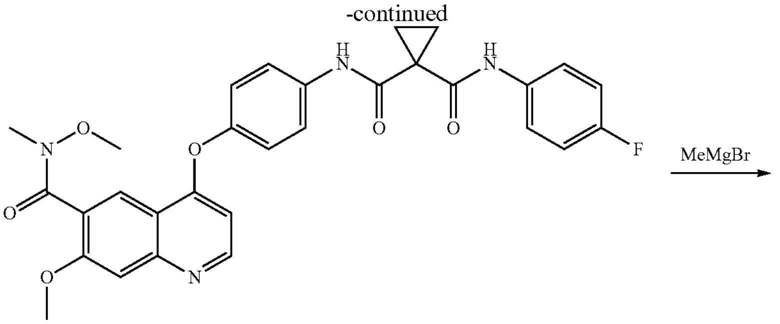

33

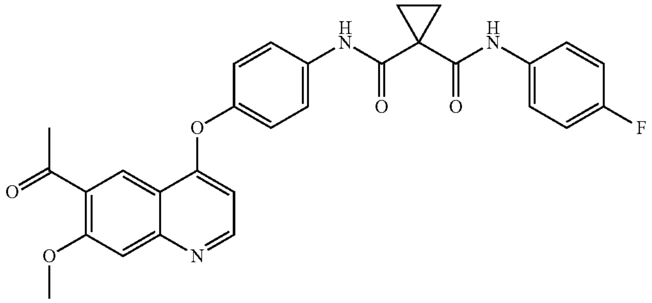

34

N-(4-Fluorophenyl)-N-(4-((7-methoxy-6-(methoxy (methyl)carbamoyl)quinolin-4-yl)oxy)phenyl)cyclopropane-1,1-dicarboxamide (33): To a solution of Compound 6 (300 mg, 581.97 μmol, 1 eq) and N, O-dimethylhydroxylamine hydrochloride (170.30 mg, 1.75 mmol, 3 eq) in DMF (3 mL) were added HATU (442.57 mg, 1.16 mmol, 2 eq) and DIEA (225.65 mg, 1.75 mmol, 304.11 uL, 3 eq). The resulting mixture was stirred at 20° C. for 3 h to give a brown solution. The mixture was diluted with EtOAc (60 mL) and washed with water (2×20 mL) and aq saturated NaCl (20 mL). The organic phase was concentrated in vacuo, and the resulting residue was purified by flash silica gel chromatography (ISCO®; 5 g SepaFlash® Silica Flash Column, Eluent of 0 to approximately 20% MeOH/DCM gradient at 10 mL/min) to give Compound 33 (300 mg, 89.52% yield. MS (EI) for $C_{30}H_{27}FN_4O_6$. found 559.2 (MH+).

1-N-[4-(6-Acetyl-7-methoxyquinolin-4-yl)oxyphenyl]-1-N'-(4-fluorophenyl)cyclopropane-1,1-dicarboxamide (34): To a solution of Compound 33 (280 mg, 501.29 μmol, 1 eq) in THF (5 mL) was added MeMgBr (3 M, 1.67 mL, 10 eq) at 0° C. under an atmosphere of nitrogen. The resulting mixture was stirred at 20° C. for 15 h to give a brown suspension. The reaction mixture was quenched with aq saturated $NH_4Cl$ (20 mL), extracted with EtOAc (3×15 mL), and concentrated. The resulting residue was purified by flash silica gel chromatography (ISCO®; 4 g SepaFlash® Silica Flash Column, Eluent of 0 4% MeOH/DCM gradient @ 10 mL/min). The resulting crude product was further purified (ISCO®; 4 g SepaFlash® Silica Flash Column, Eluent of 0 to approximately 60% EtOAc/petroleum ether gradient @ 10 mL/min) to give Compound 34 (190 mg, 73.81% yield). $^1H$ NMR (400 MHz, $CDCl_3$) δ 9.40 (br s, 1H), 8.90 (br s, 1H), 8.68 (s, 1H), 7.51 (d, 1H), 7.63-7.66 (m, 2H), 7.45-7.50 (m, 3H), 7.14-7.16 (m, 2H), 7.02-7.07 (m, 2H), 6.43 (d, 1H), 4.05 (s, 3H), 2.71 (s, 3H), 1.16-1.72 (m, 4H); MS (EI) for $C_{29}H_{24}FN_3O_5$. found 536.1 $(MH+Na)^+$.

Example 10: 1-N'-(4-Fluorophenyl)-1-N-[4-[7-methoxy-6-[(E)-N-methoxy-C-methylcarbonimidoyl]quinolin-4-yl]oxyphenyl]cyclopropane-1,1-dicarboxamide (35) and 1-N'-(4-Fluorophenyl)-1-N-[4-[7-methoxy-6-[(Z)—N-methoxy-C-methylcarbonimidoyl]quinolin-4-yl]oxyphenyl] cyclopropane-1,1-dicarboxamide (36)

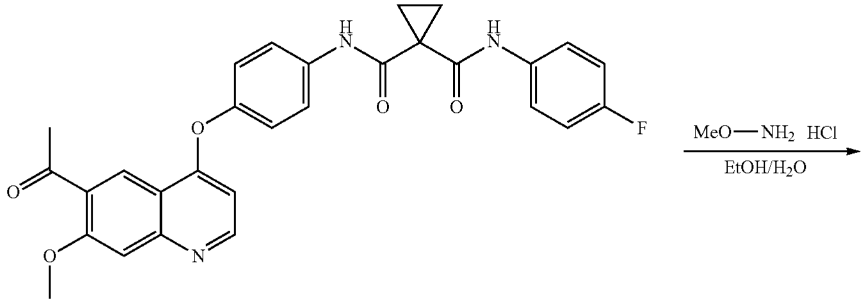

34

-continued

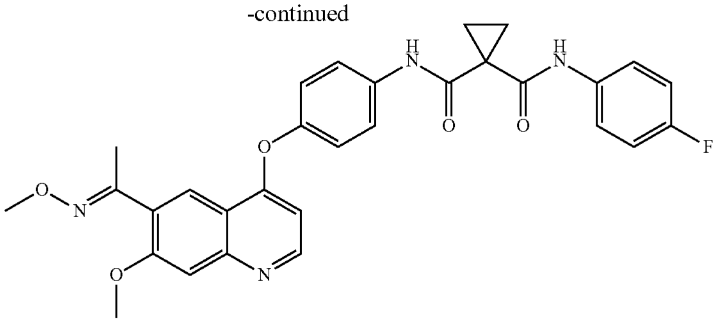

35

+

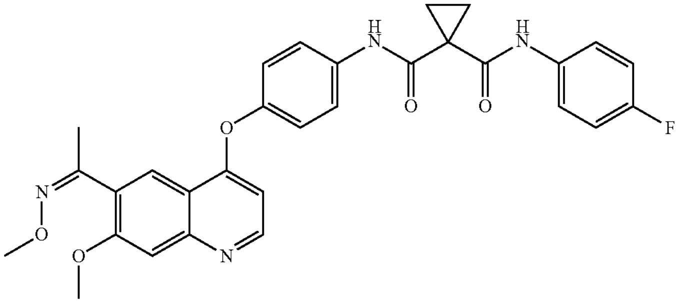

36

To a solution of Compound 34 (140 mg, 272.63 μmol, 1 eq) in water (2.5 mL) and EtOH (2.5 mL) was added methoxyamine hydrochloride (45.54 mg, 545.26 μmol, 41.40 uL, 2 eq), and the resulting mixture was stirred at 50° C. for 2 h to give a brown solution. The reaction mixture was diluted with EtOAc (50 mL), washed with water (2×20 mL), and concentrated. The resulting residue was purified by flash silica gel chromatography (ISCO®; 4 g SepaFlash® Silica Flash Column, Eluent of 0 to approximately 80% EtOAc/Petroleum ether gradient @ 10 mL/min) twice. Compounds 35 and 36 were recovered as a mixture of Z and E isomers (110 mg, 69.7% yield)(MS (EI) for $C_{30}H_{27}FN_4O_5$. found 542.9 (MH+). The Z and E isomers were separated by prep-HPLC (column: Agela DuraShell 150 mm*25 mm*5 μm; mobile phase: [water (0.05% ammonia hydroxide v/v)-ACN]; B %: 47%-87%, 10 min) to give Compound 35 (54.7 mg, 52.10% yield) and Compound 36 (6.4 mg, 6.10% yield). Compound 35: $^1$H NMR (400 MHz, DMSO-$d_6$) δ 10.21 (br s, 1H), 10.07 (br s, 1H), 8.63 (d, 1H), 8.09 (s, 1H), 7.77 (d, 2H), 7.65-7.68 (m, 2H), 7.49 (s, 1H), 7.77 (d, 2H), 7.16 (t, 2H), 6.44 (d, 1H), 3.99 (s, 3H), 3.91 (s, 3H), 2.16 (s, 3H), 1.48 (s, 4H). Compound 36: $^1$H NMR (400 MHz, DMSO-$d_6$) δ 10.21 (br s, 1H), 10.07 (br s, 1H), 8.61 (d, 1H), 7.97 (s, 1H), 7.77 (d, 2H), 7.63-7.66 (m, 2H), 7.47 (s, 1H), 7.25 (d, 2H), 7.16 (t, 2H), 6.43 (d, 1H), 3.95 (s, 3H), 3.70 (s, 3H), 2.15 (s, 3H), 1.48 (s, 4H).

Example 11: 1-N-[4-(6-Cyano-7-methoxyquinolin-4-yl)oxyphenyl]-1-N'-(4-fluorophenyl)cyclopropane-1,1-dicarboxamide (37)

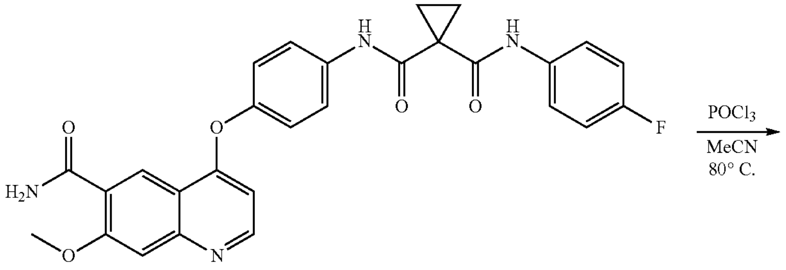

7

-continued

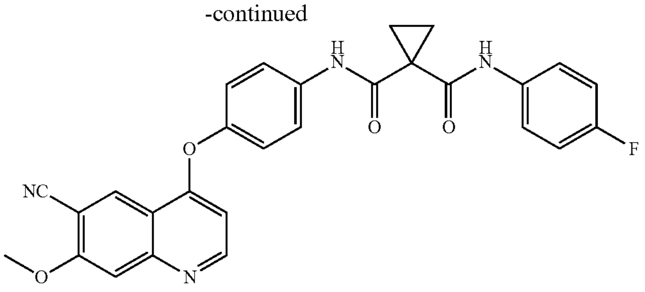

37

1-N-[4-(6-Cyano-7-methoxyquinolin-4-yl)oxyphenyl]-1-N'-(4-fluorophenyl)cyclopropane-1,1-dicarboxamide (37): To Compound 7 (200 mg, 379.12 μmol, 1 equiv) in MeCN (10 mL) was added $POCl_3$ (7.78 g, 50.74 mmol, 4.72 mL, 134 equiv). The mixture was stirred at 80° C. for 3 h. The reaction mixture was filtered, and the filtrate was concentrated and dried under vacuum. The residue was diluted with water (5 mL), the pH was adjusted to 8-9 with aq $Na_2CO_3$, and the residue was extracted with DCM (3x20 mL). The combined organic layers were concentrated and then dried under vacuum. The residue was purified by prep HPLC to give Compound 37 (80.3 mg, 42.37% yield). $^1H$ NMR (400 MHz, DMSO-$d_6$) δ 10.23 (br s, 1H), 10.05 (br s, 1H), 8.79-8.72 (m, 2H), 7.79 (br d, 2H), 7.68-7.58 (m, 3H), 7.27 (d, 2H), 7.15 (t, 2H), 6.52 (d, 1H), 4.07 (s, 3H), 1.48 (s, 4H); MS (EI) for $C_{28}H_{21}FN_4O_4$. found 497.1 (MH+).

Example 12: N-(4-((6-Bromo-7-methoxyquinolin-4-yl)oxy)phenyl)-N-(4-fluorophenyl)cyclopropane-1,1-dicarboxamide (43)

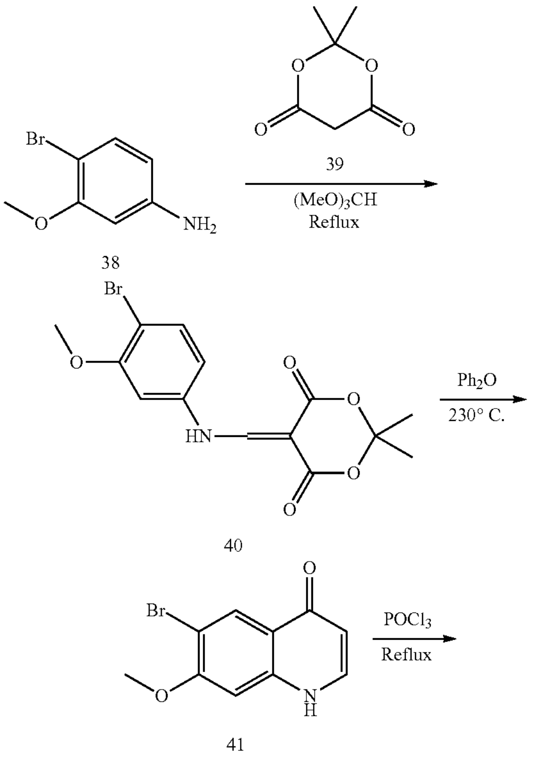

-continued

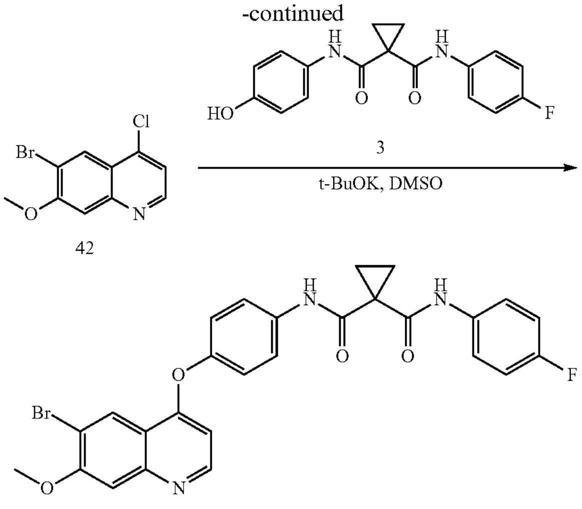

5-(((4-Bromo-3-methoxyphenyl)amino)methylene)-2,2-dimethyl-1,3-dioxane-4,6-dione (40): Compound 39 (4.10 g, 28.46 mmol, 1.15 eq) in trimethoxymethane (25 mL, 228.04 mmol, 9.22 eq) was heated to reflux at 105° C. for 1 h. Compound 38 (5 g, 24.75 mmol, 1 eq) was then added, and the reflux continued at 105° C. for another 1 h. The resulting suspension was filtered, washed with MeOH, and vacuum dried to yield Compound 40 (7.7 g, 87.4% yield), which was used in the next step without further purification. $^1H$ NMR (400 MHz, $CDCl_3$) δ 11.24-11.20 (d, 1H), 8.62-9.59 (d, 1H), 7.57-7.54 (d, 1H), 6.77-6.74 (m, 2H), 3.94 (s, 3H), 1.76 (s, 3H), 1.74 (s, 3H).

6-Bromo-7-methoxyquinolin-4(1H)-one (41): To $Ph_2O$ (35 mL) at 230° C. was added Compound 40 (7.7 g, 21.62 mmol, 1 eq), and the mixture was stirred for 1 h. After cooling to room temperature, the reaction mixture was poured into hexane (20 mL), and the resulting precipitate was filtered and washed with hexane. The resulting residue was dried under vacuum to give Compound 41 (6.2 g, 75.8% yield, 67.2% purity). $^1H$ NMR (400 MHz, DMSO-$d_6$) δ 11.78 (s, 1H), 8.18 (s, 1H), 7.88-7.86 (d, 1H), 7.05 (s, 1H), 6.03-6.01 (d, 1H), 3.92 (s, 3H); MS (EI) for $C_{10}H_8BrNO_2$. found 254.2 (MH+).

6-Bromo-4-chloro-7-methoxyquinoline (42): Compound 41 (6.2 g, 16.40 mmol, 1 eq) in $POCl_3$ (15 mL, 161.41 mmol, 9.84 eq) was stirred at 110° C. for 1 h. After cooling, the reaction mixture was cautiously poured into a mixture of aq saturated $Na_2CO_3$ and ice with stirring. The resulting suspension was filtered, washed with water, and dried under vacuum to give Compound 42 (7.78 g, 57.4% purity, 99.9% yield), which was used in subsequent steps without further purification. MS (EI) for $C_{10}H_7BrClNO$, found 272.2 (MH+).

N-(4-((6-Bromo-7-methoxyquinolin-4-yl)oxy)phenyl)-N-(4-fluorophenyl)cyclopropane-1,1-dicarboxamide (43): A mixture of Compound 42 (5.72 g, 12.05 mmol, 1.26 eq), Compound 3 (3.00 g, 9.54 mmol, 1 eq), and t-BuOK (3.21 g, 28.63 mmol, 3 eq) in DMSO (30 mL) was stirred at 150° C. for 2 h. Aq saturated $NH_4Cl$ (200 mL) was added, and the mixture was extracted with EtOAc (3×250 mL). The combined organic phases were dried over anhyd $Na_2SO_4$ and concentrated in vacuo. The resulting residue was purified by flash silica gel chromatography (ISCO®; 40 g SepaFlash® Silica Flash Column, Eluent of 0 to approximately 100% EtOAc/Petroleum ether gradient at 40 mL/min). The resulting residue was triturated with MeOH (50 mL) and filtered to give Compound 43 (3.0 g, 57.11% yield). $^1H$ NMR (400 MHz, $CDCl_3$) δ 9.33 (s, 1H), 8.66 (br s, 1H), 8.60 (d, 1H), 8.58 (s, 1H), 7.64 (d, 2H), 7.48 (dd, 2H), 7.45 (s, 1H), 7.18 (d, 2H), 7.07 (t, 2H), 6.45 (d, 1H), 4.07 (s, 3H), 1.78-1.72 (m, 2H), 1.71-1.65 (m, 2H).

The following compound was synthesized in a manner analogous to Compound 43 in the last step of Example 12, substituting Compound 42 with 6-bromo-4-chloroquinoline.

N-(4-((6-Bromoquinolin-4-yl)oxy)phenyl)-N-(4-fluorophenyl)cyclopropane-1,1-dicarboxamide (44). MS (EI) for $C_{26}H_{19}BrFN_3O_3$. found 520.0 (MH+).

Example 13: 1-N'-(4-Fluorophenyl)-1-N-[4-[7-methoxy-6-(1,3-oxazol-2-yl)quinolin-4-yl]oxyphenyl]cyclopropane-1,1-dicarboxamide (45)

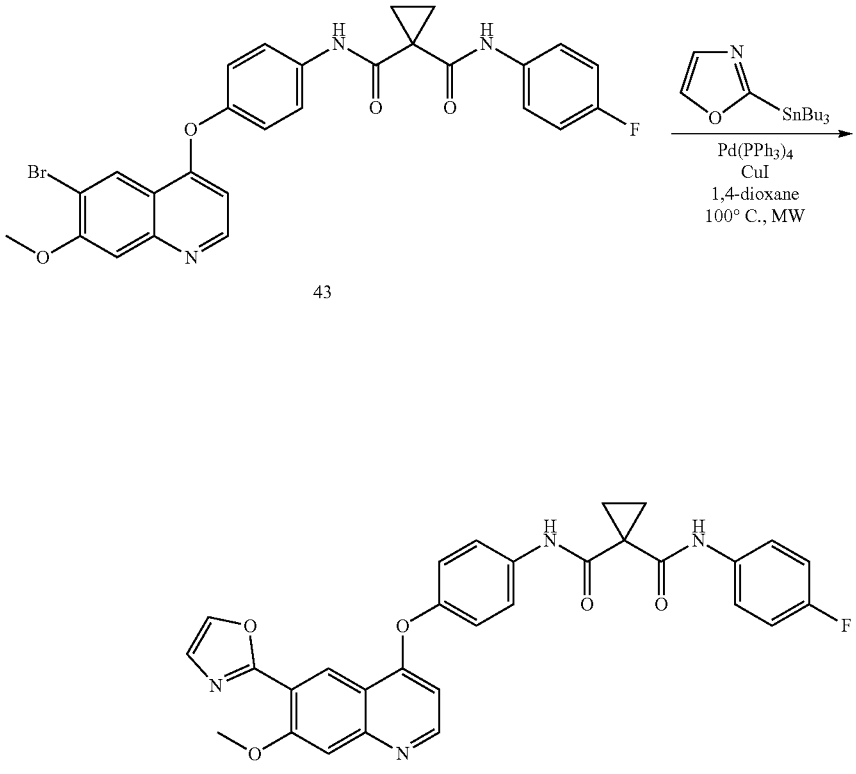

43

45

1-N'-(4-Fluorophenyl)-1-N-[4-[7-methoxy-6-(1,3-oxazol-2-yl)quinolin-4-yl]oxyphenyl]cyclopropane-1,1-dicarboxamide (45): Compound 43 (200 mg, 363.39 μmol, 1 equiv), tributyl(oxazol-2-yl)stannane (200.0 mg, 558.5 μmol, 1.5 equiv), CuI (8 mg, 42.0 μmol, 0.12 equiv), and $Pd(PPh_3)_4$ (48.0 mg, 41.5 μmol, 0.11 equiv) were combined in 1,4-dioxane (5 mL) in a sealed tube, which was then heated at 100° C. under microwave irradiation for 30 min. The reaction mixture was concentrated under vacuum, and the resulting residue was purified initially by flash silica gel chromatography (0~100% EtOAc/Petroleum ether) and subsequently by prep HPLC to give Compound 45 (81.5 mg, 41.3% yield). $^1H$ NMR (400 MHz, $CDCl_3$) δ 9.36 (s, 1H), 8.98 (s, 1H), 8.75 (br s, 1H), 8.63 (d, 1H), 7.82 (s, 1H), 7.65 (d, 2H), 7.57 (s, 1H), 7.48 (dd, 2H), 7.36 (s, 1H), 7.19 (d, 2H), 7.06 (t, 2H), 6.46 (d, 1H), 4.13 (s, 3H), 1.77-1.74 (m, 2H), 1.73-1.69 (m, 2H); MS (EI) for $C_{30}H_{23}FN_4O_5$. found 539.1 (MH+).

Example 14: 1-N'-(4-Fluorophenyl)-1-N-[4-[7-(2-hydroxyethoxy)-6-(1,3-oxazol-2-yl)quinolin-4-yl]oxyphenyl]cyclopropane-1,1-dicarboxamide (50)

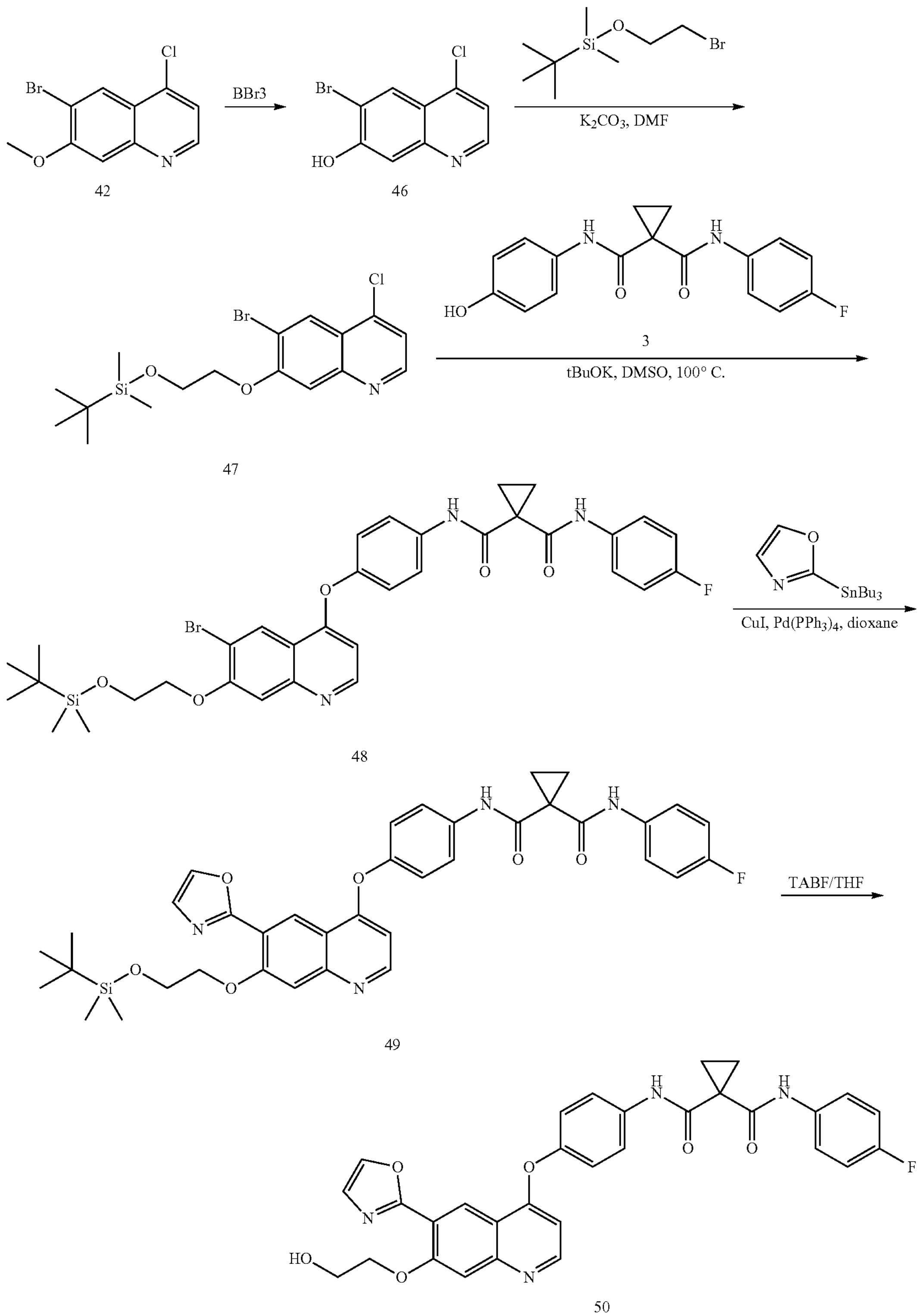

42, 46, 3, 47, 48, 49, 50

6-Bromo-4-chloroquinolin-7-ol (46): A mixture of Compound 42 (5 g, 18.35 mmol, 1 eq) and $BBr_3$ (13.00 g, 51.89 mmol, 5 mL, 2.83 eq) in DCE (15 mL) was stirred under an atmosphere of nitrogen at 90° C. for 2.5 h. The reaction mixture was cooled to room temperature and poured into aq saturated $NaHCO_3$ with vigorous stirring. The resulting residue was filtered, washed with water, dissolved in methyl tert-butyl ether, and dried. The solvent was removed under reduced pressure to give Compound 46 (7 g), which was used in subsequent reactions without further purification. $^1$H NMR (400 MHz, DMSO-$d_6$) δ 9.03 (d, 1H), 8.49 (s, 1H), 7.93 (d, 1H), 7.69 (s, 1H), 6.08 (s, 1H); MS (EI) for $C_9H_5BrClNO$, found 260.2 (MH+).

6-Bromo-7-(2-((tert-butyldimethylsilyl)oxy)ethoxy)-4-chloroquinoline (47): To a mixture of Compound 46 (1 g, 3.87 mmol, 1 eq) and 2-bromoethoxy-tert-butyl-dimethyl-silane (1.15 g, 4.8 mmol, 1.24 eq) in DMF (10 mL) was added $K_2CO_3$ (1.05 g, 7.60 mmol, 1.96 eq) and NaI (720 mg, 4.80 mmol, 1.24 eq), and the mixture was heated to 80° C. with stirring for 2 h. The reaction mixture was partitioned between water (20 mL) and EtOAc (2×20 mL). The combined organic phases were washed with aq saturated NaCl (10 mL), dried over anhyd $Na_2SO_4$, and concentrated. The resulting residue was purified by flash silica gel chromatography (ISCO®; 12 g SepaFlash® Silica Flash Column, Eluent of 0 to approximately 20% EtOAc/Petroleum ether gradient at 30 mL/min) to give Compound 47 (560 mg, 34.73% yield). $^1$H NMR (400 MHz, $CDCl_3$) δ 8.71 (d, 1H), 8.45 (s, 1H), 7.47 (s, 1H), 7.37 (d, 1H), 4.29-4.26 (m, 2H), 4.13-4.11 (m, 2H), 0.93-0.92 (m, 9H), 0.16-0.14 (m, 6H); MS (EI) for $C_{17}H_{23}BrClNO_2Si$, found 417.8 (MH+).

N-(4-((6-Bromo-7-(2-((tert-butyldimethylsilyl)oxy)ethoxy)quinolin-4-yl)oxy)phenyl)-N-(4-fluorophenyl)cyclopropane-1,1-dicarboxamide (48): Compound 48 was made in a manner analogous to the preparation of Compound 43 from Compound 42 in Example 12. Compound 48 was recovered (400 mg, 48% yield). $^1$H NMR (400 MHz, DMSO-$d_6$) δ 10.20 (s, 1H), 10.01 (s, 1H), 8.63 (d, 1H), 8.47 (s, 1H), 7.77 (d, 2H), 7.65-7.62 (m, 2H), 7.55 (s, 1H), 7.25 (d, 2H), 7.17-7.13 (m, 2H), 6.46 (d, 1H), 4.32-4.30 (t, 2H), 4.05-4.03 (t, 2H), 1.47 (s, 4H), 0.88 (s, 9H), 0.10 (s, 6H); MS (EI) for $C_{34}H_{37}BrFN_3O_5Si$, found 696.1 (MH+).

N-(4-((7-(2-((tert-Butyldimethylsilyl)oxy)ethoxy)-6-(oxazol-2-yl)quinolin-4-yl)oxy)phenyl)-N-(4-fluorophenyl)cyclopropane-1,1-dicarboxamide (49): Compound 49 was made in a manner analogous to the preparation of Compound 45 from Compound 43 in Example 13. Compound 49 was recovered (400 mg, crude). $^1$H NMR (400 MHz, $CDCl_3$) δ 10.20 (s, 1H), 10.06 (s, 1H), 8.74 (s, 1H), 8.67 (d, 1H), 8.25 (s, 1H), 7.78 (d, 2H), 7.62-7.59 (m, 3H), 7.43 (s, 1H), 7.28 (d, 2H), 7.19-7.09 (m, 2H), 6.48 (d, 1H), 4.41-4.25 (m, 2H), 4.04-4.02 (m, 2H), 1.47 (s, 4H), 0.83 (s, 9H), 0.02 (s, 6H); MS (EI) for $C_{37}H39FN_4O_6Si$, found 683.3 (MH+).

1-N'-(4-Fluorophenyl)-1-N-[4-[7-(2-hydroxyethoxy)-6-(1,3-oxazol-2-yl)quinolin-4-yl]oxyphenyl]cyclopropane-1,1-dicarboxamide (50): To a mixture of Compound 49 (350 mg, 512.6 μmol, 1 eq) in THF (20 mL) was added tetrabutyl ammonium fluoride (1 M, 1.40 mL, 2.73 eq), and the resulting reaction mixture was stirred for 0.5 h at 0-20° C., after which it was poured into aq saturated $NaHCO_3$ with vigorous stirring. The resulting mixture was partitioned between water (20 mL) and EtOAc (2×20 mL). The combined organic phases were separated, washed with aq saturated NaCl (10 mL), dried over anhyd $Na_2SO_4$, and concentrated. The resulting residue was recrystallized from MeOH to give Compound 50 (174.3 mg, 58.6% yield). $^1$H NMR (400 MHz, DMSO-$d_6$) δ 10.20 (s, 1H), 10.06 (s, 1H), 8.77 (s, 1H), 8.67 (d, 1H), 8.30 (s, 1H), 7.78 (d, 2H), 7.66-7.63 (m, 3H), 7.45 (s, 1H), 7.28 (d, 2H), 7.17-7.13 (m, 2H), 6.47 (d, 1H), 4.97-4.94 (t, 1H), 4.32-4.30 (t, 2H), 3.86-3.82 (m, 2H), 1.47 (s, 4H); MS (EI) for $C_{31}H_{25}FN_4O_6$. found 569.2 (MH+).

Example 15: 1-N-[4-(6-Dimethylphosphoryl-7-methoxyquinolin-4-yl)oxyphenyl]-1-N'-(4-fluorophenyl)cyclopropane-1,1-dicarboxamide (51)

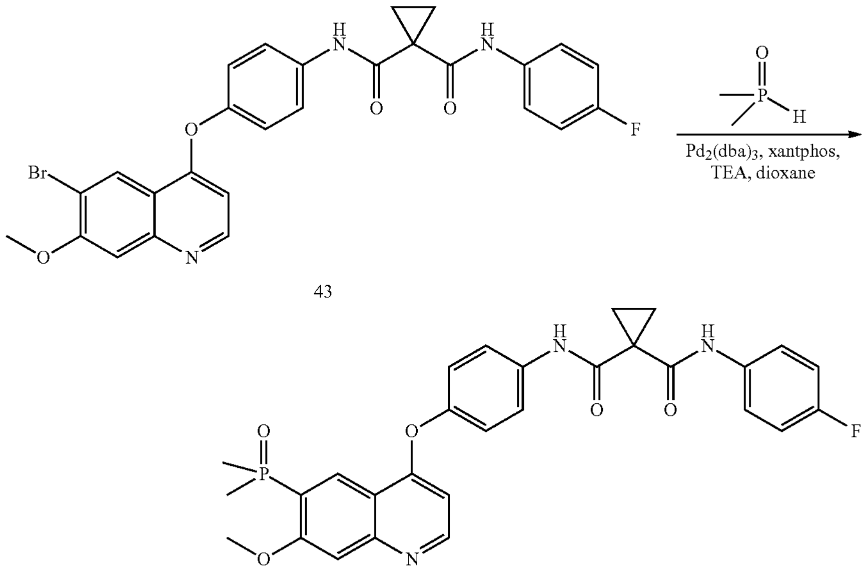

43

51

1-N-[4-(6-Dimethylphosphoryl-7-methoxyquinolin-4-yl)oxyphenyl]-1-N'-(4-fluorophenyl)cyclopropane-1,1-dicarboxamide (51): To a solution of Compound 43 (100 mg, 181.7 μmol, 1 eq) in dioxane (2 mL) was added methylphosphonoylmethane (21.27 mg, 272.5 μmol, 1.5 eq), 4,5-bis(diphenylphosphino)-9,9-dimethylxanthene (Xantphos) (21.03 mg, 36.3 μmol, 0.2 eq), tris(dibenzylideneacetone)dipalladium(0) ($Pd_2(dba)_3$) (33.28 mg, 36.3 μmol, 0.2 eq), and $Et_3N$ (91.93 mg, 908.5 μmol, 126.5 uL, 5 eq). The resulting mixture was stirred at 110° C. for 1 h under an atmosphere of nitrogen. The mixture was concentrated in vacuo and triturated with EtOH (5 mL). The resulting residue was filtered, dried, and purified by prep-HPLC (YMC-Actus Triart C18 150*30 mm*5 μm; mobile phase: [water (0.225% FA)-ACN]; B %: 20%-60%, 10 min) to give Compound 51 (26.2 mg, 26.34% yield, 100% purity). $^{1}$H NMR (400 MHz, DMSO-$d_6$) δ 10.24 (s, 1H), 10.10 (s, 1H), 8.76 (d, 1H), 8.69 (d, 1H), 7.80 (d, 2H), 7.65 (dd, 2H), 7.52 (d, 1H), 7.28 (d, 2H), 7.16 (t, 2H), 6.48 (d, 1H), 4.04 (s, 3H), 1.75 (s, 3H), 1.72 (s, 3H), 1.48 (s, 4H); MS (EI) for $C_{29}H_{27}FN_3O_5P$, found 548.1 (MH+).

Example 16: Methyl 4-(4-(1-((4-fluorophenyl)carbamoyl)cyclopropane-1-carboxamido)phenoxy)quinoline-6-carboxylate (56)

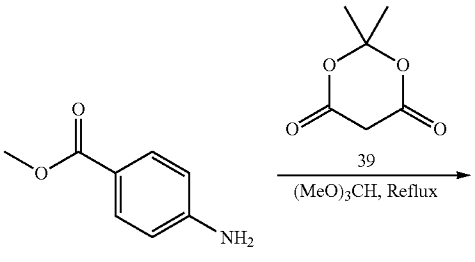

52

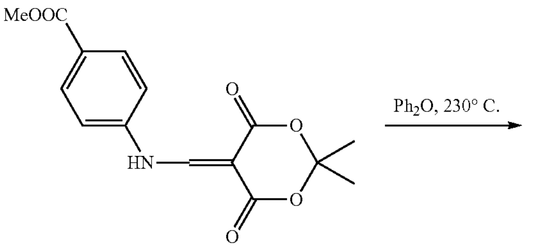

53

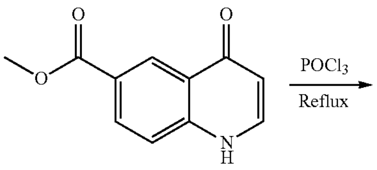

54

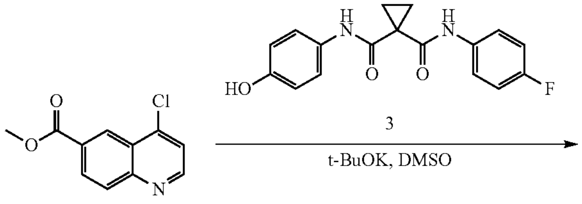

55

-continued

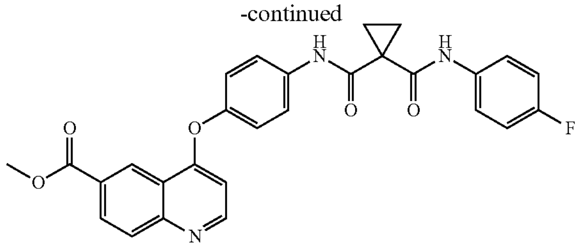

56

Methyl 4-(((2,2-dimethyl-4,6-dioxo-1,3-dioxan-5-ylidene)methyl)amino)benzoate (53): Compound 53 was synthesized from Compounds 52 and 39 in a manner analogous to the preparation of Compound 40 from Compounds 38 and 39 in Example 12. Compound 53 was obtained (9 g, 89.1% yield). $^{1}$H NMR (400 MHz, $CDCl_3$) δ 11.32 (br d, 1H), 8.70 (d, 1H), 8.13 (d, 2H), 7.31 (d, 2H), 3.94 (s, 3H), 1.77 (s, 6H).

Methyl 4-oxo-1,4-dihydroquinoline-6-carboxylate (54): Compound 54 was synthesized from Compound 53 in a manner analogous to the preparation of Compound 41 from Compound 40 in Example 12. Compound 54 was obtained (1.3 g, crude). $^{1}$H NMR (400 MHz, DMSO-$d_6$) δ 12.03 (s, 1H), 8.74-8.64 (m, 1H), 8.14 (dd, 1H), 8.01-7.93 (m, 1H), 7.64-7.58 (m, 1H), 6.11 (d, 1H), 3.88 (s, 3H).

Methyl 4-chloroquinoline-6-carboxylate (55): Compound 55 was synthesized from Compound 54 in a manner analogous to the preparation of Compound 42 from Compound 41 in Example 12. Compound 55 was obtained (0.5 g, 35.3% yield). $^{1}$E1 NMR (400 MHz, $CDCl_3$) δ 9.00 (d, 1H), 8.89 (d, 1H), 8.38 (dd, 1H), 8.19 (d, 1H), 7.58 (d, 1H), 4.03 (s, 3H); MS (EI) for $C_{11}H_8ClNO_2$. found 221.9 (MH+).

Methyl 4-(4-(1-((4-fluorophenyl)carbamoyl)cyclopropane-1-carboxamido)phenoxy)quinoline-6-carboxylate 56: Compound 56 was synthesized from Compounds 55 and 3 in a manner analogous to the preparation of Compound 43 from Compounds 42 and 3 in Example 12. Compound 56 was obtained (0.9 g, 99.8% yield). MS (EI) for $C_{28}H_{22}FN_3O_5$. found 500.4 (MH+).

Example 17: 4-(4-(1-((4-Fluorophenyl)carbamoyl)cyclopropane-1-carboxamido)phenoxy)quinoline-6-carboxylic acid (57)

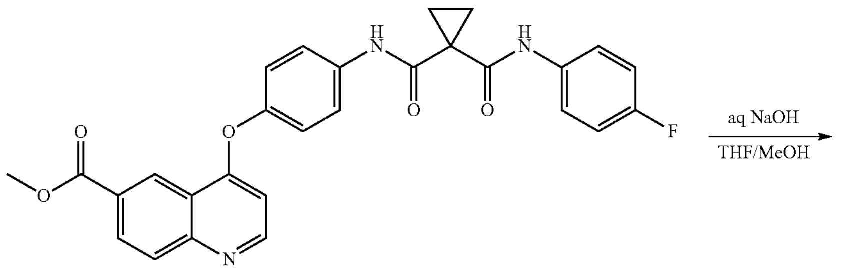

56

-continued

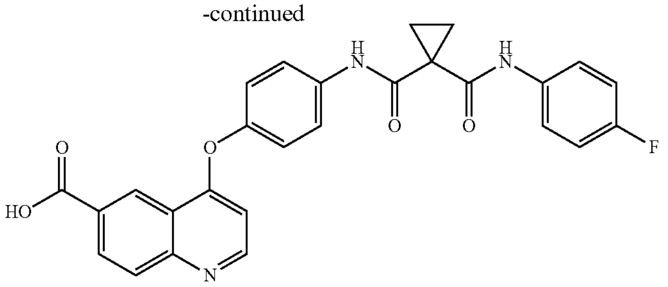

57

4-(4-(1-((4-Fluorophenyl)carbamoyl)cyclopropane-1-carboxamido)phenoxy)quinoline-6-carboxylic acid (57): Compound 57 was synthesized from Compound 56 in a manner analogous to the preparation of Compound 6 from Compound 5 in Example 2. Compound 57 was obtained (0.5 g, 57.2% yield). MS (EI) for $C_{27}H_{20}FN_3O_5$. found 486.0 (MH+).

Example 18: 1-N-[4-(6-Carbamoylquinolin-4-yl)oxyphenyl]-1-N'-(4-fluorophenyl)cyclopropane-1,1-dicarboxamide (58)

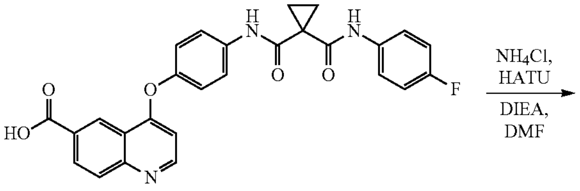

57

-continued

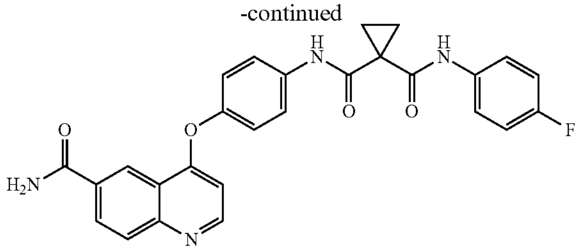

58

N-(4-((6-Carbamoylquinolin-4-yl)oxy)phenyl)-N-(4-fluorophenyl)cyclopropane-1,1-dicarboxamide (58): Compound 58 was synthesized from Compound 57 in a manner analogous to the preparation of Compound 7 from Compound 6 in Example 3. Compound 58 was obtained (26 mg, 26.0% yield). $^1H$ NMR (400 MHz, DMSO-$d_6$) δ 10.22 (s, 1H), 10.06 (s, 1H), 8.90 (d, 1H), 8.74 (d, 1H), 8.34 (br s, 1H), 8.26 (dd, 1H), 8.06 (d, 1H), 7.80 (d, 2H), 7.64 (dd, 2H), 7.56 (br s, 1H), 7.29 (d, 2H), 7.15 (t, 2H), 6.61 (d, 1H), 1.48 (s, 4H); MS (EI) for $C_{27}H_{21}FN_4O_4$. found 485.1 (MH+).

Example 19: 1-N'-(4-Fluorophenyl)-1-N-[4-[6-(methylcarbamoyl)quinolin-4-yl]oxyphenyl]cyclopropane-1,1-dicarboxamide (59)

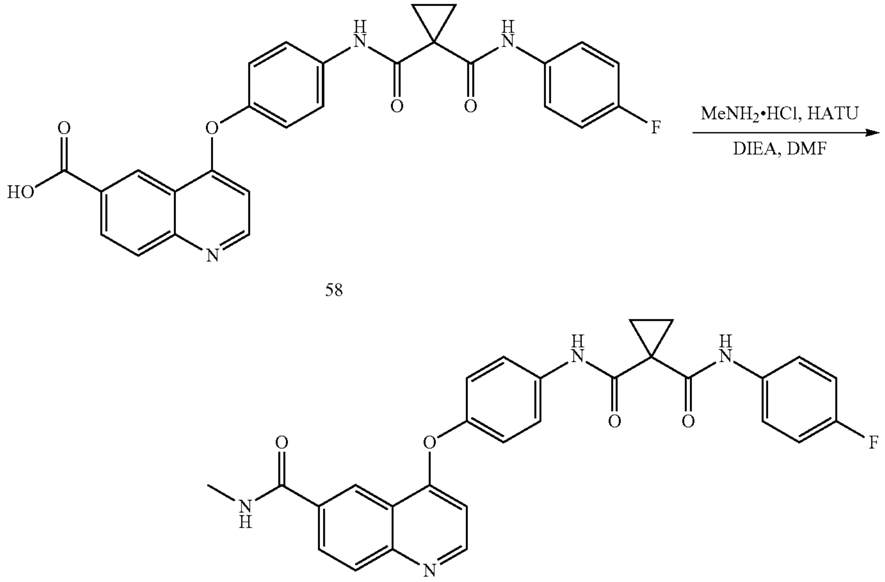

58

59

1-N'-(4-Fluorophenyl)-1-N-[4-[6-(methylcarbamoyl)quinolin-4-yl]oxyphenyl]cyclopropane-1,1-dicarboxamide (59): Compound 59 was synthesized from Compound 58 in a manner analogous to the preparation of Compound 8 from Compound 6 in Example 4. Compound 59 was obtained (31.1 mg, 30.3% yield). $^1$H NMR (400 MHz, DMSO-d$_6$) δ 10.22 (s, 1H), 10.05 (s, 1H), 8.86 (d, 1H), 8.81 (br d, 1H), 8.74 (d, 1H), 8.23 (dd, 1H), 8.07 (d, 1H), 7.80 (d, 2H), 7.64 (dd, 2H), 7.29 (d, 2H), 7.15 (t, 2H), 6.61 (d, 1H), 2.85 (d, 3H), 1.48 (s, 4H); MS (EI) for $C_{28}H_{23}FN_4O_4$. found 499.1 (MH+).

The following compound was prepared by a method analogous to the preparation of Compound 59 in Example 19:

1-N'-(4-Fluorophenyl)-1-N-[4-[6-[(1-methylazetidin-3-yl)carbamoyl]quinolin-4-yl]oxyphenyl]cyclopropane-1,1-dicarboxamide (60): $^1$H NMR (400 MHz, DMSO-d$_6$) δ 10.23 (s, 1H), 10.05 (s, 1H), 9.23-9.14 (m, 1H), 8.89 (s, 1H), 8.75 (d, 1H), 8.25 (d, 1H), 8.08 (d, 1H), 7.81 (br d, 2H), 7.68-7.62 (m, 2H), 7.30 (d, 2H), 7.16 (t, 2H), 6.61 (d, 1H), 4.60-4.44 (m, 1H), 3.69-3.60 (m, 2H), 3.31 (s, 3H), 3.20-3.09 (m, 2H), 1.48 (s, 4H); MS (D) for $C_{31}H_{28}FN_5O_4$. found 554.1 (MH+).

Example 20: Methyl 7-fluoro-4-(4-(1-((4-fluorophenyl)carbamoyl)cyclopropane-1-carboxamido)phenoxy)quinoline-6-carboxylate (65)

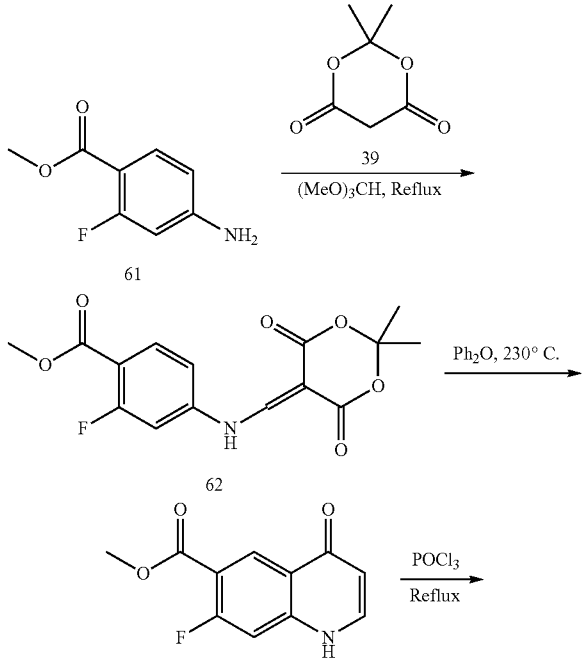

61

62

63

-continued

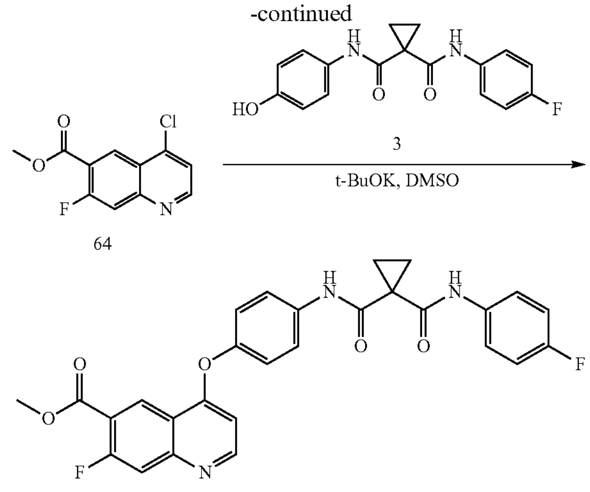

64

65

Methyl 4-(((2,2-dimethyl-4,6-dioxo-1,3-dioxan-5-ylidene)methyl)amino)-2-fluorobenzoate (62): Compound 62 was synthesized from Compounds 61 and 39 in a manner analogous to the preparation of Compound 40 from Compounds 38 and 39 in Example 12. Compound 62 was obtained (4.8 g, 50.2% yield). $^1$H NMR (400 MHz, DMSO-d$_6$) δ 11.28 (s, 1H), 8.65 (s, 1H), 7.91 (t, 1H), 7.72 (dd, 1H), 7.52 (dd, 1H), 3.84 (s, 3H), 1.68 (s, 6H).

Methyl 7-fluoro-4-oxo-1,4-dihydroquinoline-6-carboxylate (63): Compound 63 was synthesized from Compound 62 in a manner analogous to the preparation of Compound 41 from Compound 40 in Example 12. Compound 63 was obtained (0.8 g, 58.5% yield). MS (D) for $C_{11}H_8FNO_3$. found 222.2 (MH+).

Methyl 4-chloro-7-fluoroquinoline-6-carboxylate (64): Compound 64 was synthesized from Compound 63 in a manner analogous to the preparation of Compound 42 from Compound 41 in Example 12. Compound 64 was obtained (110 mg, 31% yield). $^1$H NMR (400 MHz, $CDCl_3$) δ 8.90 (d, 1H), 8.85 (d, 1H), 7.84 (d, 1H), 7.53 (d, 1H), 4.03 (s, 3H); MS (EI) for $C_{11}H_7ClFNO_2$. found 240.0 (MH+).

Methyl 4-(4-(1-((4-fluorophenyl)carbamoyl)cyclopropane-1-carboxamido)phenoxy)quinoline-6-carboxylate (65): Compound 65 was synthesized from Compounds 64 and 3 in a manner analogous to the preparation of Compound 43 from Compounds 42 and 3 in Example 12. Compound 65 was obtained (90 mg, 92.6% yield). MS (EI) for $C_{28}H_{21}F_2N_3O_5$. found 518.3 (MH+).

Example 21: 7-Fluoro-4-(4-(1-((4-fluorophenyl)carbamoyl)cyclopropane-1-carboxamido)phenoxy)quinoline-6-carboxylic Acid (66)

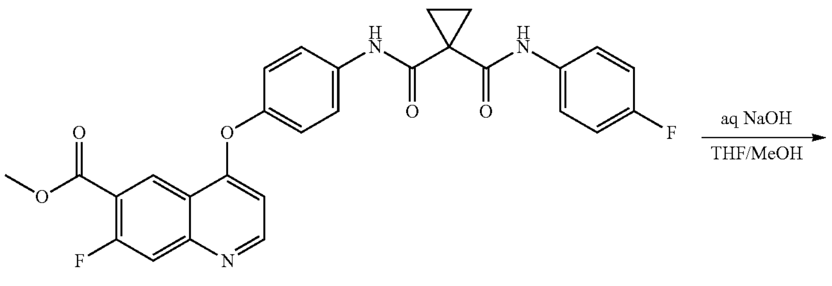

65

-continued

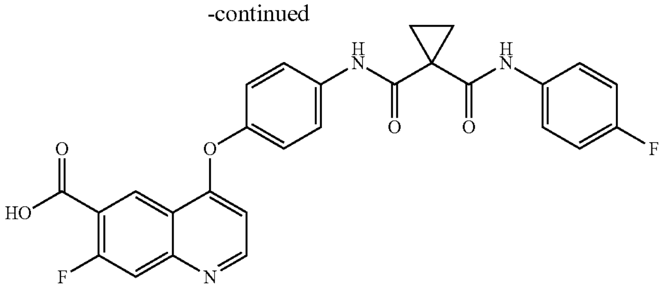

66

7-Fluoro-4-(4-(1-((4-fluorophenyl)carbamoyl)cyclopropane-1-carboxamido)phenoxy)quinoline-6-carboxylic acid (66): Compound 66 was synthesized from Compound 65 in a manner analogous to the preparation of Compound 6 from Compound 5 in Example 2. Compound 66 was obtained (50 mg, 57.1% yield). MS (EI) for $C_{27}H_{19}F_2N_3O_5$. found 504.4 (MH+).

Example 22: 1-N-[4-(6-Carbamoyl-7-fluoroquinolin-4-yl)oxyphenyl]-1-N'-(4-fluorophenyl)cyclopropane-1,1-dicarboxamide (67)

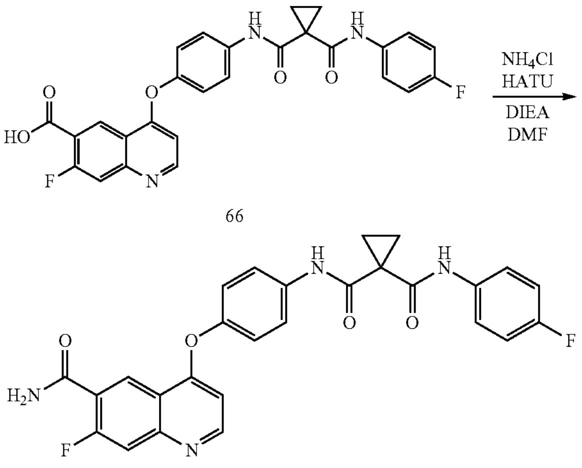

66

67

1-N-[4-(6-Carbamoyl-7-fluoroquinolin-4-yl)oxyphenyl]-1-N'-(4-fluorophenyl)cyclopropane-1,1-dicarboxamide (67): Compound 67 was synthesized from Compound 66 in a manner analogous to the preparation of Compound 7 from Compound 6 in Example 3. Compound 67 was obtained (7.6 mg, 15.2% yield). $^1H$ NMR (400 MHz, $CDCl_3$) δ 9.47 (s, 1H), 9.24 (d, 1H), 8.84 (s, 1H), 8.71 (d, 1H), 7.79 (d, 1H), 7.67 (d, 2H), 7.48 (dd, 2H), 7.15 (d, 2H), 7.04 (t, 2H), 6.86 (d, 1H), 6.54 (d, 1H), 6.06 (s, 1H), 1.76-1.68 (m, 4H); MS (EI) for $C_{27}H_{20}F_2N_4O_4$. found 503.1 (MH+).

The following compounds were prepared by a sequence analogous to that taken to prepare Compound 67 from Compound 61 in Examples 20-22, substituting Compound 61 with the appropriate methyl 4-amino-2-halobenzoate:

1-N-[4-(6-Carbamoyl-7-chloroquinolin-4-yl)oxyphenyl]-1-N'-(4-fluorophenyl)cyclopropane-1,1-dicarboxamide (68): $^1H$ NMR (400 MHz, DMSO-$d_6$) δ 10.23 (s, 1H), 10.05 (s, 1H), 8.75 (d, 1H), 8.35 (s, 1H), 8.14 (s, 2H), 7.88-7.73 (m, 3H), 7.64 (dd, 2H), 7.27 (d, 2H), 7.15 (t, 2H), 6.64 (d, 1H), 1.47 (s, 4H); MS (EI) for $C_{27}H_{20}ClFN_4O_4$. found 519.4 (MH+).

1-N-[4-(7-Bromo-6-carbamoylquinolin-4-yl)oxyphenyl]-1-N'-(4-fluorophenyl)cyclopropane-1,1-dicarboxamide (69): $^1H$ NMR (400 MHz, DMSO-$d_6$) δ 10.24 (br s, 1H), 10.07 (br s, 1H), 8.75 (d, 1H), 8.30 (d, 2H), 8.14 (br s, 1H), 7.80 (d, 2H), 7.64-7.67 (m, 2H), 7.27 (d, 2H), 7.18 (t, 3H), 6.65 (d, 1H), 1.48 (s, 4H); MS (EI) for $C_{27}H_{20}BrFN_4O_4$. found 563.3 (MH+).

Example 23: 1-N-[4-[6-Carbamoyl-7-(2-methoxyethylamino)quinolin-4-yl]oxyphenyl]-1-N'-(4-fluorophenyl)cyclopropane-1,1-dicarboxamide (70)

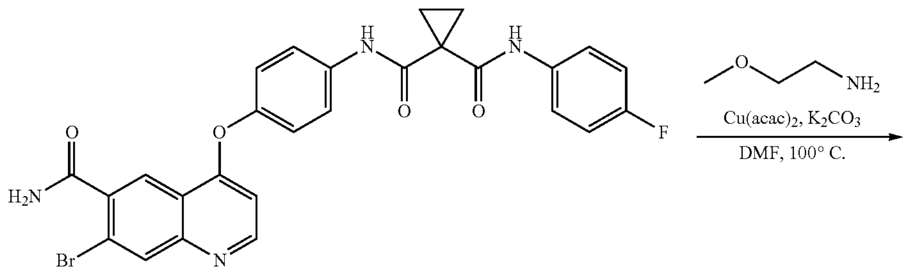

69

-continued

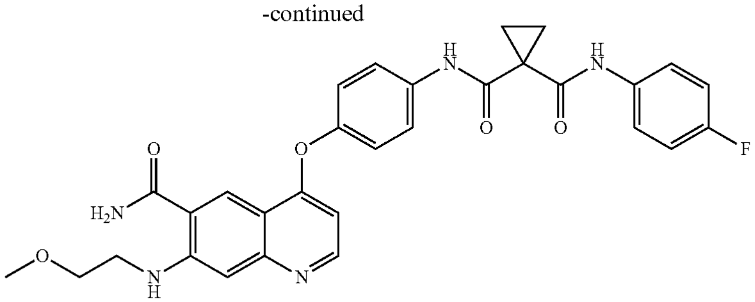

70

1-N-[4-[6-Carbamoyl-7-(2-methoxyethylamino)quinolin-4-yl]oxyphenyl]-1-N'-(4-fluorophenyl)cyclopropane-1,1-dicarboxamide (70): To a mixture of Compound 69 (200 mg, 337.25 μmol, 1 eq), 2-methoxyethan-1-amine (50.66 mg, 674.51 μmol, 2 eq), and $K_2CO_3$ (93.22 mg, 674.51 μmol, 2 eq) in DMF (10 mL) was added bis[(Z)-1-methyl-3-oxo-but-1-enoxy]copper (70.62 mg, 269.80 μmol, 0.8 eq) at 10° C. under nitrogen atmosphere. The resulting mixture was stirred for 2 h at 100° C. under nitrogen atmosphere. Heating was discontinued, and once the reaction mixture reached ambient temperature, it was quenched with aq saturated $NH_4OH$ (50 mL) and extracted with EtOAc (3×30 mL). The combined extracts were dried over anhyd $Na_2SO_4$, filtered, and concentrated. The residue was purified by prep HPLC to give Compound 70 (22.2 mg, 11.33% yield). $^1H$ NMR (400 MHz, $CD_3OD$) δ 8.62 (s, 1H), 8.43 (d, 1H), 7.72 (d, 2H), 7.56 (dd, 2H), 7.23 (d, 2H), 7.07 (t, 2H), 6.99 (s, 1H), 6.32 (d, 1H), 3.72 (t, 2H), 3.43 (s, 5H), 1.64 (s, 4H); MS (EI) for $C_{30}H_{28}FN_5O_5$. found 558.1 (MH+).

The following compounds were prepared in a method analogous to Compound 70 in Example 23:

1-N-[4-[6-Carbamoyl-7-(3-morpholin-4-ylpropylamino)quinolin-4-yl]oxyphenyl]-1-N'-(4-fluorophenyl)cyclopropane-1,1-dicarboxamide (71): $^1H$ NMR (400 MHz, $CD_3OD$) δ 8.60 (s, 1H), 8.42 (d, 1H), 7.71 (d, 2H), 7.59-7.53 (m, 2H), 7.22 (d, 2H), 7.07 (t, 2H), 6.97 (s, 1H), 6.30 (d, 1H), 3.73 (t, 4H), 3.38-3.33 (m, 2H), 2.61-2.45 (m, 6H), 2.00-1.91 (m, 2H), 1.64 (s, 4H); MS (EI) for $C_{34}H_{35}FN_6O_5$. found 627.2 (MH+).

1-N-[4-[7-(Azetidin-1-yl)-6-carbamoylquinolin-4-yl]oxyphenyl]-1-N'-(4-fluorophenyl)cyclopropane-1,1-dicarboxamide (72): $^1H$ NMR (400 MHz, $CD_3OD$) δ 8.46 (d, 1H), 8.32 (s, 1H), 7.71 (d, 2H), 7.59-7.53 (m, 2H), 7.21 (d, 2H), 7.11-7.04 (m, 2H), 6.86 (s, 1H), 6.37 (d, 1H), 4.11 (t, 4H), 2.42 (m, 2H), 1.64 (s, 4H); MS (EI) for $C_{30}H_{26}FN_5O_4$. found 540.1 (MH+).

Example 24: Ethyl 7-bromo-4-(4-(1-((4-fluorophenyl)carbamoyl)cyclopropane-1-carboxamido)phenoxy)quinoline-6-carboxylate (79)

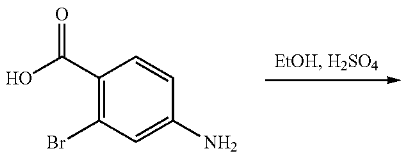

73

-continued

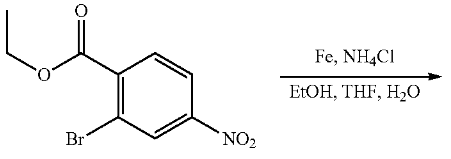

74

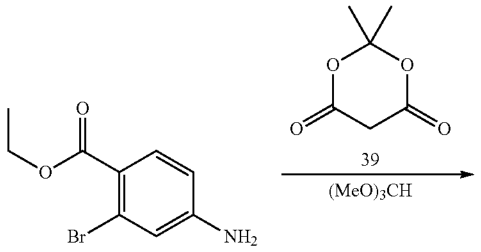

75

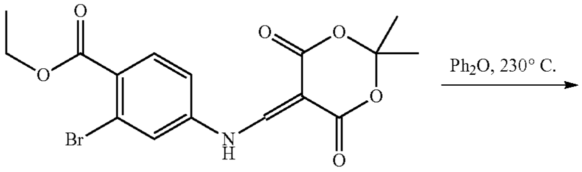

76

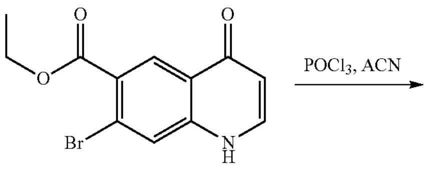

77

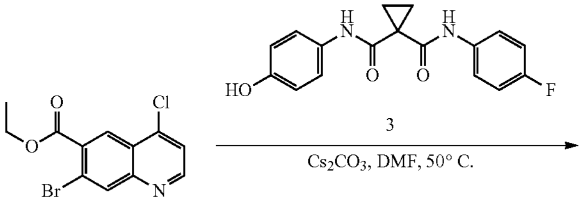

78

-continued

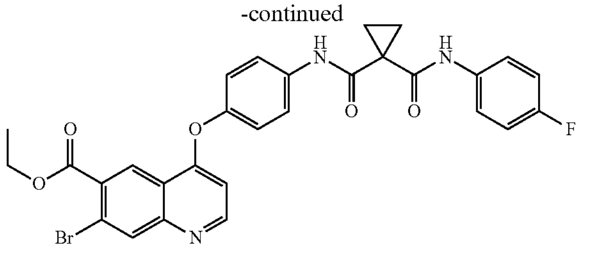

79

Ethyl 2-bromo-4-nitrobenzoate (74): To a solution of Compound 73 (20.0 g, 79.67 mmol, 1 eq) in EtOH (78.80 g, 1.71 mol, 100.00 mL, 21.47 eq) was added $H_2SO_4$ (7.81 g, 79.67 mmol, 4.25 mL, 1 eq) and the reaction was stirred at 80° C. for 24 h. The reaction mixture was concentrated, and the residue was partitioned between water (200 mL) and DCM (100 mL). The phases were separated and the aq phase was extracted with DCM (3×100 mL). The combined organic phases were dried over anhyd $Na_2SO_4$ and concentrated in vacuo to afford Compound 74 (21.0 g, 91.37% yield). $^1H$ NMR (400 MHz, DMSO-$d_6$) δ 8.52-8.47 (m, 1H), 8.33-8.28 (m, 1H), 7.97 (d, 1H), 4.38 (q, 2H), 1.34 (t, 3H); MS (EI) for $C_9H_8BrNO_4$. found 274.0 (MH+).

Ethyl 4-amino-2-bromobenzoate (75): To a stirred solution of Compound 74 (2, 5.00 g, 17.3 mmol, 1 eq) in EtOH (22 mL), THF (22 mL), and water (11 mL) were added iron (2.03 g, 36.4 mmol, 2.1 eq) and $NH_4Cl$ (1.95 g, 36.4 mmol, 1.27 mL, 2.1 eq), and the reaction mixture was heated to 80° C. for 3 h. The reaction was repeated in the exact same manner on a scale that used 16.0 g of Compound 74. The two reactions were combined and filtered through Celite® (diatomaceous earth), and the filter cake was washed with EtOH (3×30 mL) and EtOAc (3×30 mL). The filtrate was concentrated, and diluted with aq saturated $NaHCO_3$ (200 mL) ensuring the pH was approximately 8, and extracted with EtOAc (3×150 mL). The combined extracts were dried over anhyd $Na_2SO_4$ and concentrated to afford crude product (19 g). The crude product was suspended in EtOAc (5 mL) and petroleum ether (25 mL) and stirred for 20 min at room temperature. The precipitate was collected by filtration and washed with petroleum ether (2×10 mL) to afford Compound 75 (16.0 g, 85.54% yield, 95% purity). $^1H$ NMR (400 MHz, DMSO-$d_6$) δ 7.62 (d, 1H), 6.84 (d, 1H), 6.54 (dd, 1H), 6.13 (s, 2H), 4.19 (q, 2H), 1.27 (t, 3H); MS (EI) for $C_9H_{10}BrNO_2$. found 243.9 (MH+).

Ethyl 2-bromo-4-(((2,2-dimethyl-4,6-dioxo-1,3-dioxan-5-ylidene)methyl)amino)benzoate (76): Compound 76 was synthesized from Compounds 75 and 39 in a manner analogous to the preparation of Compound 40 from Compounds 38 and 39 in Example 12. Compound 76 was obtained (23 g, 88.1% yield). $^1H$ NMR (400 MHz, $CDCl_3$) δ 11.23 (d, 1H), 8.63 (d, 1H), 7.92 (d, 1H), 7.56 (d, 1H), 7.23 (dd, 1H), 4.40 (q, 2H), 1.76 (s, 6H), 1.41 (t, 3H).

Ethyl 7-bromo-4-oxo-1,4-dihydroquinoline-6-carboxylate (77): Compound 77 was synthesized from Compound 76 in a manner analogous to the preparation of Compound 41 from Compound 40 in Example 12. Compound 77 was obtained (20 g, 94.4% yield, 60% purity) and used in subsequent reactions without further purification. MS (EI) for $C_{12}H_{10}BrNO_3$. found 296.0 (MH+).

Ethyl 7-bromo-4-chloroquinoline-6-carboxylate (78): Compound 78 was prepared from Compound 77 as described for Compound 42 in Example 12, except that instead of using neat $POCl_3$, the reaction was run in MeCN with 4.21 eq of $POCl_3$ at 90° C. for 1.5 h (4.2 g, 33% yield). $^1H$ NMR (400 MHz, $CD_3OD$) δ 8.84 (d, 1H), 8.62 (s, 1H), 8.45 (s, 1H), 7.55 (d, 1H), 4.50 (q, 2H), 1.47 (t, 3H); MS (EI) for $C_{12}H9BrClNO_2$. found 313.8 (MH+).

Ethyl 7-bromo-4-(4-(1-((4-fluorophenyl)carbamoyl)cyclopropane-1-carboxamido)phenoxy)quinoline-6-carboxylate (79): Compound 79 was prepared from Compound 78 and 3 as described in Example 12 for Compound 43 except that cesium carbonate was substituted for the potassium t-butoxide and the reaction mixture was heated only to 50° C. (6.7 g, 80.5% yield). $^1H$ NMR (400 MHz, $CD_3OD$) δ 9.55 (s, 1H), 8.79 (s, 1H), 8.70 (d, 1H), 8.55 (s, 1H), 8.40 (s, 1H), 7.67 (d, 2H), 7.47 (dd, 2H), 7.18 (d, 2H), 7.06 (t, 2H), 6.56 (d, 1H), 4.48 (q, 2H), 1.79-1.73 (m, 2H), 1.68-1.62 (m, 2H), 1.46 (t, 3H); MS (EI) for $C_{29}H_{23}BrFN_3O_5$. found 592.0 (MH+).

Example 25: 4-[4-[[1-[(4-Fluorophenyl)carbamoyl]cyclopropane-carbonyl]amino]phenoxy]-7-(methylamino)quinoline-6-carboxylic Acid (81)

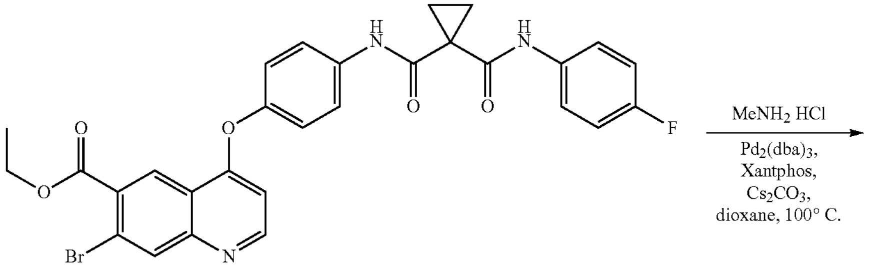

79

-continued

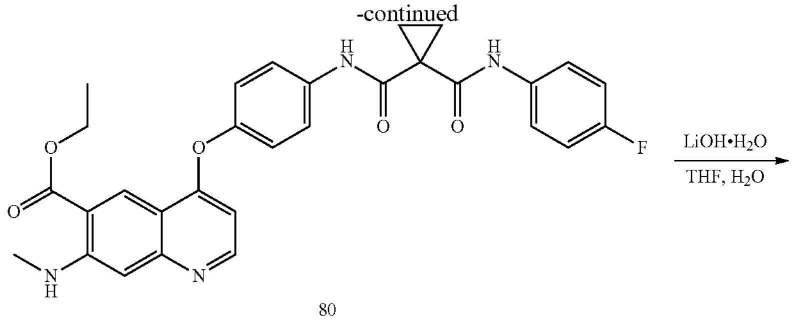

80

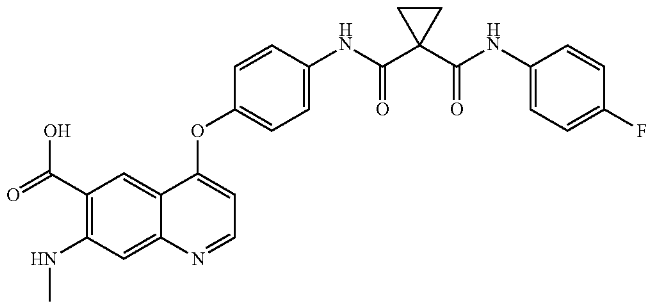

81

Ethyl 4-(4-(1-((4-fluorophenyl)carbamoyl)cyclopropane-1-carboxamido)phenoxy)-7-(methylamino)quinoline-6-carboxylate (80): To a mixture of Compound 79 (1.00 g, 1.60 mmol, 1 eq), methanamine hydrogen chloride (216.55 mg, 3.21 mmol, 2 eq), $Cs_2CO_3$ (1.57 g, 4.81 mmol, 3 eq), and Xantphos (556.73 mg, 962.17 μmol, 0.6 eq) in 1,4-dioxane (25 mL) was added $Pd_2(dba)_3$ (440.54 mg, 481.08 μmol, 0.3 eq) at 10° C. under a nitrogen atmosphere. The resulting mixture was stirred for 3 h at 100° C. under a nitrogen atmosphere. The reaction mixture was allowed to cool and then diluted with water (50 mL) and EtOAc (50 mL), neutralized to a pH of approximately 8 with aq saturated $NH_4Cl$ solution, and filtered. The filter cake was washed with EtOAc. The phases of the filtrate were separated, and the aq phase was extracted with EtOAc (3×30 mL). The combined EtOAc phases were dried over anhyd $Na_2SO_4$ and concentrated. The residue was purified by flash silica gel chromatography (0-80% EtOAc:petroleum ether, then 0-15% EtOH in DCM) followed by further purification by prep HPLC to give Compound 80 (250 mg, 27.30% yield). $^1H$ NMR (400 MHz, $CDCl_3$) δ 10.27 (s, 1H), 9.00 (s, 2H), 8.42 (s, 2H), 7.80 (d, 2H), 7.51 (dd, 2H), 7.39 (s, 1H), 7.17 (d, 2H), 7.03 (t, 2H), 6.38 (d, 1H), 4.44 (q, 2H), 3.11 (s, 3H), 1.85 (s, 2H), 1.73 (s, 2H), 1.48-1.43 (m, 3H); MS (EI) for $C_{30}H_{27}FN_4O_5$. found 543.1 (MH+).

4-[4-[[1-[(4-Fluorophenyl)carbamoyl]cyclopropane-carbonyl]amino]phenoxy]-7-(methylamino)quinoline-6-carboxylic acid (81): A mixture of Compound 80 (250. mg, 437.4 μmol, 1 eq) and lithium hydroxide:hydrate (183.69 mg, 4.38 mmol, 10 eq) in THF (10.0 mL) and water (10.0 mL) was stirred for 20 h at 10° C. The reaction was diluted with water (40 mL), acidified to a pH of approximately 6 with aq saturated $NH_4Cl$, and extracted with EtOAc (4×40 mL). The combined extracts were dried over anhyd $Na_2SO_4$ and concentrated under reduced pressure to afford crude product which was subsequently purified by prep HPLC (column: Xtimate C18 150*25 mm*5 μm; mobile phase: [water (0.05% HCl)-ACN]; B %: 16%-46%, 9.5 min) to give Compound 81 HCl salt (120 mg, 47.3% yield). $^1H$ NMR (400 MHz, $CD_3OD$) δ 9.13 (s, 1H), 8.57 (d, 1H), 7.81 (d, 2H), 7.56 (dd, 2H), 7.34 (d, 2H), 7.07 (t, 2H), 6.88 (s, 1H), 6.61 (d, 1H), 3.07 (s, 3H), 1.66 (s, 4H); MS (EI) for $C_{28}H_{23}FN_4O_5$. found 515.1 (MH+).

Example 26: 1-N-[4-[6-Carbamoyl-7-(methylamino)quinolin-4-yl]oxyphenyl]-1-N'-(4-fluorophenyl)cyclopropane-1,1-dicarboxamide (82)

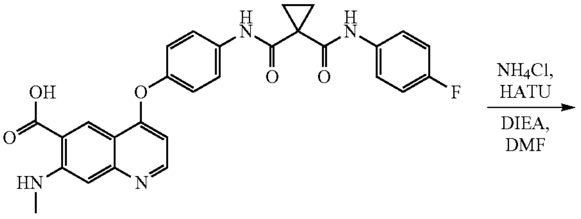

81

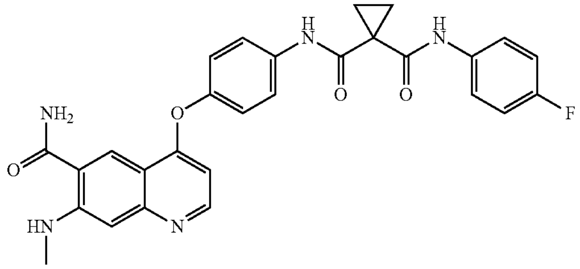

82

1-N-[4-[6-Carbamoyl-7-(methylamino)quinolin-4-yl]oxyphenyl]-1-N'-(4-fluorophenyl)cyclopropane-1,1-dicarboxamide (82): Compound 82 was synthesized from Compound 81 in a manner analogous to the preparation of Compound 7 from Compound 6 in Example 3 (29.9 mg, 24% yield). $^1H$ NMR (400 MHz, $CD_3OD$) δ 8.61 (s, 1H), 8.43 (d, 1H), 7.72 (d, 2H), 7.59-7.54 (m, 2H), 7.23 (d, 2H), 7.07 (t, 2H), 6.94 (s, 1H), 6.31 (d, 1H), 2.97 (s, 3H), 1.64 (s, 4H); MS (EI) for $C_{28}H_{24}FN_5O_4$. found 514.1 (MH+).

Example 27: 1-N'-(4-Fluorophenyl)-1-N-[4-[7-(methylamino)-6-(methylcarbamoyl)quinolin-4-yl]oxyphenyl]cyclopropane-1,1-dicarboxamide (83)

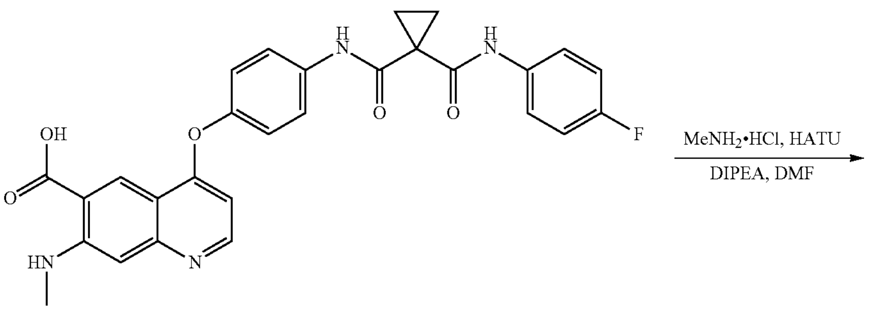

81

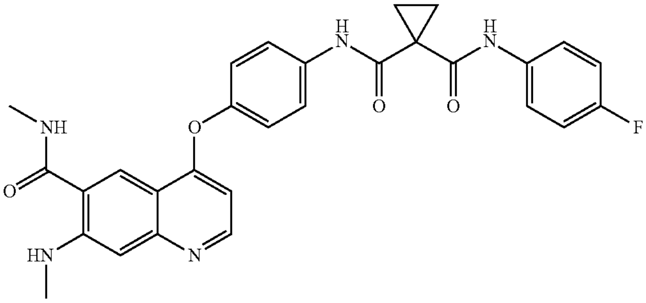

83

1-N'-(4-Fluorophenyl)-1-N-[4-[7-(methylamino)-6-(methylcarbamoyl)quinolin-4-yl]oxyphenyl]cyclopropane-1,1-dicarboxamide (83): Compound 83 was synthesized from Compound 81 in a manner analogous to the preparation of Compound 8 from Compound 6 in Example 4 (33.3 mg, 26% yield). $^1$H NMR (400 MHz, $CD_3OD$) δ 8.47 (s, 1H), 8.42 (d, 1H), 7.71 (d, 2H), 7.59-7.54 (m, 2H), 7.22 (d, 2H), 7.07 (t, 2H), 6.94 (s, 1H), 6.32 (d, 1H), 2.96 (s, 3H), 2.92 (s, 3H), 1.64 (s, 4H); MS (EI) for $C_{29}H_{26}FN_5O_4$. found 528.1 (MH+).

Example 28: Methyl 4-[4-[[1-[(4-fluorophenyl)carbamoyl]cyclopropane-carbonyl]amino]phenoxy]-7-(methylamino)quinoline-6-carboxylate (84)

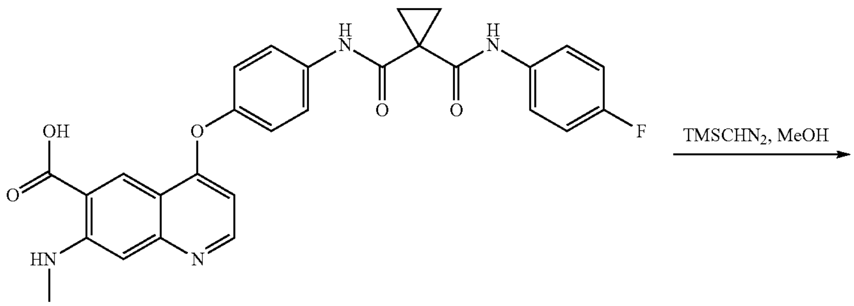

81

-continued

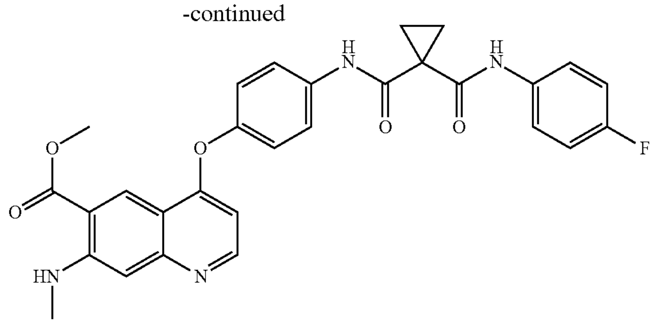

84

Methyl 4-[4-[[1-[(4-fluorophenyl)carbamoyl]cyclopropane-carbonyl]amino]phenoxy]-7-(methylamino)quinoline-6-carboxylate (84): To a solution of Compound 81 (30 mg, 55.39 μmol, 1 eq) in MeOH (5 mL) was added $TMSCHN_2$ (2 M, 276.97 uL, 10 eq) at 10° C., and the reaction was stirred at 10° C. for 6 h. The reaction was repeated in an identical fashion on another 45 mg of Compound 81. The reaction solutions from both batches were combined and concentrated in vacuo. The resulting residue was purified by prep HPLC to give Compound 84 (25.5 mg, 55.16% yield). $^1H$ NMR (400 MHz, $CD_3OD$) δ 8.99 (s, 1H), 8.45 (d, 1H), 7.72 (d, 2H), 7.57 (dd, 2H), 7.23 (d, 2H), 7.07 (t, 2H), 6.97 (s, 1H), 6.29 (d, 1H), 3.95 (s, 3H), 3.01 (s, 3H), 1.64 (s, 4H); MS (EI) for $C_{29}H_{25}FN_4O_5$. found 529.1 (MH+).

Example 29: 7-((tert-Butoxycarbonyl)amino)-4-(4-(1-((4-fluorophenyl)carbamoyl)cyclopropane-1-carboxamido)phenoxy)quinoline-6-carboxylic Acid (86)

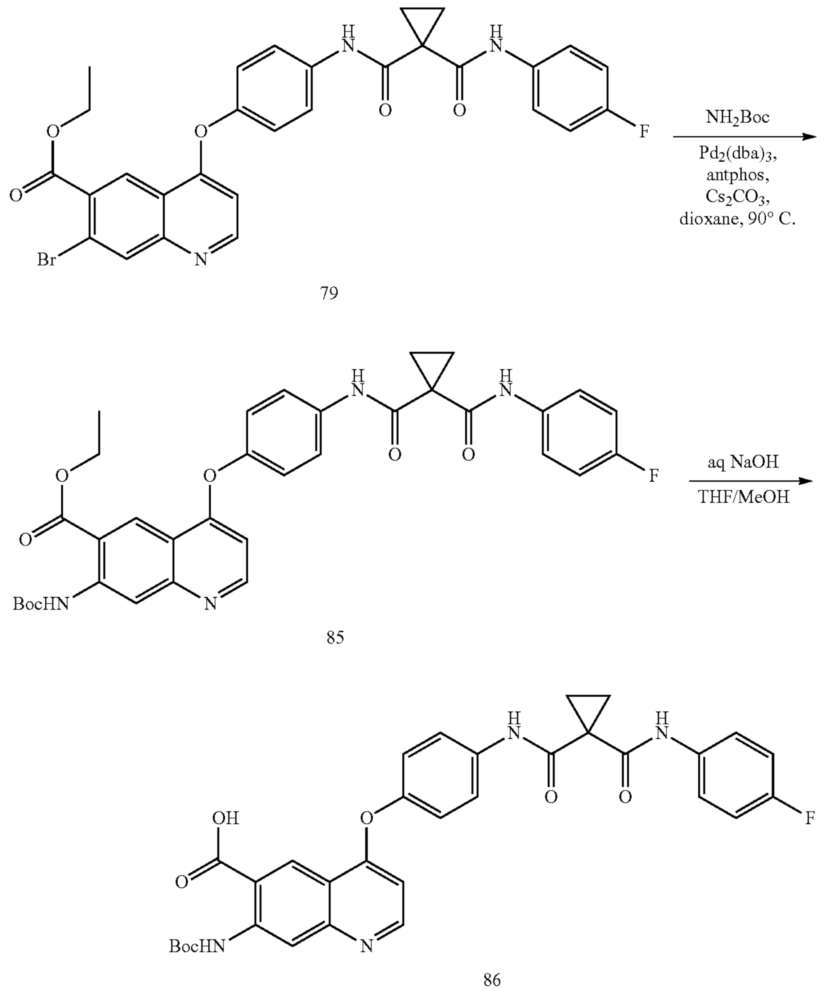

Ethyl 7-((tert-butoxycarbonyl)amino)-4-(4-(1-((4-fluorophenyl)carbamoyl)cyclopropane-1-carboxamido)phenoxy) quinoline-6-carboxylate (85): A mixture of Compound 79 (1.5 g, 2.53 mmol, 1 eq), $NH_2Boc$ (355.95 mg, 3.04 mmol, 1.2 eq), Xantphos (586.03 mg, 1.01 mmol, 0.4 eq), $Pd_2(dba)_3$ (463.72 mg, 506.40 μmol, 0.2 equiv), and $Cs_2CO_3$ (2.47 g, 7.60 mmol, 3 equiv) in dioxane (20 mL) was degassed and purged with nitrogen three times, followed by stirring at 90° C. for 16 h under an atmosphere of nitrogen. The mixture was filtered and concentrated, and the residue was purified by flash silica gel chromatography (10-100% EtOAc in Petroleum ether) to give Compound 85 (1.3 g, 79.14% yield). $^1H$ NMR (400 MHz, DMSO-$d_6$) δ 10.28 (s, 1H), 10.23 (s, 1H), 10.06 (s, 1H), 8.94 (s, 1H), 8.72 (d, 1H), 8.69 (s, 1H), 7.79 (d, 2H), 7.64 (dd, 2H), 7.30 (d, 2H), 7.16 (t, 2H), 6.46 (d, 1H), 4.42 (q, 2H), 1.53 (s, 9H), 1.48 (s, 4H), 1.38 (t, 3H); MS (EI) for $C_{34}H_{33}FN_4O_7$. found 629.2 (MH+).

7-((tert-Butoxycarbonyl)amino)-4-(4-(1-((4-fluorophenyl)carbamoyl)cyclopropane-1-carboxamido)phenoxy)quinoline-6-carboxylic acid (86): Compound 86 was synthesized from Compound 85 in a manner analogous to the preparation of Compound 6 by the hydrolysis of the methyl ester of Compound 5 in Example 2 (0.7 g, 82.4% yield). $^1H$ NMR (400 MHz, $CD_3OD$) δ 9.13 (s, 1H), 8.57 (d, 1H), 7.81 (d, 2H), 7.56 (dd, 2H), 7.34 (d, 2H), 7.07 (t, 2H), 6.88 (s, 1H), 6.61 (d, 1H), 3.07 (s, 3H), 1.66 (s, 4H); MS (EI) for $C_{32}H_{29}FN_4O_7$. found 601.1 (MH+).

Example 30: 1-N-[4-(7-Amino-6-carbamoylquinolin-4-yl)oxyphenyl]-1-N'-(4-fluorophenyl)cyclopropane-1,1-dicarboxamide (87)

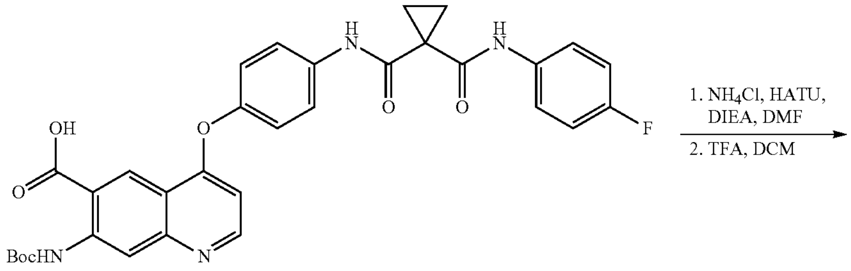

86

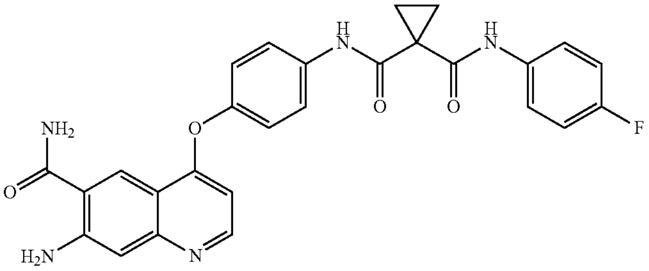

87

1-N-[4-(7-Amino-6-carbamoylquinolin-4-yl)oxyphenyl]-1-N'-(4-fluorophenyl)-cyclopropane-1,1-dicarboxamide (87): Compound 87 was synthesized from Compound 86 in two steps. The first step followed a manner analogous to the preparation of Compound 7 from Compound 6 in Example 3. Step 2 involved TFA-mediated BOC-deprotection using a standard procedure such as that employed in Example 5 which provided the final Compound 87 (41.9 mg, 35% yield over 2 steps). $^1H$ NMR (400 MHz, $CD_3OD$) δ 8.63 (s, 1H), 8.43 (d, 1H), 7.73 (d, 2H), 7.66-7.52 (m, 2H), 7.32-7.22 (m, 2H), 7.15 (s, 1H), 7.12-7.05 (m, 2H), 6.31 (d, 1H), 1.66 (s, 4H); MS (EI) for $C_{27}H_{22}FN_5O_4$. found 500.0 (MH+).

Example 31: 1-N-[4-[7-Amino-6-(methylcarbamoyl)quinolin-4-yl]oxyphenyl]-1-N'-(4-fluorophenyl)cyclopropane-1,1-dicarboxamide (88)

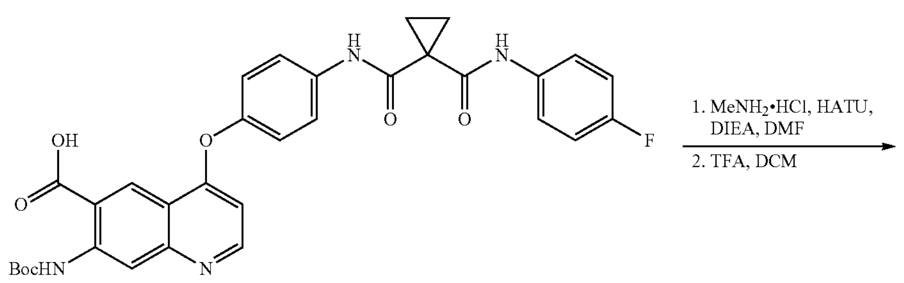

86

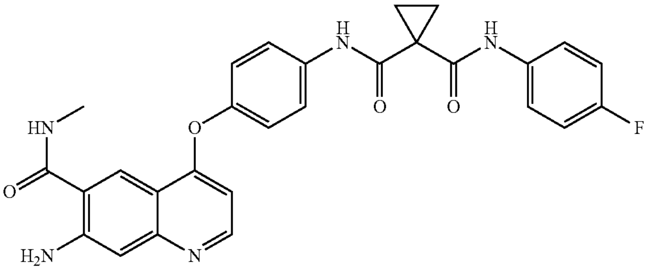

88

1-N-[4-[7-Amino-6-(methylcarbamoyl)quinolin-4-yl]oxyphenyl]-1-N'-(4-fluorophenyl)cyclopropane-1,1-dicarboxamide (88): Compound 88 was synthesized from Compound 86 in two steps. The first step followed a manner analogous to the preparation of Compound 8 from Compound 6 in Example 4. Step 2 involved TFA-mediated BOC-deprotection using a standard procedure such as that employed in Example 5 which provided the final Compound 88 (50.9 mg, 42% yield over 2 steps). $^1$H NMR (400 MHz, DMSO-$d_6$) δ 10.19 (s, 1H), 10.05 (s, 1H), 8.70 (br d, 1H), 8.52-8.38 (m, 2H), 7.77 (d, 2H), 7.69-7.59 (m, 2H), 7.30-7.06 (m, 5H), 6.55 (s, 2H), 6.17 (d, 1H), 2.79 (d, 3H), 1.48 (s, 4H); MS (EI) for $C_{28}H_{24}FN_5O_4$. found 514.1 (MH+).

Example 32: 7-Amino-4-[4-[[1-[(4-fluorophenyl)carbamoyl]cyclopropane-carbonyl]amino]phenoxy]quinoline-6-carboxylic Acid (89)

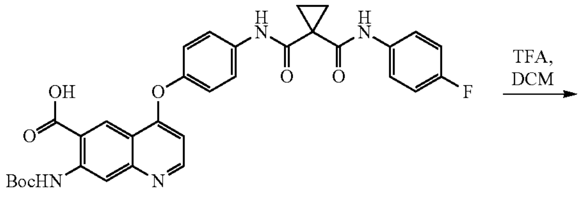

86

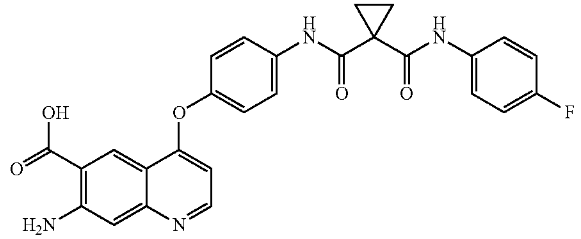

89

7-Amino-4-[4-[[1-[(4-fluorophenyl)carbamoyl]cyclopropane-carbonyl]amino]phenoxy]quinoline-6-carboxylic acid (89): Compound 89 was synthesized from Compound 86 via TFA mediated BOC-deprotection as described in Example 5. $^1$H NMR (400 MHz, DMSO-$d_6$) δ 10.19 (s, 1H), 10.07 (s, 1H), 8.80 (s, 1H), 8.48 (d, 1H), 7.76 (d, 2H), 7.69-7.58 (m, 2H), 7.24 (d, 2H), 7.19-7.10 (m, 3H), 6.16 (d, 1H), 1.48 (s, 4H); MS (EI) for $C_{27}H_{21}FN_4O_5$. found 501.1 (MH+).

Example 33: Methyl 7-amino-4-[4-[[1-[(4-fluorophenyl)carbamoyl]-cyclopropanecarbonyl]amino]phenoxy]quinoline-6-carboxylate (90)

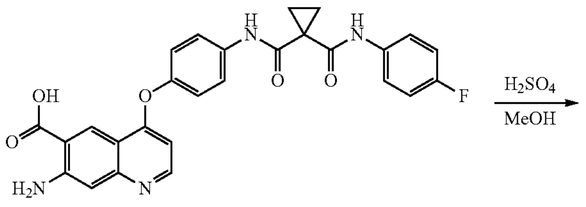

89

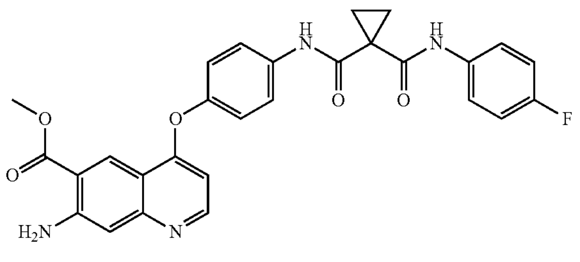

90

Methyl 7-amino-4-[4-[[1-[(4-fluorophenyl)carbamoyl]cyclopropane-carbonyl]amino]phenoxy]quinoline-6-carboxylate (90): A solution of Compound 89 (100 mg, 199.81 μmol, 1 eq) in MeOH (3 mL) and H2504 (0.1 mL) was stirred at 70° C. for 40 h. The reaction was concentrated in vacuo, and the resulting residue was purified by prep HPLC to give Compound 90 (28.5 mg, 26.88% yield). $^{1}$H NMR (400 MHz, DMSO-$d_6$) δ 10.20 (br s, 1H), 10.07 (br s, 1H), 8.81 (s, 1H), 8.50 (d, 1H), 7.77 (br d, 2H), 7.65 (br dd, 2H), 7.25 (br d, 2H), 7.21-7.06 (m, 3H), 6.83 (s, 2H), 6.15 (d, 1H), 3.90 (s, 3H), 1.48 (s, 4H); MS (EI) for $C_{28}H_{23}FN_4O_5$. found 515.2 (MH+).

Example 34: N-(4-((6-Carbamoyl-7-hydroxyquinolin-4-yl)oxy)phenyl)-N-(4-fluorophenyl)cyclopropane-1,1-dicarboxamide (91)

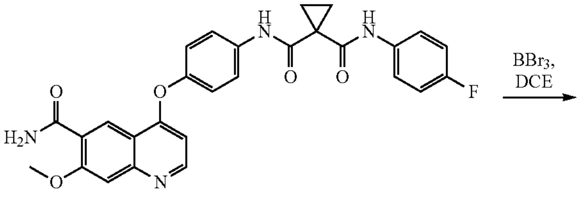

7

(91): A mixture of Compound 7 (250 mg, 485.91 μmol, 1 eq) and $BBr_3$ (1.04 g, 4.15 mmol, 0.4 mL, 8.54 eq) in 1,2-dichloroethane (2 mL) was stirred under an atmosphere of nitrogen at 50° C. for 1 h. The reaction mixture was cooled to room temperature and poured into aq saturated $NaHCO_3$ with vigorous stirring. The resulting residue was filtered, washed with water and then methyl t-butyl ether, and dried. The resulting crude compound was purified by prep HPLC to give Compound 91 (69.5 mg, 27.3% yield). $^{1}$H NMR (400 MHz, DMSO-$d_6$) δ 12.91 (s, 1H), 10.20 (s, 1H), 10.04 (s, 1H), 8.97 (s, 1H), 8.84 (s, 1H), 8.60-8.59 (d, 1H), 7.79 (s, 1H), 7.77-7.64 (d, 2H), 7.63-7.62 (d, 2H), 7.30-7.26 (m, 3H), 7.17-7.13 (m, 2H), 6.63-6.33 (d, 1H), 1.47 (s, 4H); MS (EI) for $C_{27}H_{21}FN_4O_5$. found 501.1 (MH+).

Example 35: 1-N'-(4-Fluorophenyl)-1-N-[4-[(2-methyl-4-oxo-2,3-dihydropyrido[3,2-g][1,3]benzoxazin-6-yl)oxy]phenyl]cyclopropane-1,1-dicarboxamide (92)

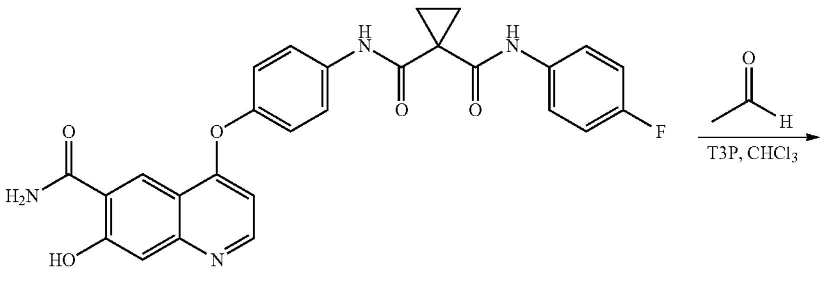

91

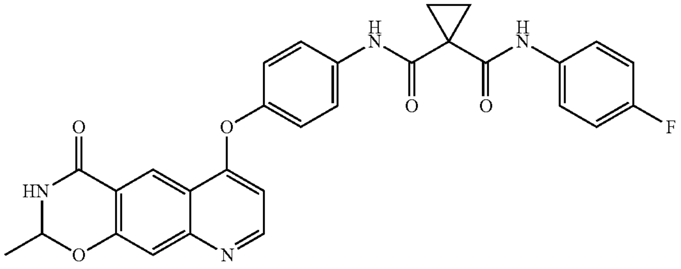

92

-continued

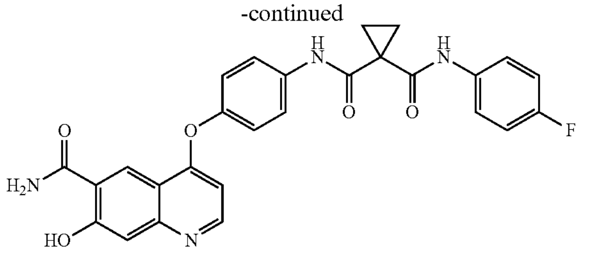

91

N-(4-((6-Carbamoyl-7-hydroxyquinolin-4-yl)oxy)phenyl)-N-(4-fluorophenyl)cyclopropane-1,1-dicarboxamide 1-N'-(4-Fluorophenyl)-1-N-[4-[(2-methyl-4-oxo-2,3-dihydropyrido[3,2-g][1,3]benzoxazin-6-yl)oxy]phenyl]cyclopropane-1,1-dicarboxamide (92): To a solution of Compound 91 (130 mg, 259.75 μmol, 1 eq) in $CHCl_3$ (5 mL) was added $T_3P$ (535 mg, 1.68 mmol, 0.5 mL, 6.47 eq) and acetaldehyde (393 mg, 8.91 mmol, 0.5 mL, 34.30 eq). The resulting mixture was stirred at 50° C. for 3 h then concentrated in vacuo. The residue was purified by prep HPLC to give Compound 92 (30.7 mg, 22.45% yield). $^{1}$H NMR (400 MHz, DMSO-$d_6$) δ 10.22 (s, 1H), 10.07 (s, 1H), 9.05 (s, 1H), 8.78 (s, 1H), 8.70 (d, 1H), 7.72 (d, 2H), 7.65 (d, 2H), 7.50 (s, 1H), 7.28 (d, 2H), 7.17 (d, 2H), 6.50 (d, 1H), 5.62-5.58 (m, 1H), 1.57 (d, 3H), 1.48 (s, 4H); MS (EI) for $C_{29}H_{23}FN_4O_5$. found 527.2 (MH+).

Example 36: 1-N-[4-[(2-Ethyl-4-oxo-2,3-dihydropyrido[3,2-g][1,3]benzoxazin-6-yl)oxy]phenyl]-1-N'-(4-fluorophenyl)cyclopropane-1,1-dicarboxamide (96)

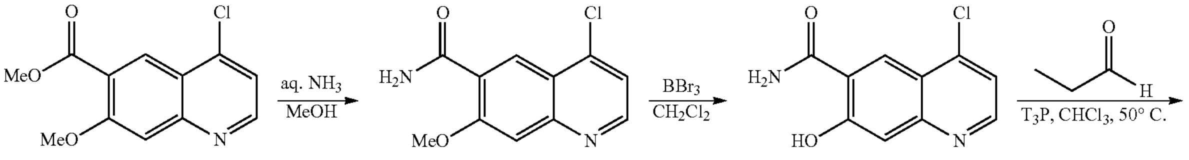

4

93

94

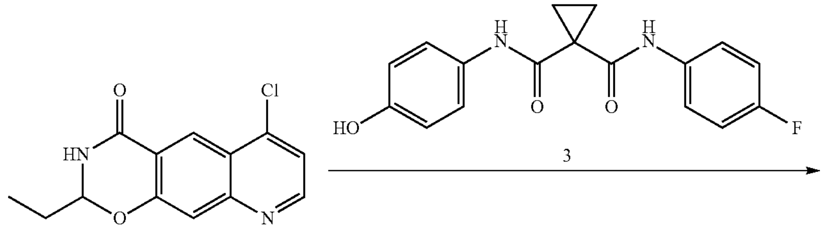

3

95

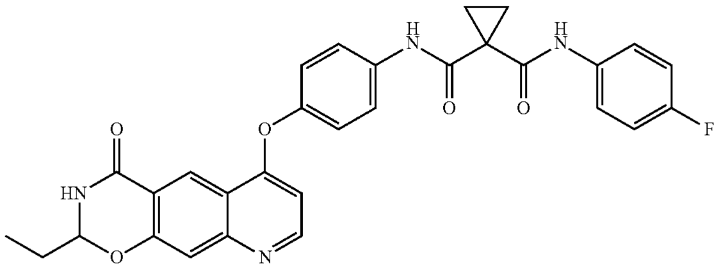

96

4-Chloro-7-methoxyquinoline-6-carboxamide (93): To a mixture of Compound 4 (2.00 g, 7.55 mmol, 1 eq) in MeOH (20 mL) was added $NH_3.H_2O$ (10.58 g, 75.50 mmol, 11.63 mL, 10 eq) at 10° C. The mixture was stirred for 72 h at 70° C. The resulting precipitate was collected by filtration and dried under vacuum to give Compound 93 (1.30 g, 69.1% yield); MS (EI) for $C_{11}H_9ClN_2O_2$. found 237.0 (MH+).

4-Chloro-7-hydroxyquinoline-6-carboxamide (94): To a mixture of Compound 93 (1.30 g, 5.22 mmol, 1 eq) in DCM (30 mL) was added $BBr_3$ (6.54 g, 26.09 mmol, 2.51 mL, 5 eq) in portions at 0° C. The mixture was stirred for 6 h at 0° C. The reaction was quenched with aq saturated $NaHCO_3$ (150 mL) and filtered. The resulting residue was dried under vacuum to give Compound 94 (1.00 g, 81.77% yield). MS (EI) for $C_{10}H_7ClN_2O_2$. found 222.8 (MH+).

6-Chloro-2-ethyl-2,3-dihydro-4H-[1,3]oxazino[5,6-g]quinolin-4-one (95): To a solution of Compound 94 (2 g, 8.98 mmol, 1 eq) in $CHCl_3$ (15 mL) was added propionaldehyde (1.60 g, 27.48 mmol, 2 mL, 3.06 eq) and $T_3P$ (10.42 g, 32.76 mmol, 9.74 mL, 3.65 eq). The resulting mixture was stirred at 50° C. for 15 h followed by further addition of propionaldehyde (1.60 g, 27.48 mmol, 2 mL, 3.06 eq) and continued stirring at 50° C. for an additional 15 h. The mixture was then concentrated to remove solvent to give crude Compound 95 as a yellow solid (2.2 g, 85.8% yield) which was used into the next step without further purification. $^1H$ NMR (400 MHz, DMSO-$d_6$) δ 9.16 (br s, 1H), 8.87 (d, 1H), 8.66 (s, 1H), 7.72 (d, 1H), 7.62 (s, 1H), 5.45-5.47 (m, 1H), 1.38-1.44 (m, 2H), 1.06 (t, 3H); MS (EI) for $C_{13}H_{11}ClN_2O_2$. found 262.9 (MH+).

1-N-[4-[(2-Ethyl-4-oxo-2,3-dihydropyrido[3,2-g][1,3]benzoxazin-6-yl)oxy]phenyl]-1-N'-(4-fluorophenyl)cyclopropane-1,1-dicarboxamide (96): A solution of Compound 95 (95 mg, 361.64 umol, 1 eq) and Compound 3 (284.17 mg, 904.10 umol, 2.5 eq) in chlorobenzene (10 mL) was stirred at 140° C. for 15 h. The mixture was diluted with EtOAc (60 mL) and washed with aq 2 N NaOH (3×20 mL). The combined water phases were extracted with EtOAc (30 mL). The combined organic phases were concentrated, and the resulting residue was purified by prep-HPLC (column: YMC-Triart Prep C18 150*40 mm*7 um; mobile phase: [water (0.05% ammonia hydroxide v/v)-ACN]; B %: 53%-73%, 10 min) to give Compound 96 as a white solid (7.1 mg, 3.6% yield). $^1H$ NMR (400 MHz, DMSO-$d_6$) δ 10.23 (s, 1H), 10.07 (s, 1H), 9.05 (s, 1H), 8.78 (s, 1H), 8.69 (s, 1H), 7.78-7.86 (m, 2H), 7.64-7.67 (m, 2H), 7.51 (s, 1H), 7.28-7.30 (m, 2H), 7.14-7.18 (m, 2H), 6.49-6.51 (m, 1H), 5.43 (s, 1H), 1.88-1.91 (m, 2H), 1.48 (s, 4H), 1.06 (t, 3H); MS (EI) for $C_{30}H_{25}FN_4O_5$. found 541.1 (MH+).

Example 37: 1-N-[4-[6-Carbamoyl-7-(3-morpholin-4-ylpropoxy)quinolin-4-yl]oxyphenyl]-1-N'-(4-fluorophenyl)cyclopropane-1,1-dicarboxamide (98)

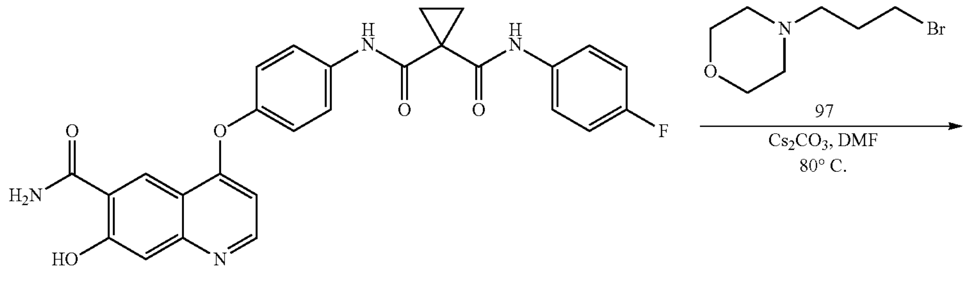

91

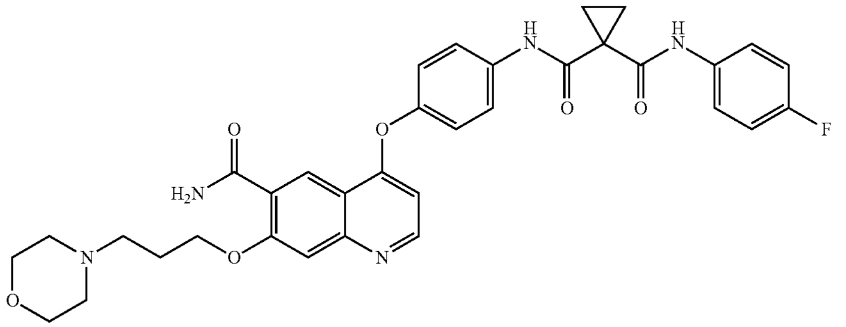

98

4-(3-Bromopropyl)morpholine (97): 3-Morpholinopropan-1-ol (2.0 g, 13.77 mmol, 1 eq) and $PPh_3$ (4.0 g, 15.25 mmol, 1.11 eq) were dissolved in THF (20 mL), and the reaction mixture chilled in an ice water bath under nitrogen. $CBr_4$ (5.0 g, 15.08 mmol, 1.09 eq) was added in portions over 15 min. After stirring for 30 min, the mixture was warmed to 30° C. for 18 h. The reaction was quenched with water (10 mL) and EtOAc (30 mL). The layers were separated, and the organic layer was extracted with 1 N HCl (2×15 mL). The pH of the combined aq extracts was adjusted to 10-11 with 4 N NaOH. The aq phase was extracted with EtOAc (3×30 mL). The combined EtOAc extracts were dried over anhyd $Na_2SO_4$ and concentrated to give Compound 97 (1.8 g, 63% yield) which was used in subsequent reactions without further purification. $^1H$ NMR (400 MHz, $CDCl_3$) δ 3.72-3.69 (m, 4H), 3.49-3.46 (t, 2H), 2.50-2.43 (m, 6H), 2.06-1.99 (m, 2H).

1-N-[4-[6-Carbamoyl-7-(3-morpholin-4-ylpropoxy)quinolin-4-yl]oxyphenyl]-1-N'-(4-fluorophenyl)cyclopropane-1,1-dicarboxamide (98): To a mixture of Compound 91 (45 mg, 85.87 μmol, 1 eq) and Compound 97 (53.48 mg, 257.00 μmol, 2.99 eq) in DMF (2 mL) was added $Cs_2CO_3$ (81.18 mg, 249.14 μmol, 2.90 eq) under nitrogen. The mixture was stirred at 80° C. for 2 h. The reaction mixture was diluted with water (50 mL) and extracted with EtOAc (2×20 mL). The combined organic phases were separated, washed with aq saturated NaCl, dried over anhyd $Na_2SO_4$, concentrated, and purified by prep HPLC to give Compound 98 (16.2 mg, 29.70% yield). $^1H$ NMR (400 MHz, DMSO-$d_6$) δ 9.36 (s, 1H), 9.29-9.27 (d, 1H), 9.00 (s, 1H), 8.64-8.63 (d, 1H), 7.99-7.98 (d, 1H), 7.69-67 (d, 2H), 7.54 (s, 1H), 7.51-7.47 (m, 2H), 7.17-7.14 (d, 2H), 7.07-7.01 (m, 2H), 6.46-6.45 (d, 1H), 5.98-5.97 (d, 1H), 4.40-4.37 (t, 2H), 3.76-3.70 (m, 4H), 2.26-2.58 (m, 2H), 2.50 (s, 4H), 2.20-2.13 (m, 2H), 1.74-1.70 (m, 4H); MS (EI) for $C_{34}H_{34}FN_5O_6$. found 628.5 (MH+).

Example 38: 1-N-[4-[6-Carbamoyl-7-(2-methoxyethoxy)quinolin-4-yl]oxyphenyl]-1-N'-(4-fluorophenyl)cyclopropane-1,1-dicarboxamide (103)

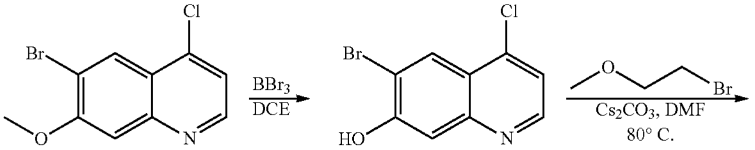

42 99

-continued

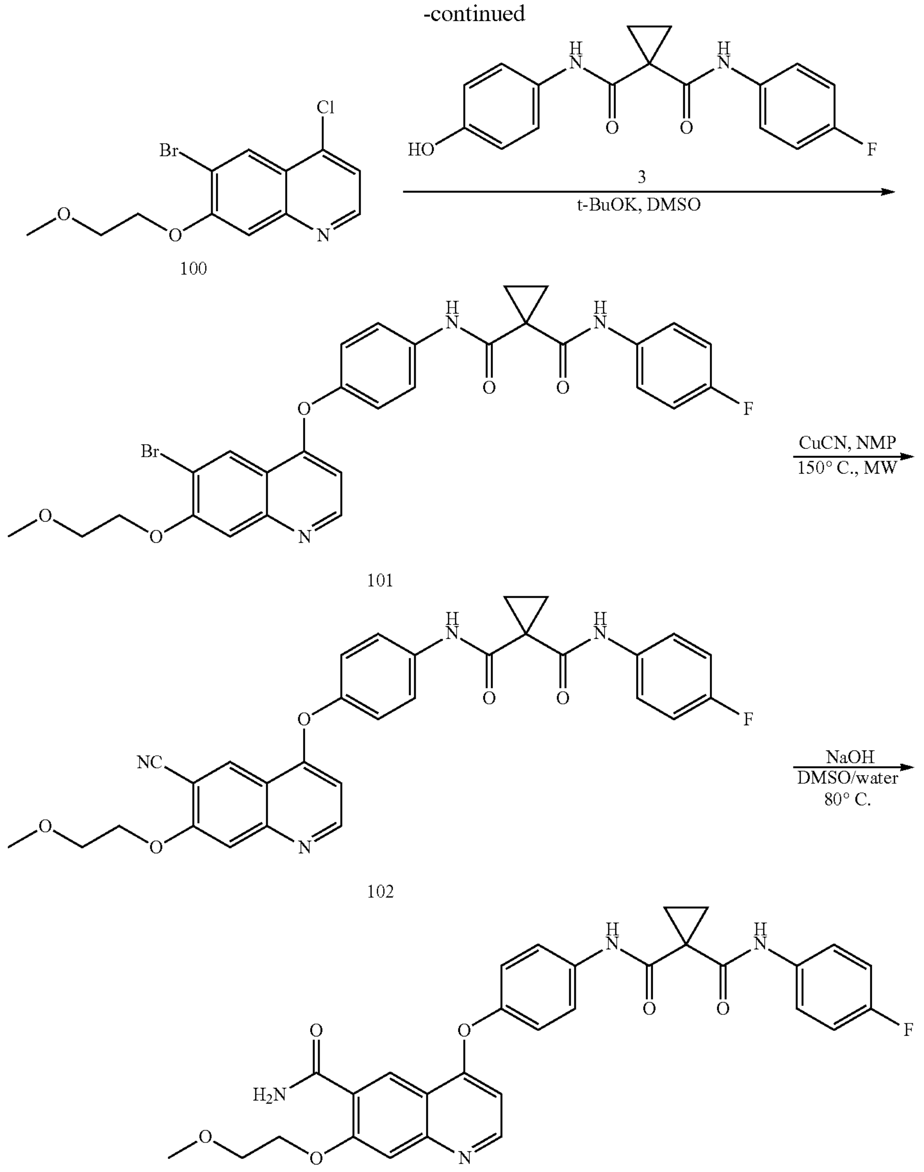

100

101

102

103

6-Bromo-4-chloroquinolin-7-ol (99): A mixture of Compound 42 (5 g, 18.35 mmol, 1 eq) and $BBr_3$ (13.0 g, 51.89 mmol, 5 mL, 2.83 eq) in 1,2-dichloroethane (15 mL) was stirred under an atmosphere of nitrogen at 90° C. for 2.5 h. The reaction mixture was cooled to room temperature and poured into aq saturated $NaHCO_3$ with vigorous stirring. The resulting residue was filtered, washed with water and then methyl t-butyl ether, and dried under vacuum to give Compound 99 (7 g, crude), which was used in subsequent steps without further purification. $^1H$ NMR (400 MHz, DMSO-$d_6$) δ 9.04-9.03 (d, 1H), 8.49 (s, 1H), 7.93-7.92 (d, 1H), 7.69 (s, 1H), 6.08 (s, 1H); MS (EI) for $C_9H_5BrClNO$, found 258.2 (MH+).

6-Bromo-4-chloro-7-(2-methoxyethoxy)quinoline (100): A mixture of Compound 99 (500 mg, 1.93 mmol, 1 eq), 1-bromo-2-methoxy-ethane (1.08 g, 7.73 mmol, 726.35 μL, 4 eq), and $Cs_2CO_3$ (1.90 g, 5.83 mmol, 3.01 eq) in DMF (4 mL) was stirred under an atmosphere of nitrogen at 80° C. for 2 h. The reaction mixture was cooled to room temperature, and water (2 mL) was added. The resulting residue was filtered, washed with water, and dried under vacuum to give Compound 100 (590 mg, 96% yield), which was used in subsequent reactions without further purification. $^1H$ NMR (400 MHz, DMSO-$d_6$) δ 8.80-8.79 (d, 1H), 8.37 (s, 1H), 7.65-7.64 (d, 1H), 7.62 (s, 1H), 4.39-4.37 (t, 2H), 3.79-3.77 (t, 2H), 3.37 (s, 3H); MS (EI) for $C_{12}H_{11}BrClNO_2$. found 315.8 (MH+).

N-(4-((6-Bromo-7-(2-methoxyethoxy)quinolin-4-yl)oxy)phenyl)-N-(4-fluorophenyl)cyclopropane-1,1-dicarboxamide (101): Compound 101 was synthesized from Compounds 100 and 3 in a manner analogous to the preparation of Compound 43 from Compounds 42 and 3 in Example 12 (65 mg, 69.2% yield). MS (EI) for $C_{29}H_{25}BrFN_3O_5$. found 594.1 (MH+).

N-(4-((6-Cyano-7-(2-methoxyethoxy)quinolin-4-yl)oxy)phenyl)-N-(4-fluorophenyl)cyclopropane-1,1-dicarboxamide (102): Compound 101 (65 mg, 109.35 μmol, 1 eq) and CuCN (15 mg, 167.48 μmol, 36.59 μL, 1.53 eq) were combined in N-Methyl-2-pyrrolidone (NMP) (2 mL) in a sealed tube and heated at 150° C. under microwave irradiation for 45 min. The reaction mixture was partitioned between water (10 mL), $NH_4OH$ (5 mL), and EtOAc (20 mL), the phases were separated, and the aq phase was further extracted with EtOAc. The combined organic phases were washed with aq saturated NaCl, dried over anhyd $Na_2SO_4$, and concentrated to give Compound 102 (40 mg, 68% yield) which was used in subsequent steps without further purification. MS (EI) for $C_{30}H_{25}FN_4O_5$. found 541.5 (MH+).

1-N-[4-[6-Carbamoyl-7-(2-methoxyethoxy)quinolin-4-yl]oxyphenyl]-1-N'-(4-fluorophenyl)cyclopropane-1,1-dicarboxamide (103): Compound 102 (40 mg, 74.00 μmol, 1 eq) and NaOH (100 mg, 2.50 mmol, 33.79 eq) were dissolved in DMSO (1.5 mL) and water (0.5 mL). The resulting mixture was heated at 80° C. for 1 h. The reaction mixture was partitioned between water (10 mL) and EtOAc (20 mL), the phases were separated, and the aq phase further extracted with EtOAc. The combined organic phases were washed with aq saturated NaCl, dried over anhyd $Na_2SO_4$, and concentrated. The residue was purified by flash silica gel chromatography (50~100% EtOAc/Petroleum ether) to give Compound 103 (18.6 mg, 44% yield). $^1H$ NMR (400 MHz, $CDCl_3$) δ 9.30 (s, 1H), 9.27 (s, 1H), 9.02 (s, 1H), 8.64-8.63 (d, 1H), 8.15 (s, 1H), 7.69-7.66 (d, 2H), 7.51-7.48 (m, 3H), 7.17-7.15 (d, 2H), 7.07-7.03 (m, 2H), 6.47-6.45 (d, 1H), 5.92 (s, 1H), 4.44-4.42 (t, 2H), 3.91-3.89 (t, 2H), 3.50 (s, 3H), 1.75-1.68 (m, 4H); MS (EI) for $C_{30}H_{27}FN_4O_6$. found 559.4 (MH+).

Example 39: 1-N-[4-[6-Carbamoyl-7-(2-hydroxyethoxy)quinolin-4-yl]oxyphenyl]-1-N'-(4-fluorophenyl)cyclopropane-1,1-dicarboxamide (106)

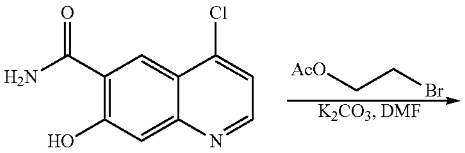

42

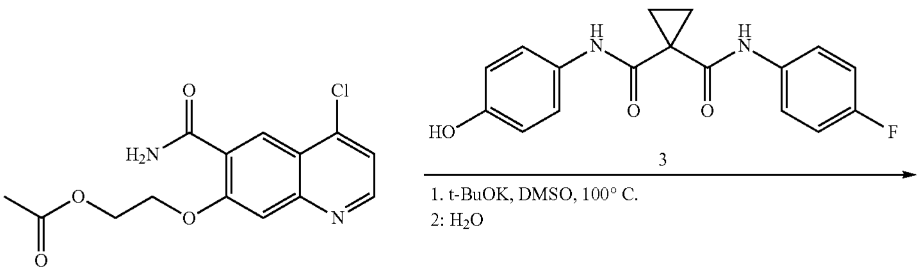

104

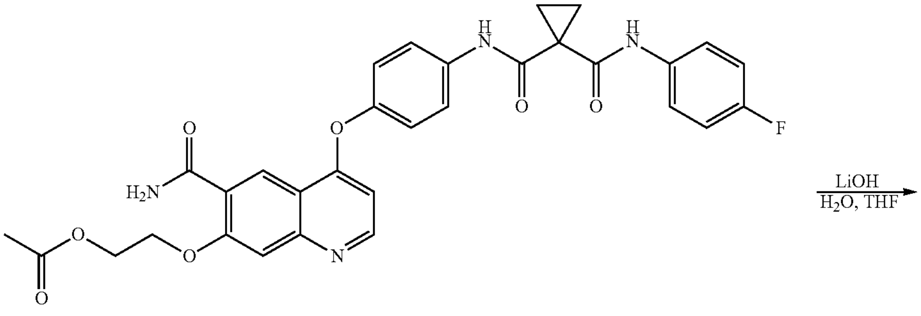

105

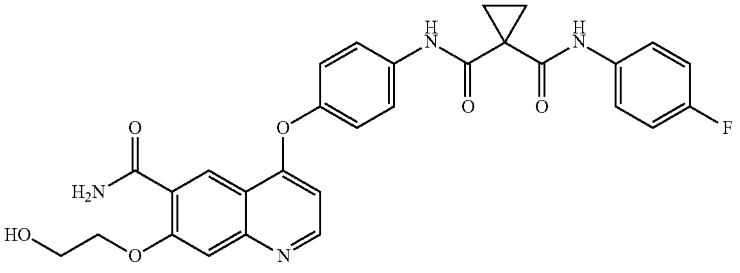

106

2-((6-Carbamoyl-4-chloroquinolin-7-yl)oxy)ethyl acetate (104): To a mixture of Compound 94 (200 mg, 853.44 μmol, 1 eq) and $K_2CO_3$ (589.77 mg, 4.27 mmol, 5 eq) in DMF (10 mL) was added 2-bromoethyl acetate (285.05 mg, 1.71 mmol, 187.53 uL, 2.00 eq) at 10° C. The resulting mixture was stirred for 1 h at 70° C. After cooling, the reaction mixture was diluted with water (50 mL) and extracted with EtOAc (3x30 mL). The combined extracts were washed with aq saturated NaCl (3x100 mL), dried over anhyd $Na_2SO_4$, and concentrated in vacuo to give Compound 104 (220 mg, 79.33% yield). MS (EI) for $C_{14}H_{13}ClN_2O_4$. found 309.0 (MH+).

2-((6-Carbamoyl-4-(4-(1-((4-fluorophenyl)carbamoyl) cyclopropane-1-carboxamido)phenoxy)quinolin-7-yl)oxy) ethyl acetate (105): Compound 104 (200 mg, 615.45 µmol) was converted to Compound 105 by reaction with Compound 3 using a manner analogous to the preparation of Compound 43 from Compounds 42 and 3 in Example 12. The resulting reaction mixture was treated with water at 100° C. for 4 h before employing the usual reaction work-up as outlined in Example 12. The resulting product was a mixture of Compound 105 and Compound 106. The mixture was separated by flash silica gel chromatography to give Compound 105 (100 mg, 24.93% yield), which was used in the next reaction, and Compound 106 (100 mg, 25.36% yield, 85% purity), which was combined with the product of the next reaction for final purification. For Compound 105: MS (EI) for $C_{31}H_{27}FN_4O_7$. found 587.1 (MH+).

1-N-[4-[6-Carbamoyl-7-(2-hydroxyethoxy)quinolin-4-yl] oxyphenyl]-1-N'-(4-fluorophenyl)cyclopropane-1,1-dicarboxamide (106): To a solution of Compound 105 (isolated from the previous reaction (100 mg, 153.44 µmol, 1 eq)) in THF (5 mL) and water (1 mL) was added $LiOH.H_2O$ (64.39 mg, 1.53 mmol, 10 eq). The resulting mixture was stirred for 1 h at 70° C. After allowing the reaction mixture to cool to room temperature, the mixture was acidified to a pH of approximately 7 with aq saturated $NH_4Cl$ solution, diluted with water (30 mL), and extracted with EtOAc (3x20 mL). The combined organic phases were dried over anhyd $Na_2SO_4$ and concentrated in vacuo to give crude Compound 106 (90 mg, 91.56% yield, 85% purity). This material was combined with the Compound 106 isolated from the previous step and purified by flash silica gel chromatography. The resulting product was suspended in a 1:1 mixture of DCM: MeCN and stirred for 10 min. The resulting solid was filtered, washed with MeCN followed by DCM, and dried in vacuo give Compound 106 (65.8 mg, 38.7% yield). $^1H$ NMR (400 MHz, DMSO-$d_6$) δ 10.20 (s, 1H), 10.06 (s, 1H), 8.83 (s, 1H), 8.66 (d, 1H), 7.96 (s, 1H), 7.84 (s, 1H), 7.78 (d, 2H), 7.64 (dd, 2H), 7.56 (s, 1H), 7.27 (d, 2H), 7.15 (t, 2H), 6.47 (d, 1H), 5.14 (t, 1H), 4.32 (t, 2H), 3.86 (dd, 2H), 1.47 (s, 4H); MS (EI) for $C_{29}H_{25}FN_4O_6$. found 545.1 (MH+).

Example 40: 1-N'-(4-Fluorophenyl)-1-N-[4-[7-(2-hydroxyethoxy)-6-(methylcarbamoyl)quinolin-4-yl] oxyphenyl]cyclopropane-1,1-dicarboxamide (110)

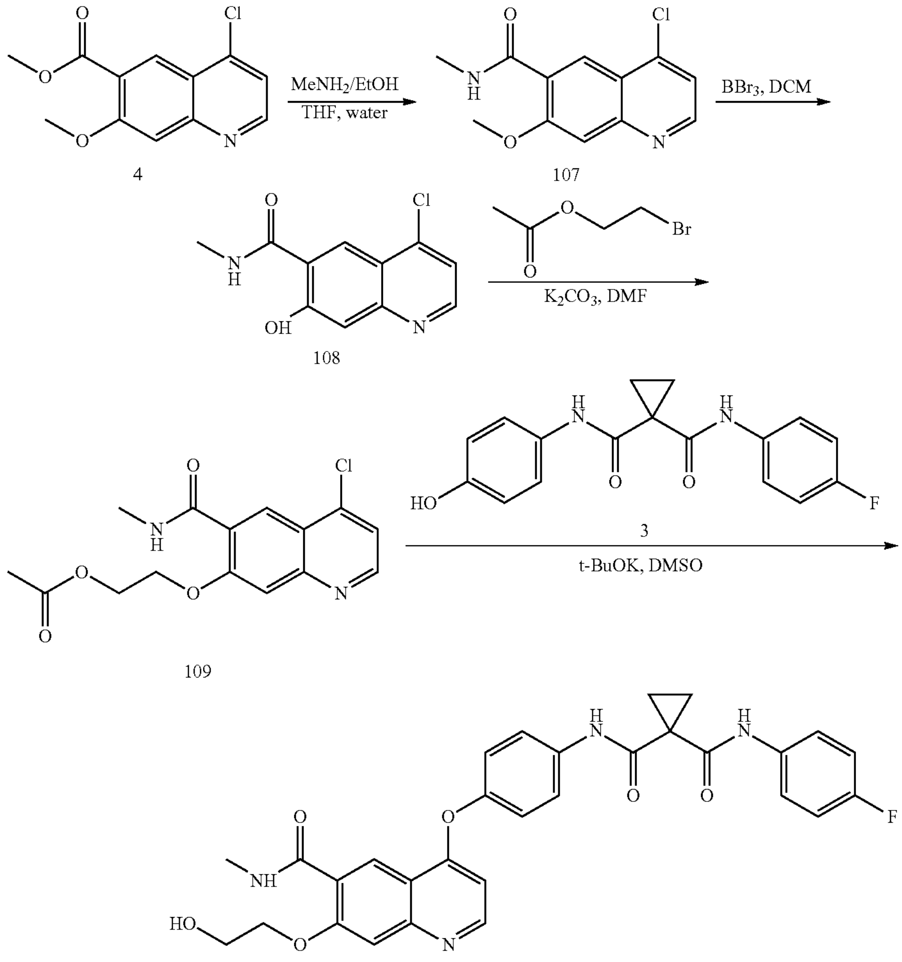

4

107

108

109

3

110

4-Chloro-7-methoxy-N-methylquinoline-6-carboxamide (107): Methylamine (8 M, 50 mL, 10.07 eq) in EtOH was added to a solution of Compound 4 (10 g, 39.74 mmol, 1 eq) in THF (150 mL) at 30° C. and stirred at that temperature for 25 h. The reaction mixture was concentrated under vacuum. The residue was slurried with warm water (100 mL), and the resulting residue was filtered and dried under vacuum to give Compound 107 (9 g, 90.4% yield). MS (EI) for $C_{12}H_{11}ClN_2O_2$. found 251.0 (MH+).

4-Chloro-7-hydroxy-N-methylquinoline-6-carboxamide (108): Compound 108 was synthesized from Compound 107 in a manner analogous to the preparation of Compound 94 from Compound 93 in Example 36 (730 mg, 62% yield). MS (EI) for $C_{11}H_9ClN_2O_2$. found 237.0 (MH+).

2-((4-Chloro-6-(methylcarbamoyl)quinolin-7-yl)oxy) ethyl acetate (109): Compound 109 was synthesized from Compound 108 in a manner analogous to the preparation of Compound 104 from Compound 94 in Example 39 (200 mg, crude). MS (EI) for $C_{15}H_{15}ClN_2O_4$. found 323.1 (MH+).

1-N'-(4-Fluorophenyl)-1-N-[4-[7-(2-hydroxyethoxy)-6-(methylcarbamoyl)quinolin-4-yl]oxyphenyl]cyclopropane-1,1-dicarboxamide (110): t-BuOK (70 mg, 623.83 μmol, 2.01 eq) was added to a mixture of Compound 3 (107 mg, 340.43 μmol, 1.10 eq) and Compound 109 (100 mg, 309.84 μmol, 1 eq) in DMSO (10 mL). The resulting mixture was heated at 100° C. with stirring for 2 h. After cooling to room temperature, the reaction mixture was diluted with water (50 mL) and extracted with EtOAc (3×50 mL). The combined organic phases were washed with aq saturated NaCl (2×100 mL), dried over anhyd $Na_2SO_4$, and concentrated under vacuum. The residue was purified by flash silica gel chromatography (0-20% MeOH in EtOAc) to give the crude product, which was purified by prep-TLC (20% MeOH in DCM, $R_f$=0.3) to give the Compound 110 (54.8 mg, 100% purity). $^1$H NMR (400 MHz, DMSO-$d_6$) δ 10.22 (s, 1H), 10.07 (s, 1H), 8.75 (s, 1H), 8.66 (d, 1H), 8.49 (q, 1H), 7.78 (d, 2H), 7.64 (dd, 2H), 7.57 (s, 1H), 7.27 (d, 2H), 7.15 (t, 2H), 6.46 (d, 1H), 5.19 (t, 1H), 4.32 (t, 2H), 3.86 (br d, 2H), 2.87 (d, 3H), 1.47 (s, 4H); MS (EI) for $C_{30}H_{27}FN_4O_6$. found 559.1 (MH+).

Example 41: 1-N-[4-[6-Carbamoyl-7-(2-hydroxypropoxy)quinolin-4-yl]oxyphenyl]-1-N'-(4-fluorophenyl)cyclopropane-1,1-dicarboxamide (115)

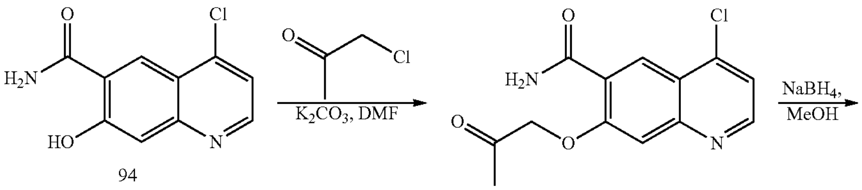

94

111

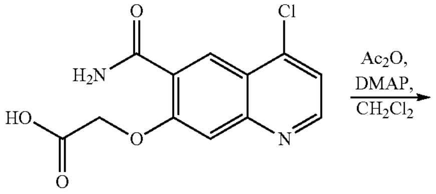

112

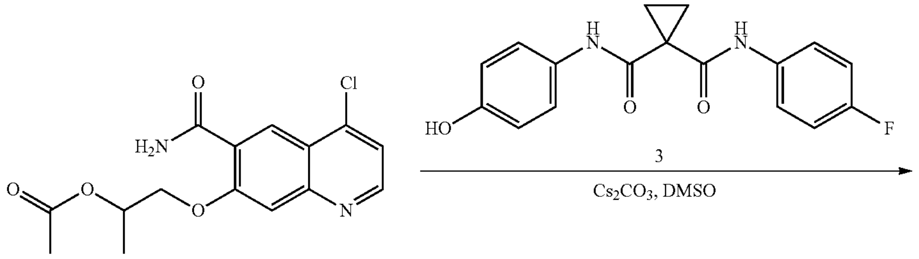

113

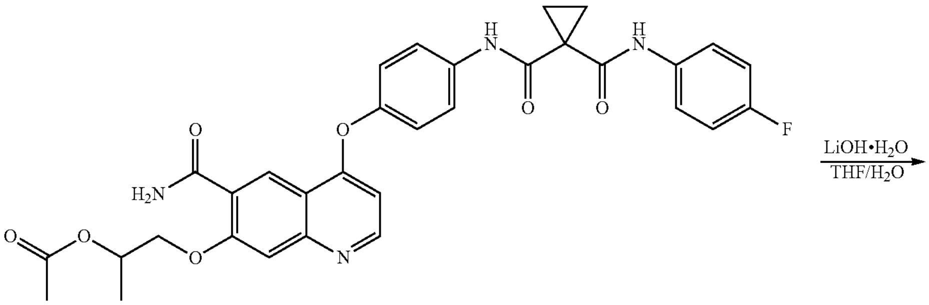

114

-continued

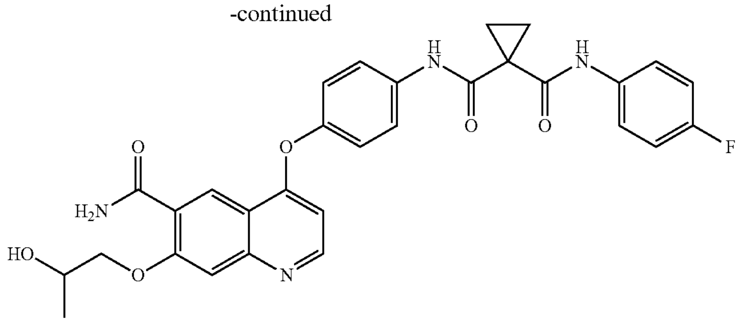

115

4-Chloro-7-(2-oxopropoxy)quinoline-6-carboxamide (111): To a mixture of Compound 94 (200 mg, 853.4 μmol, 1 eq) and $K_2CO_3$ (589.76 mg, 4.27 mmol, 5 eq) in DMF (10 mL) was added 1-chloropropan-2-one (1.45 g, 15.7 mmol, 11.97 μL, 18.4 eq) at 10° C. The reaction mixture was then stirred for 1 h at 65° C. The reaction mixture was diluted with water (50 mL) and extracted with EtOAc (3×30 mL). The combined extracts were washed with aq saturated NaCl (3×100 mL), dried over anhyd $Na_2SO_4$, and concentrated. The resulting residue was purified by flash silica gel chromatography (0-10% MeOH in DCM). The resulting yellow residue was further purified prep HPLC (column: Waters Xbridge 150 mm*25 mm*5 μm; mobile phase: [water (0.05% ammonia hydroxide v/v)-ACN]; B %: 17%-47%, 7.8 min) to give Compound 111 (55 mg, 30.0% yield). MS (EI) for $C_{13}H_{11}ClN_2O_3$. found 279.0 (MH+).

4-Chloro-7-(2-hydroxypropoxy)quinoline-6-carboxamide (112): To a mixture of Compound 111 (50 mg, 170.44 μmol, 1 eq) in MeOH (10 mL) was added $NaBH_4$ (12.90 mg, 340.88 μmol, 2 eq) at 10° C. The reaction mixture was then stirred for 1 h at 50° C. The reaction mixture was quenched with aq saturated $NH_4Cl$ (30 mL) and extracted with EtOAc/i-PrOH (v/v=3:1, 5×20 mL). The combined extracts were dried over anhyd $Na_2SO_4$ and concentrated under reduced pressure to give Compound 112 (50 mg, 99.3% yield). MS (EI) for $C_{13}H_{13}ClN_2O_3$. found 302.8 $(MH+Na)^+$.

1-((6-Carbamoyl-4-chloroquinolin-7-yl)oxy)propan-2-yl acetate (113): To a mixture of Compound 112 (45 mg, 128.25 μmol, 1 eq) in DCM (10 mL) were added $Ac_2O$ (65.46 mg, 641.24 μmol, 60.06 μL, 5 eq) and DMAP (15.67 mg, 128.25 μmol, 1 eq) at 10° C. The mixture was then stirred for 16 h at 10° C. The reaction mixture was diluted with water (30 mL) and extracted with DCM (5×20 mL). The combined extracts were dried over anhyd $Na_2SO_4$ and concentrated. The residue was purified by flash silica gel chromatography (0-3% MeOH in EtOAc) to afford Compound 113 (45 mg, 86.98% yield, 80% purity). MS (EI) for $C_{15}H_{15}ClN_2O_4$. found 344.8 $(MH+Na)^+$.

1-((6-Carbamoyl-4-(4-(1-((4-fluorophenyl)carbamoyl)cyclopropane-1-carboxamido)phenoxy)quinolin-7-yl)oxy)propan-2-yl acetate (114): Compound 114 was synthesized from Compounds 113 and 3 in a similar manner as described for Compound 43 in Example 12 except that cesium carbonate was substituted for potassium t-butoxide and the reaction mixture was heated to 100° C. for 2 h (40 mg, 72.9% yield). MS (EI) for $C_{32}H_{29}FN_4O_7$. found 601.1 (MH+).

1-N-[4-[6-Carbamoyl-7-(2-hydroxypropoxy)quinolin-4-yl]oxyphenyl]-1-N'-(4-fluorophenyl)cyclopropane-1,1-dicarboxamide (115): To a solution of Compound 114 (40 mg, 63.27 μmol, 1 eq) in THF (5 mL) and water (1 mL) was added $LiOH.H_2O$ (26.55 mg, 632.71 μmol, 10 eq). The mixture was stirred for 1 h at 70° C. After cooling to room temperature, the reaction was diluted with DCM (30 mL), dried over anhyd $Na_2SO_4$, and concentrated under reduced pressure. The product was suspended in MeCN (1 mL) and stirred for 5 min at 10° C. The resulting precipitate was collected by filtration and dried under vacuum to give Compound 115 (16.7 mg, 46.78% yield). $^1H$ NMR (400 MHz, DMSO-$d_6$) δ 10.20 (s, 1H), 10.06 (s, 1H), 8.81 (s, 1H), 8.66 (d, 1H), 8.02 (d, 1H), 7.84 (s, 1H), 7.78 (d, 2H), 7.64 (dd, 2H), 7.54 (s, 1H), 7.27 (d, 2H), 7.15 (t, 2H), 6.47 (d, 1H), 5.15 (d, 1H), 4.27-4.21 (m, 1H), 4.17-4.04 (m, 2H), 1.47 (s, 4H), 1.22 (d, 3H); MS (EI) for $C_{30}H_{27}FN_4O_6$. found 559.1 (MH+).

The following compound was prepared by a sequence analogous to that taken to prepare Compound 115 from Compound 94 in Examples 41, substituting Compound 94 with Compound 108:

1-N'-(4-Fluorophenyl)-1-N-[4-[7-(2-hydroxypropoxy)-6-(methylcarbamoyl)quinolin-4-yl]oxyphenyl]cyclopropane-1,1-dicarboxamide (116). $^1H$ NMR (400 MHz, DMSO-$d_6$) δ 10.27 (s, 1H), 10.13 (s, 1H), 8.80 (s, 1H), 8.73 (d, 1H), 8.62 (d, 1H), 7.85 (d, 2H), 7.71 (dd, 2H), 7.62 (s, 1H), 7.33 (d, 2H), 7.22 (t, 2H), 6.54 (d, 1H), 5.28 (d, 1H), 4.31 (dd, 1H), 4.23-4.10 (m, 2H), 2.94 (d, 3H), 1.54 (s, 4H), 1.29 (d, 3H); MS (EI) for $C_{31}H_{29}FN_4O_6$. found 573.1 (MH+).

Example 42: 1-N'-(4-Fluorophenyl)-1-N-[4-[7-(2-hydroxypropoxy)-6-(1,3-oxazol-2-yl)quinolin-4-yl]oxyphenyl]cyclopropane-1,1-dicarboxamide (125)

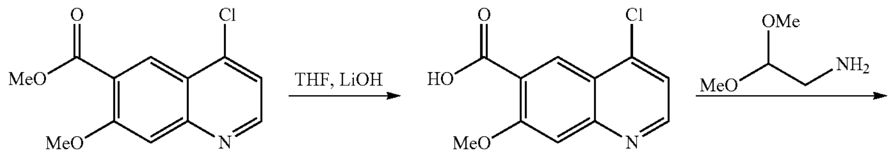

4 117

-continued
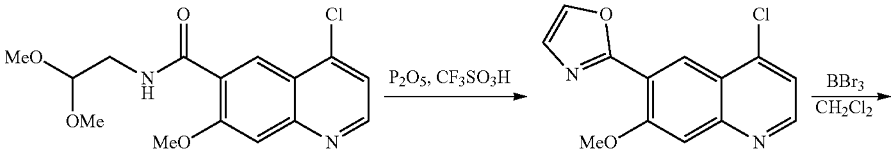
118
119
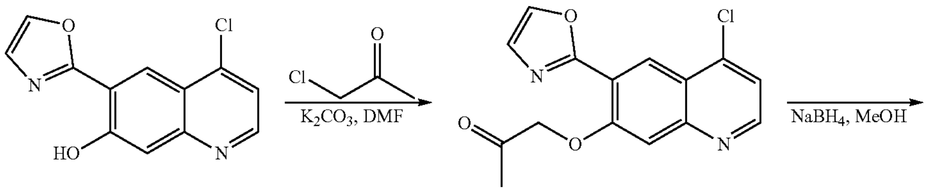
120
121
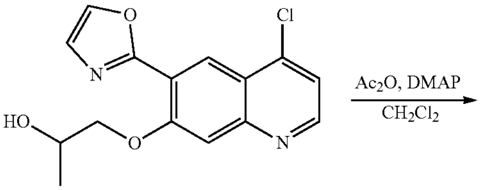
122
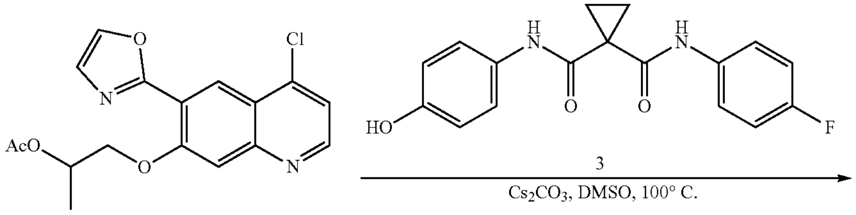
123
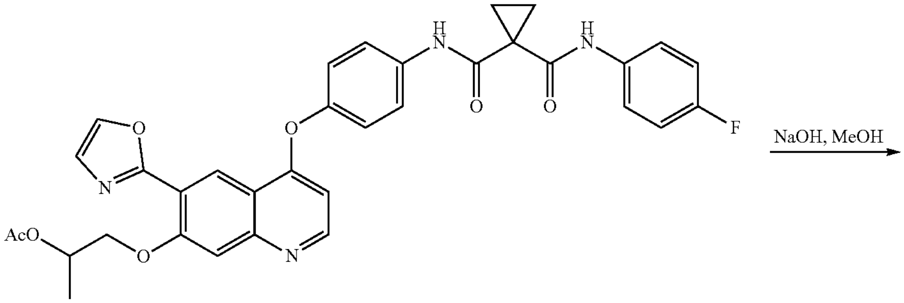
124
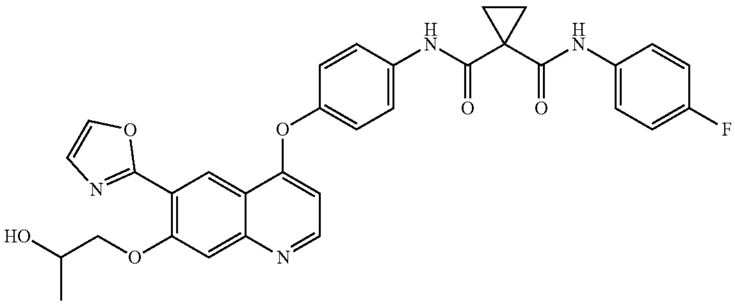
125
4-Chloro-7-methoxyquinoline-6-carboxylic acid (117): To a solution of Compound 4 (4.0 g, 15.89 mmol, 1 eq) in THF (30 mL) and water (6 mL) was added $LiOH.H_2O$ (1.33 g, 31.79 mmol, 2 eq), and the resulting mixture was stirred at 20° C. for 10 h. The resulting solid was filtered to give crude Compound 117 as a white solid (4.4 g) which was used in the next step without further purification. MS (EI) for $C_{11}H_8ClNO_3$. found 238.0 (MH+).

4-Chloro-N-(2,2-dimethoxyethyl)-7-methoxyquinoline-6-carboxamide (118): To a solution of Compound 117 (4 g, 16.83 mmol, 1 eq) and 2,2-dimethoxyethanamine (7.08 g, 67.33 mmol, 7.34 mL, 4 eq) in THF (40 mL) was added $T_3P$ (16.07 g, 50.50 mmol, 15.02 mL, 3 eq) and DIPEA (8.70 g, 67.33 mmol, 11.73 mL, 4 eq). The resulting reaction mixture was stirred at 20° C. for 15 h. Additional $T_3P$ (5 mL) and 2,2-dimethoxyethanamine (3 mL) were added to the mixture, and stirring continued at 20° C. for 25 h. The mixture was quenched with water (30 mL) and adjusted to pH 9-10 with aq 1 M NaOH. The resulting aq mixture was extracted with EtOAc (3×40 mL). The combined organic extracts were washed with aq saturated NaCl (15 mL) and concentrated to give crude Compound 118 a sa white solid (4.1 g, 73.5% yield) which was used in the next step without further purification. MS (EI) for $C_{15}H_{17}ClN_2O_4$. found 325.1 (MH+).

2-(4-Chloro-7-methoxyquinolin-6-yl)oxazole (119): To Compound 118 (2.5 g, 7.70 mmol, 1 eq) at 20° C. under nitrogen was added Eaton's Reagent (7.7 wt % phosphorus pentoxide solution in methanesulfonic acid, 23.09 mmol, 46.97 mL, 3 eq). The resulting mixture was heated at 145° C. for 7 h. The mixture was quenched with water (100 mL) and adjusted to pH 8-9 with $Et_3N$. The resulting mixture was extracted with EtOAc (4×40 mL). The combined organic extracts were washed with aq saturated NaCl (40 mL) and concentrated. The residue was purified by flash silica gel chromatography (ISCO®; 20 g SepaFlash® Silica Flash Column, Eluent of 0~80% Ethyl acetate/Petroleum ether gradient @ 32 mL/min) to give Compound 119 as a white solid (1.38 g, 68.8% yield). $^1H$ NMR (400 MHz, $CDCl_3$) δ 8.43 (s, 1H), 8.76 (d, 1H), 7.86 (s, 1H), 7.62 (s, 1H), 7.42 (d, 1H), 7.40 (s, 1H), 4.14 (s, 3H); MS (EI) for $C_{13}H_9ClN_2O_2$. found 261.0 (MH+).

4-Chloro-6-(oxazol-2-yl)quinolin-7-ol (120): Compound 120 was synthesized from Compound 119 in a manner analogous to the way Compound 94 was synthesized from Compound 93 in Example 36. MS (EI) for $C_{12}H_7ClN_2O_2$. found 246.7 (MH+).

1-((4-Chloro-6-(oxazol-2-yl)quinolin-7-yl)oxy)propan-2-one (121): Compound 121 was synthesized from Compound 120 in a manner analogous to the way Compound 111 was synthesized from Compound 94 in Example 41. MS (EI) for $C_{15}H_{11}ClN_2O_3$. found 302.7 (MH+).

1-((4-Chloro-6-(oxazol-2-yl)quinolin-7-yl)oxy)propan-2-ol (122): Compound 122 was synthesized from Compound 121 in a manner analogous to the way Compound 112 was synthesized from Compound 111 in Example 41. MS (EI) for $C_{15}H_{13}ClN_2O_3$. found 326.9 $[M+Na]^+$.

1-((4-Chloro-6-(oxazol-2-yl)quinolin-7-yl)oxy)propan-2-yl acetate (123): Compound 123 was synthesized from Compound 122 in a manner analogous to the way Compound 113 was synthesized from Compound 112 in Example 41. $^1H$ NMR (400 MHz, $CDCl_3$) δ 8.83 (s, 1H), 7.23 (d, 1H), 7.83 (s, 1H), 7.54 (s, 1H), 7.40 (d, 1H), 7.34 (s, 1H), 5.41-5.49 (m, 1H), 4.25 (d, 2H), 2.06 (s, 3H), 1.43 (d, 3H); MS (EI) for $C_{17}H_{15}ClN_2O_4$. found 347.1 (MH+).

1-((4-(4-(1-((4-Fluorophenyl)carbamoyl)cyclopropane-1-carboxamido)phenoxy)-6-(oxazol-2-yl)quinolin-7-yl)oxy) propan-2-yl acetate (124): Compound 124 was synthesized from Compounds 123 and 3 using a variation of the manner that Compound 43 was synthesized from Compounds 42 and 3 in Example 12. Cesium carbonate was substituted for the potassium t-butoxide and the reaction mixture was heated to 100° C. for 3 h. MS (EI) for $C_{34}H_{29}FN_4O_7$. found 625.0 (MH+).

1-N'-(4-Fluorophenyl)-1-N-[4-[7-(2-hydroxypropoxy)-6-(1,3-oxazol-2-yl)quinolin-4-yl]oxyphenyl]cyclopropane-1,1-dicarboxamide (125): To a solution of Compound 124 (400 mg, 640.4 umol, 1 eq) in water (5 mL) and MeOH (5 mL) was added NaOH (51.23 mg, 1.28 mmol, 2 eq), and the mixture was stirred at 20° C. for 5 h. The mixture was diluted with water (30 mL). The resulting precipitate was filtered and washed with water (2×5 mL) and MeOH (3 mL). The solid was then lyophilized to give Compound 125 as a white solid (238.5 mg, 63.9% yield). $^1H$ NMR (400 MHz, DMSO-$d_6$) δ 10.22 (s, 1H), 10.07 (s, 1H), 8.79 (s, 1H), 8.68 (d, 1H), 8.32 (s, 1H), 7.79 (d, 2H), 7.65 (t, 2H), 7.60 (s, 1H), 7.47 (s, 1H), 7.29 (d, 2H), 7.18 (t, 2H), 6.49 (d, 1H), 5.02 (d, 1H), 4.15-4.10 (m, 3H), 1.48 (s, 4H), 1.26 (d, 3H); MS (EI) for $C_{32}H_{27}FN_4O_6$. found 583.3 (MH+).

Example 43: Methyl 4-[2-chloro-4-[[1-[(4-fluorophenyl)carbamoyl]cyclopropane-carbonyl]amino]phenoxy]-7-methoxyquinoline-6-carboxylate (128)

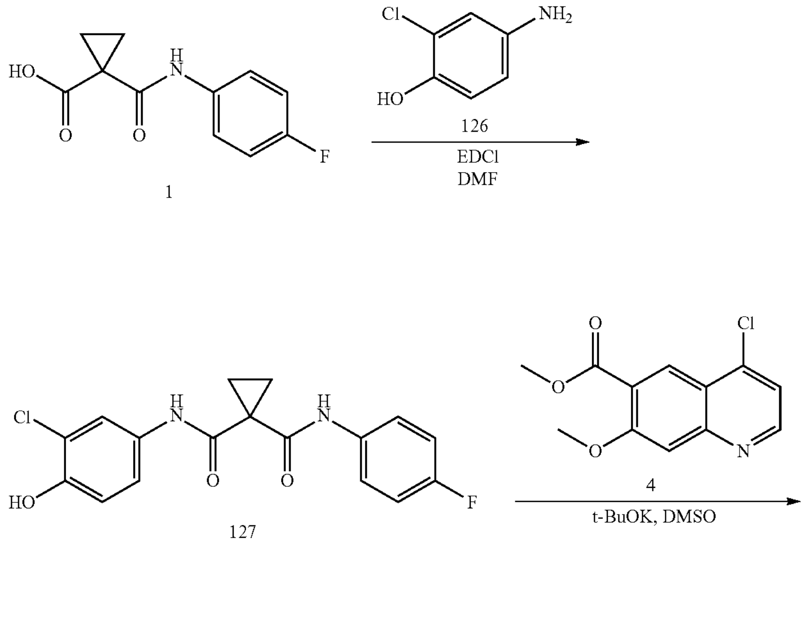

-continued

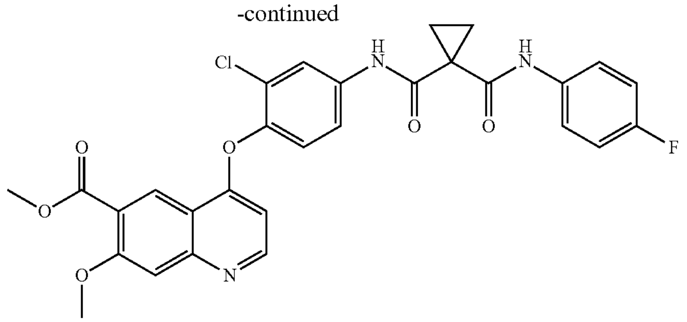

128

N-(3-Chloro-4-hydroxyphenyl)-N-(4-fluorophenyl)cyclopropane-1,1-dicarboxamide (127): Compound 127 was synthesized from Compounds 1 and 126 in a manner analogous to the preparation of Compound 3 from Compounds 1 and 2 in Example 1 (1.9 g, 73.5% yield). $^1$H NMR (400 MHz, $CDCl_3$) δ 9.03-8.85 (m, 2H), 7.68 (d, 1H), 7.50-7.40 (m, 2H), 7.18 (dd, 1H), 7.08-7.00 (m, 2H), 6.97 (d, 1H), 5.53 (s, 1H), 1.64 (s, 4H); MS (EI) for $C_{17}H_{14}ClFN_2O_3$. found 349.0 (MH+).

Methyl 4-[2-chloro-4-[[1-[(4-fluorophenyl)carbamoyl]cyclopropane-carbonyl]amino]phenoxy]-7-methoxyquinoline-6-carboxylate (128): Compound 128 was synthesized from Compounds 127 and 4 in a manner analogous to the preparation of Compound 43 from Compounds 42 and 3 in Example 12 (0.8 g, 32.1% yield). $^1$H NMR (400 MHz, $CDCl_3$) δ 10.08 (s, 1H), 8.83 (s, 1H), 8.63 (d, 1H), 8.20 (s, 1H), 7.92 (d, 1H), 7.55-7.48 (m, 2H), 7.48-7.41 (m, 2H), 7.21 (d, 1H), 7.10-7.02 (m, 2H), 6.30 (d, 1H), 4.04 (s, 3H), 3.97 (s, 3H), 1.85-1.78 (m, 2H), 1.66-1.58 (m, 2H); MS (EI) for $C_{29}H_{23}ClFN_3O_6$. found 564.4 (MH+).

The following compound was prepared in two steps in a sequence analogous to the way Compound 128 was synthesized in Example 43, replacing Compound 126 with 4-amino-2-fluorophenol:

Methyl 4-[2-fluoro-4-[[1-[(4-fluorophenyl)carbamoyl]cyclopropane-carbonyl]amino]phenoxy]-7-methoxyquinoline-6-carboxylate (129): $^1$H NMR (400 MHz, $CDCl_3$) δ 10.05 (s, 1H), 8.83 (s, 1H), 8.65 (d, 1H), 8.09 (s, 1H), 7.78 (dd, 1H), 7.50 (s, 1H), 7.48-7.42 (m, 2H), 7.27-7.19 (m, 2H), 7.10-7.04 (m, 2H), 6.40 (d, 1H), 4.05 (s, 3H), 3.97 (s, 3H), 1.84-1.81 (m, 2H), 1.63-1.60 (m, 2H); MS (EI) for $C_{29}H_{23}F_2N3O6$. found 548.4 (MH+).

Example 44: 4-[2-Chloro-4-[[1-[(4-fluorophenyl)carbamoyl]cyclopropane-carbonyl]amino]phenoxy]-7-methoxyquinoline-6-carboxylic Acid (130)

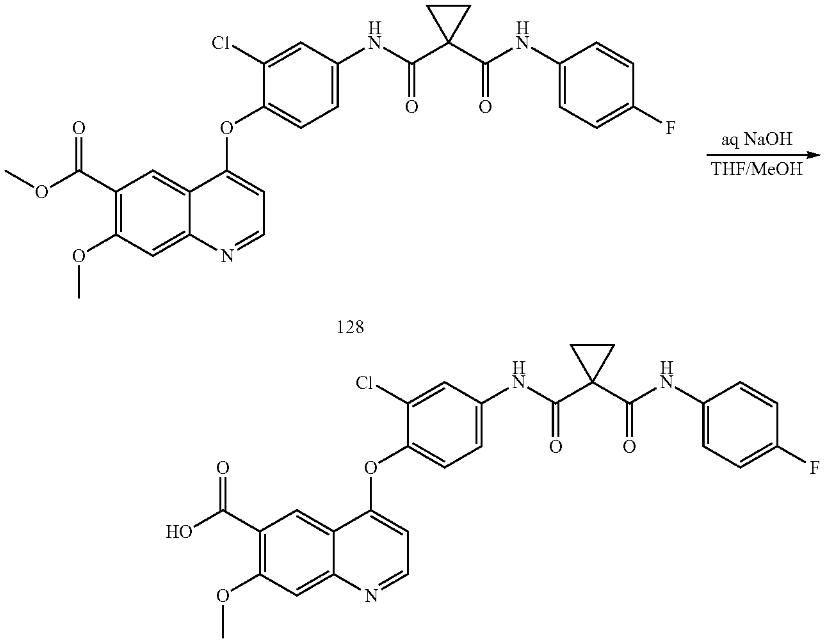

128

130

4-[2-Chloro-4-[[1-[(4-fluorophenyl)carbamoyl]cyclopropane-carbonyl]amino]phenoxy]-7-methoxyquinoline-6-carboxylic acid (130): Compound 130 was synthesized from Compound 128 in a manner analogous to the preparation of Compound 6 from Compound 5 in Example 2 (0.55 g, 76.6% yield). $^1$H NMR (400 MHz, DMSO-$d_6$) δ 10.41 (s, 1H), 10.10 (s, 1H), 8.58 (d, 1H), 8.25 (s, 1H), 8.10 (d, 1H), 7.75-7.59 (m, 3H), 7.47-7.37 (m, 2H), 7.16 (t, 2H), 6.32 (d, 1H), 3.92 (s, 3H), 1.47 (s, 4H); MS (EI) for $C_{28}H_{21}ClFN_3O_6$. found 550.1 (MH+).

The following compound was prepared from Compound 129 by a method analogous to the preparation of Compound 130 was synthesized from Compound 128 in Example 44:

4-[2-Fluoro-4-[[1-[(4-fluorophenyl)carbamoyl]cyclopropane-carbonyl]amino]phenoxy]-7-methoxyquinoline-6-carboxylic acid (131): $^1$H NMR (400 MHz, DMSO-$d_6$) δ 13.20 (s, 1H), 10.42 (s, 1H), 10.01 (s, 1H), 8.72 (d, 1H), 8.59 (s, 1H), 7.93 (d, 1H), 7.64 (dd, 2H), 7.56-7.51 (m, 2H), 7.50-7.44 (m, 1H), 7.15 (t, 2H), 6.54 (d, 1H), 3.99 (s, 3H), 1.47 (d, 4H); MS (EI) for $C_{28}H_{21}F_2N306$. found 534.4 (MH+).

Example 45: 1-N'-[4-(6-Carbamoyl-7-methoxyquinolin-4-yl)oxy-3-chlorophenyl]-1-N-(4-fluorophenyl)cyclopropane-1,1-dicarboxamide (132)

1-N'-[4-(6-Carbamoyl-7-methoxyquinolin-4-yl)oxy-3-chlorophenyl]-1-N-(4-fluorophenyl)cyclopropane-1,1-dicarboxamide (132): Compound 132 was synthesized from Compound 130 in a manner analogous to the preparation of Compound 7 from Compound 6 in Example 3 (43.1 mg, 40.9% yield). $^1$H NMR (400 MHz, DMSO-$d_6$) δ 10.38 (s, 1H), 10.04 (s, 1H), 8.71 (s, 1H), 8.67 (d, 1H), 8.11 (d, 1H), 7.89 (br s, 1H), 7.78 (br s, 1H), 7.73-7.61 (m, 3H), 7.54 (s, 1H), 7.46 (d, 1H), 7.16 (t, 2H), 6.37 (d, 1H), 4.04 (s, 3H), 1.47 (s, 4H); MS (EI) for $C_{28}H_{22}ClFN_4O_5$. found 549.4 (MH+).

The following compound was prepared from Compound 131 by a method analogous to the preparation of Compound 132 from Compound 130 in Example 45:

1-N'-[4-(6-Carbamoyl-7-methoxyquinolin-4-yl)oxy-3-fluorophenyl]-1-N-(4-fluorophenyl)cyclopropane-1,1-dicarboxamide (133): $^1$H NMR (400 MHz, DMSO-$d_6$) δ 10.40 (s, 1H), 10.01 (s, 1H), 8.67 (m, 2H), 7.93-7.88 (m, 2H), 7.76 (s, 1H), 7.64 (dd, 2H), 7.53-7.52 (m, 2H), 7.47-7.43 (m, 1H), 7.15 (t, 2H), 6.48 (d, 1H), 4.03 (s, 3H), 1.47 (s, 4H); MS (EI) for $C_{28}H_{22}F_2N_4O_5$. found 533.5 (MH+).

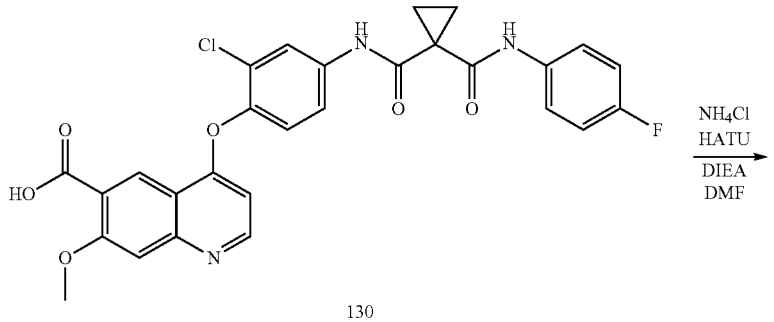

130

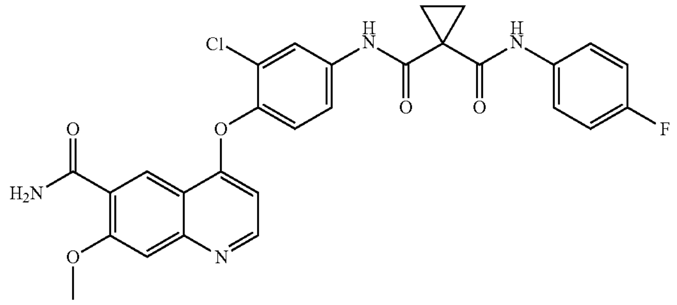

132

Example 46: 1-N'-[3-Chloro-4-[7-methoxy-6-(methylcarbamoyl)quinolin-4-yl]oxyphenyl]-1-N-(4-fluorophenyl)cyclopropane-1,1-dicarboxamide (134)

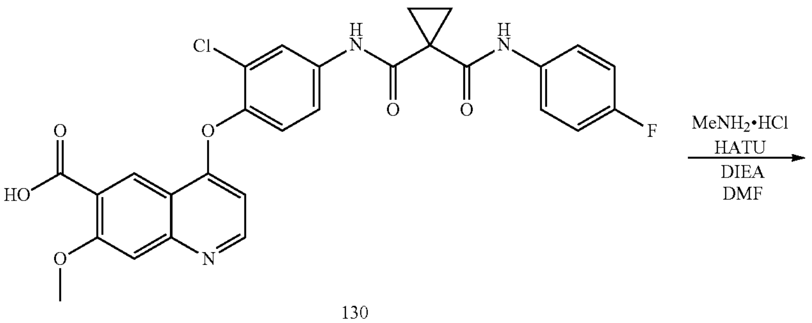

130

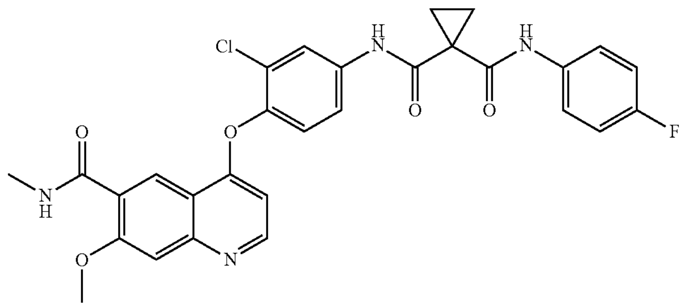

134

1-N'-[3-Chloro-4-[7-methoxy-6-(methylcarbamoyl)quinolin-4-yl]oxyphenyl]-1-N-(4-fluorophenyl)cyclopropane-1,1-dicarboxamide (134): Compound 134 was synthesized from Compound 130 in a manner analogous to the preparation of Compound 8 from Compound 6 in Example 4 (49.7 mg, 48.6% yield). $^1$H NMR (400 MHz, DMSO-$d_6$) δ 10.38 (s, 1H), 10.04 (s, 1H), 8.66 (d, 1H), 8.63 (s, 1H), 8.40 (br d, 1H), 8.11 (d, 1H), 7.72-7.61 (m, 3H), 7.54 (s, 1H), 7.46 (d, 1H), 7.20-7.12 (m, 2H), 6.37 (d, 1H), 4.03 (s, 3H), 2.85 (d, 3H), 1.48 (s, 4H); MS (EI) for $C_{29}H_{24}ClFN_4O_5$. found 563.1 (MH+).

The following compound was prepared from Compound 131 by a method analogous to the preparation of Compound 134 from Compound 130 in Example 46:

1-N'-[3-Fluoro-4-[7-methoxy-6-(methylcarbamoyl)quinolin-4-yl]oxyphenyl]-1-N-(4-fluorophenyl)cyclopropane-1,1-dicarboxamide (135): $^1$H NMR (400 MHz, DMSO-$d_6$) δ 10.40 (s, 1H), 10.01 (s, 1H), 8.67 (d, 1H), 8.61 (s, 1H), 8.39 (d, 1H), 7.91 (d, 1H), 7.64 (dd, 2H), 7.53-7.52 (m, 2H), 7.47-7.42 (m, 1H), 7.15 (t, 2H), 6.48 (d, 1H), 4.02 (s, 3H), 2.84 (d, 3H), 1.47 (s, 4H); MS (EI) for $C_{29}H_{24}F_2N_4O_5$. found 547.5 (MH+).

Example 47: Methyl 4-[4-[[1-[(4-fluorophenyl)carbamoyl]cyclopropane-carbonyl]amino]phenoxy]-6-methylquinoline-7-carboxylate (140)

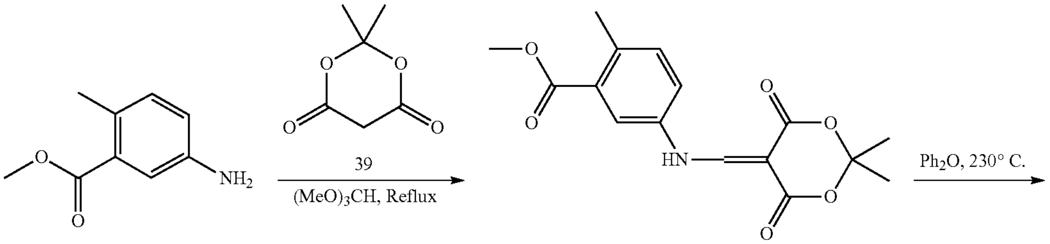

136

137

-continued

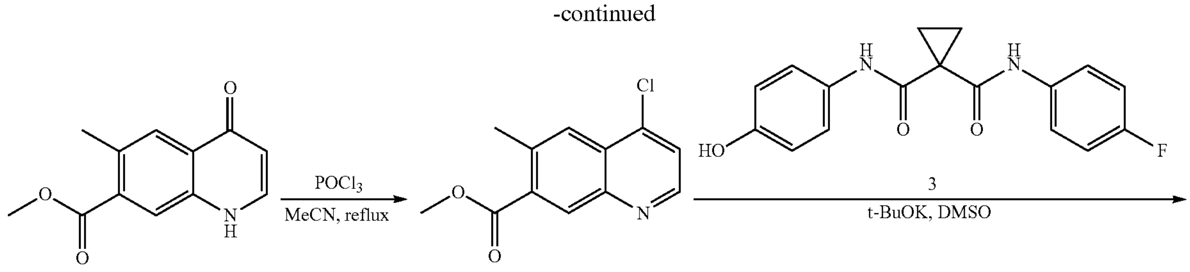

138

139

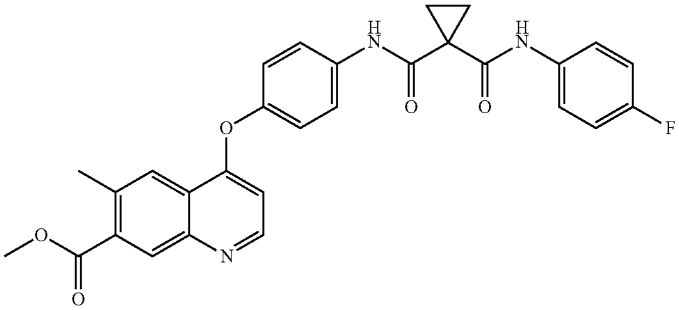

140

Methyl 5-(((2,2-dimethyl-4,6-dioxo-1,3-dioxan-5-ylidene)methyl)amino)-2-methylbenzoate (137): Compound 137 was synthesized from Compounds 136 and 39 in a manner analogous to the preparation of Compound 40 from Compound 38 and 39 in Example 12 (4.74 g, 81.7% yield). $^1$H NMR (400 MHz, DMSO-$d_6$) δ 11.28 (s, 1H), 8.53 (s, 1H), 8.01-7.88 (d, 1H), 7.75-7.61 (dd, 1H), 7.45-7.30 (d, 1H), 3.85 (s, 3H), 2.49 (s, 3H), 1.67 (s, 6H).

Methyl 6-methyl-4-oxo-1,4-dihydroquinoline-7-carboxylate (138): Compound 138 was synthesized from Compound 137 in a manner analogous to the preparation of Compound 41 from Compound 40 in Example 12 (625 mg, 25.9% yield). MS (EI) for $C_{12}H_{11}NO_3$. found 218.1 (MH+).

Methyl 4-chloro-6-methylquinoline-7-carboxylate (139): Compound 139 was synthesized from Compound 138 in a manner similar to that described for Compound 42 in Example 12 except Compound 138 was heated in a mixture of MeCN (10 mL) and $POCl_3$ (3 mL) instead of neat $POCl_3$ (445 mg, 65.6% yield). MS (EI) for $C_{12}H_{10}ClNO_2$. found 236.3 (MH+).

Methyl 4-[4-[[1-[(4-fluorophenyl)carbamoyl]cyclopropane-carbonyl]amino]phenoxy]-6-methylquinoline-7-carboxylate (140): Compound 140 was synthesized from Compounds 139 and 3 in a manner analogous to the preparation of Compound 43 from synthesized from Compound 42 and 3 in Example 12 (320 mg, 36.7% yield). $^1$H NMR (400 MHz, $CD_3OD$) δ 8.66-8.61 (d, 1H), 8.52 (s, 1H), 8.28 (s, 1H), 7.78-7.71 (d, 2H), 7.60-7.54 (m, 2H), 7.28-7.22 (d, 2H), 7.11-7.03 (m, 2H), 6.71-6.67 (d, 1H), 3.98 (s, 3H), 2.76 (s, 3H), 1.64 (s, 4H); MS (EI) for $C_{29}H_{24}FN_3O_5$. found 514.1 (MH+).

Example 48: 4-[4-[[1-[(4-Fluorophenyl)carbamoyl]cyclopropane-carbonyl]amino]phenoxy]-6-methylquinoline-7-carboxylic Acid (141)

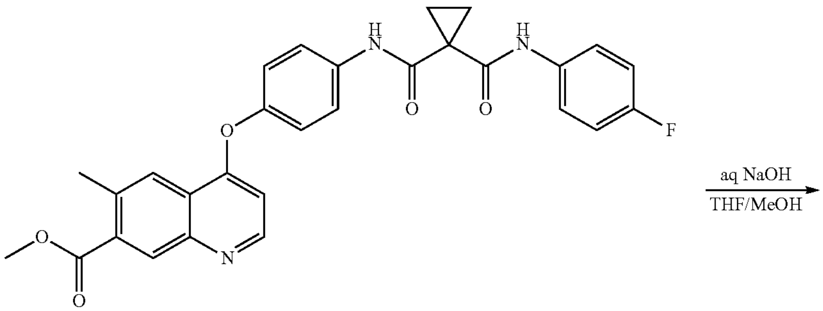

140

-continued

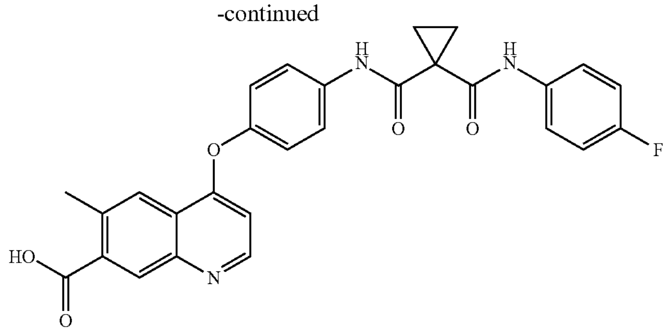

141

4-[4-[[1-[(4-Fluorophenyl)carbamoyl]cyclopropane-carbonyl]amino]phenoxy]-6-methylquinoline-7-carboxylic acid (141): Compound 141 was synthesized from Compound 140 in a manner analogous to the preparation of Compound 6 from Compound 5 in Example 2 (100 mg, 93.5% yield). $^1$H NMR (400 MHz, $CD_3OD$) δ 8.66-8.61 (d, 1H), 8.47 (s, 1H), 8.27 (s, 1H), 7.78-7.73 (d, 2H), 7.78-7.71 (dd, 2H), 7.28-7.24 (d, 2H), 7.11-7.03 (t, 2H), 6.73-6.69 (d, 1H), 2.76 (s, 3H), 1.65 (s, 4H); MS (EI) for $C_{28}H_{22}FN_3O_5$. found 500.5 (MH+).

Example 49: 1-N-[4-(7-Carbamoyl-6-methylquinolin-4-yl)oxyphenyl]-1-N'-(4-fluorophenyl)cyclopropane-1,1-dicarboxamide (142)

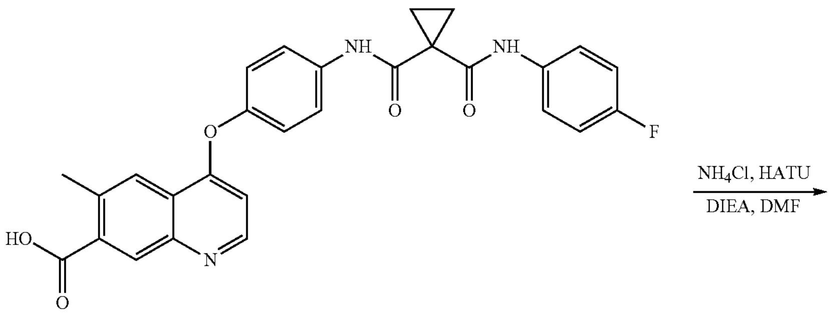

141

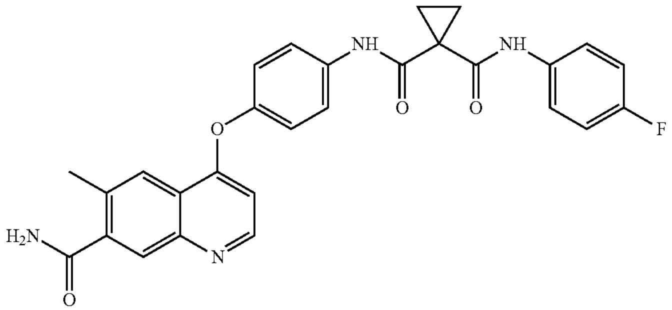

142

1-N-[4-(7-Carbamoyl-6-methylquinolin-4-yl)oxyphenyl]-1-N'-(4-fluorophenyl)cyclopropane-1,1-dicarboxamide (142): Compound 142 was synthesized from Compound 141 in a manner analogous to the preparation of Compound 7 in Example 3 (17.4 mg, 34.9% yield). $^1$H NMR (400 MHz, $CD_3OD$) δ 8.65-8.57 (d, 1H), 8.26 (s, 1H), 8.05 (s, 1H), 7.78-7.70 (d, 2H), 7.62-7.51 (m, 2H), 7.30-7.20 (m, 2H), 7.13-7.03 (m, 2H), 6.69-6.63 (d, 1H), 2.65 (s, 3H), 1.64 (s, 4H); MS (EI) for $C_{28}H_{23}FN_4O_4$. found 499.1 (MH+).

Example 50: 1-N'-(4-Fluorophenyl)-1-N-[4-[6-methyl-7-(methylcarbamoyl)quinolin-4-yl]oxyphenyl]cyclopropane-1,1-dicarboxamide (143)

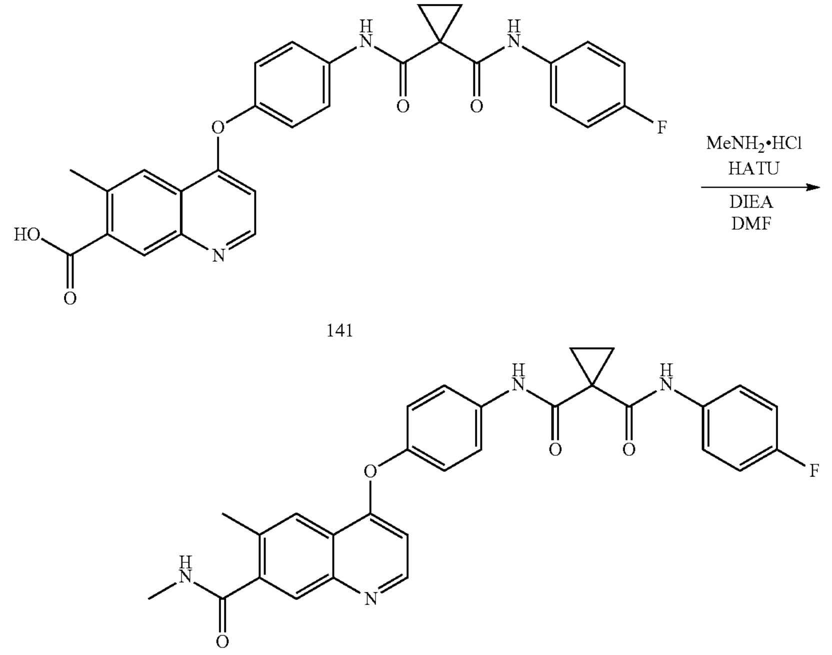

141

143

1-N'-(4-Fluorophenyl)-1-N-[4-[6-methyl-7-(methylcarbamoyl)quinolin-4-yl]oxyphenyl]cyclopropane-1,1-dicarboxamide (143): Compound 143 was synthesized from Compound 141 in a manner analogous to the preparation of Compound 8 in Example 4 (11.9 mg, 17.8% yield). $^1$H NMR (400 MHz, $CD_3OD$) δ 8.64-8.55 (d, 1H), 8.25 (s, 1H), 7.97 (s, 1H), 7.78-7.68 (d, 2H), 7.61-7.50 (m, 2H), 7.28-7.18 (d, 2H), 7.11-7.02 (m, 2H), 6.70-6.61 (d, 1H), 2.98 (s, 3H), 2.60 (s, 3H), 1.64 (s, 4H); MS (EI) for $C_{29}H_{25}FN_4O_4$. found 513.1 (MH+).

Example 51: Methyl 4-[4-[[1-[(4-fluorophenyl)carbamoyl]cyclopropane-carbonyl]amino]phenoxy]-6-methoxyquinoline-7-carboxylate (150)

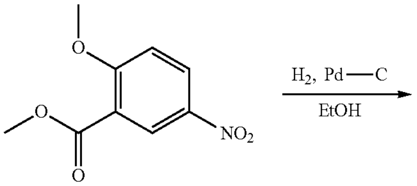

144

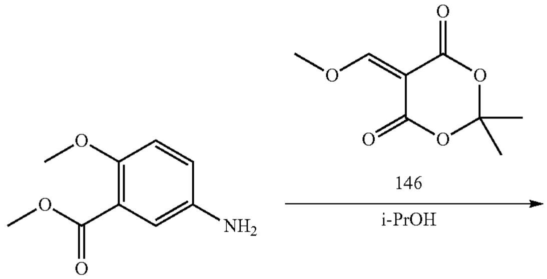

146

145

-continued

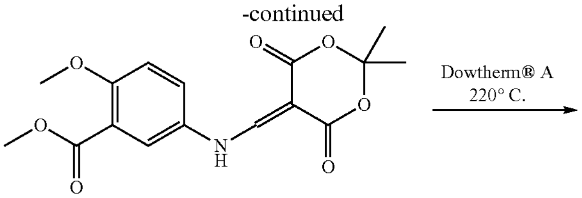

147

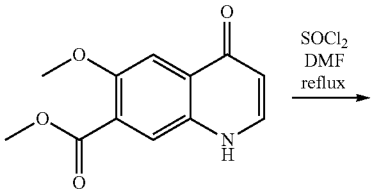

148

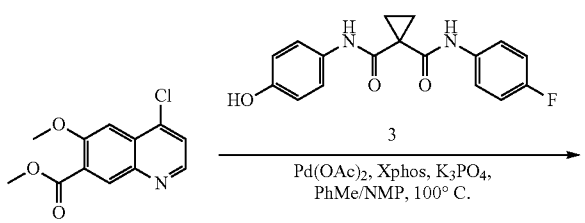

3

149

-continued

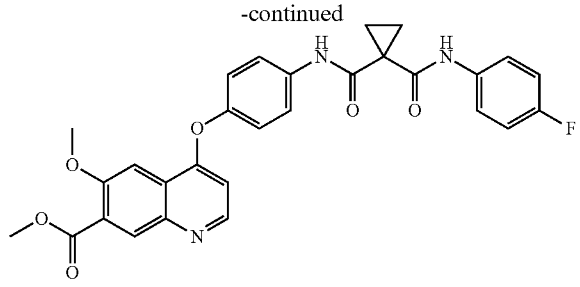

150

Methyl 5-amino-2-methoxybenzoate (145): To a solution of Compound 144 (5.00 g, 23.68 mmol, 1 eq) in EtOH (50 mL) was added 10% Pd/C (500 mg), and the resulting mixture was degassed and purged under H2. The reaction mixture was stirred under H2 (15 psi) at 25° C. for 12 h. The reaction mixture was filtered, and the filtrate was concentrated to give Compound 145 (4.5 g, 99.6% yield), which was used in subsequent steps without further purification. $^1H$ NMR (400 MHz, $CDCl_3$) δ 7.16 (t, 1H), 6.86-6.82 (m, 2H), 3.88 (s, 3H), 3.83 (s, 3H), 3.09 (br s, 2H).

Methyl 5-(((2,2-dimethyl-4,6-dioxo-1,3-dioxan-5-ylidene)methyl)amino)-2-methoxybenzoate (147): To a suspension of Compound 146 (1.95 g, 10.49 mmol, 1 eq) in isopropanol (40 mL) was added Compound 145 (2 g, 10.49 mmol, 1 eq) portionwise at 20° C. The reaction was heated at 80° C. for 30 min. The mixture was cooled to 20° C., and the precipitate was collected, washed with tert-butyl methyl ether (50 mL), and dried to give Compound 147 (3.3 g, 93.82% yield). $^1H$ NMR (400 MHz, $CDCl_3$) δ 11.25 (d, 1H), 8.57 (d, 1H), 7.75 (d, 1H), 7.37 (dd, 1H), 7.05 (d, 1H), 3.95 (s, 3H), 3.93 (s, 3H), 1.76 (s, 6H).

Methyl 6-methoxy-4-oxo-1,4-dihydroquinoline-7-carboxylate (148): To DOWTHERM® A (eutectic mixture of 26.5% diphenyl+73.5% diphenyl oxide)(CAS Reg. No. 8004-13-5) (10 mL) at 220° C. was added Compound 147 (1.0 g, 2.98 mmol, 1 eq) portionwise. The reaction was stirred at 220° C. for 10 min. The reaction was cooled to 20-25° C. and then diluted with petroleum ether (50 mL). The resulting residue was collected, washed with petroleum ether (3x30 mL), and dried to give Compound 148 (800 mg, 69.07% yield, 60% purity). $^1H$ NMR (400 MHz, DMSO-$d_6$) δ 12.22 (d, 1H), 7.94 (d, 1H), 7.92 (s, 1H), 7.61 (s, 1H), 6.06 (d, 1H), 3.87 (s, 3H), 3.84 (s, 3H).

Methyl 4-chloro-6-methoxyquinoline-7-carboxylate (149): To a mixture of Compound 148 (700 mg, 1.80 mmol, 1 eq) in $SOCl_2$ (10 mL) was added 5 drops of DMF. The resulting mixture was stirred at 80° C. for 1 h. The reaction mixture was concentrated in vacuo, and the resulting residue was diluted with aq saturated $NaHCO_3$ (20 mL) and extracted with EtOAc (3x30 mL). The combined organic phases were washed with aq saturated NaCl (50 mL), dried over anhyd $Na_2SO_4$, and concentrated. The residue was purified by flash silica gel chromatography (ISCO®; 4 g SepaFlash® Silica Flash Column, Eluent of 0~30% EtOAc/Petroleum ether gradient at 25 mL/min) to give Compound 149 (220 mg, 46.14% yield, 95% purity). $^1H$ NMR (400 MHz, $CDCl_3$) δ 8.71 (d, 1H), 8.49 (s, 1H), 7.55-7.49 (m, 2H), 4.07 (s, 3H), 3.99 (s, 3H); MS (EI) for $C_{12}H_{10}ClNO_3$. found 252.3 (MH+).

Methyl 4-[4-[[1-[(4-fluorophenyl)carbamoyl]cyclopropanecarbonyl]amino]phenoxy]-6-methoxyquinoline-7-carboxylate (150): To a mixture of Compound 149 (190 mg, 679.47 μmol, 1 eq), Compound 3 (235 mg, 747.67 μmol, 1.1 eq), $K_3PO_4$ (190 mg, 895.10 μmol, 1.32 eq), and 2-dicyclohexylphosphino-2',4',6'-triisopropylbiphenyl (XPhos) (33 mg, 69.22 μmol, 0.1 eq) in toluene (3 mL) and 1-methyl-2-pyrrolidinone (0.5 mL) was added $Pd(OAc)_2$ (8 mg, 35.63 μmol, 0.05 eq) under nitrogen. The reaction was stirred at 100° C. for 3 h. The mixture was diluted with EtOAc (30 mL), and any insoluble material was filtered off. The filtrate was diluted with water (30 mL) and extracted with EtOAc (3x30 mL). The combined organic phases were washed with aq saturated NaCl (50 mL), dried over anhyd $Na_2SO_4$, and concentrated. The residue was purified by flash silica gel chromatography (ISCO®; 4 g SepaFlash® Silica Flash Column, Eluent of 0 to approximately 50% EtOAc/Petroleum ether gradient at 25 mL/min) to give Compound 150 (170 mg, 46.06% yield, 97.49% purity). $^1H$ NMR (400 MHz, $CDCl_3$) δ 9.46 (s, 1H), 8.59 (d, 2H), 8.47 (s, 1H), 7.71-7.62 (m, 3H), 7.52-7.44 (m, 2H), 7.20 (d, 2H), 7.07 (t, 2H), 6.57 (d, 1H), 4.05 (s, 3H), 3.99 (s, 3H), 1.79-1.74 (m, 2H), 1.69-1.64 (m, 2H); MS (EI) for $C_{29}H_{24}FN_3O_6$. found 530.2 (MH+).

Example 52: 4-[4-[[1-[(4-Fluorophenyl)carbamoyl]cyclopropanecarbonyl]-amino]phenoxy]-6-methoxyquinoline-7-carboxylic Acid (151)

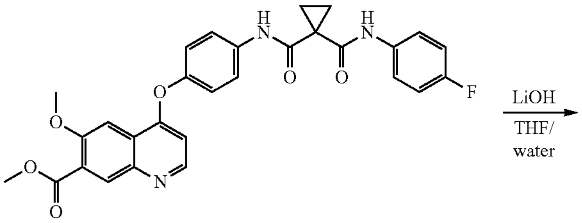

150

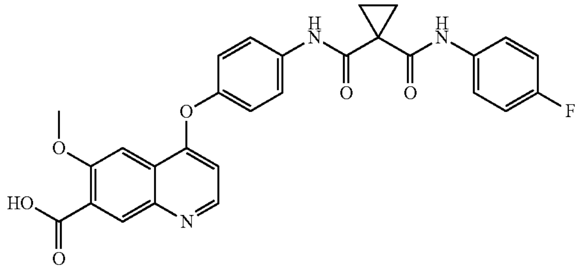

151

4-[4-[[1-[(4-Fluorophenyl)carbamoyl]cyclopropanecarbonyl]-amino]phenoxy]-6-methoxyquinoline-7-carboxylic acid (151): Compound 151 was synthesized from Compound 150 in a manner analogous to the preparation of Compound 81 from Compound 80 in Example 25 (110 mg, 75.2% yield). $^{1}H$ NMR (400 MHz, DMSO-$d_6$) δ 10.21 (s, 1H), 10.05 (s, 1H), 8.60 (d, 1H), 8.18 (s, 1H), 7.79 (d, 2H), 7.69-7.59 (m, 3H), 7.27 (d, 2H), 7.15 (t, 2H), 6.60 (d, 1H), 3.97 (s, 3H), 1.53-1.42 (m, 4H); MS (EI) for $C_{28}H_{22}FN_3O_6$. found 516.1 (MH+).

Example 53: 1-N-[4-(7-Carbamoyl-6-methoxyquinolin-4-yl)oxyphenyl]-1-N'-(4-fluorophenyl)cyclopropane-1,1-dicarboxamide (152)

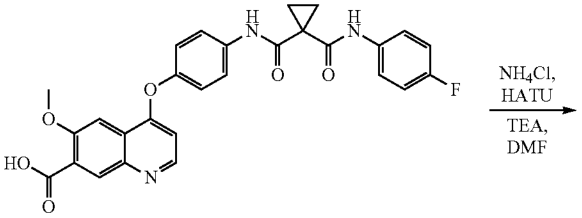

151

-continued

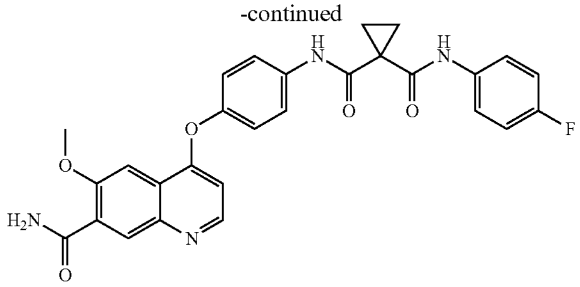

152

1-N-[4-(7-Carbamoyl-6-methoxyquinolin-4-yl)oxyphenyl]-1-N'-(4-fluorophenyl)cyclopropane-1,1-dicarboxamide (152): Compound 152 was synthesized from Compound 151 in a manner analogous to the preparation of Compound 7 from Compound 6 in Example 3 (25.6 mg, 30.7% yield). $^{1}H$ NMR (400 MHz, DMSO-$d_6$) δ 10.20 (s, 1H), 10.04 (s, 1H), 8.58 (d, 1H), 8.25 (s, 1H), 7.87 (br s, 1H), 7.78 (d, 2H), 7.72 (br s, 1H), 7.67-7.60 (m, 3H), 7.26 (d, 2H), 7.15 (t, 2H), 6.58 (d, 1H), 4.01 (s, 3H), 1.52-1.46 (m, 4H); MS (EI) for $C_{28}H_{23}FN_4O_5$. found 515.1 (MH+).

Example 54: 1-N'-(4-Fluorophenyl)-1-N-[4-[6-methoxy-7-(methylcarbamoyl)quinolin-4-yl]oxyphenyl]cyclopropane-1,1-dicarboxamide (153)

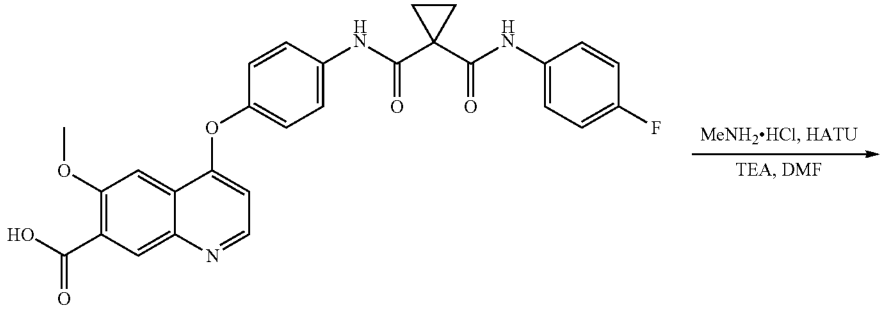

151

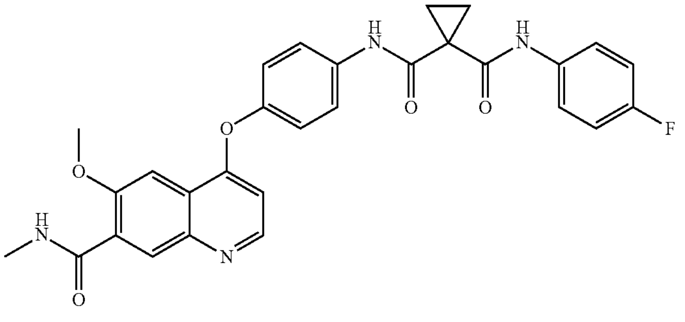

153

1-N'-(4-Fluorophenyl)-1-N-[4-[6-methoxy-7-(methylcarbamoyl)quinolin-4-yl]oxyphenyl]cyclopropane-1,1-dicarboxamide (153): Compound 153 was synthesized from Compound 151 in a manner analogous to the preparation of Compound 8 from Compound 6 in Example 4 (25.2 mg, 53.1% yield). $^{1}$H NMR (400 MHz, DMSO-$d_6$) δ 10.23 (s, 1H), 10.07 (s, 1H), 8.58 (d, 1H), 8.39 (q, 1H), 8.20 (s, 1H), 7.79 (d, 2H), 7.69-7.60 (m, 3H), 7.26 (d, 2H), 7.15 (t, 2H), 6.58 (d, 1H), 4.00 (s, 3H), 2.84 (d, 3H), 1.52-1.44 (m, 4H); MS (EI) for $C_{29}H_{25}FN_4O_5$. found 529.1 (MH+).

Example 56: Methyl 4-[4-[[1-[(4-fluorophenyl)carbamoyl]cyclopropane-carbonyl]amino]phenoxy]quinoline-7-carboxylate (162)

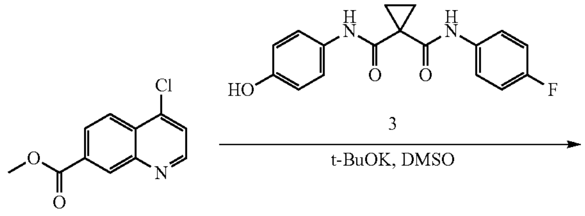

161

-continued

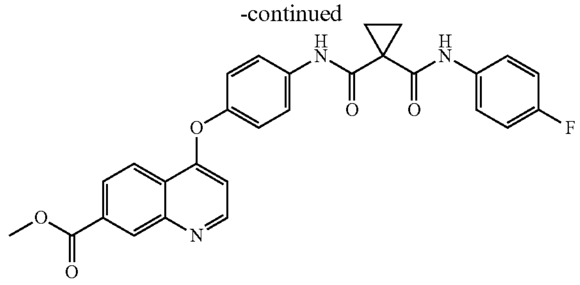

162

Methyl 4-[4-[[1-[(4-fluorophenyl)carbamoyl]cyclopropane-carbonyl]amino]phenoxy]quinoline-7-carboxylate (162): Compound 162 was synthesized from Compounds 161 and 3 in a manner analogous to the preparation of Compound 43 from Compounds 42 and 3 in Example 12 (20 mg, 16% yield). $^{1}$H NMR (400 MHz, $CDCl_3$) δ 9.42 (s, 1H), 8.81 (d, 1H), 8.75 (d, 1H), 8.60 (br s, 1H), 8.43 (d, 1H), 8.19 (dd, 1H), 7.69-7.63 (m, 2H), 7.51-7.44 (m, 2H), 7.23-7.18 (m, 2H), 7.07 (t, 2H), 6.63 (d, 1H), 4.03 (s, 3H), 1.79-1.74 (m, 2H), 1.69-1.65 (m, 2H); MS (EI) for $C_{28}H_{22}FN_3O_5$. found 500.1 (MH+).

Example 57: 4-[4-[[1-[(4-Fluorophenyl)carbamoyl]cyclopropane-carbonyl]amino]phenoxy]quinoline-7-carboxylic Acid (163)

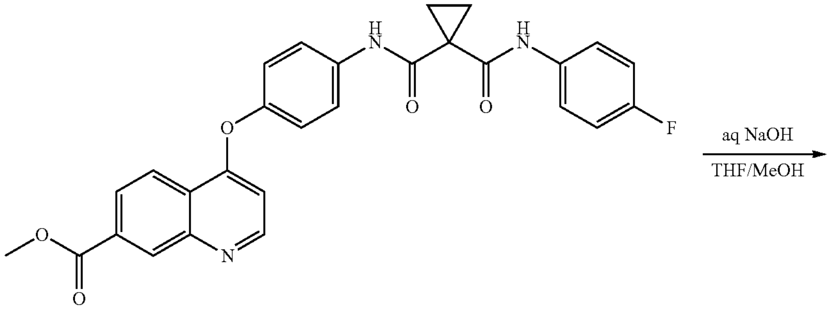

162

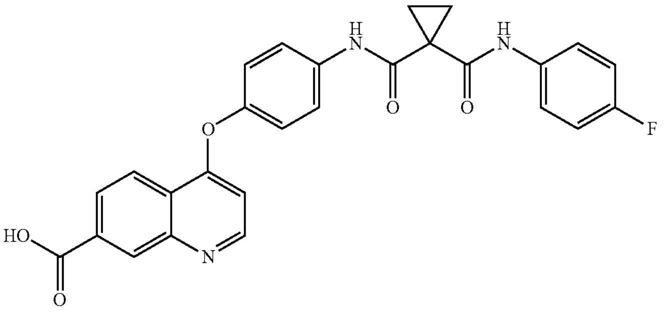

163

4-[4-[[1-[(4-Fluorophenyl)carbamoyl]cyclopropane-carbonyl]amino]phenoxy]quinoline-7-carboxylic acid (163): Compound 163 was synthesized from Compound 162 in a manner analogous to the preparation of Compound 6 from Compound 5 in Example 2 (70 mg, 68.4% yield). $^1$H NMR (400 MHz, DMSO-$d_6$) δ 10.22 (s, 1H), 10.06 (s, 1H), 8.79 (d, 1H), 8.58 (s, 1H), 8.43 (d, 1H), 8.17-8.10 (m, 1H), 7.79 (d, 2H), 7.65 (dd, 2H), 7.29 (d, 2H), 7.16 (t, 2H), 6.69 (d, 1H), 1.48 (s, 4H); MS (EI) for $C_{27}H_{20}FN_3O_5$. found 486.1 (MH+).

Example 58: 1-N-[4-(7-Carbamoylquinolin-4-yl)oxyphenyl]-1-N'-(4-fluorophenyl)cyclopropane-1,1-dicarboxamide (164)

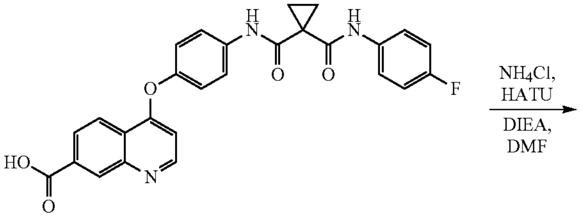

163

-continued

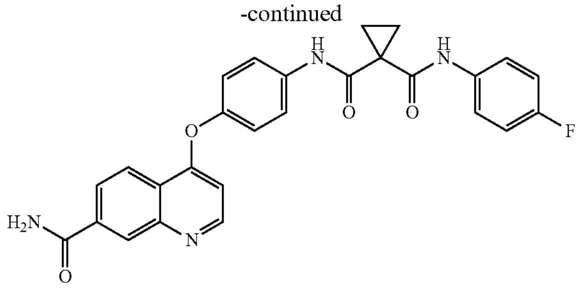

164

1-N-[4-(7-Carbamoylquinolin-4-yl)oxyphenyl]-1-N'-(4-fluorophenyl)-cyclopropane-1,1-dicarboxamide (164): Compound 164 was synthesized from Compound 163 in a manner analogous to the preparation of Compound 7 from Compound 6 in Example 3 (17.7 mg, 56.2% yield). $^1$H NMR (400 MHz, $CDCl_3$) δ 9.47 (s, 1H), 8.73 (d, 1H), 8.60 (br s, 1H), 8.50-8.43 (m, 2H), 8.08 (dd, 1H), 7.66 (d, 2H), 7.51-7.43 (m, 2H), 7.19 (d, 2H), 7.06 (t, 2H), 6.62 (d, 1H), 6.36 (br s, 1H), 5.73 (br s, 1H), 1.80-1.73 (m, 2H), 1.70-1.65 (m, 2H); MS (EI) for $C_{27}$H21F$N_4O_4$. found 485.1 (MH+).

Example 59: 1-N'-(4-Fluorophenyl)-1-N-[4-[7-(methylcarbamoyl)quinolin-4-yl]oxyphenyl]cyclopropane-1,1-dicarboxamide (165)

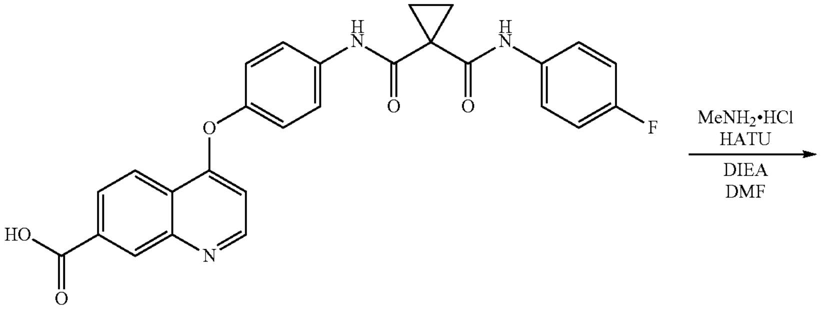

163

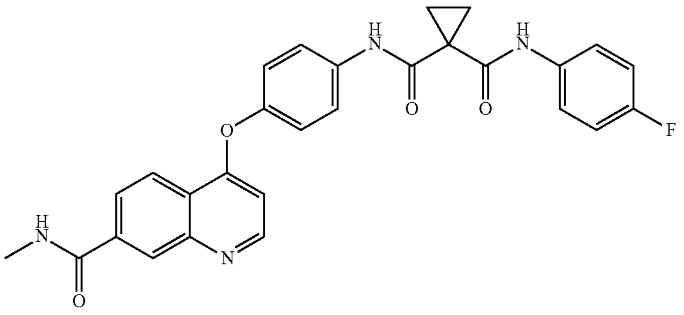

165

1-N'-(4-Fluorophenyl)-1-N-[4-[7-(methylcarbamoyl)quinolin-4-yl]oxyphenyl]cyclopropane-1,1-dicarboxamide (165): Compound 165 was synthesized from Compound 163 in a manner analogous to the preparation of Compound 8 from Compound 6 in Example 4 (16.5 mg, 33.9% yield). $^{1}$H NMR (400 MHz, $CDCl_3$) δ 9.45 (br s, 1H), 8.71 (d, 1H), 8.63 (br s, 1H), 8.43 (d, 1H), 8.37 (d, 1H), 8.04 (d, 1H), 7.65 (d, 2H), 7.50-7.44 (m, 2H), 7.19 (d, 2H), 7.06 (t, 2H), 6.60 (d, 1H), 6.40 (br s, 1H), 3.11 (d, 3H), 1.79-1.74 (m, 2H), 1.69-1.64 (m, 2H); MS (EI) for $C_{28}H_{23}FN_4O_4$. found 499.1 (MH+).

Example 60: 1-N'-(4-Fluorophenyl)-1-N-[4-[7-(2-hydroxyethoxycarbamoyl)-quinolin-4-yl]oxyphenyl]cyclopropane-1,1-dicarboxamide (166)

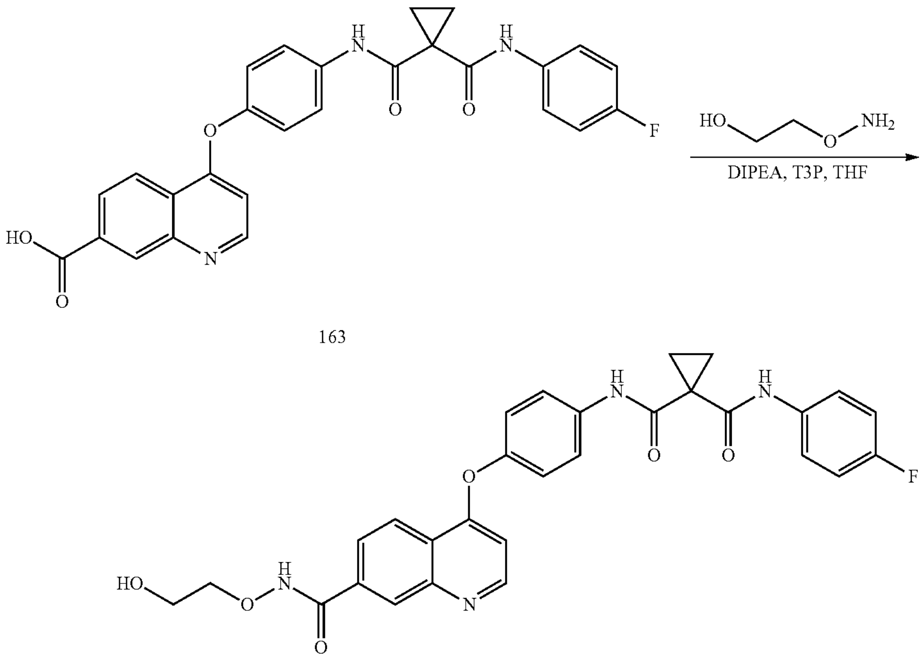

163

166

1-N'-(4-Fluorophenyl)-1-N-[4-[7-(2-hydroxyethoxycarbamoyl)-quinolin-4-yl]oxyphenyl]cyclopropane-1,1-dicarboxamide (166): Compound 166 was synthesized from Compound 163 in a manner analogous to the preparation of Compound 26 from Compound 6 in Example 6 (27 mg, 46.2% yield). $^{1}$H NMR (400 MHz, $CD_3OD$) δ 8.73 (d, 1H), 8.53 (d, 1H), 8.44 (d, 1H), 8.03 (dd, 1H), 7.77 (d, 2H), 7.59 (dd, 2H), 7.28 (d, 2H), 7.10 (t, 2H), 6.75 (d, 1H), 4.17-4.12 (m, 2H), 3.88-3.83 (m, 2H), 1.66 (s, 4H); MS (EI) for $C_{29}H_{25}FN_4O_6$. found 545.1 (MH+).

The following compounds were prepared in a method analogous to Compound 166 in Example 60:

1-N'-(4-Fluorophenyl)-1-N-[4-[7-(oxetan-3-yloxycarbamoyl)quinolin-4-yl]oxyphenyl]cyclopropane-1,1-dicarboxamide (167): $^{1}$H NMR (400 MHz, $CD_3OD$) δ 8.72 (d, 1H), 8.50 (d, 1H), 8.43 (d, 1H), 8.02 (dd, 1H), 7.79-7.73 (m, 2H), 7.62-7.56 (m, 2H), 7.31-7.25 (m, 2H), 7.09 (t, 2H), 6.74 (d, 1H), 5.19 (s, 1H), 4.93 (m, 2H), 4.88-4.81 (m, 2H), 1.70-1.63 (m, 4H); MS (EI) for $C_{30}H_{25}FN_4O_6$. found 557.1 (MH+).

N-(4-((7-(((2,2-Dimethyl-1,3-dioxolan-4-yl)methoxy)carbamoyl)quinolin-4-yl)oxy)phenyl)-N-(4-fluorophenyl)cyclopropane-1,1-dicarboxamide (168): MS (EI) for $C_{29}H_{25}FN_4O_6$. found 615.3 (MH+).

Example 61: 1-N-[4-[7-[[(2R)-2,3-Dihydroxypropoxy]carbamoyl]quinolin-4-yl]oxyphenyl]-1-N'-(4-fluorophenyl)cyclopropane-1,1-dicarboxamide (169) and 1-N-[4-[7-[[(2S)-2,3-Dihydroxypropoxy]carbamoyl]quinolin-4-yl]oxyphenyl]-1-N'-(4-fluorophenyl)cyclopropane-1,1-dicarboxamide (170)

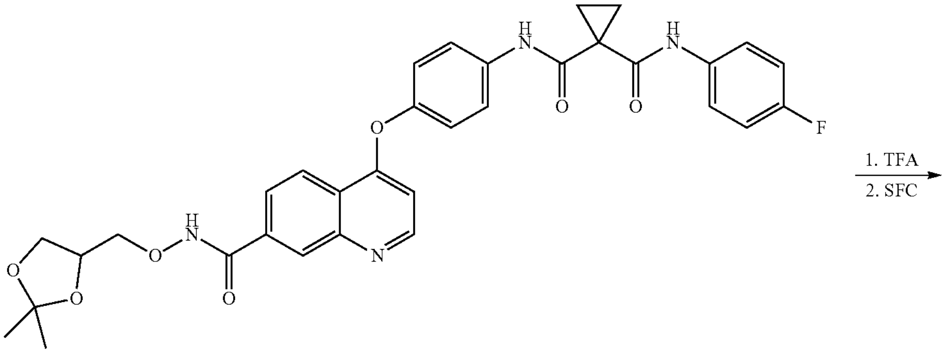

168

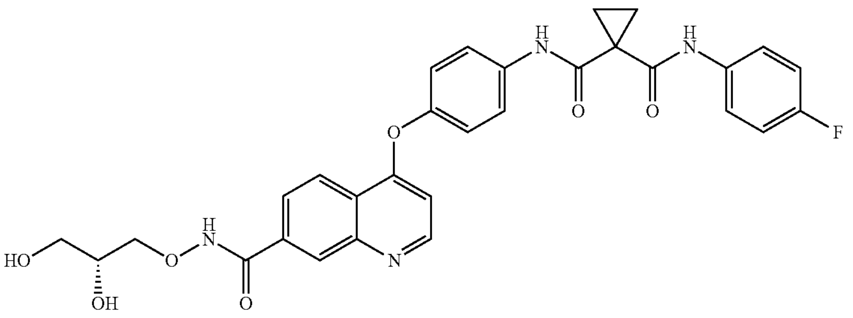

169 and

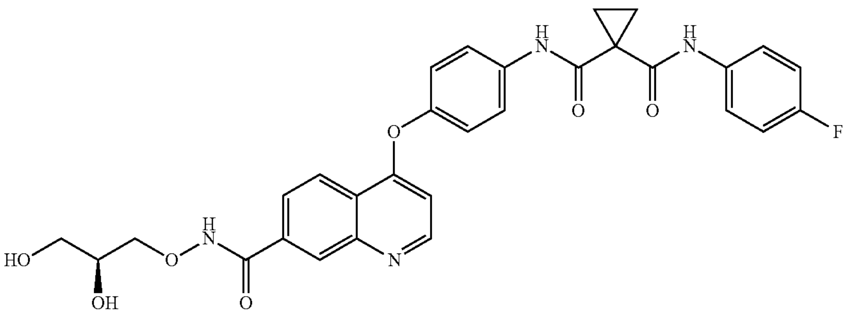

170

1-N-[4-[7-[[(2R)-2,3-Dihydroxypropoxy]carbamoyl]quinolin-4-yl]oxyphenyl]-1-N'-(4-fluorophenyl)cyclopropane-1,1-dicarboxamide (169) and 1-N-[4-[7-[[(2S)-2,3-Dihydroxypropoxy]carbamoyl]quinolin-4-yl]oxyphenyl]-1-N'-(4-fluorophenyl)cyclopropane-1,1-dicarboxamide (170): Compounds 169 and 170 were synthesized from Compound 168 in a manner analogous to the preparation of Compounds 30 and 31 from Compound 28 in Example 7. Compound 169: $^{1}H$ NMR (400 MHz, $CD_3OD$) δ 8.73 (d, 1H), 8.52 (d, 1H), 8.44 (d, 1H), 8.02 (dd, 1H), 7.77 (d, 2H), 7.62-7.55 (m, 2H), 7.30-7.25 (m, 2H), 7.09 (t, 2H), 6.75 (d, 1H), 4.21-4.15 (m, 1H), 4.06 (s, 1H), 4.02-3.96 (m, 1H), 3.68 (m, 2H), 1.66 (d, 4H); MS (EI) for $C_{30}H_{27}FN_4O_7$. found 575.2 (MH+).

Compound 170: $^{1}H$ NMR (400 MHz, $CD_3OD$) δ 8.73 (d, 1H), 8.52 (d, 1H), 8.43 (d, 1H), 8.02 (dd, 1H), 7.77 (d, 2H), 7.62-7.54 (m, 2H), 7.28 (d, 2H), 7.14-7.04 (m, 2H), 6.75 (d, 1H), 4.22-4.14 (m, 1H), 4.12-3.92 (m, 2H), 3.73-3.64 (m, 2H), 1.66 (s, 4H); MS (EI) for $C_{30}H_{27}FN_4O_7$. found 575.1 (MH+).

Example 62: 4-((6-Bromo-7-methoxyquinolin-4-yl)oxy)aniline (171)

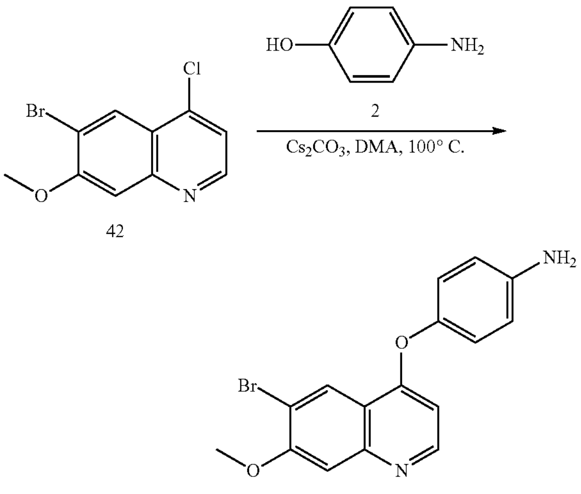

42

171

4-((6-Bromo-7-methoxyquinolin-4-yl)oxy)aniline (171): To a mixture of Compound 42 (1.75 g, 6.38 mmol) and 4-aminophenol 2 (1.1 g, 10 mmol) in DMA (15 mL) was added $Cs_2CO_3$ (3.3 g, 10 mmol) at room temperature. The mixture was stirred at 100° C. for 2 h. The mixture was allowed to cool to 20° C., diluted with water, and filtered. The crude residue was purified by flash silica gel chromatography to give Compound 171 (900 mg, 40% yield). MS (EI) for $C_{16}H_{13}BrN_2O_2$. found: 345 (MH+).

Example 63: 4-((7-Methoxy-6-(4,4,5,5-tetramethyl-1,3,2-dioxaborolan-2-yl)quinolin-4-yl)oxy)aniline (172)

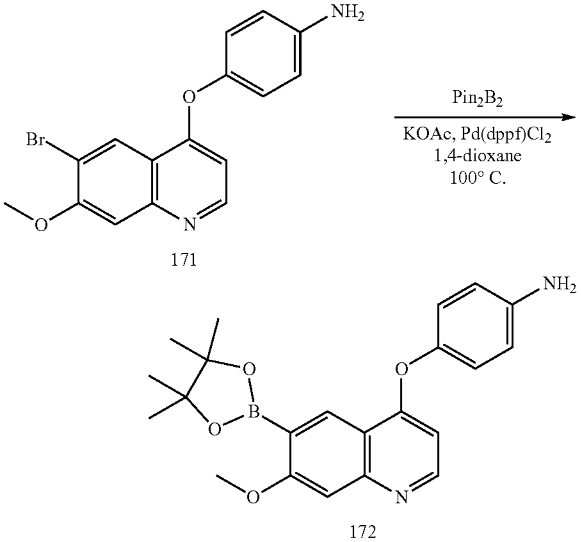

171

172

4-((7-Methoxy-6-(4,4,5,5-tetramethyl-1,3,2-dioxaborolan-2-yl)quinolin-4-yl)oxy)aniline (172): To a mixture of Compound 171 (200 mg, 0.58 mmol), bis(pinacolato)diboron (220 mg, 0.87 mmol), and potassium acetate (170 mg, 1.7 mmol) in 1,4-dioxane (3 mL) was added Pd(dppf)$C_{12}$ (42 mg, 0.06 mmol). The resulting mixture was heated at 100° C. for 2 h. After cooling, the reaction mixture was diluted with EtOAc, washed with water followed by aq saturated NaCl, concentrated, and purified by flash silica gel chromatography to give Compound 172 (43% yield). MS (EI) for $C_{22}H_{25}BN_2O_4$. found: 393 (MH+).

Example 64: 1-N-[4-[6-(3-Cyano-2-fluorophenyl)-7-methoxyquinolin-4-yl]oxyphenyl]-1-N'-(4-fluorophenyl)cyclopropane-1,1-dicarboxamide (175)

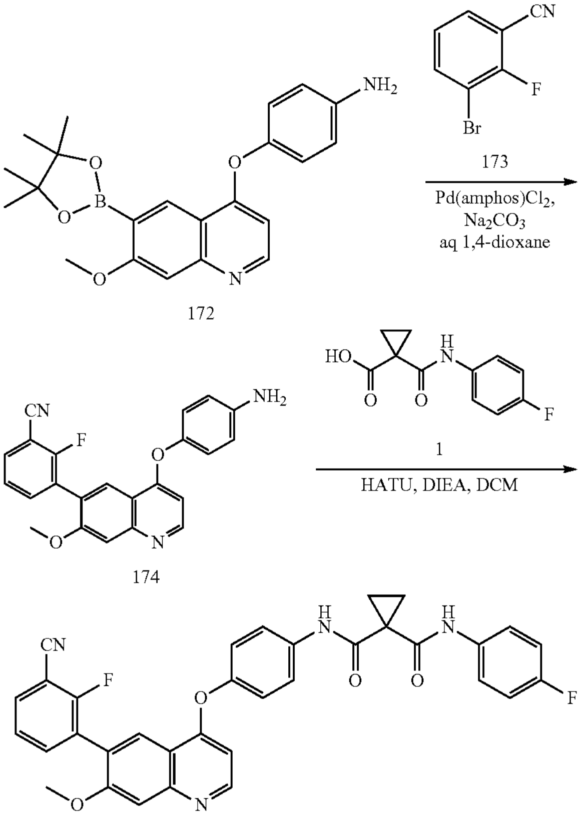

172

174

175

3-(4-(4-Aminophenoxy)-7-methoxyquinolin-6-yl)-2-fluorobenzonitrile (174): In a microwave reaction tube were mixed Compound 172 (50 mg, 0.13 mmol), Compound 173 (25 mg, 0.13 mmol), $Na_2CO_3$ (41 mg, 0.39 mmol), bis(di-tert-butyl(4-dimethylaminophenyl)phosphine)dichloropalladium(II) (9 mg, 0.013 mmol), 1,4-dioxane (2 mL), and water (0.4 mL). The reaction mixture was irritated in a microwave reactor for 5 min at 150° C. After cooling, the mixture was extracted with EtOAc, washed with aq saturated NaCl, and concentrated. The crude product was purified by flash column chromatography to give Compound 174. MS (EI) for $C_{23}H_{16}FN_3O_2$. found: 386 (MH+).

1-N-[4-[6-(3-Cyano-2-fluorophenyl)-7-methoxyquinolin-4-yl]oxyphenyl]-1-N'-(4-fluorophenyl)cyclopropane-1,1-dicarboxamide (175): To a mixture of Compound 174, Compound 1 (22 mg, 0.1 mmol) and DIEA (25 mg, 0.2 mmol) in DCM (2 mL) was added HATU (38 mg, 0.1 mmol). The mixture was stirred at room temperature until the reaction was complete and then diluted with EtOAc, washed with aq saturated $NaHCO_3$, and concentrated. The crude product was purified by flash column chromatography to give Compound 175. MS (EI) for $C_{34}H_{24}F_2N_4O_4$. found 591 (MH+).

The following compounds were prepared in a manner analogous to the method used to synthesize Compound 175 in two steps from Compound 172 in Example 64:

1-N'-(4-Fluorophenyl)-1-N-[4-(7-methoxy-6-pyridin-2-ylquinolin-4-yl)oxyphenyl]cyclopropane-1,1-dicarboxamide (176): 2-Bromopyridine was used in place of Compound 173. MS (EI) for $C_{32}H_{25}FN_4O_4$. found 549 (MH+).

1-N'-(4-Fluorophenyl)-1-N-[4-[7-methoxy-6-(1-methylimidazol-4-yl)quinolin-4-yl]oxyphenyl]cyclopropane-1,1-dicarboxamide (177). 4-Bromo-1-methyl-1H-imidazole was used in place of Compound 173. MS (EI) for $C_{31}H_{26}FN_5O_4$. found 552 (MH+).

Example 65: 1-N'-(4-Fluorophenyl)-1-N-[4-[7-methoxy-6-(5-methylfuran-2-yl)quinolin-4-yl]oxyphenyl]cyclopropane-1,1-dicarboxamide (180)

rated NaCl, and concentrated. The crude product was purified by flash column chromatography to give Compound 179. MS (EI) for $C_{21}H_{18}N_2O_3$. found: 347 (MH+).

1-N'-(4-Fluorophenyl)-1-N-[4-[7-methoxy-6-(5-methylfuran-2-yl)quinolin-4-yl]oxyphenyl]cyclopropane-1,1-dicarboxamide (180): Compound 180 was synthesized from Compound 179 in a manner analogous to the method used to synthesize Compound 175 from Compound 174 in Example 64. MS (EI) for $C_{32}H_{26}FN_3O_5$. found 552 (MH+).

The following compounds were prepared in a manner analogous to the method used to synthesize Compound 180 in two steps from Compound 171 in Example 65:

tert-Butyl 2-[4-[4-[[1-[(4-fluorophenyl)carbamoyl]cyclopropanecarbonyl]-amino]phenoxy]-7-methoxyquinolin-6-yl]pyrrole-1-carboxylate (181): t-Butyl 2-(trifluoro-14-boraneyl)-1H-pyrrole-1-carboxylate, potassium salt was used in place of Compound 178. MS (D) for $C_{36}H_{33}FN_4O_6$. found 637 (MH+).

1-N'-(4-Fluorophenyl)-1-N-[4-[7-methoxy-6-(1-methylpyrazol-4-yl)quinolin-4-yl]oxyphenyl]cyclopropane-1,1-dicarboxamide (182): 1-Methyl-4-(4,4,5,5-tetramethyl-1,3,2-dioxaborolan-2-yl)-1H-pyrazole was used in place of Compound 178. MS (D) for $C_{31}H_{26}FN_5O_4$. found 552 (MH+).

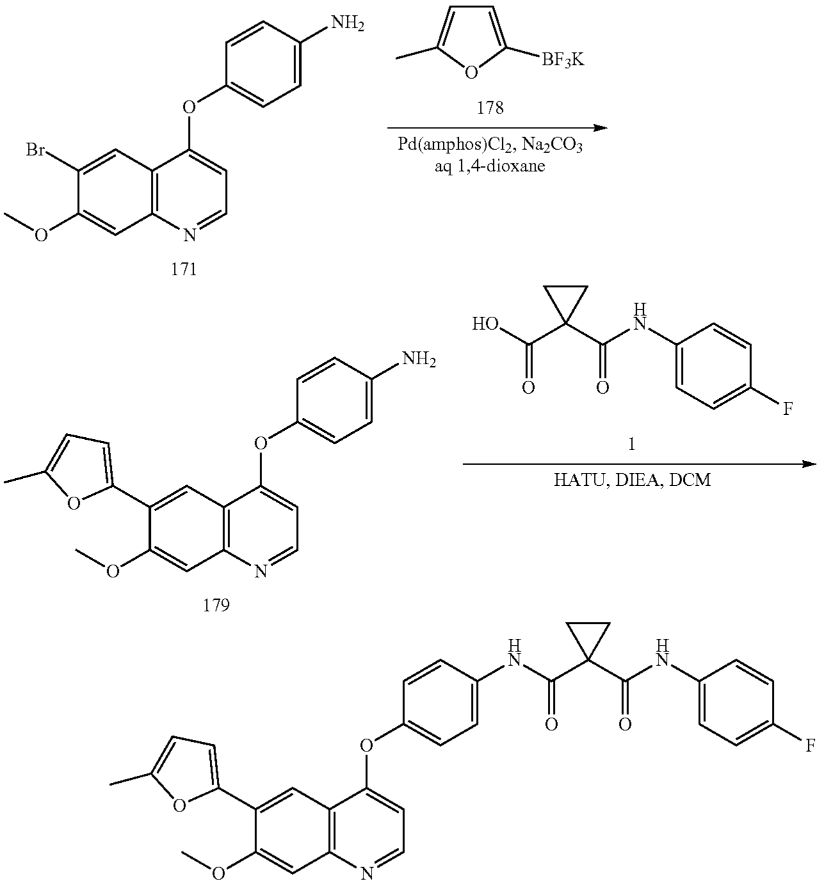

171

178

179

1

180

4-((7-Methoxy-6-(5-methylfuran-2-yl)quinolin-4-yl)oxy)aniline (179): In a microwave reaction tube were mixed Compound 171 (100 mg, 0.29 mmol), Compound 178 (82 mg, 0.43 mmol), $Na_2CO_3$ (92 mg, 0.9 mmol), bis(di-tert-butyl(4-dimethylaminophenyl)phosphine)dichloropalladium(II) (20 mg, 0.029 mmol), 1,4-dioxane (2.5 mL), and water (0.5 mL). The resulting mixture was irradiated in a microwave reactor for 5 min at 150° C. After cooling, the mixture was extracted with EtOAc, washed with aq satu- 1-N'-(4-Fluorophenyl)-1-N-[4-[7-methoxy-6-(1,2-oxazol-4-yl)quinolin-4-yl]oxyphenyl]cyclopropane-1,1-dicarboxamide (183): 4-(4,4,5,5-Tetramethyl-1,3,2-dioxaborolan-2-yl)isoxazole was used in place of Compound 178. MS (D) for $C_{30}H_{23}FN_4O_5$, found: 539 (MH+).

1-N-[4-[6-(3,5-Dimethyl-1,2-oxazol-4-yl)-7-methoxy-quinolin-4-yl]oxyphenyl]-1-N'-(4-fluorophenyl)cyclopropane-1,1-dicarboxamide (184): 3,5-Dimethyl-4-(4,4,5,5-tetramethyl-1,3,2-dioxaborolan-2-yl)isoxazole was used in place of Compound 178. MS (D) for $C_{32}H_{27}FN_4O_5$. found 567 (MH+).

1-N'-(4-Fluorophenyl)-1-N-[4-[7-methoxy-6-(1H-pyrazol-5-yl)quinolin-4-yl]oxyphenyl]cyclopropane-1,1-dicarboxamide (185): 5-(Trifluoro-14-boraneyl)-1H-pyrazole, potassium salt was used in place of Compound 178. MS (D) for $C_{30}H_{24}FN_5O_4$. found 538 (MH+).

1-N'-(4-Fluorophenyl)-1-N-[4-[7-methoxy-6-(1H-pyrazol-4-yl)quinolin-4-yl]oxyphenyl]cyclopropane-1,1-dicarboxamide (186): 4-(Trifluoro-14-boraneyl)-1H-pyrazole, potassium salt was used in place of Compound 178. MS (D) for $C_{30}H_{24}FN_5O_4$; found 538 (MH+).

1-N-[4-(6-Cyclopropyl-7-methoxyquinolin-4-yl)oxyphenyl]-1-N'-(4-fluorophenyl)cyclopropane-1,1-dicarboxamide (187): Cyclopropyltrifluoro-14-borane, potassium salt was used in place of Compound 178. MS (D) for $C_{30}H_{26}FN_3O_4$. found 512 (MH+).

Example 66: 1-N'-(4-Fluorophenyl)-1-N-[4-[7-methoxy-6-(1H-pyrrol-2-yl)quinolin-4-yl]oxyphenyl]cyclopropane-1,1-dicarboxamide (188)

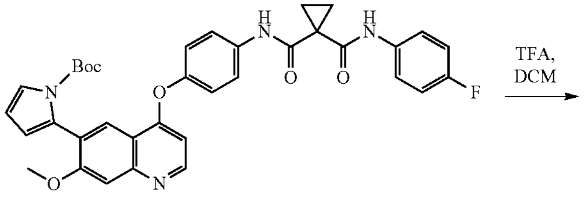

181

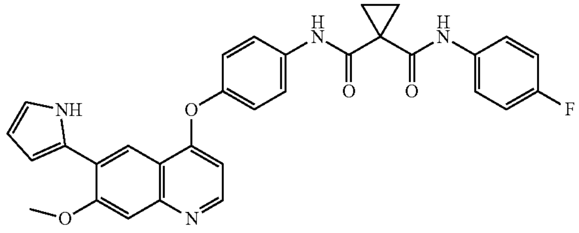

188

1-N'-(4-Fluorophenyl)-1-N-[4-[7-methoxy-6-(1H-pyrrol-2-yl)quinolin-4-yl]oxyphenyl]cyclopropane-1,1-dicarboxamide (188): Compound 181 and excess TFA were stirred in DCM at room temperature until the reaction was complete. The mixture was concentrated and purified by prep HPLC to give Compound 188 (50% yield). MS (EI) for $C_{31}H_{25}FN_4O_4$. found: 537 (MH+).

Example 67: N-(4-Fluorophenyl)-N-(4-((6-formyl-7-methoxyquinolin-4-yl)oxy)phenyl)cyclopropane-1,1-dicarboxamide (190)

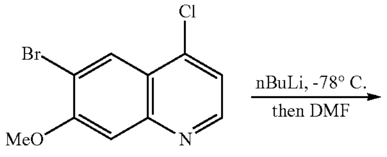

42

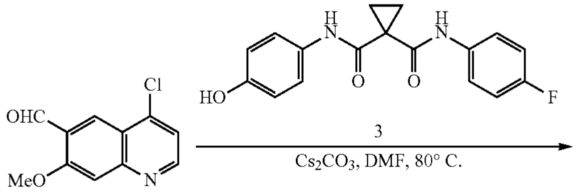

189

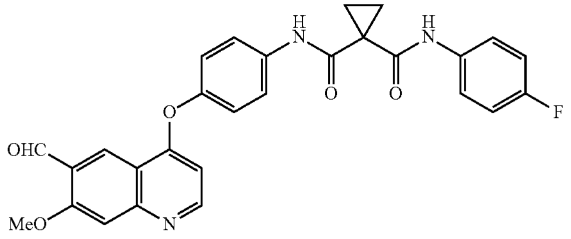

190

4-Chloro-7-methoxyquinoline-6-carbaldehyde (189): To a −78° C. mixture of Compound 42 (320 mg, 1.17 mmol) in THF (8 mL) was added nBuLi (0.6 mL, 2.5 M in THF, 1.5 mmol). The mixture was stirred at −78° C. for 45 min, and then DMF (0.5 mL) was added. The mixture was warmed to 0° C., and the stirring was continued for 1 h. The reaction was quenched with saturated $NH_4Cl$ and extracted with EtOAc. The organic phase was concentrated, and the crude residue was purified by flash silica gel chromatography to give Compound 189 (130 mg, 50% yield). MS (EI) for $C_{11}H_8ClNO_2$. found 222 (MH+).

N-(4-Fluorophenyl)-N-(4-((6-formyl-7-methoxyquinolin-4-yl)oxy)phenyl)cyclopropane-1,1-dicarboxamide (190): Compound 190 was synthesized from Compound 189 using a modification of the method used to synthesize Compound 43 from Compound 42 in Example 12, substituting the potassium t-butoxide with cesium carbonate and using DMF as the solvent.

Example 68: 1-N'-(4-Fluorophenyl)-1-N-[4-[6-(1H-imidazol-2-yl)-7-methoxyquinolin-4-yl]oxyphenyl]cyclopropane-1,1-dicarboxamide (191)

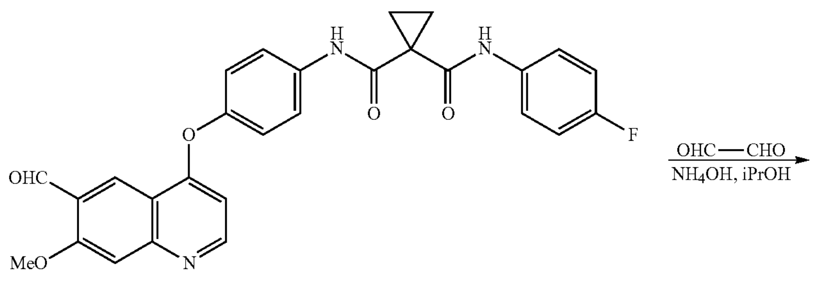

190

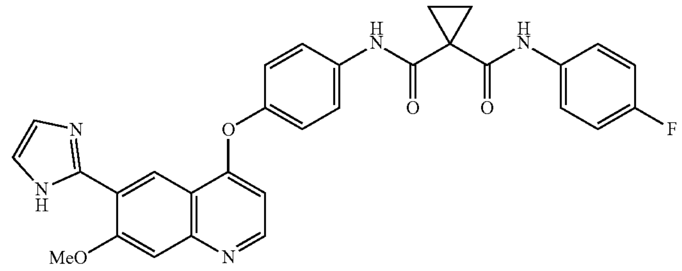

191

1-N'-(4-Fluorophenyl)-1-N-[4-[6-(1H-imidazol-2-yl)-7-methoxyquinolin-4-yl]oxyphenyl]cyclopropane-1,1-dicarboxamide (191): Compound 190 (60 mg, 0.12 mmol), glyoxal (60 mg, 40% in water) and ammonium hydroxide (130 mg, 30% in water) were mixed in iPrOH (1.5 mL). The resulting mixture was stirred at ambient (room) temperature for 12 h. The mixture was extracted with EtOAc and washed with aq saturated NaCl. The organic phase was concentrated and purified by prep HPLC to give Compound 191 (35 mg, 54% yield). MS (EI) for $C_{30}H_{24}FN_5O_4$. found 538.1 (MH+).

Example 69: 1-N'-(4-Fluorophenyl)-1-N-[4-[7-methoxy-6-(1,3-oxazol-5-yl)quinolin-4-yl]oxyphenyl]cyclopropane-1,1-dicarboxamide (192)

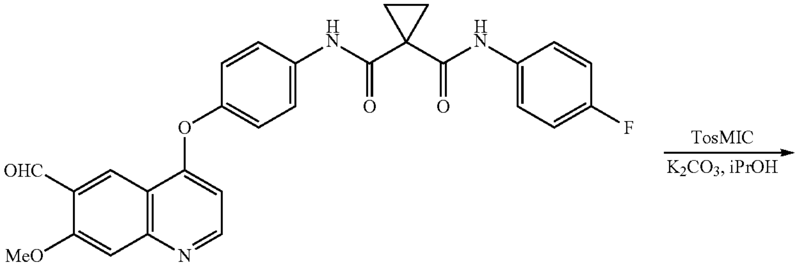

190

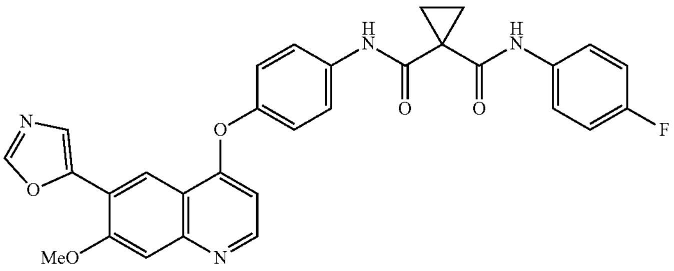

192

1-N'-(4-Fluorophenyl)-1-N-[4-[7-methoxy-6-(1,3-oxazol-5-yl)quinolin-4-yl]oxyphenyl]cyclopropane-1,1-dicarboxamide (192): Compound 190 (30 mg, 0.06 mmol), TosMIC (15 mg, 0.08 mmol), and $K_2CO_3$ (15 mg, 0.11 mmol) were mixed in iPrOH (1 mL). The resulting mixture was stirred at 80° C. for 30 min. The mixture was concentrated to dryness. The residue was extracted with EtOAc. The organic layer was washed with water and concentrated. The crude product was purified by prep HPLC to give Compound 192 (14 mg, 43% yield). MS (EI) for $C_{30}H_{23}FN_4O_5$. found 539 (MH+).

Example 70: 1-N'-(4-Fluorophenyl)-1-N-[4-[7-methoxy-6-[(E)-methoxyiminomethyl]quinolin-4-yl]oxyphenyl]cyclopropane-1,1-dicarboxamide (193)

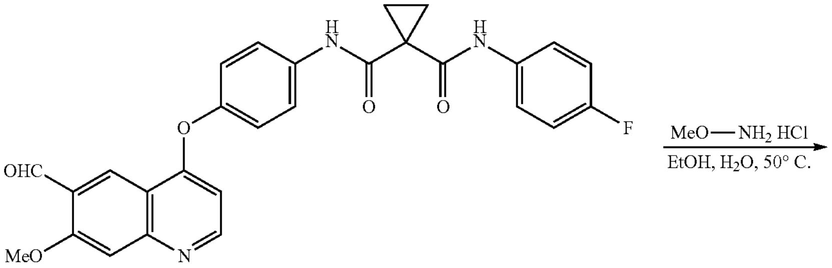

190

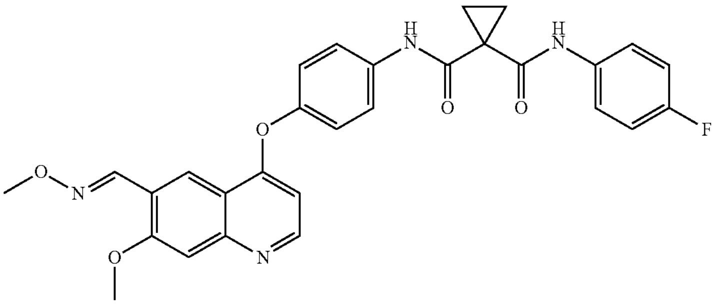

193

1-N'-(4-Fluorophenyl)-1-N-[4-[7-methoxy-6-[(E)-methoxyiminomethyl]quinolin-4-yl]oxyphenyl]cyclopropane-1,1-dicarboxamide (193): To a mixture of Compound 190 (150 mg, 300.31 μmol, 1 eq) in EtOH (3 mL) and water (0.6 mL) was added O-methylhydroxylamine-HCl (41.74 mg, 500 μmol, 1.7 eq). The mixture was stirred at 50° C. for 2 h. The resulting precipitate was filtered, slurried in 50 mL of water, and filtered again. The filter cake was lyophilized to obtain Compound 193 (125.0 mg, 73.2% yield). $^1H$ NMR (400 MHz, DMSO-$d_6$) δ 10.32 (s, 1H), 10.05 (s, 1H), 8.87 (s, 1H), 8.68 (s, 1H), 8.51 (s, 1H), 7.85 (d, 2H), 7.72-7.58 (m, 3H), 7.37 (d, 2H), 7.16 (t, 2H), 6.72 (br d, 1H), 4.07 (s, 3H), 3.99 (s, 3H), 1.49 (s, 4H); MS (EI) for $C_{29}H_{25}FN_4O_5$. found 529.2 (MH+).

Example 71: tert-Butyl 3-[4-[4-[[1-[(4-fluorophenyl)carbamoyl]cyclopropane-carbonyl]amino]phenoxy]-7-methoxyquinolin-6-yl]-3-hydroxyazetidine-1-carboxylate (195)

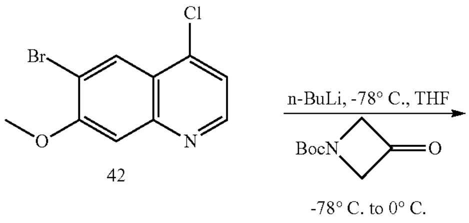

42

-continued

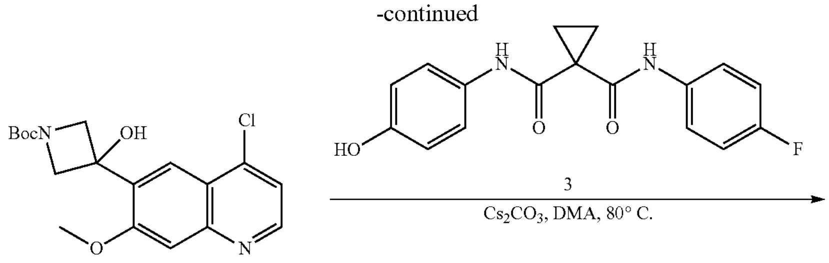

194

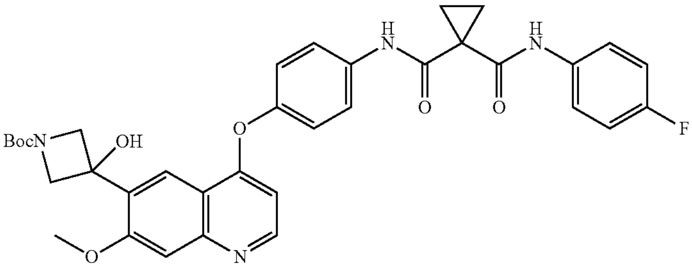

195 t-Butyl 3-(4-chloro-7-methoxyquinolin-6-yl)-3-hydroxyazetidine-1-carboxylate (194): A mixture of Compound 42 (200 mg, 0.73 mmol) and THF (4 mL) was cooled to −78° C. n-BuLi (0.4 mL, 1.0 mmol, 2.5 M in THF) was slowly added. The resulting mixture was stirred at −78° C. for 40 min. A solution of N-Boc 3-oxoazetidine (125 mg, 0.73 mmol) in THF (0.5 mL) was added. The reaction mixture was warmed to 0° C., and the stirring was continued for 1 h. The reaction was quenched with water and extracted with EtOAc. The organic phase was washed with aq saturated NaCl, concentrated, and purified by flash silica gel chromatography to give Compound 194 (38% yield). MS (EI) for $C_{18}H_{21}ClN_2O_4$. found: 365 (MH+).

tert-Butyl 3-[4-[4-[[1-[(4-fluorophenyl)carbamoyl]cyclopropane-carbonyl]amino]phenoxy]-7-methoxyquinolin-6-yl]-3-hydroxyazetidine-1-carboxylate (195): Compound 195 was synthesized from Compound 194 in a manner similar to the preparation of Compound 43 from Compound 42 in Example 12, except cesium carbonate was used instead of t-butoxide, DMF was the solvent, the reaction temperature was 80° C., and the reaction time was 12 h. Compound 195 was obtained in 68% yield. MS (EI) for $C_{35}H_{35}FN_4O_7$. found 643 (MH+).

The following compound was made in a manner analogous to Compound 195 in Example 71 with oxetan-3-one replacing the Boc protected azetidin-3-one:

1-N'-(4-Fluorophenyl)-1-N-[4-[6-(3-hydroxyoxetan-3-yl)-7-methoxyquinolin-4-yl]oxyphenyl]cyclopropane-1,1-dicarboxamide (196). MS (EI) for $C_{30}H_{26}FN_3O_6$. found 544 (MH+).

Example 72: 1-N'-(4-Fluorophenyl)-1-N-[4-[6-(3-hydroxyazetidin-3-yl)-7-methoxyquinolin-4-yl]oxyphenyl]cyclopropane-1,1-dicarboxamide (197)

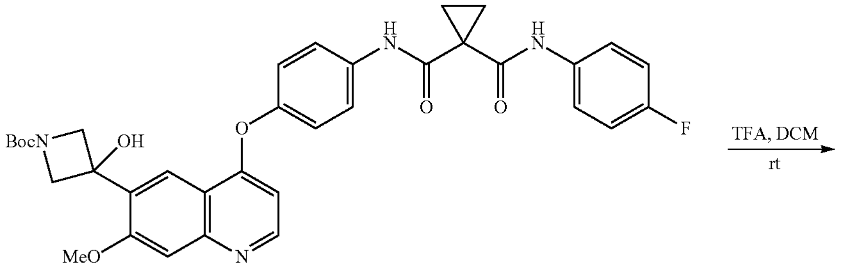

195

-continued

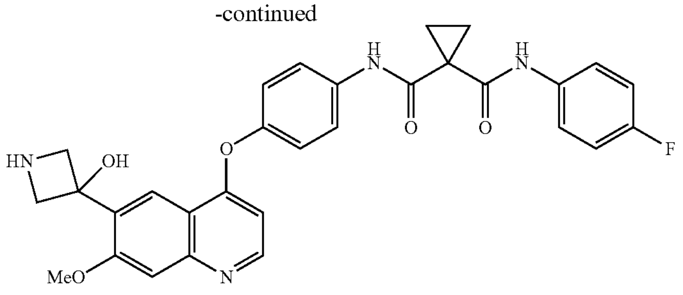

197

1-N'-(4-Fluorophenyl)-1-N-[4-[6-(3-hydroxyazetidin-3-yl)-7-methoxyquinolin-4-yl]oxyphenyl]cyclopropane-1,1-dicarboxamide (197): Compound 197 was synthesized from Compound 195 in a manner analogous to the preparation of Compound 188 from Compound 181 in Example 66 (55% yield). MS (EI) for $C_{30}H_{27}FN_4O_5$. found 543 (MH+).

Example 73: 1-N-[4-[6-(Azetidin-1-yl)-7-methoxyquinolin-4-yl]oxyphenyl]-1-N'-(4-fluorophenyl)cyclopropane-1,1-dicarboxamide (198)

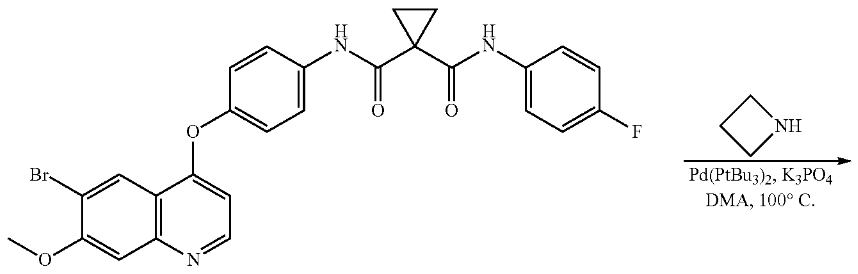

43

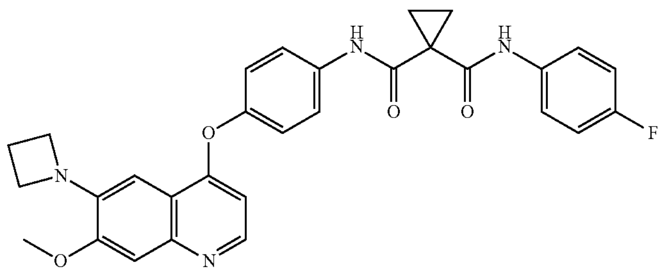

198

1-N-[4-[6-(Azetidin-1-yl)-7-methoxyquinolin-4-yl]oxyphenyl]-1-N'-(4-fluorophenyl)cyclopropane-1,1-dicarboxamide (198): To a mixture of Compound 43 (150 mg, 0.27 mmol), azetidine (300 mg, 5.25 mmol), and $K_3PO_4$ (212 mg, 1.0 mmol) in DMA (2 mL) was added bis(tri-tert-butylphosphine)palladium(0). The resulting mixture was stirred at 100° C. for 12 h. After cooling, water was added, and the mixture was extracted with EtOAc, washed with aq saturated NaCl and concentrated. The crude product was purified by prep HPLC to give Compound 198. MS (EI) for $C_{30}H_{27}FN_4O_4$. found 527 (MH+).

The following compounds were prepared from Compound 43 in a method analogous to the synthesis of Compound 198 from Compound 43 in Example 73:

1-N'-(4-Fluorophenyl)-1-N-[4-[6-(3-hydroxyazetidin-1-yl)-7-methoxyquinolin-4-yl]oxyphenyl]cyclopropane-1,1-dicarboxamide (199): Azetidin-3-ol was used in place of azetidine. MS (EI) for $C_{30}H_{27}FN_4O_5$. found 543 (MH+).

1-N-[4-[6-(3,3-Difluoroazetidin-1-yl)-7-methoxyquinolin-4-yl]oxyphenyl]-1-N'-(4-fluorophenyl)cyclopropane-1,1-dicarboxamide (200): The HCl salt of 3,3-difluoroazetidine was used in place of azetidine. MS (EI) for $C_{30}H_{25}F_3N_4O_4$. found 563 (MH+).

Example 74: 1-N'-(4-Fluorophenyl)-1-N-[4-(7-methoxy-6-pyridin-3-ylquinolin-4-yl)oxyphenyl]cyclopropane-1,1-dicarboxamide (201)

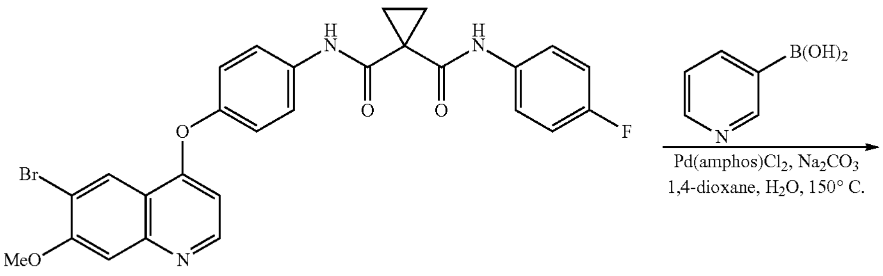

43

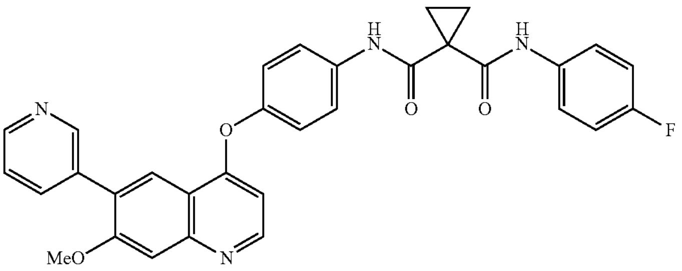

201

1-N'-(4-Fluorophenyl)-1-N-[4-(7-methoxy-6-pyridin-3-ylquinolin-4-yl)oxyphenyl]cyclopropane-1,1-dicarboxamide (201): In a microwave reaction tube were mixed Compound 43 (50 mg, 0.09 mmol), 3-pyridinylboronic acid (16 mg, 0.13 mmol), $Na_2CO_3$ (28 mg, 0.27 mmol), Bis(di-tert-butyl(4-dimethylaminophenyl)phosphine)dichloropalladium(II) (6 mg, 0.009 mmol), 1,4-dioxane (1.5 mL), and water (0.3 mL). The reaction mixture was irritated in a microwave reactor for 10 min at 150° C. After cooling, the mixture was extracted with EtOAc, washed with aq saturated NaCl, and concentrated. The crude product was purified by prep HPLC to give Compound 201. MS (EI) for $C_{32}H_{25}FN_4O_4$. found 549 (MH+).

The following compounds prepared from Compound 43 in a manner analogous to the method used to prepare Compound 201 from Compound 43 in Example 74:

1-N'-(4-Fluorophenyl)-1-N-[4-(7-methoxy-6-pyridin-4-ylquinolin-4-yl)oxyphenyl]cyclopropane-1,1-dicarboxamide (202): Pyridin-4-ylboronic acid was used in place of 3-pyridinylboronic acid. MS (EI) for $C_{32}H_{25}FN_4O_4$. found 549 (MH+).

The following compound was prepared from Compound 44 and the potassium salt of 5-(trifluoro-14-boraneyl)-1H-pyrazole in a manner analogous to the preparation of Compound 201 from Compound 43 and 3-pyridinylboronic acid in Example 74:

1-N'-(4-Fluorophenyl)-1-N-[4-[6-(1H-pyrazol-5-yl)quinolin-4-yl]oxyphenyl]cyclopropane-1,1-dicarboxamide (204): MS (EI) for $C_{29}H_{22}FN_5O_3$. found 508 (MH+).

Example 75: 1-N'-(4-Fluorophenyl)-1-N-[4-(7-methoxy-6-sulfamoylquinolin-4-yl)oxyphenyl]cyclopropane-1,1-dicarboxamide (206)

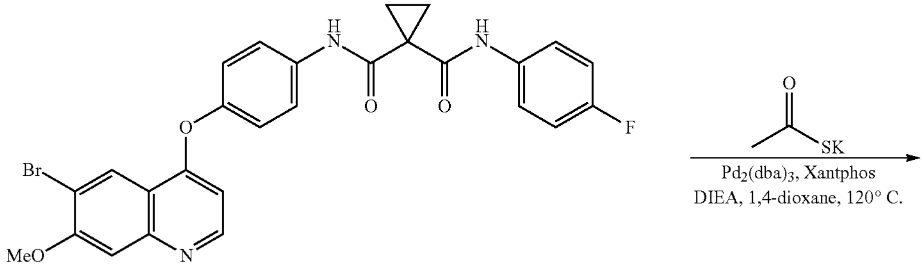

43

-continued

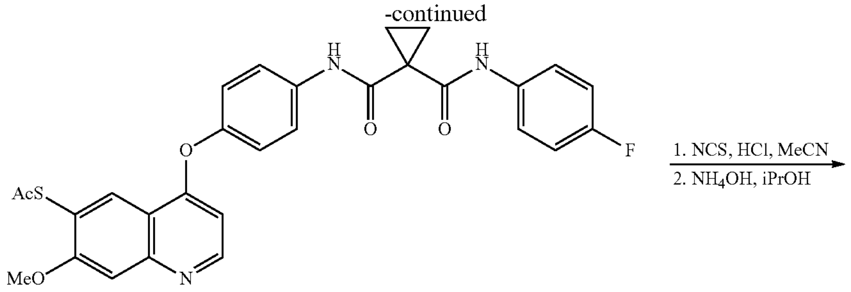

205

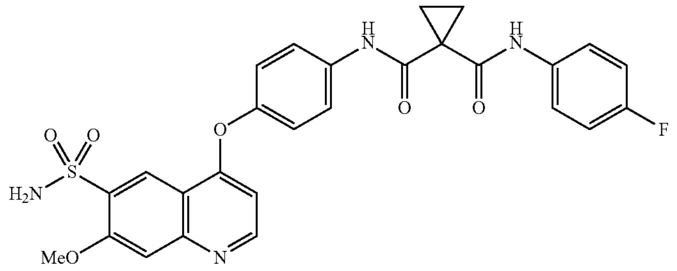

206

S-(4-(4-(1-((4-Fluorophenyl)carbamoyl)cyclopropane-1-carboxamido)phenoxy)-7-methoxyquinolin-6-yl) ethanethioate (205): To a mixture of Compound 43 (200 mg, 0.36 mmol), potassium ethanethioate (83 mg, 0.72 mmol), and DIEA (0.5 mL) in 1,4-dioxane (4 mL) was added $Pd_2(dba)_3$ (16 mg, 0.017 mmol) and Xantphos (20 mg, 0.035 mmol). The resulting mixture was stirred at 120° C. under microwave irradiation for 15 min. After cooling, EtOAc and water were added. Any insoluble material was filtered. The filtrate was washed with aq saturated NaCl and concentrated. The crude product was purified by flash silica gel chromatography to give Compound 205 (37% yield plus 50% of Compound 43 recovered).

1-N'-(4-Fluorophenyl)-1-N-[4-(7-methoxy-6-sulfamoylquinolin-4-yl)oxyphenyl]cyclopropane-1,1-dicarboxamide (206): N-Chlorosuccinimide (80 mg, 0.6 mmol) was added to a mixture of 2N HCl (0.5 mL) and MeCN (3 mL), and the resulting mixture was cooled to 0° C. A solution of Compound 205 (80 mg, 0.15 mmol) in MeCN (1.5 mL) was added. After stirring at 0° C. for 2 h, the reaction mixture was extracted with EtOAc. The organic phase was washed with aq saturated NaCl and concentrated. The resulting crude sulfonyl chloride was dissolved in i-PrOH (2 mL), to which was added excess $NH_4OH$ at room temperature. After the reaction was complete, the mixture was concentrated, and the crude product was purified by prep HPLC to give Compound 206 (60% yield). MS (EI) for $C_{27}H_{23}FN_4O_6S$, found 551 (MH+).

The following compounds were made from Compound 205 by a manner analogous to the way Compound 206 was made from Compound 205 in the second step of Example 75:

1-N'-(4-Fluorophenyl)-1-N-[4-[7-methoxy-6-(methylsulfamoyl)quinolin-4-yl]oxyphenyl]cyclopropane-1,1-dicarboxamide (207): The $NH_4OH$ was replaced by methylamine. $^1H$ NMR (400 MHz, DMSO-$d_6$) δ 10.22 (s, 1H), 10.06 (s, 1H), 8.71 (d, 1H), 8.69 (s, 1H), 7.78 (d, 2H), 7.64-7.62 (m, 2H), 7.60 (s, 1H), 7.30-7.28 (m, 3H), 7.17-7.12 (m, 2H), 6.50 (d, 1H), 4.04 (s, 3H), 2.47 (s, 3H), 1.47 (s, 4H); MS (EI) for $C_{28}H_{25}FN_4O_6S$, found 565.1 (MH+)

1-N-[4-[6-(Ethylsulfamoyl)-7-methoxyquinolin-4-yl]oxyphenyl]-1-N'-(4-fluorophenyl)cyclopropane-1,1-dicarboxamide (208): The $NH_4OH$ was replaced by ethylamine. MS (EI) for $C_{29}H_{27}FN_4O_6S$, found 579 (MH+).

The following compound was made from Compound 44 in a manner analogous to the way Compound 206 was made from Compound 43 in Example 75:

1-N'-(4-Fluorophenyl)-1-N-[4-(6-sulfamoylquinolin-4-yl)oxyphenyl]cyclopropane-1,1-dicarboxamide (209). MS (EI) for $C_{26}H_{21}FN_4O_5S$, found 521 (MH+).

Example 76: 1-N'-(4-Fluorophenyl)-1-N-[4-(7-methoxy-6-methylsulfonylquinolin-4-yl)oxyphenyl]cyclopropane-1,1-dicarboxamide (210)

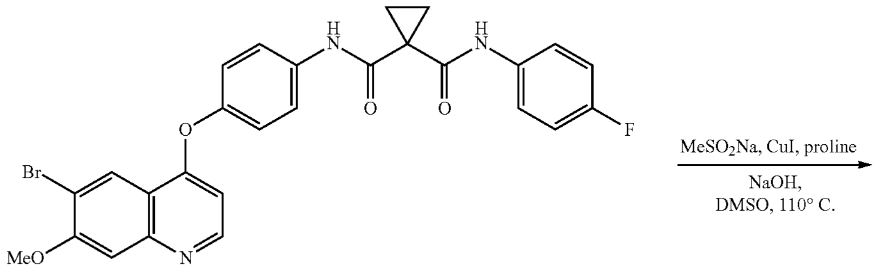

43

-continued

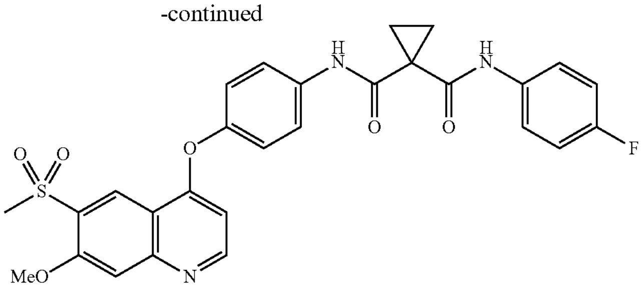

210

1-N'-(4-Fluorophenyl)-1-N-[4-(7-methoxy-6-methylsulfonylquinolin-4-yl)oxyphenyl]cyclopropane-1,1-dicarboxamide (210): Compound 43 (100 mg, 0.18 mmol), sodium methanesulfinate (40 mg, 0.36 mmol), CuI (5 mg), proline (6 mg), and NaOH (3 mg) were mixed in DMSO (1 mL). The resulting mixture was stirred at 110° C. for 14 h. After cooling to room temperature, water was added. The mixture was filtered through Celite® and washed with EtOAc. The EtOAc filtrate was concentrated and purified by prep HPLC to give Compound 210 (8% yield). MS (EI) for $C_{28}H_{24}FN_3O_6S$, found 550 (MH+).

Example 77: 1-N'-(4-Fluorophenyl)-1-N-[4-[7-(methoxycarbamoyl)quinolin-4-yl]oxyphenyl]cyclopropane-1,1-dicarboxamide (213)

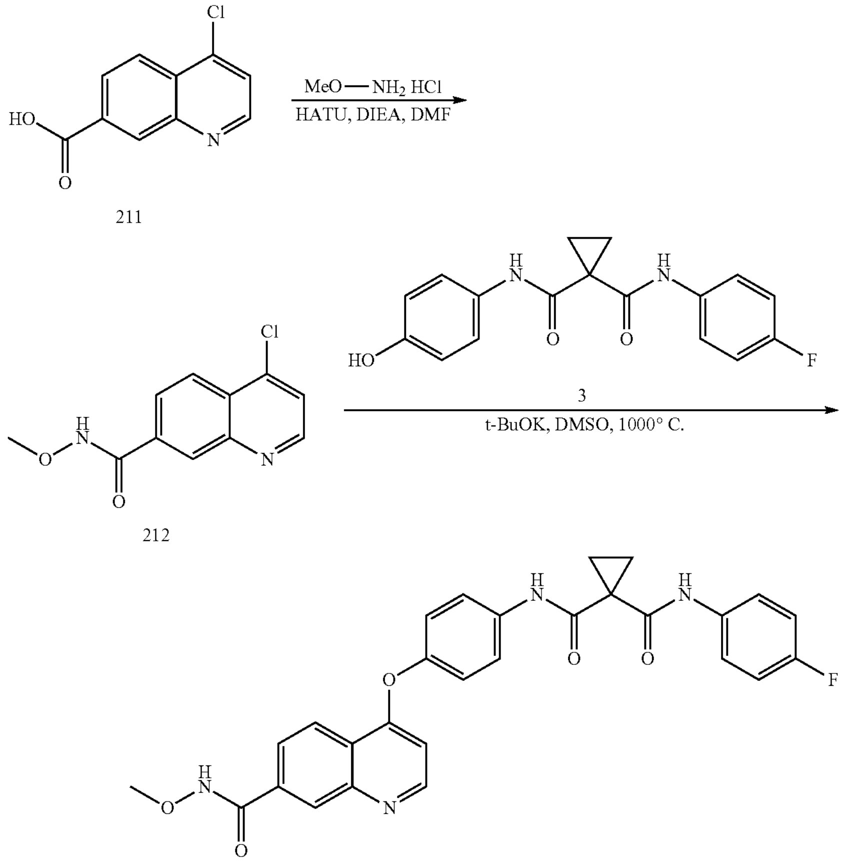

211

212

213

4-Chloro-N-methoxyquinoline-7-carboxamide (212): To a mixture of Compound 211 (60 mg, 289.00 μmol, 1 eq), HATU (180.00 mg, 473.40 μmol, 1.64 eq) and DIEA (150.00 mg, 1.16 mmol, 202.16 μL, 4.02 eq) in DMF (5 mL) was added O-methylhydroxylamine hydrochloride (54.00 mg, 646.57 μmol, 49.09 uL, 2.24 eq) in one portion. The mixture was stirred at 20-30° C. for 0.5 h and then partitioned between water (10 mL) and EtOAc (2×10 mL). The organic extracts were separated, washed with aq saturated NaCl (10 mL), dried with anhyd $Na_2SO_4$, and concentrated to give Compound 212 (140 mg, crude), which was used for the next step directly without further purification. MS (EI) for $C_{11}H_9ClN_2O_2$. found 236.9 (MH+).

1-N'-(4-Fluorophenyl)-1-N-[4-[7-(methoxycarbamoyl)quinolin-4-yl]oxyphenyl]cyclopropane-1,1-dicarboxamide (213): To a mixture of Compound 212 (140 mg, 591.58 μmol, 1 eq) and Compound 3 (280.00 mg, 890.84 μmol, 1.51 eq) in DMSO (5 mL) was added t-BuOK (133 mg, 1.19 mmol, 2.00 eq) in one portion, and the resulting mixture was stirred at 100° C. for 1 h. The reaction mixture was partitioned between water (10 mL) and EtOAc (2x10 mL). The combined organic extracts were washed with aq saturated NaCl (10 mL), dried with anhyd $Na_2SO_4$, and concentrated. The residue was purified by prep HPLC (basic conditions; column: Waters Xbridge 150*25 5 u; mobile phase: [water (0.05% ammonia hydroxide v/v)-ACN]; B %: 32%-57%, 6.5 min) to give Compound 213 (7.9 mg, 2.54% yield). $^1H$ NMR (400 MHz, DMSO-$d_6$) δ 12.11 (s, 1H), 10.22 (s, 1H), 10.06 (s, 1H), 8.77 (d, 1H), 8.44-8.37 (m, 2H), 7.99 (d, 1H), 7.79 (d, 2H), 7.65 (dd, 2H), 7.28 (d, 2H), 7.16 (t, 2H), 6.66 (d, 1H), 3.78 (s, 3H), 1.48 (s, 4H); MS (EI) for $C_{28}H_{23}FN_4O_5$. found 515.1 (MH+).

The following compound was prepared from Compound 211 in a manner analogous to the method used to prepare Compound 213 from Compound 211 in Example 77:

1-N-[4-[7-(Ethylcarbamoyl)quinolin-4-yl]oxyphenyl]-1-N'-(4-fluorophenyl)cyclopropane-1,1-dicarboxamide (214): The O-methylhydroxylamine hydrochloride in the first step was replaced with ethylamine hydrochloride. $^1H$ NMR (400 MHz, DMSO-$d_6$) δ 10.21 (s, 1H), 10.06 (s, 1H), 8.84 (t, 1H), 8.75 (d, 1H), 8.53 (d, 1H), 8.38 (d, 1H), 8.07 (dd, 1H), 7.78 (d, 2H), 7.64 (dd, 2H), 7.28 (d, 2H), 7.15 (t, 2H), 6.63 (d, 1H), 3.31 (br s, 2H), 1.47 (s, 4H), 1.18 (t, 3H); MS (EI) for $C_{29}H_{25}FN_4O_4$. found 513.1 (MH+).

Example 78: 1-N'-(4-Fluorophenyl)-1-N-[4-[7-methoxy-6-(1,3,4-oxadiazol-2-yl)quinolin-4-yl]oxyphenyl]cyclopropane-1,1-dicarboxamide (220)

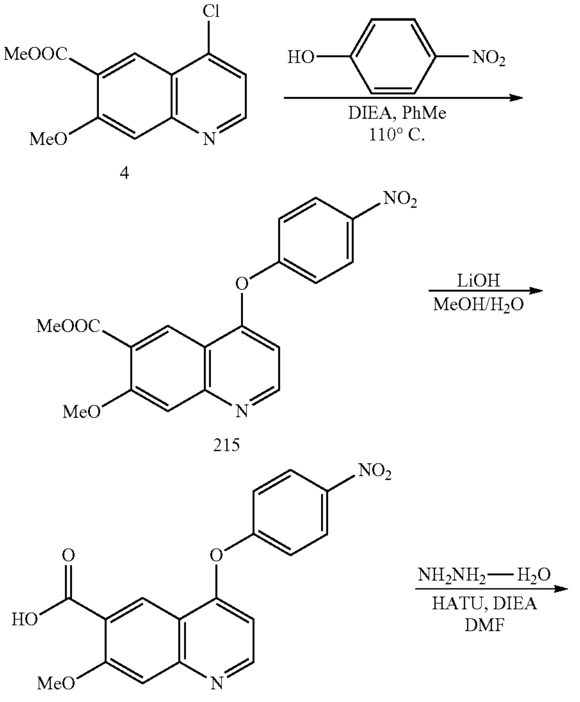

4

215

216

-continued

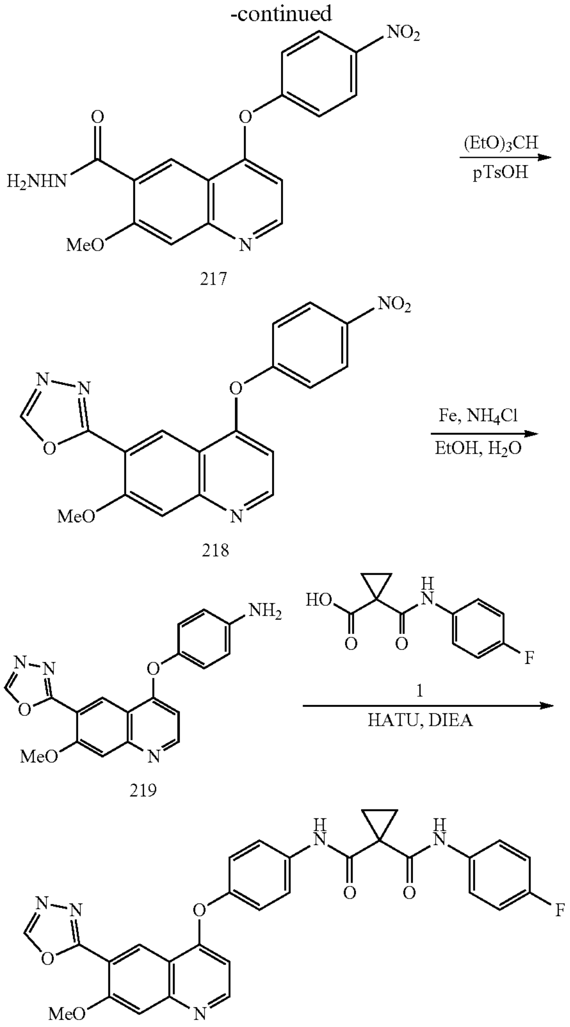

217

218

219

220

Methyl 7-methoxy-4-(4-nitrophenoxy)quinoline-6-carboxylate (215): Compound 4 (300 mg, 1.2 mmol), 4-nitrophenol (200 mg, 1.42 mmol), and DIEA (230 mg, 1.78 mmol) were mixed in toluene (1 mL). The resulting mixture was stirred at 110° C. for 12 h. After cooling, water was added, and the mixture was extracted with EtOAc. The organic phase was washed with aq saturated NaCl, concentrated and purified by flash silica gel chromatography to give Compound 215 (150 mg, 36%). MS (EI) for $C_{18}H_{14}N_2O_6$. found: 355 (MH+).

7-Methoxy-4-(4-nitrophenoxy)quinoline-6-carboxylic acid (216): Compound 216 was synthesized in a manner analogous to the preparation of Compound 81 in Example 25. MS (EI) for $C_{17}H_{12}N_2O_6$. found: 341 (MH+).

7-Methoxy-4-(4-nitrophenoxy)quinoline-6-carbohydrazide (217): To a solution of Compound 216 (45 mg, 0.13 mmol) and DIEA (51 mg, 0.4 mmol) in DMF (2 mL) was added HATU (100 mg, 0.26 mmol). The resulting mixture was stirred at room temperature for 10 min, then excess $NH_2NH_2H_2O$ was added. After the reaction was complete, water was added. The precipitate was filtered and dried under vacuum to give crude Compound 217, which was used in the next step without further purification. MS (EI) for $C_{17}H_{14}N_4O_5$. found: 355 (MH+).

2-(7-Methoxy-4-(4-nitrophenoxy)quinolin-6-yl)-1,3,4-oxadiazole (218): Compound 217 (66 mg, 0.18 mmol) and p-TsOH.$H_2O$ (4 mg, 0.02) were mixed in triethyl orthoformate (1 mL). The resulting mixture was stirred at 120° C. for 5 h. After cooling, the mixture was concentrated, and aq saturated $NaHCO_3$ was added. The precipitate was filtered and washed with EtOAc to give crude Compound 218, which was used in the next step without further purification. MS (EI) for $C_{18}H_{12}N_4O_5$. found: 365 (MH+).

4-((7-Methoxy-6-(1,3,4-oxadiazol-2-yl)quinolin-4-yl)oxy)aniline (219): Crude Compound 218 was mixed with Fe powder (50 mg, 0.9 mmol) and $NH_4Cl$ (20 mg, 0.36 mmol) in EtOH (2 mL). The resulting mixture was stirred at 85° C. for 3 h. After cooling, the mixture was filtered through Celite® and washed with EtOAc, and the filtrate was concentrated. The residue was purified by flash silica gel chromatography to give Compound 219 (40 mg, 66% over two steps). MS (EI) for $C_{18}H_{14}N_4O_3$. found: 335 (MH+).

1-N'-(4-Fluorophenyl)-1-N-[4-[7-methoxy-6-(1,3,4-oxadiazol-2-yl)quinolin-4-yl]oxyphenyl]cyclopropane-1,1-dicarboxamide (220): Compound 220 was synthesized in a manner analogous to the preparation of Compound 175 in Example 64. MS (EI) for $C_{29}H_{22}FN_5O_5$. found: 540 (MH+).

The following compound was made in a manner analogous to the synthesis of Compound 220 in Example 78, replacing Compound 4 with Compound 55:

1-N'-(4-Fluorophenyl)-1-N-[4-[6-(1,3,4-oxadiazol-2-yl)quinolin-4-yl]oxyphenyl]cyclopropane-1,1-dicarboxamide (221): MS (EI) for $C_{28}H_{20}FN_5O_4$. found 510 (MH+).

Example 81: N-(4-((7-Bromoquinolin-4-yl)oxy)phenyl)-N-(4-fluorophenyl)cyclopropane-1,1-dicarboxamide (232)

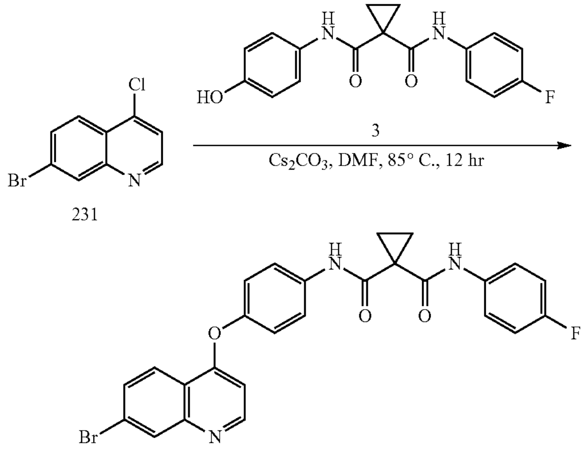

231

232

N-(4-((7-Bromoquinolin-4-yl)oxy)phenyl)-N-(4-fluorophenyl)cyclopropane-1,1-dicarboxamide (232): To a mixture of Compound 231 (1 g, 4.13 mmol) and Compound 3 (1.3 g, 4.13 mmol) in DMF (8 mL) was added $Cs_2CO_3$ (2.7 g, 8.26 mmol). The resulting mixture was stirred at 85° C. for 12 h. The mixture was cooled to room temperature, diluted with water, and filtered. The residue was purified by flash column chromatography to give Compound 232 (1.5 g, 69% yield). MS (EI) for $C_{26}H_{19}BrFN_3O_3$. found 520, 522 (MH+)

Example 85: 1-N'-(4-Fluorophenyl)-1-N-[4-(7-sulfamoylquinolin-4-yl)oxyphenyl]cyclopropane-1,1-dicarboxamide (254)

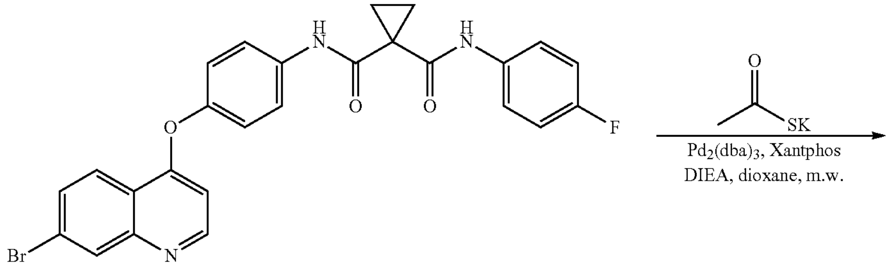

232

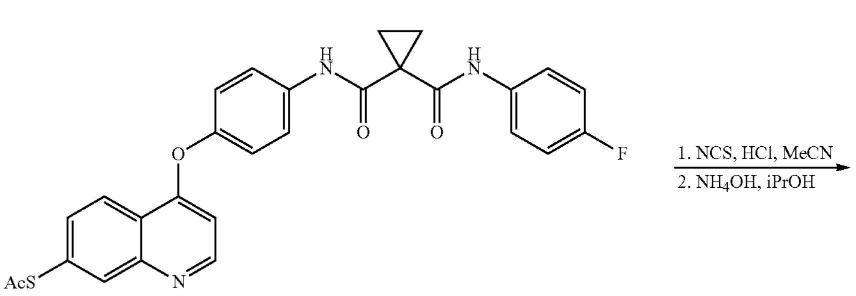

253

-continued

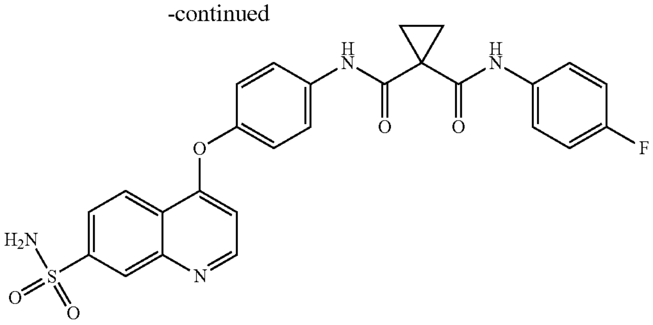

254

S-(4-(4-(1-((4-Fluorophenyl)carbamoyl)cyclopropane-1-carboxamido)phenoxy)quinolin-7-yl) ethanethioate (253): Compound 253 was synthesized from Compound 232 in a manner analogous to the preparation of Compound 205 from Compound 43 in Example 75 (170 mg, crude). MS (EI) for $C_{28}H_{22}FN_3O_4S$, found: 516.0 (MH+).

1-N'-(4-Fluorophenyl)-1-N-[4-(7-sulfamoylquinolin-4-yl)oxyphenyl]cyclopropane-1,1-dicarboxamide (254): Compound 254 was synthesized from Compound 253 in a manner analogous to the preparation of Compound 206 from Compound 205 in Example 75 (170 mg, crude). $^1H$ NMR (400 MHz, DMSO-$d_6$) δ 10.28 (s, 1H), 10.05 (s, 1H), 8.95 (d, 1H), 8.62 (d, 1H), 8.52 (d, 1H), 8.11 (dd, Hz, 1H), 7.88-7.75 (m, 4H), 7.67-7.59 (m, 2H), 7.33 (d, 2H), 7.15 (t, 2H), 6.85 (d, 1H), 1.48 (s, 4H); MS (EI) for $C_{26}H_{21}FN_4O_5S$, found: 521.0 (MH+).

Example 86: 1-N'-(4-Fluorophenyl)-1-N-[4-[7-[(E)-N-methoxy-C-methylcarbonimidoyl]quinolin-4-yl]oxyphenyl]cyclopropane-1,1-dicarboxamide (256)

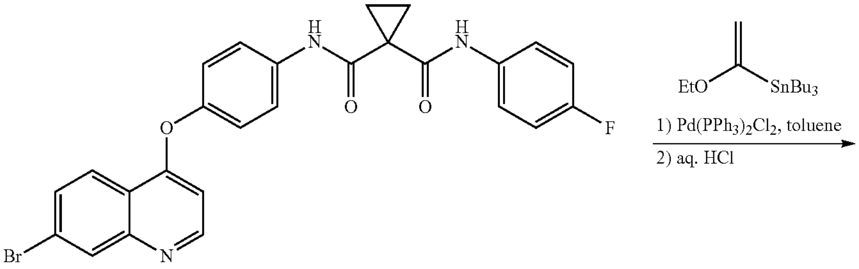

232

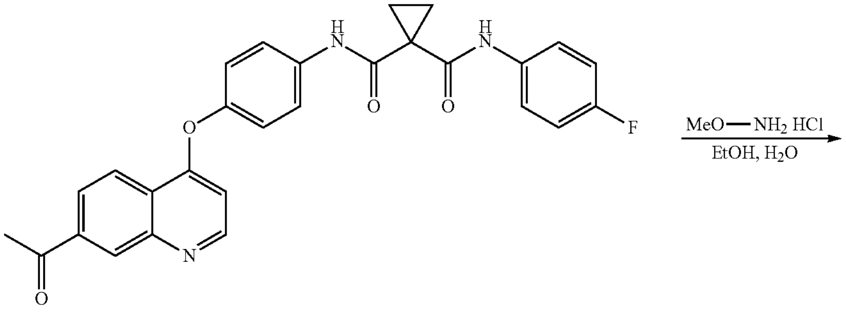

255

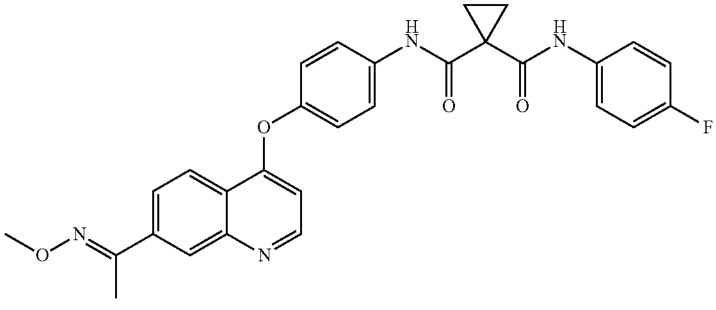

256

1-N-[4-(7-Acetylquinolin-4-yl)oxyphenyl]-1-N'-(4-fluorophenyl)cyclopropane-1,1-dicarboxamide (255): Compound 232 (100 mg, 192.18 μmol, 1 eq), tributyl(1-ethoxyvinyl)stannane (138.81 mg, 384.36 μmol, 129.73 uL, 2 eq), and $Pd(PPh_3)_2Cl_2$ (13.49 mg, 19.22 μmol, 0.1 eq) in toluene (2 mL) were degassed with nitrogen for 10 min and heated at 110° C. for 12 h under nitrogen. After cooling, KF (2 mL, 2M) was added, and the resulting mixture was stirred at room temperature for 30 min. Aq 6 M HCl (2 mL) was added to the residue, and the mixture was stirred at 25° C. for 30 min. The mixture was extracted with EtOAc. The organic layer was washed with water, aq saturated NaCl, dried ($Na_2SO_4$), and concentrated under reduced pressure. The residue was purified by prep-TLC (petroleum ether/ethyl acetate=1/1), followed by re-crystallization from MeOH (2 mL) and lyophilization to give Compound 255 (12.4 mg, 10.63% yield). $^1H$ NMR (400 MHz, $CDCl_3$) δ 9.46 (s, 1H), 8.75 (d, 1H), 8.67 (s, 1H), 8.57 (br s, 1H), 8.43 (d, 1H), 8.16 (dd, 1H), 7.66 (d, 2H), 7.51-7.45 (m, 2H), 7.20 (d, 2H), 7.10-7.04 (m, 2H), 6.64 (d, 1H), 2.78 (s, 3H), 1.76 (s, 2H), 1.67 (s, 2H); MS (EI) for $C_{28}H_{22}FN_3O_4$. found: 484.2 (MH+).

1-N'-(4-Fluorophenyl)-1-N-[4-[7-[(E)-N-methoxy-C-methylcarbonimidoyl]quinolin-4-yl]oxyphenyl]cyclopropane-1,1-dicarboxamide (256): To a mixture of Compound 255 (50 mg, 103.41 μmol, 1 eq) in EtOH (2 mL) and $H_2O$ (0.3 mL) was added O-methylhydroxylamine (43.18 mg, 517.07 μmol, 5 eq, HCl). The mixture was stirred at 50° C. for 1 h. The mixture was concentrated under vacuum, and the resulting residue was purified by column chromatography on silica-gel (petroleum ether/EtOAc=5/1 to 1/1), followed by re-purification by re-crystallization from MeOH (2 mL) to give Compound 256 (27 mg, 48.90% yield). $^1H$ NMR (400 MHz, $CDCl_3$) δ 10.24 (s, 1H), 8.82 (s, 1H), 8.72 (br d, 1H), 8.48-8.40 (m, 2H), 8.22 (s, 1H), 7.80 (d, 2H), 7.50-7.42 (m, 2H), 7.23 (br d, 2H), 7.07 (t, 2H), 6.83 (br d, 1H), 4.11 (s, 3H), 2.40 (s, 3H), 1.89-1.81 (m, 2H), 1.68-1.64 (m, 2H); MS (EI) for $C_{29}H_{25}FN_4O_4$. found: 513.1 (MH+).

Example 87: 4-(4-Amino-2-fluorophenoxy)-7-methoxy-N-methylquinoline-6-carboxamide (258)

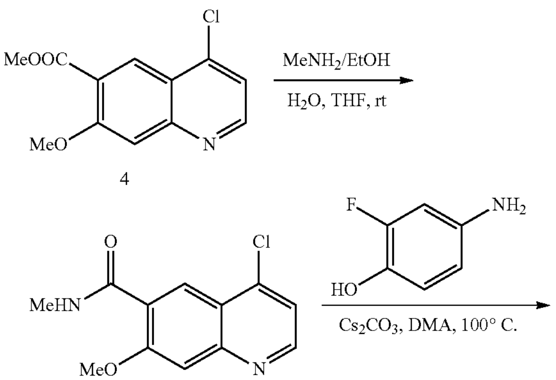

4

257

-continued

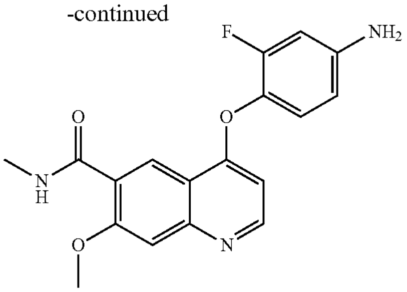

258

4-Chloro-7-methoxy-N-methylquinoline-6-carboxamide (257): Methylamine (8 M, 50 mL, 10.07 eq) in EtOH was added to a solution of Compound 4 (10 g, 39.74 mmol, 1 eq) in THF (150 mL) at 30° C. The reaction mixture was stirred at 30° C. for 25 h. The mixture was concentrated under vacuum. The residue was slurried with warm water (100 mL) and filtered. The filtered cake was dried under vacuum to give Compound 257 as a white solid (9 g, 90.35% yield). MS (EI) for $C_{12}H_{11}ClN_2O_2$. found: 251.0 (MH+).

4-(4-Amino-2-fluorophenoxy)-7-methoxy-N-methylquinoline-6-carboxamide (258): Compound 258 was synthesized from Compound 257 and 4-amino-2-fluorophenol in a manner analogous to the synthesis of Compound 171 from Compounds 42 and 2 in Example 62.

Example 88: 1-N-[3-Fluoro-4-[7-methoxy-6-(methylcarbamoyl)quinolin-4-yl]oxyphenyl]-1-N'-(4-fluorophenyl)-1-N'-methylcyclopropane-1,1-dicarboxamide (262)

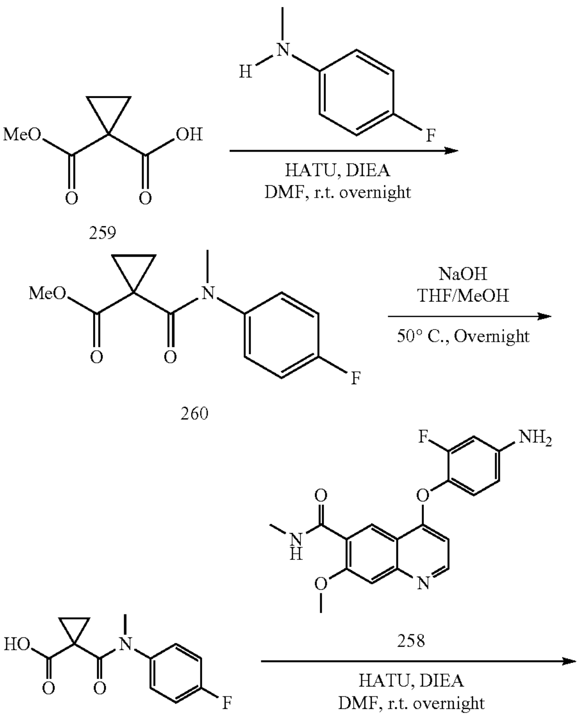

259

260

258

261

-continued

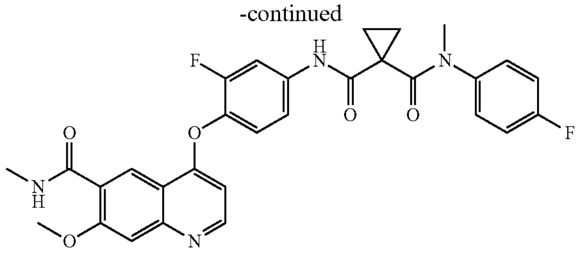

262

Methyl 1-((4-fluorophenyl)(methyl)carbamoyl)cyclopropane-1-carboxylate (260): A solution of Compound 259 (215 mg, 1.5 mmol, 1.5 eq), HATU (568 mg, 149 μmol, 1.5 eq) and DIEA (0.52 mL, 3 eq) in DMF (5 mL, 0.2M) was stirred at room temp for 15 min. 4-Fluoro-N-methylaniline (124 mg, 1.0 mmol, 1.0 eq) was added, and the mixture was stirred at room temp for 17 h. Water was added and the resulting mixture extracted with EtOAc. The two phases were separated and the organic layer dried over $Na_2SO_4$, concentrated under reduced pressure, absorbed into silica gel, and purified by CombiFlash (60:40 Hexanes:EtOAc) to give Compound 260 (221 mg, 88.7% yield). $^1H$ NMR (400 MHz, DMSO-$d_6$) δ 7.38-7.35 (m, 2H), 7.25 (m, 2H), 3.40 (s, 3H), 3.18 (s, 3H), 1.37 (d, 2H), 1.17 (bs. 2H).

1-((4-Fluorophenyl)(methyl)carbamoyl)cyclopropane-1-carboxylic acid (261): A solution of Compound 260 (60 mg, 0.23 mmol, 1.0 eq) and NaOH (20 mg, 0.5 mmol) in MeOH and THF (1 mL each) was stirred at 50° C. overnight. The reaction mixture was cooled down and concentrated under reduced pressure. To the residue, 1N HCl was added, and the resulting mixture was extracted with DCM. The two phases were separated, and the organic layer was dried over $Na_2SO_4$ and concentrated under reduced pressure to give crude Compound 261 which was used for the next step without further purification (44.7 mg, 79% yield). $^1H$ NMR (400 MHz, DMSO-$d_6$) δ 7.39 (br s, 2H), 7.25 (m, 2H), 3.17 (s, 3H), 1.24 (br s, 2H), 0.99 (br s. 2H).

1-N-[3-Fluoro-4-[7-methoxy-6-(methylcarbamoyl)quinolin-4-yl]oxyphenyl]-1-N'-(4-fluorophenyl)-1-N'-methylcyclopropane-1,1-dicarboxamide (262): A solution of Compound 261 (23.7 mg, 0.1 mmol, 1.5 eq), HATU (38 mg, 0.1 mmol, 1.5 eq) and DIEA (34 μL, 3.0 eq) in DMF (0.4 mL) was stirred at room temperature for 15 min. Compound 258 (23.7 mg, 0.06 mmol, 1.0 eq) was added, and the mixture was stirred at room temp for 17 h. Water was added to the mixture, and the resulting solid was extracted into EtOAc. The two phases were separated, and the organic layer was dried over $Na_2SO_4$, concentrated under reduced pressure, absorbed onto silica gel, and purified by CombiFlash (5:95 MeOH:DCM). The resulting product was further purified by prep HPLC to give Compound 262 (7 mg, 18.8% yield). $^1H$ NMR (400 MHz, DMSO-$d_6$) δ 9.94 (s, 1H), 8.79 (d, 1H), 8.59 (s, 1H), 8.38 (d, 1H), 7.50 (s, 1H), 7.37 (t, 2H), 7.22 (b m, 3H), 7.04 (t, 2H) 6.65 (d, 1H), 3.99 (s, 3H), 3.18 (s, 3H), 2.78 (d, 3H), 1.37 (d, 2H), 1.17 (b s, 2H); MS (EI) for $C_{30}H26F_2N_4O_5$. found 561.0 (MH+).

The following Compound 263 was made using a variation of the method used in the synthesis of Compound 262 in Example 88:

1-N'-(4-Fluorophenyl)-1-N-[4-[7-methoxy-6-(methylcarbamoyl)quinolin-4-yl]oxyphenyl]-1-N'-methylcyclopropane-1,1-dicarboxamide (263): Compound 258 was replaced by 4-(4-aminophenoxy)-7-methoxy-N-methylquinoline-6-carboxamide in the last step of the 3-step sequence of Example 88. The 4-(4-aminophenoxy)-7-methoxy-N-methylquinoline-6-carboxamide was synthesized in the same manner as Compound 258 in Example 87, replacing the 4-amino-2-fluorophenol in the second step with 4-aminophenol. $^1H$ NMR (400 MHz, DMSO-$d_6$) δ 9.69 (br s, 1H), 8.67 (d, 1H), 8.62 (s, 1H), 8.38 (d, 1H), 7.52 (s, 1H), 7.47 (s, 1H), 7.29 (m, 2H), 7.18 (d, 3H), 7.11 (t, 2H) 6.47 (d, 1H), 4.03 (s, 3H), 2.85 (d, 3H), 2.08 (s, 3H), 1.37 (d, 2H), 1.24 (br s. 2H); MS (EI) for $C_{30}H_{27}FN_4O_5$. found 543.0 (MH+).

The following compounds were made from Compound 259 and Compound 258 following the same 3-step procedure used to synthesize Compound 262 from Compound 259 and Compound 258 in Example 88:

1-N'-(2-Chloro-4-fluorophenyl)-1-N-[3-fluoro-4-[7-methoxy-6-(methylcarbamoyl)quinolin-4-yl]oxyphenyl]cyclopropane-1,1-dicarboxamide (264): The 4-fluoro-N-methylaniline in the first step was replaced with 2-chloro-4-fluoroaniline. $^1H$ NMR (400 MHz, DMSO-$d_6$) δ 10.36 (s, 1H), 10.25 (s, 1H), 8.61 (d, 1H), 8.54 (s, 1H), 8.31 (m, 1H), 7.84-7.79 (m, 2H), 7.47, (s, 2H), 7.40 (t, 2H) 7.18 (t, 1H), 6.42 (d, 1H), 3.96 (s, 3H), 2.77 (d, 3H), 1.56 (br s, 2H), 1.53 (br s. 2H); MS (EI) for $C_{29}H_{23}ClF_2N_4O_5$. found 581.0 (MH+).

1-N-[3-Fluoro-4-[7-methoxy-6-(methylcarbamoyl)quinolin-4-yl]oxyphenyl]-1-N'-(4-fluoro-2-methylphenyl)cyclopropane-1,1-dicarboxamide (265): The 4-fluoro-N-methylaniline in the first step was replaced with 4-fluoro-2-methylaniline. $^1H$ NMR (400 MHz, DMSO-$d_6$) δ 10.58 (s, 1H), 9.72 (s, 1H), 8.68 (d, 1H), 8.61 (s, 1H), 8.39 (d, 1H), 7.92 (d, 1H), 7.54 (br s, 2H), 7.47 (t, 2H), 7.1 (d, 1H), 7.03 (t, 1H) 6.49 (d, 1H), 4.03 (s, 3H), 2.85 (d, 3H), 2.22 (s, 3H), 1.54 (s, 4H); MS (EI) for $C_{30}H26F_2N_4O_5$. found 561.0 (MH+).

1-N'-(4-Fluoro-2,6-dimethylphenyl)-1-N-[3-fluoro-4-[7-methoxy-6-(methylcarbamoyl)quinolin-4-yl]oxyphenyl]cyclopropane-1,1-dicarboxamide (267): The 4-fluoro-N-methylaniline in the first step was replaced with 4-fluoro-2,6-dimethylaniline. $^1H$ NMR (400 MHz, DMSO-$d_6$) δ 10.8 (s, 1H), 9.19 (s, 1H), 8.6 (d, 1H), 8.54 (s, 1H), 8.32 (d1H), 7.87 (d1H), 7.46-7.36 (m, 3H), 6.88 (d, 2H), 6.41 (d, 1H), 3.96 (s, 3H), 2.77 (d, 3H), 2.09 (s, 6H), 1.47 (s, 4H); MS (EI) for $C_{31}H_{28}F_2N_4O_5$. found 575.0 (MH+).

1-N-[3-Fluoro-4-[7-methoxy-6-(methylcarbamoyl)quinolin-4-yl]oxyphenyl]-1-N'-(4-fluoro-2-methoxyphenyl)cyclopropane-1,1-dicarboxamide (268): The 4-fluoro-N-methylaniline in the first step was replaced with 4-fluoro-2-methoxyaniline. $^1H$ NMR (400 MHz, DMSO-$d_6$) δ 10.2 (s, 1H), 10.17 (s, 1H), 8.68 (d, 1H), 8.62 (s, 1H), 8.39 (d, 1H), 7.98-7.96 (m, 1H), 7.86 (d, 1H), 7.54-7.47 (m, 3H), 7.01 (d, 1H), 6.77 (t, 1H) 6.51 (d, 1H), 4.04 (s, 3H), 3.85 (s, 3H), 2.86 (d, 3H), 1.62 (s, 2H), 1.58 (s. 2H); MS (EI) for $C_{30}H26F_2N406$. found 577.0 (MH+).

1-N-[3-Fluoro-4-[7-methoxy-6-(methylcarbamoyl)quinolin-4-yl]oxyphenyl]-1-N'-(4-fluoro-2-propan-2-yloxyphenyl)cyclopropane-1,1-dicarboxamide (269): The 4-fluoro-N-methyl aniline in the first step was replaced with 4-fluoro-2-isopropoxyaniline. $^1H$ NMR (400 MHz, DMSO-$d_6$) δ 10.21 (s, 1H), 10.06 (s, 1H), 8.62 (d, 1H), 8.55 (s, 1H), 8.32 (d, 1H), 8.05 (t, 1H), 7.87 (d, 1H), 7.52-7.41 (m, 3H), 6.97 (d, 1H), 6.68 (t, 1H), 6.41 (d, 1H), 4.64-4.58 (m, 1H), 3.96 (s, 3H), 2.78 (d, 3H), 1.51 (s, 2H), 1.40 (s. 2H), 1.17 (s, 3H), 1.16 (s, 3H); MS (EI) for $C_{32}H_{30}F_2N406$. found 605 (MH+)

1-N'-(2-Cyclopropyl-4-fluorophenyl)-1-N-[3-fluoro-4-[7-methoxy-6-(methylcarbamoyl)quinolin-4-yl]oxyphenyl]cyclopropane-1,1-dicarboxamide (270): The 4-fluoro-N-methylaniline in the first step was replaced with 2-cyclopropyl-4-fluoroaniline. $^1H$ NMR (400 MHz, DMSO-$d_6$) δ 10.53 (br s, 1H), 9.99 (br s, 1H), 8.68 (d, 1H), 8.62 (s, 1H), 8.39 (d, 1H), 7.91 (d, 1H), 7.61 (s, 1H), 7.54 (s, 2H), 7.49 (br s, 1H), 7.01 (t, 1H) 6.82 (d, 1H), 6.49 (d, 1H), 4.04 (s, 3H), 2.85 (d, 3H), 1.97 (br s, 1H), 1.58 (s, 4H), 0.94 (d, 2H), 0.67 (d, 2H); MS (EI) for $C_{32}H_{28}F_2N_4O_5$. found 587.4 (MH+).

The 2-cyclopropyl-4-fluoroaniline used in the synthesis of Compound 270 was synthesized by the following procedure:

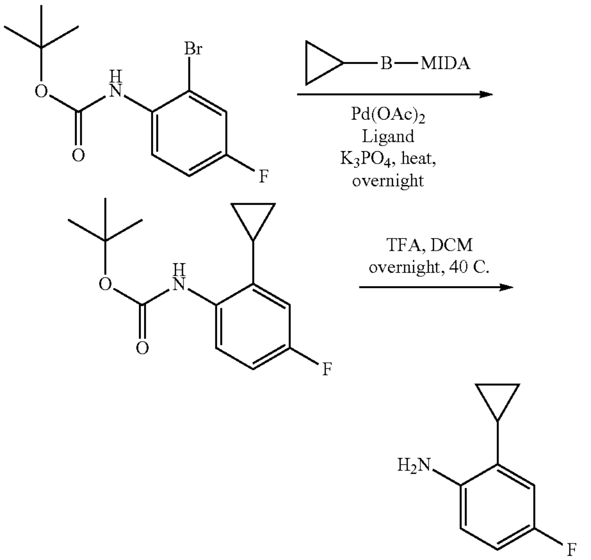

Tert-Butyl (2-bromo-4-fluorophenyl)carbamate (289 mg, 1 mmol, 1.0 eq), cyclopropyl MIDA boronate (236 mg, 1.2 mmol, 1.2 eq) and $K_3PO_4$ (636 mg, 3.0 eq) was added to toluene:water (4:1) in a thick wall reaction tube and degassed with nitrogen for 5 min. Palladium acetate (9 mg, 4 mol percent) and 2-(dicyclohexyl)phosphino biphenyl (28 mg 8 mole percent) were added to the mixture and degassed with nitrogen for another 5 min. The tube was capped, and the mixture was heated under nitrogen at 100° C. overnight. After cooling to room temperature, the two phases were separated. The organic layer was dried over anhyd $Na_2SO_4$, concentrated under reduced, absorbed into silica gel, and purified by CombiFlash using 70:30 Hexanes:DCM as gradient to give tert-butyl (2-cyclopropyl-4-fluorophenyl)carbamate as a colorless oil (90 mg, 36% yield).

A solution of tert-butyl (2-cyclopropyl-4-fluorophenyl) carbamate (86 mg, 0.3 mmol, 1.0 aq) and TFA (77 mg, 2.0 eq) in DCM (1 mL) was stirred at 40° C. overnight. The reaction solution was cooled down and concentrated under reduced pressure. To the residue, DCM (4 mL) was added, and the resulting solution was washed the with aq saturated $NaHCO_3$, dried over anhyd $Na_2SO_4$, and concentrated under reduced pressure to give crude 2-cyclopropyl-4-fluoroaniline as a nearly colorless oil (43 mg, 81% yield) which used in subsequent reactions without further purification. $^1H$ NMR (400 MHz, DMSO-$d_6$) δ 7.16-7.13 (m, 1H), 7.01 (t, 1H), 6.85 (d, 1H), 1.91-1.85 (m, 1H), 1.0 (d, 2H), 0.73 (d, 2H).

Example 89: 1-((3-Fluoro-((4-(7-methoxy-6-(methylcarbamoyl)quinolin-4-yl)oxy)phenyl)-carbamoyl)-cyclopropane-1-carboxylic Acid (272)

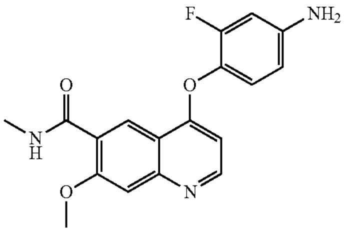

258

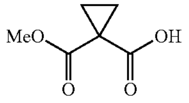

259

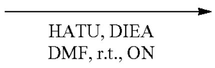

-continued

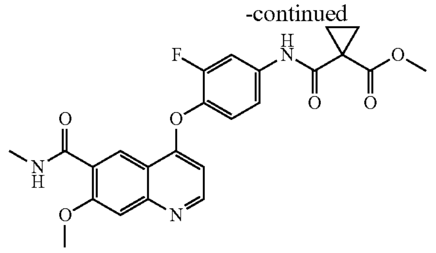

271

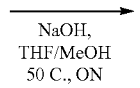

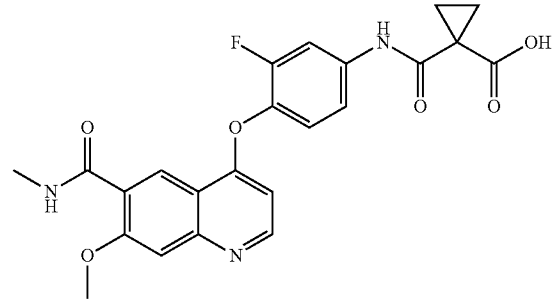

272

Methyl 1-((3-fluoro-4-((7-methoxy-6-(methylcarbamoyl) quinolin-4-yl)oxy)phenyl)-carbamoyl)cyclopropane-1-carboxylate (271): A solution of Compound 259 (108 mg, 0.7 mmol, 1.5 eq), HATU (285 mg, 0.75 mmol, 1.5 eq), and DIEA (0.26 mL, 3 eq) in DMF (2.5 mL, 0.2M) was stirred at room temperature for 15 min. Compound 258 (170 mg, 0.5 mmol, 1.0 eq) was added, and the mixture was stirred at room temperature for 17 h. Water was added, and the resulting mixture extracted with EtOAc. The organic layer was separated and washed with aq saturated NaCl, dried over anhyd $Na_2SO_4$, and concentrated under reduced pressure. The resulting residue was absorbed onto silica gel and purified by CombiFlash using 1:8 Hexanes:EtOAc followed by 1:6 Hexanes:DCM gradient. The resulting product was sonicated with Hexanes. The resulting solid was filtered, dissolved in DCM, and washed with aq 10% LiCl solution. Organic layer was dried over anhyd $Na_2SO_4$ and concentrated to give Compound 271 (90 mg, 38% yield). $^1H$ NMR (400 MHz, DMSO-$d_6$) δ 10.64 (br s, 1H), 8.67 (d, 1H), 8.61 (s, 1H), 8.39 (d, 1H), 7.88 (m, 1H), 7.54 (s, 1H), 7.51-7.44 (m, 2H), 6.52 (d, 1H), 4.03 (s, 3H), 3.71 (s, 3H), 2.85 (d, 3H), 1.46-1.45 (m, 2H), 1.43-1.42 (m, 2H).

1-((3-Fluoro-((4-(7-methoxy-6-(methylcarbamoyl)quinolin-4-yl)oxy)phenyl)carbamoyl)-cyclopropane-1-carboxylic acid (272): A solution of Compound 271 (70 mg, 0.2 mmol, 1.0 eq) and NaOH (12 mg, 0.5 mmol) in MeOH and THF (1 mL each) was stirred at 50° C. overnight. The reaction solution was allowed to cool down and then concentrated under reduced pressure. To the residue, aq 1N HCl was added, and the resulting mixture was extracted with DCM. The organic phase was dried over anhyd $Na_2SO_4$ and concentrated under reduced pressure to give crude Compound 272 (60 mg, 89% yield), which was used in subsequent reactions without further purification. $^1H$ NMR (400 MHz, DMSO-$d_6$) δ 10.85 (br s, 1H), 8.87 (d, 1H), 8.67 (s, 1H), 8.46 (d, 1H), 7.95 (m, 1H), 7.62 (s, 1H), 7.54-7.5 (m, 2H), 6.83 (d, 1H), 4.06 (s, 3H), 2.85 (d, 3H), 1.43 (s, 4H).

Example 90: 1-N'-[3-Fluoro-4-[7-methoxy-6-(methylcarbamoyl)quinolin-4-yl]oxyphenyl]-1-N-[4-(trifluoromethyl)phenyl]cyclopropane-1,1-dicarboxamide (273)

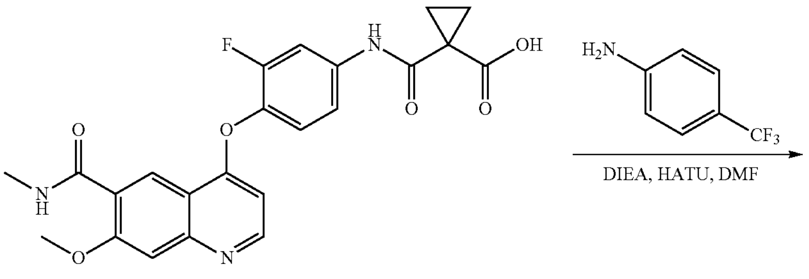

272

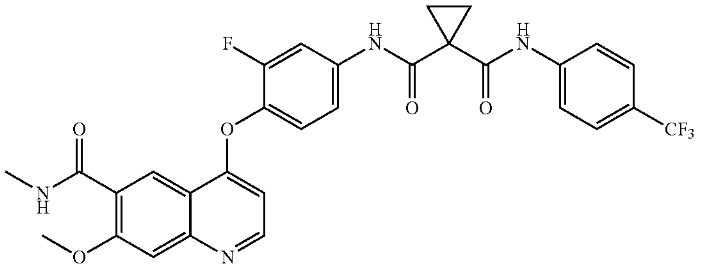

273

1-N'-[3-Fluoro-4-[7-methoxy-6-(methylcarbamoyl)quinolin-4-yl]oxyphenyl]-1-N-[4-(trifluoromethyl)phenyl]cyclopropane-1,1-dicarboxamide (273): Compound 273 was synthesized from Compound 272 and 4-(trifluoromethyl) aniline using standard HATU amide bond forming techniques such as those used in Example 3, Example 4 and the first step of Example 89. $^1$H NMR (400 MHz, $CD_3OD$) δ 8.90 (s, 1H), 8.86 (d, 1H), 7.89 (d, 1H), 7.55 (s, 1H), 7.51 (d, 2H), 7.43 (m, 2H), 7.25 (d, 2H), 6.98 (d, 1H), 4.13 (s, 3H), 2.94 (s, 3H), 1.64-1.54 (m, 4H). MS (EI) for $C_{30}H_{24}F_4N_4O_5$. found 597.2 (MH+).

The following compound was made from Compound 272 following the same procedure used to synthesize Compound 273 from Compound 272 Example 90:

1-N-(4-Chlorophenyl)-1-N'-[3-fluoro-4-[7-methoxy-6-(methylcarbamoyl)quinolin-4-yl]oxyphenyl]cyclopropane-1,1-dicarboxamide (274): The 4-(trifluoromethyl)aniline was replaced with 4-chloroaniline. $^1$H NMR (400 MHz, $CD_3OD$) δ 8.99 (s, 1H), 8.95 (d, 1H), 7.98 (d, 1H), 7.83 (d, 2H), 7.65 (d, 3H), 7.54 (q, 2H), 7.06 (d, 1H), 4.22 (s, 3H), 3.03 (s, 3H), 1.84-1.64 (m, 4H). MS (EI) for $C_{29}H_{24}ClFN_4O_5$. found 563.2 (MH+).

Example 91: 1-N'-(4-Fluorophenyl)-1-N-[4-[7-[(E)-methoxyiminomethyl]quinolin-4-yl]oxyphenyl]cyclopropane-1,1-dicarboxamide (278)

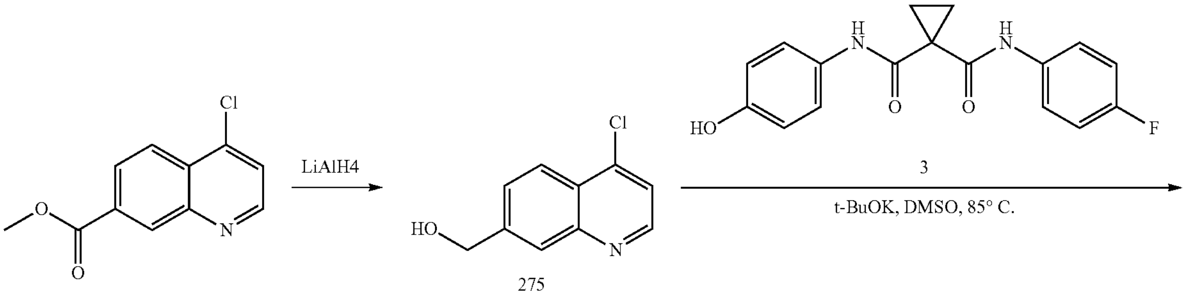

161 275

-continued

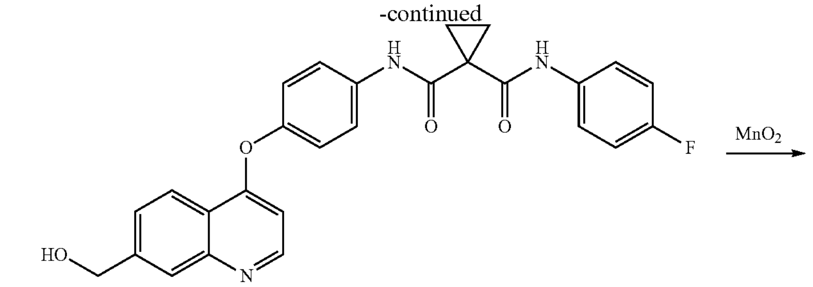

276

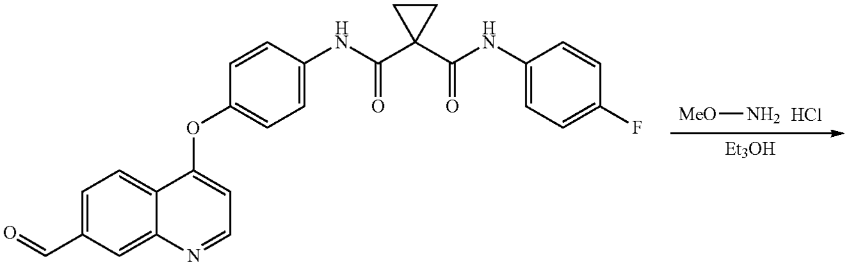

277

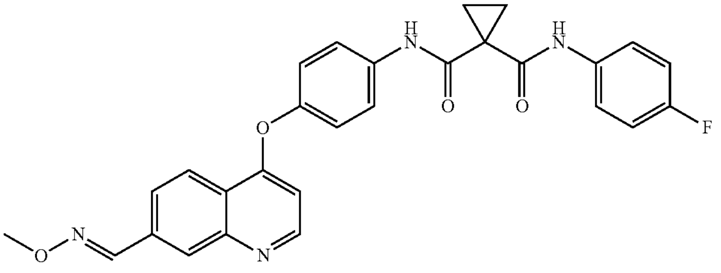

278

(4-Chloroquinolin-7-yl)methanol (275): To a solution of $LiAlH_4$ (116.45 mg, 3.07 mmol, 1.7 eq) in THF (5 mL) was added Compound 161 (400 mg, 1.80 mmol, 1 eq) in THF (2 mL) at 0° C. The mixture was stirred at 20° C. for 3 h. $Na_2SO_4.10H_2O$ (50 mg) was added, the resulting mixture was filtered, and the filtrate was dried over anhyd $Na_2SO_4$ and then concentrated in vacuo. The resulting residue was purified by flash silica gel chromatography (ISCO®; 4 g SepaFlash® Silica Flash Column, Eluent of 70100% Ethyl acetate/Petroleum ether gradient @ 25 mL/min) to give Compound 275 as a light yellow solid (150 mg, 36.5% yield). $^1H$ NMR (400 MHz, $CDCl_3$) δ 8.74 (d, 1H), 8.19 (d, 1H), 8.12 (s, 1H), 7.64 (dd, 1H), 7.47 (d, 1H), 4.94 (s, 2H), 2.99 (br s, 1H).

N-(4-Fluorophenyl)-N-(4-((7-(hydroxymethyl)quinolin-4-yl)oxy)phenyl)cyclopropane-1,1-dicarboxamide (276): Compound 276 was synthesized from Compound 275 and Compound 3 in a manner analogous to the method used to synthesize Compound 43 from Compound 42 and Compound 3 in the last step of Example 12, lowering the reaction temperature to 85° C. $^1H$ NMR (400 MHz, $CD_3OD$) δ 8.63 (d, 1H), 8.41 (d, 1H), 8.03 (s, 1H), 7.76 (d, 2H), 7.68 (dd, 1H), 7.62-7.55 (m, 2H), 7.30-7.23 (m, 2H), 7.09 (t, 2H), 6.66 (d, 1H), 4.88 (s, 2H), 1.66 (d, 4H); MS (EI) for $C_{27}H_{22}FN_3O_4$. found 472.1 (MH+).

N-(4-Fluorophenyl)-N-(4-((7-formylquinolin-4-yl)oxy)phenyl)cyclopropane-1,1-dicarboxamide (277): To a solution of Compound 276 (100 mg, 212.1 umol, 1 eq) in DCM (5 mL) was added $MnO_2$ (239.72 mg, 2.76 mmol, 13 eq). The mixture was stirred at 20° C. for 1 h. The mixture was filtered and concentrated in vacuo to give Compound 277 as a yellow oil (50 mg, 40.2% yield). MS (EI) for $C_{27}H_{20}FN_3O_4$. found 470.0 (MH+).

1-N'-(4-Fluorophenyl)-1-N-[4-[7-[(E)-methoxyiminomethyl]quinolin-4-yl]oxyphenyl]cyclopropane-1,1-dicarboxamide (278): To a mixture of Compound 277 (50 mg, 106.5 umol, 1 eq) in EtOH (3 mL) and water (0.3 mL) was added O-methylhydroxylamine (44.47 mg, 532.5 umol, 5 eq, HCl). The mixture was stirred at 50° C. for 2 h. The mixture was concentrated under vacuum, and EtOH (3 mL) was added to the residue. The resulting white solid was collected and then purified by prep-HPLC (YMC-Actus Triart C18 150*30 mm*5 um; mobile phase: [water (0.225% FA)-ACN]; B %: 37%-77%, 10 min) to give Compound 278 as a white solid (14.5 mg, 26.2% yield). $^1H$ NMR (400 MHz, DMSO-$d_6$) δ 10.22 (s, 1H), 10.07 (s, 1H), 8.72 (d, 1H), 8.51 (s, 1H), 8.34 (d, 1H), 8.18 (d, 1H), 7.97 (dd, 1H), 7.79 (d, 2H), 7.70-7.61 (m, 2H), 7.28 (d, 2H), 7.16 (t, 2H), 6.60 (d, 1H), 3.98 (s, 3H), 1.48 (s, 4H); MS (EI) for $C_{28}H_{23}FN_4O_4$. found 499.2 (MH+).

Example 92: 1-N'-(4-Fluorophenyl)-1-N-[4-[7-methoxy-6-(methylcarbamoylamino)-quinolin-4-yl]oxyphenyl]cyclopropane-1,1-dicarboxamide (279)

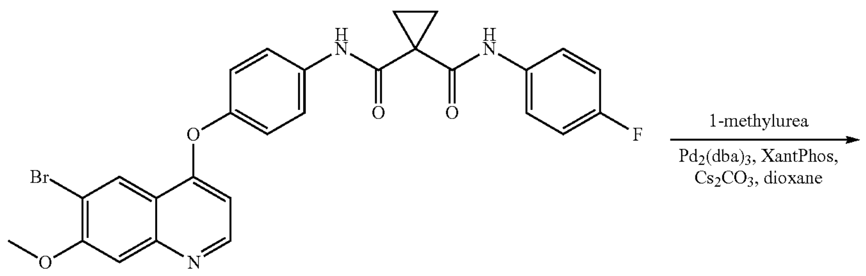

43

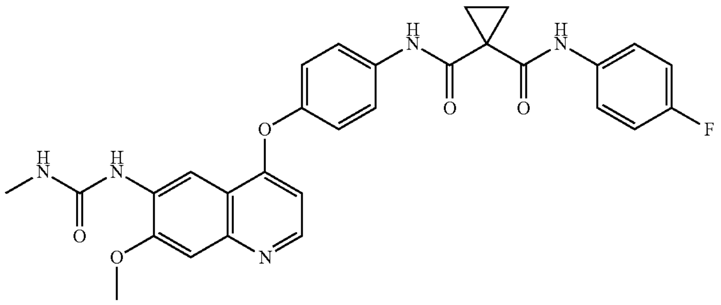

279

1-N'-(4-Fluorophenyl)-1-N-[4-[7-methoxy-6-(methylcarbamoylamino)-quinolin-4-yl]oxyphenyl]cyclopropane-1,1-dicarboxamide (279): To a mixture of Compound 43 (60 mg, 109.02 umol, 1 eq) in dioxane (3 mL) was added 1-methylurea (48.46 mg, 654.10 umol, 6 eq), $Pd_2(dba)_3$ (14.97 mg, 16.35 umol, 0.15 eq), Xantphos (18.92 mg, 32.70 umol, 0.3 eq), and $Cs_2CO_3$ (99.46 mg, 305.25 umol, 2.8 eq) under an atmosphere of nitrogen. The mixture was stirred at 100° C. for 1 h. The reaction mixture was concentrated, and water (20 mL) was added to the residue. The resulting mixture was extracted with EtOAc (3x25 mL). The combined organic extracts were dried over anhyd $Na_2SO_4$ and concentrated in vacuo, and the resulting residue was purified by prep-HPLC (column: DuraShell 150*25 mm*5 um; mobile phase: [water (0.05% ammonia hydroxide v/v)-ACN]; B %: 30%-70%, 10 min) to give Compound 279 as a white solid (12.8 mg, 20.7% yield). $^1H$ NMR (400 MHz, DMSO-$d_6$) δ 10.15 (s, 1H), 10.07 (s, 1H), 8.97 (s, 1H), 8.44 (d, 1H), 8.32 (s, 1H), 7.76 (d, 2H), 7.65 (dd, 2H), 7.40 (s, 1H), 7.24-7.12 (m, 4H), 6.95 (br d, 1H), 6.41 (d, 1H), 4.04 (s, 3H), 2.68 (s, 3H), 1.48 (br d, 4H); MS (EI) for $C_{29}H_{26}FN_5O_5$. found 544.3 (MH+).

Example 93: Methyl N-[4-[4-[[1-[(4-fluorophenyl)carbamoyl]cyclopropane-carbonyl]amino]phenoxy]-7-methoxyquinolin-6-yl]carbamate (280)

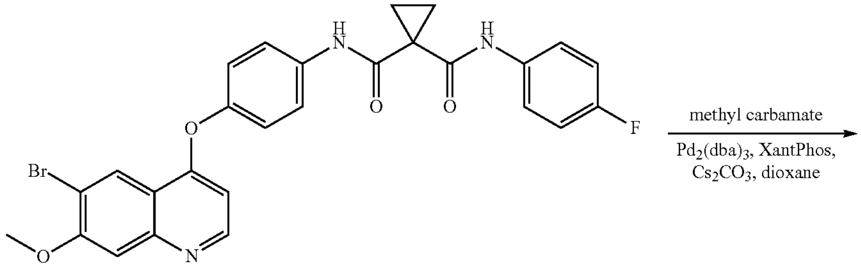

43

-continued

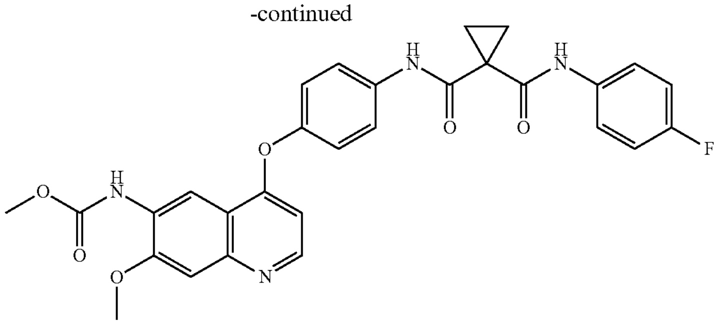

280

Methyl N-[4-[4-[[1-[(4-fluorophenyl)carbamoyl]cyclopropane-carbonyl]amino]phenoxy]-7-methoxyquinolin-6-yl]carbamate (280): Compound 280 was synthesized from Compound 43 in a manner analogous to the method used to synthesize Compound 279 from Compound 43 in Example 92, replacing the 1-methylurea with methyl carbamate. $^{1}$H NMR (400 MHz, DMSO-$d_6$) δ 10.17 (s, 1H), 10.06 (s, 1H), 8.84 (s, 1H), 8.67 (s, 1H), 8.52 (d, 1H), 7.77 (d, 2H), 7.70-7.62 (m, 2H), 7.45 (s, 1H), 7.23 (d, 2H), 7.19-7.12 (m, 2H), 6.45 (d, 1H), 4.00 (s, 3H), 3.72 (s, 3H), 1.48 (s, 4H); MS (EI) for $C_{29}H_{25}FN_4O_6$. found 567.3 $[M+Na]^+$

Example 94: 1-N'-(4-Fluorophenyl)-1-N-[4-[7-(methylcarbamoylamino)quinolin-4-yl]oxyphenyl]cyclopropane-1,1-dicarboxamide (281)

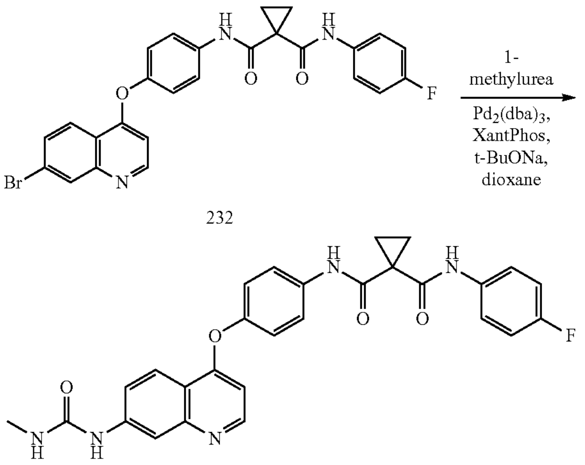

232

281

1-N'-(4-Fluorophenyl)-1-N-[4-[7-(methylcarbamoylamino)quinolin-4-yl]oxyphenyl]cyclopropane-1,1-dicarboxamide (281): A mixture of Compound 232 (100 mg, 192.18 umol, 1 eq), methylurea (42.71 mg, 576.54 umol, 3 eq), Xantphos (22.24 mg, 38.44 umol, 0.2 eq), t-BuONa (36.94 mg, 384.36 umol, 2 eq), and $Pd_2(dba)_3$ (17.60 mg, 19.22 umol, 0.1 eq) in dioxane (5 mL) was degassed and purged with nitrogen three times, followed by stirring at 100° C. for 16 h. The reaction mixture was filtered and concentrated under reduced pressure. The resulting residue was purified by prep-HPLC (column: Xtimate C18 10μ 250 mm*50 mm; mobile phase: [water (0.05% ammonia hydroxide v/v)-ACN]; B %: 39%-69%, 9 min) to give Compound 281 as a white solid (56.9 mg, 57.4% yield). $^{1}$H NMR (400 MHz, DMSO-$d_6$) δ 10.18 (s, 1H), 10.06 (s, 1H), 9.09 (s, 1H), 8.55 (d, 1H), 8.14 (d, 2H), 7.75 (d, 2H), 7.69-7.57 (m, 3H), 7.22 (d, 2H), 7.15 (t, 2H), 6.37 (d, 1H), 6.26 (d, 1H), 2.69 (d, 3H), 1.48 (s, 4H); MS (EI) for $C_{28}H_{24}FN_5O_4$. found 514.3 (MH+).

Example 95: Methyl N-[4-[4-[[1-[(4-fluorophenyl)carbamoyl]cyclopropanecarbonyl]-amino]phenoxy]quinolin-7-yl]carbamate (282)

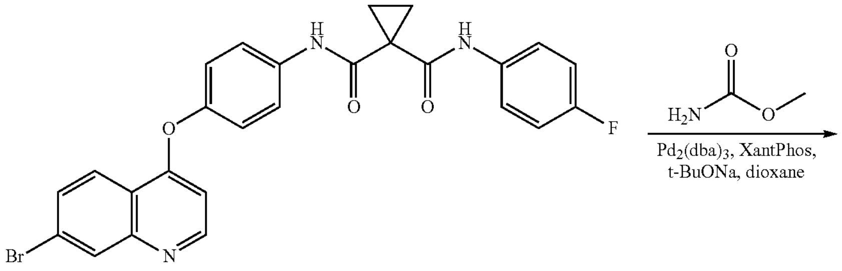

232

-continued

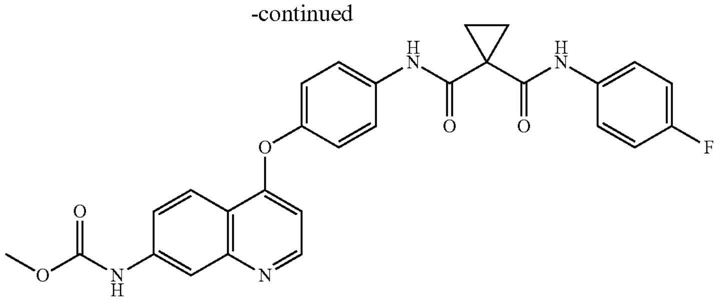

282

Methyl N-[4-[4-[[1-[(4-fluorophenyl)carbamoyl]cyclopropanecarbonyl]-amino]phenoxy]quinolin-7-yl]carbamate (282): Compound 282 was synthesized from Compound 232 in a manner analogous to the method used to synthesize Compound 281 from Compound 232 in Example 94, replacing the 1-methylurea with methyl carbamate. $^1$H NMR (400 MHz, DMSO-$d_6$) δ 10.82-10.72 (m, 1H), 10.40-10.33 (m, 1H), 10.12-10.04 (m, 1H), 8.89 (d, 1H), 8.59 (d, 1H), 8.50 (d, 1H), 7.93-7.81 (m, 3H), 7.69-7.60 (m, 2H), 7.38 (d, 2H), 7.16 (t, 2H), 6.78 (d, 1H), 3.79 (s, 3H), 1.50 (s, 4H); MS (EI) for $C_{28}H_{23}FN_4O_5$. found 515.3 (MH+).

Example 96: 1-N-[4-[6-(3-Ethyl-1,2,4-oxadiazol-5-yl)-7-methoxyquinolin-4-yl]oxyphenyl]-1-N'-(4-fluorophenyl)cyclopropane-1,1-dicarboxamide Hydrochloride (283)

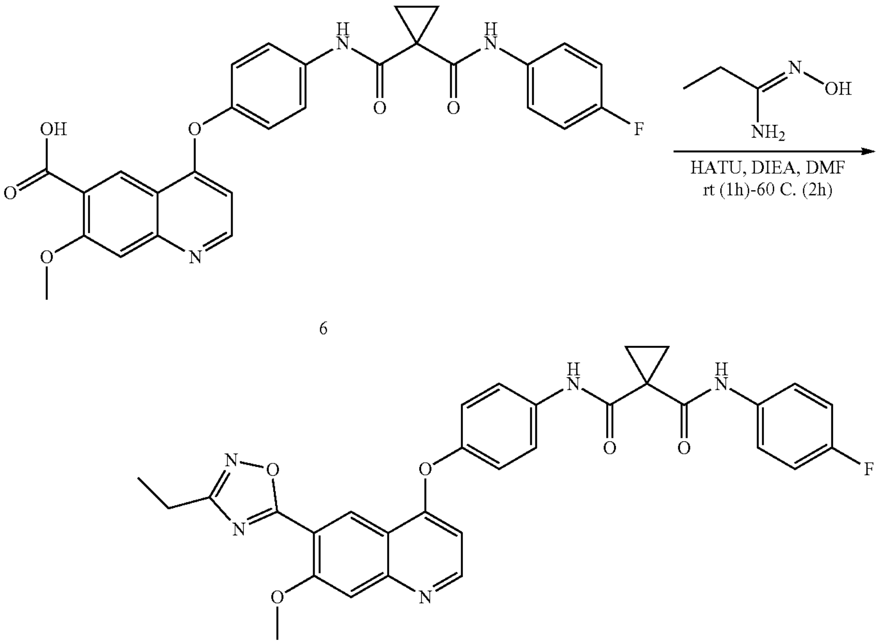

6

283

1-N-[4-[6-(3-Ethyl-1,2,4-oxadiazol-5-yl)-7-methoxyquinolin-4-yl]oxyphenyl]-1-N'-(4-fluorophenyl)cyclopropane-1,1-dicarboxamide hydrochloride (283): To a solution of Compound 6 (30 mg, 0.058 mmol), (Z)—N'-hydroxypropanimidamide (7.22 mg, 0.058 mmol), and DIEA (44 uL, 0.17 mmol) in DMF (0.5 mL) was added HATU (26.45 mg, 0.070 mmol), and the reaction was stirred at room temperature until the starting material disappeared as determined by monitoring with LC-MS. The reaction mixture was then heated to 60° C. for 2 h. Aq saturated $NaHCO_3$ was added to the resulting mixture, which was then extracted with DCM (3×). The combined organic extracts were washed with aq saturated NaCl, dried over $Na_2SO_4$, and concentrated. The resulting crude residue was subjected to HPLC purification (Gemini-NX, 10 uM, 250×30 mm, C18 column; eluent: 0.1 to 100% acetonitrile in water, both eluents containing 0.1% trifluoroacetic acid, gradient elution over 15 min) and subsequently freeze-dried. The resulting powder was brought up in 20% MeOH in DCM, passed through an Agilent PL-$HCO_3$ ion exchange column (or brought up in DCM and washed with saturated sodium bicarbonate), and concentrated under reduced pressure. HCl (4M in Dioxane, 0.5 ml; or 1M aq, 1 mL) was added, the volatile solvents were removed under reduced pressure, and the resulting residue dried under high vacuum to give the hydrochloride salt of Compound 283 (4.1 mg, 11.7% yield). $^1$H NMR (400 MHz, $CD_3OD$) δ 9.29 (s, 1H), 8.94 (d, 1H), 7.86 (q, 2H), 7.68 (s, 1H), 7.61-7.54 (m, 2H), 7.41 (d, 2H), 7.10 (t, 2H), 7.02 (d, 1H), 4.26 (s, 3H), 2.91 (q, 2H), 1.68 (s, 4H), 1.42 (t, 3H). MS (EI) for $C_{31}H_{26}FN_5O_5$. found 568.2 (MH+).

Example 97: 1-N'-[3-Fluoro-4-[6-methyl-7-(methylcarbamoyl)quinolin-4-yl]oxyphenyl]-1-N-(4-fluorophenyl)cyclopropane-1,1-dicarboxamide (289)
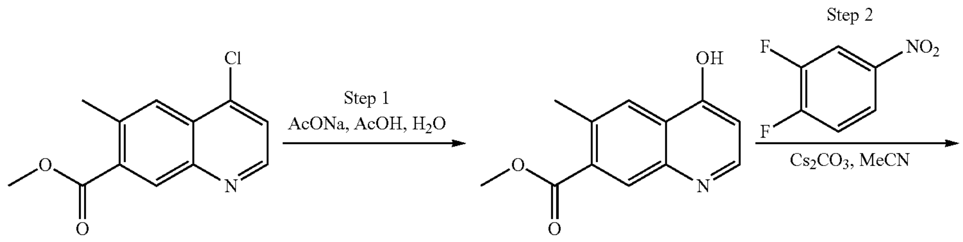
139 284
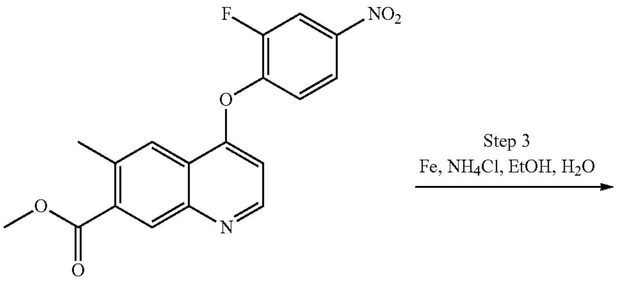
285
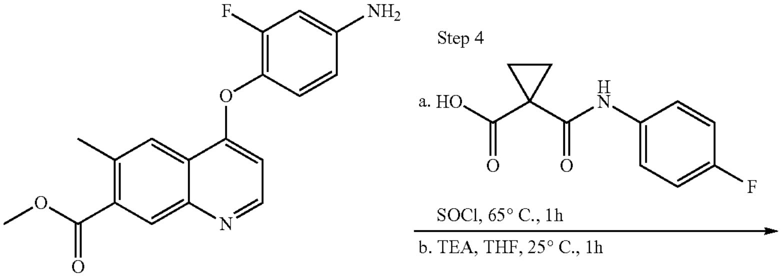
286
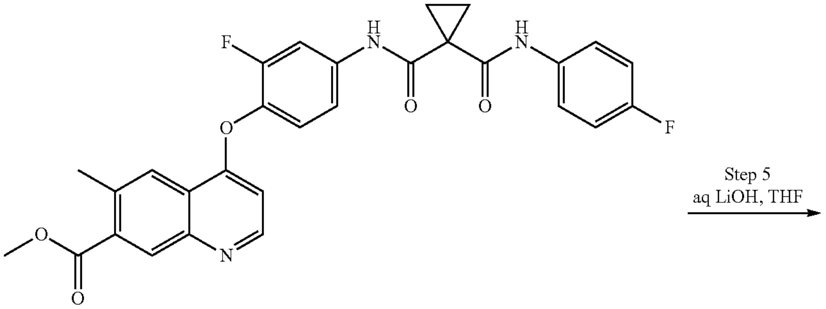
287
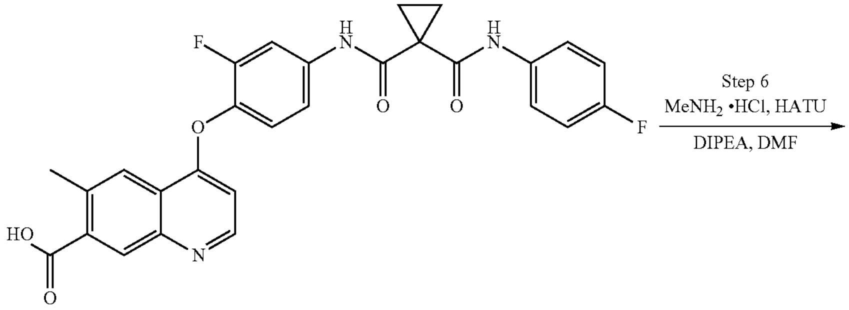
288

-continued

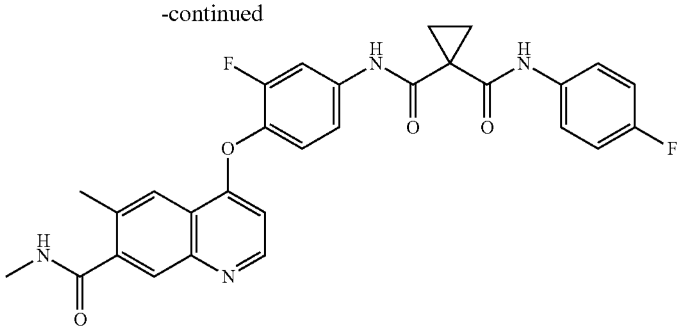

289

Methyl 4-hydroxy-6-methylquinoline-7-carboxylate (284): A mixture of Compound 139 (290 mg, 1.11 mmol, 1 eq) and AcONa (454.26 mg, 5.54 mmol, 5 eq) in AcOH (6 mL) and water (10 mL) was stirred at 90° C. for 48 h. After cooling to ambient temperature, the reaction mixture was neutralized with aq saturated $NaHCO_3$ and extracted with EtOAc (3x30 mL). The combined extracts were dried over anhyd $Na_2SO_4$ and concentrated under reduced pressure to give Compound 284 as a light yellow solid (200 mg, 74.8% yield) which was used directly in subsequent reactions without further purification. MS (EI) for $C_{12}H_{11}NO_3$. found 218.1 (MH+).

Methyl 4-(2-fluoro-4-nitrophenoxy)-6-methylquinoline-7-carboxylate (285): To a mixture of Compound 284 (200 mg, 828.65 umol, 1 eq) and 1,2-difluoro-4-nitro-benzene (197.75 mg, 1.24 mmol, 137.32 uL, 1.5 eq) in ACN (15 mL) was added $Cs_2CO_3$ (809.97 mg, 2.49 mmol, 3 eq) at 25° C., followed by stirring at 70° C. for 2 h. After being allowed to cool, the reaction mixture was diluted with water (50 mL) and extracted with EtOAc (3x30 mL). The combined organic extracts were washed with aq saturated NaCl (60 mL), dried over anhyd $Na_2SO_4$, and concentrated. The resulting residue was purified by flash chromatography on silica gel eluting with EtOAc in petroleum ether (0-60%) to give Compound 285 as a light yellow solid (120 mg, 38.6% yield). $^1H$ NMR (400 MHz, $CDCl_3$) δ 8.77 (d, 1H), 8.70 (s, 1H), 8.23-8.15 (m, 2H), 8.12 (s, 1H), 7.42-7.35 (m, 1H), 6.65 (d, 1H), 3.99 (s, 3H), 2.79 (s, 3H); MS (EI) for $C_{18}H_{13}FN_2O_5$. found 357.0 (MH+).

Methyl 4-(4-amino-2-fluorophenoxy)-6-methylquinoline-7-carboxylate (286): Compound 286 was synthesized from Compound 285 using a method analogous to that used to convert Compound 218 to Compound 219 in Example 78. MS (EI) for $C_{18}H_{15}FN_2O_3$. found 326.9 (MH+).

Methyl 4-(2-fluoro-4-(1-((4-fluorophenyl)carbamoyl)cyclopropane-1-carboxamido)phenoxy)-6-methylquinoline-7-carboxylate (287): A mixture of Compound 1 (51.30 mg, 218.34 umol, 1.5 eq) in $SOCl_2$ (8.20 g, 68.92 mmol, 5.00 mL, 473.51 eq) was stirred for 1 h at 65° C. The mixture was concentrated, and the residue was dissolved in toluene and reconcentrated. To the resulting residue was added a solution of Compound 286 (50 mg, 145.56 umol, 1.0 eq) in THF (5 mL), and then was added triethylamine (44.19 mg, 436.69 umol, 60.78 uL, 3 eq). The resulting mixture was stirred for 1 h at 25° C. The reaction mixture was quenched with water (30 mL) and extracted with EtOAc (3x20 mL). The combined extracts were dried over anhyd $Na_2SO_4$ and concentrated. The resulting residue was purified by flash chromatography on silica gel eluting with (EtOAc in petroleum ether=0-70%) to give Compound 287 as an off-white solid (70 mg, 85.95% yield). MS (D) for $C_{29}H_{23}F_2N_3O_5$. found 532.0 (MH+).

4-(2-Fluoro-4-(1-((4-fluorophenyl)carbamoyl)cyclopropane-1-carboxamido)phenoxy)-6-methylquinoline-7-carboxylic acid (288): A mixture of Compound 287 (70.0 mg, 125.12 umol, 1 eq) and $LiOH.H_2O$ (26.25 mg, 625.58 umol, 5 eq) in THF (5 mL) and water (5 mL) was stirred for 4 h at 25° C. The reaction mixture was acidified with aq 1 M HCl until a pH of 5 was achieved. The mixture was then diluted with water (30 mL) and extracted with EtOAc (3x20 mL). The combined organic extracts were dried over anhyd $Na_2SO_4$ and concentrated to give Compound 288 as a white solid (70 mg, 86.49% yield) which was used directly in subsequent reactions without further purification. MS (D) for $C_{28}H_{21}F_2N_3O_5$. found 518.1 (MH+).

1-1-N'-[3-Fluoro-4-[6-methyl-7-(methylcarbamoyl)quinolin-4-yl]oxyphenyl]-1-N-(4-fluorophenyl)cyclopropane-1,1-dicarboxamide (289): Compound 289 was synthesized from Compound 288 in a manner analogous to the preparation of Compound 8 in Example 4. $^1H$ NMR (400 MHz, DMSO-$d_6$) δ 10.39 (s, 1H), 9.99 (s, 1H), 8.67 (d, 1H), 8.48 (d, 1H), 8.16 (s, 1H), 7.95 (s, 1H), 7.91 (d, 1H), 7.63 (dd, 2H), 7.56-7.49 (m, 1H), 7.47-7.41 (m, 1H), 7.15 (t, 2H), 6.59 (d, 1H), 2.82 (d, 3H), 2.54 (s, 3H), 1.47 (d, 4H); MS (D) for $C_{29}H_{24}F_2N_4O_4$. found 531.1 (MH+).

The following compounds were made from Compound 139 using the same 6 step process used to synthesize Compound 289 in Example 97:

1-N'-[2,5-Difluoro-4-[6-methyl-7-(methylcarbamoyl)quinolin-4-yl]oxyphenyl]-1-N-(4-fluorophenyl)cyclopropane-1,1-dicarboxamide (290): The 1,2-difluoro-4-nitrobenzene in Step 2 was replaced with 1,2,4-trifluoro-5-nitrobenzene. $^1H$ NMR (400 MHz, $CDCl_3$) δ 10.09 (br s, 1H), 8.59 (d, 1H), 8.28 (dd, 1H), 8.21 (s, 1H), 8.09 (s, 1H), 8.00 (s, 1H), 7.36-7.43 (m, 2H), 6.96-7.06 (m, 3H), 6.47 (d, 1H), 5.98 (d, 1H), 3.01 (d, 3H), 2.58 (s, 3H), 1.72-1.78 (m, 2H), 1.59-1.62 (m, 2H); MS (EI) for $C_{29}H_{23}F_3N_4O_4$. found 549.1 (MH+).

1-N'-[2-Chloro-5-fluoro-4-[6-methyl-7-(methylcarbamoyl)quinolin-4-yl]oxyphenyl]-1-N-(4-fluorophenyl)cyclopropane-1,1-dicarboxamide (291): The 1,2-difluoro-4-nitrobenzene in Step 2 was replaced with 1-chloro-4,5-difluoro-2-nitrobenzene. $^1H$ NMR (400 MHz, $CDCl_3$) δ 10.08 (s, 1H), 8.66 (d, 1H), 8.61 (s, 1H), 8.44 (d, 1H), 8.15 (s, 1H), 8.07 (s, 1H), 7.52-7.45 (m, 2H), 7.36 (d, 1H), 7.06 (t, 2H), 6.54 (d, 1H), 6.15-6.07 (m, 1H), 3.08 (d, 3H), 2.65 (s, 3H), 1.82-1.72 (m, 4H); MS (EI) for $C_{29}H_{23}ClF_2N_4O_4$. found 565.1 (MH+).

1-N-(4-Fluorophenyl)-1-N'-[2,3,5-trifluoro-4-[6-methyl-7-(methylcarbamoyl)quinolin-4-yl]oxyphenyl]cyclopropane-1,1-dicarboxamide (292): The 1,2-difluoro-4-nitrobenzene in Step 2 was replaced with 1,2,3,4-tetrafluoro-5-nitrobenzene. $^1$H NMR (400 MHz, DMSO-$d_6$) δ 11.33 (s, 1H), 9.77 (s, 1H), 8.71 (d, 1H), 8.54-8.48 (m, 1H), 8.18 (s, 1H), 8.08-8.02 (m, 1H), 7.98 (s, 1H), 7.63-7.56 (m, 2H), 7.23-7.14 (m, 2H), 6.89 (d, 1H), 2.83 (d, 3H), 2.55 (s, 3H), 1.72-1.65 (m, 2H), 1.62-1.57 (m, 2H); MS (EI) for $C_{29}H_{22}F_4N_4O_4$. found 567.1 (MH+).

Example 98: 1-N'-[4-(7-Carbamoyl-6-methylquinolin-4-yl)oxy-3-fluorophenyl]-1-N-(4-fluorophenyl) cyclopropane-1,1-dicarboxamide (293)

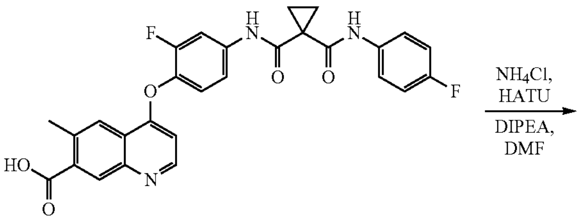

288

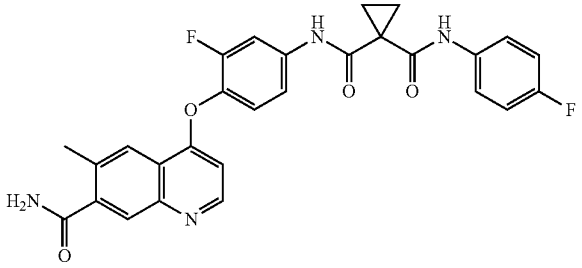

293

1-N'-[4-(7-Carbamoyl-6-methylquinolin-4-yl)oxy-3-fluorophenyl]-1-N-(4-fluorophenyl)cyclopropane-1,1-dicarboxamide (293): Compound 293 was synthesized from Compound 288 in a manner analogous to the preparation of Compound 7 in Example 3. $^1$H NMR (400 MHz, DMSO-$d_6$) δ 10.40 (s, 1H), 10.00 (s, 1H), 8.67 (d, 1H), 8.16 (s, 1H), 8.03 (s, 1H), 7.99 (s, 1H), 7.91 (d, 1H), 7.64 (dd, 2H), 7.58 (s, 1H), 7.56-7.51 (m, 1H), 7.47-7.41 (m, 1H), 7.15 (t, 2H), 6.59 (d, 1H), 2.58 (s, 3H), 1.47 (d, 4H); MS (EI) for $C_{28}H_{22}F_2N_4O_4$. found 517.1 (MH+).

The following compound was made using a similar process to that used to synthesize Compound 293 from Compound 288 in Example 98:

1-N'-[4-(7-Carbamoyl-6-methylquinolin-4-yl)oxy-2,5-difluorophenyl]-1-N-(4-fluorophenyl)cyclopropane-1,1-dicarboxamide (294): Compound 288 was replaced with 4-(2,5-difluoro-4-(1-((4-fluorophenyl)carbamoyl)cyclopropane-1-carboxamido)phenoxy)-6-methylquinoline-7-carboxylic acid, which was made using the same multistep procedure used to synthesize Compound 288 in Example 97, replacing the 1,2-difluoro-4-nitrobenzene in Step 2 with 1,2,4-trifluoro-5-nitrobenzene. $^1$H NMR (400 MHz, $CDCl_3$) δ 10.19 (br s, 1H), 8.67 (d, 1H), 8.36 (dd, 1H), 8.26 (br s, 1H), 8.19 (s, 2H), 7.47 (dd, 2H), 7.03-7.12 (m, 3H), 6.55 (d, 1H), 6.04 (br s, 1H), 5.78 (br s, 1H), 2.70 (s, 3H), 1.75-1.90 (m, 2H), 1.67-1.69 (m, 2H); MS (EI) for $C_{28}H21F_3N_4O_4$. found 535.1 (MH+).

Example 99: 1-N'-[3-Fluoro-4-[7-(2-hydroxyethoxycarbamoyl)quinolin-4-yl]oxyphenyl]-1-N-(4-fluorophenyl)cyclopropane-1,1-dicarboxamide (301)

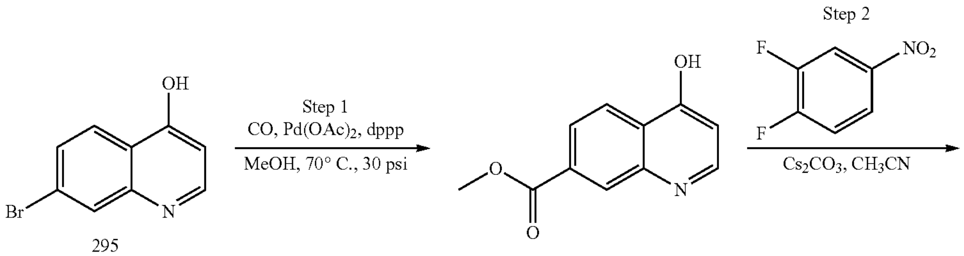

295

296

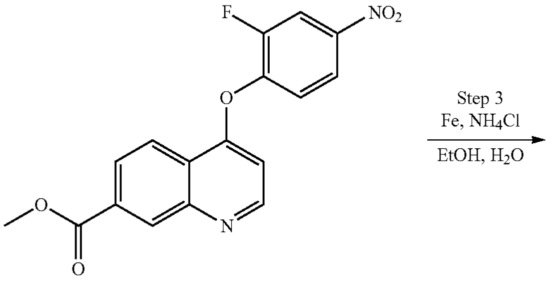

297

-continued

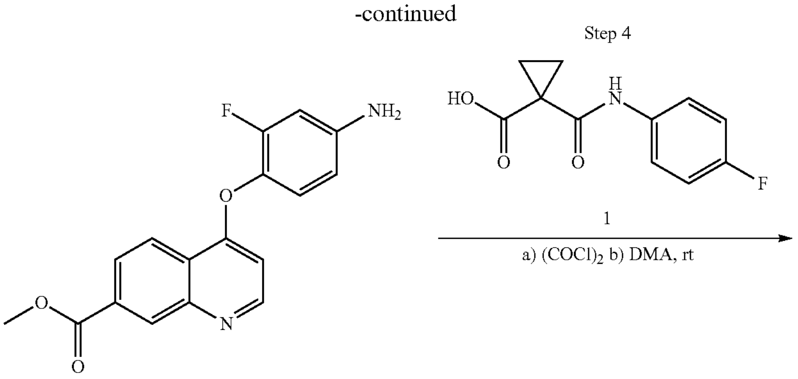

298

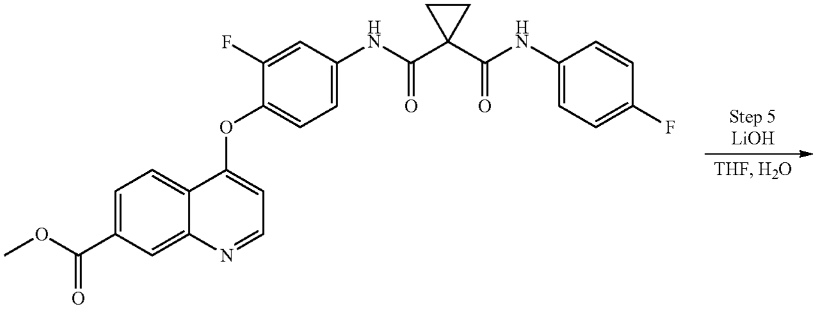

299

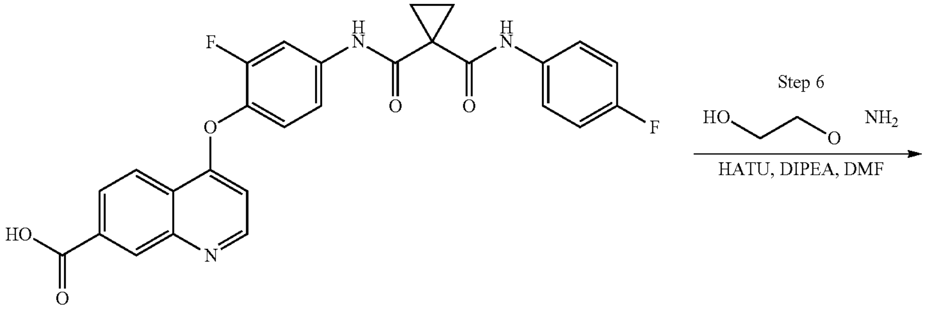

300

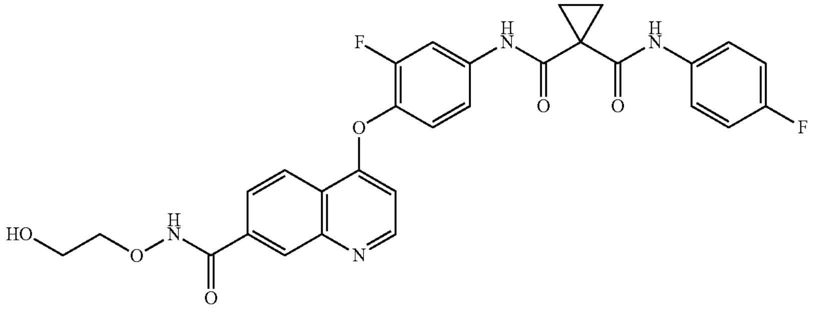

301

Methyl 4-hydroxyquinoline-7-carboxylate (296): To a round-bottom flask was added Compound 295 (5 g, 22.32 mmol, 1 eq) and TEA (22.58 g, 223.16 mmol, 31.06 mL, 10 eq) in MeOH (60 mL) and DMSO (20 mL). DPPP (1.84 g, 4.46 mmol, 0.2 eq) and $Pd(OAc)_2$ (1.00 g, 4.46 mmol, 0.2 eq) were then added. The flask was purged with carbon monoxide twice and left under 30 psi of carbon monoxide while heated at 70° C. for 12 h. MeOH (100 mL) was added, the resulting suspension was filtered through a pad of Celite, and the filter cake was washed with MeOH (3×50 mL). The combined filtrates were concentrated, and the resulting crude product was washed with water (50 mL), triturated with MeOH (15 mL), and filtered to give Compound 296 as a yellow solid (3.5 g, 77.19% yield). $^1H$ NMR (400 MHz, $CDCl_3$) δ 11.98 (br s, 1H), 8.23-8.15 (m, 2H), 8.01 (dd, 1H), 7.81 (br d, 1H), 6.11 (d, 1H), 3.90 (s, 3H); MS (EI) for $C_{11}H_9NO_3$. found 203.9 (MH+).

Methyl 4-(2-fluoro-4-nitrophenoxy)quinoline-7-carboxylate (297): Compound 297 was made from Compound 296 in a manner analogous to the way Compound 285 was made from Compound 284 in Example 97. $^1$H NMR (400 MHz, $CDCl_3$) δ 8.88-8.83 (m, 2H), 8.37 (d, 1H), 8.25-8.16 (m, 3H), 7.43 (t, 1H), 6.70 (d, 1H), 4.04 (s, 3H); MS (EI) for $C_{17}H_{11}FN_2O_5$. found 343.2 (MH+).

Methyl 4-(4-amino-2-fluorophenoxy)quinoline-7-carboxylate (298): Compound 298 was synthesized from Compound 297 using a method analogous to that used to convert Compound 218 to Compound 219 in Example 78. MS (EI) for $C_{17}H_{13}FN_2O_3$. found 312.9 (MH+).

Methyl 4-(2-fluoro-4-(1-((4-fluorophenyl)carbamoyl)cyclopropane-1-carboxamido)phenoxy)quinoline-7-carboxylate (299): Compound 1 (428.83 mg, 1.92 mmol, 3 eq) was suspended in anhyd DCM (10 mL) at 25° C. DMF (4.68 mg, 64.04 umol, 4.93 uL, 0.1 eq) was added with stirring under nitrogen, followed by $(COCl)_2$ (290.00 mg, 2.28 mmol, 0.2 mL, 3.57 eq). The mixture was stirred at 25° C. for 30 min. Toluene (5.0 mL) was added, and the solvent was removed under reduced pressure. The resulting acyl chloride product was dissolved in anhyd THF (1.0 mL). A solution of Compound 298 (200 mg, 640.42 umol, 1 eq) in DMA (6 mL) was added the above prepared acyl chloride in THF with stirring under nitrogen. The reaction was stirred at 25° C. for 0.5 h. The reaction mixture was poured into aq saturated $NaHCO_3$ (100 mL) and extracted with DCM (3×50 mL). The combined organic extracts were washed with aq saturated $NaHCO_3$ (15 mL) and then aq saturated NaCl (15 mL), dried with anhyd $Na_2SO_4$, and concentrated in vacuum to give Compound 299 as a yellow solid (270 mg, 81.47% yield) which was used in subsequent reactions without further purification. MS (EI) for $C_{28}H_{21}F_2N_3O_5$. found 518.1 (MH+).

4-(2-Fluoro-4-(1-((4-fluorophenyl)carbamoyl)cyclopropane-1-carboxamido)-phenoxy)quinoline-7-carboxylic acid (300): Compound 300 was made from Compound 299 in a manner analogous to the way Compound 288 was made from Compound 287 in Example 97. MS (EI) for $C_{27}H_{19}F_2N_3O_5$. found 504.1 (MH+).

1-N'-[3-Fluoro-4-[7-(2-hydroxyethoxycarbamoyl)quinolin-4-yl]oxyphenyl]-1-N-(4-fluorophenyl)cyclopropane-1,1-dicarboxamide (301): To a solution of Compound 300 (80 mg, 158.90 umol, 1 eq) in DMF (3 mL) was added HATU (72.50 mg, 190.68 umol, 1.2 eq) and DIEA (61.61 mg, 476.71 umol, 83.03 uL, 3 eq), and the resulting mixture was stirred at 25° C. for 30 min. 2-aminooxyethanol (14.70 mg, 190.68 umol, 1.2 eq) was added, and the reaction mixture was stirred at 25° C. for another 2 h. The reaction mixture was poured into aq saturated $NH_4Cl$ (50 mL) and extracted with DCM (3×30 mL). The combined organic extracts were concentrated under vacuum, and the resulting residue was purified by prep-HPLC (Column: Boston Prime C18 150*30 mm*5 um, gradient: 43-63% of acetonitrile in water (0.05% $NH_3H_2O$), flow rate: 25 mL/min) to give Compound 301 as a white solid (46.8 mg, 52.36% yield). $^1$H NMR (400 MHz, DMSO-$d_6$) δ 12.09 (br s, 1H), 10.41 (br s, 1H), 10.01 (br s, 1H), 8.78 (d, 1H), 8.45-8.40 (m, 2H), 8.01 (dd, 1H), 7.92 (dd, 1H), 7.68-7.60 (m, 2H), 7.56-7.51 (m, 1H), 7.50-7.44 (m, 1H), 7.20-7.11 (m, 2H), 6.68 (d, 1H), 4.80 (br s, 1H), 4.00 (t, 2H), 3.66 (t, 2H), 1.51-1.43 (m, 4H); MS (EI) for $C_{29}H_{24}F_2N406$. found 563.1 (MH+).

The following compounds were made from Compound 295 using the same 6 step process used to synthesize Compound 301 in Example 99:

1-N'-[2,5-Difluoro-4-[7-(2-hydroxyethoxycarbamoyl)quinolin-4-yl]oxyphenyl]-1-N-(4-fluorophenyl)cyclopropane-1,1-dicarboxamide (302): The 1,2-difluoro-4-nitrobenzene in Step 2 was replaced with 1,2,4-trifluoro-5-nitrobenzene. $^1$H NMR (400 MHz, DMSO-$d_6$) δ 12.13 (br s, 1H), 11.17 (br s, 1H), 9.78 (br s, 1H), 8.81 (d, 1H), 8.46 (s, 1H), 8.40 (m, 1H), 8.19 (m, 1H), 8.04 (d, 1H), 7.73 (m, 1H), 7.61 (dd, 2H), 7.19 (t, 2H), 6.83 (d, 1H), 4.81 (m, 1H), 4.00 (m, 2H), 3.68 (m, 2H), 1.69 (m, 2H), 1.61 (m, 2H); MS (EI) for $C_{29}H_{23}F_3N406$. found 581.1 (MH+).

BIOLOGICAL EXAMPLES

Example A: Kinase Assays

Kinase activity and compound inhibition were investigated using the $^{33}$P-Phosphoryl transfer radiometric kinase assay, performed using the KinaseProfiler™ service of Eurofins Pharma Discovery Services UK Limited. Dose-response experiments were performed using nine compound concentrations in a 96-well microtiter plate. For each assay, all compounds were prepared to a 50× final assay concentration (50 μM) in 100% DMSO, then diluted in a half-log series, with the final top concentration at 1 μM. This working stock of the compound was added to the assay well as the first component in the reaction, followed by the remaining components as detailed in the following assay protocols below. The positive control wells (100% kinase activity) contain all components of the reaction including 2% DMSO (control for solvent effects), except the compound of interest. Blank wells contain all components of the reaction, with the reference inhibitor, staurosporine. This reference compound was used to abolish kinase activity and generated the 0% kinase activity base-line. $IC_{50}$ values were calculated by nonlinear regression analysis using the sigmoidal dose-response (variable slope) curve fit on XLFit version 5.3 (ID Business Solutions).

Example B: Human AXL Kinase Assay

Human Axl (residues H473-A894 with Q764R, 161 nM) was incubated with 8 mM MOPS pH 7.0, 0.2 mM EDTA, 250 μM KKSRGDYMTMQIG (SEO ID NO. 43) 10 mM magnesium acetate and 10 μM [γ-33P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 μL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example C: Human KDR Kinase Assay

Human KDR (residues K790-V1356, 55 nM) was incubated with 8 mM MOPS pH 7.0, 0.2 mM EDTA, 0.33 mg/mL myelin basic protein, 10 mM magnesium acetate, and 10 μM [γ-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 μL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example D: Human Mer Kinase Assay

Human Mer (residues R557-E882 with H628Q and R794A, 0.7 nM) was incubated with 8 mM MOPS pH 7.0, 0.2 mM EDTA, 30 mM NaCl, 250 μM GGMEDIYFEFMGGKKK (SEO ID NO. 44). 10 mM magnesium acetate, and 10 μM [γ-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 μL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example E: Human Met Kinase Assay

Human Met (residues R974-S1390 with A1209G and V1290L, 3.4 nM) was incubated with 8 mM MOPS pH 7.0, 0.2 mM EDTA, 250 μM KKKGQEEEYVFIE (SEO ID NO. 45), 1 mM sodium orthovanadate, 5 mM sodium-6-glycerophosphate, 10 mM magnesium acetate, and 10 μM [γ-33P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 sL was then spotted onto a P30 filtermat and washed four times for 4 minutes in 0.425% phosphoric acid and once in methanol prior to drying and scintillation counting. Incorporated 33P was measured using the Wallac Microbeta scintillation counter (Perkin Elmer).

Activity data obtained for the Example compounds using the kinase assays in Examples A, B, D and E is provided in Table 2 (A: $IC_{50}$≤10 nM; B: 10 nM<IC50≤100 nM; C: 100 nM<$IC_{50}$≤1000 nM; D: $IC_{50}$>1000 nM).

TABLE 2

Activity data for selected compounds of the invention

| Compound No. | Name | Axl $IC_{50}$ (nM) | Mer $IC_{50}$ (nM) | c-Met $IC_{50}$ (nM) |
|---|---|---|---|---|
| 5 | methyl 4-[4-[[1-[(4-fluorophenyl)carbamoyl]cyclopropanecarbonyl]amino]phenoxy]-7-methoxyquinoline-6-carboxylate | B | A | A |
| 6 | 4-[4-[[1-[(4-fluorophenyl)carbamoyl]cyclopropanecarbonyl]amino]phenoxy]-7-methoxyquinoline-6-carboxylic acid | C | B | A |
| 7 | 1-N-[4-(6-carbamoyl-7-methoxyquinolin-4-yl)oxyphenyl]-1-N'-(4-fluorophenyl)cyclopropane-1,1-dicarboxamide | A | A | A |
| 8 | 1-N'-(4-fluorophenyl)-1-N-[4-[7-methoxy-6-(methylcarbamoyl)quinolin-4-yl]oxyphenyl]cyclopropane-1,1-dicarboxamide | A | A | A |
| 10 | 1-N-[4-[6-[2-(dimethylamino)ethylcarbamoyl]-7-methoxyquinolin-4-yl]oxyphenyl]-1-N'-(4-fluorophenyl)cyclopropane-1,1-dicarboxamide | B | A | A |
| 11 | 1-N'-(4-fluorophenyl)-1-N-[4-[7-methoxy-6-(2-piperidin-1-ylethylcarbamoyl)quinolin-4-yl]oxyphenyl]cyclopropane-1,1-dicarboxamide | A | A | A |
| 12 | 1-N'-(4-fluorophenyl)-1-N-[4-[7-methoxy-6-(2-morpholin-4-ylethylcarbamoyl)quinolin-4-yl]oxyphenyl]cyclopropane-1,1-dicarboxamide | A | A | A |
| 13 | 1-N'-(4-fluorophenyl)-1-N-[4-[7-methoxy-6-(oxetan-3-ylcarbamoyl)quinolin-4-yl]oxyphenyl]cyclopropane-1,1-dicarboxamide | B | A | A |
| 14 | 1-N'-(4-fluorophenyl)-1-N-[4-[7-methoxy-6-[(1-methylazetidin-3-yl)carbamoyl]quinolin-4-yl]oxyphenyl]cyclopropane-1,1-dicarboxamide | B | A | A |
| 15 | 1-N-[4-[6-(azetidine-1-carbonyl)-7-methoxyquinolin-4-yl]oxyphenyl]-1-N'-(4-fluorophenyl)cyclopropane-1,1-dicarboxamide | B | A | B |
| 16 | 1-N'-(4-fluorophenyl)-1-N-[4-[6-(3-hydroxyazetidine-1-carbonyl)-7-methoxyquinolin-4-yl]oxyphenyl]cyclopropane-1,1-dicarboxamide | B | A | A |
| 21 | 1-N'-(4-fluorophenyl)-1-N-[4-[7-methoxy-6-[[(2R)-pyrrolidin-2-yl]methylcarbamoyl]quinolin-4-yl]oxyphenyl]cyclopropane-1,1-dicarboxamide | A | A | A |
| 22 | 1-N'-(4-fluorophenyl)-1-N-[4-[7-methoxy-6-[[(2S)-pyrrolidin-2-yl]methylcarbamoyl]quinolin-4-yl]oxyphenyl]cyclopropane-1,1-dicarboxamide | A | A | A |
| 37 | 1-N-[4-(6-cyano-7-methoxyquinolin-4-yl)oxyphenyl]-1-N'-(4-fluorophenyl)cyclopropane-1,1-dicarboxamide | B | A | B |
| 45 | 1-N'-(4-fluorophenyl)-1-N-[4-[7-methoxy-6-(1,3-oxazol-2-yl)quinolin-4-yl]oxyphenyl]cyclopropane-1,1-dicarboxamide | A | A | A |
| 58 | 1-N-[4-(6-carbamoylquinolin-4-yl)oxyphenyl]-1-N'-(4-fluorophenyl)cyclopropane-1,1-dicarboxamide | B | B | B |
| 59 | 1-N'-(4-fluorophenyl)-1-N-[4-[6-(methylcarbamoyl)quinolin-4-yl]oxyphenyl]cyclopropane-1,1-dicarboxamide | B | B | B |
| 60 | 1-N'-(4-fluorophenyl)-1-N-[4-[6-[(1-methylazetidin-3-yl)carbamoyl]quinolin-4-yl]oxyphenyl]cyclopropane-1,1-dicarboxamide | B | B | B |

TABLE 2-continued

Activity data for selected compounds of the invention

| Compound No. | Name | Axl $IC_{50}$ (nM) | Mer $IC_{50}$ (nM) | c-Met $IC_{50}$ (nM) |
|---|---|---|---|---|
| 67 | 1-N-[4-(6-carbamoyl-7-fluoroquinolin-4-yl)oxyphenyl]-1-N'-(4-fluorophenyl)cyclopropane-1,1-dicarboxamide | B | B | B |
| 68 | 1-N-[4-(6-carbamoyl-7-chloroquinolin-4-yl)oxyphenyl]-1-N'-(4-fluorophenyl)cyclopropane-1,1-dicarboxamide | C | B | B |
| 69 | 1-N-[4-(7-bromo-6-carbamoylquinolin-4-yl)oxyphenyl]-1-N'-(4-fluorophenyl)cyclopropane-1,1-dicarboxamide | C | B | B |
| 98 | 1-N-[4-[6-carbamoyl-7-(3-morpholin-4-ylpropoxy)quinolin-4-yl]oxyphenyl]-1-N'-(4-fluorophenyl)cyclopropane-1,1-dicarboxamide | A | A | A |
| 103 | 1-N-[4-[6-carbamoyl-7-(2-methoxyethoxy)quinolin-4-yl]oxyphenyl]-1-N'-(4-fluorophenyl)cyclopropane-1,1-dicarboxamide | B | A | A |
| 128 | methyl 4-[2-chloro-4-[[1-[(4-fluorophenyl)carbamoyl]cyclopropanecarbonyl]amino]phenoxy]-7-methoxyquinoline-6-carboxylate | A | A | A |
| 130 | 4-[2-chloro-4-[[1-[(4-fluorophenyl)carbamoyl]cyclopropanecarbonyl]amino]phenoxy]-7-methoxyquinoline-6-carboxylic acid | B | B | B |
| 132 | 1-N'-[4-(6-carbamoyl-7-methoxyquinolin-4-yl)oxy-3-chlorophenyl]-1-N-(4-fluorophenyl)cyclopropane-1,1-dicarboxamide | A | A | A |
| 134 | 1-N'-[3-chloro-4-[7-methoxy-6-(methylcarbamoyl)quinolin-4-yl]oxyphenyl]-1-N-(4-fluorophenyl)cyclopropane-1,1-dicarboxamide | A | A | A |
| 129 | methyl 4-[2-fluoro-4-[[1-[(4-fluorophenyl)carbamoyl]cyclopropanecarbonyl]amino]phenoxy]-7-methoxyquinoline-6-carboxylate | A | A | A |
| 131 | 4-[2-fluoro-4-[[1-[(4-fluorophenyl)carbamoyl]cyclopropanecarbonyl]amino]phenoxy]-7-methoxyquinoline-6-carboxylic acid | B | B | A |
| 133 | 1-N'-[4-(6-carbamoyl-7-methoxyquinolin-4-yl)oxy-3-fluorophenyl]-1-N-(4-fluorophenyl)cyclopropane-1,1-dicarboxamide | A | A | A |
| 135 | 1-N'-[3-fluoro-4-[7-methoxy-6-(methylcarbamoyl)quinolin-4-yl]oxyphenyl]-1-N-(4-fluorophenyl)cyclopropane-1,1-dicarboxamide | A | A | A |
| 140 | methyl 4-[4-[[1-[(4-fluorophenyl)carbamoyl]cyclopropanecarbonyl]amino]phenoxy]-6-methylquinoline-7-carboxylate | B | A | B |
| 141 | 4-[4-[[1-[(4-fluorophenyl)carbamoyl]cyclopropanecarbonyl]amino]phenoxy]-6-methylquinoline-7-carboxylic acid | D | D | D |
| 142 | 1-N-[4-(7-carbamoyl-6-methylquinolin-4-yl)oxyphenyl]-1-N'-(4-fluorophenyl)cyclopropane-1,1-dicarboxamide | A | A | A |
| 143 | 1-N'-(4-fluorophenyl)-1-N-[4-[6-methyl-7-(methylcarbamoyl)quinolin-4-yl]oxyphenyl]cyclopropane-1,1-dicarboxamide | B | A | A |
| 150 | methyl 4-[4-[[1-[(4-fluorophenyl)carbamoyl]cyclopropanecarbonyl]amino]phenoxy]-6-methoxyquinoline-7-carboxylate | B | A | A |
| 151 | 4-[4-[[1-[(4-fluorophenyl)carbamoyl]cyclopropanecarbonyl]amino]phenoxy]-6-methoxyquinoline-7-carboxylic acid | C | B | B |
| 152 | 1-N-[4-(7-carbamoyl-6-methoxyquinolin-4-yl)oxyphenyl]-1-N'-(4-fluorophenyl)cyclopropane-1,1-dicarboxamide | B | A | A |
| 153 | 1-N'-(4-fluorophenyl)-1-N-[4-[6-methoxy-7-(methylcarbamoyl)quinolin-4-yl]oxyphenyl]cyclopropane-1,1-dicarboxamide | B | A | B |
| 162 | methyl 4-[4-[[1-[(4-fluorophenyl)carbamoyl]cyclopropanecarbonyl]amino]phenoxy]quinoline-7-carboxylate | B | A | B |
| 163 | 4-[4-[[1-[(4-fluorophenyl)carbamoyl]cyclopropanecarbonyl]amino]phenoxy]quinoline-7-carboxylic acid | C | C | B |
| 164 | 1-N-[4-(7-carbamoylquinolin-4-yl)oxyphenyl]-1-N'-(4-fluorophenyl)cyclopropane-1,1-dicarboxamide | A | A | A |
| 165 | 1-N'-(4-fluorophenyl)-1-N-[4-[7-(methylcarbamoyl)quinolin-4-yl]oxyphenyl]cyclopropane-1,1-dicarboxamide | A | A | A |
| 175 | 1-N-[4-[6-(3-cyano-2-fluorophenyl)-7-methoxyquinolin-4-yl]oxyphenyl]-1-N'-(4-fluorophenyl)cyclopropane-1,1-dicarboxamide | B | A | B |

TABLE 2-continued

Activity data for selected compounds of the invention

| Compound No. | Name | Axl $IC_{50}$ (nM) | Mer $IC_{50}$ (nM) | c-Met $IC_{50}$ (nM) |
|---|---|---|---|---|
| 176 | 1-N'-(4-fluorophenyl)-1-N-[4-(7-methoxy-6-pyridin-2-ylquinolin-4-yl)oxyphenyl]cyclopropane-1,1-dicarboxamide | A | A | B |
| 180 | 1-N'-(4-fluorophenyl)-1-N-[4-[7-methoxy-6-(5-methylfuran-2-yl)quinolin-4-yl]oxyphenyl]cyclopropane-1,1-dicarboxamide | B | A | B |
| 181 | tert-butyl 2-[4-[4-[[1-[(4-fluorophenyl)carbamoyl]cyclopropanecarbonyl]amino]phenoxy]-7-methoxyquinolin-6-yl]pyrrole-1-carboxylate | C | B | B |
| 182 | 1-N'-(4-fluorophenyl)-1-N-[4-[7-methoxy-6-(1-methylpyrazol-4-yl)quinolin-4-yl]oxyphenyl]cyclopropane-1,1-dicarboxamide | B | A | A |
| 183 | 1-N'-(4-fluorophenyl)-1-N-[4-[7-methoxy-6-(1,2-oxazol-4-yl)quinolin-4-yl]oxyphenyl]cyclopropane-1,1-dicarboxamide | B | A | A |
| 184 | 1-N-[4-[6-(3,5-dimethyl-1,2-oxazol-4-yl)-7-methoxyquinolin-4-yl]oxyphenyl]-1-N'-(4-fluorophenyl)cyclopropane-1,1-dicarboxamide | B | A | B |
| 185 | 1-N'-(4-fluorophenyl)-1-N-[4-[7-methoxy-6-(1H-pyrazol-5-yl)quinolin-4-yl]oxyphenyl]cyclopropane-1,1-dicarboxamide | B | A | A |
| 186 | 1-N'-(4-fluorophenyl)-1-N-[4-[7-methoxy-6-(1H-pyrazol-4-yl)quinolin-4-yl]oxyphenyl]cyclopropane-1,1-dicarboxamide | B | A | A |
| 187 | 1-N-[4-(6-cyclopropyl-7-methoxyquinolin-4-yl)oxyphenyl]-1-N'-(4-fluorophenyl)cyclopropane-1,1-dicarboxamide | A | A | B |
| 188 | 1-N'-(4-fluorophenyl)-1-N-[4-[7-methoxy-6-(1H-pyrrol-2-yl)quinolin-4-yl] oxyphenyl]cyclopropane-1,1-dicarboxamide | B | A | A |
| 195 | tert-butyl 3-[4-[4-[[1-[(4-fluorophenyl)carbamoyl]cyclopropanecarbonyl]amino]phenoxy]-7-methoxyquinolin-6-yl]-3-hydroxyazetidine-1-carboxylate | B | A | B |
| 196 | 1-N'-(4-fluorophenyl)-1-N-[4-[6-(3-hydroxyoxetan-3-yl)-7-methoxyquinolin-4-yl]oxyphenyl]cyclopropane-1,1-dicarboxamide | A | A | A |
| 197 | 1-N'-(4-fluorophenyl)-1-N-[4-[6-(3-hydroxyazetidin-3-yl)-7-methoxyquinolin-4-yl]oxyphenyl]cyclopropane-1,1-dicarboxamide | B | A | A |
| 198 | 1-N-[4-[6-(azetidin-1-yl)-7-methoxyquinolin-4-yl]oxyphenyl]-1-N'-(4-fluorophenyl)cyclopropane-1,1-dicarboxamide | B | A | B |
| 199 | 1-N'-(4-fluorophenyl)-1-N-[4-[6-(3-hydroxyazetidin-1-yl)-7-methoxyquinolin-4-yl]oxyphenyl]cyclopropane-1,1-dicarboxamide | A | A | A |
| 200 | 1-N-[4-[6-(3,3-difluoroazetidin-1-yl)-7-methoxyquinolin-4-yl]oxyphenyl]-1-N'-(4-fluorophenyl)cyclopropane-1,1-dicarboxamide | B | A | B |
| 201 | 1-N'-(4-fluorophenyl)-1-N-[4-(7-methoxy-6-pyridin-3-ylquinolin-4-yl)oxyphenyl]cyclopropane-1,1-dicarboxamide | A | A | A |
| 202 | 1-N'-(4-fluorophenyl)-1-N-[4-(7-methoxy-6-pyridin-4-ylquinolin-4-yl)oxyphenyl]cyclopropane-1,1-dicarboxamide | B | A | A |
| 206 | 1-N'-(4-fluorophenyl)-1-N-[4-(7-methoxy-6-sulfamoylquinolin-4-yl)oxyphenyl]cyclopropane-1,1-dicarboxamide | A | A | A |
| 210 | 1-N'-(4-fluorophenyl)-1-N-[4-(7-methoxy-6-methylsulfonylquinolin-4-yl)oxyphenyl]cyclopropane-1,1-dicarboxamide | A | A | A |
| 220 | 1-N'-(4-fluorophenyl)-1-N-[4-[7-methoxy-6-(1,3,4-oxadiazol-2-yl)quinolin-4-yl]oxyphenyl]cyclopropane-1,1-dicarboxamide | A | A | A |

Example F: AXL Autophosphorylation ELISA in A-172 Cells

A-172 glioblastoma cells (ATCC #CRL-1620) were seeded at $2.5\times10^5$ cells/well onto 24-well plates (Greiner #662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061) and 1% Penicillin Streptomycin (Thermo Fisher #15140-122). A-172 cells were incubated at 37° C., 5% $CO_2$ for 24 h and then starved for 24 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 1 μg/mL recombinant human Gas6 (R&D Systems #885-GSB-500) for 15 min, washed with cold PBS and immediately lysed with 150 μL of cold 1× lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 μL/well added into the human phospho-AXL DuoSet IC ELISA (R&D Systems #DYC2228-2). Assay was performed according to manufacturer's instructions and sample phospho-AXL concentrations were extrapolated using human phospho-AXL control (R&D Systems #841645) as a standard. Positive control wells (100% activity) contained Gash-stimulated, DMSO-treated cell lysates. Negative control wells (0% activity) contained Gash-stimulated, reference inhibitor-treated cell lysates. IC50 values were calculated by nonlinear regression analysis using a 4-parameter logistic curve fit in ActivityBase XE (IDBS).

Example G: Met Autophosphorylation ELISA in PC-3 Cells

PC-3 prostate cancer cells (ATCC #CRL-1435) were seeded at $4\times10^4$ cells/well onto 24-well plates (Greiner #662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). PC-3 cells were incubated at 37° C., 5% $CO_2$ for 24 h and then starved for 3 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human HGF (R&D Systems #294-HG-250) for 10 min, washed with cold PBS and immediately lysed with 130 μL of cold 1× lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 100 μL/well added into the PathScan phospho-Met (panTyr) Sandwich ELISA (Cell Signaling Technology #7333). Assay was performed according to manufacturer's instructions. Positive control wells (100% activity) contained HGF-stimulated, DMSO-treated cell lysates. Negative control wells (0% activity) contained HGF-stimulated, reference inhibitor-treated cell lysates. IC50 values were calculated by nonlinear regression analysis using a 4-parameter logistic curve fit in ActivityBase XE (IDBS).

Example H: KDR Autophosphorylation ELISA in HUVEC Cells

Human umbilical vein endothelial cells or HUVEC (Lonza #C2519A) were seeded at $2\times10^4$ cells/well onto 96-well plates (Corning #3904), in EGM-2 growth medium (Lonza #CC-3162) containing 1% Penicillin Streptomycin (Thermo Fisher #15140-122). HUVEC cells were incubated at 37° C., 5% $CO_2$ for 24 h and then starved for 24 h in serum-free EBM-2 basal medium (Lonza #CC-3156) containing 1% Penicillin Streptomycin. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human VEGF165 (R&D Systems #293-VE-500) for 5 min, washed with cold PBS, and immediately lysed with 130 μL of cold 1× lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 μL/well added into the human phospho-KDR DuoSet IC ELISA (R&D Systems #DYC1766-2). Assay was performed according to manufacturer's instructions and sample phospho-KDR concentrations were extrapolated using human phospho-KDR control (R&D Systems #841421) as a standard. Positive control wells (100% activity) contained VEGF165-stimulated, DMSO-treated cell lysates. Negative control wells (0% activity) contained non-stimulated cell lysates. IC50 values were calculated by nonlinear regression analysis using a 4-parameter logistic curve fit in ActivityBase XE (IDBS).

Example I: Mer Autophosphorylation ELISA in Transient Transfected 293A Cells 293A cells (Thermo Fisher #R70507) were seeded at $1.5\times10^6$ cells/well onto 100 mm dish (Greiner #664169), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). 293A cells were incubated at 37° C., 5% $CO_2$ for 24 h and then transfected with 6 μg MERTK DNA (Genecopoeia #EX-Z8208-M02) using TransIT LT1 transfection reagent (Mirus-Bio #MIR2305). After 24 h incubation, the transfected 293A cells were seeded at $1\times10^5$ cells/well onto 96-well plates (Corning #3904) in DMEM growth medium overnight. Test compounds were serially diluted to produce an 8-point dose curve in fresh serum-free medium to a final concentration of 0.3% DMSO (vehicle) and added to the cells and incubated for 1 h. Cells were then immediately lysed with 150 μL of cold 1× lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 50 μL/well added into the human phospho-Mer DuoSet IC ELISA (R&D Systems #DYC2579-2). Assay was performed according to manufacturer's instructions and sample phospho-Mer concentrations were extrapolated using human phospho-Mer control (R&D Systems #841793) as a standard. Positive control wells (100% activity) contained DMSO-treated cell lysates. Negative control wells (0% activity) contained reference inhibitor-treated cell lysates. $IC_{50}$ values were calculated by nonlinear regression analysis using a 4-parameter logistic curve fit in ActivityBase XE (IDBS).

Compounds of the present disclosure, as exemplified herein, showed $IC_{50}$ values in the following ranges: A: $IC_{50}\leq10$ nM; B: 10 nM$<IC_{50}\leq100$ nM; C: 100 nM$<IC_{50}\leq300$ nM; D: $IC_{50}>300$ nM. "NT" means not tested Activity data obtained for the Example compounds using cell based kinase assays in Examples F, G, H and I is provided in Table 3.

TABLE 3

Cellular activity data for selected compounds of the invention

| Compound No. | Axl $IC_{50}$ (nM) | Mer $IC_{50}$ (nM) | c-Met $IC_{50}$ (nM) | KDR $IC_{50}$ (nM) |
|---|---|---|---|---|
| 5 | B | NT | B | A |
| 6 | NT | NT | D | D |

TABLE 3-continued

Cellular activity data for selected compounds of the invention

| Compound No. | Axl $IC_{50}$ (nM) | Mer $IC_{50}$ (nM) | c-Met $IC_{50}$ (nM) | KDR $IC_{50}$ (nM) |
|---|---|---|---|---|
| 7 | A | A | A | A |
| 8 | A | A | B | A |
| 9 | A | A | B | A |
| 10 | NT | NT | NT | NT |
| 11 | A | NT | B | A |
| 12 | A | NT | B | A |
| 13 | B | NT | B | A |
| 14 | A | NT | A | B |
| 15 | B | NT | C | D |
| 16 | B | NT | C | C |
| 17 | B | B | B | A |
| 20 | B | B | B | B |
| 21 | A | NT | B | B |
| 22 | A | NT | B | B |
| 26 | B | B | B | A |
| 27 | A | B | B | A |
| 30 | C | D | C | B |
| 31 | B | D | C | B |
| 32 | A | A | B | A |
| 34 | A | A | B | A |
| 35 | C | NT | C | C |
| 36 | C | NT | C | D |
| 37 | B | NT | B | B |
| 45 | A | A | A | A |
| 50 | A | A | A | A |
| 51 | B | C | B | C |
| 58 | B | NT | C | C |
| 59 | C | NT | C | C |
| 60 | C | NT | C | D |
| 67 | C | NT | C | C |
| 68 | NT | NT | NT | NT |
| 69 | NT | NT | NT | NT |
| 70 | B | NT | B | B |
| 71 | B | B | B | B |
| 81 | D | NT | D | D |
| 82 | B | NT | B | B |
| 83 | B | NT | B | B |
| 84 | A | NT | B | A |
| 87 | C | NT | C | D |
| 88 | C | NT | C | D |
| 89 | D | NT | D | D |
| 90 | B | NT | B | B |
| 92 | B | NT | C | C |
| 96 | B | B | C | C |
| 98 | A | B | A | A |
| 103 | A | NT | B | A |
| 106 | A | NT | B | A |
| 110 | A | B | A | A |
| 115 | A | B | B | A |
| 116 | A | B | B | A |
| 125 | A | A | B | B |
| 128 | B | NT | B | A |
| 129 | A | NT | B | A |
| 130 | D | NT | D | D |
| 131 | D | NT | D | D |
| 132 | A | A | A | A |
| 133 | A | A | A | A |
| 134 | A | A | A | A |
| 135 | A | A | A | A |
| 140 | B | NT | B | B |
| 141 | NT | NT | NT | NT |
| 142 | B | B | B | B |
| 143 | B | NT | B | C |
| 150 | B | NT | B | A |
| 151 | NT | NT | NT | D |
| 152 | B | NT | C | C |
| 153 | B | NT | C | B |
| 162 | D | NT | C | B |
| 163 | NT | NT | NT | NT |
| 164 | A | B | A | B |
| 165 | B | B | A | A |
| 166 | B | NT | B | C |
| 167 | C | NT | C | C |
| 169 | C | D | C | C |
| 170 | C | NT | D | C |

TABLE 3-continued

Cellular activity data for selected compounds of the invention

| Compound No. | Axl $IC_{50}$ (nM) | Mer $IC_{50}$ (nM) | c-Met $IC_{50}$ (nM) | KDR $IC_{50}$ (nM) |
|---|---|---|---|---|
| 175 | B | NT | B | C |
| 176 | B | NT | B | B |
| 177 | A | NT | B | A |
| 180 | A | NT | B | B |
| 181 | NT | NT | NT | NT |
| 182 | A | A | B | A |
| 183 | B | NT | B | B |
| 184 | C | NT | B | D |
| 185 | B | A | B | A |
| 186 | A | NT | B | A |
| 187 | B | NT | B | B |
| 188 | A | NT | B | B |
| 191 | A | A | B | A |
| 192 | A | A | B | A |
| 193 | B | NT | C | C |
| 195 | C | NT | B | B |
| 196 | B | NT | B | B |
| 197 | C | NT | C | D |
| 198 | B | NT | B | B |
| 199 | A | NT | A | A |
| 200 | B | NT | B | B |
| 201 | B | NT | B | B |
| 202 | B | NT | B | B |
| 204 | B | NT | B | B |
| 206 | A | B | A | A |
| 207 | B | B | B | B |
| 208 | B | B | B | B |
| 209 | C | NT | C | B |
| 210 | B | NT | B | A |
| 213 | B | B | B | C |
| 214 | B | B | B | B |
| 220 | A | A | B | A |
| 221 | B | NT | C | C |
| 254 | C | NT | C | D |
| 255 | D | NT | C | D |
| 256 | C | NT | C | C |
| 262 | D | NT | D | D |
| 263 | D | NT | D | D |
| 264 | B | B | B | B |
| 265 | A | B | B | B |
| 267 | B | NT | C | C |
| 268 | A | B | B | A |
| 269 | B | B | C | B |
| 270 | B | B | B | B |
| 273 | C | NT | C | B |
| 274 | B | A | B | A |
| 278 | C | C | C | C |
| 279 | A | A | B | A |
| 280 | A | A | B | A |
| 281 | C | NT | B | C |
| 282 | C | NT | C | D |
| 283 | B | B | B | B |
| 289 | B | B | B | B |
| 290 | A | A | A | C |
| 291 | B | B | B | D |
| 292 | B | B | B | D |
| 293 | B | B | B | B |
| 294 | A | A | A | B |
| 301 | B | B | B | B |
| 302 | B | C | A | C |

Example J: Pharmacokinetic Studies

Pharmacokinetic properties of select compounds were assessed in male Sprague-Dawley rats.

The non-GLP study was designed to investigate the pharmacokinetics of chosen compounds in plasma following an intravenous or oral dose administration to male Sprague Dawley rats.

Two groups of male Sprague-Dawley rats (three animals per group) received either an intravenous or oral (gavage) dose of compound at target dose levels of 3 mg/kg. Animals were observed for any clinically relevant abnormalities during dosing and at each sample collection period.

Animals in the PO group were fasted overnight prior to dose administration. Food was returned following the collection of the 4-hour blood sample. Water was not withheld.

Immediately prior to dosing, the body weight of each animal was recorded. Doses (rounded to the nearest 0.001 mL) were calculated based on the pretreatment body weight (kg) and a dose volume of 2.5 mL/kg for intravenous administration and 5 mL/kg for oral administration. Intravenous formulations were administered via a jugular vein cannula. Immediately after dosing, the cannula was flushed with saline and the line was tied off. The oral dose was administered via a ball-tipped feeding needle. Dosing syringe volumes for administration were second-person verified prior to dosing and that volume along with the results for the concentration verification analysis were used to calculate the actual dose administered. Dosing syringes were weighed immediately prior to and immediately after dosing each animal as a gravimetric check.

Serial blood samples (approximately 200 μL per sample) were collected from each animal at 0.083 (IV dosing only), 0.25, 0.5, 1, 2, 4, 6 (PO dosing only), 8, 24, 32, 48, and 72 hours after dosing. Blood samples were collected into tubes containing $K_2$EDTA via the non-dosing jugular-vein cannula (JVC), which was flushed with an approximately equal volume of saline following each collection.

Blood samples were stored on wet ice until processed to plasma by centrifugation (3500 rpm at 5° C. for 10 minutes) within 1 hour of collection. Plasma samples were transferred into matrix tubes and then stored in a −80° C. freezer.

Plasma samples and dose formulation samples were analyzed for the compounds of interest using liquid chromatography-tandem mass spectrometry (LC-MS/MS) methods. Pharmacokinetic parameter estimates were calculated from the individual animal plasma concentration-time data using the actual dose based on the analysis of the dosing formulations, nominal sampling times (all collections were within an acceptable range of target), and non-compartmental methods. The concentration-time data were analyzed to fit either an intravenous-bolus (IV) plasma analysis model (201) or extra-vascular (P0) dosing plasma analysis model (200) using the software WinNonlin Phoenix version 6.3 (Pharsight). The single-dose pharmacokinetic parameters assessed include, as appropriate: $C_{max}$ (observed peak or maximum concentration); $T_{max}$ (observed time of peak concentration); $T_{1/2}$ (terminal half-life); $V_z$ (volume of distribution based on the terminal phase); $V_{ss}$ (volume of distribution at steady state); $AUC_{INF}$ (area under the concentration-time curve computed from time zero to infinity); $AUC_{last}$ (area under the concentration-time curve computed from time zero to the time of the last quantifiable concentration); $C_0$ (back-extrapolated concentration at time zero); CL (total body clearance); Vz/F (volume of distribution for extravascular administration based on the terminal phase); CL/F (total body clearance for extravascular administration); F % (bioavailability); and $MRT_{last}$ (mean residence time).

Areas-under-the-plasma concentration-time curves (AUC) were estimated using the linear-log trapezoidal rule. The area through the time ($T_{last}$) of the last observable concentration ($C_{last}$) is reported as $AUC_{last}$. AUC extrapolated to infinity, ($AUC_{INF}$) was estimated by adding $AUC_{last}$ and the ratio of $C_{last}/\lambda_z$, where $\lambda_z$ is the terminal rate constant. Apparent terminal half-life ($T_{1/2}$) was calculated as $\ln(2)/\lambda_z$ and determined using the slope of the log-linear terminal phase of the concentration-time curve, defined by a minimum of three plasma concentration-time points. Half-lives are reported if the correlation for the regression line, as measured by r squared, is ≥0.9 when rounded. After IV administration, volume of distribution (Vz) was calculated as Dose/$\lambda_{z*}$ $AUC_{INF\text{-}obs}$, clearance (CL) was calculated as Dose/$AUC_{INF\text{-}obs}$ and volume of distribution at steady state ($V_{ss}$) was estimated as $MRT_{INF}$*CL. Mean residence time (MRT) from the time of dosing to the time of the last measurable concentration was calculated as $AUMC_{last}/AUC_{last}$. For model 200 the bioavailability (i.e. fraction of total dose that reaches the systemic circulation) cannot be calculated. Consequently, volume and clearance for this model is Vz/F or CL/F, respectively; where F is defined as bioavailability (i.e. fraction of total dose that reaches the systemic circulation; (Average $AUC_{last\text{-}po}$/Average $AUC_{last\text{-}iv}$)*[$Dose_{IV}$/$Dose_{PO}$]*100).

Pharmacokinetic data produced by the procedure above for some compounds of the invention are provided in Table 4 below.

TABLE 4

Rat Pharmacokinetic data for selected compounds of the invention

| Compound No. | Rat PK Parameters |
|---|---|
| 7 | IV (1 mg/kg)<br>t½ = 3.1 hr<br>Cl = 89 mL/hr/kg<br>PO (3 mg/kg)<br>t½ = 7.3 hr<br>Cmax = 8.8 uM<br>F = 72% |
| 8 | IV (3 mg/kg)<br>t½ = 5.4 hr<br>Cl = 43 mL/hr/kg<br>PO (3 mg/kg)<br>t½ = 7.1 hr<br>Cmax = 11.4 uM<br>F = 62% |
| 9 | IV (3 mg/kg)<br>t½ = 2.8 hr<br>Cl = 152 mL/hr/kg<br>PO (3 mg/kg)<br>t½ = 2.6 hr<br>Cmax = 3.9 uM<br>F = 69% |
| 17 | IV (3.0 mg/kg)<br>t½ = 3.0 hr<br>Cl = 102 mL/hr/kg<br>PO (3.2 mg/kg)<br>t½ = 4.5 hr<br>Cmax = 3.4 uM<br>F = 46% |
| 45 | IV (1 mg/kg)<br>t½ = 10.1 hr<br>Cl = 41 mL/hr/kg<br>PO (3 mg/kg)<br>t½ = 5.7 hr<br>Cmax = 15.3 uM<br>F = 133% |
| 191 | IV (3.0 mg/kg)<br>t½ = 9.9 hr<br>Cl = 63 mL/hr/kg<br>PO (3.1 mg/kg)<br>t½ = 6.8 hr<br>Cmax = 4.6 uM<br>F = 38% |
| 206 | IV (3 mg/kg)<br>t½ = 2.1 hr<br>Cl = 511 mL/hr/kg<br>PO (3 mg/kg)<br>t½ = 2.9 hr<br>Cmax = 0.7 uM<br>F = 37% |

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

The invention claimed is:

1. A compound which is:

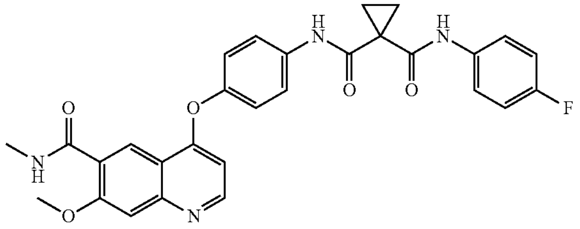 [SMILES: CNC(=O)c1cc2c(Oc3ccc(NC(=O)C4(C(=O)Nc5ccc(F)cc5)CC4)cc3)ccnc2cc1OC]

or a pharmaceutically acceptable salt thereof.

2. A compound which is 1-N'-(4-fluorophenyl)-1-N-[4-[7-methoxy-6-(methylcarbamoyl)quinolin-4-yl]oxyphenyl] cyclopropane-1,1-dicarboxamide or a pharmaceutically acceptable salt thereof.

* * * * *